US007910595B2

(12) United States Patent
Betebenner et al.

(10) Patent No.: US 7,910,595 B2
(45) Date of Patent: *Mar. 22, 2011

(54) ANTI-VIRAL COMPOUNDS

(75) Inventors: David A. Betebenner, Libertyville, IL (US); David A. DeGoey, Salem, WI (US); Clarence J. Maring, Palatine, IL (US); Allan C. Krueger, Gurnee, IL (US); Nobuhiko Iwasaki, Buffalo Grove, IL (US); Todd W. Rockway, Grayslake, IL (US); Curt S. Cooper, Vernon Hills, IL (US); David D. Anderson, Kenosha, WI (US); Pamela L. Donner, Mundelein, IL (US); Brian E. Green, Wonder Lake, IL (US); Dale J. Kempf, Libertyville, IL (US); Dachun Liu, Waukegan, IL (US); Keith F. McDaniel, Wauconda, IL (US); Darold L. Madigan, Elk Grove Village, IL (US); Christopher E. Motter, Oak Creek, WI (US); John K. Pratt, Kenosha, WI (US); Jason P. Shanley, Chicago, IL (US); Michael D. Tufano, Chicago, IL (US); Rolf Wagner, Antioch, IL (US); Rong Zhang, Niskayuna, NY (US); Akhteruzzaman Molla, Gurnee, IL (US); Hongmei Mo, Foster City, CA (US); Tami J. Pilot-Matias, Green Oaks, IL (US); Sherie V L. Masse, Kenosha, WI (US); Robert J. Carrick, Pleasant Prairie, WI (US); Wenping He, Libertyville, IL (US); Liangjun Lu, Kildeer, IL (US); David J. Grampovnik, Waukegan, IL (US)

(73) Assignee: Abbott Laboratories, Abbott Park, IL (US)

(*) Notice: Subject to any disclaimer, the term of this patent is extended or adjusted under 35 U.S.C. 154(b) by 96 days.

This patent is subject to a terminal disclaimer.

(21) Appl. No.: 11/613,810

(22) Filed: Dec. 20, 2006

(65) Prior Publication Data
US 2007/0232627 A1 Oct. 4, 2007

Related U.S. Application Data

(60) Provisional application No. 60/752,473, filed on Dec. 21, 2005.

(51) Int. Cl.
C07D 471/04 (2006.01)
A01N 31/519 (2006.01)
A61P 31/12 (2006.01)
(52) U.S. Cl. ............... 514/264.11; 544/279; 514/264.1
(58) Field of Classification Search ............... 514/264.1, 514/264.11; 544/279
See application file for complete search history.

(56) References Cited

U.S. PATENT DOCUMENTS

| 3,021,332 | A | * | 2/1962 | Hitchings et al. | ............. | 544/279 |
|---|---|---|---|---|---|---|
| 4,871,851 | A | * | 10/1989 | Beck | ............................. | 544/279 |
| 5,034,393 | A | * | 7/1991 | Hackler et al. | ............. | 514/262.1 |
| 5,350,749 | A | | 9/1994 | Hackler et al. | | |
| 5,464,781 | A | | 11/1995 | Armitage et al. | | |
| 5,654,307 | A | | 8/1997 | Bridges et al. | | |
| 5,925,644 | A | | 7/1999 | Jakobi et al. | | |
| 5,965,563 | A | * | 10/1999 | Buzzetti et al. | ............. | 514/263.2 |
| 6,130,217 | A | | 10/2000 | Arnold et al. | | |
| 6,169,091 | B1 | * | 1/2001 | Cockerill et al. | ......... | 514/228.2 |
| 6,174,889 | B1 | | 1/2001 | Cockerill et al. | | |
| 6,184,226 | B1 | | 2/2001 | Chakravarty et al. | | |
| 6,277,989 | B1 | | 8/2001 | Chakravarty et al. | | |
| 6,284,764 | B1 | | 9/2001 | Kath et al. | | |
| 6,323,180 | B1 | | 11/2001 | Llinas-Brunet et al. | | |
| 6,348,587 | B1 | | 2/2002 | Schinazi et al. | | |
| 6,395,733 | B1 | * | 5/2002 | Arnold et al. | ............. | 514/234.2 |
| 6,413,971 | B1 | | 7/2002 | Arnold et al. | | |
| 6,476,031 | B1 | | 11/2002 | Chakravarty et al. | | |
| 6,541,481 | B2 | | 4/2003 | Kath et al. | | |
| 6,610,677 | B2 | * | 8/2003 | Davies et al. | ................. | 514/183 |
| 6,703,403 | B2 | | 3/2004 | Norbeck et al. | | |
| 6,703,421 | B1 | * | 3/2004 | Nunokawa et al. | ........... | 514/532 |
| 6,723,726 | B1 | | 4/2004 | Cockerill et al. | | |
| 6,784,174 | B1 | * | 8/2004 | Cumming | ................... | 514/234.2 |
| 6,809,097 | B1 | | 10/2004 | Thomas et al. | | |
| 6,903,096 | B2 | | 6/2005 | Chakravarty et al. | | |
| 7,037,913 | B2 | | 5/2006 | Wang et al. | | |
| 7,183,302 | B2 | | 2/2007 | Romine et al. | | |

(Continued)

FOREIGN PATENT DOCUMENTS

EP 0 404 355 12/1990

(Continued)

OTHER PUBLICATIONS

Elneairy, et al., Journal of Sulfur Chemistry (2005), 26(4-5), 381-391.*
Monge, et al., Arzneimittel-Forschung (1990), 40(11), 1230-3.*
Iwamura, et al., Journal of Medicinal Chemistry (1985), 28(5), 577-83.*
Chen, et al., Yaoxue Xuebao (1982), 17(2), 112-17.*
Godefroy, et al., Journal of Heterocyclic Chemistry (1973), 10(6), 1077-8.*

(Continued)

Primary Examiner — James O Wilson
Assistant Examiner — Cecilia M Jaisle
(74) Attorney, Agent, or Firm — Xu Zhang

(57) ABSTRACT

Compounds effective in inhibiting replication of Hepatitis C virus ("HCV") or other viruses are disclosed. This invention is also directed to compositions comprising such compounds, co-formulation or co-administration of such compounds with other anti-viral or therapeutic agents, processes and intermediates for the syntheses of such compounds, and methods of using such compounds for the treatment of HCV or other viral infections.

20 Claims, No Drawings

U.S. PATENT DOCUMENTS

| | | | |
|---|---|---|---|
| 2003/0125343 | A1 | 7/2003 | Gambacorti-Passerini et al. |
| 2004/0242604 | A1 | 12/2004 | Bhattacharya et al. |
| 2004/0265792 | A1 | 12/2004 | Glenn et al. |
| 2005/0075331 | A1 | 4/2005 | Pratt et al. |
| 2005/0090522 | A1 | 4/2005 | Wang et al. |
| 2005/0107364 | A1 | 5/2005 | Hutchinson et al. |
| 2005/0215575 | A1* | 9/2005 | Bakthavatchalam et al. ............ 514/266.21 |
| 2006/0035965 | A1 | 2/2006 | Dalton et al. |
| 2007/0197558 | A1 | 8/2007 | Betebenner et al. |
| 2007/0232645 | A1 | 10/2007 | Rockway et al. |

FOREIGN PATENT DOCUMENTS

| | | | |
|---|---|---|---|
| EP | 404355 | * | 12/1990 |
| EP | 0 414 386 | | 2/1991 |
| EP | 0 912 570 | | 5/1999 |
| EP | 1 162 196 | | 12/2001 |
| ES | 2009217 | * | 9/1989 |
| GB | 774094 | * | 5/1957 |
| JP | 47025076 | * | 7/1972 |
| WO | 93/13097 | | 7/1993 |
| WO | 95/00511 | | 1/1995 |
| WO | 95/19774 | | 7/1995 |
| WO | 96/09294 | | 3/1996 |
| WO | 96/40142 | | 12/1996 |
| WO | 97/13771 | | 4/1997 |
| WO | 98/02428 | | 1/1998 |
| WO | 98/02437 | | 1/1998 |
| WO | 98/02438 | | 1/1998 |
| WO | 98/05661 | | 2/1998 |
| WO | 98/08846 | | 3/1998 |
| WO | 98/13350 | | 4/1998 |
| WO | 98/22444 | | 5/1998 |
| WO | 98/23613 | | 6/1998 |
| WO | WO 9846605 | * | 10/1998 |
| WO | 99/59587 | | 11/1999 |
| WO | 00/12497 | | 3/2000 |
| WO | 2007/076035 | | 7/2000 |
| WO | 00/44728 | | 8/2000 |
| WO | 00/56738 | | 9/2000 |
| WO | 01/32153 | | 5/2001 |
| WO | 01/32632 | | 5/2001 |
| WO | 01/57040 | | 8/2001 |
| WO | 01/60315 | | 8/2001 |
| WO | 01/90121 | | 11/2001 |
| WO | 02/04425 | | 1/2002 |
| WO | WO 03051366 | * | 6/2003 |
| WO | WO 03059913 | * | 7/2003 |
| WO | WO 03062209 | * | 7/2003 |
| WO | WO 03097615 | * | 11/2003 |
| WO | 2004/055004 | | 1/2004 |
| WO | 2004/014313 | | 2/2004 |
| WO | 2004/014852 | | 2/2004 |
| WO | 2004/024693 | | 3/2004 |
| WO | 2004/047818 | | 6/2004 |
| WO | WO 2004055003 | * | 7/2004 |
| WO | WO 2004055004 | * | 7/2004 |
| WO | 2004/065392 | | 8/2004 |
| WO | WO 2004071460 | * | 8/2004 |
| WO | 2004/087056 | | 10/2004 |
| WO | WO 2006067614 | * | 12/2004 |
| WO | WO 2006071875 | * | 12/2004 |
| WO | 2005/007652 | | 1/2005 |
| WO | WO 2005003100 | * | 1/2005 |
| WO | WO 2005023807 | * | 3/2005 |
| WO | WO 2006100310 | * | 3/2005 |
| WO | WO 2006105063 | * | 3/2005 |
| WO | WO 2005032481 | * | 4/2005 |
| WO | 2005/047288 | | 5/2005 |
| WO | WO 2005042498 | * | 5/2005 |
| WO | WO 2006120252 | * | 5/2005 |
| WO | 2005/082865 | | 9/2005 |
| WO | WO 2005049033 | * | 9/2005 |
| WO | WO 2005082865 | * | 9/2005 |
| WO | WO 2005087227 | * | 9/2005 |
| WO | 2005/105761 | | 11/2005 |
| WO | WO 2007060404 | * | 11/2005 |
| WO | 2006/012333 | | 2/2006 |
| WO | 2006/035061 | | 4/2006 |
| WO | 2006/038039 | | 4/2006 |
| WO | 2006/120251 | | 11/2006 |
| WO | 2006/120252 | | 11/2006 |
| WO | 2007/035010 | | 3/2007 |

OTHER PUBLICATIONS

Ahmed, et al., Journal of Heterocyclic Chemistry (2002), 39(2), 309-314.*

Rewcastle, et al., Journal of Medicinal Chemistry (1996), 39(9), 1823-35.*

Nishikawa, et al., Bioscience, Biotech., and Biochem. (1994), 58(9), 1709-10.*

Soloducho, Archiv der Pharmazie (Weinheim, Germany) (1990), 323(8), 513-15.*

Iwamura, et al., Phytochemistry (Elsevier) (1979), 18(8), 1265-8.*

Hayashi, et al., Yakugaku Zasshi (1977), 97(9), 1022-33.*

Nishikawa, et al., Chem. & Pharm. Bulletin (1976), 24(9), 2057-77.*

Godefroy, et al., Comptes Rendus des Seances de l'Academie des Sciences, Serie B: Sciences Physiques (1973), 277(16), 703-6.*

Blight, K.J., et al., "Efficient Initiation of HCV RNA Replication in Cell Culture", *Science*, 290:1972-1974 (2000).

Bundgaard, H., "Design of prodrugs", pp. 7-9 & 21-24 (1985).

Cortese, F. & Bauman, L., "A Synthesis of Conjugatred Bile Acids. I. Glycocholic Acid", *JACS*, 57:1393-1395 (1935).

Cross, L.C. & Klyne, W., "Rules for the Nomenclature of Organic Chemistry—Section E: Stereochemistry", *Pure Appl. Chem.*, 45:11-30 (1976).

Das, S., et al., "A Small yeast RNA Blocks Hepatitis C Virus Internal Ribosome Entry Site (HCV IRES)-Mediated Translation and Inhibits Replication of a Chimeric Poliovirus under Translational control of the HCV IRES Element", *J of Virology*, 72(7):5638-5647 (1998).

Deeb, A., et al., "Pyridazine Derivatives and Related Comp9unds Part 5. Pyrazolo[3,4-c]Pyridazine: Synthesis and Some Reactoins", *Heterocycles*, 32(5):895-900 (1991).

Gomtsyan, A., et al., "Design, Synthesis, and Structure-Activity Relationship of 6-Alkynylpyrimidines as Potent Adenosine Kinase Inhibitors", *J. Med. Chem.*, 45:3639-3648 (2002).

Greene & Wuts, *Protective Groups in Organic Synthesis*, 3$^{rd}$ Ed.:Tbl of Cont., (1999).

Hoover, J.E., *Remington's Pharmaceutical Sciences*, Tbl of Cont., (1975).

Ikeda, M., et al., "Selectable Subgenomic and Genome-Length Dicistronic RNAs Derived from an Infectious Molecular Clone of the HCV-N Strain of Hepatitis C Virus Replicate Efficiently in Clutured Huh7 Cells", *J. of Virology*, 76(6):2997-3006 (2002).

Jacques, et al., *Enantiomers, Racemates, and Resolutions*, Tble of Cont., (1981).

Janout, V., et al., "Design and Synthesis of Molecular Umbrellas", *J. Am. Chem. Soc.*, 119:640-647 (1997).

Lieberman, H.A. & Lachman, L., *Pharmaceutical Dosage Forms*, vol. 1:Tbl of Cont., (1980).

McKenzie, A. & Clough, G.W., "XLVIII.-Experiments on the Ealden Inversion. Part VIII. α-Amino-a-phenylpropionic Acids", *J. Chem. Soc.*, 101:390-397 (1912).

Miranda, E.I., et al., "Thiols, Unsymmetrical Sulfides and Thioacetals From the New Reagent: Trisopropysilanethiol", *Tetrahedron Ltrs.*, 35(20):3221-3224 (1994).

Nakamura, S., "Studies on Growth Inhibition of hiochi-bacteria, Specific Saprophytes of Sake", *Agr. Biol. Chem.*, 25(8):665-670 (1961).

Prakash, G.K.Su., et al., "Facile preparation of di- and monofluoromethyl ketones form trifluoromethyl ketones via fluorinated enol silyl ethers", *J. of Fluorine Chem.*, 112:357-362 (2001).

Refai, M., et al., "New Synthesis of Some 1,8- Naphthoyridines of Possible Lantimicrobial Lactivity", *Egypt. J. Pharm. Sci.*, 37(1-6):241-249 (1996).

Shuman, R.T., et al., "Structure-Activity Study of Tripeptide Thrombin Inhibitors Using α-Alkyl Amino Lacids and Other Conformationally Constrained Amino Acid Substitutions", *J. Med. Chem.*,38:4446-4453 (1995).

Yi, M., et al., "Subjenomic Hepatitis C Virus Replicaons Inducting Expression of a Secreted Enzymatic Reporter Protein", *Virology*, 304:197-210 (2002).

International Search Report for PCT/US2006/049079 dated Aug. 17, 2007.

International Search Report for PCT/US2006/048685 dated Oct. 30, 2007.

International Search Report for PCT/uS2006/049080 dated Aug. 23, 2007.

U.S. Appl. No. 11/960,298, filed Dec. 19, 2007.

Barlin, B.B. & Tan, W-L., "Potential Antimalarials. I 1,8-Naphthyridines", Aust. J. Chem., 37:1065-1073 (1984).

Chandrakumar, Nizal S., First Office Action for U.S. Appl. No. 11/613,836 dated Apr. 23, 2008.

Chandrakumar, Nizal S., Second Office Action for U.S. Appl. No. 11/613,836 dated Nov. 4, 2008.

Dorwald, F.Z., "Side Reactions in Organic Synthesis—a Guid to Successful Synthesis Design", 9-16 (2005).

Jaisle, Cecilia M., First Office Action for U.S. Appl. No. 11/613,825 dated Jun. 2, 2008.

Jaisle, Cecilia M., Second Office Action for U.S. Appl. No. 11/613,825 dated Oct. 28, 2008.

Martini, C., et al., :"Specific Inhibition of Benzodiazepine Receptor Binding by Some 1,2,3-Triazole Derivatives", J. of Pharm. Sci., 77(11):977-980 (1988).

Nishikawa, S., et al., "Cytokinin Activity of 4-Aminopyridopyrimidines toward the Growth of Tobacco Callus", Biosci. Biotech. Biochem., 58(9):1709-1710 (1994).

Nishikawa, et al., Chem. & Pharm. Bulletin 24(9):2057-2077 (1976).

Rewcastle, G.W., et al., "Tyrosine Kinase Inhibitors. 10. Isomeric 4-[(3-Bromophyenyl)amino]pyrido[d]-pyrimidines Are Potent ATP Binding Site Inhibitors of the Tyrosine Kinase Function of the Epidermal Growth Factor Receptor", J. Med. Chem., 39:1823-1835 (1996).

Soloducho, J., "Synthesis of Some Pyrido[2,3-d]pyrimidine and Pyrido[3,2-d]pyrimidine Derivatives", Arch. Pharm. (weinheim), 323:513-515 (1990).

USPQ, "*Graham v. John Deere Co. of Kansas City*", USPQ, 148:459-478 (1966).

Livi et al., "Farmaco, STN Document No. 86:89704; Abstract of Edizione Scientifica ," vol. 31 (11), pp. 797-808, 1976.

US Office Action dated Jul. 7, 2009 from U.S. Appl. No. 11/613,836, filed Dec. 20, 2006.

US Office Action dated Jul. 23, 2009 from U.S. Appl. No. 11/613,825, filed Dec. 20, 2006.

\* cited by examiner

ANTI-VIRAL COMPOUNDS

This application claims the benefit and incorporates herein by references the entire content of U.S. Provisional Application No. 60/752,473, filed Dec. 21, 2005.

FIELD

The present invention relates to compounds effective in inhibiting replication of Hepatitis C virus ("HCV"). The present invention also relates to methods of making such compounds, compositions comprising such compounds, intermediates for the syntheses of such compounds, and methods of using such compounds/compositions for the treatment of HCV infection or conditions/symptoms associated therewith. In addition, the present invention relates to use of such compounds for the manufacture of medicaments for the treatment of HCV infection.

BACKGROUND

HCV, a human pathogen, is an RNA virus belonging to the *Hepacivirus* genus in the Flaviviridae family. As is characteristic with all other members of the Flaviviridae family, HCV has enveloped virions that contain a positive stranded RNA genome encoding all known virus-specific proteins in one single, uninterrupted, open reading frame. The open reading frame comprises approximately 9500 nucleotides encoding a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B. A cellular protease cleaves the viral protein at the NS2—NS3 junction allowing a viral protease (NS3 protease) to mediate subsequent cleavages. The NS3 protein also exhibits nucleoside triphosphatase and RNA helicase activities. NS2 and NS4A may, too, be involved in proteolytic activity. NS5A is a phosphoprotein involved in replication. NS5B is a RNA-dependent RNA polymerase. U.S. Patent Pub. No. 2004/0265792, published 30 Dec. 2004, mentions that inhibition of the aforementioned non-structural proteins may inhibit HCV replication.

HCV infection is associated with progressive liver pathology, including cirrhosis and hepatocellular carcinoma. HCV-associated end-stage liver disease is the most frequent indication for liver transplantation among adults. Chronic hepatitis C may be treated with a once-weekly injection of peginterferon-alpha in combination with daily ribavarin. Peginterferon-alpha is interferon-alpha attached to polyethylene glycol to slow elimination of the drug from the body. This results in enhanced compliance and clinically superior anti-viral activity when compared to treatments of interferon-alpha daily injections. Substantial limitations to efficacy and tolerability remain as many users suffer from side effects and viral elimination from the body is often inadequate.

Attempts have been made to design drugs that specifically inhibit functions of the hepatitis C virus. Boehringer Ingelheim U.S. Pat. No. 6,323,180 mentions tri-peptide compounds as HCV serine protease inhibitors proposed for treatment of HCV infection.

Another approach is ISIS-14803 (Isis Pharmaceuticals), an antisense inhibitor complementary to a conserved sequence of the hepatitis C virus RNA. This molecule binds to the viral RNA and inhibits the expression of proteins required for replication.

Inhibition of HCV translation, by a yeast RNA that binds to cellular polypeptides and prevents their interaction with the viral internal ribosome entry site (IRES), is described in Das et al, J. VIROLOGY, 72(7):5638-5647 (1998).

Fused-bicyclic heterocyclic compounds have been proposed for diverse life-science-related uses. Examples of such heterocyclic compounds include naphthyridine, pyridopyrimidine, pyrimidopyrimidine, pyrazolopyrimidine and thiazolo/thienopyrimidine compounds.

Naphthyridine-type fused-bicyclic compounds have been investigated for disease-treatment uses. For example, Boots WO 93/13097, published 8 Jul. 1993, mentions [1,8]naphthyridine compounds, such as ethyl 4-(4-methoxyanilino)-6-ethoxy-7-methyl-1,8-naphthyridine-3-carboxylate hydrochloride, proposed for use as anti-rheumatic agents. Boots WO 95/00511, published 5 Jan. 1995, mentions substituted ring-fused 4-aminopyridines, such as 3-ethoxy-5-(2-ethoxy-5-pyridylamino)-2-methyl-1,8-naphthyridine, proposed for use as anti-rheumatic agents. Zeneca WO 98/13350, published 2 Apr. 1998, mentions [1,8]naphthyridine compounds, such as 2-acetamido-5-(2-fluoro-5-hydroxy-4-methylanilino)-1,8-naphthyridine hydrochloride, proposed as anti-angiogenic agents. Neurogen WO 2004/055004, published 1 Jul. 2004, mentions naphthyridine compounds as capsaicin-receptor modulators, specific compounds being 5-(4-trifluoromethyl-phenylamino)-2-(3-trifluoromethyl-pyridin-2-yl)-[1,6]naphthyridine-7-carboxylic acid, and 2-methoxymethyl-4-(4-trifluoromethyl-phenylamino)-7-(3-trifluoromethyl-pyridin-2-yl)-[1,8]naphthyridine-3-carboxylic acid.

Pyridopyrimidine-type fused-bicyclic compounds have been investigated for various disease-treatment uses. For example, Pfizer WO 98/05661, published 12 Feb. 1998, mentions substituted pyridopyrimidine compounds, such as [8-(1-ethyl-propyl)-2-methyl-5,6,7,8-tetrahydro-pyrido(2,3-d)pyrimidin-4-yl]-(2,4,6-trimethyl-phenyl)-amine, as corticotrophin releasing factor (hormone) CRF (CRH) antagonists proposed for treatment of Alzheimer's Disease and obesity. Pfizer WO 98/23613, published 4 Jun. 1998, mentions fused-bicyclic pyrimidine compounds, including pyridopyrimidinyl-aminophenyl compounds, such as (3-ethynyl-phenyl)-pyrido[3,4-d]pyrimidin-4-yl-amine, proposed for treatment of hyperproliferative diseases such as cancer. Glaxo Wellcome U.S. Pat. No. 6,169,091, issued 2 Jan. 2001, mentions bicyclic heteroaromatic compounds, such as 4-(4-benzyloxyanilino)pyrido[2,3-d]-pyrimidine, as tyrosine kinase inhibitors proposed for treatment of fibrosis, inflammation, nervous system diseases and cancer. Eli Lilly WO 01/32632, published 10 May 2001, mentions 4-substituted pyrimidine compounds, including 2-trifluoromethyl-4-[2-(2-(2-chlorophenyl)ethylamino]pyrido-[2,3-d]pyrimidine hydrochloride, as mGluR1 antagonists proposed for treatment of neurological disorders associated with glutamate dysfunction such as convulsions, migraine, psychosis, anxiety and pain. Abbott Laboratories WO 01/57040 published 9 Aug. 2001, mentions 6,7-disubstituted-4-aminopyrido[2,3-d]pyrimidine compounds, such as 4-amino-6-(4-methylphenyl)-7-(4-bromophenyl)pyrido[2,3-d]pyrimidine, as adenosine kinase inhibitors proposed for treatment of pain and inflammation. Neurogen WO 2004/055004, published 1 Jul. 2004, mentions pyridopyrmidinyl-aminophenyl compounds, such as 2-methyl-2-{4-[2-methyl-7-(3-methyl-pyridin-2-yl)-pyrido[2,3-d]pyrimidin-4-ylamino]-phenyl}-propionic acid, as capsaicin-receptor modulators. Pfizer U.S. Pat. No. 6,395,733, issued 28 May 2002, mentions heterocyclic ring-fused pyrimidine compounds, such as 3-chloro-phenyl-pyrido[2,3-d]pyrimidin-4-yl-amine, proposed for treatment of hyperproliferative disease, such as cancer.

Pyrimidopyrimidine-type fused bicyclic compounds have been investigated for both pest-control and disease-treatment uses. For example, Dow Elanco U.S. Pat. No. 5,350,749, issued 27 Sep. 1994, mentions 4-substituted-pyrimido[2,3-d] pyrimidine compounds proposed for use as fungicides, insecticides and miticides. Warner-Lambert WO 95/19774, published 27 Jul. 1995, mentions pyrimidopyrimidine compounds, such as 4-benzylamino-7-methylaminopyrimido[4,5-d]pyrimidine, as tyrosine kinase inhibitors proposed for treatment of cancer, vascular restenosis and psoriasis.

Thienopyrimidine-type fused-bicyclic compounds have been investigated for various disease-treatment uses. For example, Warner-Lambert WO 95/19774, published 27 Jul. 1995, mentions fused heterocyclic pyrimidine compounds, including 4-(3-bromoanilino)thieno[2,3-d]pyrimidine, as tyrosine kinase inhibitors proposed for treatment of cancer, vascular restenosis and psoriasis. Glaxo Wellcome U.S. Pat. No. 6,169,091, issued 2 Jan. 2001, mentions bicyclic heteroaromatic compounds, such as 5-methyl-4-(4-phenoxyanilino)thieno[2,3-d]pyrimidine hydrochloride as tyrosine kinase inhibitors, proposed for treatment of fibrosis, inflammation, nervous system diseases and cancer. Eli Lilly WO 01/32632, published 10 May 2001, mentions 4-substituted-pyrimidine compounds, such as 6-methyl-4-[2,6-dichlorobenzylthio)ethylamino]thieno[2,3-d]pyrimidine hydrochloride, as mGluR1 antagonists proposed for treatment of neurological disorders associated with glutamate dysfunction such as convulsions, migraine, psychosis, anxiety and pain.

Bristol-Myers Squibb WO 2004/014852, published 19 Feb. 2004, mentions iminothiazolidinones, including fused-bicyclic derivatives of 2-(4-aminophenyl)-5H-thiazolo[2,3-6]quinazolin-3-one, as NS5A-protein-inhibitors proposed to prevent HCV replication.

Bristol-Myers Squibb WO 2004/014313, published 19 Feb. 2004, mentions combination therapies for treatment of viral diseases, including iminothiazolidinone NS5A-protein-inhibiting anti-HCV compounds in combination with other agents capable of interfering with HCV function.

SUMMARY

The present invention features compounds having Formulae I, I(a), I(b), I(c), I(d), I(e), I(f), I(g) or I(h), tautomers of these compounds, and pharmaceutically acceptable salts of these compounds or tautomers. These compounds, tautomers or salts can be used, either individually or in combination with other drugs or agents, to inhibit the replication of HCV or other viruses. These compounds, tautomers or salts can also be used, either individually or in combination with other drugs or agents, to disrupt functions of HCV or other viruses.

The present invention also features compositions that comprise the compounds, tautomers or salts of the present invention. A composition of the present invention can include one or more compounds, tautomers or salts of the present invention. A composition of the present invention can also include one or more other antiviral or therapeutic agents.

In addition, the present invention features methods of using the compounds, tautomers or salts of the present invention, or compositions comprising the same, to inhibit the replication of HCV or other viruses. These methods comprise contacting HCV or another virus, or cells infected with HCV or said another virus, with an effective amount of a compound, tautomer or salt of the present invention, thereby inhibiting the replication of HCV or said another virus.

The present invention further features methods of using the compounds, tautomers or salts of the present invention, or compositions comprising the same, to inhibit the proliferation or transmission of HCV or other viruses. These methods comprise contacting HCV or another virus, or contacting cells infected with HCV or another virus, with an effective amount of a compound, tautomer or salt of the present invention, thereby inhibiting the proliferation or transmission of HCV or said another virus.

Moreover, the present invention features methods of using the compounds, tautomers or salts of the present invention, or compositions comprising the same, to treat HCV or other viral infections. These methods comprise administering to a patient in need of such treatment an effective amount of a compound, tautomer or salt of the present invention, thereby reducing the blood or tissue level of HCV or other viruses in the patient.

The present invention also features use of the compounds, tautomers or salts of the present invention for the manufacture of medicaments for the treatment of HCV or other viral infections.

Furthermore, the present invention features processes of making the compounds, tautomers or salts of the present invention, and intermediates employed in these processes.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The following description is exemplary in nature and is not intended to limit the present disclosure, application, or uses.

Compounds

The present invention features compounds having Formula I, tautomers thereof, and pharmaceutically acceptable salts of the compounds or tautomers,

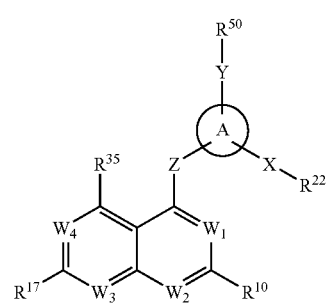

wherein:
$W_1$, $W_2$, $W_3$ and $W_4$ are each independently selected from N or C($R^{33}$);
Z is a bond, —$CR^{41}R^{41'}$— or —$NR^{41}$—, wherein $R^{41}$ and $R^{41'}$ are each independently selected from the group consisting of hydrogen, alkyl, alkenyl and alkynyl;
A is a carbocyclyl or heterocyclyl, and is optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, $-L_S-O-R_S$, $-L_S-S-R_S$, $-L_S-C(O)R_S$, $-L_S-OC(O)R_S$, $-L_S-C(O)OR_S$, $-L_S-N(R_SR_{S'})$, $-L_S-C(=NR_S)R_{S'}$, $-L_S-S(O)R_S$, $-L_S-SO_2R_S$, $-L_S-C(O)N(R_SR_{S'})$, $-L_S-N(R_S)C(O)R_{S'}$, $-L_S-C(=NR_S)N(R_{S'}R_{S''})$, $-L_S-N(R_{S'})C(=NR_S)R_{S'}$, $-L_S-N(R_S)C(O)N(R_{S'}R_{S''})$, $-L_S-N(R_S)SO_2R_{S'}$, $-L_S-SO_2N(R_SR_{S'})$, and $-L_S-N(R_S)SO_2N(R_{S'}R_{S''})$;

$R^{10}$, $R^{17}$, $R^{33}$ and $R^{35}$ are each independently selected at each occurrence from the group consisting of hydrogen, halogen, oxo, thioxo, hydroxy, mercapto, nitro, cyano, amino, carboxy, formyl, phosphate, azido, alkyl, alkenyl, alkynyl, carbocyclyl, heterocyclyl, $-L_S-O-R_S$, $-L_S-S-R_S$, $-L_S-C(O)R_S$, $-L_S-OC(O)R_S$, $-L_S-C(O)OR_S$, $-L_S-N(R_SR_{S'})$, $-L_S-C(=NR_S)R_{S'}$, $-L_S-S(O)R_S$, $-L_S-SO_2R_S$, $-L_S-C(O)N(R_SR_{S'})$, $-L_S-N(R_S)C(O)R_{S'}$, $-L_S-C(=NR_S)N(R_{S'}R_{S''})$, $-L_S-N(R_{S'})C(=NR_S)R_{S''}$, $-L_S-N(R_S)C(O)N(R_{S'}R_{S''})$, $-L_S-N(R_S)SO_2R_{S'}$, $-L_S-SO_2N(R_SR_{S'})$, $-L_S-N(R_S)SO_2N(R_{S'}R_{S''})$, $-L_E-Q-L_{E'}-(C_3-C_{18}$carbocyclyl) and $-L_E-Q-L_{E'}-(M_3-M_{18}$heterocyclyl);

X is selected from the group consisting of a bond, $-L_S-O-$, $-L_S-S-$, $-L_S-C(O)-$, $-L_S-N(R_S)-$, $-L_S-N(R_S)C(O)-$, $-L_S-C(O)N(R_S)-$, $-L_S-N(R_S)C(O)O-$, $-L_S-OC(O)N(R_S)-$, $-L_S-N(R_S)C(O)N(R_{S'})-$, $-L_S-C(=NR_S)N(R_{S'})-$, $-L_S-N(R_{S'})C(=NR_S)-$, $-L_S-S(O)-$, $-L_S-SO_2-$, $-L_S-C(O)O-$ and $-L_S-OC(O)-$;

$R^{22}$ is carbocyclyl or heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, $-L_S-O-R_S$, $-L_S-S-R_S$, $-L_S-C(O)R_S$, $-L_S-OC(O)R_S$, $-L_S-C(O)OR_S$, $-L_S-N(R_{SR}S_{S'})$, $-L_S-C(=NR_S)R_{S'}$, $-L_S-S(O)R_S$, $-L_S-SO_2R_S$, $-L_S-C(O)N(R_SR_{S'})$, $-L_S-N(R_S)C(O)R_{S'}$, $-L_S-C(=NR_S)N(R_{S'}R_{S''})$, $-L_S-N(R_{S'})C(=NR_S)R_{S''}$, $-L_S-N(R_S)C(O)N(R_{S'}R_{S''})$, $-L_S-N=C(NR_SR_{S'})(NR_{S'}R_{S'})$, $-L_S-N(R_S)SO_2R_{S'}$, $-L_S-SO_2N(R_SR_{S'})$, $-L_S-N(R_S)SO_2N(R_{S'}R_{S''})$, $-L_E-Q-L_{E'}-(C_3-C_{18}$carbocyclyl) and $-L_E-Q-L_{E'}-(M_3-M_{18}$heterocyclyl); or $R^{22}$ is alkyl, alkenyl or alkynyl, and is optionally substituted with one or more $R^{26}$; or $R^{22}$ is hydrogen;

Y is selected from the group consisting of a bond, $-O-$, $-C(O)-$, $-S(O)_2-$, $-S(O)-$, $-OS(O)_2-$, $-OS(O)-$, $-C(O)O-$, $-OC(O)-$, $-OC(O)O-$, $-C(O)N(R^{15})-$, $-N(R^{15})C(O)-$, $-C(O)N(R^{15})O-$, $-N(R^{15})C(O)O-$, $-C(O)N(R^{15})N(R^{15'})-$, $-S-$, $-C(S)-$, $-C(S)O-$, $-OC(S)-$, $-C(S)N(R^{15})-$, $-N(R^{15})-$, $-N(R^{15})C(S)-$, $-N(R^{15})S(O)-$, $-N(R^{15})S(O)_2-$, $-S(O)_2N(R^{15})-$, $-S(O)N(R^{15})-$, $-C(S)N(R^{15})O-$, and $-C(S)N(R^{15'})N(R^{15'})-$, wherein $R^{15}$ and $R^{15'}$ are each independently selected at each occurrence from the group consisting of hydrogen, alkyl, alkenyl and alkynyl;

$R^{50}$ is $-L^1-A^1$, wherein $A^1$ is selected from the group consisting of carbocyclyl, heterocyclyl, alkyl, alkenyl and alkynyl, and $L^1$ is selected from the group consisting of a bond, alkylene, alkenylene and alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, $-L_S-O-R_S$, $-L_S-S-R_S$, $-L_S-C(O)R_S$, $-L_S-OC(O)R_S$, $-L_S-C(O)OR_S$, $-L_S-N(R_SR_{S'})$, $-L_S-C(=NR_S)R_{S'}$, $-L_S-S(O)R_S$, $-L_S-SO_2R_S$, $-L_S-C(O)N(R_SR_{S'})$, $-L_S-N(R_S)C(O)R_{S'}$, $-L_S-C(=NR_S)N(R_{S'}R_{S''})$, $-L_S-N(R_{S'})C(=NR_S)R_{S''}$, $-L_S-N(R_S)C(O)N(R_{S'}R_{S''})$, $-L_S-N(R_S)SO_2R_{S'}$, $-L_S-SO_2N(R_SR_{S'})$, $-L_S-N(R_S)SO_2N(R_{S'}R_{S''})$, $-L_E-Q-L_{E'}-(C_3-C_{18}$carbocyclyl) and $-L_E-Q-L_{E'}-(M_3-M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, alkoxy, thioalkoxy, alkylcarbonyl, alkoxycarbonyl, alkylcarbonyloxy, alkylamino, alkoxycarbonylamino, $-L_S-O-R_S$, $-L_S-S-R_S$, $-L_S-C(O)R_S$, $-L_S-OC(O)R_S$, $-L_S-C(O)OR_S$, $-L_S-N(R_SR_{S'})$, $-L_S-C(=NR_S)R_{S'}$, $-L_S-S(O)R_S$, $-L_S-SO_2R_S$, $-L_S-C(O)N(R_SR_{S'})$, $-L_S-N(R_S)C(O)R_{S'}$, $-L_S-C(=NR_S)N(R_{S'}R_{S''})$, $-L_S-N(R_{S'})C(=NR_S)R_{S''}$, $-L_S-N(R_S)C(O)N(R_{S'}R_{S''})$, $-L_S-N(R_S)SO_2R_{S'}$, $-L_S-SO_2N(R_SR_{S'})$, $-L_S-N(R_S)SO_2N(R_{S'}R_{S''})$, carbocyclyl, heterocyclyl, carbocyclylalkyl, heterocyclylalkyl, $-L_E-Q-L_{E'}-(C_3-C_{18}$carbocyclyl) and $-L_E-Q-L_{E'}-(M_3-M_{18}$heterocyclyl);

$L_S$ is independently selected at each occurrence from the group consisting of a bond, alkylene, alkenylene and alkynylene;

$R_S$, $R_{S'}$ and $R_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

$L_E$ and $L_{E'}$ are each independently selected at each occurrence from the group consisting of a bond, alkylene, alkenylene and alkynylene;

Q is independently selected at each occurrence from the group consisting of a bond, alkylene, alkenylene, alkynylene, $-S-$, $-O-$, $-C(O)-$, $-N(R_S)-$, $-N(R_S)C(O)-$, $-C(O)N(R_S)-$, $-N(R_S)C(O)O-$, $-OC(O)N(R_S)-$, $-N(R_S)C(O)N(R_{S'})-$, $-C(=NR_S)N(R_{S'})-$, $-N(R_{S'})C(=NR_S)-$, $-S(O)-$, $-SO_2-$, $-O-SO_2-$, $-SO_2-O-$, $-O-S(O)-$, $-S(O)-O-$, $-C(O)O-$ and $-OC(O)-$;

$R^{10}$, $R^{15}$, $R^{15'}$, $R^{17}$, $R^{18}$, $R^{26}$, $R^{30}$, $R^{33}$, $R^{35}$, $R^{38}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate and azido; and each $C_3-C_{18}$carbocyclyl and $M_3-M_{18}$heterocyclyl moiety in $-L_E-Q-L_{E'}-(C_3-C_{18}$carbocyclyl) and $-L_E-Q-L_{E'}-(M_3-M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl.

In one embodiment, the present invention features compounds having Formula I, tautomers thereof, and pharmaceutically acceptable salts of the compounds or tautomers, wherein:

$W_1$, $W_2$, $W_3$ and $W_4$ are each independently selected from N or $C(R^{33})$;

Z is a bond, $-CR^{41}R^{41'}-$ or $-NR^{41}-$, wherein $R^{41}$ and $R^{41'}$ are each independently selected from the group consisting of hydrogen, $C_1-C_6$alkyl, $C_2-C_6$alkenyl and $C_2-C_6$alkynyl;

A is a carbocyclyl or heterocyclyl, and is optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O-$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), and -$L_S$-N($R_S$)SO$_2$N($R_{S'} R_{S''}$);

$R^{10}$, $R^{17}$, $R^{33}$ and $R^{35}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

X is selected from the group consisting of a bond, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_{S'}$)C(=N$R_S$)—, -$L_S$-S(O)—, -$L_S$-SO$_2$-, -$L_S$-C(O)O— and -$L_S$-OC(O)—;

$R^{22}$ is carbocyclyl or heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N=C(N$R_S R_{S'}$)(N$R_S R_{S'}$), -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl); or $R^{22}$ is $C_1$-$C_6$alkyl, $C_2$-$C_6$alkenyl or $C_2$-$C_6$alkynyl, and is optionally substituted with one or more $R^{26}$; or $R^{22}$ is hydrogen;

Y is selected from the group consisting of a bond, —O—, —C(O)—, —S(O)$_2$—, —S(O)—, —OS(O)$_2$—, —OS(O)—, —C(O)O—, —OC(O)—, —OC(O)O—, —C(O)N($R^{15}$)—, —N($R^{15}$)C(O)—, —C(O)N($R^{15}$)O—, —N($R^{15}$)C(O)O—, —C(O)N($R^{15}$)N($R^{15'}$)—, —S—, —C(S)—, —C(S)O—, —C(S)N($R^{15}$)—, —N($R^{15}$)—, —N($R^{15}$)C(S)—, —N($R^{15}$)S(O)—, —N($R^{15}$)S(O)$_2$—, —S(O)$_2$N($R^{15}$)—, —S(O)N($R^{15}$)—, —C(S)N($R^{15}$)O—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl and $C_2$-$C_6$alkynyl;

$R^{50}$ is -$L^1$-$A^1$, wherein $A^1$ is selected from the group consisting of carbocyclyl, heterocyclyl, $C_1$-$C_6$alkyl, $C_2$-$C_6$alkenyl and $C_2$-$C_6$alkynyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —C(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{17}$, $R^{18}$, $R^{26}$, $R^{30}$ $R^{33}$, $R^{35}$, $R^{38}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate, and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl.

In one example of this embodiment, $W_1$, $W_2$ and $W_3$ are N, $W_4$ is $C(R^{33})$, and Z is —$NR^{41'}$.

In another example of this embodiment, A is a $C_5$-$C_6$carbocyclyl optionally substituted with one or more $R^{18}$.

In yet another example of this embodiment, A is a $M_5$-$M_6$heterocyclyl optionally substituted with one or more $R^{18}$.

In still another example of this embodiment, Y is —C(O)N($R^{15}$)— or —N($R^{15}$)C(O)—, $R^{15}$ is hydrogen, $C_1$-$C_6$alkyl, $C_2$-$C_6$alkenyl or $C_2$-$C_6$alkynyl, and $L^1$ is $C_1$-$C_6$alkylene optionally substituted with one or more $R^{38}$, wherein $A^1$ is a $C_4$-$C_6$carbocyclyl or $M_4$-$M_6$heterocyclyl and is optionally substituted with one or more $R^{30}$.

In still yet another example of this embodiment, Y is —C(O)N($R^{15}$)— or —N($R^{15}$)C(O)—, $R^{15}$ is hydrogen, $C_1$-$C_6$alkyl, $C_2$-$C_6$alkenyl or $C_2$-$C_6$alkynyl, and $L^1$ is a bond (i.e., $R^{50}$ is -$A^1$), wherein $A^1$ is a $C_4$-$C_6$carbocyclyl or $M_4$-$M_6$heterocyclyl and is optionally substituted with one or more $R^{30}$.

In a further example of this embodiment, Y is —C(O)N($R^{15}$)— or —N($R^{15}$)C(O)—, $R^{15}$ is hydrogen, $C_1$-$C_6$alkyl, $C_2$-$C_6$alkenyl or $C_2$-$C_6$alkynyl, and $L^1$ is a bond (i.e., $R^{50}$ is -$A^1$) or $C_1$-$C_6$alkylene optionally substituted with one or more $R^{38}$, wherein $A^1$ is a bicyclic ring (e.g., a fused bicyclic ring or a bridged bicyclic ring) which has from 6 to 14 ring atoms and is optionally substituted with one or more $R^{30}$.

In another example of this embodiment, X is —O— or —S—, and $R^{22}$ is $C_5$-$C_6$carbocyclyl or $M_5$-$M_6$heterocyclyl and is optionally substituted with one or more $R^{26}$.

In still another example of this embodiment, $R^{10}$, $R^{33}$, $R^{35}$, $R^{41}$ and $R^{41'}$ are each independently selected at each occurrence from hydrogen, halogen or $C_1$-$C_6$alkyl, and $R^{17}$ is $C_1$-$C_6$alkyl.

In yet another example of this embodiment, $R^{10}$ is hydrogen and $R^{17}$ is $C_1$-$C_6$alkyl.

In still another example of this embodiment, $W_1$, $W_2$ and $W_3$ are N, $W_4$ is $C(R^{33})$, and Z is —$NR^{41}$—, wherein:
  $R^{33}$ and $R^{35}$ are each independently selected from hydrogen, halogen or $C_1$-$C_6$alkyl;
  $R^{41}$ is selected from hydrogen or $C_1$-$C_6$alkyl;
  $R^{10}$ is hydrogen;
  $R^{17}$ is $C_1$-$C_6$alkyl or $C_3$-$C_6$cycloalkyl;
  A is a $C_5$-$C_6$carbocyclyl or $M_5$-$M_6$heterocyclyl and is optionally substituted with one or more $R^{18}$;
  X is —S— or —O—;
  $R^{22}$ is

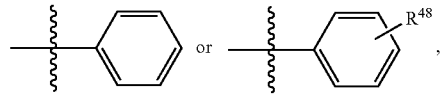

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl; and $R^{50}$ is -$L^1$-$A^1$, wherein:
  $L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a bicyclic ring (e.g., a fused bicyclic ring or a bridged bicyclic ring) having from 6 to 12 ring atoms and is optionally substituted with one or more $R^{30}$.

In another example of this embodiment, $W_1$, $W_2$ and $W_3$ are N, $W_4$ is $C(R^{33})$, and Z is —$NR^{41}$—, wherein:
  $R^{33}$ and $R^{35}$ are each independently selected from hydrogen, halogen or $C_1$-$C_6$alkyl;
  $R^{41}$ is selected from hydrogen or $C_1$-$C_6$alkyl;
  $R^{10}$ is hydrogen;
  $R^{17}$ is $C_1$-$C_6$alkyl or $C_3$-$C_6$cycloalkyl;
  A is a $C_5$-$C_6$carbocyclyl or $M_5$-$M_6$heterocyclyl and is optionally substituted with one or more $R^{18}$;
  X is —S— or —O—;
  $R^{22}$ is

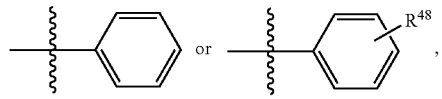

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;

Y is —C(O)O— or —OC(O)—; and $R^{50}$ is -$L^1$-$A^1$, wherein:
  $L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is hydrogen; or
  $L^1$ is a bond (i.e., $R^{50}$ is -$A^1$), and $A^1$ is a bicyclic ring (e.g., a fused bicyclic ring or a bridged bicyclic ring) having from 6 to 12 ring atoms and is optionally substituted with one or more $R^{30}$.

The ring member(s) in the moiety

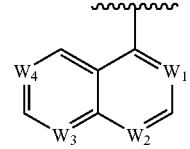

may be substituted with S or other heteroatoms.

In another embodiment, the present invention features compounds having a formula selected from the group consisting of Formulae I(a), I(b), I(c) and I(d), tautomers of these compounds, and pharmaceutically acceptable salts of these compounds or tautomers,

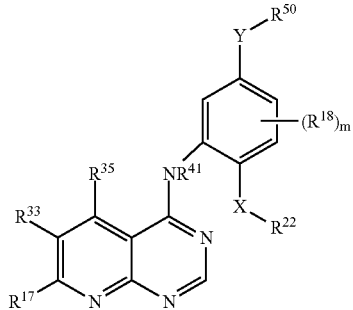

I(a)

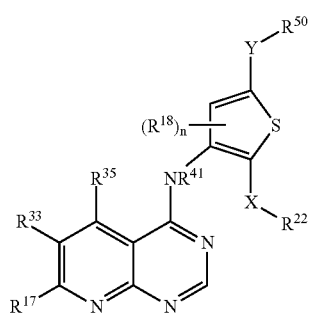

I(b)

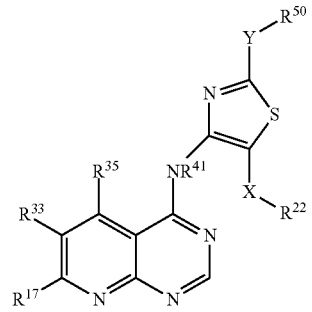

I(c)

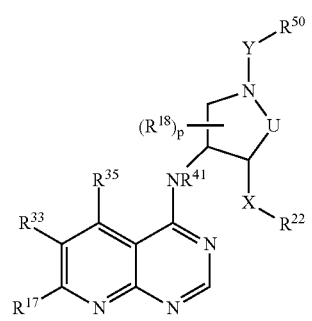

I(d)

wherein:
$R^{17}$, $R^{33}$ and $R^{35}$ are each independently selected from hydrogen, halogen, $C_1$-$C_6$alkyl or $C_3$-$C_6$cycloalkyl;
$R^{41}$ is selected from hydrogen or $C_1$-$C_6$alkyl;
X is —S— or —O—;

$R^{22}$ is

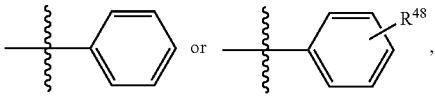

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;
Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;
$R^{50}$ is -$L^1$-$A^1$, wherein:
  $L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a bicyclic ring (e.g., a fused bicyclic ring or a bridged bicyclic ring) having from 6 to 12 ring atoms and is optionally substituted with one or more $R^{30}$; or
  $L^1$ is $C_1$-$C_6$alkyl optionally substituted with one or more $R^{38}$, and $A^1$ is hydrogen or $C_1$-$C_6$alkyl optionally substituted with one or more $R^{30}$;
$R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_S$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_S$)C(=N$R_S$)$R_{S''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), and -$L_S$-N($R_S$)SO$_2$N($R_S R_{S''}$);
$R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S''}$, -$L_S$-S(O)$R_S$, -$L_S$-SO$_2$$R_S$, -$L_S$-C(O)N($R_S R_{S''}$), -$L_S$-N($R_S$)C(O)$R_{S'}$, -$L_S$-C(=N$R_S$)N($R_S R_{S''}$), -$L_S$-N($R_S$)C(=N$R_S$)$R_{S''}$, -$L_S$-N=C(N$R_S R_{S'}$)(N$R_S R_{S'}$), -$L_S$-N($R_S$)C(O)N($R_S R_{S''}$), -$L_S$-N($R_S$)SO$_2$$R_{S''}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);
$R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S''}$, -$L_S$-S(O)$R_S$, -$L_S$-SO$_2$$R_S$, -$L_S$-C(O)N($R_S R_{S'}$), -$L_S$-N($R_S$)C(O)$R_{S''}$, -$L_S$-C(=N$R_S$)N($R_S R_{S''}$), -$L_S$-N($R_S$)C(=N$R_S$)$R_{S''}$, -$L_S$-N($R_S$)C(O)N($R_S R_{S''}$), -$L_S$-N($R_S$)SO$_2$$R_{S''}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);
$R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, amino$C_1$-$C_6$alkyl, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —C(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, O—S(O)—, —S(O)—O—, —C(O)O— and —OC(O)—;

$R^{15}$, $R^{17}$, $R^{18}$, $R^{26}$, $R^{30}$ $R^{33}$, $R^{35}$, $R^{38}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido;

each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

m is 0, 1, 2, or 3;
n is 0 or 1;
p is 0, 1, 2, or 3; and
U is —CH$_2$— or —CH$_2$—CH$_2$— and is optionally substituted with one or more $R^{18}$.

In yet another embodiment, the present invention features compounds having a formula selected from the group consisting of Formulae I(a), I(b), I(c) and I(d), tautomers of these compounds, and pharmaceutically acceptable salts of these compounds or tautomers, wherein:

$R^{17}$, $R^{33}$ and $R^{35}$ are each independently selected from hydrogen, halogen or $C_1$-$C_6$alkyl;

$R^{41}$ is selected from hydrogen or $C_1$-$C_6$alkyl;

X is —S— or —O—;

$R^{22}$ is $C_4$-$C_{12}$carbocyclyl or $M_4$-$M_{12}$heterocyclyl (e.g., indole or imidazole), and is optionally substituted with one or more $R^{26}$;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or $L^1$ is a bond (i.e., $R^{50}$ is -$A^1$), and $A^1$ is a $C_4$-$C_{12}$carbocyclyl or $M_4$-$M_{12}$heterocyclyl and is optionally substituted with one or more $R^{30}$; or $L^1$ is a bond (i.e., $R^{50}$ is -$A^1$), and $A^1$ is a bicyclic ring (e.g., a fused bicyclic ring or a bridged bicyclic ring) having from 6 to 12 ring atoms and is optionally substituted with one or more $R^{30}$; or $L^1$ is $C_1$-$C_6$alkylene optionally substituted with one or more $R^{38}$, and $A^1$ is hydrogen or $C_1$-$C_6$alkyl optionally substituted with one or more $R^{30}$;

$R^{18}$, $R^{26}$, $R^{30}$, $R^{38}$, m, n, p and U are as defined in the embodiment immediately above; and $R^{15}$, $R^{17}$, $R^{18}$, $R^{26}$, $R^{30}$ $R^{33}$, $R^{35}$, $R^{38}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido.

In one example of this embodiment, $L^1$ is $C_1$-$C_6$alkylene and is substituted with at least one phosphate, and $A^1$ is hydrogen.

In another example of this embodiment, $L^1$ is $C_1$-$C_6$alkylene and substituted with at least one phosphate, $A^1$ is hydrogen, X is —S— or —O—, $R^{22}$ is

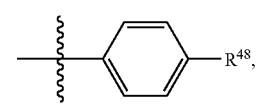

$R^{48}$ is amino and is optionally substituted with one or more $R^{26}$, $R^{17}$ is $C_1$-$C_6$alkyl (e.g., methyl, isopropyl or butyl), and $R^{41}$, $R^{33}$ and $R^{35}$ are independently hydrogen or halogen. In many instances, Y is —C(O)N($R^{15}$)— and $R^{15}$ is hydrogen. In many other instances, Y is —C(O)N($R^{15}$)— and $R^{15}$ is $C_1$-$C_6$alkyl or $C_2$-$C_6$alkenyl (e.g., —CH$_3$ or —CH$_3$—CH$_2$=CH$_2$). In still some instances, $R^{48}$ is substituted with at least one $R^{26}$. Non-limiting examples of suitable $R^{26}$ include —C(O)—O—$C_1$-$C_6$alkyl, —SO$_2$—$C_1$-$C_6$alkyl, —C(O)—$C_1$-$C_6$alkylene-$C_3$-$C_{18}$carbocyclyl (e.g., —C(O)—$C_1$-$C_6$alkylene-phenyl) or —C(O)—$C_1$-$C_6$alkylene-$M_3$-$M_{18}$heterocyclyl, wherein the $C_3$-$C_{18}$carbocyclyl and $M_3$-$M_{18}$heterocyclyl can be further optionally substituted with one or more moieties, such as halogen, $C_1$-$C_6$alkyl or $C_1$-$C_6$haloalkyl.

In still another example of this embodiment, $L^1$ is $C_1$-$C_6$alkylene and substituted with at least one $R^{38}$, and $A^1$ is hydrogen. No-limiting examples of suitable $R^{38}$ include halogen, oxo, thioxo, hydroxy, mercapto, amino, $C_5$-$C_6$carbocyclyl-O— or $M_5$-$M_6$heterocyclyl-O—.

In another embodiment, the present invention features compounds having a formula selected from the group consisting of Formulae I(a), I(b), I(c) and I(d), tautomers of these compounds, and pharmaceutically acceptable salts of these compounds or tautomers, wherein:

$R^{17}$, $R^{33}$ and $R^{35}$ are each independently selected from hydrogen, halogen or $C_1$-$C_6$alkyl;

$R^{41}$ is selected from hydrogen or $C_1$-$C_6$alkyl;

X is —S— or —O—;

$R^{22}$ is

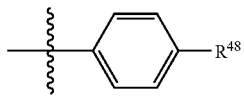

and is optionally substituted with one or more $R^{26}$, wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;

$R^{50}$ is -$L^1$-$A^1$, wherein $L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$;

$R^{18}$, $R^{26}$, $R^{30}$, $R^{38}$, m, n, p and U as defined in the embodiment immediately above; and $R^{15}$, $R^{17}$, $R^{18}$, $R^{26}$, $R^{30}$ $R^{33}$, $R^{35}$, $R^{38}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido.

In one example of this embodiment, X is —O—.

In another example of this embodiment, X is —S—.

In still another example of this embodiment, $R^{48}$ is amino and is optionally substituted with one or more $R^{26}$.

In yet another example of this embodiment, $R^{17}$ is $C_1$-$C_6$alkyl (e.g., methyl, isopropyl or butyl), and $R^{41}$, $R^{33}$ and $R^{35}$ are independently hydrogen or halogen.

In a further example of this embodiment, $A^1$ is $C_5$-$C_6$carbocyclyl (e.g., phenyl) or $M_5$-$M_6$heterocyclyl (e.g., pyridinyl or thiofuranyl), and is optionally substituted with one or more $R^{30}$ (e.g., —F, —Br, —$CH_3$, or —$CF_3$).

In still another example of this embodiment, $R^{48}$ is amino and is substituted with at least one $R^{26}$. Non-limiting examples of suitable $R^{26}$ include —C(O)—O—$C_1$-$C_6$alkyl, —$SO_2$—$C_1$-$C_6$alkyl, —C(O)—$C_1$-$C_6$alkylene-$C_3$-$C_{18}$carbocyclyl (e.g., —C(O)—$C_1$-$C_6$alkylene-phenyl) or —C(O)—$C_1$-$C_6$alkylene-$M_3$-$M_{18}$heterocyclyl, wherein the $C_3$-$C_{18}$carbocyclyl and $M_3$-$M_{18}$heterocyclyl can be further substituted with at least one phosphate and optionally substituted with one or more other moieties, such as halogen, $C_1$-$C_6$alkyl or $C_1$-$C_6$haloalkyl.

In still yet another example of this embodiment, $L^1$ is $C_1$-$C_6$alkylene (e.g., —$CH_2$—, —CH($CH_3$)—, —$CH_2$—$CH_2$—, —C($CH_3$)$_2$—, —CH($CH_2CH_3$)—, —C($CH_3$)($CH_2CH_3$)—, —C($CH_2CH_3$)($CH_2CH_3$)— or —$CH_2$—CH($CH_3$)—) and is optionally substituted with one or more $R^{38}$ (e.g., phosphate, halogen, hydroxy, —$CO_2$—$C_1$-$C_6$alkyl or —$CO_2$—O—$C_1$-$C_6$alkyl), X is —S—, $R^{48}$ is amino and is optionally substituted with one or more $R^{26}$, $R^{17}$ is $C_1$-$C_6$alkyl (e.g., methyl, isopropyl or butyl), $R^{41}$, $R^{33}$ and $R^{35}$ are independently hydrogen or halogen, and $A^1$ is $C_5$-$C_6$carbocyclyl (e.g., phenyl) or $M_5$-$M_6$heterocyclyl (e.g., pyridinyl or thiofuranyl) and is optionally substituted with one or more $R^{30}$ (e.g., —F, —Br, —$CH_3$, or —$CF_3$)— In many instances, Y is —C(O)N($R^{15}$)— and $R^{15}$ is hydrogen. In many other instances, Y is —C(O)N($R^{15}$)— and $R^{15}$ is $C_1$-$C_6$alkyl or $C_2$-$C_6$alkenyl (e.g., —$CH_3$ or —$CH_3$—$CH_2$=$CH_2$). In still some instances, $R^{48}$ is substituted with at least one $R^{26}$. Non-limiting examples of suitable $R^{26}$ include —C(O)—O $C_1$-$C_6$alkyl, —$SO_2C_1$-$C_6$alkyl, —C(O)—$C_1$-$C_6$alkylene-$C_3$-$C_{18}$carbocyclyl (e.g., —C(O)—$C_1$-$C_6$alkylene-phenyl) or —C(O)—$C_1$-$C_6$alkylene-$M_3$-$M_{18}$heterocyclyl, wherein the $C_3$-$C_{18}$carbocyclyl and $M_3$-$M_{18}$heterocyclyl can be further substituted with at least one phosphate and optionally substituted with one or more other moieties, such as halogen, $C_1$-$C_6$alkyl or $C_1$-$C_6$haloalkyl.

In yet another example of this embodiment, $L^1$ is $C_1$-$C_6$alkylene (e.g., —$CH_2$—, —CH($CH_3$)—, —$CH_2$—$CH_2$—, —C($CH_3$)$_2$—, —CH($CH_2CH_3$)—, —C($CH_3$)($CH_2CH_3$)—, —C($CH_2CH_3$)($CH_2CH_3$)— or —$CH_2$—CH($CH_3$)—) and is optionally substituted with one or more $R^{38}$ (e.g., phosphate, halogen, hydroxy, —$CO_2$—$C_1$-$C_6$alkyl or —$CO_2$—O—$C_1$-$C_6$alkyl), X is —O—, $R^{48}$ is amino and is optionally substituted with one or more $R^{26}$, $R^{17}$ is $C_1$-$C_6$alkyl (e.g., methyl, isopropyl or butyl), $R^{41}$, $R^{33}$ and $R^{35}$ are independently hydrogen or halogen, and $A^1$ is $C_5$-$C_6$carbocyclyl (e.g., phenyl) or $M_5$-$M_6$heterocyclyl (e.g., pyridinyl or thiofuranyl) and is optionally substituted with one or more $R^{30}$ (e.g., —F, —Br, —$CH_3$, or —$CF_3$). In many instances, Y is —C(O)N($R^{15}$)— and $R^{15}$ is hydrogen. In many other instances, Y is —C(O)N($R^{15}$)— and $R^{15}$ is $C_1$-$C_6$alkyl or $C_2$-$C_6$alkenyl (e.g., —$CH_3$ or $CH_3$—$CH_2$=$CH_2$). In still some instances, $R^{48}$ is substituted with at least one $R^{26}$. Non-limiting examples of suitable $R^{26}$ include —C(O)—O—$C_1$-$C_6$alkyl, —$SO_2$—$C_1$-$C_6$alkyl, —C(O)—$C_1$-$C_6$alkylene-$C_3$-$C_{18}$carbocyclyl (e.g., —C(O)—$C_1$-$C_6$alkylene-phenyl) or —C(O)—$C_1$-$C_6$alkylene-$M_3$-$M_{18}$heterocyclyl, wherein the $C_3$-$C_{18}$carbocyclyl and $M_3$-$M_{18}$heterocyclyl can be further substituted with at least one phosphate and optionally substituted with one or more other moieties, such as halogen, $C_1$-$C_6$alkyl or $C_1$-$C_6$haloalkyl.

In yet another embodiment, the present invention features compounds having a formula selected from the group consisting of Formulae I(a), I(b), I(c) and I(d), tautomers of these compounds, and pharmaceutically acceptable salts of these compounds or tautomers, wherein:

$R^{17}$, $R^{33}$ and $R^{35}$ are each independently selected from hydrogen, halogen or $C_1$-$C_6$alkyl;

$R^{41}$ is selected from hydrogen or $C_1$-$C_6$alkyl;

X is —S— or —O—;

$R^{22}$ is

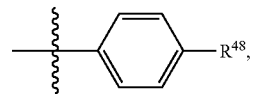

and is optionally substituted with one or more $R^{26}$, wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;

$R^{50}$ is -$A^1$, wherein $A^1$ is a bicyclic ring (e.g., a fused bicyclic ring or a bridged bicyclic ring) having from 6 to 12 ring atoms and is optionally substituted with one or more $R^{30}$;

$R^{18}$, $R^{26}$, $R^{30}$, m, n, p and U as defined in the embodiment immediately above; and $R^{15}$, $R^{17}$, $R^{18}$, $R^{26}$, $R^{30}$ $R^{33}$, $R^{35}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido.

In one example of this embodiment, $A^1$ is a bicyclic ring having from 9 to 11 ring atoms (e.g., 2,3-dihydro-1H-indenyl) and is optionally substituted with one or more $R^{30}$ (e.g., hydroxy$C_1$-$C_6$alkyl), X is —S—, $R^{48}$ is amino and is optionally substituted with one or more $R^{26}$, $R^{17}$ is $C_1$-$C_6$alkyl (e.g., methyl, isopropyl or butyl), and $R^{41}$, $R^{33}$ and $R^{35}$ are independently hydrogen or halogen. In many instances, Y is —C(O)N($R^{15}$)— and $R^{15}$ is hydrogen. In many other instances, Y is —C(O)N($R^{15}$)— and $R^{15}$ is $C_1$-$C_6$alkyl or $C_2$-$C_6$alkenyl (e.g., —$CH_3$ or —$CH_3$—$CH_2$=$CH_2$). In still some instances, $R^{48}$ is substituted with at least one $R^{26}$. Non-limiting examples of suitable $R^{26}$ include —C(O)—O—$C_1$-$C_6$alkyl, —$SO_2$—$C_1$-$C_6$alkyl, —C(O)—$C_1$-$C_6$alkylene-$C_3$-$C_{18}$carbocyclyl (e.g., —C(O)—$C_1$-$C_6$alkylene-phenyl) or —C(O)—$C_1$-$C_6$alkylene-$M_3$-$M_{18}$heterocyclyl, wherein the $C_3$-$C_{18}$carbocyclyl and $M_3$-$M_{18}$heterocyclyl can be further substituted with at least one phosphate and optionally substituted with one or more other moieties, such as halogen, $C_1$-$C_6$alkyl or $C_1$-$C_6$haloalkyl.

In another example of this embodiment, $A^1$ is a bicyclic ring having from 9 to 11 ring atoms (e.g., 2,3-dihydro-1H-indenyl) and is optionally substituted with one or more $R^{30}$ (e.g., hydroxy$C_1$-$C_6$alkyl), X is —O—, $R^{48}$ is amino and is optionally substituted with one or more $R^{26}$, $R^{17}$ is $C_1$-$C_6$alkyl (e.g., methyl, isopropyl or butyl), and $R^{41}$, $R^{33}$ and $R^{35}$ are independently hydrogen or halogen. In many instances, Y is —C(O)N($R^{15}$)— and $R^{15}$ is hydrogen. In many other instances, Y is —C(O)N($R^{15}$)— and $R^{15}$ is $C_1$-$C_6$alkyl or $C_2$-$C_6$alkenyl (e.g., —$CH_3$ or —$CH_3$—$CH_2$=$CH_2$). In still some instances, $R^{48}$ is substituted with at least one $R^{26}$. Non-limiting examples of suitable $R^{26}$ include —C(O)—O—$C_1$-$C_6$alkyl, —$SO_2$—$C_1$-$C_6$alkyl, —C(O)—$C_1$-$C_6$alkylene-$C_3$-$C_{18}$carbocyclyl (e.g., —C(O)—$C_1$-$C_6$alkylene-phenyl) or —C(O)—$C_1$-$C_6$alkylene-$M_3$-$M_{18}$heterocyclyl, wherein the $C_3$-$C_{18}$carbocyclyl and $M_3$-$M_{18}$heterocyclyl can be further substituted with at least one phosphate and optionally substituted with one or more other moieties, such as halogen, $C_1$-$C_6$alkyl or $C_1$-$C_6$haloalkyl.

In still yet another embodiment, the present invention features compounds having a formula selected from the group consisting of Formulae I(a), I(b), I(c) and I(d), tautomers of these compounds, and pharmaceutically acceptable salts of these compounds or tautomers, wherein:

$R^{17}$, $R^{33}$ and $R^{35}$ are each independently selected from hydrogen, halogen or $C_1$-$C_6$alkyl;

$R^{41}$ is selected from hydrogen or $C_1$-$C_6$alkyl;

X is —S— or —O—;

$R^{22}$ is $C_4$-$C_{12}$carbocyclyl or $M_4$-$M_{12}$heterocyclyl (e.g.,

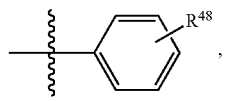

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy), and is optionally substituted with one or more $R^{26}$;

Y is —C(O)N($R^{15}$)N($R^{15'}$)—, —N($R^{15}$)C(O)O—, C(O)O—, —O—, —C(O)—, —OC(O)O—, —OS(O)$_2$— or —N($R^{15}$)S(O)$_2$—, wherein $R^{15}$ and $R^{15'}$ are each independently selected from hydrogen, $C_1$-$C_6$alkyl, $C_2$-$C_6$alkenyl or $C_2$-$C_6$alkynyl;

$R^{50}$ is -$L^1$-$A^1$, wherein:
  $L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a bicyclic ring (e.g., a fused bicyclic ring or a bridged bicyclic ring) having from 6 to 12 ring atoms and is optionally substituted with one or more $R^{30}$; or
  $L^1$ is $C_1$-$C_6$alkylene optionally substituted with one or more $R^{38}$, and $A^1$ is hydrogen or $C_1$-$C_6$alkyl optionally substituted with one or more $R^{30}$;

$R^{18}$, $R^{26}$, $R^{30}$, $R^{38}$, m, n, p and U are as defined in the embodiment immediately above; and $R^{15}$, $R^{15'}$, $R^{17}$, $R^{18}$, $R^{26}$, $R^{30}$ $R^{33}$, $R^{35}$, $R^{38}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido.

In another embodiment, the present invention features compounds having a formula selected from the group consisting of Formulae I(a), I(b), I(c) and I(d), tautomers of these compounds, and pharmaceutically acceptable salts of these compounds or tautomers, wherein:

$R^{17}$, $R^{33}$ and $R^{35}$ are each independently selected from hydrogen, halogen or $C_1$-$C_6$alkyl;

$R^{41}$ is selected from hydrogen or $C_1$-$C_6$alkyl;

X is a bond;

$R^{22}$ is $C_1$-$C_6$alkyl, $C_2$-$C_6$alkenyl or $C_2$-$C_6$alkynyl, and is optionally substituted with one or more $R^{26}$; or $R^{22}$ is hydrogen;

Y is —C(O)N($R^{15}$)—, —N($R^{15}$)C(O)—, —C(O)O—, —O—, C(O)—, —OC(O)O—, —N($R^{15}$)S(O)$_2$—, —N($R^{15}$)C(O)O—, —OS(O)$_2$— or —C(O)N($R^{15}$)N($R^{15'}$)—, wherein $R^{15}$ and $R^{15'}$ are each independently selected from hydrogen, $C_1$-$C_6$alkyl, $C_2$-$C_6$alkenyl or $C_2$-$C_6$alkynyl;

$R^{50}$ is -$L^1$-$A^1$, wherein:
  $L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a $C_4$-$C_{12}$carbocyclyl or $M_4$-$M_{12}$heterocyclyl and is optionally substituted with one or more $R^{30}$; or
  $L^1$ is a bond (i.e., $R^{50}$ is -$A^1$), and $A^1$ is a bicyclic ring (e.g., a fused bicyclic ring or a bridged bicyclic ring)

having from 6 to 12 ring atoms and is optionally substituted with one or more $R^{30}$; or $L^1$ is $C_1$-$C_6$alkylene optionally substituted with one or more $R^{38}$, and $A^1$ is hydrogen or $C_1$-$C_6$alkyl optionally substituted with one or more $R^{30}$;

$R^{18}$, $R^{26}$, $R^{30}$, $R^{38}$, m, n, p and U are as defined in the embodiment immediately above; and $R^{15}$, $R^{15'}$, $R^{17}$, $R^{18}$, $R^{26}$, $R^{30}$ $R^{33}$, $R^{35}$, $R^{38}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido.

In still another embodiment, the present invention features compounds having Formula I(e), tautomers thereof, and pharmaceutically acceptable salts of the compounds or tautomers,

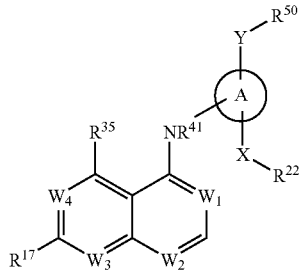

I(e)

wherein:

$W_1$, $W_2$, $W_3$ and $W_4$ are each independently selected from N or $C(R^{33})$ (e.g., $W_1$, $W_2$ and $W_3$ are N, $W_4$ is $C(R^{33})$);

$R^{17}$, $R^{33}$ and $R^{35}$ are each independently selected at each occurrence from hydrogen, halogen, $C_1$-$C_6$alkyl or $C_3$-$C_6$cycloalkyl;

$R^{41}$ is selected from hydrogen or $C_1$-$C_6$alkyl;

A is a $C_5$-$C_{12}$carbocyclyl or $M_5$-$M_{12}$heterocyclyl (e.g., benzooxazolyl or phenyl), and is optionally substituted with one or more $R^{18}$;

X is —S— or —O—;

$R^{22}$ is $C_4$-$C_{12}$carbocyclyl or $M_4$-$M_{12}$heterocyclyl (e.g., phenyl or

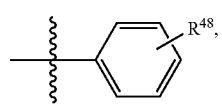

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy), and $R^{22}$ is optionally substituted with one or more $R^{26}$;

Y is a bond, —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or $L^1$ is a bond, and $A^1$ is a $C_4$-$C_{12}$carbocyclyl or $M_4$-$M_{12}$heterocyclyl and is optionally substituted with one or more $R^{30}$; or $L^1$ is a bond, and $A^1$ is a bicyclic ring (e.g., a fused bicyclic ring or a bridged bicyclic ring) having from 6 to 12 ring atoms and is optionally substituted with one or more $R^{30}$; or $L^1$ is $C_1$-$C_6$alkylene optionally substituted with one or more $R^{38}$, and $A^1$ is hydrogen or $C_1$-$C_6$alkyl optionally substituted with one or more $R^{30}$;

$R^{18}$, $R^{26}$, $R^{30}$ and $R^{38}$ are as defined in the embodiment immediately above; and $R^{15}$, $R^{17}$, $R^{18}$, $R^{26}$, $R^{30}$ $R^{33}$, $R^{35}$, $R^{38}$, and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, and azido.

In one example of this embodiment, $W_1$, $W_2$ and $W_3$ are N, $W_4$ is $C(R^{33})$, A is a $C_7$-$C_{10}$carbocyclyl or $M_7$-$M_{10}$heterocyclyl (e.g., a bicyclic ring such as benzooxazolyl), and Y is a bond.

In the examples and embodiments described herein, $A^1$ can be selected, by way of illustration and not of limitation, from the group consisting of phenyl, pyridinyl, thiazolyl, thienyl, furyl, tetrahydrofuryl, pyrrolyl, pyrazinyl, cyclobutyl, cyclohexyl, naphthyl, indolinyl, indenyl, 2,3-dihydro-1H-indenyl, chromanyl, benzo[d][1,3]dioxolyl, 2,3-dihydrobenzo[b][1,4]dioxanyl, 3,4-dihydro-2H-benzo[b][1,4]dioxepinyl, 1,2,3,4-tetrahydronaphthyl, 2,3-dihydrobenzofuryl, 4,5,6,7-tetrahydrobenzofuryl, norbornanyl and adamantyl. Likewise, by way of illustration only and not of limitation, $R^{18}$, $R^{26}$ and $R^{30}$ can be each independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino and $C_1$-$C_6$alkoxycarbonylamino$C_1$-$C_6$alkyl, and $R^{38}$ can be independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, $C_1$-$C_6$alkoxycarbonylamino$C_1$-$C_6$alkyl, $C_3$-$C_5$cycloalkyl, and $C_3$-$C_5$cycloalkyl$C_1$-$C_6$alkyl.

In yet another embodiment, the present invention features compounds having Formula I(a), I(b), I(c), I(d) or I(e), tautomers of the compounds, and pharmaceutically acceptable salts of these compounds or tautomers, wherein:

$R^{17}$ is hydrogen, $C_1$-$C_6$alkyl (e.g., $R^{17}$ is $C_1$-$C_6$alkyl, such as isopropyl or methyl), or $C_3$-$C_6$cycloalkyl;

$R^{41}$ is selected from hydrogen or $C_1$-$C_6$alkyl (e.g., $R^{41}$ is hydrogen);

A is a $C_5$-$C_6$carbocyclyl or $M_5$-$M_6$heterocyclyl and is optionally substituted with one or more $R^{18}$, and $W_1$, $W_2$, $W_3$ and $W_4$ are each independently selected from N or $C(R^{33})$ (e.g., $W_1$, $W_2$ and $W_3$ are N, $W_4$ is $C(R^{33})$);

$R^{33}$ and $R^{35}$ are each independently selected from hydrogen, halogen or $C_1$-$C_6$alkyl (e.g., $R^{33}$ and $R^{35}$ are hydrogen);

X is —S— or O— (e.g., X is —S—);

$R^{22}$ is

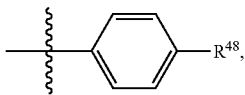

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy (e.g., $R^{48}$ is amino), and $R^{22}$ is optionally substituted with one or more $R^{26}$;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl (e.g., $R^{15}$ is hydrogen);

$R^{50}$ is -$L^1$-$A^1$, wherein:
- $L^1$ is $C_1$-$C_6$alkylene (e.g., $L^1$ is —$CH_2$— or —CH($CH_3$)—) and is optionally substituted with one or more $R^{38}$, and $A^1$ is a $C_4$-$C_{12}$carbocyclyl or $M_4$-$M_{12}$heterocyclyl (such as phenyl, pyridinyl, thiazolyl, thienyl, furyl, tetrahydrofuryl, pyrrolyl, pyrazinyl, cyclobutyl, cyclohexyl or naphthyl), wherein $A^1$ is optionally substituted with one or more $R^{30}$, or
- $L^1$ is a bond, and $A^1$ is a bicyclic ring having from 6 to 12 ring atoms (such as naphthyl, indolinyl, indenyl, 2,3-dihydro-1H-indenyl, chromanyl, benzo[d][1,3]dioxolyl, 2,3-dihydrobenzo[b][1,4]dioxanyl, 3,4-dihydro-2H-benzo[b][1,4]dioxepinyl, 1,2,3,4-tetrahydronaphthyl, 2,3-dihydrobenzofuryl, 4,5,6,7-tetrahydrobenzofuryl, norbornanyl or adamantyl), wherein $A^1$ is optionally substituted with one or more $R^{30}$;

$R^{18}$, $R^{26}$ and $R^{30}$ are each independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino and $C_1$-$C_6$alkoxycarbonylamino$C_1$-$C_6$alkyl;

$R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, $C_1$-$C_6$alkoxycarbonylamino$C_1$-$C_6$alkyl, $C_3$-$C_5$cycloalkyl, and $C_3$-$C_5$cycloalkyl$C_1$-$C_6$alkyl;

m is 0, 1, 2, or 3;

n is 0 or 1;

p is 0, 1, 2, or 3; and

U is —$CH_2$— or —$CH_2$—$CH_2$— and is optionally substituted with one or more $R^{18}$.

In still yet another embodiment, the present invention features compounds having Formula I(a), I(b), I(c), I(d) or I(e), tautomers of these compounds, and pharmaceutically acceptable salts of these compounds or tautomers, wherein:

$R^{17}$ is $C_1$-$C_6$alkyl (e.g., isopropyl) or $C_3$-$C_6$cycloalkyl;

$R^{33}$ and $R^{35}$ are hydrogen;

$R^{41}$ is hydrogen;

$W_1$, $W_2$ and $W_3$ are N, $W_4$ is C(H), and A is a $C_5$-$C_6$carbocyclyl or $M_5$-$M_6$heterocyclyl and is optionally substituted with one or more $R^{18}$, X is —S—;

$R^{22}$ is

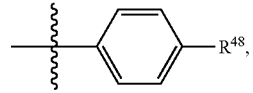

wherein $R^{48}$ is amino, and $R^{22}$ is optionally substituted with one or more $R^{26}$;

Y is —C(O)N($R^{15}$)—, wherein $R^{15}$ is hydrogen, $C_1$-$C_6$alkyl, $C_2$-$C_6$alkenyl or $C_2$-$C_6$alkynyl;

$R^{50}$ is -$L^1$-$A^1$, wherein:
- $L^1$ is $C_1$-$C_6$alkylene (e.g., —$CH_2$— or —CH($CH_3$)—) and is optionally substituted with one or more $R^{38}$, and $A^1$ is a $C_4$-$C_{12}$carbocyclyl or $M_4$-$M_{12}$heterocyclyl (such as phenyl, pyridinyl, thiazolyl, thienyl, furyl, tetrahydrofuryl, pyrrolyl, pyrazinyl, cyclobutyl, cyclohexyl or naphthyl) and is optionally substituted with one or more $R^{30}$, or
- $L^1$ is a bond, and $A^1$ is a bicyclic ring having from 6 to 12 ring atoms (such as naphthyl, indolinyl, indenyl, 2,3-dihydro-1H-indenyl, chromanyl, benzo[d][1,3]dioxolyl, 2,3-dihydrobenzo[b][1,4]dioxanyl, 3,4-dihydro-2H-benzo[b][1,4]dioxepinyl, 1,2,3,4-tetrahydronaphthyl, 2,3-dihydrobenzofuryl, 4,5,6,7-tetrahydrobenzofuryl, norbornanyl or adamantyl), and is optionally substituted with one or more $R^{30}$;

$R^{18}$, $R^{26}$ and $R^{30}$ are each independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino and $C_1$-$C_6$alkoxycarbonylamino$C_1$-$C_6$alkyl;

$R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, $C_1$-$C_6$alkoxycarbonylamino$C_1$-$C_6$alkyl, $C_3$-$C_5$cycloalkyl, and $C_3$-$C_5$cycloalkyl$C_1$-$C_6$alkyl;

m is 0, 1, 2, or 3;
n is 0 or 1;
p is 0, 1, 2, or 3; and
U is —CH$_2$— or —CH$_2$—CH$_2$— and is optionally substituted with one or more R$^{18}$.

As non-limiting examples of the above-described embodiments, the compounds, tautomers thereof, or pharmaceutically acceptable salts of the compounds or tautomers, are characterized by at least one of the following features, or any appropriate combination thereof:
(a) W$_1$, W$_2$ and W$_3$ are N, W$_4$ is C(R$^{33}$), and Z is —NR$^{41}$—;
(b) A is a C$_5$-C$_6$carbocyclyl optionally substituted with one or more R$^{18}$;
(c) A is a M$_5$-M$_6$heterocyclyl optionally substituted with one or more R$^{18}$;
(d) Y is —C(O)N(R$^{15}$)— or —N(R$^{15}$)C(O)—, L$^1$ is C$_1$-C$_6$alkylene optionally substituted with one or more R$^{38}$, and A$^1$ is a C$_4$-C$_6$carbocyclyl or M$_4$-M$_6$heterocyclyl and is optionally substituted with one or more R$^{30}$, wherein R$^{15}$ is hydrogen, C$_1$-C$_6$alkyl, C$_2$-C$_6$alkenyl or C$_2$-C$_6$alkynyl;
(e) Y is —C(O)N(R$^{15}$)— or —N(R$^{15}$)C(O)—, R$^{15}$ is hydrogen, C$_1$-C$_6$alkyl, C$_2$-C$_6$alkenyl or C$_2$-C$_6$alkynyl, L$^1$ is a bond or C$_1$-C$_6$alkylene optionally substituted with one or more R$^{38}$, and A$^1$ is a bicyclic ring which has from 6 to 14 ring atoms and is optionally substituted with one or more R$^{30}$;
(f) X is —O— or —S—, and R$^{22}$ is C$_5$-C$_6$carbocyclyl or M$_5$-M$_6$heterocyclyl and is optionally substituted with one or more R$^{26}$;
(g) R$^{10}$, R$^{33}$, R$^{35}$, R$^{41}$ and R$^{41'}$ are each independently selected from hydrogen or C$_1$-C$_6$alkyl, and R$^{17}$ is C$_1$-C$_6$alkyl;
(h) R$^{10}$ is hydrogen and R$^{17}$ is C$_1$-C$_6$alkyl;
(i) A$^1$ is selected from the group consisting of phenyl, pyridinyl, thiazolyl, thienyl, furyl, tetrahydrofuryl, pyrrolyl, pyrazinyl, cyclobutyl, cyclohexyl, naphthyl, indolinyl, indenyl, 2,3-dihydro-1H-indenyl, chromanyl, benzo[d][1,3]dioxolyl, 2,3-dihydrobenzo[b][1,4]dioxanyl, 3,4-dihydro-2H-benzo[b][1,4]dioxepinyl, 1,2,3,4-tetrahydronaphthyl, 2,3-dihydrobenzofuryl, 4,5,6,7-tetrahydrobenzofuryl, norbornanyl and adamantyl;
(j) R$^{18}$, R$^{26}$ and R$^{30}$ are each independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, C$_1$-C$_6$haloalkyl, C$_1$-C$_6$hydroxyalkyl, C$_1$-C$_6$alkoxy, C$_1$-C$_6$thioalkoxy, C$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino and C$_1$-C$_6$alkoxycarbonylaminoC$_1$-C$_6$alkyl;
(k) R$^{38}$ is independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, C$_1$-C$_6$haloalkyl, C$_1$-C$_6$hydroxyalkyl, C$_1$-C$_6$alkoxy, C$_1$-C$_6$thioalkoxy, C$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino, C$_1$-C$_6$alkoxycarbonylaminoC$_1$-C$_6$alkyl, C$_3$-C$_5$cycloalkyl, and C$_3$-C$_5$cycloalkylC$_1$-C$_6$alkyl; and/or
(l) the compounds have a formula selected from Formulae I(a), I(b), I(c), I(d) or I(e).

In yet another embodiment, the present invention features pyridopyrimidinyl-aminophenyl amide compounds, the tautomers of the compounds, and pharmaceutically acceptable salts of the compounds or tautomers, wherein the compounds correspond in structure to Formula I(f):

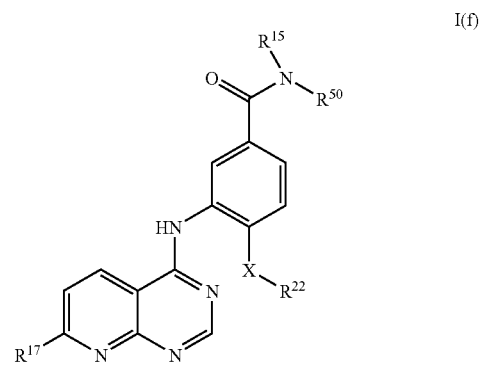

I(f)

wherein:
X is selected from the group consisting of O and S;
R$^{50}$ is selected from the group consisting of

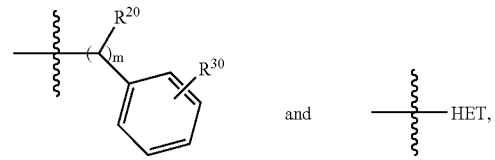

wherein HET is heterocyclo optionally substituted with R$^{30}$;
R$^{30}$ is one or more substituents independently selected from the group consisting of hydrogen, halogen, alkyl, haloalkyl, alkoxy, hydroxy, alkoxyiminoalkyl, cyano, alkylamino, haloalkylcycloalkyl, and aminocarbonyl;
R$^{20}$ is selected from the group consisting of hydrogen and alkyl;
m is an integer selected from the group consisting of zero and one;
or R$^{50}$ and R$^{15}$, taken together with the nitrogen to which they are bound, form a 5-12-membered monocyclic heterocycle containing one or more heteroatoms selected from the group consisting of O, N, and S; wherein the heterocycle is optionally substituted with at least one alkyl group; or R$^{15}$ is selected from the group consisting of hydrogen and alkyl;
R$^{17}$ is selected from the group consisting of hydrogen and alkyl;
R$^{22}$ is selected from the group consisting of aryl and heterocycle; wherein R$^{22}$ is optionally substituted with one or more substituents independently selected from R$^{26}$;
R$^{26}$ is selected from the group consisting of hydrogen, hydroxy, heteroaryl, alkoxycarbonylamino, amino, alkyl, heterocyclocarbonylamino, alkylheteroarylamino, aminocarbonylamino, alkoxycarbonylamino, halogen, alkylcarbonylamino, aminoalkylcarbonylamino, alkylsulfonylamino, haloalkoxycarbonylamino, alkylheteroarylamino, alkylamino, alkylaminocarbonyl, alkylaminoalkoxycarbonyl, morpholinoalkoxycarbonylamino, alkylheteroarylalkoxycarbonylamino, alkylaminoalkoxycarbonylamino, alkylaminohydroxyalkoxycarbonylamino, dialkylamino, monoalkylamino, alkoxycarbonyaminoimino, aminoimino, [2-(alkylheteroarylamino)-4-(haloheteroarylaminocarbonyl)]-(arylthio)arylureido, heteroarylcarbonylamino, arylalkylaminocarbonylamino, cycloalkylaminocarbonylamino, heteroarylalkylaminocarbonylamino, alkoxyalkylaminocarbonylamino, arylalkoxycarbonylamino, heteroarylalkoxycarbonylamino, heterocycloalkoxycarbonylamino, alkoxycarbonylaminopropylamino, arylcarbonylamino, alkoxyalkylcarbonylamino, alkoxyarylalkylcarbonylamino, hydroxyalkylarylalkylcarbonylamino,

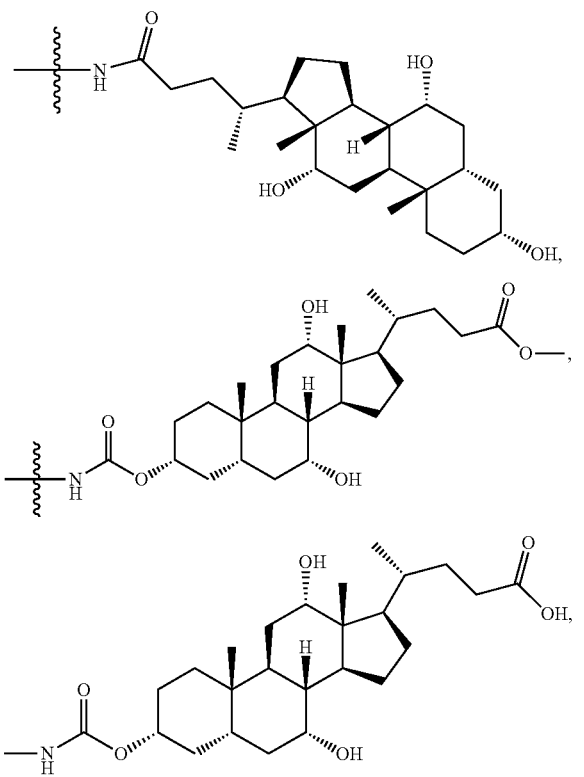

azido, alkylaminoalkyl, morpholinocarbonylamino, alkylaminocarbonylamino, arylalkylaminocarbonylamino, and cycloalkylalkylamino.

In one example of this embodiment, $R^{22}$ is selected from the group consisting of

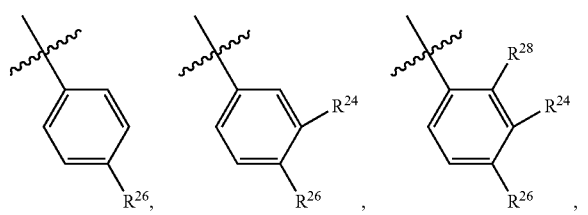

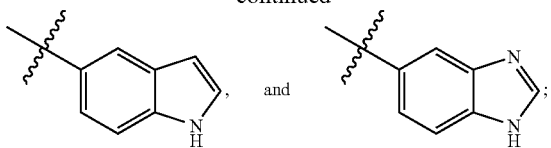

$R^{24}$ is selected from the group consisting of hydrogen, hydroxy, heteroaryl, alkoxycarbonylamino, amino, alkyl, heterocyclocarbonylamino, alkylheteroarylamino, aminocarbonylamino, alkoxycarbonylamino, and halogen;

$R^{26}$ is selected from the group consisting of hydrogen, hydroxy, heteroaryl, alkoxycarbonylamino, amino, alkyl, heterocyclocarbonylamino, alkylheteroarylamino, aminocarbonylamino, alkoxycarbonylamino, halogen, alkylcarbonylamino, aminoalkylcarbonylamino, alkylsulfonylamino, haloalkoxycarbonylamino, alkylheteroarylamino, alkylamino, alkylaminocarbonyl, alkylaminoalkoxycarbonyl, morpholinoalkoxycarbonylamino, alkylheteroarylalkoxycarbonylamino, alkylaminoalkoxycarbonylamino, alkylaminohydroxyalkoxycarbonylamino, dialkylamino, monoalkylamino, alkoxycarbonyaminoimino, aminoimino, [2-(alkylheteroarylamino)-4-(haloheteroarylaminocarbonyl)]-(arylthio)arylureido, heteroarylcarbonylamino, arylalkylaminocarbonylamino, cycloalkylaminocarbonylamino, heteroarylalkylaminocarbonylamino, alkoxyalkylaminocarbonylamino, arylalkoxycarbonylamino, heteroarylalkoxycarbonylamino, heterocycloalkoxycarbonylamino, alkoxycarbonylaminopropylamino, arylcarbonylamino, alkoxyalkylcarbonylamino, alkoxyarylalkylcarbonylamino, hydroxyalkylarylalkylcarbonylamino,

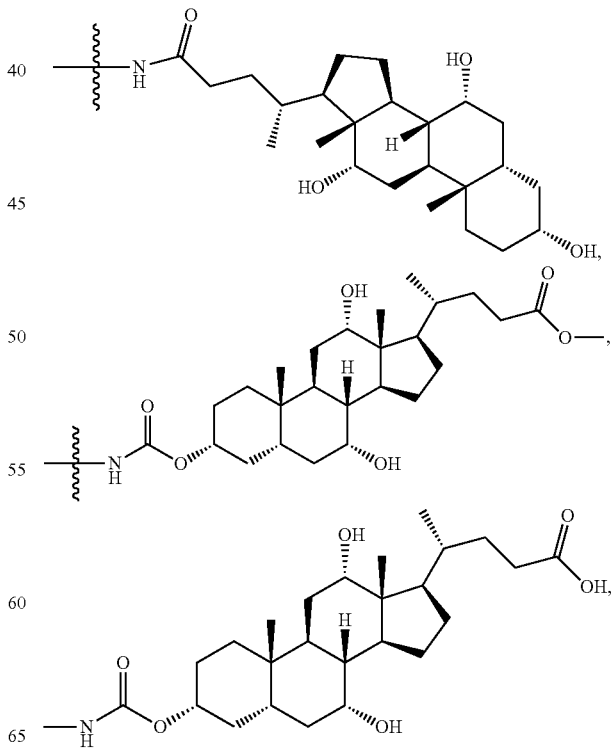

azido, alkylaminoalkyl, morpholinocarbonylamino, alkylaminocarbonylamino, arylalkylaminocarbonylamino, and cycloalkylalkylamino;

$R^{28}$ is selected from the group consisting of hydrogen, halogen, and alkyl.

In another example of this embodiment, HET is selected from the group consisting of pyridinyl, thiazolyl, thiadiazolyl, isothiazolyl, and morpholinyl; or $R^{50}$ taken together with $R^{15}$ form morpholinyl optionally substituted with one or more methyl;

$R^{15}$ is selected from the group consisting of hydrogen, methyl, and isopropyl;

$R^{17}$ is selected from the group consisting of hydrogen, methyl, isopropyl, and t-butyl;

$R^{20}$ is selected from the group consisting of hydrogen and methyl;

$R^{22}$ is as described above in relation to Formula I(f);

$R^{24}$ is selected from the group consisting of hydrogen, hydroxy, 1H-indolyl, t-butoxycarbonylamino, amino, pyrrolidnylcarbonylamino, isopropylpyrido[2,3-d]pyrimidinylamino, aminocarbonylamino, fluoro, and methyl;

$R^{26}$ is selected from the group consisting of hydrogen, amino, hydroxy, t-butoxycarbonylamino, propylcarbonylamino, pyrrolidnylcarbonylamino, aminoethylcarbonylamino, methylsulfanylamino, trichloroethoxycarbonylamino, isopropylpyrido[2,3-d]pyrimidinylamino, N,N-dimethylaminocarbonyl, methoxy, N,N-dimethylamino-ethoxycarbonyl, morpholinylethoxycarbonylamino, 1-methylpyrrolidinyl-ethoxycarbonylamino, 1-methyl-piperidinyl-methoxycarbonylamino, N,N-dimethylamino-propoxycarbonylamino, trichloroethoxy-carbonylamino, N,N-dimethylamino-2-hydroxypropoxycarbonylamino, aminopropoxycarbonylamino, propylamino, N-methyl-N-propylamino, N-ethyl-N-propylamino, N,N-dimethylamino, pyrrolyl, bis-t-butoxycarbonylaminoimino, diaminoimino, [2-(7-isopropylpyrido[2,3-d]pyrimidin-4-ylamino)-4-(5-bromopyridin-2-ylaminocarbonyl)-phenylsulfanyl]phenylaminocarbonylamino, piperidinylcarbonylamino, phenylmethylaminocarbonylamino, pentylaminocarbonylamino, phenylethylaminoacarbonylamino, thienylmethylaminocarbonylamino, furanylmethylaminocarbonylamino, methoxyethylaminocarbonylamino, phenylmethoxycarbonylamino, thienylmethoxycarbonylamino, butoxycarbonylamino, tetrahydrofuranylmethoxycaronbylamino, methoxyethoxy-2-ethoxycarbonylamino, phenylcarbonylamino, ethoxymethylcarbonylamino, dimethoxyphenylmethylcarbonylamino, hydroxymethylphenylmethylcarbonylamino, azido, methylsulfanylamino, N,N-dipropylamino, 7-isopropylpyrido[2,3-d]pyrimidin-4-ylamino, morpholinylcarbonylamino, methylaminocarbonylamino, N,N-dimethylaminocarbonylamino, ethylaminocarbonylamino, piperidinylcarbonylamino, cyclopentylaminocarbonylamino, cyclopropylaminocarbonylamino, N-butyl-N-methylaminocarbonylamino, pentylaminocarbonylamino, ethoxyethylaminocarbonylamino, N-phenylmethyl-N-methylaminocarbonylamino, N,N-diisopropylaminocarbonylamino, N,N-diethylamino, 2,2-dimethylpropylamino, cyclopropylmethylamino, piperidinyl, and piperidinylcarbonylamino;

$R^{28}$ is selected from the group consisting of hydrogen, chloro, and methyl;

$R^{30}$ is one or more substituent selected from the group consisting of hydrogen, bromo, fluoro, methyl, hydroxy, methoxy, methoxyiminoethyl, cyano, trifluoromethyl, N,N-dimethylamino, trifluoromethylcyclohexyl, and aminocarbonyl.

A non-limiting example of compounds within Formula I(f) is 4-(4-Amino-phenylsulfanyl)-N-(5-bromo-pyridin-2-yl)-3-(7-isopropyl-pyrido[2,3-d]pyrimidin-4-ylamino)-benzamide.

In still another embodiment, the present invention features pyridopyrimidinyl-aminophenyl reverse amide compounds, tautomers of the compounds, or pharmaceutically acceptable salts of the compounds or tautomers, wherein the compounds of this embodiment correspond in structure to Formula I(g):

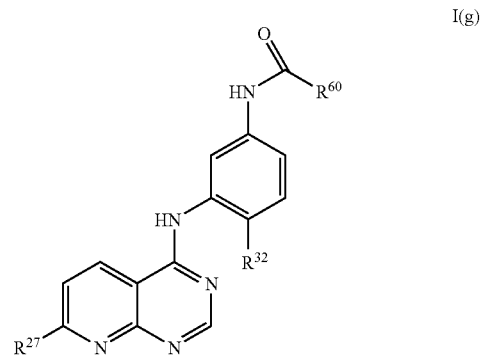

I(g)

wherein:

$R^{27}$ is selected from the group consisting of hydrogen and alkyl;

$R^{32}$ is selected from the group consisting of arylsulfanyl and aryloxy; wherein $R^{32}$ is optionally substituted with one or more substituents independently selected from $R^{36}$;

$R^{36}$ is selected from the group consisting of hydrogen, hydroxy, amino, dialkylamino, haloalkoxycarbonylamino, alkyl, and arylalkoxy;

$R^{60}$ is selected from the group consisting of aryl and heterocyclo; wherein $R^{60}$ is optionally substituted with $R^{40}$;

$R^{40}$ is selected from the group consisting of hydrogen, halogen, haloalkyl, alkoxy, haloalkoxy, dialkylamino, monoalkylamino, hydroxy, alkylcarbonylamino, and alkyl.

In a subset of this embodiment within Formula I(g), $R^{32}$ is selected from the group consisting of

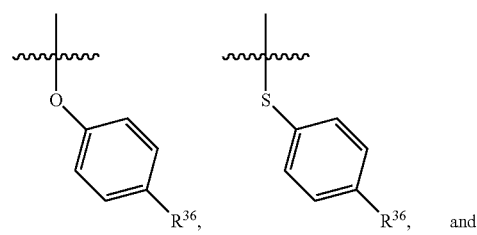

and

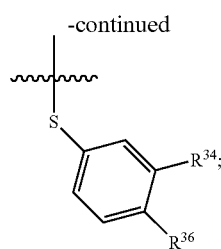

$R^{34}$ is selected from the group consisting of hydrogen and hydroxy;

$R^{36}$ is selected from the group consisting of hydrogen, hydroxy, amino, dialkylamino, haloalkoxycarbonylamino, alkyl, and arylalkoxy.

In a further subset of the embodiment within Formula I(g), $R^{27}$ is selected from the group consisting of hydrogen, methyl, ethyl, and isopropyl;

$R^{32}$ is as described above in relation to Formula I(g);

$R^{34}$ is selected from the group consisting of hydrogen and hydroxy;

$R^{36}$ is selected from the group consisting of hydrogen, hydroxy, amino, N,N-dimethylamino, dichloroethoxycarbonylamino, t-butyl, methyl, and phenylmethoxy;

$R^{40}$ is one or more substituents selected from the group consisting of hydrogen, trifluoromethyl, bromo, chloro, fluoro, methoxy, trifluoromethoxy, N,N-dimethylamino, hydroxy, methylcarbonylamino, and methyl;

$R^{60}$ is selected from the group consisting of phenyl, furanyl, pyrazinyl, pyridinyl, thienyl, and pyrrolyl.

In a further embodiment, the present invention features pyridopyrimidinyl-amino heteroaryl compounds, tautomers thereof, and pharmaceutically acceptable salts of the compounds or tautomers, wherein the compounds of this embodiment correspond in structure to Formula I(h):

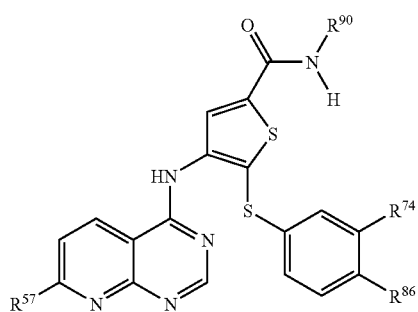

I(h)

wherein:

$R^{57}$ is selected from the group consisting of alkyl and hydroxyalkyl;

$R^{74}$ is selected from the group consisting of hydrogen and hydroxy;

$R^{86}$ is selected from the group consisting of hydrogen, hydroxy, haloalkoxycarbonylamino, and amino;

$R^{90}$ is selected from the group consisting of haloaryl and aryl.

In a subset family of this embodiment within Formula I(h), $R^{57}$ is selected from the group consisting of methyl, isopropyl, and hydroxymethylethyl;

$R^{74}$ is selected from the group consisting of hydrogen and hydroxy;

$R^{86}$ is selected from the group consisting of hydrogen, hydroxyl, amino, and trichloroethoxycarbonylamino;

$R^{90}$ is selected from the group consisting of phenyl and bromophenyl.

Salts of the Compounds of this Invention

The compounds of the present invention, or tautomers thereof, can be used in the form of salts. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient, the salt preferably is pharmaceutically acceptable. Pharmaceutically acceptable salts include, but are not limited to, salts commonly used to form alkali metal salts and/or to form addition salts of free acids or free bases. In general, these salts typically may be prepared by conventional means with a compound of this invention by reacting, for example, the appropriate acid or base with the compound.

Pharmaceutically acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxyic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts of the compounds of this invention include, for example, metallic salts and organic salts. Preferred metallic salts include, but are not limited to, alkali metal (group Ia) salts, alkaline earth metal (group IIa) salts, and other physiological acceptable metal salts. Such salts may be made from aluminum, calcium, lithium, magnesium, potassium, sodium, and zinc. Non-limiting examples of preferred organic salts can be made from tertiary amines and quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Solvates, Prodrugs, and Isomers

The compounds of the present invention, tautomers thereof, and their salts, may also exist in the form of solvates with water, for example hydrates, or with organic solvents such as methanol, ethanol or acetonitrile to form, respectively, a methanolate, ethanolate or acetonitrilate. The compounds of the present invention may exist in each form of solvate or mixtures thereof.

In one aspect, the compounds, tautomers or salts of the present invention may be in the form of prodrugs. Some are aliphatic or aromatic esters derived from acidic groups on compounds of this invention. Others are aliphatic or aromatic esters of hydroxyl or amino groups on compounds of this invention. Phosphate prodrugs of hydroxyl groups on compounds of this invention are preferred prodrugs.

The compounds of the invention may comprise asymmetrically substituted carbon atoms known as chiral centers. These chiral centers are designated as "R" or "S" depending on the configuration of substituents around the chiral carbon atom. The terms "R" and "S" used herein are configurations as defined in Nomenclature of Organic Chemistry, Section E: Stereochemistry, Recommendations 1974, PURE APPL. CHEM., 45:11-30 (1976). The compounds of this invention may exist, without limitation, as single stereoisomers (e.g., single enantiomers or single diastereomer), mixtures of stereoisomers (e.g. any mixture of enantiomers or diastereomers), or racemic mixtures. All such single stereoisomers, mixtures and racemates are encompassed within the scope of the invention. Compounds identified herein as single stereoisomers are meant to describe compounds that are present in a form that is substantially free from other stereoisomers (e.g., other enantiomers or diastereomers). By "substantially free," it means that at least 80% of the compound in a composition is the desired stereoisomer; preferably, at least 90% of the compound in a composition is the desired stereoisomer; and more preferably, at least 95%, 96%, 97%, 98% or 99% of the compound in a composition is the desired stereoisomer. Where the stereochemistry of the chiral carbon(s) present in a chemical structure is not specified, the chemical structure is intended to encompass compounds containing either stereoisomer of each chiral center present in the chemical structure.

Individual stereoisomers of the compounds of this invention can be prepared using many methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished on chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The compounds of the invention includes each conformational isomer of these compounds and mixtures thereof.

Certain compounds of the invention may also exist in zwitterionic form and the invention includes each zwitterionic form of these compounds and mixtures thereof.

Definitions

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., $R^{17}$, $A^1$, $L^1$, X, Y, or Z). Unless otherwise specified, each variable within such a formula is defined independently of any other variable, and any variable that occurs more than one time in a formula is defined independently at each occurrence. If substituents are described as being "independently selected" from a group, each substituent is selected independently from the other. Each substituent therefore can be identical to or different from the other substituent(s).

The number of carbon atoms in a hydrocarbyl substituent can be indicated by the prefix "$C_x$-$C_y$," where x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "alkylaryl" contains two components: alkyl and aryl. Thus, for example, $C_1$-$C_6$alkylaryl refers to a $C_1$-$C_6$alkyl appended to the parent molecular moiety through an aryl group. Likewise, alkyl$C_6$-$C_{10}$aryl refers to an alkyl group appended to the parent molecular moiety through a $C_6$-$C_{10}$aryl group. Similarly, the prefix "halo" on haloalkoxyalkyl indicates that the alkoxy component is substituted with one or more halogen radicals, while the prefix "halo" on alkoxyhaloalkyl indicates that the alkyl component is substituted with one or more halogen radicals.

When words are used to describe a linking element between two other elements of a depicted chemical structure, the leftmost-described component of the linking element is the component that is bound to the left element in the depicted structure. To illustrate, if the chemical structure is X-L-Y and L is described as methylarylethyl, then the chemical would be X-methyl-aryl-ethyl-Y.

If a linking element in a depicted structure is a bond, then the left element in the depicted structure is bound directly to the right element in the depicted structure. For example, if a chemical structure is depicted as X-L-Y and L is selected as a bond, then the chemical structure would be X—Y. For another example, if a chemical moiety is depicted as -L-X and L is selected as a bond, then the chemical moiety would be —X. For yet another example, if a chemical structure is depicted as X-$L_1$-$L_2$-Y, X-$L_1$-$L_2$-$L_3$-Y or X-$L_1$-$L_2$... -$L_N$-Y, and $L_1$, $L_2$, $L_3$, ... $L_N$ are selected as bonds, then the chemical structure would be X—Y.

When a chemical formula is used to describe a substituent, the dash on the right (or left) side of the formula indicates the portion of the substituent that has the free valence(s).

If a substituent is described as being "substituted," a non-hydrogen radical is in the place of one or more hydrogen radials on a carbon, nitrogen or oxygen of the substituent. Thus, for example, a substituted alkyl substituent is an alkyl substituent wherein at least one non-hydrogen radical is in the place of a hydrogen radical(s) on the alkyl substituent. To illustrate, monofluoroalkyl is alkyl substituted with one fluoro radical, and difluoroalkyl is alkyl substituted with two fluoro radicals. It should be recognized that if there are two or more substitutions on a substituent, each of the non-hydrogen radicals may be identical or different unless otherwise stated.

A substituent is "substitutable" if it comprises at least one carbon, nitrogen or oxygen atom that is bonded to one or more hydrogen atoms.

If a substituent is described as being "optionally substituted", the substituent may be either substituted or not substituted. If a substituent is described as being optionally substituted with up to a particular number of non-hydrogen radicals, that substituent may be either not substituted, or substituted by up to that particular number of non-hydrogen radicals or by up to the maximum number of substitutable positions on the substituent, whichever is less. Thus, for example, if a substituent is described as a heteroaryl optionally substituted with up to three non-hydrogen radicals, then any heteroaryl with less than three substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" (alone or in combination with another term(s)) means a straight- or branched-chain hydrocarbyl substituent containing one or more double bonds and typically from 2 to 20 carbon atoms, more typically from 2 to 8 carbon atoms, and even more typically from 2 to 6 carbon atoms. Each carbon-carbon double bond may have either cis or trans geometry within the alkenyl moiety, relative to groups substituted on the double bond carbons. Non-limiting examples of such substituents include ethenyl (vinyl), 2-propenyl, 3-propenyl, 1,4-pentadienyl, 1,4-butadienyl, 1-butenyl, 2-butenyl, and 3-butenyl.

The term "alkenylene" (alone or in combination with another term(s)) refers to a divalent unsaturated hydrocarbyl group which may be linear or branched and which has at least one carbon-carbon double bond. An alkenylene group typically contains 2 to 20 carbon atoms, more typically from 2 to 8 carbon atoms, and even more typically from 2 to 6 carbon atoms. Non-limiting examples of alkenylene groups include —C(H)═C(H)—, —C(H)═C(H)—CH$_2$—, —C(H)═C(H)—CH$_2$—CH$_2$—, —CH$_2$—C(H)═C(H)—CH$_2$—, —C(H)═C(H)—CH(CH$_3$)—, and —CH$_2$—C(H)═C(H)—CH(CH$_2$CH$_3$)—.

The term "alkoxy" (alone or in combination with another term(s)) refers to an alkyl group appended to the parent molecular moiety through an oxy moiety (i.e., —O-alkyl). Non-limiting examples of such a substituent include methoxy (—O—CH$_3$), ethoxy, n-propoxy, isopropoxy, n-butoxy, isobutoxy, sec-butoxy, and tert-butoxy.

The term "alkoxyalkyl" (alone or in combination with another term(s)) refers to an alkoxy group appended to the parent molecular moiety through an alkylene group. Non-limiting examples of alkoxyalkyl include tert-butoxymethyl, 2-ethoxyethyl, 2-methoxyethyl, and methoxymethyl.

The term "alkoxycarbonyl" (alone or in combination with another term(s)) refers to an alkoxy group appended to the parent molecular moiety through a carbonyl group (i.e., —C(O)—O-alkyl). Representative examples of alkoxycarbonyl include, but are not limited to, methoxycarbonyl, ethoxycarbonyl

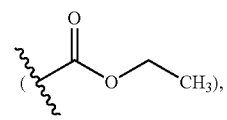

and tert-butoxycarbonyl.

The term "alkoxycarbonylamino" (alone or in combination with another term(s)) refers to N(R$_A$R$_B$)—, where R$_A$ is alkyl-O—C(O)—, and R$_B$ is alkyl-O—C(O)— or hydrogen. R$_A$ and R$_B$ may be identical or different.

The term "alkoxycarbonylaminoalkyl" (alone or in combination with another term(s)) refers to N($R_A R_B$)-alkylene-, where $R_A$ is alkyl-O—C(O)—, and $R_B$ is alkyl-O—C(O)— or hydrogen. $R_A$ and $R_B$ may be identical or different.

The term "alkoxycarbonylalkyl" (alone or in combination with another term(s)) refers to an alkoxycarbonyl group appended to the parent molecular moiety through an alkylene group. Representative examples of alkoxycarbonylalkyl include, but are not limited to, 2-methoxy-2-oxoethyl, 2-ethoxy-2-oxoethyl, 3-methoxy-3-oxopropyl, 3-ethoxy-3-oxopropyl, 4-ethoxy-2-(ethoxycarbonyl)-4-oxobutyl, 5-methoxy-5-oxopentyl, and 6-methoxy-6-oxohexyl.

The term "alkyl" (alone or in combination with another term(s)) means a straight- or branched-chain saturated hydrocarbyl substituent typically containing from 1 to 20 carbon atoms, more typically from 1 to 8 carbon atoms, and even more typically from 1 to 6 carbon atoms. Non-limiting examples of such substituents include methyl, ethyl, n-propyl, isopropyl, n-butyl, isobutyl, sec-butyl, t-butyl, pentyl, iso-amyl, hexyl, and octyl.

The term "alkylamino" (alone or in combination with another term(s)) refers to —$NR_A R_B$, wherein $R_A$ is alkyl, and $R_B$ is hydrogen or alkyl. $R_A$ and $R_B$ may be identical or different. For instance, $C_1$-$C_6$alkylamino refers to —$NR_A R_B$, wherein $R_A$ is $C_1$-$C_6$alkyl, and $R_B$ is hydrogen or $C_1$-$C_6$alkyl.

The term "alkylaminoalkyl" (alone or in combination with another term(s)) refers to N($R_A R_B$)-alkylene-, wherein $R_A$ is alkyl, and $R_B$ is hydrogen or alkyl. $R_A$ and $R_B$ may be identical or different. Thus, $C_1$-$C_6$alkylamino$C_1$-$C_6$alky refers to N($R_A R_B$)—$C_1$-$C_6$alkylene-, wherein $R_A$ is $C_1$-$C_6$alkyl, and $R_B$ is hydrogen or $C_1$-$C_6$alkyl.

The term "alkylcarbonyl" (alone or in combination with another term(s)) refers to an alkyl group appended to the parent molecular moiety through a carbonyl group (i.e., —C(O)-alkyl). Representative examples of alkylcarbonyl include, but are not limited to, acetyl, ethylcarbonyl

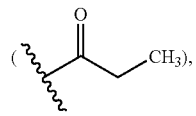

1-oxopropyl, 2,2-dimethyl-1-oxopropyl, 1-oxobutyl, and 1-oxopentyl.

The term "alkylcarbonylalkyl" (alone or in combination with another term(s)) refers to an alkylcarbonyl group appended to the parent molecular moiety through an alkylene group. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" (alone or in combination with another term(s)) refers to an alkylcarbonyl group appended to the parent molecular moiety through an oxy moiety. Representative examples of alkylcarbonyloxy include, but are not limited to, acetyloxy, ethylcarbonyloxy, and tert-butylcarbonyloxy.

The term "alkylcarbonyloxyalkyl" (alone or in combination with another term(s)) refers to an alkylcarbonyloxy group appended to the parent molecular moiety through an alkylene moiety. Representative examples of alkylcarbonyloxyalkyl include, but are not limited to, 2-(acetyloxy)ethyl, 3-(acetyloxy)propyl, and 3-(propionyloxy)propyl.

The terms "alkylene" or "alkylenyl" (alone or in combination with another term(s)) denote a divalent group derived from a straight or branched saturated hydrocarbyl chain typically containing from 1 to 20 carbon atoms, more typically from 1 to 8 carbon atoms, and even more typically from 1 to 6 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" (alone or in combination with another term(s)) means a straight- or branched-chain hydrocarbyl substituent containing one or more triple bonds and typically from 2 to 20 carbon atoms, more typically from 2 to 8 carbon atoms, and even more typically from 2 to 6 carbon atoms. Non-limiting examples of such substituents include ethynyl, 1-propynyl, 2-propynyl, 3-propynyl, decynyl, 1-butynyl, 2-butynyl, and 3-butynyl.

The terms "alkynylene" (alone or in combination with another term(s)) refers to a divalent unsaturated hydrocarbon group which may be linear or branched and which has at least one carbon-carbon triple bonds. Representative alkynylene groups include, by way of example, —C≡C—, —C≡C—$CH_2$—, —C≡C—$CH_2$—$CH_2$—, —$CH_2$—C≡C—$CH_2$—, —C≡C—CH($CH_3$)—, and —$CH_2$—C≡C—CH($CH_2CH_3$)—.

The term "amino" (alone or in combination with another term(s)) means —$NH_2$. The term "monosubstituted amino" (alone or in combination with another term(s)) means an amino substituent wherein one of the hydrogen radicals is replaced by a non-hydrogen substituent. The term "disubstituted amino" (alone or in combination with another term(s)) means an amino substituent wherein both of the hydrogen atoms are replaced by non-hydrogen substituents, which may be identical or different.

The term "aminocarbonyl" (alone or in combination with another term(s)) means —C(O)—$NH_2$, which also may be depicted as:

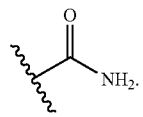

The term "aminoalkyl" (alone or in combination with another term(s)) means -alkylene-$NH_2$.

The term "aminoalkylcarbonyl" (alone or in combination with another term(s)) means —C(O)-alkylene-$NH_2$. For example, "aminomethylcarbonyl" may be depicted as:

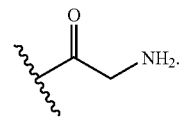

The term "aminosulfonyl" (alone or in combination with another term(s)) means —S(O)$_2$—$NH_2$, which also may be depicted as:

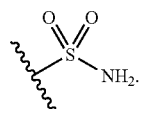

The term "aryl" (alone or in combination with another term(s)) refers to an aromatic carbocyclyl containing from 6 to 14 carbon ring atoms. Non-limiting examples of aryls include phenyl, naphthalenyl, anthracenyl, and indenyl. An aryl group can be connected to the parent molecular moiety through any substitutable carbon atom of the group.

The term "arylalkyl" (alone or in combination with another term(s)) refers to an aryl group appended to the parent molecular moiety through an alkylene group. Representative examples of substituted/unsubstituted arylalkyl include, but are not limited to, benzyl, 4-(benzyloxy)benzyl, 4-methoxybenzyl, 4-hydroxybenzyl, 3-(1,3-benzodioxol-5-yl)-2-methylpropyl, 3-(phenoxy)benzyl, 3-(1,3-benzodioxol-5-yl)propyl, 2-phenylethyl, 3-phenylpropyl, 2-naphthylmethyl, 3,5-ditert-butyl-2-hydroxybenzyl, 3-methoxybenzyl, 3,4-dimethoxybenzyl, 4-(dimethylamino)benzyl, 4-[3-(dimethylamino)propoxy]benzyl, (6-methoxy-2-naphthyl)methyl, and 2-naphth-2-ylethyl.

The term "arylalkylcarbonyl" (alone or in combination with another term(s)) refers to an arylalkyl group appended to the parent molecular moiety through a carbonyl group (i.e., arylalkyl-C(O)—). Representative examples of arylalkylcarbonyl include, but are not limited to, 2-naphthylacetyl and phenylacetyl.

The term "arylalkoxy" (alone or in combination with another term(s)) refers to an arylalkyl group appended to the parent molecular moiety through an oxy moiety (i.e., arylalkyl-O—). Representative examples of arylalkoxy include, but are not limited to, 2-phenylethoxy, 3-naphth-2-ylpropoxy, and 5-phenylpentyloxy.

The term "arylalkoxyalkyl" (alone or in combination with another term(s)) refers to an arylalkoxy group appended to the parent molecular moiety through an alkylene group. Representative examples of arylalkoxyalkyl include, but are not limited to, benzyloxymethyl, 2-(benzyloxy)ethyl, and (2-phenylethoxy)methyl.

The term "arylalkoxycarbonyl" (alone or in combination with another term(s)) refers to an arylalkoxy group appended to the parent molecular moiety through a carbonyl group. Representative examples of arylalkoxycarbonyl include, but are not limited to, benzyloxycarbonyl, and naphth-2-ylmethoxycarbonyl.

The term "arylcarbonyl" (alone or in combination with another term(s)) refers to an aryl group appended to the parent molecular moiety through a carbonyl group. Representative examples of arylcarbonyl include, but are not limited to, benzoyl and naphthoyl.

The term "aryloxy" (alone or in combination with another term(s)) refers to an aryl group appended to the parent molecular moiety through an oxy moiety. Representative examples of substituted/unsubstituted aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" (alone or in combination with another term(s)) refers to an aryloxy group appended to the parent molecular moiety through an alkylene group. Representative examples of aryloxyalkyl include, but are not limited to, 2-phenoxyethyl, 3-naphth-2-yloxypropyl, and phenoxymethyl.

The term "aryloxycarbonyl" (alone or in combination with another term(s)) refers to an aryloxy group appended to the parent molecular moiety through a carbonyl group.

The term "arylthio" (alone or in combination with another term(s)) refers to an aryl group appended to the parent molecular moiety through a sulfur atom (i.e., aryl-S—). Representative examples of arylthio include, but are not limited to, phenylthio, naphthalen-1-ylthio, and naphthalen-2-ylthio.

The term "arylthioalkyl" (alone or in combination with another term(s)) refers to aryl-S-alkylene-. Representative examples of arylthioalkyl include, but are not limited to, (phenylthio)methyl, 2-(phenylthio)ethyl, and 3-(phenylthio)propyl.

The term "arylthioalkoxy" (alone or in combination with another term(s)) refers to an arylthioalkyl group appended to the parent molecular moiety through an oxy group.

The term "arylthioalkoxyalkyl" (alone or in combination with another term(s)) refers to an arylthioalkoxy group appended to the parent molecular moiety through an alkylene group.

The terms "carbocycle" or "carbocyclic" or "carbocyclyl" (alone or in combination with another term(s)) refer to a saturated (e.g., "cycloalkyl"), partially saturated (e.g., "cycloalkenyl" or "cycloalkynyl") or completely unsaturated (e.g., "aryl") ring system containing zero heteroatom ring atom and typically from 3 to 18 carbon ring atoms. "Ring atoms" or "ring members" are the atoms bound together to form the ring or rings of a cyclic substituent. A carbocyclyl may be, without limitation, a single ring, or two or more fused rings, or bridged or spiro rings. A carbocyclyl may contain from 3 to 14 ring members (i.e., $C_3$-$C_{14}$carbocyclyl, such as $C_3$-$C_{14}$cycloalkyl), from 3 to 10 ring members (i.e., $C_3$-$C_{10}$carbocyclyl, such as $C_3$-$C_{10}$cycloalkyl), from 3 to 8 ring members (i.e., $C_3$-$C_8$carbocyclyl, such as $C_3$-$C_8$cycloalkyl), from 3 to 6 ring members (i.e., $C_3$-$C_6$carbocyclyl, such as $C_3$-$C_6$cycloalkyl), from 4 to 10 ring members (i.e., $C_4$-$C_{10}$carbocyclyl, such as $C_4$-$C_{10}$cycloalkyl and $C_4$-$C_{10}$cycloalkenyl), from 4 to 8 ring members (i.e., $C_4$-$C_8$carbocyclyl, such as $C_4$-$C_8$cycloalkyl and $C_4$-$C_8$cycloalkenyl), or from 5 to 7 ring members (i.e., $C_5$-$C_7$carbocyclyl, such as $C_5$-$C_7$cycloalkyl, $C_5$-$C_7$cycloalkenyl and phenyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydroindenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl. A carbocyclyl group can be attached to the parent molecular moiety through any substitutable carbon atom of the group.

The term "carbocyclylalkyl" (alone or in combination with another term(s)) refers to a carbocyclyl group appended to the parent molecular moiety through an alkylene group. For instance, $C_3$-$C_{10}$carbocyclyl$C_1$-$C_6$alkyl refers to a $C_3$-$C_{10}$carbocyclyl group appended to the parent molecular moiety through $C_1$-$C_6$alkylene. Likewise, $C_5$-$C_7$carbocyclyl$C_1$-$C_6$alkyl refers to a $C_5$-$C_7$carbocyclyl group appended to the parent molecular moiety through $C_1$-$C_6$alkylene.

The term "carbocyclylalkoxy" (alone or in combination with another term(s)) refers to a carbocyclylalkyl group appended to the parent molecular moiety through an oxy group (i.e., carbocyclyl-alkylene-O—). For instance, $C_3$-$C_{10}$carbocyclyl$C_1$-$C_6$alkoxy refers to a $C_3$-$C_{10}$carbocyclyl$C_1$-$C_6$alkyl group appended to the parent molecular moiety through an oxy group. Likewise, a $C_5$-$C_7$carbocyclyl$C_1$-$C_6$alkoxy group refers to a $C_5$-$C_7$carbocyclyl$C_1$-$C_6$alkyl group appended to the parent molecular moiety through an oxy group.

The term "carbocyclylalkoxyalkyl" (alone or in combination with another term(s)) refers to a carbocyclylalkoxy group appended to the parent molecular moiety through an alkylene group (i.e., carbocyclyl-alkylene-O-alkylene-). For instance, $C_3$-$C_{10}$carbocyclyl$C_1$-$C_6$alkoxy$C_1$-$C_6$alkyl refers to $C_3$-$C_{10}$carbocyclyl$C_1$-$C_6$alkoxy group appended to the parent molecular moiety through a $C_1$-$C_6$alkylene group.

The term "carbocyclylalkoxycarbonyl" (alone or in combination with another term(s)) refers to a carbocyclylalkoxy group appended to the parent molecular moiety through a carbonyl group (i.e., —C(O)—O-alkylene-carbocyclyl). For instance, $C_3$-$C_{10}$carbocyclyl$C_1$-$C_6$alkoxycarbonyl refers to a $C_3$-$C_{10}$carbocyclyl$C_1$-$C_6$alkoxy group appended to the parent molecular moiety through a carbonyl group. As a non-limiting example, "phenylethoxycarbonyl" may be depicted as:

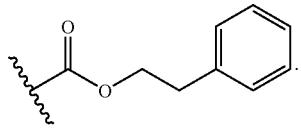

The term "carbocyclylalkylcarbonyl" (alone or in combination with another term(s)) refers to a carbocyclylalkyl group appended to the parent molecular moiety through a carbonyl group (i.e., —C(O)-alkylene-carbocyclyl). For example, "phenylethylcarbonyl" may be depicted as:

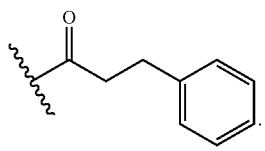

The term "carbocyclylcarbonyl" (alone or in combination with another term(s)) refers to a carbocyclyl group appended to the parent molecular moiety through a carbonyl group (i.e., carbocyclyl-C(O)—). For example, "phenylcarbonyl" may be depicted as:

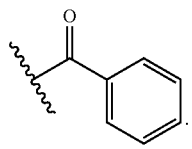

The term "carbocyclyloxy" (alone or in combination with another term(s)) refers to a carbocyclyl group appended to the parent molecular moiety through an oxy moiety (i.e., carbocyclyl-O—).

The term "carbocyclyloxyalkyl" (alone or in combination with another term(s)) refers to a carbocyclyloxy group appended to the parent molecular moiety through an alkylene group (i.e., carbocyclyl-O-alkylene-).

The term "carbocyclyloxycarbonyl" (alone or in combination with another term(s)) refers to a carbocyclyloxy group appended to the parent molecular moiety through a carbonyl group (i.e., —C(O)—O-carbocyclyl). For example, "phenyloxycarbonyl" may be depicted as:

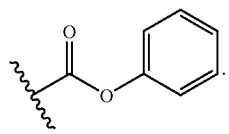

The term "carbocyclylthio" (alone or in combination with another term(s)) refers to a carbocyclyl group appended to the parent molecular moiety through a sulfur atom (i.e., carbocyclyl-S—).

The term "carbocyclylthioalkoxy" (alone or in combination with another term(s)) refers to carbocyclyl-alkylene-S—.

The term "carbocyclylthioalkoxyalkyl" (alone or in combination with another term(s)) refers to carbocyclyl-alkylene-S-alkylene-.

The term "carbocyclylthioalkyl" (alone or in combination with another term(s)) refers to a carbocyclylthio group appended to the parent molecular moiety through an alkylene group (i.e., carbocyclyl-S-alkylene-).

The term "carbocyclylcarbocyclyl" (alone or in combination with another term(s)) refers to a carbocyclyl group appended to the parent molecular moiety through another carbocyclyl group (i.e., carbocyclyl-carbocyclyl-). For instance, $C_3$-$C_{10}$carbocyclyl$C_5$-$C_7$carbocyclyl refers to a $C_3$-$C_{10}$carbocyclyl group appended to the parent molecular moiety through a $C_5$-$C_7$carbocyclyl group (i.e., $C_3$-$C_{10}$carbocyclyl-$C_5$-$C_7$carbocyclyl-).

The term "carbocyclylcarbocyclylalkyl" (alone or in combination with another term(s)) refers to a carbocyclylcarbocyclyl group appended to the parent molecular moiety through an alkylene group.

The term "carbocyclylalkoxycarbocyclylalkyl" (alone or in combination with another term(s)) refers to carbocyclyl-alkylene-O-carbocyclyl-alkylene-. For instance, $C_3$-$C_{10}$carbocyclyl$C_1$-$C_6$alkoxy$C_5$-$C_7$carbocyclyl$C_3$-$C_4$alkyl refers to $C_3$-$C_{10}$carbocyclyl-$C_1$-$C_6$alkylene-O—$C_5$-$C_7$carbocyclyl-$C_3$-$C_4$alkylene-.

The term "(carbocyclylalkyl)carbocyclylalkyl" (alone or in combination with another term(s)) refers to carbocyclyl-alkylene-carbocyclyl-alkylene-. For instance, $C_3$-$C_{10}$carbocyclyl$C_1$-$C_6$alkyl$C_5$-$C_7$carbocyclyl$C_3$-$C_4$alkyl refers to $C_3$-$C_{10}$carbocyclyl-$C_1$-$C_6$alkylene-$C_5$-$C_7$carbocyclyl-$C_3$-$C_4$alkylene-.

The term "carbocyclylalkoxyheterocycloalkyl" (alone or in combination with another term(s)) refers to carbocyclyl-alkylene-O-heterocyclyl-alkylene-.

The term "carbocyclylcarbonylheterocycloalkyl" (alone or in combination with another term(s)) refers to carbocyclyl-C(O)-heterocyclyl-alkylene-.

The term "carbocyclylheterocycloalkyl" (alone or in combination with another term(s)) refers to carbocyclyl-heterocyclyl-alkylene-.

The term "carbocyclylcarbonylcarbocyclylalkyl" (alone or in combination with another term(s)) refers to carbocyclyl-C(O)-carbocyclyl-alkylene-. For instance, $C_3$-$C_{10}$carbocyclylcarbonyl$C_4$-$C_8$carbocyclyl$C_1$-$C_6$alkyl refers to $C_3$-$C_{10}$carbocyclyl-C(O)—$C_4$-$C_8$carbocyclyl-$C_1$-$C_6$alkylene-.

The term "(carbocyclylalkyl)heterocycloalkyl" (alone or in combination with another term(s)) refers to carbocyclyl-alkylene-heterocyclyl-alkylene.

The term "carbonyl" (alone or in combination with another term(s)) refers to —C(O)—, which also may be depicted as:

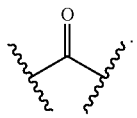

The term "carboxy" (alone or in combination with another term(s)) means —C(O)—OH, which also may be depicted as:

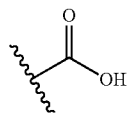

The term "carboxyalkyl" (alone or in combination with another term(s)) refers to a carboxy group appended to the parent molecular moiety through an alkylene group. Representative examples of carboxyalkyl include, but are not limited to, carboxymethyl, 2-carboxyethyl, and 3-carboxypropyl.

The term "cyclic amino" (alone or in combination with another term(s)) means a heterocyclyl moiety comprising at least one nitrogen ring atom, with the remaining ring atoms being carbon and optionally nitrogen or sulfur. Non-limiting examples of such moieties include piperidinyl, piperazinyl, and thiazine groups.

The term "cycloalkenyl" (alone or in combination with another term(s)) refers to a non-aromatic, partially unsaturated carbocyclyl substituent having zero heteroatom ring member and typically from 4 to 18 carbon ring members. Representative examples of cycloalkenyl groups include, but are not limited to, cyclobutenyl, cyclopentenyl, cyclohexenyl, and octahydronaphthalenyl.

The term "cycloalkyl" (alone or in combination with another term(s)) refers to a saturated carbocyclyl group containing zero heteroatom ring member and typically from 3 to 18 carbon ring members. Non-limiting examples of cycloalkyls include cyclopropyl, cyclobutyl, cyclopentyl, cyclohexyl, cycloheptyl, cyclooctyl, decalinyl and norpinanyl.

The term "cycloalkylcarbonyl" (alone or in combination with another term(s)) refers to a cycloalkyl group appended to the parent molecular moiety through a carbonyl group.

The term "cyano" (alone or in combination with another term(s)) means —CN, which also may be depicted as

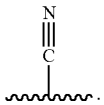

The term "dialkylamino" (alone or in combination with another term(s)) refers to —NR$_A$R$_B$, wherein R$_A$ and R$_B$ are independently selected from alkyl groups.

The term "dialkylaminocarbonyl" (alone or in combination with another term(s)) refers to a dialkylamino group appended to the parent molecular moiety through a carbonyl group (i.e., N(R$_A$R$_B$)—C(O)—, wherein R$_A$ and R$_B$ are independently selected from alkyl groups).

The term "formyl" (alone or in combination with another term(s)) refers to a —C(O)H group.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

The prefix "halo" indicates that the substituent to which the prefix is attached is substituted with one or more independently selected halogen radicals. For example, "haloalkyl" (alone or in combination with another term(s)) means an alkyl substituent wherein at least one hydrogen radical is replaced with a halogen radical. Non-limiting examples of haloalkyls include chloromethyl, 1-bromoethyl, fluoromethyl, difluoromethyl, trifluoromethyl, and 1,1,1-trifluoroethyl. Illustrating further, "haloalkoxy" (alone or in combination with another term(s)) means an alkoxy substituent wherein at least one hydrogen radical is replaced by a halogen radical. Non-limiting examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical. Non-limiting examples of perfluoroalkyl substituents include trifluoromethyl (—CF$_3$), perfluoroisopropyl, perfluorobutyl, perfluorodecyl, and perfluorododecyl. To illustrate further, the term "perfluoroalkoxy" means an alkoxy substituent wherein each hydrogen radical is replaced with a fluorine radical. Non-limiting examples of perfluoroalkoxy substituents include trifluoromethoxy (—O—CF$_3$), perfluoroisopropoxy, perfluorobutoxy, perfluorodecoxy, and perfluorododecoxy.

The terms "heterocycle" or "heterocyclo" or "heterocyclyl" (alone or in combination with another term(s)) refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results.

A heterocyclyl may be, without limitation, a single ring, which typically contains from 3 to 14 ring atoms (i.e., M$_3$-M$_{14}$heterocyclyl), from 3 to 8 ring atoms (i.e., M$_3$-M$_8$heterocyclyl), from 3 to 6 ring atoms (i.e., M$_3$-M$_6$heterocyclyl), or from 5 to 6 ring atoms (i.e., M$_5$-M$_6$heterocyclyl). Non-limiting examples of single-ring heterocyclyls include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl may also include, without limitation, two or more rings fused together, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocyclyls include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), tetrahydroisoquinolinyl, carbazolyl, xanthenyl, and acridinyl.

The term "two-fused-ring" heterocyclyl (alone or in combination with another term(s)) means a saturated, partially saturated, or aromatic heterocyclyl containing two fused rings. Non-limiting examples of two-fused-ring heterocyclyls include naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl, pteridinyl, indolyl, isoindolyl, indoleninyl, isoindazolyl, benzazinyl, phthalazinyl, quinolinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzoimidazolyl, benzotriazolyl, benzoxazinyl, benzoisoxazinyl, and tetrahydroisoquinolinyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

As used herein, the number of ring atoms in a heterocyclyl moiety can be identified by the prefix "$M_x$-$M_y$," where x is the minimum and y is the maximum number of ring atoms in the heterocyclyl moiety.

The term "heterocycloalkoxy" (alone or in combination with another term(s)) refers to a heterocycloalkyl group appended to the parent molecular moiety through an oxy group.

The term "heterocycloalkoxyalkyl" (alone or in combination with another term(s)) refers to a heterocycloalkoxy group appended to the parent molecular moiety through an alkylene group (i.e., heterocyclyl-alkylene-O-alkylene-).

The term "heterocycloalkoxycarbonyl" (alone or in combination with another term(s)) refers to a heterocycloalkoxy group appended to the parent molecular moiety through a carbonyl group (i.e., heterocyclyl-alkylene-O—C(O)—).

The term "heterocycloalkyl" (alone or in combination with another term(s)) refers to a heterocyclyl appended to the parent molecular moiety through an alkylene group (e.g., heterocyclo$C_1$-$C_6$alkyl).

The term "heterocycloalkylcarbonyl" (alone or in combination with another term(s)) refers to a heterocycloalkyl group appended to the parent molecular moiety through a carbonyl group (i.e., —C(O)-alkylene-heterocyclyl).

The term "heterocyclocarbonyl" (alone or in combination with another term(s)) refers to a heterocyclyl appended to the parent molecular moiety through a carbonyl group (i.e., —C(O)-heterocyclyl).

The terms "heterocyclyloxy" or "(heterocyclo)oxy" (alone or in combination with another term(s)) refers to a heterocyclyl group appended to the parent molecular moiety through an oxy moiety.

The term "(heterocyclyo)oxyalkyl" (alone or in combination with another term(s)) refers to a heterocyclyloxy group appended to the parent molecular moiety through an alkylene group (i.e., heterocyclyl-O-alkylene-).

The term "(heterocyclo)oxycarbonyl" (alone or in combination with another term(s)) refers to a (heterocyclo)oxy group appended to the parent molecular moiety through a carbonyl group (i.e., heterocyclyl-O—C(O)—).

The term "heterocyclothio" (alone or in combination with another term(s)) refers to a heterocyclyl appended to the parent molecular moiety through —S—.

The term "heterocyclothioalkoxy" (alone or in combination with another term(s)) refers to heterocyclyl-alkylene-S—.

The term "heterocyclothioalkoxyalkyl" (alone or in combination with another term(s)) refers to heterocyclyl-alkylene-S-alkylene-.

The term "heterocyclothioalkyl" (alone or in combination with another term(s)) refers to a heterocyclothio group appended to the parent molecular moiety through an alkylene group (i.e., heterocyclyl-S-alkylene-).

The term "heterocyclocarbocyclyl" (alone or in combination with another term(s)) refers to a heterocyclyl appended to the parent molecular moiety through a carbocyclyl group (i.e., heterocyclo-carbocyclyl-).

The term "heterocyclocarbocyclylalkyl" (alone or in combination with another term(s)) refers to a heterocyclocarbocyclyl group appended to the parent molecular moiety through an alkylene group (i.e., heterocyclyl-carbocyclyl-alkylene-).

The term "(heterocyclo)alkoxycarbocyclylalkyl" (alone or in combination with another term(s)) refers to heterocycloalkylene-O-carbocyclyl-alkylene-.

The term "(heterocyclo)carbonylcarbocyclylalkyl" (alone or in combination with another term(s)) refers to heterocyclo-C(O)-carbocyclyl-alkylene-.

The term "(heterocyclo)heterocycloalkyl" (alone or in combination with another term(s)) refers to heterocyclo-heterocyclo-alkylene-.

The term "(heterocyclo)alkoxyheterocycloalkyl" (alone or in combination with another term(s)) refers to heterocycloalkylene-O-heterocyclo-alkylene-.

The term "(heterocyclo)carbonylheterocycloalkyl" (alone or in combination with another term(s)) refers to heterocyclo-C(O)-heterocyclo-alkylene-.

The term "(heterocycloalkyl)carbocyclylalkyl" (alone or in combination with another term(s)) refers to heterocycloalkylene-carbocyclyl-alkylene-.

The term "(heterocycloalkyl)heterocycloalkyl" (alone or in combination with another term(s)) refers to heterocycloalkylene-heterocyclo-alkylene-. Thus, for example, ($M_3$-$M_{10}$heterocyclo$C_1$-$C_6$alkyl)$M_5$-$M_6$heterocyclo$C_1$-$C_3$alkyl means $M_3$-$M_{10}$heterocyclo-$C_1$-$C_6$alkylene-$M_5$-$M_6$heterocyclo-$C_1$-$C_3$alkylene-.

The term "heteroaryl" (alone or in combination with another term(s)) means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3, 4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heteroarylalkoxy" (alone or in combination with another term(s)) refers to a heteroarylalkyl appended to the parent molecular moiety through an oxy group (i.e., heteroaryl-alkylene-O—). Representative examples of heteroarylalkoxy include, but are not limited to, 2-pyridin-3-ylethoxy, 1,3-thiazol-5-ylmethoxy, 3-quinolin-3-ylpropoxy, and 5-pyridin-4-ylpentyloxy.

The term "heteroarylalkoxyalkyl" (alone or in combination with another term(s)) refers to a heteroarylalkoxy group appended to the parent molecular moiety through an alkylene group (i.e., heteroaryl-alkylene-O-alkylene-). Representative examples of heteroarylalkoxyalkyl include, but are not limited to, (2-pyridin-3-ylethoxy)methyl, (3-quinolin-3-ylpropoxy)methyl, (1,3-thiazol-5-ylmethoxy)methyl, and 2-(5-pyridin-4-ylpentyloxy)ethyl.

The term "heteroarylalkoxycarbonyl" (alone or in combination with another term(s)) refers to a heteroarylalkoxy group appended to the parent molecular moiety through a carbonyl group (i.e., heteroaryl-alkylene-O—C(O)—). Representative examples of heteroarylalkoxycarbonyl include, but are not limited to, (2-pyridin-3-ylethoxy)carbonyl, (3-quinolin-3-ylpropoxy)carbonyl, 2-(1,3-thiazol-5-ylmethoxy)carbonyl, and (5-pyridin-4-ylpentyloxy)carbonyl.

The term "heteroarylalkyl" (alone or in combination with another term(s)) refers to a heteroaryl group appended to the parent molecular moiety through an alkylene group. Representative examples of heteroarylalkyl include, but are not limited to, 3-quinolinylmethyl, 3-pyridinylmethyl, 4-pyridinylmethyl, 1H-imidazol-4-ylmethyl, 1H-pyrrol-2-ylmethyl, pyridin-3-ylmethyl, and 2-pyrimidin-2-ylpropyl.

The term "heteroarylalkylcarbonyl" (alone or in combination with another term(s)) refers to a heteroarylalkyl group appended to the parent molecular moiety through a carbonyl group (i.e., heteroaryl-alkylene-C(O)—).

The term "heteroarylcarbonyl" (alone or in combination with another term(s)) refers to a heteroaryl group appended to the parent molecular moiety through a carbonyl group. Representative examples of heteroarylcarbonyl include, but are not limited to, pyridin-3-ylcarbonyl, (1,3-thiazol-5-yl)carbonyl, and quinolin-3-ylcarbonyl.

The term "heteroaryloxy" (alone or in combination with another term(s)) refers to a heteroaryl group appended to the parent molecular moiety through an oxy moiety. Representative examples of heteroaryloxy include, but are not limited to, pyridin-3-yloxy, and quinolin-3-yloxy.

The term "heteroaryloxyalkyl" (alone or in combination with another term(s)) refers to a heteroaryloxy group appended to the parent molecular moiety through an alkylene group (i.e., heteroaryl-O-alkylene-).

The term "heteroaryloxycarbonyl" (alone or in combination with another term(s)) refers to a heteroaryloxy group appended to the parent molecular moiety through a carbonyl group (i.e., heteroaryl-O—C(O)—).

The term "heteroarylthio" (alone or in combination with another term(s)) refers to a heteroaryl group appended to the parent molecular moiety through —S—.

The term "heteroarylthioalkoxy" (alone or in combination with another term(s)) refers to heteroaryl-alkylene-S—.

The term "heteroarylthioalkoxyalkyl" (alone or in combination with another term(s)) refers to heteroaryl-alkylene-S-alkylene-.

The term "heteroarylthioalkyl" (alone or in combination with another term(s)) refers to a heteroarylthio group appended to the parent molecular moiety through an alkylene group (i.e., heteroaryl-S-alkylene-).

The term "hydrogen" (alone or in combination with another term(s)) refers to a hydrogen radical, and may be depicted as —H.

The term "hydroxy" (alone or in combination with another term(s)) refers to —OH.

The term "hydroxyalkyl" (alone or in combination with another term(s)) refers to an alkyl substituent wherein one or more hydrogen radicals are replaced with —OH. Representative examples of hydroxyalkyl include, but are not limited to, hydroxymethyl, 2-hydroxyethyl, 3-hydroxypropyl, and 2-ethyl-4-hydroxyheptyl.

The term "keto" (alone or in combination with another term(s)) means an oxo radical, and may be depicted as =O.

The term "iminoalkyl" (alone or in combination with another term(s)) refers to a radical of the formula

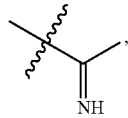

wherein the H may be optionally substituted with alkyl or hydroxy, in which case the substituent would be alkyliminoalkyl or hydroxyiminoalkyl respectively.

The term "nitro" (alone or in combination with another term(s)) means —NO$_2$.

The term "oxo" (alone or in combination with another term(s)) refers to a =O moiety

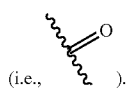

(i.e.,         ).

The term "oxy" (alone or in combination with another term(s)) means —O—.

The term "propargyl" (alone or in combination with another term(s)) means the monovalent radical depicted as: —CH$_2$—CH≡CH.

The term "sulfonyl" (alone or in combination with another term(s)) means —S(O)$_2$—, which also may be depicted as:

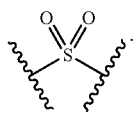

The term "sulfinyl" (alone or in combination with another term(s)) means —S(O)—, which also may be depicted as:

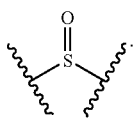

The term "thio" or "thia" (alone or in combination with another term(s)) means —S—.

The term "thiol," "mercapto" or "sulfhydryl" (alone or in combination with another term(s)) means a sulfhydryl substituent, (i.e., —SH). Thus, for example, thiolalkyl means an alkyl substituent wherein one or more hydrogen radicals are replaced with —SH, while alkylthio means alkyl-S—.

The term "thioalkoxy" (alone or in combination with another term(s)) refers to an alkyl group appended to the parent molecular moiety through —S—. Representative examples of thioalkoxy include, but are not limited to, methylthio, ethylthio, and butylthio.

The term "thioalkoxyalkyl" (alone or in combination with another term(s)) refers to a thioalkoxy group appended to the parent molecular moiety through an alkylene group (i.e., alkyl-S-alkylene-).

The term "thiocarbonyl" (alone or in combination with another term(s)) means a carbonyl wherein the oxygen atom has been replaced with a sulfur. Such a substituent may be depicted as —C(S)—, and also may be depicted as:

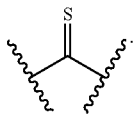

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). The prodrug derivative form often offers advantages of solubility, tissue compatibility, or delayed release in a mammalian organism (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "chiral" refers to molecules that do not have a plane of symmetry and are therefore not superimposable on their mirror image. A chiral molecule may exists in two forms, one right-handed and one left-handed.

The term "stereoisomer" refers to isomers that have their atoms connected in the same order but have different three-dimensional arrangements. The term stereoisomer includes, for example, enantiomers and diastereomers.

The term "cis-trans isomer" refers to stereoisomers that differ in their stereochemistry about a double bond or ring. Cis-trans isomers are also called geometric isomers.

The term "enantiomer" refers to stereoisomers of a chiral substance that have a mirror-image relationship.

The term "diastereomer" refers to stereoisomers that are not enantiomers, or mirror images of each other.

The term "racemic mixture" refers to a mixture consisting of equal parts (+) and (−) enantiomers of a chiral substance. Even though the individual molecules are chiral, racemic mixtures are optically inactive.

The term "tautomer" refers to isomers that are interconvertable. For example, enols and ketones are tautomers because they are interconverted by treatment with either acid or base.

The term "position isomer" refers to any of two or more constitutional isomers that differ in the position of a particular substituent or group. Functional groups can be attached at structurally nonequivalent positions on a carbon skeleton. For example, [1,3]imidazole, depicted as

and [1,4]imidazole, depicted as

are position isomers.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS (3rd ed., John Wiley & Sons, NY (1999), which is incorporate herein by reference in its entirety. Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The following abbreviations are used in the General Synthetic Methods and Examples described below:
AcOH=acetic acid
atm=atmospheres
Boc=N-t-butoxycarbonyl (protecting group)
CDI=1,1'-carbonyldiimidazole
CH$_2$Cl$_2$=methylene chloride (dichloromethane)
CuI=cuprous iodide [copper (I) iodide]
DCE=1,2-dichloroethane
DEAD=diethyl azodicarboxylate
DMA=N-N-dimethylacetamide
DMAP=4-dimethylaminopyridine
DMF=N,N-dimethylformamide
DMSO=dimethylsulfoxide
EDCI=(N-ethyl-N'-(3-dimethylaminopropyl)carbodiimide hydrochloride
EMME=2-ethoxymethylene-malonic acid diethyl ester
Et$_3$N=triethylamine
Ether=diethyl ether
EtI=ethyl iodide
EtOAc=ethyl acetate
EtOH=ethanol
Fe=iron
Fe(AcAc)3=Iron(III)-acetylacetonate
Fmoc chloride=9-fluorenylmethyl chloroformate
HOBt=N-Hydroxybenzotriazole
Hunig's base=N,N-diisopropylethylamine
IPA=isopropyl alcohol
K$_2$CO$_3$=potassium carbonate
KOH=potassium hydroxide
LDA=lithium diisopropylamine
MeOH=methanol
MsCl=methanesulfonyl chloride
NaH=sodium hydride
NH$_2$OH.HCl=hydroxylamine hydrochloride
NMP=1-methyl-2-pyrrolidinone
Mg$_2$SO$_4$=magnesium sulfate
Na$_2$SO$_4$=sodium sulfate
NH$_3$=ammonia
NH$_4$Cl=ammonium chloride
NH$_4$OH=ammonium hydroxide
PG=protecting group such as Boc- or Troc-
POCl$_3$=phosphorous oxy chloride
R—MgCl=Grignard reagent
R—I=alkyl iodide or substituted alkyl iodide
SnCl2=Stannous chloride (Tin (II) chloride)
TFA=trifluoroacetic acid
THF=tetrahydrofuran
TLC=thin layer chromatography
Triflic Anhydride=trifluoromethanesulfonic anhydride
Troc=2,2,2-trichloroethoxycarbonyl-(protecting group)

GENERAL SYNTHETIC METHODS AND EXAMPLES

The following synthetic methods and schemes illustrate the general methods by which the compounds of the present invention can be prepared. Starting materials can be obtained from commercial sources or prepared using methods well known to those of ordinary skill in the art. By way of example, synthetic routes similar to those shown hereinbelow may be used, together with synthetic methods known in the art of synthetic organic chemistry, or variations thereon, as appreciated by those skilled in the art.

The present invention is intended to encompass compounds prepared by either synthetic processes or metabolic processes. Metabolic processes include those occurring in the human or animal body (in vivo), or those occurring in vitro.

If a substituent described herein is not compatible with the synthetic methods of this invention, the substituent may be protected with a suitable protecting group that is stable to the reaction conditions used in these methods. The protecting group may be removed at a suitable point in the reaction sequence to provide a desired intermediate or target compound. Suitable protecting groups and methods for protecting

Preparation of 7-Substituted-4-Substituted-[1,8]Naphthyridine Compounds or deprotecting substituents are well know in the art, examples of which can be found in Greene and Wuts, supra.

Shown in Schemes 1, 2, 3 and 4 below is a representative method for the preparation of these [1,8]naphthyridine-type compounds.

The 7-substituted-4-substituted-[1,8]naphthyridine compounds are generally synthesized (Scheme 4) by coupling a 7-substituted-4-chloro-[1,8]naphthyridine compound 8 with a coupling compound such as 10, 11 and 12 (Scheme 3). Other 4-substituted [1,8]naphthyridines can be prepared in a similar manner utilizing the appropriate coupling compounds.

Preparation of 6-Substituted-2-aminopyridines

In a typical preparation described in Scheme 1, a solution of 2,6-dichloropyridine is treated with ammonium hydroxide in a sealed metal reactor at about 180° C. for about 40 hours. After cooling to room temperature the product is filtered giving 6-chloro-2-aminopyridine. A solution of this product and hexane-2,5-dione in benzene is treated with acetic acid, heated under reflux conditions with azeotropic removal of water for about 20 hours. This reaction mixture is cooled to room temperature, diluted with diethyl ether, washed with dilute hydrochloric acid and water. The organic layer is dried over magnesium sulfate, filtered and concentrated under vacuum to give 6-chloro-2-(2,5-dimethyl-pyrrol-1-yl-pyridine 1. Compound 1 is treated with a Grignard reagent (R—MgX) in dry tetrahydrofuran (THF) and 1-methyl-2-pyrrolidinone (NMP) at room temperature under a nitrogen atmosphere and iron (III) acetylacetonate [Fe(AcAc)$_3$] is added and the mixture is stirred at room temperature for about 18 hours. During the reaction two addition charges of the Grignard reagent and iron catalyst are added. The reaction is quenched by pouring unto 5% acetic acid and extracting with ether. The ether layer is dried over sodium sulfate, filtered and concentrated under vacuum to give 6-substituted-2-(2,5-dimethyl-pyrrol-1-yl)-pyridine 2. Compound 2 can be directly converted to a 6-substituted-2-aminopyridine 4 or it can be further functionalized by reacting it with an alkyl iodide or a substituted alkyl iodide in the presence of lithium diisopropylamide (LDA). In this case, a solution of compound 2 in dry tetrahydrofuran is added dropwise over about 30 minutes to a stirred solution of lithium diisopropylamide in dry tetrahydrofuran at −30° C. An alkyl iodide or a substituted alky iodide (R—I) in tetrahydrofuran is then added dropwise over about 30 minutes then warmed to room temperature. After two hours the reaction mixture is quenched by pouring into saturated sodium chloride solution and extracted with ether. The ether solution is dried over magnesium sulfate, filtered and concentrated under vacuum giving the 6-substituted-2-(2,5-dimethyl-pyrrol-1-yl)pyridine 3. A solution of either compound 2 or 3 and hydroxylamine hydrochloride in ethanol and water is heated at about 100° C. for about 16 hours, cooled to room temperature and extracted with methylene chloride, dried over magnesium sulfate, filtered and concentrated under vacuum giving the 6-substituted-aminopyridine 4 used in Scheme 2. The 6-substituent in Scheme 1 is $R^7$ which is described before.

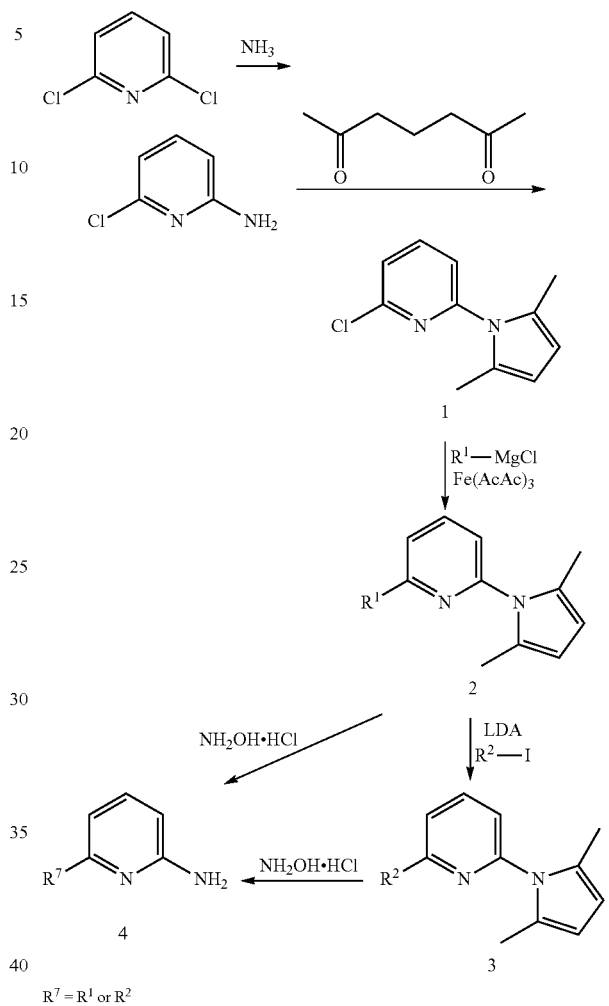

Scheme 1: Method of Preparation of 6-Substituted-2-Aminopyridines $R^7 = R^1$ or $R^2$

Preparation of 7-Substituted-4-Chloro-[1,8]Naphthyridines

A typical preparation described in Scheme 2 consists of mixing a 6-substituted 2-aminopyridine 4 and 2-ethoxymethylene-malonic acid diethyl ester (EMME) and heating to about 100° C. with stirring for about 2.5 hours. The reaction mixture is cooled to room temperature and diluted with hexane, the resulting solid is filtered and dried under vacuum to give the aminomethylene malonic acid ester 5. Compound 5 is then dissolved in diphenylether and the resulting solution heated to 250° C. for about 30 minutes. After cooling to room temperature, diluting with hexane the resulting solid is filtered and dried under vacuum giving the substituted 7-substituted-4-oxo-1,4-dihydro-[1,8]naphthyridine-3-carboxylic acid ethyl ester "E". A solution of compound 6 and potassium hydroxide (KOH) is heated in a sealed metal reactor at 180° C. for about 16 hours, cooled to room temperature and adjusted to pH 6 with 1N hydrochloric acid. The resulting precipitate is filtered and dried giving the 7-substituted [1,8]napthyridin-4-ol 7. A mixture of compound 7 is mixed with phosphorous oxychloride (POCl$_3$) and heated to about 50° C. with stirring for 6 hours, cooled quenched by pouring unto ice. It is cooled then adjusted to pH 10 with concentrated ammonium hydroxide and extracted with methylene chloride, dried over anhydrous sodium sulfate, filtered and concentrated under vacuum giving the 7-substituted-4-chloro-[1,8]naphthyridine 8. The substituents for compound 8 are shown in Scheme 2 as $R^7$ which has been described before.

Scheme 2: Method for preparation of substituted 4-chloro-[1,8]naphthyridines.

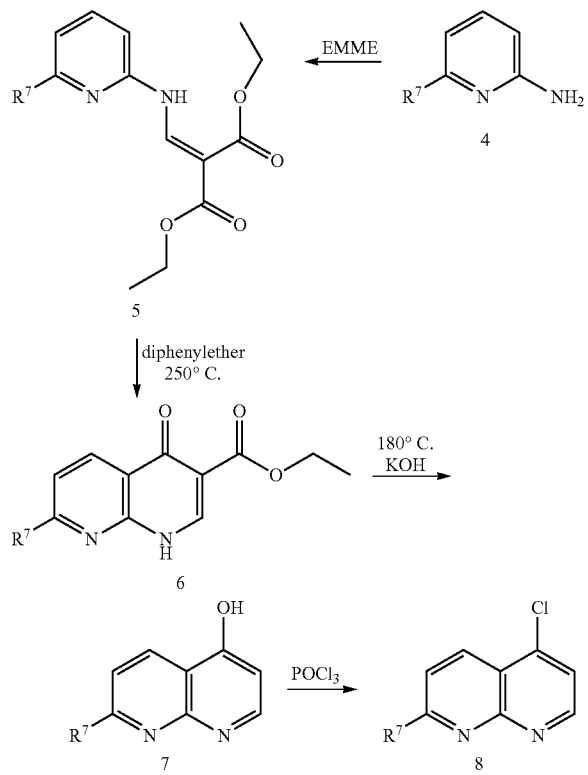

Preparation of Aminophenyl Coupling Agents (10, 11 and 12)

A wide variety of aminophenyl coupling agents are possible. The agents in Scheme 3 are exemplary of this variety.

In a typical preparation, a substituted 2-chloro-nitrobenzene compound in dimethylformamide (DMF) is treated with a sodium thiophenolate at about 50° C. for about 2 hours, is cooled and diluted with methylene chloride, washed with water, dried over sodium sulfate, filtered and concentrated under vacuum to give the substituted-2-phenylsulfanyl-nitrobenzene compound. This nitrobenzene compound is then reduced with stannous chloride ($SnCl_2$) or iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenylsulfanyl-aminobenzene compound 10.

Similarly, the corresponding substituted-2-hydroxy-nitrobenzene compound is dissolved in dimethylformamide reacted with a sodium phenoxide solution, stirred and heated to 100° C. for about 5 days. The reaction mixture is cooled and diluted with methylene chloride, washed with water, dried over sodium sulfate, filtered and concentrated under vacuum to give the substituted-2-phenoxy-nitrobenzene compound. This nitrobenzene compound is then reduced with stannous chloride ($SnCl_2$) and iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenoxy-aminobenzene compound 12.

Similarly, either compound 10 where $R^9$ is hydroxy- or protected hydroxyl- can be further modified by alkylating the hydroxy-group using a substituted benzyl bromide to give the corresponding 5-substituted-phenoxy-2-substituted-phenylsulfanyl-aminobenzene compound 11.

Scheme 3: Preparation of Aminophenyl Coupling Agents

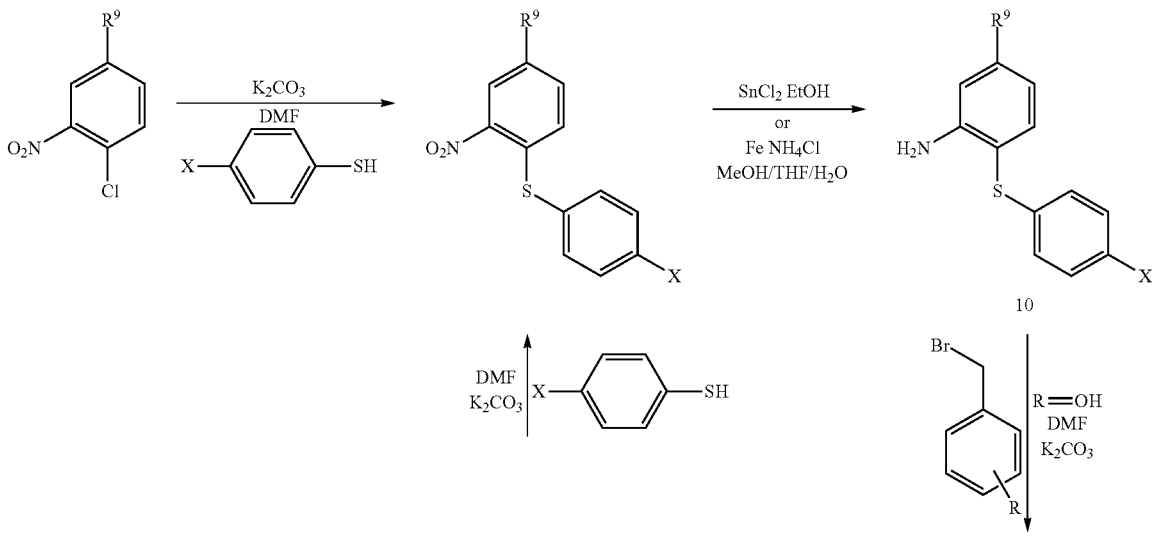

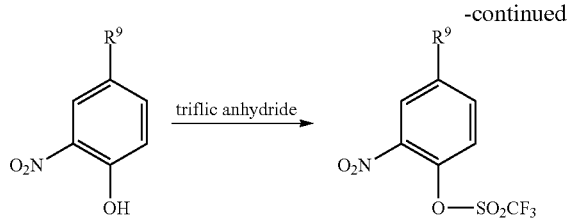

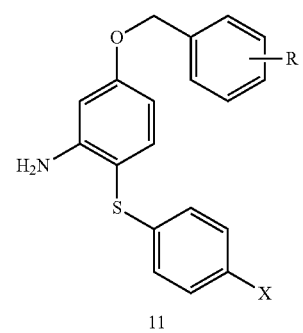

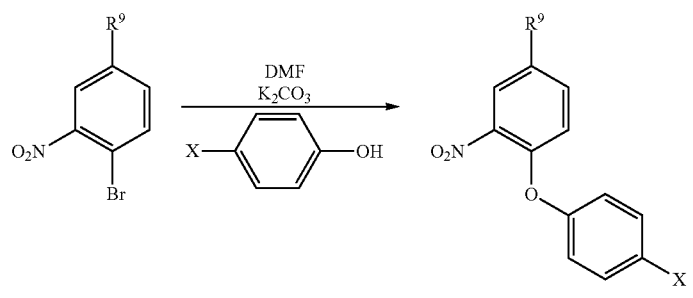

$R^9$ is defined above;
X is OH, NH$_2$, NHR, halo, alkyl, or alkoxy
R is alkyl, alkoxy, bromo, fluoro, chloro, or cyano Preparation of
7-Substituted-4-aminophenyl-[1,8]naphthyridines As shown in Scheme 4, the coupling agent (compound 10, 11, 12 or the like) appropriate for the synthesis of the desired 7-substituted-4-aminophenyl-[1,8]naphthyridine is dissolved in ethanol and reacted with compound 8 in ethanol at 80° C. for about 7 hours. The reaction mixture is concentrated under vacuum and recrystallized from tetrahydrofuran with a few drops of methanol. Filtration gives the desired 7-substituted-4-aminophenyl-[1,8]naphthyridine 13, 14 or 15.

Scheme 4: Coupling of Substituted 4-Chloro-[1,8]naphthyridines with Substituted Aminophenyl Agents

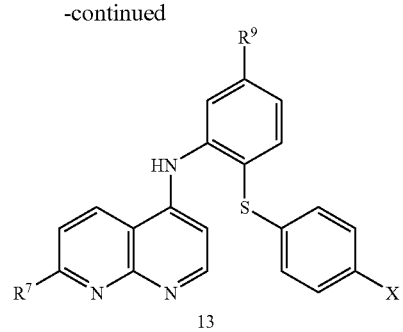

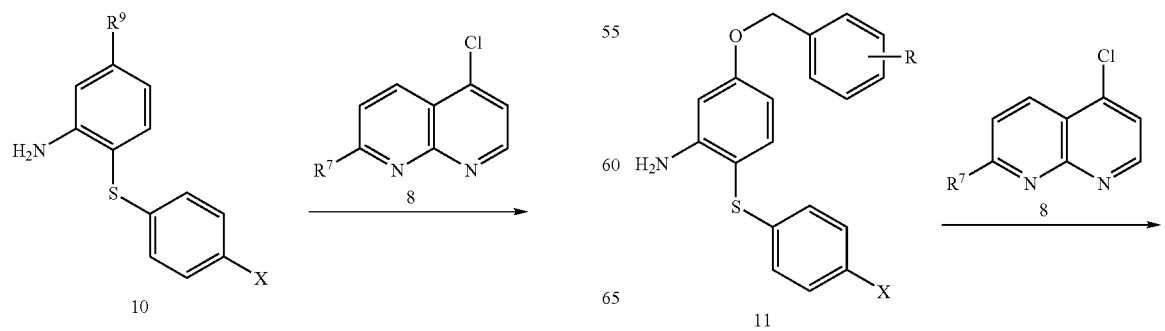

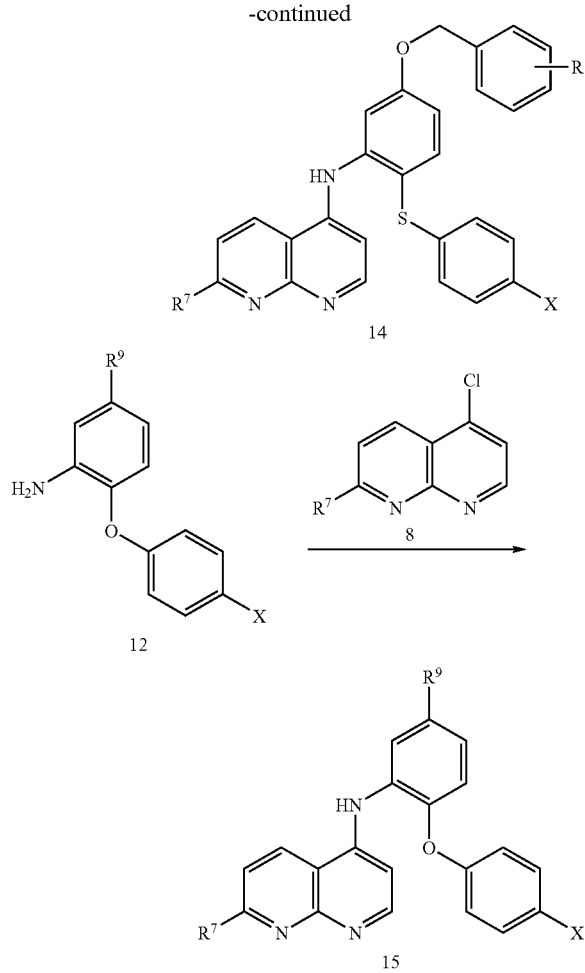

R[9] is defined above;
X is defined above;
R is defined above

Preparation of 7-Substituted-4-Aminophenyl-substituted-pyrido[2,3-d]pyrimidine Compounds A typical preparation of 7-substituted-4-aminophenyl-substituted-pyrido[2,3-d]pyrimidine compounds (Scheme 8) involves the coupling reaction of a substituted aminophenyl coupling agent (described in Schemes 3, 5, and 6) with a 6-substituted-2-amidino-3-cyanopyridine compound 9 (Scheme 7).

Preparation of Amide Coupling Agents

As described in Scheme 3, a wide variety of aminophenyl coupling agents are possible. In Scheme 5, aminophenyl compounds with amide substitution in the 3-phenyl position are described.

A substituted aniline in methylene chloride is treated with 4-chloro-3-nitrobenzoyl chloride and N,N-diisopropylamine and stirred at room temperature for about 17 hours. The solvent is removed under vacuum, the residue dissolved in ethyl acetate, washed with water and brine, dried over sodium sulfate, filtered and concentrated under vacuum to give the N-substituted phenyl-4-chloro-3-nitrobenzamide 16.

Compound 16 can be further modified by displacement of the 4-chloro group to produce the 3-amino-4-substituted phenoxybenzamides 17 and the 3-amino-4-substituted phenylsulfanylbenzamides 18.

Compounds 17 can typically be prepared by reacting the benzamide 16 in anhydrous N,N-dimethylformamide with 4-(N-t-butoxycarbonyl)aminophenol (N-Boc-4-hydroxyaniline) and potassium carbonate at room temperature, then heated to about 80° C. for about 5 hours. The reaction is cooled to room temperature, the solvent removed under vacuum, the residue taken up in ethyl acetate, washed with water and brine. The organic layer is dried over sodium sulfate, filtered and concentrated under vacuum to produce the 4-N-t-butoxycarbonylamino substituted compound 17. The Boc protecting group can be removed under a variety of methods to produce compounds of structure 17.

In a similar manner, compound 16 can be reacted with 4-aminothiophenol and anhydrous sodium acetate in anhydrous ethanol heating under reflux four about 19 hours. Upon cooling to room temperature the ethanol is removed under vacuum, the residue taken up in water and extracted with ethyl acetate. The organic extracts are washed with brine, dried over sodium sulfate, filtered and concentrated under vacuum. Trituration of the solid with ethylacetate-methylene chloride afforded compound 18.

Scheme 5: Preparation of Amide Coupling Agents

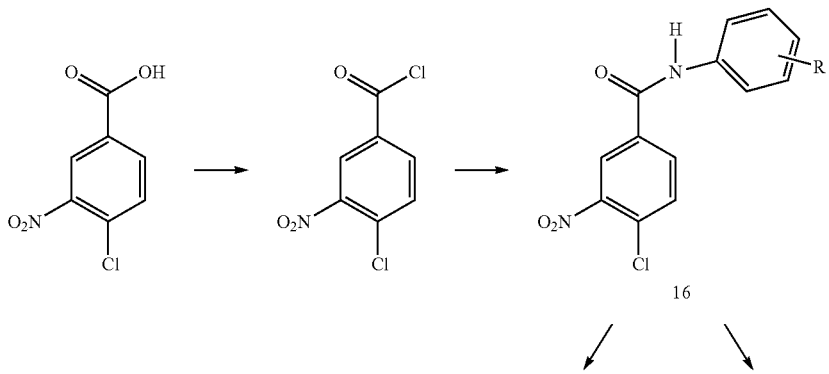

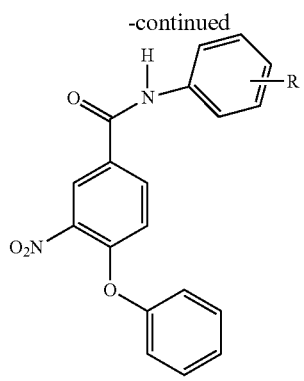
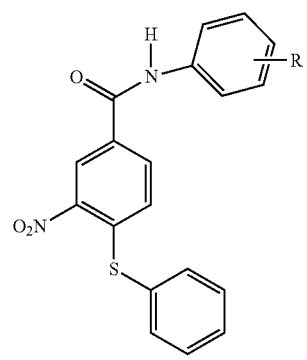

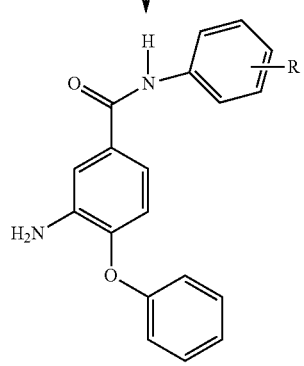
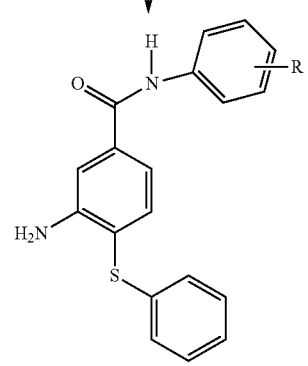

17    18

The amide phenyl ring, the phenyoxy ring and the phenylsuflanyl ring can be substituted as described above. Some examples will require the use of protecting groups followed by removal of the protecting group at the appropriate time.
R is as defined above.

Preparation of Reverse Amide Coupling Agents

The preparation of reverse amide agents for coupling is shown in Scheme 6. In a typical preparation 4-fluoro-3-nitroaniline is reacted with a substituted benzoyl chloride, Hunig's base (N,N-diisopropylethylamine) in tetrahydrofuran with stirring at room temperature for about 1 hour. Water is added to the solution and the resulting solid (compound 19) is collected by filtration and dried in a vacuum oven.

A solution of compound 19, 4-hydroxythiophenol and potassium carbonate in N,N-dimethylformamide is heated to about 80° C. for about 2 hours. After cooling to room temperature, the mixture is poured unto ice water, extracted with ethyl acetate, the extracts dried over magnesium sulfate, filtered and concentrated under vacuum to give the 4-hydroxyphenylsulfanyl intermediate. A solution of this intermediate, iron powder and ammonium chloride in tetrahydrofuran and water is heated to reflux for about 3 hours. The resulting mixture is cooled and diluted with methanol and filtered. The filtrate is diluted with water and extracted with methylene chloride. The methylene chloride extracts are dried over magnesium sulfate, filtered and concentrated under vacuum to give the 4-hydroxy analog of compound 23.

Similarly a compound 19 can be reacted with 4-aminothiophenol and cesium carbonate in N,N-dimethylformamide at about 90° C. for about 4 hours. After cooling to room temperature the mixture is poured into ice water and acidified to pH 5 with 1 N hydrochloric acid. The solution is extracted with ethyl acetate, the extracts dried over sodium sulfate, filtered and concentrated under vacuum to give the corresponding 4-aminophenylsulfanyl-3-nitroanilide. A methylene chloride solution of this anilide is then reacted with 2,2,2-trichloroethyl chloroformate and pyridine for about 16 hours. The solution is then washed with water, then brine and then the extracts are dried over sodium sulfate, filtered and concentrated under vacuum. The residue is triturated with hexane and ethyl acetate to give the corresponding Troc-amino-protected compound 22. This Troc-protected amino compound is then dissolved in ethanol and tetrahydrofuran and reacted with iron powder and ammonium chloride at reflux for about 6 hours. The resultant mixture is cooled diluted with ethanol and filtered. The filtrates are concentrated under vacuum to give the Troc-amino protected compound 23.

Similarly a solution of compound 19 in anhydrous N,N-dimethylformamide can also be reacted with the 4-t-butoxycarbonylaminophenol (N-Boc-4-hydroxyaniline) and potassium carbonate at room temperature, and then heated to about 80° C. for about 5 hours. The reaction is cooled to room temperature, the solvent removed under vacuum and the residue taken up in ethyl acetate, washed with water and brine dried over sodium sulfate, filtered and concentrated under vacuum to give the N-Boc protected compound 20. Compound 20 is then dissolved in ethanol, tetrahydrofuran and water and reacted with iron powder and ammonium chloride heating the mixture at about 90° C. for about 2 hours. After cooling to room temperature the mixture is diluted with ethyl acetate, filtered and the filtrate washed with water and brine. The organic phase is dried over sodium sulfate, filtered and concentrated under vacuum to give the coupling agent compound 22.

Scheme 6: Preparation of Reverse Amide Coupling Agents
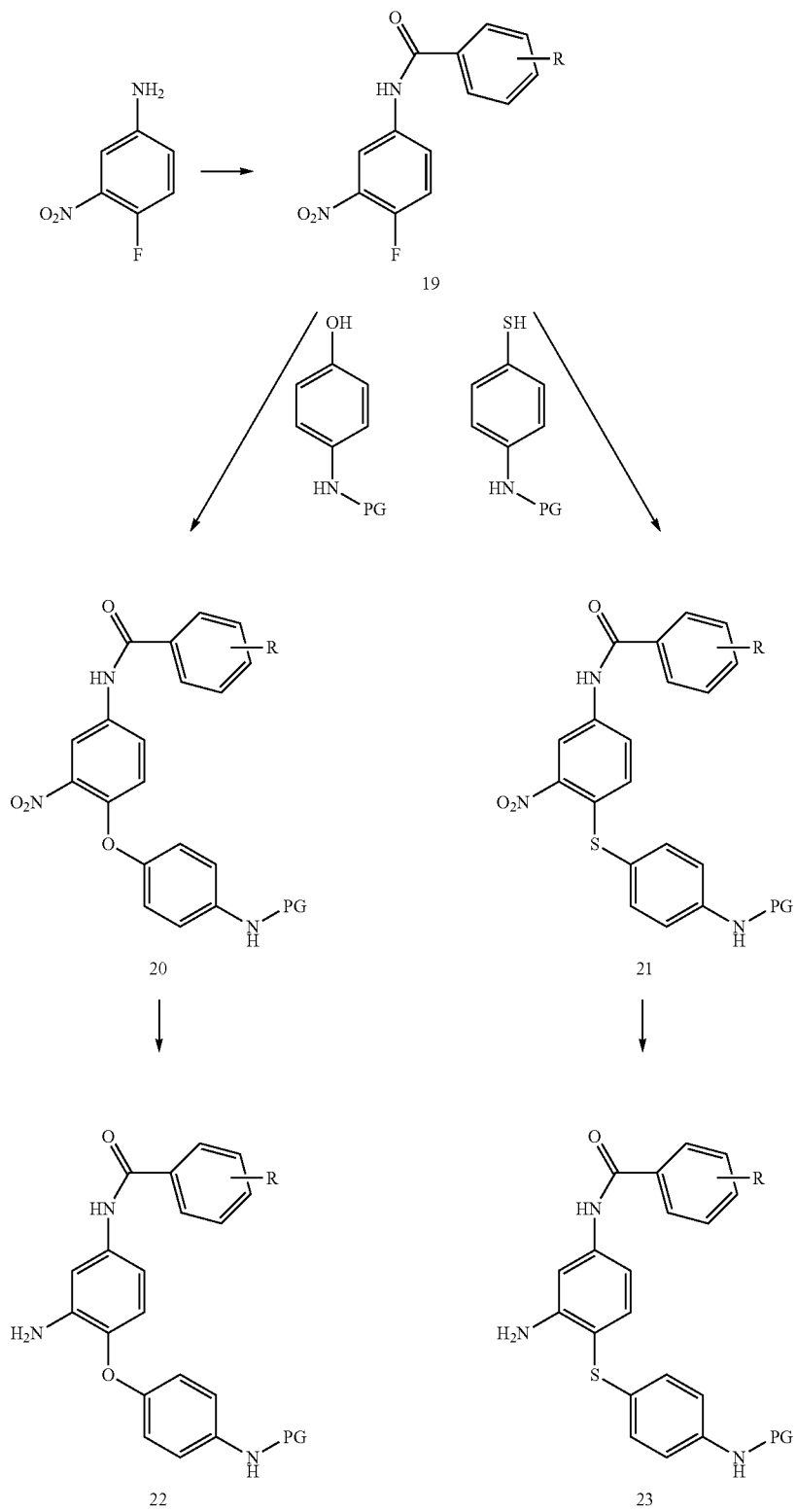
PG = Protecting Group
such as Boc-, Troc- and the like.
R is as defined above

Preparation of the N,N-Dimethylformamidine Coupling Agent 9

Preparation of the 7-substituted-4-aminophenyl-substituted-pyrido[2,3-d]pyrimidines can be accomplished by coupling a N,N-dimethylformamidino compound 9 with a variety of coupling agents some of which are described in Schemes 3, 5, and 6.

Preparation of the N,N-dimethylformamidine compounds 9 can be accomplished as described in Scheme 7. A substituted alkyl methyl ketone and ethyl formate are added to a diethyl ether solution of sodium hydride (or sodium metal) at about 0° C. for about 2 hours. After the addition the reaction is allowed to stir at room temperature overnight. Additional diethyl ether is added and the precipitate is quickly isolated by vacuum filtration died in a vacuum desiccator. This material was dissolved in water with 2-cyanoacetamide. A piperidine acetate solution is added and the resulting solution is heated at reflux for about 2 hours. The mixture is cooled to room temperature and adjusted to pH 4 with glacial acetic acid. The resulting solid is isolated by vacuum filtration rinsed with water and dried and identified as the 6-substituted-2-oxo-1,2-dihydropyridine-3-carbonitrile 24. Compound 24 can either be converted to the 2-chloro-pyridine with phosphorous oxychloride (as shown in Scheme 7) or the 2-bromopyridine. The 2-bromoyridine is prepared by taking a toluene solution of compound 24 and reacting with tetrabutylammonium bromide and phosphorous pentoxide at reflux for about 5 hours. The reaction mixture is cooled, water added and the mixture stirred for about 2 hours at room temperature. The reaction mixture was diluted with toluene, the organic layer separated, washed with brine and dried over magnesium sulfate, filtered and concentrated under vacuum to give the 2-bromopyridine. An ethanol solution of either the 2-chloropyridine or the 2-bromopyridine and liquid ammonia are reacted in a sealed high pressure vessel at about 130° C. for about 20 hours. The reaction mixture is concentrated under vacuum and the residue washed with water and dried to give the 6-substituted-2-amino-nicotinonitrile 25. Compound 25 and N,N-dimethylformamide dimethyl acetal is dissolved in toluene and heated to reflux for about 3 hours. The resulting solution is cooled to room temperature and concentrated under vacuum to give the 6-substituted-3-cyano-pyridin-2-yl-N,N-dimethylformamidine 9.

Scheme 7: Preparation of N,N-Dimethyl Formamidine Coupling Agents

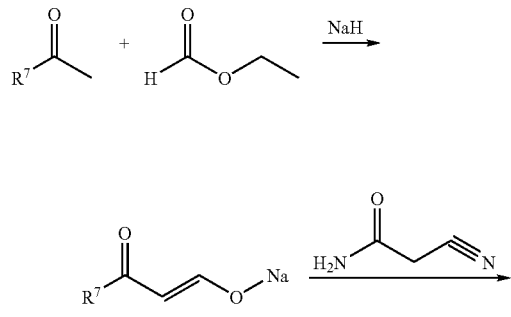

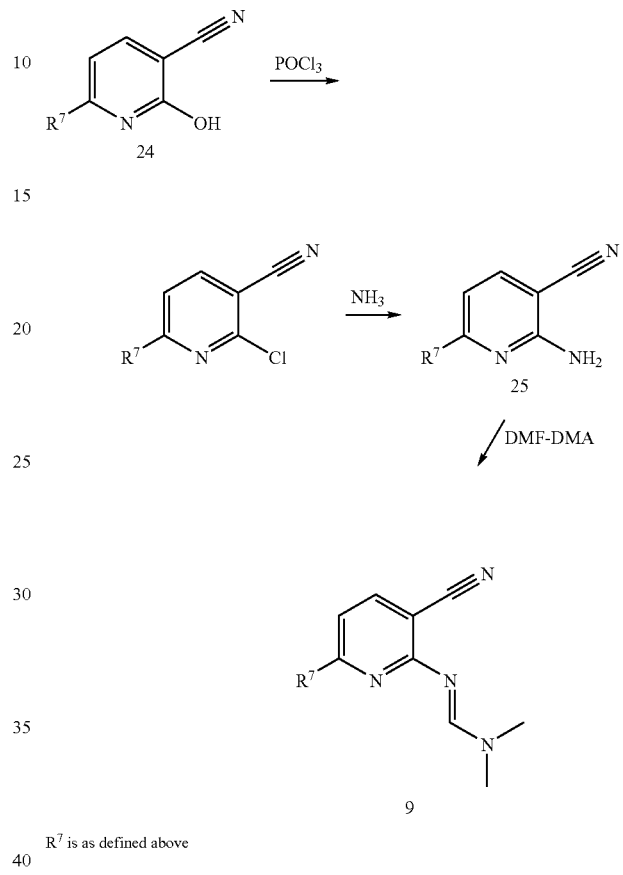

$R^7$ is as defined above

Preparation of 7-Substituted-4-aminophenyl-substituted-pyrido[2,3-d]pyrimidines As described above, the preparation of 7-substituted-4-aminophenyl-substituted-pyrido[2,3-d]pyrimidines can be accomplished by coupling the substituted 6-substituted-3-cyano-pyridin-2-yl-N,N-dimethylformamidine 9 as shown in Scheme 7 with a variety of coupling agents some of which are described in Schemes 3, 5 and 6. This coupling reaction is described in Scheme 8.

In a typical preparation, compound 9 and an aminophenyl coupling agent similar to those described in Schemes 3, 5 and 6 are dissolved in acetic acid and stirred at about 130° C. for about 15 minutes. The mixture is cooled to room temperature, the acetic acid removed under vacuum and the resulting residue purified by reverse phase chromatography. At this point any functional protecting group such as the Boc, Troc or other group can be removed by known methods to give the final products.

Scheme 8: 7-Substituted-4-Aminophenyl-Substituted Pyrido[2,3-d]pyrimidines
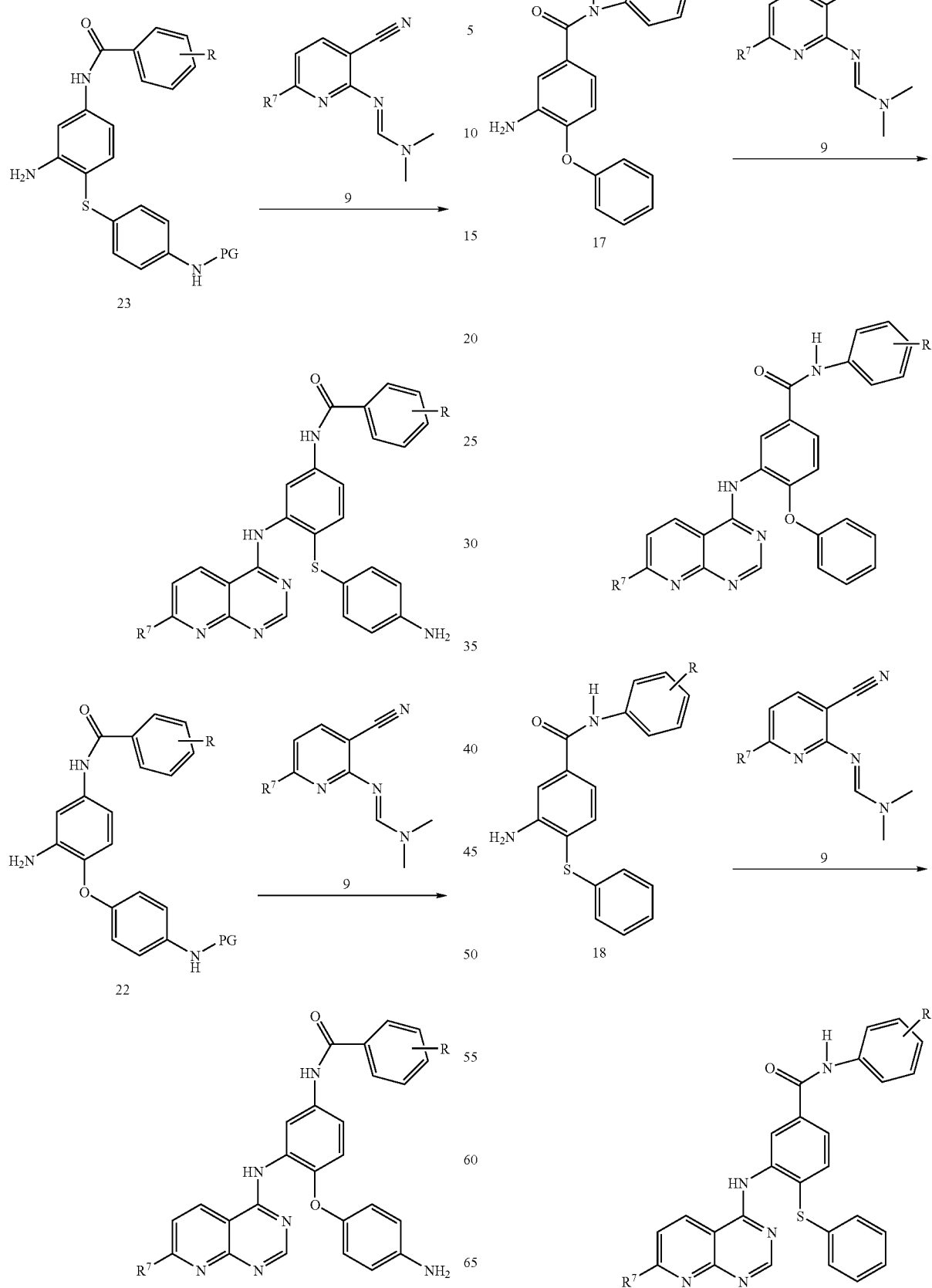

-continued

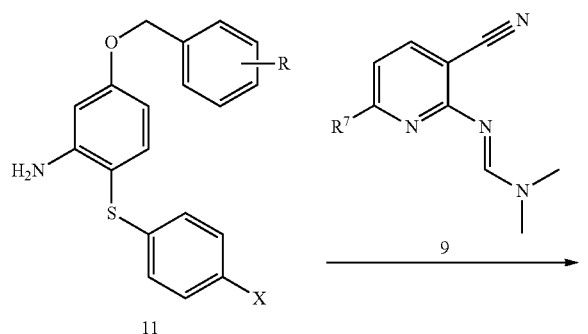

11

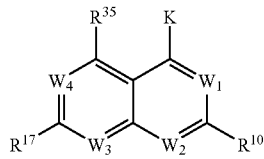

9

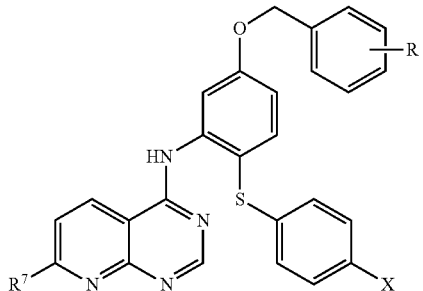

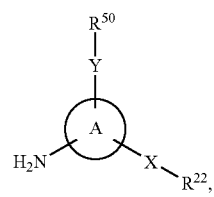

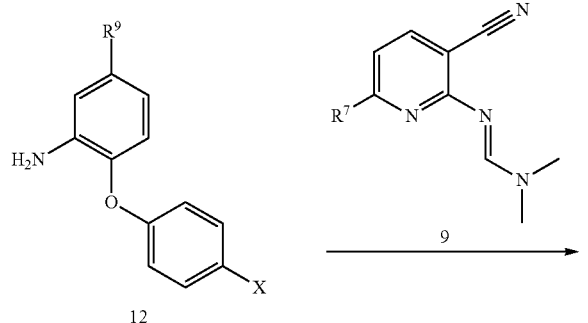

12

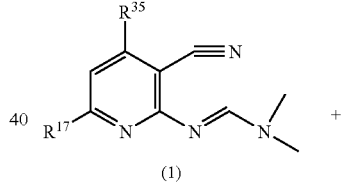

9

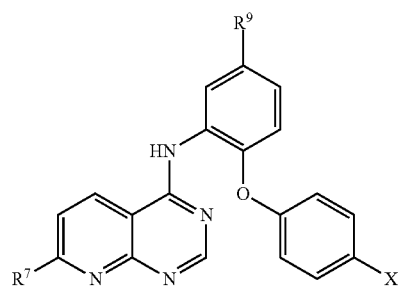

The amide phenyl ring, the phenyoxy ring and the phenylsuflanyl ring can be substituted as described above. Some examples will require the use of protecting groups followed by removal of the protecting group at the appropriate time.

$R^7$, $R^9$, X and R are as defined above

Preparation of Compounds of Formulae I, I(a), I(b), I(c), I(d) and I(e)

The synthesis of compounds of Formulae I, I(a), I(b), I(c), I(d) or I(e) generally involves reaction of

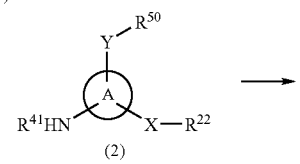

with

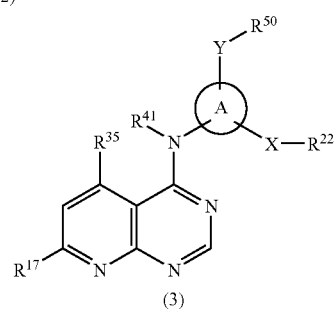

wherein $W_1$, $W_2$, $W_3$, $W_4$, A, X, Y, $R^{10}$, $R^{17}$, $R^{22}$, $R^{35}$, and $R^{50}$ have the meanings as set forth in the above embodiments or examples, and K is Cl or another halogen. The synthesis of compounds of Formulae I, I(a), I(b), I(c), I(d) or I(e) as described in the above embodiments or examples is also exemplified in Schemes 9-12.

Representative compounds of Formulae I, I(a), I(b), I(c), I(d) or I(e) wherein $W_4$ is CH, $W_1$, $W_2$ and $W_3$ are N, and Z is $NR^{41}$ can be prepared using the procedure as outlined in Scheme 9.

Scheme 9

(1)

+

(2)

→

(3)

Amines of formula (2) wherein $R^{41}$ is hydrogen can be treated with N,N-dimethylformamidine compounds of formula (1) in the presence of an acid such as, but not limited to, acetic acid, at elevated temperature (for example, from about 80° C. to about 150° C.), thereby producing compounds of formula (3). The acetic acid can function as a solvent. Other suitable solvents can also be used in the reaction.

N alkylation of compounds of formula (2) wherein $R^{41}$ is hydrogen provides formula (2) and (3) wherein $R^{41}$ is alkyl. This process can be facilitated with an alkylating reagent of formula $R^{41}X^1$, wherein $X^1$ is halogen, tosylate, triflate or mesylate, in the presence of a base such as, but not limited to, an organic base such as triethylamine or diisopropylamine, or an inorganic base such as sodium, cesium or potassium carbonate, in a suitable solvent, and at a temperature ranging from about room temperature to about 100° C.

Scheme 10

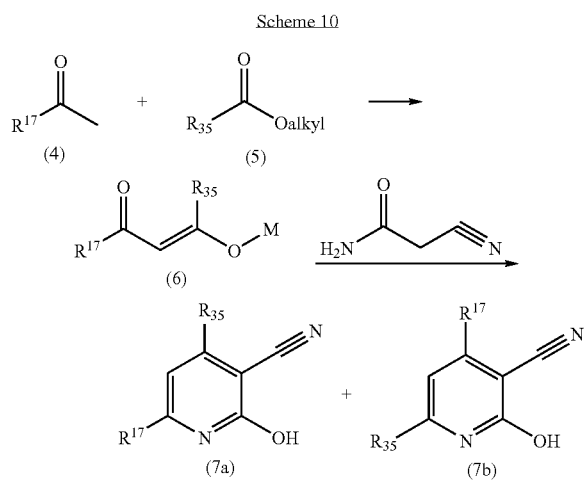

Preparation of the N,N-dimethylformamidine compounds of formula (1) can be accomplished as described in Scheme 10. Ketones of formula (4) and esters of formula (5), in the presence of a base such as, but not limited to, sodium or potassium hydride (or sodium metal) at about 0° C. in a suitable solvent such as, but not limited to, diethyl ether, provide a salt of formula (6) wherein M is potassium or sodium. Treatment of formula (6) with 2-cyanoacetamide in the presence of piperidine acetate, at about reflux gives nitriles of formula (7a) and (7b). The regioisomers (7a) and (7b) can be separated at this point or later in the synthetic route, using purification techniques known to those skilled in the art. Compounds of formula (7a) can either be converted to compounds of formula (8) wherein $X^2$ is Cl by treatment with phosphorous oxychloride or to compounds of formula (8) wherein $X^2$ is Br by treatment with tetrabutylammonium bromide and phosphorous pentoxide in a suitable solvent, at reflux. A solution of compounds of formula (8) wherein $X^2$ is Cl or Br and liquid ammonia are reacted in a sealed high pressure vessel at elevated temperature, for example, at about 130° C. to provide compounds of formula (9). Compounds of formula (9) and N,N-dimethylformamide dimethyl acetal in a solvent such as, but not limited to, toluene, at reflux yield the N,N-dimethylformamidine compounds of formula (1).

Scheme 11

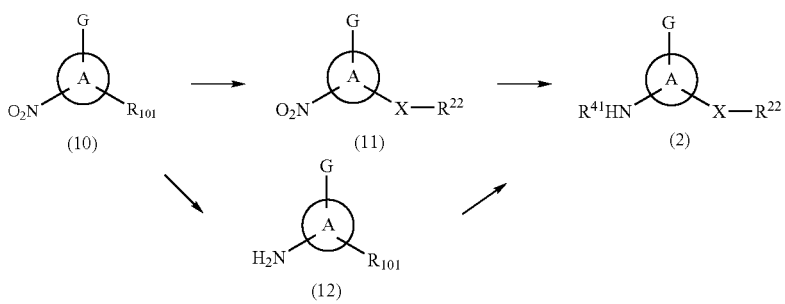

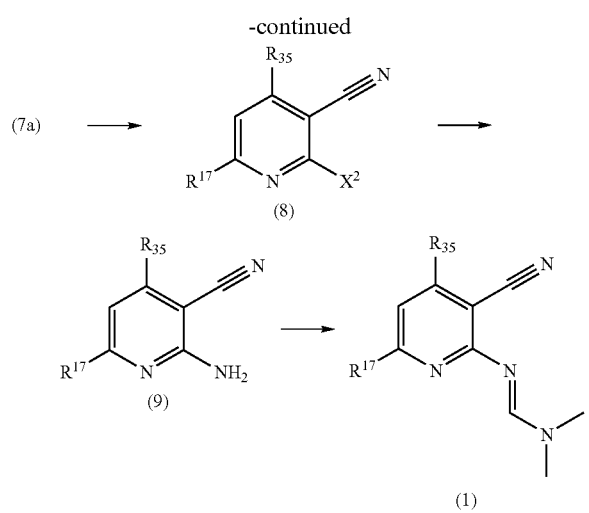

Compounds of formula (2) wherein $R^{41}$ is hydrogen and X is O or S, can be prepared from compounds of formula (10) according to Scheme 11, wherein $R_{101}$ is a leaving group such as, but not limited to, halogen, triflate or mesylate (the latter two can be prepared from the corresponding alcohol using methodologies known to one skilled in the art), via a two-step synthesis, namely, reduction of the nitro group followed by displacement of $R_{101}$, or displacement of $R_{101}$ followed by reduction of the nitro group.

Displacement of $R_{101}$ with $R^{22}XH$ wherein X is O or S can be facilitated in the presence of a suitable base such as, but not limited to, potassium, cesium or sodium carbonate or bicarbonate, or sodium or potassium hydride, and optionally in the presence of 18-crown-6, at elevated temperature. The reaction can generally be performed in a solvent such as, but not limited to, N,N-dimethylformamide or dimethylsulfoxide, at a temperature from about room temperature to about 180° C. The reaction can generally be performed in a solvent such as, but not limited to, N,N-dimethylformamide or dimethylsulfoxide, at a temperature from about room temperature to about 180° C. The reaction can also be conducted in a microwave oven. It is appreciated compounds of formula (11) can also be obtained from the reaction of formula (10) wherein Rio, is —X—H with compounds of formula $R^{22}X^3$ wherein $X^3$ is a leaving group such as, but not limited to, halogen, triflate or mesylate, using the aforementioned reaction conditions. The displacement reactions can also be effected in the presence of a metal catalyst such as, but not limited to, copper metal, CuI, or palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, pyridine, triethylamine, sodium tert-butoxide, cesium carbonate, or sodium hydride. The reaction is generally performed at a temperature from about room temperature to about 180° C., in a solvent such as, but not limited to, toluene or N,N-dimethylformamide.

Reduction of the nitro group can be accomplished by treatment of nitro compound with a reducing agent such as, but not limited to, iron powder/ammonium chloride or tin(II) chloride, in a suitable solvent.

It is also appreciated that compounds of formula (10) can also be converted to compounds of formula (2) by first reducing the nitro functionality, followed by the displacement reaction, using reaction conditions as described hereinabove.

Scheme 12

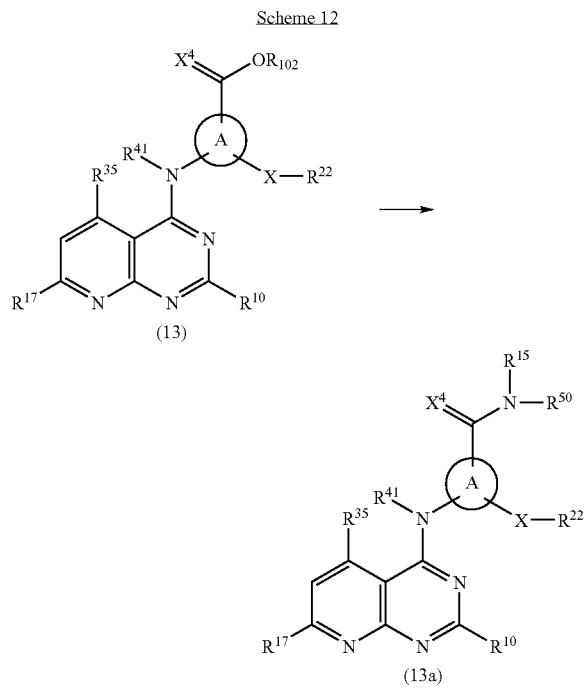

Scheme 12 illustrates the preparation of compounds of Formula I wherein $W_4$ is CH, $W_1$, $W_2$ and $W_3$ are N, Z is $NR^{41}$ and Y is —C(O)N($R^{15}$) or C(S)N($R^{15}$).

Acids of formula (13) wherein $X^4$ is oxygen and $R_{102}$ is hydrogen, obtained from hydrolysis or hydrogenation of the corresponding alkyl or benzyl esters, can be transformed to compounds of formula (13a). This can be accomplished by coupling with an appropriate amine. Standard coupling reaction conditions are known to one skilled in the art. One such conditions is to first convert the acid to an activated ester, for example, by treating the acid with N-hydroxyl succinamide, N-(3-dimethylaminopropyl)-N'-ethylcarbodiimide hydrochloride, or TBTU, and a base such as, but not limited to, N-methyl morpholine or diisopropylethyl amine, in a solvent such as, but not limited to, dichloromethane or dimethyl sulfoxide, and without isolation, followed by treatment of the activated ester with amines of formula N(H)($R^w$)($R^3$) or of formula $NR^{15}R^{50}H$. Such procedures can also be made on compounds of formula (2) before reacting with compounds of formula (1) in Scheme 9.

Conversion of compounds of formulas (13) or (13a) wherein $X^4$ is O to formulas (13) or (13a) wherein $X^4$ is S can be achieved by treatment with Lawesson reagent.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Reactions may be worked up in the convention manner, e.g. by eliminating the solvent from the residue and further purified according to methodologies generally known in the art such as, but not limited to, crystallization, distillation, extraction, trituration and chromatography.

It should be understood that the above-described embodiments and schemes and the following examples are given by way of illustration, not limitation. Various changes and modifications within the scope of the present invention will become apparent to those skilled in the art from the present description.

Example 1

N-(4-Fluoro-3-methyl-phenyl)-3-(7-isopropyl-pyrido[2,3-d]pyrimidin-4-ylamino)-4-(4-methoxy-phenyl-sulfanyl)-benzamide The product from Example 137B was reacted with 4-fluoro-3-methylaniline according to the procedure from Example 137C substituting 4-fluoro-3-methylaniline for 5-amino-o-cresol to provide the title compound as an off white solid after trituration of the reaction product from methanol (61 mg, 68%). 1H NMR (300 MHz, DMSO-D6) δ ppm 10.21 (s, 1 H), 10.19 (s, 1 H), 8.86 (d, J=8.46 Hz, 1 H), 8.59 (s, 1 H), 7.98 (s, 1 H), 7.80 (dd, J=8.46, 1.47 Hz, 1 H), 7.62-7.68 (m, 2 H), 7.52-7.59 (m, 1 H), 7.40 (d, J=8.82 Hz, 2 H), 7.11 (t, J=9.19 Hz, 1 H), 6.96-7.04 (m, J=8.92 Hz, 3 H), 3.77 (s, 3 H), 3.17-3.29 (m, 1 H), 2.22 (d, J=1.47 Hz, 3 H), 1.34 (d, J=6.99 Hz, 6 H); MS (ESI$^+$) m/z 554.2 (M+H)$^+$, (ESI$^-$) m/z 552.2 (M−H)$^-$.

Example 2

N-(4-Fluoro-3-methyl-phenyl)-4-(4-hydroxy-phenyl-sulfanyl)-3-(7-isopropyl-pyrido[2,3-d]pyrimidin-4-ylamino)-benzamide The product from Example 1 was reacted according to the procedure from Example 150 substituting the product from Example 1 for the product from Example 138 to provide a residue which was purified by trituration from methanol to provide the title compound as an off white solid (9.6 mg, 20%). 1H NMR (300 MHz, DMSO-D6) δ ppm: 10.20 (s, 1 H), 10.15 (s, 1 H), 9.95 (s, 1 H), 8.84 (s, 1 H), 8.57 (s, 1 H), 7.95 (s, 1 H), 7.71-7.87 (m, 1 H), 7.65 (dd, J=7.71, 2.39 Hz, 1 H), 7.61 (s, 1 H), 7.52-7.59 (m, 1 H), 7.31 (d, J=8.46 Hz, 2 H), 7.10 (t, J=9.19 Hz, 1 H), 6.91 (s, 1 H), 6.85 (d, J=8.82 Hz, 2 H), 3.19-3.27 (m, J=0.74 Hz, 1 H), 2.22 (s, 3 H), 1.33 (d, J=6.99 Hz, 6 H); MS (ESI$^+$) m/z 540.2 (M+H)$^+$, (ESI$^-$) m/z 538.2 (M−H)$^-$.

Example 3

3-(7-Isopropyl-pyrido[2,3-d]pyrimidin-4-ylamino)-4-(4-methoxy-phenylsulfanyl)-N-(3-trifluoromethyl-phenyl)-benzamide The product from Example 137B was reacted with 3-(trifluoromethyl)aniline according to the procedure from Example 137C substituting 3-(trifluoromethyl)aniline for 5-amino-o-cresol to provide the title compound as an off white solid after trituration of the reaction product from methanol (73 mg, 77%). 1H NMR (300 MHz, DMSO-D6) δ ppm: 10.54 (s, 1 H), 8.93 (d, J=8.46 Hz, 1 H), 8.67 (s, 1 H), 8.22 (s, 1 H), 8.04 (d, J=8.09 Hz, 1 H), 7.99 (s, 1 H), 7.85 (d, J=7.72 Hz, 1 H), 7.74 (d, J=8.46 Hz, 1 H), 7.59 (t, J=8.09 Hz, 1 H), 7.45 (d, J=8.46 Hz, 1 H), 7.41 (d, J=8.82 Hz, 2 H), 6.92-7.11 (m, 4 H), 3.77 (s, 3 H), 3.20-3.31 (m, 1 H), 1.35 (d, J=6.62 Hz, 6 H); MS (ESI+) m/z 590.3 (M+H)+, (ESI−) m/z 588.1 (M−H)−.

Example 4

4-(4-Hydroxy-phenylsulfanyl)-3-(7-isopropyl-pyrido[2,3-d]pyrimidin-4-ylamino)-N-(3-trifluoromethyl-phenyl)-benzamide The product from Example 3 was reacted according to the procedure from Example 150 substituting the product from Example 3 for the product from Example 138 to provide a residue which was purified by trituration from methanol to provide the title compound as an off white solid (16.7 mg, 28%). 1H NMR (300 MHz, DMSO-D6) δ ppm: 10.48 (s, 1 H), 10.21 (s, 1 H), 9.97 (s, 1 H), 8.88 (d, J=9.19 Hz, 1 H), 8.59 (s, 1 H), 8.21 (s, 1 H), 7.95-8.10 (m, 2 H), 7.83 (d, J=8.46 Hz, 1 H), 7.62-7.69 (m, J=6.80, 2.39 Hz, 1 H), 7.59 (t, J=8.09 Hz, 1 H), 7.44 (d, J=7.35 Hz, 1 H), 7.32 (d, J=8.46 Hz, 2 H), 6.90-6.99 (m, 1 H), 6.86 (d, J=8.46 Hz, 2 H), 3.20-3.29 (m, 1 H), 1.34 (d, J=6.99 Hz, 6 H); MS (ESI+) m/z 576.2 (M+H)+, (ESI−) m/z 574.2 (M−H)−.

Example 5

3-(7-Isopropyl-pyrido[2,3-d]pyrimidin-4-ylamino)-4-(4-methoxy-phenylsulfanyl)-N-(4-trifluoromethyl-phenyl)-benzamide The product from Example 137B was reacted with 4-(trifluoromethyl)aniline according to the procedure from Example 137C substituting 4-(trifluoromethyl)aniline for 5-amino-o-cresol to provide the title compound as an off white solid after trituration of the reaction product from methanol (62 mg, 65%). 1H NMR (300 MHz, DMSO-D6) δ ppm: 10.86 (s, 1 H), 10.56 (s, 1 H), 8.92 (d, J=6.99 Hz, 1 H), 8.66 (s, 1 H), 7.99 (d, J=8.46 Hz, 2 H), 7.84 (d, J=7.72 Hz, 1 H), 7.58-7.78 (m, 3 H), 7.36-7.50 (m, 2 H), 7.23-7.36 (m, 1 H), 6.86-7.14 (m, 3 H), 3.77 (s, 3 H), 3.20-3.29 (m, 1 H), 1.35 (d, J=6.62 Hz, 6 H); MS (ESI+) m/z 590.6 (M+H)+, (ESI−) m/z 588.2 (M−H)−.

Example 6

4-(4-Hydroxy-phenylsulfanyl)-3-(7-isopropyl-pyrido[2,3-d]pyrimidin-4-ylamino)-N-(4-trifluoromethyl-phenyl)-benzamide The product from Example 5 was reacted according to the procedure from Example 150 substituting the product from Example 5 for the product from Example 138 to provide a residue which was purified by trituration from methanol to provide the title compound as an off white solid (7.7 mg, 16%). 1H NMR (300 MHz, DMSO-D6) δ ppm 9.15 (d, J=8.82 Hz, 1 H), 9.01 (s, 1 H), 7.93-8.10 (m, 5 H), 7.71 (d, J=8.82 Hz, 2 H), 7.34 (d, J=8.46 Hz, 2 H), 7.10 (d, J=8.46 Hz, 1 H), 6.83-6.90 (m, 2 H), 3.27-3.44 (m, 1 H), 1.40 (d, J=6.99 Hz, 6 H) [added one drop TFA to NMR tube to sharpen resolution—therefore no NH or OH peaks]; MS (ESI+) m/z 576.2 (M+H)+, (ESI−) m/z 574.2 (M−H)−.

Example 7

N-(3-Dimethylamino-phenyl)-3-(7-isopropyl-pyrido[2,3-d]pyrimidin-4-ylamino)-4-(4-methoxy-phenyl-sulfanyl)-benzamide The product from Example 137B was reacted with N,N-dimethyl-1,3-phenylenediamine according to the procedure from Example 137C substituting N,N-dimethyl-1,3-phenylenediamine for 5-amino-o-cresol to provide the title compound as an off white solid after trituration of the reaction product from methanol (53 mg, 58%). 1H NMR (300 MHz, DMSO-D6) δ ppm 10.33 (s, 1 H), 9.99 (s, 1 H), 8.87 (s, 1 H), 8.61 (s, 1 H), 7.98 (s, 1 H), 7.80 (s, 1 H), 7.65 (d, J=6.62 Hz, 1 H), 7.40 (d, J=8.82 Hz, 2 H), 7.09-7.19 (m, 3 H), 6.94-7.05 (m, 3 H), 6.41-6.53 (m, 1 H), 3.77 (s, 3 H), 3.18-3.30 (m, 1 H), 2.88 (s, 6 H), 1.34 (d, J=6.99 Hz, 6 H); MS (ESI+) m/z 565.3 (M+H)+, (ESI−) m/z 563.3 (M−H)−.

Example 8

3-[4-(4-Hydroxy-phenylsulfanyl)-3-(7-isopropyl-pyrido[2,3-d]pyrimidin-4-ylamino)-phenoxymethyl]-benzonitrile

Example 8A

4-Methyl-3-oxo-pentanal, sodium salt

A flame-dried 100-mL flask equipped with a 25-mL addition funnel was purged with nitrogen gas and charged with anhydrous diethyl ether (40 mL) followed by the addition of sodium slivers (1.65 g, 0.0725 mol). The reaction mixture was cooled to ice/water bath temperature and a solution of methyl isopropyl ketone (6.244 g, 0.0725 mol) and ethyl formate (5.481 g, 0.0725 mol) in anhydrous diethyl ether (5 mL) was added slowly dropwise over 1.5 hours, at 0° C. After the addition was complete the cooling bath was removed and the reaction mixture stirred at room temperature overnight. Additional ether (10 mL) was then added to break up the resulting precipitate, and the solid was isolated quickly by vacuum filtration. The solid was rinsed with small amounts of ether and then dried in a vacuum desiccator for one hour to provide the title product as an off-white solid (5.35 g, 54% yield). This material was used in the next step without further purification.

Example 8B

6-Isopropyl-2-oxo1,2-dihydro-pyridine-3-carbonitrile

To a solution of the product of Example 8A (5.35 g, 0.0393 mol) and 2-cyanoacetamide (3.47 g, 0.0413 mol) in water (35 mL) was stirred at room temperature for 10 minutes. To this mixture was added 2.5 mL of a stock piperidine acetate solution (prepared from 9.8 mL of piperidine, 6 mL of acetic acid and 10 mL of water), and the solution was heated under reflux for 2 hours. The mixture was then cooled to room temperature and taken to pH 4 by the addition of glacial acetic acid. The resulting light yellow solid was isolated by vacuum filtration, rinsed with water (2×30 mL), and dried under vacuum to provide the title product (4.36 g, 68%).

Example 8C

2-Bromo-6-isopropyl-nicotinonitrile

To a solution of the product of Example 8B (4.35 g, 0.0269 mol), tertrabutylammonium bromide (10.4 g, 0.0323 mol) and phosphorous pentoxide (8.01 g, 1.05 mol) in toluene (80 mL) was heated under reflux for 5 hours. The reaction mixture was then cooled to room temperature, water (80 mL) was added, and the mixture was stirred for 2 h at room temperature. The reaction mixture was diluted with toluene (20 mL) and the organic layer separated. The aqueous layer was washed with toluene (50 mL) and the combined organic layers were washed with brine (50 mL), dried over anhydrous magnesium sulfate, filtered, and concentrated under vacuum to provide the title product as a yellow oil (5.64 g, 93%).

Example 8D

2-Amino-6-isopropyl-nicotinonitrile

To a solution of the product of Example 8C (21 g, 0.093 mol) and liquid ammonia (250 mL) in 500 mL of ethanol were reacted in a sealed high-pressure vessel at 130° C. for 20 hours. The reaction mixture was concentrated under vacuum and the residue ground to a fine powder then washed with water (2×50 mL) and dried in a vacuum oven for 24 hours to provide the title compound as a beige solid (14 g, 93%).

Example 8E

N'-(3-Cyano-6-isopropyl-pyridin-2-yl)-N-N-dimethyl-formamidine

To a solution of the product of Example 8D (7.1 g, 0.044 mol) and N,N-Dimethylformamide dimethyl acetal (6.44 mL, 0.0484 mol) in toluene (100 mL) was heated at reflux for 3 hours. The resulting solution was cooled to room temperature and concentrated under vacuum to provide the title compound (9.5 g, 100%) as a thick brown oil that solidified upon standing. Although this material appears to be pure by NMR, it contains small amounts of highly colored impurities. It can be chromatographed on silica gel (ethyl acetate/hexane gradient) to provide a slightly yellow oil that solidifies upon standing (about 70% recovery from chromatography).

Example 8F 3-(4-Chloro-3-nitro-phenoxymethyl)-benzonitrile

The title compound was prepared according to the procedure of Example 9C substituting 3-bromomethyl-benzonitrile for 1-chloromethyl-4-methoxy-benzene (0.813 g, 98%).

Example 8G

3-[4-(4-Hydroxy-phenylsulfanyl)-3-nitro-phenoxymethyl]-benzonitrile

The title compound was prepared according to the procedure of Example 9D substituting 3-(4-Chloro-3-nitro-phenoxymethyl)-benzonitrile for 1-Chloro-4-(4-methoxy-benzyloxy)-2-nitro-benzene (1.07 g, 100%).

Example 8H

3-[3-Amino-4-(4-hydroxy-phenylsulfanyl)-phenoxymethyl]-benzonitrile

The title compound was prepared according to the procedure of Example 9E substituting 3-[4-(4-Hydroxy-phenylsulfanyl)-3-nitro-phenoxymethyl]-benzonitrile for 4-[4-(4-Methoxy-benzyloxy)-2-nitro-phenylsulfanyl]-phenol (0.97 g, 98%).

Example 8I

3-[4-(4-Hydroxy-phenylsulfanyl)-3-(7-isopropyl-pyrido[2,3-d]pyrimidin-4-ylamino)-phenoxymethyl]-benzonitrile A solution of the product of Example 8E (47.4 mg, 0.219 mmol), and the product of Example 8H (76.3 mg, 0.219 mmol) in acetic acid (1 mL) was stirred in an oil bath preheated to 130° C. for 15 minutes. The mixture was then cooled to room temperature, the acetic acid removed under vacuum, and the resultant residue purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as a trifluoroacetic acid salt (14 mg, 10%). $^1$H NMR (300 MHz, DMSO-$d_6$) δ ppm: 10.94 (s, 1 H), 9.69 (s, 1 H), 8.88 (d, J=8.46 Hz, 1 H), 8.70 (s, 1 H), 7.92 (s, 1 H), 7.72-7.87 (m, 3 H), 7.62 (t, J=7.72 Hz, 1 H), 7.15-7.28 (m, J=8.82 Hz, 2 H), 7.08-7.15 (m, 2 H), 6.99-7.06 (m, 1 H), 6.61-6.72 (m, 2 H), 5.18 (s, 2 H), 3.19-3.30 (m, 1 H, 1.34 (d, J=6.99 Hz, 6 H); MS(ESI) m/z 520.3 (M+H)+, (ESI−) m/z 518.3 (M−H)−.

Example 9

4-[4-(4-Methoxy-benzyloxy)-2-(7-methyl-pyrido[2,3-d]pyrimidin-4-ylamino)-phenylsulfanyl]-phenol

Example 9A

2-Amino-6-methyl-nicotinonitrile

2-Chloro-6-methyl-nicotinonitrile (25 g, 0.164 mol) and liquid ammonia (250 mL) in 500 mL of ethanol were reacted in a sealed high-pressure vessel at 130° C. for 20 hours. The reaction mixture was concentrated under vacuum and the residue washed with water (2×50 mL) then dried in a vacuum oven for 24 hours to provide the title compound as a light yellow solid (18 g, 82%). $^1$H NMR (300 MHz, DMSO-$d_6$) δ ppm: 2.30 (s, 3H), 6.52 (d, J=7.7 Hz, 1H), 6.78 (s, 2H), 7.73 (d, J=7.7 Hz, 1H).

Example 9B

N'-(3-Cyano-6-methyl-pyridin-2-yl)-N,N-dimethyl-formamidine

A solution of the product of Example 9A (10 g, 75.19 mmol) and N,N-Dimethylformamide dimethyl acetal (11 mL, 82.71 mmol) in toluene (100 mL) was heated at reflux for 6 hours. After cooling to room temperature, the solution was concentrated under vacuum to provide the title compound as a yellow solid (13.78 g, 98%). $^1$H NMR (300 MHz, DMSO-$d_6$) δ ppm: 2.41 (s, 3H), 3.06 (s, 3H), 3.14 (s, 3H), 6.87 (d, J=7.7 Hz, 1H), 7.89 (d, J=8.1 Hz, 1H), 8.59 (s, 1H).

Example 9C

1-Chloro-4-(4-methoxy-benzyloxy)-2-nitro-benzene

A solution of 4-chloro-3-nitro-phenol (0.5 g, 2.88 mmol), 1-chloromethyl-4-methoxy-benzene (0.496 g, 3.17 mmol), potassium carbonate (1.19 g, 8.64 mmol) and tetrabutylammonium iodide (0.005 g, 0.0135 mmol) in N,N-dimethylformamide (5 ml) was stirred at room temperature for 16 hours. Afterwards ice water (10 mL) was added to the solution and the resultant solid was collected by filtration and dried in a vacuum oven to provide the title compound (0.812 g, 96%).

Example 9D

4-[4-(4-Methoxy-benzyloxy)-2-nitro-phenylsulfanyl]-phenol

A solution of the product of Example 9C (0.812 g, 2.76 mmol), 4-hydroxythiophenol (0.419, 3.32 mmol) and cesium carbonate (2.16 g, 6.64 mmol) in N,N-dimethylformamide (5 mL) was heated to 100° C. for 16 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over magnesium sulfate, filtered and concentrated under vacuum to provide the title compound (1.06 g, 100%).

Example 9E

4-[2-Amino-4-(4-methoxy-benzyloxy)-phenylsulfanyl]-phenol

A solution of the product of Example 9D (1.06 g, 2.76 mmol), iron powder (0.63 g, 11.04 mmol) and ammonium chloride (0.18 g, 3.31 mmol) in a methanol (18 mL), tetrahydrofuran (18 mL), and water (6 mL) solution was heated to reflux for 3 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over magnesium sulfate, filtered and concentrated under vacuum to provide the title compound (0.99 g, 100%).

Example 9F

4-[4-(4-Methoxy-benzyloxy)-2-(7-methyl-pyrido[2,3-d]pyrimidin-4-ylamino)-phenylsulfanyl]-phenol A solution of the product of Example 9B (28.4 mg, 0.151 mmol), and the product of Example 9E (53.3 mg, 0.151 mmol) in acetic acid (1 mL) was stirred in an oil bath preheated to 130° C. for 20 minutes. The mixture was then cooled to room temperature, the acetic acid removed under vacuum, and the resultant residue triturated with methanol to provide the title compound as a tan solid (26.5 mg, 35%). $^1$H NMR (300 MHz, DMSO-$d_6$) δ ppm: 9.92 (s, 1 H), 9.63 (s, 1 H), 8.70 (d, J=8.09 Hz, 1 H), 8.55 (s, 1 H), 7.52 (d, J=8.46 Hz, 1 H), 7.38 (d, J=8.82 Hz, 2 H), 7.27 (s, 1 H), 7.06-7.18 (m, 3 H), 6.94 (d, J=8.46 Hz, 3 H), 6.61-6.72 (m, 2 H), 5.02 (s, 2 H), 3.75 (s, 3 H), 2.66 (s, 3 H); MS (ESI+) m/z 497.2 (M+H)+, (ESI−) m/z 495.3 (M−H)−.

Example 10

4-(4-Amino-phenoxy)-N-(4-bromo-phenyl)-3-(7-isopropyl-pyrido[2,3-d]pyrimidin-4-ylamino)-benzamide Example 10A N-(4-Bromo-phenyl)-4-chloro-3-nitro-benzamide A mixture of 4-bromoaniline (2.58 g 14.99 mmol) in dry methylene chloride (100 mL) was treated with 4-chloro-3-nitrobenzoyl chloride (3.60 g, 17.99 mmol) and N,N-diisopropylethylamine (3.14 mL, 17.99 mmol), and the resulting mixture stirred at room temperature for 17 hours. The solvent was removed by rotary evaporation in vacuo, the residue taken up in ethyl acetate (100 mL) and washed with water (2×50 mL) and brine. Dried the organic extract over anhydrous sodium sulfate, filtered, and concentrated in vacuo to give the product as a tan solid (5.132 g, 14.45 mmol, 96%)

Example 10B

{4-[4-(4-Bromo-phenylcarbamoyl)-2-nitro-phenoxy]phenyl}-carbamic acid tert-butyl ester A solution of the product of Example 10A (5.132 g, 14.45 mmol) in anhydrous N,N-dimethylformamide (50 mL) was treated with N-Boc-4-hydroxyaniline (3.024 g, 14.45 mmol) and potassium carbonate (3.994 g, 28.90 mmol) at room temperature, then heated at 80° under a nitrogen atmosphere for 4.5 hours. The reaction was cooled to room temperature and the solvent removed by rotary evaporation in vacuo. The residue was taken up in ethyl acetate (200 mL) and washed with water (4×50 mL) and brine (50 mL). The organic layer was dried over anhydrous sodium sulfate, filtered, and concentrated by rotary evaporation to give the product as a dark yellow solid (7.38 g, 13.97 mmol, 97%).

Example 10C

{4-[2-Amino-4-(4-bromo-phenylcarbamoyl)-phenoxy]-phenyl}-carbamic acid tert-butyl ester A solution of the product of Example 10B (7.383 g, 13.97 mmol), iron powder (4.80 g, 85.94 mmol) and ammonium chloride (4.896 g, 91.53 mmol) in ethanol (60 mL), tetrahydrofuran (60 mL), and water (30 mL) was heated at 80° for 1.5 hours. After cooling to room temperature, the mixture was diluted with ethyl acetate (300 mL) and washed with water (4×100 mL) and brine (50 mL). The organic phase was dried over sodium sulfate, filtered and concentrated under vacuum to provide the title compound as a light tan solid (6.658 g, 13.36 mmol, 96%).

Example 10D

{4-[4-(4-Bromo-phenylcarbamoyl)-2-(7-isopropyl-pyrido[2,3-d]pyrimidin-4-ylamino)-phenoxy]-phenyl}-carbamic acid tert-butyl ester A solution of the product of Example 8E (2.89 g, 13.36 mmol) and the product of Example 10C (6.658 g, 13.36 mmol) in acetic acid (50 mL) was stirred in an oil bath preheated to 140° C. for 20 minutes. The reaction was cooled to room temperature, diluted with hexanes (250 mL), concentrated by rotary evaporation, and co-evaporated with methylene chloride/hexanes (4×). The residue was dried on hi-vacuum overnight. The residue was purified by silica gel flash chromatography with 30% ethyl acetate/methylene chloride followed by methanol/methylene chloride to give the title compound as a brown solid (6.48 g, 72%).

Example 10E 4-(4-Amino-phenoxy)-N-(4-bromo-phenyl)-3-(7-isopropyl-pyrido[2,3-d]pyrimidin-4-ylamino)-benzamide The product of Example 10D (2.78 g, 4.152 mmol) was treated with trifluoroacetic acid (25 mL) in methylene chloride (25 mL) at room temperature for 30 minutes. The solvents were removed under vacuum by rotary evaporation and the residual oil taken up in ethyl acetate (400 mL) and washed with saturated aqueous sodium bicarbonate (2×100 mL), water (2×100 mL), and brine (100 mL). The organic phase was dried over anhydrous sodium sulfate, filtered, and concentrated in vacuo. The resulting solid was triturated with 3% methanol/methylene chloride and dried in vacuo to afford the title compound as a light beige solid (1.77 g, 75%). $^1$H NMR (300 MHz, DMSO-D6) δ ppm 1.32 (d, J=6.99 Hz, 6 H) 3.09-3.31 (m, 1 H) 5.03 (s, 2 H) 6.57 (d, J=8.82 Hz, 2 H) 6.78 (d, J=8.82 Hz, 2 H) 6.83 (d, J=8.82 Hz, 1 H) 7.53 (d, J=8.82 Hz, 2 H) 7.60 (d, J=8.82 Hz, 1 H) 7.75 (d, J=9.19 Hz, 2 H) 7.85 (dd, J=8.46, 2.21 Hz, 1 H) 8.16 (d, J=2.21 Hz, 1 H) 8.62 (s, 1 H) 8.84 (d, J=8.46 Hz, 1 H) 10.00 (s, 1 H) 10.29 (s, 1 H); MS (ESI+) m/z 569/571 (M+H)$^+$, MS (ESI−) m/z 567/569 (M−H)$^-$.

Example 11

4-(4-Amino-phenoxy)-N-(5-bromo-pyridin-2-yl)-3-(7-isopropyl-pyrido[2,3-d]pyrimidin-4-ylamino)-benzamide

Example 11A

{4-[2-Amino-4-(5-bromo-pyridin-2-ylcarbamoyl)-phenoxy]-phenyl}-carbamic acid tert-butyl ester A mixture of 4-chloro-3-nitrobenzoyl chloride was reacted with 5-Bromo-pyridin-2-ylamine to produce N-(4-Bromo-phenyl)-4-chloro-3-nitro-benzamide according to the procedure of Example 10A, which was treated sequentially using the procedures from Examples 10B and 10C to provide the title product.

Example 11B 4-(4-Amino-phenoxy)-N-(5-bromo-pyridin-2-yl)-3-(7-isopropyl-pyrido[2,3-d]pyrimidin-4-ylamino)-benzamide The product of Example 11A was reacted with the product of Example 8E using the procedure of Example 10D substituting the product of Example 11A for the product of Example 10C to provide {4-[4-(5-Bromo-pyridin-2-ylcarbamoyl)-2-(7-isopropyl-pyrido[2,3-d]pyrimidin-4-ylamino)-phenoxy]-phenyl}-carbamic acid tert-butyl ester which was reacted using the procedure of Example 10E to provide the crude title compound which was purified by column chromatography on silica gel using methanol/dichloromethane as eluent to provide the title compound (74 mg, 53%). $^1$H NMR (300 MHz, DMSO-D6) δ ppm 1.32 (d, J=6.99 Hz, 6 H) 3.13-3.30 (m, 1 H) 5.04 (s, 2 H) 6.57 (d, J=8.82 Hz, 2 H) 6.80 (d, J=8.83 Hz, 2 H) 6.78 (d, J=8.45 Hz, 1 H) 7.60 (d, J=8.46 Hz, 1 H) 7.95 (dd, J=8.64, 2.39 Hz, 1 H) 8.06 (dd, J=8.82, 2.57 Hz, 1 H) 8.18 (d, J=8.82 Hz, 1 H) 8.25 (d, J=1.84 Hz, 1 H) 8.50 (d, J=2.57 Hz, 1 H) 8.62 (s, 1 H) 8.85 (d, J=8.46 Hz, 1 H) 9.97 (s, 1 H) 10.90 (s, 1 H); MS (ESI+) m/z 570/572 (M+H)+, (ESI−) m/z 568/570 (M−H)−.

Example 12

4-(4-Amino-phenoxy)-N-(5-bromo-thiazol-2-yl)-3-(7-isopropyl-pyrido[2,3-d]pyrimidin-4-ylamino)-benzamide

Example 12A

{4-[2-Amino-4-(5-bromo-thiazol-2-ylcarbamoyl)-phenoxy]-phenyl}-carbamic acid tert-butyl ester A mixture of 4-chloro-3-nitrobenzoyl chloride was reacted with 5-Bromo-thiazol-2-ylamine to produce N-(5-Bromo-thiazol-2-yl)-4-chloro-3-nitro-benzamide according to the procedure of Example 10A, which was treated sequentially using the procedures from Examples 10B and 10C to provide the title product.

Example 12B 4-(4-Amino-phenoxy)-N-(5-bromo-thiazol-2-yl)-3-(7-isopropyl-pyrido[2,3-d]pyrimidin-4-ylamino)-benzamide The product of Example 12A was reacted with the product of Example 8E using the procedure of Example 10D substituting the product of Example 12A for the product of Example 10C to provide {4-[4-(5-Bromo-thiazol-2-ylcarbamoyl)-2-(7-isopropyl-pyrido[2,3-d]pyrimidin-4-ylamino)-phenoxy]-phenyl}-carbamic acid tert-butyl ester which was reacted using the procedure of Example 10E to provide the crude title compound which was purified by column chromatography on silica gel using methanol/dichloromethane as eluent to provide the title compound (110 mg, 72%). 1H NMR (300 MHz, DMSO-D6) δ ppm 1.32 (d, J=6.99 Hz, 6 H) 3.13-3.28 (m, 1 H) 5.06 (s, 2 H) 6.58 (d, J=8.82 Hz, 2 H) 6.79 (d, J=8.82 Hz, 2 H) 6.80 (d, J=8.45 Hz, 1 H) 7.61 (d, J=8.46 Hz, 1 H) 7.64 (s, 1 H) 8.01 (dd, J=8.82, 2.21 Hz, 1 H) 8.34 (d, J=2.21 Hz, 1 H) 8.64 (s, 1 H) 8.85 (d, J=8.46 Hz, 1 H) 9.98 (s, 1 H) 12.83 (s, 1 H); MS (ESI+) m/z 576/578 (M+H)+.

Example 13

4-(4-Amino-phenylsulfanyl)-N-(4-bromo-phenyl)-3-(7-isopropyl-pyrido[2,3-d]pyrimidin-4-ylamino)-benzamide

Example 13A 4-(4-Amino-phenylsulfanyl)-N-(4-bromo-phenyl)-3-nitro-benzamide

A mixture of the product of Example 10A (1.00 g, 2.816 mmol), 4-aminothiophenol (529 mg, 4.224 mmol) and anhydrous sodium acetate (1.155 g, 14.08 mmol) in anhydrous ethanol (30 mL) was heated at reflux under a nitrogen atmosphere for 19 hours. The reaction was cooled to room temperature and the ethanol removed by rotary evaporation. The residue was taken up in water (50 mL) and extracted with ethyl acetate (2×100 mL). The combined organic extracts were washed with brine (50 mL), dried over anhydrous sodium sulfate, filtered, and concentrated in vacuo. Trituration of the solid with 4% ethyl acetate/methylene chloride (25 mL) afforded the title compound as a yellow solid (1.091 g, 87%).

Example 13B

{4-[4-(4-Bromo-phenylcarbamoyl)-2-nitro-phenylsulfanyl]-phenyl}-carbamic acid tert-butyl ester A mixture of the product of Example 13A (1.091 g, 2.456 mmol) and di-tert-butyl dicarbonate (804 mg, 3.683 mmol) in 1,4-dioxane (16 mL) was heated at reflux under a nitrogen atmosphere for 5.5 hours, at which time additional Boc anhydride (750 mg) was added and the reaction allowed to reflux an additional 15 hours. The reaction was cooled to room temperature and the solvent removed by rotary evaporation in vacuo. The resulting solid was triturated with 2.5% ethyl acetate/methylene chloride to obtain the title compound as an orange solid (1.198 g, 90%).

Example 13C

{4-[2-Amino-4-(4-bromo-phenylcarbamoyl)-phenylsulfanyl]-phenyl}-carbamic acid tert-butyl ester A suspension of the product of Example 13B (1.198 g, 2.20 mmol), iron powder (756 mg, 13.53 mmol), and ammonium chloride (771 mg, 14.41 mmol) in water (15 mL) and ethanol (30 mL) was heated at 90° for 1 hour. The reaction was cooled to room temperature. The mixture was diluted with ethyl acetate (200 mL) and washed with water (2×50 mL) and brine (50 mL). The organic phase was dried over sodium sulfate, filtered, and concentrated under vacuum to provide the title compound as a light yellow solid (1.08 g, 95%).

Example 13D

{4-[4-(4-Bromo-phenylcarbamoyl)-2-(7-isopropyl-pyrido[2,3-d]pyrimidin-4-ylamino)-phenylsulfanyl]-phenyl}-carbamic acid tert-butyl ester A solution of the product of Example 8E (109 mg, 0.504 mmol) and the product of Example 13C (200 mg, 0.389 mmol) in acetic acid (10 mL) was stirred in an oil bath preheated to 140° C. for 15 minutes. The reaction was cooled to room temperature, diluted with hexanes (100 mL), concentrated by rotary evaporation, and co-evaporated with methylene chloride/hexanes (4×). The residue was dried on hi-vacuum. The residue was purified by silica gel flash chromatography with 20% ethyl acetate/methylene chloride followed by 4% methanol/methylene chloride to give the title compound (108 mg, 40%).

Example 13E 4-(4-Amino-phenylsulfanyl)-N-(4-bromo-phenyl)-3-(7-isopropyl-pyrido[2,3-d]pyrimidin-4-ylamino)-benzamide The product of Example 13D (106 mg, 0.1546 mmol) was treated with trifluoroacetic acid (3 mL) in methylene chloride (3 mL) at room temperature for 30 minutes. The solvents were removed by rotary evaporation and the residual oil taken up in ethyl acetate (75 mL) and washed with saturated aqueous sodium bicarbonate (50 mL), water, and brine. The organic phase was dried over anhydrous sodium sulfate, filtered, and concentrated in vacuo. Purification by silica gel flash chromatography with 5% methanol/methylene chloride provided the title compound as a light yellow solid (55 mg, 61%). $^1$H NMR (300 MHz, DMSO-D6) δ ppm: 1.34 (d, J=6.99 Hz, 6 H) 3.13-3.31 (m, 1 H) 5.60 (s, 2 H) 6.63 (d, J=8.82 Hz, 2 H) 6.88 (d, J=8.46 Hz, 1 H) 7.14 (d, J=8.46 Hz, 2 H) 7.52 (d, J=8.82 Hz, 2 H) 7.64 (d, J=8.46 Hz, 1 H) 7.73 (d, J=8.82 Hz, 2 H) 7.78 (dd, J=8.27, 1.65 Hz, 1 H) 7.94 (d, J=1.47 Hz, 1 H) 8.59 (s, 1 H) 8.88 (d, J=8.82 Hz, 1 H) 10.16 (s, 1 H) 10.28 (s, 1 H); MS (ESI+) m/z 585/587 (M+H)$^+$, MS (ESI−) m/z 583/585 (M−H)$^-$.

Example 14

4-(4-Amino-phenylsulfanyl)-N-(4-bromo-phenyl)-3-(7-methyl-pyrido[2,3-d]pyrimidin-4-ylamino)-benzamide The product of Example 13C was reacted with the product of Example 9B using the procedure of Example 13D substituting the product of Example 9B for the product of Example 8E to provide {4-[4-(4-Bromo-phenylcarbamoyl)-2-(7-methyl-pyrido[2,3-d]pyrimidin-4-ylamino)-phenylsulfanyl]-phenyl}-carbamic acid tert-butyl ester which was reacted using the procedure of Example 13E to provide the crude title compound which was purified by HPLC using ammonium acetate to provide the title product (22 mg, 36%). 1H NMR (300 MHz, DMSO-D6) δ ppm: 2.68 (s, 3 H) 5.59 (s, 2 H) 6.63 (d, J=8.82 Hz, 2 H) 6.87 (d, J=6.62 Hz, 1 H) 7.14 (br d, J=8.46 Hz, 2 H) 7.46-7.61 (br m, 1 H) 7.52 (d, J=8.82 Hz, 2 H) 7.69-7.86 (br m, 1 H) 7.73 (d, J=9.19 Hz, 2 H) 7.94 (br m, 1 H) 8.58 (br s, 1 H) 8.82 (br s, 1 H) 10.15 (br s, 1 H) 10.26 (br s, 1 H).

Example 15

{4-[4-(5-Bromo-thiazol-2-ylcarbamoyl)-2-(7-isopropyl-pyrido[2,3-d]pyrimidin-4-ylamino)-phenylsulfanyl]-phenyl}-carbamic acid tert-butyl ester Example 15A {4-[2-Amino-4-(5-bromo-thiazol-2-ylcarbamoyl)-phenylsulfanyl]-phenyl}-carbamic acid tert-butyl ester A mixture of 4-chloro-3-nitrobenzoyl chloride was reacted with 5-Bromo-thiazol-2-ylamine to produce N-(5-Bromo-thiazol-2-yl)-4-chloro-3-nitro-benzamide according to the procedure of Example 10A, which was treated sequentially using the procedures from Examples 13A, 13B and 13C to provide the title product.

Example 15B

{4-[4-(5-Bromo-thiazol-2-ylcarbamoyl)-2-(7-isopropyl-pyrido[2,3-d]pyrimidin-4-ylamino)-phenylsulfanyl]-phenyl}-carbamic acid tert-butyl ester The product of Example 15A was reacted with the product of Example 8E using the procedure of Example 13D substituting the product of Example 15A for the product of Example 13C to provide the crude title compound which was purified by column chromatography on silica gel using methanol/dichloromethane as eluent to provide the title compound (50 mg, 25%). $^1$H NMR (300 MHz, DMSO-D6) δ ppm: 1.34 (d, J=6.62 Hz, 6 H) 1.49 (s, 9 H) 3.16-3.30 (m, 1 H) 6.93 (d, J=8.46 Hz, 1 H) 7.40 (m, 3 H) 7.56 (d, J=8.46 Hz, 2 H) 7.61-7.71 (m, 1 H) 7.93 (dd, J=8.46, 1.84 Hz, 1 H) 8.14 (d, J=1.47 Hz, 1 H) 8.59 (s, 1 H) 8.87 (d, J=8.82 Hz, 1 H) 9.64 (s, 1 H) 10.21 (s, 1 H) 12.89 (s, 1 H); MS (ESI+) m/z 692/694 (M+H)+.

Example 16

4-(4-Amino-phenylsulfanyl)-N-(5-bromo-thiazol-2-yl)-3-(7-isopropyl-pyrido[2,3-d]pyrimidin-4-ylamino)-benzamide The product of Example 15B was reacted with trifluoroacetic acid using the procedure form Example 13E to provide the crude title compound which was purified by column chromatography on silica gel using methanol/dichloromethane as eluent to provide the title compound (120 mg, 76%). 1H NMR (300 MHz, DMSO-D6) δ ppm: 1.34 (d, J=6.99 Hz, 6 H) 3.15-3.30 (m, 1 H) 5.64 (s, 2 H) 6.65 (d, J=8.46 Hz, 2 H) 6.84 (d, J=8.46 Hz, 1 H) 7.15 (d, J=8.46 Hz, 2 H) 7.65 (d, J=8.46 Hz, 1 H) 7.64 (s, 1 H) 7.92 (dd, J=8.46, 1.84 Hz, 1 H) 8.10 (d, J=1.47 Hz, 1 H) 8.59 (s, 1 H) 8.89 (d, J=8.46 Hz, 1 H) 10.14 (s, 1 H) 12.85 (s, 1 H); MS (ESI+) m/z 592/594 (M+H)+.

Example 17

-(4-Amino-phenylsulfanyl)-N-(5-bromo-pyridin-2-yl)-3-(7-isopropyl-pyrido[2,3-d]pyrimidin-4-ylamino)-benzamide

Example 17A

N-(5-Bromo-pyridin-2-yl)-4-chloro-3-nitro-benzamide

A mixture of 4-chloro-3-nitrobenzoyl chloride (22.0 g, 0.1 mol) and 2-amino-5-bromopyridine (17.3 g, 0.1 mol) in toluene (250 mL) was refluxed for 4 hours, allowing gaseous HCl to escape the reaction vessel through an open, water cooled condenser. The reaction mixture was cooled to room temperature, diluted with hexanes (200 mL) and filtered to give the title compound (33.9 g, 95%).

Example 17B

4-(4-Amino-phenylsulfanyl)-N-(5-bromo-pyridin-2-yl)-3-nitro-benzamide

A mixture of the product from Example 17 A (24.2 g, 0.0678 mol), 4-amino-benzenethiol (12.7 g, 0.102 mol, 1.5 eq), and sodium acetate trihydrate (46.1 g, 0.339 mol, 5.0 eq) in 500 mL of ethanol was heated under reflux under nitrogen with stirring for 2 h. The reaction mixture was then allowed to cool to room temperature and 200 mL of water added. The mixture was stirred for 30 min, filtered, and dried in vacuo to give the title compound (29.8 g, 99%).

Example 17C

{4-[4-(5-Bromo-pyridin-2-ylcarbamoyl)-2-nitro-phenylsulfanyl]-phenyl}-carbamic acid 2,2,2-trichloro-ethyl ester A mixture of the product from Example 17B (68.2 g, 0.15 mol) and pyridine (23.7 g, 24 mL, 0.3 mol, 2 eq) in dichloromethane (1.2 L) was stirred at room temperature. To this mixture was added in small portions 9-fluorenylmethoxycarbonyl chloride (42.7 g, 0.165 mol, 1.1 eq) over 1 h. The reaction mixture was stirred at room temperature for 3.5 h, during which time the product precipitated as a yellow solid. The mixture was filtered and the filter cake was rinsed with dichloromethane and dried in vacuo to give the title compound (98.6 g, 98%) as a yellow solid.

Example 17D

{4-[2-Amino-4-(5-bromo-pyridin-2-ylcarbamoyl)-phenylsulfanyl]-phenyl}-carbamic acid 9H-fluoren-9-ylmethyl ester A 5 liter, 3-neck round bottom flask equipped with a water condenser, heating mantle and overhead stirrer was charged with glacial acetic acid (0.75 L) and 200 proof ethanol (0.75 L) followed by addition of the product from Example 17C (40.0 g, 60 mmol) and iron powder (13.3 g, 240 mmol). The mixture was then heated to reflux for 6 hours, cooled to ambient temperature and diluted with 1.0-1.5 L of EtOAc, stirred for 10-15 minutes and diluted with 1.0 L of water. The two-phase mix was stirred vigorously for 5-10 minutes and the layers were allowed to separate. The red aqueous layer was removed and discarded. The remaining EtOAc layer with suspended solids was washed 6×1.0 L with water eventually removing all of the red color. The EtOAc layer was then filtered to collect a cream colored solid which was rinsed with 300 mL EtOAc and dried to constant mass in a vacuum oven (40° C., house vacuum, 24 hours) to give of the title compound (37 g, 97%).

Example 17E

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid 9H-fluoren-9-ylmethyl ester A mixture of the product from Example 17D (23.9 g, 37.4 mmol) and N'-(3-cyano-6-isopropyl-pyridin-2-yl)-N,N-dimethyl-formamidine (9.71 g, 44.9 mmol, 1.2 eq) in 450 mL of glacial acetic acid was heated in an oil bath at 150° C. for 2 h and then cooled to room temperature. The reaction mixture was evaporated in vacuo and the residue was dissolved in approximately 70 mL of dichloromethane. This material was purified by silica gel chromatography using a Biotage Flash 75M cartridge, eluting first with 1:4 ethyl acetate/dichloromethane followed by 98:2 dichloromethane/methanol. The resulting product triturated with dichloromethane and filtered to provide the title compound as a white solid (17.6 g, 58%).

Example 17F

4-(4-Amino-phenylsulfanyl)-N-(5-bromo-pyridin-2-yl)-3-(7-isopropyl-pyrido[2,3-d]pyrimidin-4-ylamino)-benzamide A 3 liter, 3-neck round bottom flask under $N_2$ equipped with an addition funnel and overhead stirrer was charged with the product from Example 17E (32.35 g, 40.0 mmol) and anhydrous tetrahydrofuran (0.5 L). To the yellow solution was added tetrabutylammonium fluoride (1.0 M in THF, 32.0 mL, 32 mmol) at a fast drip rate. After the addition was completed the red, transparent solution was stirred for 3 hours, diluted with 1.0 L of water and 400 mL of EtOAc and stirred vigorously for 5 minutes. The layers were allowed to separate and the aqueous layer was removed and discarded. The organic layer was washed with a second liter of water and again the water was removed. The mix was diluted again with 1 L of water and 400 mL of EtOAc and stirred vigorously for 5 minutes to give an emulsion. The emulsion was broken by adding 50-100 mL of saturated brine and stirring gently. The organic layer was washed 4×1 L with water using brine as necessary to break the emulsions. After the final aqueous wash 400 mL of EtOAc was added and the suspension was stirred for 1 hour and the solid was collected by filtration, rinsed with 400 mL of EtOAc, rinsed with 500 mL of water and dried to constant mass in a vacuum oven (60° C., house vacuum, 24 hours) to give the title compound (22.6 g, 96%) as a cream colored powder.

Example 18

4-(4-Amino-phenylsulfanyl)-N-(4-bromo-3-fluoro-phenyl)-3-(7-isopropyl-pyrido[2,3-d]pyrimidin-4-ylamino)-benzamide Example 18A {4-[2-Amino-4-(4-bromo-3-fluoro-phenylcarbamoyl)-phenylsulfanyl]-phenyl}-carbamic acid tert-butyl ester A mixture of 4-chloro-3-nitrobenzoyl chloride was reacted with 4-Bromo-3-fluoro-phenylamine to produce N-(4-Bromo-3-fluoro-phenyl)-4-chloro-3-nitro-benzamide according to the procedure of Example 10A, which was treated sequentially using the procedures from Examples 13A, 13B and 13C to provide the title product.

Example 18B 4-(4-Amino-phenylsulfanyl)-N-(4-bromo-3-fluoro-phenyl)-3-(7-isopropyl-pyrido[2,3-d]pyrimidin-4-ylamino)-benzamide The product of Example 18A was reacted with the product of Example 8E using the procedure of Example 13D substituting the product of Example 18A for the product of Example 13C to provide {4-[4-(4-Bromo-3-fluoro-phenylcarbamoyl)-2-(7-isopropyl-pyrido[2,3-d]pyrimidin-4-ylamino)-phenylsulfanyl]-phenyl}-carbamic acid tert-butyl ester which was reacted using the procedure of Example 13E to provide the crude title compound which was purified by HPLC using ammonium acetate to provide the title product (8 mg, 7%).

Example 19

4-(4-Amino-phenylsulfanyl)-N-(5-chloro-pyridin-2-yl)-3-(7-isopropyl-pyrido[2,3-d]pyrimidin-4-ylamino)-benzamide Example 19A 4-(4-Amino-phenylsulfanyl)-3-nitro-benzoic acid A solution of 4-chloro-3-nitrobenzoic acid (2.00 g, 10.0 mmol), 4-aminothiophenol (10.0 mmol), and cesium carbonate (6.52 g, 20.0 mmol) in anhydrous N,N-dimethylformamide (10 mL) was heated at 90° C. under a nitrogen atmosphere for 2 hours. The reaction was cooled to room temperature and poured into 50 mL of ice water and ethyl acetate (100 mL). The mixture was stirred while adjusting the pH to 2 with concentrated hydrochloric acid. The layers were separated and the organic phase washed with water (2×50 mL) and brine (50 mL), dried over anhydrous sodium sulfate, filtered, and concentrated by rotary evaporation in vacuo. The residue was co-evaporated with methylene chloride/hexanes and the residue triturated with methylene chloride to provide the title compound as a dark yellow solid (2.115 g, 73%).

Example 19B

4-[4-(9H-Fluoren-9-ylmethoxycarbonylamino)-phenylsulfanyl]-3-nitro-benzoic acid

A suspension of the product of Example 19A (1.00 g, 3.445 mmol) in anhydrous methylene chloride (40 mL) was treated with N,O-bis(trimethylsilyl)acetamide (1.77 mL, 7.234 mmol) dropwise, and the resulting orange-colored solution was stirred at room temperature for 30 minutes under a nitrogen atmosphere. Anhydrous pyridine (0.557 mL, 6.89 mmol) was then added, followed by solid 9-fluorenylmethoxycarbonyl chloride (1.114 g, 4.306 mmol) in three portions. The reaction was stirred for 30 minutes, then poured into water (75 mL) and adjusted the pH to 1 with 1N aqueous hydrochloric acid. After stirring for 15 minutes at room temperature, the mixture was transferred to a separatory funnel and extracted with ethyl acetate (500 mL, followed by 2×150 mL). The combined organic extracts were washed with water (2×50 mL) and brine (50 mL), dried over anhydrous sodium sulfate, filtered, and concentrated by rotary evaporation in vacuo. Trituration with methylene chloride provided the title compound as a yellow solid (1.29 g, 73%).

Example 19C

[4-(4-Chlorocarbonyl-2-nitro-phenylsulfanyl)-phenyl]-carbamic acid 9H-fluoren-9-ylmethyl ester A suspension of the product of Example 19B (500 mg, 0.976 mmol) in anhydrous methylene chloride (10 mL) and tetrahydrofuran (5 mL) was treated with oxalyl chloride (2M in methylene chloride, 0.976 mL, 1.951 mmol) and N,N-dimethylformamide (3 drops), and the resulting solution was stirred under a nitrogen atmosphere for 2 hours at room temperature. The solvent was removed by rotary evaporation in vacuo and the residue dried on hi-vacuum to give the title compound as a yellow solid (0.571 g).

Example 19D

{4-[4-(5-Chloro-pyridin-2-ylcarbamoyl)-2-nitro-phenylsulfanyl]-phenyl}-carbamic acid 9H-fluoren-9-ylmethyl ester A solution of the product of Example 19C (471 mg, 0.861 mmol) in anhydrous tetrahydrofuran (8 mL) was treated with 5-chloro-2-aminopyridine (125 mg, 0.972 mmol) and diisopropylethylamine (0.232 mL, 1.332 mmol), and stirred at room temperature under a nitrogen atmosphere for 18 hours. The solvent was removed by rotary evaporation in vacuo, the residue taken up in ethyl acetate (250 mL) and washed with saturated aqueous sodium bicarbonate (50 mL), water (2×50 mL), and brine (50 mL). The organic phase was dried over anhydrous sodium sulfate, filtered, and concentrated in vacuo. Trituration with methylene chloride provided the title compound as a yellow solid (373 mg, 61%).

Example 19E

{4-[2-Amino-4-(5-chloro-pyridin-2-ylcarbamoyl)-phenylsulfanyl]-phenyl}-carbamic acid 9H-fluoren-9-ylmethyl ester The product of Example 19D (371 mg, 0.5954 mmol), ammonium chloride (208.6 mg, 3.900 mmol), and iron powder (204.5 mg, 3.662 mmol) in a mixture of water (6 mL), ethanol (12 mL) and tetrahydrofuran (12 mL) was heated at 90° under a nitrogen atmosphere for 3 hours. The reaction was cooled to room temperature, diluted with ethyl acetate (200 mL), and washed with water (2×50 mL) and brine (50 mL). The organic was dried over anhydrous sodium sulfate, filtered, and concentrated by rotary evaporation in vacuo to give the product as an off-white solid (321 mg, 91%).

Example 19F

{4-[4-(5-Chloro-pyridin-2-ylcarbamoyl)-2-(7-isopropyl-pyrido[2,3-d]pyrimidin-4-ylamino)-phenylsulfanyl]-phenyl}-carbamic acid 9H-fluoren-9-ylmethyl ester A solution of the product of Example 8E (88 mg, 0.4063 mmol) and the product of Example 19E (241 mg, 0.4063 mmol) in acetic acid (10 mL) was stirred in an oil bath preheated to 140° C. for 1.5 hour. The reaction was cooled to room temperature, diluted with hexanes (100 mL), concentrated by rotary evaporation, and co-evaporated with methylene chloride/hexanes (4×). The residue was dried on hi-vacuum, then purified by silica gel flash chromatography with 2% methanol/methylene chloride to afford the title compound as a yellow solid (168 mg, 54%).

Example 19G 4-(4-Amino-phenylsulfanyl)-N-(5-chloro-pyridin-2-yl)-3-(7-isopropyl-pyrido[2,3-d]pyrimidin-4-ylamino)-benzamide A solution of the product of Example 19F (167 mg, 0.2185 mmol) in 1,4-dioxane (4 mL) was treated with a solution of lithium hydroxide monohydrate (18.3 mg, 0.437 mmol) in water (2 mL) at ambient temperature, then heated at 60° for 40 minutes. The reaction was cooled to room temperature, diluted with ethyl acetate (100 mL) and water (30 mL), adjusted the aqueous pH to 6 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel flash chromatography with 5% methanol/methylene chloride afforded the title compound as a yellow solid (84 mg, 71%). $^1$H NMR (300 MHz, DMSO-D6) δ ppm: 1.34 (d, J=6.99 Hz, 6 H) 3.15-3.30 (m, 1 H) 5.62 (s, 2 H) 6.65 (d, J=8.46 Hz, 2 H) 6.77-6.89 (m, 1 H) 7.15 (d, J=8.46 Hz, 2 H) 7.64 (d, J=8.09 Hz, 1 H) 7.87 (d, J=8.46 Hz, 1 H) 7.95 (dd, J=8.82, 2.57 Hz, 1 H) 8.04 (s, 1 H) 8.21 (d, J=9.19 Hz, 1 H) 8.42 (d, J=2.57 Hz, 1 H) 8.58 (s, 1 H) 8.89 (d, J=8.46 Hz, 1 H) 10.13 (s, 1 H) 10.92 (s, 1 H); MS (ESI+) m/z 542/544 (M+H)$^+$.

Example 20

4-(4-Amino-phenylsulfanyl)-3-(7-isopropyl-pyrido[2,3-d]pyrimidin-4-ylamino)-N-(4-trifluoromethyl-thiazol-2-yl)-benzamide

Example 20A

{4-[2-Amino-4-(4-trifluoromethyl-thiazol-2-ylcarbamoyl)-phenylsulfanyl]-phenyl}-carbamic acid 9H-fluoren-9-ylmethyl ester A mixture of the product from Example 19C was reacted with 4-Trifluoromethyl-thiazol-2-ylamine using the procedure of Example 19D substituting 4-Trifluoromethyl-thiazol-2-ylamine for 5-chloro-2-aminopyridine followed by reduction of the nitro group following the procedure of Example 19E to provide the title product.

Example 20B 4-(4-Amino-phenylsulfanyl)-3-(7-isopropyl-pyrido[2,3-d]pyrimidin-4-ylamino)-N-(4-trifluoromethyl-thiazol-2-yl)-benzamide The product of Example 20A was reacted with the product of Example 8E using the procedure of Example 19F substituting the product of Example 20A for the product of Example 19E to provide {4-[2-(7-Isopropyl-pyrido[2,3-d]pyrimidin-4-ylamino)-4-(4-trifluoromethyl-thiazol-2-ylcarbamoyl)-phenylsulfanyl]-phenyl}-carbamic acid 9H-fluoren-9-ylmethyl ester which was reacted using the procedure of Example 19G to provide the crude title compound which was purified by trituration with 3% methanol/methylene chloride to provide the title compound (73 mg, 68%). 1H NMR (300 MHz, DMSO-D6) δ ppm: 1.34 (d, J=6.99 Hz, 6 H) 3.17-3.32 (m, 1 H) 5.65 (s, 2 H) 6.66 (d, J=8.46 Hz, 2 H) 6.84 (d, J=8.46 Hz, 1 H) 7.16 (d, J=8.46 Hz, 2 H) 7.65 (d, J=8.46 Hz, 1 H) 7.96 (dd, J=8.46, 1.84 Hz, 1 H) 8.01 (s, 1 H) 8.13 (d, J=1.47 Hz, 1 H) 8.59 (s, 1 H) 8.90 (d, J=8.46 Hz, 1 H) 10.14 (s, 1 H) 13.02 (s, 1 H); MS (ESI+) m/z 582 (M+H)+.

Example 21

4-(4-Amino-phenylsulfanyl)-N-(3-fluoro-phenyl)-3-(7-isopropyl-pyrido[2,3-d]pyrimidin-4-ylamino)-benzamide

Example 21A

{4-[2-Amino-4-(3-fluoro-phenylcarbamoyl)-phenylsulfanyl]-phenyl}-carbamic acid 9H-fluoren-9-ylmethyl ester A mixture of the product from Example 19C was reacted with 3-Fluoro-phenylamine using the procedure of Example 19D substituting 3-Fluoro-phenylamine for 5-chloro-2-aminopyridine followed by reduction of the nitro group following the procedure of Example 19E to provide the title product.

Example 21B 4-(4-Amino-phenylsulfanyl)-N-(3-fluoro-phenyl)-3-(7-isopropyl-pyrido[2,3-d]pyrimidin-4-ylamino)-benzamide The product of Example 21A was reacted with the product of Example 8E using the procedure of Example 19F substituting the product of Example 21A for the product of Example 19E to provide {4-[4-(3-Fluoro-phenylcarbamoyl)-2-(7-isopropyl-pyrido[2,3-d]pyrimidin-4-ylamino)-phenylsulfanyl]-phenyl}-carbamic acid 9H-fluoren-9-ylmethyl ester which was reacted using the procedure of Example 19G to provide the crude title compound which was purified by column chromatography on silica gel using methanol/dichloromethane as eluent to provide the title product (9 mg, 55%). 1H NMR (300 MHz, DMSO-D6) δ ppm: 1.34 (d, J=6.62 Hz, 6 H) 3.13-3.35 (m, 1 H) 5.60 (s, 2 H) 6.64 (d, J=8.46 Hz, 2 H) 6.84-6.98 (m, 2 H) 7.15 (d, J=8.46 Hz, 2 H) 7.37 (q, J=7.97 Hz, 1 H) 7.53 (d, J=8.09 Hz, 1 H) 7.64 (dd, J=8.09, 0.74 Hz, 1 H) 7.68-7.83 (m, 2 H) 7.95 (s, 1 H) 8.59 (s, 1 H) 8.89 (d, J=8.82 Hz, 1 H) 10.16 (s, 1 H) 10.34 (s, 1 H); MS (ESI+) m/z 525 (M+H)+.

Example 22

N-(4-Bromo-phenyl)-4-(4-hydroxy-phenylsulfanyl)-3-(7-isopropyl-pyrido[2,3-d]pyrimidin-4-ylamino)-benzamide Example 22A N-(4-Bromo-phenyl)-4-(4-hydroxy-phenylsulfanyl)-3-nitro-benzamide A solution of the product of Example 10A (553 mg, 1.557 mmol) in anhydrous N,N-dimethylformamide (15 mL) was treated with 4-mercaptophenol (196 mg, 1.557 mmol) and cesium carbonate (1.015 g, 3.114 mmol) at room temperature, then heated at 100° under a nitrogen atmosphere for 3 hours. The reaction was cooled to room temperature and the solvent removed by rotary evaporation in vacuo. The residue was taken up in H$_2$O (30 mL) and the pH adjusted to 3 with 1N aqueous HCl. The aqueous was extracted with ethyl acetate (2×50 mL), and the combined organic extracts washed with brine (25 mL). The organic layer was dried over anhydrous sodium sulfate, filtered, and concentrated by rotary evaporation. The residue was purified by trituration with methylene chloride and silica gel flash chromatography with a gradient of 6% to 30% ethyl acetate/methylene chloride to give the product as a dark yellow solid (517 mg, 75%).

Example 22B

3-Amino-N-(4-bromo-phenyl)-4-(4-hydroxy-phenylsulfanyl)-benzamide

A suspension of the product of Example 22A (409.9 mg, 0.9205 mmol) and iron powder (206 mg, 3.682 mmol) in acetic acid (7 mL) and ethanol (7 mL) was heated at reflux under a nitrogen atmosphere for 1 hour. The reaction was cooled to room temperature. The mixture was diluted with water (30 mL), the pH adjusted to 6 with solid sodium carbonate, and the aqueous extracted with ethyl acetate (2×50 mL). The combined organic extracts were washed with brine (25 mL), dried over sodium sulfate, filtered, and concentrated under vacuum to provide the title compound as a tan solid (290 mg, 0.6983 mmol, 76%).

Example 22C

N-(4-Bromo-phenyl)-4-(4-hydroxy-phenylsulfanyl)-3-(7-isopropyl-pyrido[2,3-d]pyrimidin-4-ylamino)-benzamide A solution of the product of Example 8E (21 mg, 0.0963 mmol) and the product of Example 22B (40 mg, 0.0963 mmol) in acetic acid (1 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4×). The residue was re-concentrated under hi-vacuum. The residue was purified by silica gel flash chromatography with 4% methanol/methylene chloride to provide the title compound as a yellow solid (29 mg, 0.0494 mmol, 51%). $^1$H NMR (300 MHz, DMSO-D6) δ ppm: 1.34 (d, J=6.99 Hz, 6 H) 3.18-3.29 (m, 1 H) 6.85 (d, J=8.82 Hz, 2 H) 6.89-6.97 (m, 1 H) 7.31 (d, J=8.46 Hz, 2 H) 7.52 (d, J=9.19 Hz, 2 H) 7.58-7.69 (m, 1 H) 7.73 (d, J=9.19 Hz, 2 H) 7.76-7.84 (m, 1 H) 7.86-8.07 (m, 1 H) 8.59 (s, 1 H) 8.76-9.01 (m, 1 H) 9.96 (s, 1 H) 10.20 (s, 1 H) 10.31 (s, 1 H); MS (ESI+) m/z 586/588 (M+H)$^+$, MS (ESI−) m/z 584/586 (M−H)$^−$.

Example 23

N-(5-Bromo-pyridin-2-yl)-4-(4-hydroxy-phenylsulfanyl)-3-(7-isopropyl-pyrido[2,3-d]pyrimidin-4-ylamino)-benzamide Example 23A 3-Amino-N-(5-bromo-pyridin-2-yl)-4-(4-hydroxyphenylsulfanyl)-benzamide A mixture of 4-chloro-3-nitrobenzoyl chloride was reacted with 5-Bromo-pyridin-2-ylamine to produce N-(4-Bromophenyl)-4-chloro-3-nitro-benzamide according to the procedure of Example 10A, which was treated sequentially using the procedures from Examples 22A and 22B to provide the title product.

Example 23B

N-(5-Bromo-pyridin-2-yl)-4-(4-hydroxy-phenylsulfanyl)-3-(7-isopropyl-pyrido[2,3-d]pyrimidin-4-ylamino)-benzamide The product of Example 23A was reacted with the product of Example 8E using the procedure of Example 22C substituting the product of Example 23A for the product of Example 22B to provide the crude title compound which was purified by HPLC with TFA to provide the title compound as a trifluoroacetic acid salt (42 mg, 43%). 1H NMR (300 MHz, DMSO-D6) δ ppm: 1.35 (d, J=6.99 Hz, 6 H) 3.17-3.36 (m, 1 H) 6.84-6.88 (m, 2 H) 6.90 (d, J=8.46 Hz, 1 H) 7.33 (d, J=8.46 Hz, 2 H) 7.81 (d, J=8.09 Hz, 1 H) 7.86-7.97 (m, 1 H) 8.04 (s, 1 H) 8.06 (dd, J=8.82, 2.57 Hz, 1 H) 8.16 (d, J=8.83 Hz, 1 H) 8.50 (d, J=2.57 Hz, 1 H) 8.75 (br s, 1 H) 8.96 (d, J=8.82 Hz, 1 H) 10.02 (s, 1 H) 10.96 (s, 1 H); MS (ESI+) m/z 587/589 (M+H)+.

Example 24

N-(5-Bromo-pyrimidin-2-yl)-4-(4-hydroxy-phenylsulfanyl)-3-(7-isopropyl-pyrido[2,3-d]pyrimidin-4-ylamino)-benzamide Example 24A 3-Amino-N-(5-bromo-pyrimidin-2-yl)-4-(4-hydroxyphenylsulfanyl)-benzamide A mixture of 4-chloro-3-nitrobenzoyl chloride was reacted with 5-Bromo-pyrimidin-2-ylamine to produce N-(5-Bromopyrimidin-2-yl)-4-chloro-3-nitro-benzamide according to the procedure of Example 10A, which was treated sequentially using the procedures from Examples 22A and 22B to provide the title product.

Example 24B

N-(5-Bromo-pyrimidin-2-yl)-4-(4-hydroxy-phenyl-sulfanyl)-3-(7-isopropyl-pyrido[2,3-d]pyrimidin-4-ylamino)-benzamide The product of Example 24A was reacted with the product of Example 8E using the procedure of Example 22C substituting the product of Example 24A for the product of Example 22B to provide the crude title compound which was purified by HPLC with TFA to provide the title compound as a trifluoroacetic acid salt (34 mg, 33%). 1H NMR (300 MHz, DMSO-D6) δ ppm: 1.36 (d, J=6.99 Hz, 6 H) 3.07-3.50 (m, 1 H) 6.86 (d, J=8.46 Hz, 2 H) 6.92 (d, J=8.09 Hz, 1 H) 7.33 (d, J=8.46 Hz, 2 H) 7.86 (d, J=8.09 Hz, 2 H) 7.96 (s, 1 H) 8.81 (s, 1 H) 8.88 (s, 2 H) 8.99 (d, J=9.19 Hz, 1 H) 10.03 (s, 1 H) 11.18 (s, 1 H); MS (ESI+) m/z 588/590 (M+H)+.

Example 25

N-(5-Bromo-pyridin-2-yl)-4-(4-hydroxy-phenylsul-fanyl)-3-(7-methyl-pyrido[2,3-d]pyrimidin-4-ylamino)-benzamide The product of Example 23A was reacted with the product of Example 9B using the procedure of Example 22C substituting the product of Example 23A for the product of Example 22B and substituting the product of Example 9B for the product of Example 8E to provide the crude title compound which was purified by HPLC with TFA to provide the title compound as a trifluoroacetic acid salt (41 mg, 43%). 1H NMR (300 MHz, DMSO-D6) δ ppm: 2.77 (s, 3 H) 6.85 (d, J=8.46 Hz, 2 H) 6.95 (d, J=8.46 Hz, 1 H) 7.32 (d, J=8.82 Hz, 2 H) 7.86 (d, J=8.46 Hz, 1 H) 7.97 (dd, J=8.46, 1.84 Hz, 1 H) 8.02-8.11 (m, 2 H) 8.19 (d, J=9.19 Hz, 1 H) 8.51 (d, J=1.84 Hz, 1 H) 8.89 (s, 1 H) 9.00 (d, J=8.82 Hz, 1 H) 10.05 (br s, 1 H) 10.99 (s, 1 H) 11.73 (br s, 1 H); MS (ESI+) m/z 559/561 (M+H)+.

Example 26

N-(3-Bromo-phenyl)-4-(4-hydroxy-phenylsulfanyl)-3-(7-isopropyl-pyrido[2,3-d]pyrimidin-4-ylamino)-benzamide Example 26A 3-Amino-N-(3-bromo-phenyl)-4-(4-hydroxy-phenyl-sulfanyl)-benzamide A mixture of 4-chloro-3-nitrobenzoyl chloride was reacted with 3-Bromo-phenylamine to produce N-(3-Bromo-phenyl)-4-chloro-3-nitro-benzamide according to the procedure of Example 10A, which was treated sequentially using the procedures from Examples 22A and 22B to provide the title product.

Example 26B

N-(3-Bromo-phenyl)-4-(4-hydroxy-phenylsulfanyl)-3-(7-isopropyl-pyrido[2,3-d]pyrimidin-4-ylamino)-benzamide The product of Example 26A was reacted with the product of Example 8E using the procedure of Example 22C substituting the product of Example 26A for the product of Example 22B to provide the crude title compound which was purified by column chromatography on silica gel using methanol/dichloromethane as eluent to provide the title product (24 mg, 42%). MS (ESI+) m/z 586/588 (M+H)+.

Example 27

N-(3-Bromo-phenyl)-4-(4-hydroxy-phenylsulfanyl)-3-(7-methyl-pyrido[2,3-d]pyrimidin-4-ylamino)-benzamide The product of Example 26A was reacted with the product of Example 9B using the procedure of Example 22C substituting the product of Example 26A for the product of Example 22B and substituting the product of Example 9B for the product of Example 8E to provide the crude title compound which was purified by column chromatography on silica gel using methanol/dichloromethane as eluent to provide the title product (22 mg, 47%). ¹H NMR (300 MHz, DMSO-D6) δ ppm: 2.68 (s, 3 H) 6.81-6.89 (m, 2 H) 6.89-7.01 (m, 1 H) 7.22-7.38 (m, 4 H) 7.49-7.64 (m, 1 H) 7.67-7.89 (m, 2 H) 7.92-8.03 (m, 1 H) 8.04-8.17 (m, 1 H) 8.58 (s, 1 H) 8.70-8.91 (m, 1 H) 9.96 (s, 1 H) 10.20 (s, 1 H) 10.31 (s, 1 H); MS (ESI+) m/z 558/560 (M+H)+.

Example 28

N-(4-Bromo-phenyl)-4-(4-hydroxy-phenylsulfanyl)-3-(7-methyl-pyrido[2,3-d]pyrimidin-4-ylamino)-benzamide Example 28A 3-Amino-N-(4-bromo-phenyl)-4-(4-hydroxy-phenyl-sulfanyl)-benzamide A solution of the product from Example 10A was treated sequentially using the procedures from Examples 22A and 22B to provide the title product.

Example 28B

N-(4-Bromo-phenyl)-4-(4-hydroxy-phenylsulfanyl)-3-(7-methyl-pyrido[2,3-d]pyrimidin-4-ylamino)-benzamide The product of Example 28A was reacted with the product of Example 9B using the procedure of Example 22C substituting the product of Example 28A for the product of Example 22B and substituting the product of Example 9B for the product of Example 8E to provide the crude title compound which was purified by column chromatography on silica gel using methanol/dichloromethane as eluent to provide the title product (24 mg, 51%). ¹H NMR (300 MHz, DMSO-D6) δ ppm: 2.68 (s, 3 H) 6.85 (d, J=8.46 Hz, 2 H) 6.89-7.00 (m, 1 H) 7.31 (d, J=8.82 Hz, 2 H) 7.45-7.64 (m, 3 H) 7.67-7.88 (m, 3 H) 7.97 (s, 1 H) 8.58 (s, 1 H) 8.70-8.92 (m, 1 H) 9.96 (s, 1 H) 10.19 (s, 1 H) 10.29 (s, 1 H); MS (ESI+) m/z 558/560 (M+H)+.

Example 29

4-[4-(3-Fluoro-benzyloxy)-2-(pyrido[2,3-d]pyrimidin-4-ylamino)-phenylsulfanyl]-phenol

Example 29A

N'-(3-cyano-pyridin-2-yl)-N,N-dimethyl-formamidine

A solution of 2-Amino-nicotinonitrile (5 g, 42 mmol) and N,N-Dimethylformamide dimethyl acetal (6.13 mL, 46.2 mmol) in toluene (20 mL) was heated at reflux for 3 hours. After cooling to room temperature, the solution was concentrated under vacuum to provide the title compound (7.3 g, 100%).

Example 29B

1-Chloro-4-(3-fluoro-benzyloxy)-2-nitro-benzene

The title compound was prepared according to the procedure of Example 9C substituting 1-Bromomethyl-3-fluoro-benzene for 1-chloromethyl-4-methoxy-benzene (0.56 g, 100%).

Example 29C

4-[4-(3-Fluoro-benzyloxy)-2-nitro-phenylsulfanyl]-phenol

The title compound was prepared according to the procedure of Example 9D substituting 1-Chloro-4-(3-fluoro-benzyloxy)-2-nitro-benzene for 1-Chloro-4-(4-methoxy-benzyloxy)-2-nitro-benzene (0.57 g, 77%).

Example 29D

4-[2-Amino-4-(3-fluoro-benzyloxy)-phenylsulfanyl]-phenol

The title compound was prepared according to the procedure of Example 9E substituting 4-[4-(3-Fluoro-benzyloxy)-2-nitro-phenylsulfanyl]-phenol for 4-[4-(4-Methoxy-benzyloxy)-2-nitro-phenylsulfanyl]-phenol (0.501 g, 96%).

Example 29E

4-[4-(3-Fluoro-benzyloxy)-2-(pyrido[2,3-d]pyrimidin-4-ylamino)-phenylsulfanyl]-phenol A solution of the product from Example 29A (35 mg, 0.2 mmol) and the product from Example 29D (68 mg, 0.2 mmol) in acetic acid (1 mL) was gradually heated form room temperature to 130° C. in an oil bath over a 15 minute time period, followed by heating at 130° C. for an additional 1.5 hours. The mixture was then cooled to room temperature, concentrated under vacuum to provide the crude title compound which was purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as the trifluoroacetic acid salt (28 mg, 30%). $^1$H NMR (300 MHz, DMSO-d$_6$) δ ppm: 5.14 (s, 2 H) 6.65 (m, 2 H) 7.14 (m, 8 H) 7.49 (m, 1 H) 7.66 (m, 1 H) 8.61 (s, 1 H) 8.88 (d, J=7.47 Hz, 1 H) 9.07 (s, 1 H) 9.65 (s, 1 H) 10.34 (s, 1 H); MS (ESI) m/z 471 (M+H)+.

Example 30

N-(4-Bromo-phenyl)-4-(4-hydroxy-phenylsulfanyl)-3-(pyrido[2,3-d]pyrimidin-4-ylamino)-benzamide The product of Example 28A was reacted with the product of Example 29A using the procedure of Example 22C substituting the product of Example 28A for the product of Example 22B and substituting the product of Example 29A for the product of Example 8E to provide the crude title compound which was purified by column chromatography on silica gel using methanol/dichloromethane as eluent to provide the title product (11 mg, 24%). 1H NMR (300 MHz, DMSO-D6) δ ppm: 6.85 (d, J=8.82 Hz, 2 H) 6.88-7.01 (br m, 1 H) 7.31 (d, J=8.46 Hz, 2 H) 7.52 (d, J=8.82 Hz, 2 H) 7.61-7.87 (br m, 2 H) 7.73 (d, J=9.19 Hz, 2 H) 7.92-8.09 (br m, 1 H) 8.54-8.72 (br m, 1 H) 8.87-9.04 (br m, 1 H) 9.03-9.19 (br m, 1 H) 9.96 (br s, 1 H) 10.31 (br d, J=9.56 Hz, 2 H); MS (ESI+) m/z 544/546 (M+H)+.

Example 31

N-(2-Bromo-benzyl)-4-(4-hydroxy-phenylsulfanyl)-3-(7-methyl-pyrido[2,3-d]pyrimidin-4-ylamino)-benzamide

Example 31A

3-Amino-N-(2-bromo-benzyl)-4-(4-hydroxy-phenylsulfanyl)-benzamide

A mixture of 4-chloro-3-nitrobenzoyl chloride was reacted with 2-Bromo-benzylamine to produce N-(2-Bromo-benzyl)-4-chloro-3-nitro-benzamide according to the procedure of Example 10A, which was treated sequentially using the procedures from Examples 22A and 22B to provide the title product.

Example 31B

N-(2-Bromo-benzyl)-4-(4-hydroxy-phenylsulfanyl)-3-(7-methyl-pyrido[2,3-d]pyrimidin-4-ylamino)-benzamide The product of Example 31A was reacted with the product of Example 9B using the procedure of Example 22C substituting the product of Example 31A for the product of Example 22B and substituting the product of Example 9B for the product of Example 8E to provide the crude title compound which was purified by column chromatography on silica gel using methanol/dichloromethane as eluent to provide the title product (60 mg, 71%). 1H NMR (300 MHz, DMSO-D6) δ ppm: 2.68 (s, 3 H) 4.48 (d, J=5.52 Hz, 2 H) 6.84 (d, J=8.82 Hz, 2 H) 6.87-6.96 (m, 1 H) 7.16-7.25 (m, 1 H) 7.25-7.40 (m, 4 H) 7.56 (d, J=8.09 Hz, 1 H) 7.61 (d, J=8.82 Hz, 1 H) 7.76 (d, J=8.82 Hz, 1 H) 7.93 (s, 1 H) 8.58 (s, 1 H) 8.74-8.85 (m, 1 H) 8.94-9.21 (m, 1 H) 9.94 (s, 1 H) 10.16 (s, 1 H); MS (ESI+) m/z 572/574 (M+H)+.

Example 32

N-(2-Bromo-benzyl)-4-(4-hydroxy-phenylsulfanyl)-3-(pyrido[2,3-d]pyrimidin-4-ylamino)-benzamide The product of Example 31A was reacted with the product of Example 29A using the procedure of Example 22C substituting the product of Example 3 1A for the product of Example 22B and substituting the product of Example 29A for the product of Example 8E to provide the crude title compound which was purified by column chromatography on silica gel using methanol/dichloromethane as eluent to provide the title product (58 mg, 60%). 1H NMR (300 MHz, DMSO-D6) δ ppm: 4.48 (d, J=5.88 Hz, 2 H) 6.84 (d, J=8.46 Hz, 2 H) 6.87-7.02 (m, 1 H) 7.13-7.44 (m, 5 H) 7.58-7.64 (m, 1 H) 7.64-7.84 (m, 2 H) 7.93 (s, 1 H) 8.62 (d, J=1.84 Hz, 1 H) 8.82-9.20 (m, 3 H) 9.94 (s, 1 H) 10.30 (s, 1 H); MS (ESI+) m/z 558/560 (M+H)+.

Example 33

N-(4-Bromo-benzyl)-4-(4-hydroxy-phenylsulfanyl)-3-(7-methyl-pyrido[2,3-d]pyrimidin-4-ylamino)-benzamide Example 33A 3-Amino-N-(4-bromo-benzyl)-4-(4-hydroxy-phenylsulfanyl)-benzamide A mixture of 4-chloro-3-nitrobenzoyl chloride was reacted with 4-Bromo-benzylamine to produce N-(4-Bromo-benzyl)-4-chloro-3-nitro-benzamide according to the procedure of Example 10A, which was treated sequentially using the procedures from Examples 22A and 22B to provide the title product.

Example 33B

N-(4-Bromo-benzyl)-4-(4-hydroxy-phenylsulfanyl)-3-(7-methyl-pyrido[2,3-d]pyrimidin-4-ylamino)-benzamide The product of Example 33A was reacted with the product of Example 9B using the procedure of Example 22C substituting the product of Example 33A for the product of Example 22B and substituting the product of Example 9B for the product of Example 8E to provide the crude title compound which was purified by column chromatography on silica gel using methanol/dichloromethane as eluent to provide the title product (40 mg, 40%). 1H NMR (500 MHz, DMSO-D6) δ ppm: 2.67 (s, 3 H) 4.41 (d, J=6.22 Hz, 2 H) 6.83 (d, J=8.82 Hz, 2 H) 6.86-6.95 (m, 1 H) 7.25 (d, J=8.30 Hz, 2 H) 7.28 (d, J=8.82 Hz, 2 H) 7.50 (d, J=8.30 Hz, 2 H) 7.52-7.59 (m, 1 H) 7.65-7.80 (m, 1 H) 7.81-7.98 (m, 1 H) 8.49-8.63 (m, 1 H) 8.69-8.84 (m, 1 H) 8.93-9.01 (m, 1 H) 9.83-9.97 (m, 1 H) 10.11 (s, 1 H); MS (ESI+) m/z 572/574 (M+H)+.

Example 34

N-(4-Bromo-benzyl)-4-(4-hydroxy-phenylsulfanyl)-3-(pyrido[2,3-d]pyrimidin-4-ylamino)-benzamide The product of Example 33A was reacted with the product of Example 29A using the procedure of Example 22C substituting the product of Example 33A for the product of Example 22B and substituting the product of Example 29A for the product of Example 8E to provide the crude title compound which was purified by column chromatography on silica gel using methanol/dichloromethane as eluent to provide the title product (26 mg, 26%). 1H NMR (300 MHz, DMSO-D6) δ ppm: 4.41 (d, J=5.88 Hz, 2 H) 6.76-6.96 (m, 1 H) 6.83 (d, J=8.46 Hz, 2 H) 7.20-7.33 (m, 4 H) 7.51 (d, J=8.46 Hz, 2 H) 7.58-7.80 (m, 2 H) 7.82-7.97 (m, 1 H) 8.52-8.69 (m, 1 H) 8.86-9.18 (m, 3 H) 9.94 (s, 1 H) 10.28 (s, 1 H); MS (ESI+) m/z 558/560 (M+H)+.

Example 35

N-Benzyl-4-(4-hydroxy-phenylsulfanyl)-3-(7-methyl-pyrido[2,3-d]pyrimidin-4-ylamino)-benzamide Example 35A 3-Amino-N-benzyl-4-(4-hydroxy-phenylsulfanyl)-benzamide A mixture of 4-chloro-3-nitrobenzoyl chloride was reacted with Benzylamine to produce N-Benzyl-4-chloro-3-nitro-benzamide according to the procedure of Example 10A, which was treated sequentially using the procedures from Examples 22A and 22B to provide the title product.

Example 35B

N-Benzyl-4-(4-hydroxy-phenylsulfanyl)-3-(7-methyl-pyrido[2,3-d]pyrimidin-4-ylamino)-benzamide The product of Example 35A was reacted with the product of Example 9B using the procedure of Example 22C substituting the product of Example 35A for the product of Example 22B and substituting the product of Example 9B for the product of Example 8E to provide the crude title compound which was purified by column chromatography on silica gel using methanol/dichloromethane as eluent to provide the title product (50 mg, 54%). 1H NMR (300 MHz, DMSO-D6) δ ppm: 2.67 (s, 3 H) 4.45 (d, J=5.88 Hz, 2 H) 6.78-6.96 (m, 1 H) 6.83 (d, J=8.46 Hz, 2 H) 7.15-7.40 (m, 7 H) 7.55 (d, J=7.35 Hz, 1 H) 7.73 (d, J=5.88 Hz, 1 H) 7.90 (s, 1 H) 8.56 (s, 1 H) 8.80 (d, J=8.09 Hz, 1 H) 9.01 (s, 1 H) 9.94 (s, 1 H) 10.14 (s, 1 H); MS (ESI+) m/z 494(M+H)+, (ESI−) m/z 492 (M−H)−.

Example 36

N-Benzyl-4-(4-hydroxy-phenylsulfanyl)-3-(pyrido[2,3-d]pyrimidin-4-ylamino)-benzamide The product of Example 35A was reacted with the product of Example 29A using the procedure of Example 22C substituting the product of Example 35A for the product of Example 22B and substituting the product of Example 29A for the product of Example 8E to provide the crude title compound which was purified by column chromatography on silica gel using methanol/dichloromethane as eluent to provide the title product (39 mg, 55%). 1H NMR (300 MHz, DMSO-D6) δ ppm: 4.45 (d, J=5.88 Hz, 2 H) 6.83 (d, J=8.82 Hz, 2 H) 6.82-6.93 (m, 1 H) 7.16-7.44 (m, 7 H) 7.56-7.81 (m, 2 H) 7.90 (br s, 1 H) 8.61 (br s, 1 H) 8.79-9.22 (br m, 3 H) 9.94 (br s, 1 H) 10.28 (br s, 1 H); MS (ESI+) m/z 480 (M+H)+.

Example 37

N-(4-Bromo-phenyl)-4-(4-hydroxy-phenoxy)-3-(7-isopropyl-pyrido[2,3-d]pyrimidin-4-ylamino)-benzamide Example 37A 4-(4-Hydroxy-phenoxy)-3-nitro-benzoic acid A solution of hydroquinone (3.00 g, 0.0272 mol) and potassium hydroxide (2.293 g, 0.0409 mol) in anhydrous dimethylsulfoxide (20 mL) was heated at 120° for 30 minutes under a nitrogen atmosphere. A solution of 4-chloro-3-nitrobenzoic acid (5.49 g, 0.0272 mol) in dimethylsulfoxide (25 mL) was added dropwise over a 30 minute period at 120°, then let the reaction stir an additional 2 hours at the same temperature. The reaction was then cooled in an ice bath and poured into 100 mL of ice-water. The mixture was acidified with concentrated HCl to pH 3 and extracted with ethyl ether (3×100 mL). The combined ethereal extracts were washed with water (3×150 mL), dried over anhydrous sodium sulfate, filtered, and concentrated by rotary evaporation in vacuo. Purification of the residue by silica gel flash chromatography with a gradient of 2% to 3% methanol/methylene chloride containing 0.5% acetic acid afforded the product as an orange solid after co-evaporation with methylene chloride/hexanes (2.432 g, 32%).

Example 37B

N-(4-Bromo-phenyl)-4-(4-hydroxy-phenoxy)-3-nitro-benzamide

A mixture of the product of Example 37A (200 mg, 0.7267 mmol) and 4-bromoaniline (193.3 mg, 1.090 mmol) in anhydrous toluene (6 mL) at 50° under a nitrogen atmosphere was treated with phosphorus trichloride (0.052 mL, 0.5814 mmol), then heated at reflux for 2 hours. The reaction was cooled to room temperature and water (30 mL) was added. Extracted the mixture with ethyl acetate (3×25 mL), then washed the combined organic extracts with brine, dried over anhydrous sodium sulfate, filtered, and concentrated by rotary evaporation in vacuo. Purification by silica gel flash chromatography with 10% ethyl acetate/methylene chloride afforded the product as a light orange solid (124 mg, 40%).

Example 37C

3-Amino-N-(4-bromo-phenyl)-4-(4-hydroxy-phenoxy)-benzamide

A solution of the product of Example 37B (116.6 mg, 0.2717 mmol) and iron powder (60.7 mg, 1.087 mmol) in acetic acid (2 mL) and ethanol (2 mL) was heated at reflux under a nitrogen atmosphere for 1 hour. The reaction was then cooled to room temperature. The mixture was diluted with water (20 mL), the pH adjusted to 6 with solid sodium carbonate, and the aqueous extracted with ethyl acetate (2×50 mL). The combined organic extracts were washed with brine (25 mL), dried over sodium sulfate, filtered, and concentrated under vacuum to provide the title compound as a beige solid (100 mg, 92%).

Example 37D

N-(4-Bromo-phenyl)-4-(4-hydroxy-phenoxy)-3-(7-isopropyl-pyrido[2,3-d]pyrimidin-4-ylamino)-benzamide A solution of the product of Example 8E (15.4 mg, 0.0714 mmol) and the product of Example 37C (28.5 mg, 0.0714 mmol) in acetic acid (1 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4×). After drying on hi-vacuum, the residue was purified by silica gel flash chromatography with 5% methanol/methylene chloride to afford the title product (24 mg, 59%). $^1$H NMR (300 MHz, DMSO-D6) δ ppm: 1.32 (d, J=6.62 Hz, 6 H) 3.14-3.29 (m, 1 H) 6.75 (d, J=8.82 Hz, 2 H) 6.83-6.98 (m, 3 H) 7.53 (d, J=8.82 Hz, 2 H) 7.60 (d, J=8.46 Hz, 1 H) 7.76 (d, J=8.82 Hz, 2 H) 7.87 (dd, J=8.82, 1.84 Hz, 1 H) 8.17 (d, J=1.47 Hz, 1 H) 8.61 (s, 1 H) 8.82 (d, J=8.82 Hz, 1 H) 9.39 (s, 1 H) 10.02 (s, 1 H) 10.31 (s, 1 H); MS (ESI+) m/z 570/572 (M+H)$^+$, MS (ESI-) m/z 568/570 (M-H)$^-$.

Example 38

N-(4-Bromo-phenyl)-4-(4-hydroxy-phenoxy)-3-(7-methyl-pyrido[2,3-d]pyrimidin-4-ylamino)-benzamide The product of Example 37C was reacted with the product of Example 9B using the procedure of Example 37D substituting the product of Example 9B for the product of Example 8E to provide the crude title compound which was purified by column chromatography on silica gel using methanol/dichloromethane as eluent to provide the title product (42 mg, 49%). 1H NMR (300 MHz, DMSO-D6) δ ppm: 2.66 (s, 3 H) 6.75 (d, J=8.82 Hz, 2 H) 6.89 (t, J=8.27 Hz, 3 H) 7.53 (d, J=8.82 Hz, 3 H) 7.75 (d, J=9.19 Hz, 2 H) 7.86 (dd, J=8.64, 1.65 Hz, 1 H) 8.18 (d, J=1.47 Hz, 1 H) 8.61 (s, 1 H) 8.77 (d, J=8.46 Hz, 1 H) 9.39 (s, 1 H) 10.00 (s, 1 H) 10.30 (s, 1 H); MS (ESI+) m/z 542/544 (M+H)+.

Example 39

N-(3-Bromo-phenyl)-4-(4-hydroxy-phenoxy)-3-(7-isopropyl-pyrido[2,3-d]pyrimidin-4-ylamino)-benzamide Example 39A 3-Amino-N-(3-bromo-phenyl)-4-(4-hydroxy-phenoxy)-benzamide A mixture of 4-chloro-3-nitrobenzoic acid was reacted with hydroquinone to produce 4-(4-Hydroxy-phenoxy)-3-nitro-benzoic acid according to the procedure of Example 37A, which was treated sequentially with 3-Bromo-phenylamine using the procedure from Example 37B and reduced using the procedure from Example 37C to provide the title product.

Example 39B

N-(3-Bromo-phenyl)-4-(4-hydroxy-phenoxy)-3-(7-isopropyl-pyrido[2,3-d]pyrimidin-4-ylamino)-benzamide The product of Example 39A was reacted with the product of Example 8E using the procedure of Example 37D substituting the product of Example 39A for the product of Example 37C to provide the crude title compound which was purified by column chromatography on silica gel using methanol/dichloromethane as eluent to provide the title product (27 mg, 62%). 1H NMR (300 MHz, DMSO-D6) δ ppm: 1.32 (d, J=6.99 Hz, 6 H) 3.14-3.29 (m, 1 H) 6.75 (d, J=8.82 Hz, 2) 6.82-6.96 (m, 3 H) 7.23-7.41 (m, 2 H) 7.60 (d, J=8.46 Hz, 1 H) 7.70-7.81 (m, 1 H) 7.87 (d, J=8.82 Hz, 1 H) 8.10 (s, 1 H) 8.17 (s, 1 H) 8.61 (s, 1 H) 8.82 (d, J=8.46 Hz, 1 H) 9.39 (s, 1 H) 10.02 (s, 1 H) 10.33 (s, 1 H); MS (ESI+) m/z 570/572 (M+H)+.

Example 40

N-(3-Bromo-phenyl)-4-(4-hydroxy-phenoxy)-3-(7-methyl-pyrido[2,3-d]pyrimidin-4-ylamino)-benzamide The product of Example 39A was reacted with the product of Example 9B using the procedure of Example 37D substituting the product of Example 39A for the product of Example 37C and substituting the product of Example 9B for Example 8E to provide the crude title compound which was purified by column chromatography on silica gel using methanol/dichloromethane as eluent to provide the title product (32 mg, 75%). 1H NMR (300 MHz, DMSO-D6) δ ppm: 2.67 (s, 3 H) 6.75 (d, J=8.82 Hz, 2 H) 6.82-6.98 (m, 3 H) 7.20-7.38 (m, 2 H) 7.54 (d, J=8.46 Hz, 1 H) 7.69-7.81 (m, 1 H) 7.87 (dd, J=8.64, 2.02 Hz, 1 H) 8.10 (s, 1 H) 8.19 (d, J=1.84 Hz, 1 H) 8.61 (s, 1 H) 8.78 (d, J=8.46 Hz, 1 H) 9.39 (s, 1 H) 10.01 (s, 1 H) 10.32 (s, 1 H); MS (ESI+) m/z 542/544 (M+H)+.

Example 41

4-(4-Hydroxy-phenoxy)-3-(7-isopropyl-pyrido[2,3-d]pyrimidin-4-ylamino)-N-phenyl-benzamide

Example 41A

3-Amino-4-(4-hydroxy-phenoxy)-N-phenyl-benzamide

A mixture of 4-chloro-3-nitrobenzoic acid was reacted with hydroquinone to produce 4-(4-Hydroxy-phenoxy)-3-nitro-benzoic acid according to the procedure of Example 37A, which was treated sequentially with Phenylamine using the procedure from Example 37B and reduced using the procedure from Example 37C to provide the title product.

Example 41B 4-(4-Hydroxy-phenoxy)-3-(7-isopropyl-pyrido[2,3-d]pyrimidin-4-ylamino)-N-phenyl-benzamide The product of Example 41A was reacted with the product of Example 8E using the procedure of Example 37D substituting the product of Example 41A for the product of Example 37C to provide the crude title compound which was purified by column chromatography on silica gel using methanol/dichloromethane as eluent to provide the title product (16 mg, 42%). 1H NMR (300 MHz, DMSO-D6) δ ppm: 1.32 (d, J=6.62 Hz, 6 H) 3.12-3.30 (m, 1 H) 6.74 (d, J=8.82 Hz, 2 H) 6.89 (t, J=8.09 Hz, 3 H) 7.09 (t, J=7.35 Hz, 1 H) 7.35 (t, J=7.91 Hz, 2 H) 7.60 (d, J=8.82 Hz, 1 H) 7.76 (d, J=7.72 Hz, 2 H) 7.88 (dd, J=8.64, 2.02 Hz, 1 H) 8.17 (d, J=2.21 Hz, 1 H) 8.61 (s, 1 H) 8.82 (d, J=8.46 Hz, 1 H) 9.38 (s, 1 H) 10.02 (s, 1 H) 10.19 (s, 1 H); MS (DCI/NH3) m/z 492 (M+H)+.

Example 42

N-Benzyl-4-(4-hydroxy-phenoxy)-3-(7-isopropyl-pyrido[2,3-d]pyrimidin-4-ylamino)-N-methyl-benzamide

Example 42A

3-Amino-N-benzyl-4-(4-hydroxy-phenoxy)-N-methyl-benzamide

A mixture of 4-chloro-3-nitrobenzoic acid was reacted with hydroquinone to produce 4-(4-Hydroxy-phenoxy)-3-nitro-benzoic acid according to the procedure of Example 37A, which was treated sequentially with Benzyl-methyl-amine using the procedure from Example 37B and reduced using the procedure from Example 37C to provide the title product.

Example 42B

N-Benzyl-4-(4-hydroxy-phenoxy)-3-(7-isopropyl-pyrido[2,3-d]pyrimidin-4-ylamino)-N-methyl-benzamide The product of Example 42A was reacted with the product of Example 8E using the procedure of Example 37D substituting the product of Example 42A for the product of Example 37C to provide the crude title compound which was purified by column chromatography on silica gel using methanol/dichloromethane as eluent to provide the title product (37 mg, 45%).

Example 43

N-(2-Fluoro-phenyl)-4-(4-hydroxy-phenoxy)-3-(7-isopropyl-pyrido[2,3-d]pyrimidin-4-ylamino)-benzamide

Example 43A 4-(4-Benzyloxy-phenoxy)-3-nitro-benzoic acid

A solution of 4-Benzyloxy-phenol (2.00 g, 0.01 mol) and potassium hydroxide (1.12 g, 0.02 mol) in anhydrous dimethylsulfoxide (20 mL) was stirred at room temperature for 10 minutes under a nitrogen atmosphere. A solution of 4-chloro-3-nitrobenzoic acid (2.01 g, 0.01 mol) in dimethylsulfoxide (5 mL) was added and the mixture heated to 120° for 1 hour. The reaction was then cooled in an ice bath and poured into 100 mL of ice-water. The mixture was acidified with concentrated HCl to pH 3 then the resultant solid was colleted by vacuum filtration, washed with water and dried in a vacuum oven to provide the title product (3.5 g, 96%).

Example 43B

3-Amino-4-(4-benzyloxy-phenoxy)-benzoic acid

A solution of the product of Example 43A (0.73 g, 2.0 mmol), iron powder (1.12 g, 20 mmol) and ammonium chloride (1.08 g, 20 mmol) in methanol (20 mL), tetrahydrofuran (20 mL), and water (10 mL) was heated at 80° for 48 hours. After cooling to room temperature, the mixture was diluted with methanol (50 mL) and filtered through a pad of celite. The filtrate was concentrated under vacuum then purified by column chromatography on silica gel using methanol/dichloromethane as eluent to provide the title product (670 mg, 100%).

Example 43C 4-(4-Benzyloxy-phenoxy)-3-(7-isopropyl-pyrido[2,3-d]pyrimidin-4-ylamino)-benzoic acid A solution of the product of Example 8E (432 mg, 2.0 mmol) and the product of Example 43B (670 mg, 2.0 mmol) in acetic acid (5 mL) was stirred in an oil bath preheated to 140° C. for 30 minutes. The reaction was cooled to room temperature, concentrated by rotary evaporation, and co-evaporated with methylene chloride/hexanes (4×). After drying on hi-vacuum, the residue was purified by silica gel flash chromatography with methanol/methylene chloride to afford the title product (560 mg, 55%).

Example 43D 4-(4-Benzyloxy-phenoxy)-3-(7-isopropyl-pyrido[2,3-d]pyrimidin-4-ylamino)-benzoyl chloride A solution of the product from Example 43C (224 mg, 0.443 mmol) in thionyl chloride (2 mL) was refluxed for 1 hour. The mixture was cooled to room temperature, toluene (5 mL) was added and the mixture concentrated under vacuum to provide the title product as a solid.

Example 43E 4-(4-Benzyloxy-phenoxy)-N-(2-fluoro-phenyl)-3-(7-isopropyl-pyrido[2,3-d]pyrimidin-4-ylamino)-benzamide A solution of the product from Example 43D (53 mg, 0.1 mmol), N,N-diisopropylethylamine (0.052 mL, 0.3 mmol), 2-Fluoro-phenylamine (0.014 mL, 0.15 mmol) in dichloromethane (2 mL) was stirred at room temperature for 1 hour, then concentrated under vacuum to provide the title product.

Example 43F

N-(2-Fluoro-phenyl)-4-(4-hydroxy-phenoxy)-3-(7-isopropyl-pyrido[2,3-d]pyrimidin-4-ylamino)-benzamide A solution of the product of Example 43E and pentamethylbenzene (72 mg, 0.5 mmol) in trifluoroacetic acid (5 mL) was stirred at room temperature for 1 hour. The solvent was removed by rotary evaporation under vacuum and co-evaporated with methylene chloride/hexanes (2×) to provide the crude title compound which was purified by HPLC with TFA to provide the title compound as a trifluoroacetic acid salt (11 mg, 22%). 1H NMR (300 MHz, DMSO-D6) δ ppm: 1.34 (d, J=6.62 Hz, 6 H) 3.28 (m, 1 H) 6.77 (m, 2 H) 6.93 (m, 3 H) 7.26 (m, 3 H) 7.58 (m, 1 H) 7.88 (d, J=8.82 z, 1 H) 8.00 (dd, J=8.64, 2.02 Hz, 1 H) 8.14 (d, J=2.21 Hz, 1 H) 8.91 (s, 1 H) 9.00 (d, J=8.09 Hz, 1 H) 9.47 (s, 1 H) 10.13 (s, 1 H) 11.48 (s, 1 H); MS (ESI+) m/z 510 (M+H)+.

Example 44

4-(4-Hydroxy-phenoxy)-3-(7-isopropyl-pyrido[2,3-d]pyrimidin-4-ylamino)-N-(3-methoxy-phenyl)-benzamide A solution of the product from Example 43D and 3-Methoxy-phenylamine was reacted to provide 4-(4-Benzyloxy-phenoxy)-3-(7-isopropyl-pyrido[2,3-d]pyrimidin-4-ylamino)-N-(3-methoxy-phenyl)-benzamide using the procedure from Example 43E. The material was then deprotected using the procedure from Example 43F to provide the crude title compound which was purified by column chromatography on silica gel using methanol/dichloromethane as eluent to provide the title product (12 mg, 40%). 1H NMR (300 MHz, DMSO-D6) δ ppm: 1.32 (d, J=6.99 Hz, 6 H) 3.11-3.29 (m, 1 H) 3.75 (s, 3 H) 6.68 (dd, J=8.09, 1.84 Hz, 1 H) 6.75 (d, J=8.82 Hz, 2 H) 6.89 (t, J=8.64 Hz, 3 H) 7.24 (t, J=8.09 Hz, 1 H) 7.37 (d, J=8.09 Hz, 1 H) 7.45 (t, J=2.21 Hz, 1 H) 7.60 (d, J=8.46 Hz, 1 H) 7.86 (dd, J=8.64, 1.65 Hz, 1 H) 8.17 (s, 1 H) 8.61 (s, 1 H) 8.82 (d, J=8.46 Hz, 1 H) 9.38 (s, 1 H) 10.01 (s, 1 H) 10.15 (s, 1 H); MS (ESI+) m/z 522 (M+H)+.

Example 45

N-(3-Carbamoyl-phenyl)-4-(4-hydroxy-phenoxy)-3-(7-isopropyl-pyrido[2,3-d]pyrimidin-4-ylamino)-benzamide A solution of the product from Example 43D and 3-Amino-benzamide was reacted to provide 4-(4-Benzyloxy-phenoxy)-N-(3-carbamoyl-phenyl)-3-(7-isopropyl-pyrido[2,3-d]pyrimidin-4-ylamino)-benzamide using the procedure from Example 43E. The material was then deprotected using the procedure from Example 43F to provide the crude title compound which was purified by HPLC with TFA to provide the title compound as a trifluoroacetic acid salt (30 mg, 56%). 1H NMR (300 MHz, DMSO-D6) δ ppm: 1.35 (d, J=6.62 Hz, 6 H) 3.28 (m, 1 H) 6.78 (m, 2 H) 6.94 (m, 3 H) 7.40 (m, 2 H) 7.60 (d, J=7.72 Hz, 1 H) 7.91 (m, 3 H) 8.02 (dd, J=8.82, 2.21 Hz, 1 H) 8.17 (d, J=2.21 Hz, 1 H) 8.22 (m, 1 H) 8.91 (s, 1 H) 9.00 (d, J=8.46 Hz, 1 H) 9.48 (s, 1 H) 10.37 (s, 1 H) 11.50 (s, 1 H); MS (ESI+) m/z 535 (M+H)+.

Example 46

4-(4-Hydroxy-phenoxy)-3-(7-isopropyl-pyrido[2,3-d]pyrimidin-4-ylamino)-N-pyridin-3-yl-benzamide A solution of the product from Example 43D and Pyridin-3-ylamine was reacted to provide 4-(4-Benzyloxy-phenoxy)-3-(7-isopropyl-pyrido[2,3-d]pyrimidin-4-ylamino)-N-pyridin-3-yl-benzamide using the procedure from Example 43E. The material was then deprotected using the procedure from Example 43F to provide the crude title compound which was purified by HPLC with TFA to provide the title compound as a trifluoroacetic acid salt (23 mg, 47%). 1H NMR (300 MHz, DMSO-D6) δ ppm: 1.35 (d, J=6.99 Hz, 6 H) 3.29 (m, 1 H) 6.78 (m, 2 H) 6.95 (m, 3 H) 7.54 (dd, J=8.27, 4.96 Hz, 1 H) 7.90 (d, J=8.82 Hz, 1 H) 8.02 (dd, J=8.82, 2.21 Hz, 1 H) 8.16 (d, J=2.21 Hz, 1 H) 8.29 (m, 1 H) 8.39 (dd, J=4.78, 1.47 Hz, 1 H) 8.94 (s, 1 H) 9.04 (m, 2 H) 9.48 (s, 1 H) 10.59 (s, 1 H) 11.59 (s, 1 H); MS (ESI+) m/z 493 (M+H)+.

Example 47

4-(4-Hydroxy-phenoxy)-3-(7-isopropyl-pyrido[2,3-d]pyrimidin-4-ylamino)-N-pyridin-4-yl-benzamide A solution of the product from Example 43D and Pyridin-4-ylamine was reacted to provide 4-(4-Benzyloxy-phenoxy)-3-(7-isopropyl-pyrido[2,3-d]pyrimidin-4-ylamino)-N-pyridin-4-yl-benzamide using the procedure from Example 43E. The material was then deprotected using the procedure from Example 43F to provide the crude title compound which was purified by HPLC with TFA to provide the title compound as a trifluoroacetic acid salt (30 mg, 61%). 1H NMR (300 MHz, DMSO-D6) δ ppm: 1.34 (d, J=6.62 Hz, 6 H) 3.27 (m, 1 H) 6.78 (m, 2 H) 6.94 (m, 3 H) 7.81 (d, J=8.46 Hz, 1 H) 8.01 (dd, J=8.64, 2.02 Hz, 1 H) 8.22 (m, 3 H) 8.72 (d, J=6.99 Hz, 2 H) 8.83 (s, 1 H) 8.96 (d, J=8.46 Hz, 1 H) 9.50 (s, 1 H) 11.10 (s, 1 H) 11.35 (s, 1 H); MS (ESI+) m/z 493 (M+H)+.

Example 48

4-(4-Hydroxy-phenoxy)-3-(7-isopropyl-pyrido[2,3-d]pyrimidin-4-ylamino)-N-pyridin-2-yl-benzamide A solution of the product from Example 43D and Pyridin-2-ylamine was reacted to provide 4-(4-Benzyloxy-phenoxy)-

3-(7-isopropyl-pyrido[2,3-d]pyrimidin-4-ylamino)-N-pyridin-2-yl-benzamide using the procedure from Example 43E. The material was then deprotected using the procedure from Example 43F to provide the crude title compound which was purified by HPLC with TFA to provide the title compound as a trifluoroacetic acid salt (5 mg, 10%). 1H NMR (300 MHz, DMSO-D6) δ ppm: 1.35 (d, J=6.99 Hz, 6 H) 3.28 (m, 1 H) 6.78 (m, 2 H) 6.87 (d, J=8.82 Hz, 1 H) 6.94 (m, 2 H) 7.18 (dd, J=7.35, 4.78 Hz, 1 H) 7.88 (m, 2 H) 8.09 (dd, J=8.46, 2.21 Hz, 1 H) 8.17 (d, J=8.46 Hz, 1 H) 8.22 (d, J=2.21 Hz, 1 H) 8.38 (d, J=2.94 Hz, 1 H) 8.94 (s, 1 H) 9.03 (d, J=8.82 Hz, 1 H) 9.48 (s, 1 H) 10.80 (s, 1 H) 11.61 (s, 1 H); MS (ESI+) m/z 493 (M+H)+.

Example 49

N-(2-Carbamoyl-phenyl)-4-(4-hydroxy-phenoxy)-3-(7-isopropyl-pyrido[2,3-d]pyrimidin-4-ylamino)-benzamide A solution of the product from Example 43D and 2-Amino-benzamide was reacted to provide 4-(4-Benzyloxy-phenoxy)-N-(2-carbamoyl-phenyl)-3-(7-isopropyl-pyrido[2,3-d]pyrimidin-4-ylamino)-benzamide using the procedure from Example 43E. The material was then deprotected using the procedure from Example 43F to provide the crude title compound which was purified by HPLC with TFA to provide the title compound as a trifluoroacetic acid salt (18 mg, 34%). 1H NMR (300 MHz, DMSO-D6) δ ppm: 1.35 (d, J=6.99 Hz, 6 H) 3.28 (m, 1 H) 6.76 (m, 2 H) 6.96 (m, 3 H) 7.18 (m, 1 H) 7.57 (m, 1 H) 7.85 (m, 4 H) 8.10 (d, J=2.21 Hz, 1 H) 8.43 (s, 1 H) 8.68 (d, J=8.46 Hz, 1 H) 8.91 (s, 1 H) 9.00 (d, J=8.82 Hz, 1 H) 9.48 (s, 1 H) 11.50 (s, 1 H) 12.99 (s, 1 H); MS (ESI+) m/z 535 (M+H)+.

Example 50

N-(3-Fluoro-phenyl)-4-(4-hydroxy-phenoxy)-3-(7-isopropyl-pyrido[2,3-d]pyrimidin-4-ylamino)-benzamide A solution of the product from Example 43D and 3-Fluoro-phenylamine was reacted to provide 4-(4-Benzyloxy-phenoxy)-N-(3-fluoro-phenyl)-3-(7-isopropyl-pyrido[2,3-d]pyrimidin-4-ylamino)-benzamide using the procedure from Example 43E. The material was then deprotected using the procedure from Example 43F to provide the crude title compound which was purified by HPLC with TFA to provide the title compound as a trifluoroacetic acid salt (7 mg, 14%). 1H NMR (300 MHz, DMSO-D6) δ ppm: 1.34 (d, J=6.99 Hz, 6 H) 3.28 (m, 1 H) 6.78 (m, 2 H) 6.93 (m, 4 H) 7.39 (m, 1 H) 7.55 (m, 1 H) 7.74 (m, 1 H) 7.85 (d, J=8.46 Hz, 1 H) 7.97 (dd, J=8.82, 2.21 Hz, 1 H) 8.13 (d, J=1.84 Hz, 1 H) 8.88 (s, 1 H) 8.98 (d, J=8.46 Hz, 1 H) 9.46 (s, 1 H) 10.42 (s, 1 H) 11.34 (s, 1 H); MS (ESI+) m/z 510 (M+H)+.

Example 51

N-(4-Fluoro-phenyl)-4-(4-hydroxy-phenoxy)-3-(7-isopropyl-pyrido[2,3-d]pyrimidin-4-ylamino)-benzamide A solution of the product from Example 43D and 4-Fluoro-phenylamine was reacted to provide 4-(4-Benzyloxy-phenoxy)-N-(4-fluoro-phenyl)-3-(7-isopropyl-pyrido[2,3-d]pyrimidin-4-ylamino)-benzamide using the procedure from Example 43E. The material was then deprotected using the procedure from Example 43F to provide the crude title compound which was purified by HPLC with TFA to provide the title compound as a trifluoroacetic acid salt (27 mg, 53%). 1H NMR (300 MHz, DMSO-D6) δ ppm: 1.34 (d, J=6.62 Hz, 6 H) 3.28 (m, 1 H) 6.76 (m, 2 H) 6.92 (m, 3 H) 7.20 (m, 2 H) 7.76 (m, 2 H) 7.85 (d, J=8.82 Hz, 1 H) 7.96 (dd, J=8.64, 2.39 Hz, 1 H) 8.13 (d, J=2.21 Hz, 1 H) 8.88 (s, 1 H) 8.98 (d, J=8.46 Hz, 1 H) 9.46 (s, 1 H) 10.30 (s, 1 H) 11.35 (s, 1 H); MS (ESI+) m/z 510 (M+H)+.

Example 52

N-(2-Bromo-phenyl)-4-(4-hydroxy-phenoxy)-3-(7-isopropyl-pyrido[2,3-d]pyrimidin-4-ylamino)-benzamide A solution of the product from Example 43D and 2-Bromo-phenylamine was reacted to provide 4-(4-Benzyloxy-phenoxy)-N-(2-bromo-phenyl)-3-(7-isopropyl-pyrido[2,3-d]pyrimidin-4-ylamino)-benzamide using the procedure from Example 43E. The material was then deprotected using the procedure from Example 43F to provide the crude title compound which was purified by HPLC with TFA to provide the title compound as a trifluoroacetic acid salt (8 mg, 14%). 1H NMR (300 MHz, DMSO-D6) δ ppm: 1.34 (d, J=6.99 Hz, 6 H) 3.28 (m, 1 H) 6.77 (m, 2 H) 6.94 (m, 3 H) 7.24 (m, 1 H) 7.44 (m, 1 H) 7.54 (dd, J=7.74, 1.84 Hz, 1 H) 7.73 (dd, J=8.09, 1.50 Hz, 1 H) 7.86 (d, J=8.46 Hz, 1 H) 8.01 (dd, J=8.64, 2.02 Hz, 1 H) 8.15 (d, J=2.21 Hz, 1 H) 8.89 (s, 1 H) 8.98 (d, J=8.46 Hz, 1 H) 9.46 (s, 1 H) 10.06 (s, 1 H) 11.37 (s, 1 H); MS (ESI+) m/z 570, 572 (M+H)+.

Example 53

N-(2-Hydroxy-5-methyl-phenyl)-4-(4-hydroxy-phenoxy)-3-(7-isopropyl-pyrido[2,3-d]pyrimidin-4-ylamino)-benzamide A solution of the product from Example 43D and 2-Amino-4-methyl-phenol was reacted to provide 4-(4-Benzyloxy-phenoxy)-N-(2-hydroxy-5-methyl-phenyl)-3-(7-isopropyl-pyrido[2,3-d]pyrimidin-4-ylamino)-benzamide using the procedure from Example 43E. The material was then deprotected using the procedure from Example 43F to provide the crude title compound which was purified by HPLC with TFA to provide the title compound as a trifluoroacetic acid salt (15 mg, 29%). 1H NMR (300 MHz, DMSO-D6) δ ppm: 1.34 (d, J=6.99 Hz, 6 H) 2.22 (s, 3 H) 3.29 (m, 1 H) 6.79 (m, 4 H) 6.92 (m, 3 H) 7.47 (d, J=1.32 Hz, 1 H) 7.87 (d, J=8.82 Hz, 1 H) 7.97 (dd, J=8.46, 2.21 Hz, 1 H) 8.13 (d, J=2.21 Hz, 1 H) 8.91 (s, 1 H) 9.00 (d, J=8.46 Hz, 1 H) 9.45 (m, 3 H) 11.46 (s, 1 H); MS (ESI+) m/z 522 (M+H)+.

Example 54

4-(4-Hydroxy-phenoxy)-3-(7-isopropyl-pyrido[2,3-d]pyrimidin-4-ylamino)-N-(4-methoxy-phenyl)-benzamide A solution of the product from Example 43D and 4-Methoxy-phenylamine was reacted to provide 4-(4-Benzyloxy-phenoxy)-3-(7-isopropyl-pyrido[2,3-d]pyrimidin-4-ylamino)-N-(4-methoxy-phenyl)-benzamide using the procedure from Example 43E. The material was then deprotected using the procedure from Example 43F to provide the crude title compound which was purified by HPLC with TFA to provide the title compound as a trifluoroacetic acid salt (27 mg, 52%). 1H NMR (300 MHz, DMSO-D6) δ ppm: 1.34 (d, J=6.99 Hz, 6 H) 3.28 (m, 1 H) 3.74 (s, 3 H) 6.77 (m, 2 H) 6.92 (m, 5 H) 7.64 (m, 2 H) 7.87 (d, J=8.82 Hz, 1 H) 7.96 (dd, J=8.64, 2.02 Hz, 1 H) 8.12 (d, J=2.21 Hz, 1 H) 8.89 (s, 1 H) 8.99 (d, J=8.46 Hz, 1 H) 9.46 (s, 1 H) 10.12 (s, 1 H) 11.41 (s, 1 H); MS (ESI+) m/z 522 (M+H)+.

Example 55

N-(4-Fluoro-phenyl)-4-(4-hydroxy-phenylsulfanyl)-3-(7-isopropyl-pyrido[2,3-d]pyrimidin-4-ylamino)-benzamide Example 55A 3-Amino-N-(4-fluoro-phenyl)-4-(4-hydroxy-phenyl-sulfanyl)-benzamide A mixture of 4-chloro-3-nitrobenzoyl chloride was reacted with 4-Fluoro-phenylamine to produce 4-Chloro-N-(4-fluoro-phenyl)-3-nitro-benzamide according to the procedure of Example 10A, which was treated sequentially using the procedures from Examples 22A and 22B to provide the title product.

Example 55B

N-(4-Fluoro-phenyl)-4-(4-hydroxy-phenylsulfanyl)-3-(7-isopropyl-pyrido[2,3-d]pyrimidin-4-ylamino)-benzamide The product of Example 55A was reacted with the product of Example 8E using the procedure of Example 22C substituting the product of Example 55A for the product of Example 22B to provide the crude title compound which was purified by HPLC with TFA to provide the title compound as a trifluoroacetic acid salt (47 mg, 45%). 1H NMR (300 MHz, DMSO-D6) δ ppm: 1.36 (d, J=6.99 Hz, 6 H) 3.27 (m, 1 H) 6.84 (m, 2 H) 6.97 (d, J=8.46 Hz, 1 H) 7.18 (m, 2 H) 7.31 (m, 2 H) 7.80 (m, 4 H) 7.95 (s, 1 H) 8.75 (s, 1 H) 8.96 (d, J=8.46 Hz, 1 H) 10.00 (s, 1 H) 10.28 (s, 1 H) 11.28 (s, 1 H); MS (ESI+) m/z 526 (M+H)+.

Example 56

N-(4-Fluoro-phenyl)-4-(4-hydroxy-phenylsulfanyl)-3-(7-methyl-pyrido[2,3-d]pyrimidin-4-ylamino)-benzamide The product of Example 55A was reacted with the product of Example 9B using the procedure of Example 22C substituting the product of Example 55A for the product of Example 22B and substituting the product of Example 9B for the product of Example 8E to provide the crude title compound which was purified by HPLC with TFA to provide the title compound as a trifluoroacetic acid salt (24 mg, 24%). 1H NMR (300 MHz, DMSO-D6) δ ppm: 2.75 (s, 3 H) 6.83 (m, 2 H) 7.00 (d, J=8.46 Hz, 1 H) 7.18 (m, 2 H) 7.31 (m, 2 H) 7.76 (m, 3 H) 7.86 (d, J=8.09 Hz, 1 H) 7.96 (s, 1 H) 8.81 (s, 1 H) 8.95 (d, J=8.09 Hz, 1 H) 10.00 (s, 1 H) 10.28 (s, 1 H) 11.38 (s, 1 H); (ESI+) m/z 498 (M+H)+.

Example 57

N-(4-Fluoro-phenyl)-4-(4-hydroxy-phenylsulfanyl)-3-(pyrido[2,3-d]pyrimidin-4-ylamino)-benzamide The product of Example 55A was reacted with the product of Example 29A using the procedure of Example 22C substituting the product of Example 55A for the product of Example 22B and substituting the product of Example 29A for the product of Example 8E to provide the crude title compound which was purified by HPLC with TFA to provide the title compound as a trifluoroacetic acid salt (24 mg, 24%). 1H NMR (300 MHz, DMSO-D6) δ ppm: 6.84 (m, 2 H) 6.97 (d, J=8.46 Hz, 1 H) 7.18 (m, 2 H) 7.32 (m, 2 H) 7.79 (m, 4 H) 7.95 (s, 1 H) 8.74 (s, 1 H) 9.02 (d, J=8.09 Hz, 1 H) 9.12 (d, J=2.82 Hz, 1 H) 9.99 (s, 1 H) 10.27 (s, 1 H) 11.21 (s, 1 H); MS (ESI+) m/z 484 (M+H)+.

Example 58

N-(2-Fluoro-phenyl)-4-(4-hydroxy-phenylsulfanyl)-3-(7-isopropyl-pyrido[2,3-d]pyrimidin-4-ylamino)-benzamide Example 58A 3-Amino-N-(2-fluoro-phenyl)-4-(4-hydroxy-phenyl-sulfanyl)-benzamide A mixture of 4-chloro-3-nitrobenzoyl chloride was reacted with 2-Fluoro-phenylamine to produce 4-Chloro-N-(2-fluoro-phenyl)-3-nitro-benzamide according to the procedure of Example 10A, which was treated sequentially using the procedures from Examples 22A and 22B to provide the title product.

Example 58B

N-(2-Fluoro-phenyl)-4-(4-hydroxy-phenylsulfanyl)-3-(7-isopropyl-pyrido[2,3-d]pyrimidin-4-ylamino)-benzamide The product of Example 58A was reacted with the product of Example 8E using the procedure of Example 22C substituting the product of Example 58A for the product of Example 22B to provide the crude title compound which was purified by HPLC with TFA to provide the title compound as a trifluoroacetic acid salt (43 mg, 41%). 1H NMR (300 MHz, DMSO-D6) δ ppm: 1.36 (d, J=6.99 Hz, 6 H) 3.28 (m, 1 H) 6.84 (m, 2 H) 6.99 (d, J=8.46 Hz, 1 H) 7.26 (m, 5 H) 7.57 (t, J=7.35 Hz, 1 H) 7.87 (t, J=8.09 Hz, 2 H) 7.97 (s, 1 H) 8.81 (s, 1 H) 8.99 (d, J=8.82 Hz, 1 H) 10.01 (s, 1 H) 10.12 (s, 1 H) 11.38 (s, 1 H); MS (ESI+) m/z 526 (M+H)+.

Example 59

N-(2-Fluoro-phenyl)-4-(4-hydroxy-phenylsulfanyl)-3-(7-methyl-pyrido[2,3-d]pyrimidin-4-ylamino)-benzamide The product of Example 58A was reacted with the product of Example 9B using the procedure of Example 22C substituting the product of Example 58A for the product of Example 22B and substituting the product of Example 9B for the product of Example 8E to provide the crude title compound which was purified by HPLC with TFA to provide the title compound as a trifluoroacetic acid salt (45 mg, 45%). 1H NMR (300 MHz, DMSO-D6) δ ppm: 2.75 (s, 3 H) 6.84 (m, 2 H) 7.00 (d, J=8.46 Hz, 1 H) 7.28 (m, 5 H) 7.56 (m, 1 H) 7.80 (d, J=8.09 Hz, 1 H) 7.89 (d, J=8.46 Hz, 1 H) 7.98 (s, 1 H) 8.83 (s, 1 H) 8.95 (d, J=8.46 Hz, 1 H) 10.01 (s, 1 H) 10.12 (s, 1 H) 11.49 (s, 1 H); MS (ESI+) m/z 498 (M+H)+.

Example 60

N-(2-Fluoro-phenyl)-4-(4-hydroxy-phenylsulfanyl)-3-(pyrido[2,3-d]pyrimidin-4-ylamino)-benzamide The product of Example 58A was reacted with the product of Example 29A using the procedure of Example 22C substituting the product of Example 58A for the product of Example 22B and substituting the product of Example 29A for the product of Example 8E to provide the crude title compound which was purified by HPLC with TFA to provide the title compound as a trifluoroacetic acid salt (55 mg, 57%). 1H NMR (300 MHz, DMSO-D6) δ ppm: 6.84 (m, 2 H) 7.00 (d, J=8.09 Hz, 1 H) 7.26 (m, 5 H) 7.57 (m, 1 H) 7.89 (m, 2 H) 7.98 (s, 1 H) 8.85 (s, 1 H) 9.08 (d, J=7.72 Hz, 1 H) 9.17 (d, J=2.94 Hz, 1 H) 10.02 (s, 1 H) 10.13 (s, 1 H) 11.58 (s, 1 H); MS (ESI+) m/z 484 (M+H)+.

Example 61

N-(3-Fluoro-phenyl)-4-(4-hydroxy-phenylsulfanyl)-3-(7-isopropyl-pyrido[2,3-d]pyrimidin-4-ylamino)-benzamide

Example 61A

3-Amino-N-(3-fluoro-phenyl)-4-(4-hydroxy-phenylsulfanyl)-benzamide

A mixture of 4-chloro-3-nitrobenzoyl chloride was reacted with 3-Fluoro-phenylamine to produce 4-Chloro-N-(3-fluoro-phenyl)-3-nitro-benzamide according to the procedure of Example 10A, which was treated sequentially using the procedures from Examples 22A and 22B to provide the title product.

Example 61B

N-(3-Fluoro-phenyl)-4-(4-hydroxy-phenylsulfanyl)-3-(7-isopropyl-pyrido[2,3-d]pyrimidin-4-ylamino)-benzamide The product of Example 61A was reacted with the product of Example 8E using the procedure of Example 22C substituting the product of Example 61A for the product of Example 22B to provide the crude title compound which was purified by HPLC with TFA to provide the title compound as a trifluoroacetic acid salt (44 mg, 42%). 1H NMR (300 MHz, DMSO-D6) δ ppm: 1.36 (d, J=6.99 Hz, 6 H) 3.28 (m, 1 H) 6.90 (m, 4 H) 7.36 (m, 3 H) 7.52 (m, 1 H) 7.73 (m, 1 H) 7.84 (d, J=8.46 Hz, 2 H) 7.95 (s, 1 H) 8.78 (s, 1 H) 8.98 (d, J=8.46 Hz, 1 H) 10.01 (s, 1 H) 10.41 (s, 1 H) 11.38 (s, 1 H); MS (ESI+) m/z 526 (M+H)+.

Example 62

N-(3-Fluoro-phenyl)-4-(4-hydroxy-phenylsulfanyl)-3-(7-methyl-pyrido[2,3-d]pyrimidin-4-ylamino)-benzamide The product of Example 61A was reacted with the product of Example 9B using the procedure of Example 22C substituting the product of Example 61A for the product of Example 22B and substituting the product of Example 9B for the product of Example 8E to provide the crude title compound which was purified by HPLC with TFA to provide the title compound as a trifluoroacetic acid salt (56 mg, 56%). 1H NMR (300 MHz, DMSO-D6) δ ppm: 2.74 (s, 3 H) 6.90 (m, 4 H) 7.35 (m, 3 H) 7.52 (d, J=9.19 Hz, 1 H) 7.73 (m, 2 H) 7.85 (d, J=8.46 Hz, 1 H) 7.96 (s, 1 H) 8.78 (s, 1 H) 8.93 (d, J=8.46 Hz, 1 H) 10.01 (s, 1 H) 10.40 (s, 1 H) 11.34 (s, 1 H); MS (ESI+) m/z 498 (M+H)+.

Example 63

N-(3-Fluoro-phenyl)-4-(4-hydroxy-phenylsulfanyl)-3-(pyrido[2,3-d]pyrimidin-4-ylamino)-benzamide The product of Example 61A was reacted with the product of Example 29A using the procedure of Example 22C substituting the product of Example 61A for the product of Example 22B and substituting the product of Example 29A for the product of Example 8E to provide the crude title compound which was purified by HPLC with TFA to provide the title compound as a trifluoroacetic acid salt (54 mg, 56%). 1H NMR (300 MHz, DMSO-D6) δ ppm: 6.90 (m, 4 H) 7.35 (m, 3 H) 7.53 (d, J=9.19 Hz, 1 H) 7.72 (m, 1 H) 7.84 (m, 2 H) 7.96 (s, 1 H) 8.76 (s, 1 H) 9.03 (d, J=8.09 Hz, 1 H) 9.14 (d, J=3.31 Hz, 1 H) 10.00 (s, 1 H) 10.40 (s, 1 H) 11.26 (s, 1 H); MS (ESI+) m/z 484 (M+H)+.

Example 64

{4-[4-(3-Bromo-phenylcarbamoyl)-2-(7-isopropyl-pyrido[2,3-d]pyrimidin-4-ylamino)-phenylsulfanyl]-phenyl}-carbamic acid tert-butyl ester

Example 64A

{4-[2-Amino-4-(3-bromo-phenylcarbamoyl)-phenylsulfanyl]-phenyl}-carbamic acid tert-butyl ester A mixture of 4-chloro-3-nitrobenzoyl chloride was reacted with 3-Bromo-phenylamine to produce N-(3-Bromo-phenyl)-4-chloro-3-nitro-benzamide according to the procedure of Example 10A, which was treated sequentially using the procedures from Examples 13A, 13B and 13C to provide the title product.

Example 64B

{4-[4-(3-Bromo-phenylcarbamoyl)-2-(7-isopropyl-pyrido[2,3-d]pyrimidin-4-ylamino)-phenylsulfanyl]-phenyl}-carbamic acid tert-butyl ester The product of Example 64A was reacted with the product of Example 8E using the procedure of Example 13D substituting the product of Example 64A for the product of Example 13C to provide the crude title compound which was purified by silica gel flash chromatography with methanol/methylene chloride to provide the title compound (32 mg, 23%). 1H NMR (300 MHz, DMSO-D6) δ ppm: 1.34 (d, J=6.99 Hz, 6 H) 1.48 (s, 9 H) 3.22 (m, 1 H) 7.01 (d, J=8.09 Hz, 1 H) 7.30 (m, 2 H) 7.36 (d, J=8.46 Hz, 2 H) 7.54 (d, J=8.82 Hz, 2 H) 7.64 (d, J=8.46 Hz, 1 H) 7.73 (m, 1 H) 7.81 (d, J=8.09 Hz, 1 H) 8.00 (s, 1 H) 8.08 (s, 1 H) 8.60 (s, 1 H) 8.86 (d, J=8.46 Hz, 1 H) 9.60 (s, 1 H) 10.23 (s, 1 H) 10.35 (s, 1 H); MS (ESI+) m/z 685, 687 (M+H)+.

Example 65

4-(4-Amino-phenylsulfanyl)-N-(3-bromo-phenyl)-3-(7-isopropyl-pyrido[2,3-d]pyrimidin-4-ylamino)-benzamide The product of Example 64B was treated with trifluoroacetic acid (3 mL) in methylene chloride (3 mL) at room temperature for 30 minutes. The solvents were removed under vacuum to provide the title compound as a trifluoroacetic acid salt. 1H NMR (300 MHz, DMSO-D6) δ ppm: 1.37 (d, J=6.99 Hz, 6 H) 3.30 (m, 1 H) 6.65 (d, J=8.46 Hz, 2 H) 6.97 (d, J=8.46 Hz, 1 H) 7.16 (d, J=8.46 Hz, 2 H) 7.30 (m, 2 H) 7.72 (m, 1 H) 7.88 (dd, J=8.46, 1.84 Hz, 1 H) 7.96 (m, 2 H) 8.05 (s, 1 H) 8.92 (s, 1 H) 9.07 (d, J=8.46 Hz, 1 H) 10.37 (s, 1 H) 11.82 (s, 1 H); MS (ESI+) m/z 585, 587 (M+H)+.

Example 66

{4-[4-(3-Bromo-phenylcarbamoyl)-2-(7-methyl-pyrido[2,3-d]pyrimidin-4-ylamino)-phenylsulfanyl]-phenyl}-carbamic acid tert-butyl ester The product of Example 64A was reacted with the product of Example 9B using the procedure of Example 13D substituting the product of Example 64A for the product of Example 13C and substituting the product of Example 9B for the product of Example 8E to provide the crude title compound which was purified by column chromatography on silica gel using methanol/dichloromethane as eluent to provide the title compound (27 mg, 21%). 1H NMR (300 MHz, DMSO-D6) δ ppm: 1.48 (s, 9 H) 2.69 (s, 3 H) 7.00 (d, J=8.09 Hz, 1 H) 7.34 (m, 4 H) 7.54 (m, 3 H) 7.72 (m, 1 H) 7.81 (d, J=8.09 Hz, 1 H) 8.01 (s, 1 H) 8.07 (s, 1 H) 8.60 (s, 1 H) 8.82 (d, J=8.46 Hz, 1 H) 9.60 (s, 1 H) 10.22 (s, 1 H) 10.34 (s, 1 H); MS (ESI+) m/z 657, 659 (M+H)+.

Example 67

4-(4-Amino-phenylsulfanyl)-N-(3-bromo-phenyl)-3-(7-methyl-pyrido[2,3-d]pyrimidin-4-ylamino)-benzamide The product of Example 66 was treated with trifluoroacetic acid (3 mL) in methylene chloride (3 mL) at room temperature for 30 minutes. The solvents were removed under vacuum to provide the title compound as a trifluoroacetic acid salt. 1H NMR (300 MHz, DMSO-D6) δ ppm: 2.77 (s, 3 H) 6.65 (d, J=8.46 Hz, 2 H) 6.97 (d, J=8.46 Hz, 1 H) 7.16 (d, J=8.46 Hz, 2 H) 7.30 (m, 2 H) 7.72 (m, 1 H) 7.90 (m, 3 H) 8.05 (s, 1 H) 8.92 (s, 1 H) 9.01 (d, J=8.46 Hz, 1 H) 10.36 (s, 1 H) 11.78 (s, 1 H); MS (ESI+) m/z 557, 559 (M+H)+.

Example 68

{4-[4-(3-Bromo-phenylcarbamoyl)-2-(pyrido[2,3-d]pyrimidin-4-ylamino)-phenylsulfanyl]-phenyl}-carbamic acid tert-butyl ester The product of Example 64A was reacted with the product of Example 29A using the procedure of Example 13D substituting the product of Example 64A for the product of Example 13C and substituting the product of Example 29A for the product of Example 8E to provide the crude title compound which was purified by column chromatography on silica gel using methanol/dichloromethane as eluent to provide the title compound (31 mg, 24%). 1H NMR (300 MHz, DMSO-D6) δ ppm: 1.48 (s, 9 H) 7.01 (d, J=8.46 Hz, 1 H) 7.32 (m, 4 H) 7.54 (d, J=8.46 Hz, 1 H) 7.71 (m, 2 H) 7.82 (d, J=7.72 Hz, 1 H) 8.01 (s, 1 H) 8.08 (s, 1 H) 8.64 (s, 1 H) 8.96 (d, J=8.09 Hz, 1 H) 9.11 (d, J=2.94 Hz, 1 H) 9.61 (s, 1 H) 10.35 (s, 1 H) 10.36 (s, 1 H); MS (ESI+) m/z 643/645 (M+H)+.

Example 69

4-(4-Amino-phenylsulfanyl)-N-(3-bromo-phenyl)-3-(pyrido[2,3-d]pyrimidin-4-ylamino)-benzamide The product of Example 68 was treated with trifluoroacetic acid (3 mL) in methylene chloride (3 mL) at room temperature for 30 minutes. The solvents were removed under vacuum to provide the title compound as a trifluoroacetic acid salt. 1H NMR (300 MHz, DMSO-D6) δ ppm: 6.65 (d, J=8.82 Hz, 2 H) 6.97 (d, J=8.46 Hz, 1 H) 7.17 (d, J=8.46 Hz, 2 H) 7.30 (m, 2 H) 7.72 (m, 1 H) 7.91 (m, 3 H) 8.05 (s, 1 H) 8.91 (s, 1 H) 9.12 (d, J=8.46 Hz, 1 H) 9.19 (d, J=3.68 Hz, 1 H) 10.36 (s, 1 H) 11.72 (s, 1 H); MS (ESI+) m/z 543/545 (M+H)+.

Example 70

4-[4-(2-Amino-butyrylamino)-phenylsulfanyl]-N-(4-bromo-phenyl)-3-(7-isopropyl-pyrido[2,3-d]pyrimidin-4-ylamino)-benzamide To a solution of the product from Example 13E (59 mg, 0.1 mmol) and Boc-Abu-OH (22 mg, 0.11 mmol) in tetrohydrofuran (5 ml) was added 3-(diethoxyphosphoryloxy)-1,2,3-benzo-triazin-4(3H)-one (36 mg, 0.11 mmol) and triethylamine (0.07 ml, 0.5 mmol). The mixture was stirred at room temperature for 16 hours then poured into saturated sodium carbonate solution and extracted with ethyl acetate. The organic layer was dried with magnesium sulfate, filtered and evaporated. To the residue was added dichloromethane (2 ml) and trifluoroacetic acid (2 ml) then stirred at room temperature for 1 hour. The solvent was evaporated and the residue was purified by HPLC with NH4OH to provide the title compound. (62 mg, 85%). 1H NMR (300 MHz, DMSO-D6) δ ppm: 0.90 (t, J=7.54 Hz, 3 H) 1.33 (d, J=6.99 Hz, 6 H) 1.48 (m, 1 H) 1.66 (m, 1 H) 1.90 (s, 3 H) 3.22 (m, 2 H) 7.02 (m, 2 H) 7.40 (d, J=8.46 Hz, 2 H) 7.52 (d, J=8.46 Hz, 2 H) 7.61 (d, J=8.46 Hz, 1 H) 7.72 (m, 5 H) 7.94 (s, 1 H) 8.52 (s, 1 H) 8.79 (s, 1 H) 10.33 (s, 1 H); MS (ESI+) m/z 670, 672 (M+H)+.

Example 71

Pyrrolidine-2-carboxylic acid {4-[4-(4-bromo-phenylcarbamoyl)-2-(7-isopropyl-pyrido[2,3-d]pyrimidin-4-ylamino)-phenylsulfanyl]-phenyl}-amide The product of Example 13E was reacted with (S)-Pyrrolidine-1,2-dicarboxylic acid 1-tert-butyl ester using the procedure of Example 70 substituting (S)-Pyrrolidine-1,2-dicarboxylic acid 1-tert-butyl for Boc-Abu-OH to provide the crude title compound which was purified by HPLC with TFA to provide the title compound as a trifluoroacetic acid salt (48 mg, 53%). 1H NMR (300 MHz, DMSO-D6) δ ppm: 1.35 (d, J=6.99 Hz, 6 H) 1.95 (m, 3 H) 2.37 (m, 1 H) 3.28 (m, 3 H) 4.32 (m, 1 H) 7.14 (s, 1 H) 7.45 (d, J=8.82 Hz, 2 H) 7.54 (d, J=8.82 Hz, 2 H) 7.63 (d, J=8.82 Hz, 2 H) 7.73 (d, J=8.82 Hz, 2 H) 7.85 (s, 2 H) 8.02 (s, 1 H) 8.70 (s, 2 H) 8.92 (s, 1 H) 9.23 (s, 1 H) 10.38 (s, 1 H) 10.67 (s, 1 H) 11.10 (s, 1 H); MS (ESI+) m/z 682/684 (M+H)+.

Example 72

4-[4-(3-Amino-propionylamino)-phenylsulfanyl]-N-(4-bromo-phenyl)-3-(7-isopropyl-pyrido[2,3-d]pyrimidin-4-ylamino)-benzamide The product of Example 13E was reacted with 3-tert-Butoxycarbonylamino-propionic acid using the procedure of Example 70 substituting 3-tert-Butoxycarbonylamino-propionic acid for Boc-Abu-OH to provide the crude title compound which was purified by HPLC with TFA then neutralized with an aqueous sodium carbonate solution to provide the title compound (15 mg, 23%). 1H NMR (300 MHz, DMSO-D6) δ ppm: 1.33 (d, J=6.62 Hz, 6 H) 2.41 (t, J=6.25 Hz, 2 H) 2.83 (t, J=6.25 Hz, 2 H) 3.20 (m, 1 H) 6.97 (d, J=8.46 Hz, 1 H) 7.39 (d, J=8.46 Hz, 2 H) 7.54 (m, 3 H) 7.70 (m, 5 H) 7.95 (s, 1 H) 8.47 (s, 1 H) 8.79 (d, J=8.09 Hz, 1 H) 10.32 (s, 1 H); MS (ESI+) m/z 656/658 (M+H)+.

Example 73

4-(4-Hydroxy-phenylsulfanyl)-3-(7-isopropyl-pyrido[2,3-d]pyrimidin-4-ylamino)-N-phenyl-benzamide

Example 73A

3-Amino-4-(4-hydroxy-phenylsulfanyl)-N-phenyl-benzamide

A mixture of 4-chloro-3-nitrobenzoyl chloride was reacted with Phenylamine to produce 4-Chloro-3-nitro-N-phenyl-benzamide according to the procedure of Example 10A, which was treated sequentially using the procedures from Examples 22A and 22B to provide the title product.

Example 73B 4-(4-Hydroxy-phenylsulfanyl)-3-(7-isopropyl-pyrido[2,3-d]pyrimidin-4-ylamino)-N-phenyl-benzamide The product of Example 73A was reacted with the product of Example 8E using the procedure of Example 22C substituting the product of Example 73A for the product of Example 22B to provide the crude title compound which was purified by HPLC with TFA to provide the title compound as a trifluoroacetic acid salt (42 mg, 34%). 1H NMR (300 MHz, DMSO-D6) δ ppm: 1.36 (d, J=6.62 Hz, 6 H), 3.23-3.35 (m, 1 H), 6.84 (d, J=8.82 Hz, 2 H), 6.98 (d, J=8.46 Hz, 1 H), 7.10 (t, J=7.54 Hz, 1 H), 7.25-7.39 (m, 4 H), 7.73 (d, J=7.72 Hz, 2 H), 7.85 (s, 2 H), 7.96 (s, 1 H), 8.79 (s, 1 H), 8.98 (d, J=6.62 Hz, 1 H), 10.00 (s, 1 H), 10.22 (s, 1 H), 11.28 (s, 1); MS (ESI+) m/z 508 (M+H)+.

Example 74

4-(4-Hydroxy-phenylsulfanyl)-3-(7-methyl-pyrido[2,3-d]pyrimidin-4-ylamino)-N-phenyl-benzamide The product of Example 73A was reacted with the product of Example 9B using the procedure of Example 22C substituting the product of Example 73A for the product of Example 22B and substituting the product of Example 9B for the product of Example 8E to provide the crude title compound which was purified by HPLC with TFA to provide the title compound as a trifluoroacetic acid salt (44 mg, 37%). 1H NMR (300 MHz, DMSO-D6) δ ppm: 2.75 (s, 3 H), 6.78-6.89 (m, 2 H), 7.00 (d, J=8.09 Hz, 1 H), 7.10 (t, J=7.35 Hz, 1 H), 7.25-7.41 (m, 4 H), 7.73 (d, J=7.72 Hz, 2 H), 7.78 (d, J=8.82 Hz, 1 H), 7.87 (d, J=8.46 Hz, 1 H), 7.97 (s, 1 H), 8.81 (s, 1 H), 8.94 (d, J=9.19 Hz, 1 H), 10.00 (s, 1 H), 10.22 (s, 1 H), 11.38 (s, 1 H); MS (ESI+) m/z 480 (M+H)+.

Example 75

4-(4-Hydroxy-phenylsulfanyl)-N-phenyl-3-(pyrido[2,3-d]pyrimidin-4-ylamino)-benzamide The product of Example 73A was reacted with the product of Example 29A using the procedure of Example 22C substituting the product of Example 73A for the product of Example 22B and substituting the product of Example 29A for the product of Example 8E to provide the crude compound which was purified by HPLC with TFA to provide the title compound as a trifluoroacetic acid salt (45 mg, 39%). 1H NMR (300 MHz, DMSO-D6) δ 6.84 ppm: (d, J=8.82 Hz, 2 H), 6.99 (d, J=8.82 Hz, 1 H), 7.10 (t, J=7.35 Hz, 1 H), 7.26-7.42 (m, 4 H), 7.73 (d, J=7.35 Hz, 2 H), 7.84 (s, 2 H), 7.97 (s, 1 H), 8.81 (s, 1 H), 9.06 (s, 1 H), 9.15 (s, 1 H), 9.98 (s, 1 H), 10.21 (s, 1 H), 11.29 (s, 1 H); MS (ESI+) mz 466 (M+H)+.

Example 76

4-(4-Hydroxy-phenylsulfanyl)-3-(7-isopropyl-pyrido[2,3-d]pyrimidin-4-ylamino)-N-thiazol-2-yl-benzamide

Example 76A

3-Amino-4-(4-hydroxy-phenylsulfanyl)-N-thiazol-2-yl-benzamide

A mixture of 4-chloro-3-nitrobenzoyl chloride was reacted with Thiazol-2-ylamine to produce 4-Chloro-3-nitro-N-thiazol-2-yl-benzamide according to the procedure of Example 10A, which was treated sequentially using the procedures from Examples 22A and 22B to provide the title product.

Example 76B 4-(4-Hydroxy-phenylsulfanyl)-3-(7-isopropyl-pyrido[2,3-d]pyrimidin-4-ylamino)-N-thiazol-2-yl-benzamide The product of Example 76A was reacted with the product of Example 8E using the procedure of Example 22C substituting the product of Example 76A for the product of Example 22B to provide the crude title compound which was purified by HPLC with TFA to provide the title compound as a trifluoroacetic acid salt (38 mg, 30%). 1H NMR (300 MHz, DMSO-D6) δ ppm: 1.37 (d, J=6.62 Hz, 6 H), 3.23-3.39 (m, 1 H), 6.87 (d, J=8.46 Hz, 2 H), 6.95 (d, J=8.46 Hz, 1 H), 7.28 (d, J=3.31 Hz, 1 H), 7.31-7.38 (m, 2 H), 7.55 (d, J=3.68 Hz, 1 H), 7.91 (d, J=8.46 Hz, 1 H), 8.02 (d, J=8.46 Hz, 1 H), 8.10 (d, J=1.84 Hz, 1 H), 8.85 (s, 1 H), 9.03 (d, J=8.46 Hz, 1 H), 10.07 (s, 1 H), 12.65 (s, 1 H); MS (ESI+) m/z 515 (M+H)+.

Example 77

4-(4-Hydroxy-phenylsulfanyl)-3-(7-methyl-pyrido[2,3-d]pyrimidin-4-ylamino)-N-thiazol-2-yl-benzamide The product of Example 76A was reacted with the product of Example 9B using the procedure of Example 22C substituting the product of Example 76A for the product of Example 22B and substituting the product of Example 9B for the product of Example 8E to provide the crude title compound which was purified by HPLC with TFA to provide the title compound as a trifluoroacetic acid salt (28 mg, 23%). 1H NMR (300 MHz, DMSO-D6) δ ppm: 2.77 (s, 3 H), 6.87 (d, J=8.82 Hz, 2 H), 6.96 (d, J=8.46 Hz, 1 H), 7.28 (d, J=3.31 Hz, 1 H), 7.34 (d, J=8.82 Hz, 2 H), 7.55 (d, J=3.68 Hz, 1 H), 7.85 (d, J=8.82 Hz, 1 H), 8.02 (dd, J=8.46, 1.84 Hz, 1 H), 8.12 (d, J=1.84 Hz, 1 H), 8.89 (s, 1 H), 9.00 (d, J=8.46 Hz, 1 H), 10.09 (s, 1 H), 12.69 (s, 1 H); MS (ESI+) m/z 487 (M+H)+.

Example 78

4-(4-Hydroxy-phenylsulfanyl)-3-(pyrido[2,3-d]pyrimidin-4-ylamino)-N-thiazol-2-yl-benzamide The product of Example 76A was reacted with the product of Example 29A using the procedure of Example 22C substituting the product of Example 76A for the product of Example 22B and substituting the product of Example 29A for the product of Example 8E to provide the crude title compound which was purified by HPLC with TFA to provide the title compound as a trifluoroacetic acid salt (45 mg, 39%). 1H NMR (300 MHz, DMSO-D6) δ ppm: 6.86 (d, J=8.46 Hz, 2 H), 6.97 (d, J=8.46 Hz, 1 H), 7.28 (d, J=3.31 Hz, 1 H), 7.34 (d, J=8.82 Hz, 2 H), 7.55 (d, J=3.68 Hz, 1 H), 7.96 (dd, J=8.27, 4.60 Hz, 1 H), 8.03 (dd, J=8.46, 1.84 Hz, 1 H), 8.13 (d, J=1.84 Hz, 1 H), 8.92 (s, 1 H), 9.13 (d, J=8.09 Hz, 1 H), 9.18-9.23 (m, 1 H), 10.06 (s, 1 H), 11.85 (s, 1 H), 12.64 (s, 1 H); MS (ESI+) m/z 473 (M+H)+.

Example 79

N-(3-Bromo-phenyl)-4-(3-hydroxy-phenylsulfanyl)-3-(7-isopropyl-pyrido[2,3-d]pyrimidin-4-ylamino)-benzamide Example 79A N-(3-Bromo-phenyl)-4-(3-hydroxy-phenylsulfanyl)-3-nitro-benzamide A solution of N-(3-Bromo-phenyl)-4-chloro-3-nitro-benzamide (from Example 26A) (0.356 g, 1.0 mmol), 3-hydroxythiophenol (0.126 g, 1.0 mmol) and cesium carbonate (0.65 g, 2.0 mmol) in N,N-dimethylformamide (5 mL) was heated to 95° C. for 3 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over magnesium sulfate, filtered and concentrated under vacuum to provide the title compound (0.430 g, 97%).

Example 79B

3-Amino-N-(3-bromo-phenyl)-4-(3-hydroxy-phenylsulfanyl)-benzamide

A solution of the product of Example 79A (0.43 g, 0.97 mmol), iron powder (0.28 g, 5.0 mmol) and ammonium chloride (0.08 g, 1.5 mmol) in an ethanol (18 mL), tetrahydrofuran (18 mL), and water (6 mL) solution was heated to reflux for 3 hours. The resultant mixture was diluted with ethanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over sodium sulfate, filtered and concentrated under vacuum to provide the title compound (0.41 g, 98%).

Example 79C

N-(3-Bromo-phenyl)-4-(3-hydroxy-phenylsulfanyl)-3-(7-isopropyl-pyrido[2,3-d]pyrimidin-4-ylamino)-benzamide A solution of the product of Example 79B (62.0 mg, 0.15 mmol) and the product of Example 8E (32.0 mg, 0.15 mmol) in acetic acid (1 mL) was stirred in a preheated 140° C. oil bath for 20 minutes. The mixture was cooled and concentrated under vacuum. The resultant residue was purified by HPLC with TFA to provide the title compound as a trifluoroacetic acid salt (32 mg, 30%). 1H NMR (300 MHz, DMSO-D6) δ ppm: 1.35 (d, J=6.99 Hz, 6 H), 3.19-3.34 (m, 1 H), 6.70 (dd, J=7.72, 1.84 Hz, 1 H), 6.75 (t, J=2.02 Hz, 1 H), 6.80 (d, J=7.72 Hz, 1 H), 7.14 (t, J=7.91 Hz, 1 H), 7.24-7.38 (m, 3 H), 7.71-7.77 (m, 1 H), 7.80 (d, J=8.46 Hz, 1 H), 7.91 (d, J=8.09 Hz, 1 H), 8.01 (s, 1 H), 8.08 (s, 1 H), 8.73 (s, 1 H), 8.91 (d, J=8.46 Hz, 1 H), 9.72 (s, 1 H), 10.44 (s, 1 H), 11.26 (s, 1 H); MS (ESI+) m/z 586/588 (M+H)+.

Example 80

N-(3-Bromo-phenyl)-4-(3-hydroxy-phenylsulfanyl)-3-(7-methyl-pyrido[2,3-d]pyrimidin-4-ylamino)-benzamide The product of Example 79B was reacted with the product of Example 9B using the procedure of Example 79C substituting the product of Example 9B for the product of Example 8E to provide the crude title compound which was purified by HPLC with TFA to provide the title compound as a trifluoroacetic acid salt (35 mg, 35%). 1H NMR (300 MHz, DMSO-D6) δ ppm: 2.72 (s, 3 H), 6.71 (dd, J=7.72, 1.84 Hz, 1 H), 6.75 (t, J=2.02 Hz, 1 H), 6.81 (d, J=8.09 Hz, 1 H), 7.14 (t, J=7.91 Hz, 1 H), 7.27-7.37 (m, 3 H), 7.68-7.79 (m, 2 H), 7.90 (d, J=7.72 Hz, 1 H), 8.02 (s, 1 H), 8.08 (s, 1 H), 8.72 (s, 1 H), 8.85 (d, J=8.09 Hz, 1 H), 9.72 (s, 1 H), 10.42 (s, 1 H), 11.17 (s, 1 H); MS (ESI+) m/z 558/560 (M+H)+.

Example 81

N-(3-Bromo-phenyl)-4-(3-hydroxy-phenylsulfanyl)-3-(pyrido[2,3-d]pyrimidin-4-ylamino)-benzamide The product of Example 79B was reacted with the product of Example 29A using the procedure of Example 79C substituting the product of Example 29A for the product of Example 8E to provide the crude title compound which was purified by HPLC with TFA to provide the title compound as a trifluoroacetic acid salt (44 mg, 45%). 1H NMR (300 MHz, DMSO-D6) δ ppm: 6.70 (dd, J=8.09, 1.84 Hz, 1 H), 6.75 (s, 1 H), 6.81 (d, J=7.72 Hz, 1 H), 7.14 (t, J=7.91 Hz, 1 H), 7.26-7.38 (m, 3 H), 7.72-7.77 (m, 1 H), 7.79 (d, J=6.62 Hz, 1 H), 7.88 (d, J=6.25 Hz, 1 H), 8.01 (s, 1 H), 8.08 (s, 1 H), 8.71 (s, 1 H), 8.94 (s, 1 H), 9.10 (s, 1 H), 9.71 (s, 1 H), 10.41 (s, 1 H), 11.08 (s, 1 H): MS (ESI+) m/z 544/546 (M+H)+.

Example 82

4-(3-Hydroxy-phenylsulfanyl)-3-(7-isopropyl-pyrido[2,3-d]pyrimidin-4-ylamino)-N-phenyl-benzamide

Example 82A

3-Amino-4-(3-hydroxy-phenylsulfanyl)-N-phenyl-benzamide

To 4-Chloro-3-nitro-N-phenyl-benzamide from Example 73A was reacted using the procedures from Examples 81A and 81B to provide the title product.

Example 82B 4-(3-Hydroxy-phenylsulfanyl)-3-(7-isopropyl-pyrido[2,3-d]pyrimidin-4-ylamino)-N-phenyl-benzamide The product of Example 82A was reacted with the product of Example 8E using the procedure of Example 79C substituting the product of Example 82A for the product of Example 79B to provide the crude title compound which was purified by HPLC with TFA to provide the title compound as a trifluoroacetic acid salt (52 mg, 45%). 1H NMR (300 MHz, DMSO-D6) δ ppm: 1.35 (d, J=6.62 Hz, 6 H), 3.21-3.34 (m, 1 H), 6.69 (dd, J=7.54, 2.02 Hz, 1 H), 6.74 (t, J=1.84 Hz, 1 H), 6.80 (d, J=8.09 Hz, 1 H), 7.12 (q, J=7.60 Hz, 2 H), 7.28-7.39 (m, 3 H), 7.71-7.83 (m, 3 H), 7.91 (d, J=7.72 Hz, 1 H), 8.02 (s, 1 H), 8.72 (s, 1 H), 8.91 (d, J=8.46 Hz, 1 H), 9.71 (s, 1 H), 10.30 (s, 1 H), 11.18 (s, 1 H); MS (ESI+) m/z 508 (M+H)+.

Example 83

4-(3-Hydroxy-phenylsulfanyl)-3-(7-methyl-pyrido[2,3-d]pyrimidin-4-ylamino)-N-phenyl-benzamide The product of Example 82B was reacted with the product of Example 9B using the procedure of Example 79C substituting the product of Example 82B for the product of Example 79B and substituting the product of Example 9B for the product of Example 8E to provide the crude title compound which was purified by HPLC with TFA to provide the title compound as a trifluoroacetic acid salt (25 mg, 21%). 1H NMR (300 MHz, DMSO-D6) δ ppm: 2.74 (s, 3 H), 6.69 (dd, J=7.91, 2.02 Hz, 1 H), 6.74 (t, J=2.02 Hz, 1 H), 6.79 (d, J=7.72 Hz, 1 H), 7.07-7.17 (m, 2 H), 7.33 (d, J=3.31 Hz, 1 H), 7.36 (s, 1 H), 7.37 (d, J=4.04 Hz, 1 H), 7.76 (t, J=8.27 Hz, 3 H), 7.94 (d, J=8.09 Hz, 1 H), 8.03 (s, 1 H), 8.79 (s, 1 H), 8.90 (d, J=8.46 Hz, 1 H), 9.72 (s, 1 H), 10.31 (s, 1 H), 11.44 (s, 1 H); MS (ESI+) m/z 480 (M+H)+.

Example 84

N-(4-Bromo-phenyl)-4-(3-hydroxy-phenylsulfanyl)-3-(7-isopropyl-pyrido[2,3-d]pyrimidin-4-ylamino)-benzamide

Example 84A

3-Amino-N-(4-bromo-phenyl)-4-(3-hydroxy-phenylsulfanyl)-benzamide

To the product from Example 10A was reacted using the procedures from Examples 81A and 81B to provide the title product.

Example 84B

N-(4-Bromo-phenyl)-4-(3-hydroxy-phenylsulfanyl)-3-(7-isopropyl-pyrido[2,3-d]pyrimidin-4-ylamino)-benzamide The product of Example 84A was reacted with the product of Example 8E using the procedure of Example 79C substituting the product of Example 84A for the product of Example 79B to provide the crude title compound which was purified by HPLC with TFA to provide the title compound as a trifluoroacetic acid salt (33 mg, 31%). 1H NMR (300 MHz, DMSO-D6) δ ppm: 1.35 (d, J=6.62 Hz, 6 H), 3.22-3.34 (m, 1 H), 6.69 (dd, J=7.91, 2.02 Hz, 1 H), 6.74 (t, J=2.02 Hz, 1 H), 6.80 (d, J=8.09 Hz, 1 H), 7.12 (t, J=7.91 Hz, 1 H), 7.34 (d, J=8.09 Hz, 1 H), 7.48-7.58 m, 2 H), 7.70-7.79 (m, 2 H), 7.84 (d, J=8.46 Hz, 1 H), 7.93 (d, J=8.46 Hz, 1 H), 8.01 (s, 1 H), 8.78 (s, 1 H), 8.94 (d, J=8.46 Hz, 1 H), 9.72 (s, 1 H), 10.43 (s, 1 H), 11.43 (s, 1 H); MS (ESI+) m/z 586/588 (M+H)+.

Example 85

N-(4-Bromo-phenyl)-4-(3-hydroxy-phenylsulfanyl)-3-(7-methyl-pyrido[2,3-d]pyrimidin-4-ylamino)-benzamide The product of Example 84A was reacted with the product of Example 9B using the procedure of Example 79C substituting the product of Example 84A for the product of Example 79B and substituting the product of Example 9B for the product of Example 8E to provide the crude title compound which was purified by HPLC with TFA to provide the title compound as a trifluoroacetic acid salt (28 mg, 28%). 1H NMR (300 MHz, DMSO-D6) δ ppm: 2.73 (s, 3 H), 6.70 (dd, J=7.72, 2.21 Hz, 1 H), 6.74 (t, J=1.84 Hz, 1 H), 6.80 (d, J=7.72 Hz, 1 H), 7.13 (t, J=7.91 Hz, 1 H), 7.33 (d, J=8.09 Hz, 1 H), 7.51-7.58 (m, 2 H), 7.70-7.78 (m, 3 H), 7.91 (d, J=8.09 Hz, 1 H), 8.02 (s, 1 H), 8.75 (s, 1 H), 8.88 (d, J=8.09 Hz, 1 H), 9.72 (s, 1 H), 10.42 (s, 1 H), 11.31 (s, 1 H); MS (ESI+) m/z 558/560 (M+H)+.

Example 86

4-(4-Amino-phenoxy)-3-(7-isopropyl-pyrido[2,3-d]pyrimidin-4-ylamino)-N-p-tolyl-benzamide

Example 86A

4-Fluoro-3-nitro-benzoyl chloride

To a solution of 4-Fluoro-3-nitro-benzoic acid (1.00 g, 5.40 mmol) dissolved in 1,2-dichloroethane (30 mL) was added SOCl₂ (6.42 g, 54.0 mmol). The reaction mixture was then heated to 80° C. for 16 hrs. At this time the reaction mixture was cooled to room temperature and the solvent removed under vacuum to provide the title product.

Example 86B

4-Fluoro-3-nitro-N-p-tolyl-benzamide

To a solution of p-Tolylamine (626 mg, 5.89 mmol), and Hunig's base (2.054 ml, 11.8 mmol) in tetrahydrofuran (20 mL) was added the product from Example 86A (1.20 g, 5.89 mmol) in tetrahydrofuran (10 mL) dropwise over 10 minutes. The solution was stirred at room temperature for 1 hour, the reaction mixture diluted with water and the title compound was collected by filtration (1.77 g, 100%).

Example 86C

[4-(2-nitro-4-p-tolylcarbamoyl-phenoxy)-phenyl]-carbamic acid tert-butyl ester

To the product from Example 86B (1.77 g, 5.45 mmol), KOH (736 mg, 12.9 mmol), and (4-Hydroxy-phenyl)-carbamic acid tert-butyl ester (1.35 g, 6.45 mmol) were dissolved in DMSO and heated to 80° C. for 2 hrs. At this time the reaction mixture was cooled to room temperature and diluted with water. The title compound was then collected by filtration (380 mg, 12.7%).

Example 86D

[4-(2-Amino-4-p-tolylcarbamoyl-phenoxy)-phenyl]-carbamic acid tert-butyl ester

The product from Example 86C (380 mg, 0.819 mmol) was reduced according to the procedure of Example 10C to provide the title product (321 mg, 90%).

Example 86E

{4-[2-(7-Isopropyl-pyrido[2,3-d]pyrimidin-4-ylamino)-4-p-tolylcarbamoyl-phenoxy]-phenyl}-carbamic acid tert-butyl ester A solution of the product of Example 8E (160.0 mg, 0.739 mmol), and the product of Example 86D (321.0 mg, 0.739 mmol) in acetic acid (1 mL) was stirred in an oil bath preheated to 130° C. for 10 minutes. The mixture was then cooled to room temperature, and the acetic acid removed under vacuum to provide the title product (305 mg, 64%).

Example 86F 4-(4-Amino-phenoxy)-3-(7-isopropyl-pyrido[2,3-d]pyrimidin-4-ylamino)-N-p-tolyl-benzamide The product of Example 86E (305 mg, 0.504 mmol) was dissolved in dichloromethane (5 mL) and trifluoroacetic acid (2 mL). The solution was stirred at room temperature for 1 hour at which time the solvent was removed on the under vacuum. The resultant residue was purified by HPLC with TFA to provide the title compound as a trifluoroacetic acid salt (35 mg, 14%). $^1$H NMR (300 MHz, DMSO-D$_6$) δ ppm: 1.34 (d, J=6.99 Hz, 6 H), 2.28 (s, 3 H), 3.28 (qt, J=13.70, 6.94 Hz, 1 H), 6.82-6.88 (m, 2 H), 6.91-6.99 (m, 3 H), 7.16 (d, J=8.46 Hz, 2 H), 7.63 (d, J=8.46 Hz, 2 H), 7.86 (d, J=8.46 Hz, 1 H), 7.98 (dd, J=8.46, 2.21 Hz, 1 H), 8.13 (d, J=2.21 Hz, 1 H), 8.87 (s, 1 H), 8.98 (d, J=8.46 Hz, 1 H), 10.17 (s, 1 H); MS (ESI+) m/z 505 (M+H-TFA)+; (ESI−) m/z 503 (M−H-TFA)−.

Example 87

4-(4-Amino-phenoxy)-N-(4-fluoro-3-methyl-phenyl)-3-(7-isopropyl-pyrido[2,3-d]pyrimidin-4-ylamino)-benzamide

Example 87A

{4-[2-Amino-4-(4-fluoro-3-methyl-phenylcarbamoyl)-phenoxy]-phenyl}-carbamic acid tert-butyl ester A mixture of the product from Example 86A was reacted with 4-Fluoro-3-methyl-phenylamine to produce 4-Fluoro-N-(4-fluoro-3-methyl-phenyl)-3-nitro-benzamide according to the procedure of Example 86B, which was treated sequentially using the procedures from Examples 86C and 395D to provide the title product.

Example 87B 4-(4-Amino-phenoxy)-N-(4-fluoro-3-methyl-phenyl)-3-(7-isopropyl-pyrido[2,3-d]pyrimidin-4-ylamino)-benzamide The product of Example 87A was reacted with the product of Example 8E using the procedure of Example 86E substituting the product of Example 87A for the product of Example 86D to provide {4-[4-(4-Fluoro-3-methyl-phenylcarbamoyl)-2-(7-isopropyl-pyrido[2,3-d]pyrimidin-4-ylamino)-phenoxy]-phenyl}-carbamic acid tert-butyl ester which was reacted using the procedure of Example 86F to provide a residue which was purified by HPLC with TFA to provide the title compound as a trifluoroacetic acid salt (20 mg, 11%). 1H NMR (300 MHz, DMSO-D6) δ ppm: 1.34 (d, J=6.62 Hz, 6 H), 2.24 (s, 3 H), 3.21-3.37 (m, J=13.79, 7.17, 6.99 Hz, 1 H), 6.84-7.00 (m, 5 H), 7.12 (t, J=9.19 Hz, 1 H), 7.54-7.59 (m, 1 H), 7.66 (dd, J=6.80, 2.39 Hz, 1 H), 7.86 (d, J=8.46 Hz, 1 H), 7.98 (dd, J=8.82, 2.21 Hz, 1 H), 8.13 (d, J=2.21 Hz, 1 H), 8.88 (s, 1 H), 8.98 (d, J=8.46 Hz, 1 H), 10.23 (s, 1 H); MS (ESI+) m/z 523 (M+H-TFA)+; (ESI−) m/z 521 (M−H-TFA)−.

Example 88

4-(4-Amino-phenoxy)-3-(7-isopropyl-pyrido[2,3-d]pyrimidin-4-ylamino)-N-(3-trifluoromethyl-phenyl)-benzamide

Example 88A

{4-[2-Amino-4-(3-trifluoromethyl-phenylcarbamoyl)-phenoxy]-phenyl}-carbamic acid tert-butyl ester A mixture of the product from Example 86A was reacted with 3-Trifluoromethyl-phenylamine to produce 4-Fluoro-3-nitro-N-(3-trifluoromethyl-phenyl)-benzamide according to the procedure of Example 86B, which was treated sequentially using the procedures from Examples 86C and 86D to provide the title product.

Example 88B 4-(4-Amino-phenoxy)-3-(7-isopropyl-pyrido[2,3-d]pyrimidin-4-ylamino)-N-(3-trifluoromethyl-phenyl)-benzamide The product of Example 88A was reacted with the product of Example 8E using the procedure of Example 86E substituting the product of Example 88A for the product of Example 86D to provide {4-[2-(7-Isopropyl-pyrido[2,3-d]pyrimidin-4-ylamino)-4-(3-trifluoromethyl-phenylcarbamoyl)-phenoxy]-phenyl}-carbamic acid tert-butyl ester which was reacted using the procedure of Example 86F to provide a residue which was purified by HPLC with TFA to provide the title compound as a trifluoroacetic acid salt (55 mg, 23%). 1H NMR (300 MHz, DMSO-D6) δ ppm: 1.34 (d, J=6.99 Hz, 6 H), 3.22-3.35 (m, 1 H), 6.79-7.11 (m, 6 H), 7.47 (d, J=7.72 Hz, 1 H), 7.61 (t, J=8.09 Hz, 1 H), 7.87 (d, J=8.82 Hz, 1 H), 7.99-8.10 (m, 2 H), 8.17 (d, J=2.21 Hz, 1 H), 8.23 (s, 1 H), 8.88 (s, 1 H), 8.99 (d, J=8.82 Hz, 1 H), 10.57 (s, 1 H); MS (ESI+) m/z 559 (M+H-TFA)+; (ESI−) m/z 557 (M−H-TFA)−.

Example 89

N-(4-Bromo-phenyl)-4-(1H-indol-5-ylsulfanyl)-3-(7-isopropyl-pyrido[2,3-d]pyrimidin-4-ylamino)-benzamide

Example 89A

5-Iodo-indole-1-carboxylic acid tert-butyl ester

A solution of 5-iodoindole (2.00 g, 8.229 mmol) in dry methylene chloride (40 mL) was treated with di-tert-butyl dicarbonate (2.155 g, 9.875 mmol) and 4-dimethylaminopyridine (201 mg, 1.646 mmol) at room temperature and the solution was stirred at room temperature for 16 hours. The solvent was removed by rotary evaporation under vacuum and the residue purified by silica gel flash chromatography with 1:1 hexanes/methylene chloride to provide the title compound as a light pink oil (2.57 g, 91%).

Example 89B

5-Triisopropylsilanylsulfanyl-indole-1-carboxylic acid tert-butyl ester

A solution of the product of Example 89A (200 mg, 0.583 mmol) in anhydrous tetrahydrofuran (4 mL) under a nitrogen atmosphere was treated with [1,1'-bis(diphenylphosphino)ferrocene]dichloropalladium methylene chloride complex (5 mg) and the solution was sparged with nitrogen for several minutes. Potassium triisopropylsilanethiolate (146.5 mg, 0.6411 mmol), prepared according to *Tetrahedron Letters* 35 (20) 3221 1994, was added and the reaction was heated at reflux for 15 minutes. The reaction was cooled to room temperature and the solvent removed by rotary evaporation under vacuum to provide the title compound as a colorless oil (210 mg, 89%).

Example 89C

5-Mercapto-indole-1-carboxylic acid tert-butyl ester

A solution of the product of Example 89B (203.7 mg, 0.502 mmol) in anhydrous tetrahydrofuran (4 mL) at −20° under a nitrogen atmosphere was treated with a 1M solution of tetrabutylammonium fluoride in tetrahydrofuran (0.552 mL, 0.552 mmol) and the reaction stirred at −20° for 15 minutes. The reaction was diluted with ethyl acetate (50 mL) and washed with water (2×25 mL) and brine (25 mL). The organic was dried over anhydrous magnesium sulfate, filtered, and concentrated by rotary evaporation under vacuum to provide a yellow oil. Purification by silica gel flash chromatography using 5% ethyl acetate/hexanes as eluent afforded the title compound (42 mg, 33%).

Example 89D

5-[4-(4-Bromo-phenylcarbamoyl)-2-nitro-phenylsulfanyl]-indole-1-carboxylic acid tert-butyl ester A solution of the product of Example 89C (39.9 mg, 0.160 mmol) in anhydrous ethanol (2 mL) under a nitrogen atmosphere was treated with the product of Example 10A (56.8 mg, 0.160 mmol) and anhydrous sodium acetate (66 mg, 0.800 mmol) at room temperature, then heated at reflux for 2 hours. The reaction was cooled to room temperature and the solvent removed by rotary evaporation under vacuum. The residue was taken up in ethyl acetate (50 mL) and washed with water (2×25 mL) and brine (25 mL). The organic phase was dried over anhydrous sodium sulfate, filtered, and concentrated under vacuum. Purification by silica gel flash chromatography using methylene chloride as eluent afforded the title compound as a yellow solid (77 mg, 85%).

Example 89E

5-[2-Amino-4-(4-bromo-phenylcarbamoyl)-phenylsulfanyl]-indole-1-carboxylic acid tert-butyl ester A suspension of the product of Example 89D (75 mg, 0.132 mmol), iron powder (45.3 mg, 0.811 mmol), and ammonium chloride (46 mg, 0.864 mmol) in water (1 mL) and ethanol (2 mL) was heated at 95° for 30 minutes. The reaction was cooled to room temperature, diluted with ethyl acetate (50 mL), and washed with water (2×25 mL) and brine (25 mL). The organic phase was dried over anhydrous sodium sulfate, filtered, and concentrated by rotary evaporation under vacuum to afford the title compound as a yellow solid (65 mg, 92%).

Example 89F

N-(4-Bromo-phenyl)-4-(1H-indol-5-ylsulfanyl)-3-(7-isopropyl-pyrido[2,3-d]pyrimidin-4-ylamino)-benzamide A solution of the product of Example 8E (25 mg, 0.116 mmol) and the product of Example 89E (62.6 mg, 0.116 mmol) in acetic acid (2 mL) was stirred in an oil bath preheated to 140° C. for 1 hour. The reaction was cooled to room temperature, diluted with hexanes (50 mL), concentrated by rotary evaporation, and co-evaporated with methylene chloride/hexanes (4×). The residue was dried under vacuum, then purified by silica gel flash chromatography using 4% methanol/methylene chloride to provide the title compound (11 mg, 16%). $^1$H NMR (300 MHz, DMSO-D6) δ ppm: 1.35 (d, J=6.62 Hz, 6 H) 3.16-3.30 (m, 1 H) 6.44-6.53 (m, 1 H) 6.89 (d, J=8.46 Hz, 1 H) 7.15 (dd, J=8.46, 1.47 Hz, 1 H) 7.42-7.46 (m, 1 H) 7.46-7.55 (m, 3 H) 7.65 (d, J=8.46 Hz, 1 H) 7.69-7.78 (m, 4 H) 7.98 (d, J=1.47 Hz, 1 H) 8.61 (s, 1 H) 8.90 (d, J=8.82 Hz, 1 H) 10.22 (s, 1 H) 10.29 (s, 1 H) 11.38 (s, 1 H); MS (ESI+) m/z 609/611 (M+H)$^+$.

Example 90

4-(4-Azido-phenylsulfanyl)-N-(4-bromo-phenyl)-3-(7-isopropyl-pyrido[2,3-d]pyrimidin-4-ylamino)-benzamide A solution of the product of Example 13E (62.4 mg, 0.1066 mmol) in concentrated hydrochloric acid (2 mL) cooled to 0°-5° was treated dropwise with a solution of sodium nitrite (14.7 mg, 0.2131 mmol) in water (1 mL). After stirring at 0° for 1 hour, a solution of sodium azide (13.8 mg, 0.2131 mmol) and sodium acetate (72.6 mg, 0.885 mmol) in water (2 mL) was added dropwise at 0°, and the reaction stirred for 1 hour at 0°. The reaction was then diluted with water (25 mL) and ethyl acetate (50 mL), the aqueous pH was adjusted to 7-8 with 6N aqueous sodium hydroxide, the layers were separated, and the organic phase washed with brine (25 mL). The organic was dried over anhydrous sodium sulfate, filtered, and concentrated by rotary evaporation under vacuum. The resultant residue was purified by silica gel flash chromatography using 30% ethyl acetate/methylene chloride as eluent to afford the title compound as a yellow solid (21 mg, 32%). $^1$H NMR (300 MHz, DMSO-D6) δ ppm: 1.34 (d, J=6.62 Hz, 6 H) 3.11-3.32 (m, 1 H) 7.10 (d, J=8.46 Hz, 2 H) 7.21 (d, J=8.46 Hz, 1 H) 7.41 (d, J=8.46 Hz, 2 H) 7.53 (d, J=8.82 Hz, 2 H) 7.63 (d, J=8.46 Hz, 1 H) 7.74 (d, J=9.19 Hz, 2 H) 7.81-7.91 (m, 1 H) 8.03 (d, J=1.10 Hz, 1 H) 8.58 (s, 1 H) 8.82 (d, J=8.46 Hz, 1 H) 10.23 (s, 1 H) 10.39 (s, 1 H); MS (ESI+) m/z 611/613 (M+H)$^+$.

Example 91

N-(4-Bromo-phenyl)-3-(7-isopropyl-pyrido[2,3-d]pyrimidin-4-ylamino)-4-(4-methanesulfonylamino-phenoxy)-benzamide

Example 91A 4-(4-Amino-phenoxy)-N-(4-bromo-phenyl)-3-nitro-benzamide

A solution of the product of Example 10B (250 mg, 0.4732 mmol) in methylene chloride (5 mL) was treated with trifluoroacetic acid (5 mL) at room temperature for 30 minutes. The solvents were removed by rotary evaporation under vacuum, and the residue taken up in ethyl acetate (100 mL) and washed with saturated aqueous sodium hydrogen carbonate (2×50 mL), water (50 mL), and brine (50 mL). The organic phase was dried over anhydrous sodium sulfate, filtered, and concentrated under vacuum to provide the title compound as a light orange solid (197 mg, 97%).

Example 91B

N-(4-Bromo-phenyl)-4-(4-methanesulfonylamino-phenoxy)-3-nitro-benzamide

The product of Example 91A (195 mg, 0.4554 mmol) was dissolved in anhydrous pyridine (5 mL) under a nitrogen atmosphere, treated with methanesulfonyl chloride (0.106 mL, 1.366 mmol), and stirred at room temperature for 19 hours. The solvent was removed by rotary evaporation under vacuum, and the residue dissolved in ethyl acetate (100 mL) and washed with 1N aqueous hydrochloric acid (2×50 mL), water (50 mL), and brine (50 mL). The organic phase was dried over anhydrous sodium sulfate, filtered, and concentrated under vacuum to afford the title compound as a light orange solid (225 mg, 98%).

Example 91C

3-Amino-N-(4-bromo-phenyl)-4-(4-methanesulfonylamino-phenoxy)-benzamide

A suspension of the product of Example 91B (223 mg, 0.4404 mmol) and iron powder (98 mg, 1.762 mmol) in acetic acid (5 mL) and ethanol (5 mL) was heated at reflux under a nitrogen atmosphere for 30 minutes. The reaction was cooled to room temperature, diluted with water (50 mL), and treated with solid sodium carbonate until the pH was 6. Extracted with ethyl acetate (100 mL), washed the organic with brine (50 mL), dried over anhydrous sodium sulfate, filtered, and concentrated by rotary evaporation under vacuum. Co-evaporating the resulting oil with methylene chloride/hexanes gave the title compound as a light tan solid (195 mg, 93%).

Example 91D

N-(4-Bromo-phenyl)-3-(7-isopropyl-pyrido[2,3-d]pyrimidin-4-ylamino)-4-(4-methanesulfonylamino-phenoxy)-benzamide A solution of the product of Example 8E (22.7 mg, 0.105 mmol) and the product of Example 91C (50 mg, 0.105 mmol) in acetic acid (2 mL) was stirred in an oil bath preheated to 140° C. for 40 minutes. The reaction was cooled to room temperature, diluted with hexanes (50 mL), concentrated by rotary evaporation under vacuum, and co-evaporated with methylene chloride/hexanes (4×). The residue was dried under vacuum, then purified by silica gel flash chromatography using 5% methanol/methylene chloride as eluent to provide the title compound as a white solid (42 mg, 62%). $^1$H NMR (300 MHz, DMSO-D6) δ ppm: 1.31 (d, J=6.62 Hz, 6 H) 2.88 (s, 3 H) 3.12-3.28 (m, 1 H) 7.00 (d, J=8.82 Hz, 2 H) 7.06 (d, J=8.46 Hz, 1 H) 7.16 (d, J=8.82 Hz, 2 H) 7.48-7.61 (m, 3 H) 7.76 (d, J=8.82 Hz, 2 H) 7.91 (dd, J=8.82, 1.10 Hz, 1 H) 8.18 (s, 1 H) 8.59 (s, 1 H) 8.75 (d, J=8.46 Hz, 1 H) 9.62 (s, 1 H) 10.03 (s, 1 H) 10.36 (s, 1 H); MS (ESI+) m/z 647/649 (M+H)$^+$.

Example 92

4-(1H-Benzoimidazol-5-yloxy)-N-(4-bromo-phenyl)-3-(7-isopropyl-pyrido[2,3-d]pyrimidin-4-ylamino)-benzamide

Example 92A

1H-Benzoimidazol-5-ol

A solution of 5-methoxybenzimidazole (500 mg, 3.374 mmol) in 48% hydrobromic acid (10 mL) was refluxed for 2 hours. The reaction was cooled to room temperature, the solvent removed by rotary evaporation under vacuum, and the residue azeotroped with toluene (50 mL) to provide the title compound as a tan solid (701 mg, 96%).

Example 92B

5-Hydroxy-benzoimidazole-1-carboxylic acid tert-butyl ester

A suspension of the product of Example 92A (200 mg, 0.930 mmol) in anhydrous 1,4-dioxane (6 mL) under a nitrogen atmosphere was treated with diisopropylethylamine (0.179 mL, 1.023 mmol) and di-tert-butyl dicarbonate (223 mg, 1.023 mmol) at room temperature, and the reaction was then heated at 80° for 1 hour. The reaction was cooled to room temperature and the solvent removed by rotary evaporation under vacuum. Purification of the residue by silica gel flash chromatography using 3% methanol/methylene chloride as eluent afforded the 6-hydroxy isomer (79 mg, 36%) and the 5-hydroxy title compound (79 mg, 36%).

Example 92C

5-[4-(4-Bromo-phenylcarbamoyl)-2-nitro-phenoxy]-benzoimidazole-1-carboxylic acid tert-butyl ester The products of Example 10A (117.5 mg, 0.331 mmol) and Example 92B (77.5 mg, 0.331 mmol) were dissolved in anhydrous N,N-dimethylformamide (3 mL), treated with potassium carbonate (91.5 mg, 0.662 mmol), and heated at 80° under a nitrogen atmosphere for 30 minutes. The reaction was cooled to room temperature and the solvent removed by rotary evaporation under vacuum. Purification by silica gel chromatography using methanol/methylene chloride as eluent provided the title compound as a light yellow foam (85 mg, 46%).

Example 92D

5-[2-Amino-4-(4-bromo-phenylcarbamoyl)-phenoxy]-benzoimidazole-1-carboxylic acid tert-butyl ester The product of Example 92C was reacted using the procedure of Example 89E to provide the title product (24 mg, 30%).

Example 92E 4-(1H-Benzoimidazol-5-yloxy)-N-(4-bromo-phenyl)-3-(7-isopropyl-pyrido[2,3-d]pyrimidin-4-ylamino)-benzamide A solution of the product of Example 8E (9.3 mg, 0.043 mmol) and the product of Example 92D (22.6 mg, 0.043 mmol) in acetic acid (1 mL) was stirred in an oil bath preheated to 140° C. for 30 minutes. The reaction was cooled to room temperature, diluted with hexanes (50 mL), concentrated by rotary evaporation, and co-evaporated with methylene chloride/hexanes (4×). The residue was dried under vacuum and purified by HPLC with TFA to afford the title compound as a trifluoroacetic acid salt (17 mg, 48%). $^1$H NMR (300 MHz, DMSO-D6) δ ppm: 1.31 (d, J=6.99 Hz, 6 H) 3.11-3.30 (m, 1 H) 7.03 (d, J=8.46 Hz, 2 H) 7.28 (d, J=2.21 Hz, 1 H) 7.54 (d, J=8.82 Hz, 2 H) 7.61 (d, J=8.82 Hz, 1 H) 7.65 (d, J=8.46 Hz, 1 H) 7.76 (d, J=8.82 Hz, 2 H) 7.92 (dd, J=8.64, 2.02 Hz, 1 H) 8.17 (d, J=1.10 Hz, 1 H) 8.47 (s, 1 H) 8.69 (s, 1 H) 8.81 (d, J=8.46 Hz, 1 H) 10.36 (s, 1 H) 10.55 (br s, 1 H); MS (ESI+) m/z 594/596 (M+H)$^+$.

Example 93

N-(4-Bromo-phenyl)-4-(1H-indol-5-yloxy)-3-(7-isopropyl-pyrido[2,3-d]pyrimidin-4-ylamino)-benzamide Example 93A 5-Benzyloxy-indole-1-carboxylic acid tert-butyl ester A solution of 5-benzyloxyindole (500 mg, 2.24 mmol) in anhydrous methylene chloride was treated with di-tert-butyl dicarbonate (586.5 mg, 2.69 mmol) and 4-dimethylaminopyridine (55 mg, 0.448 mmol), and the reaction was stirred at room temperature under a nitrogen atmosphere for 15 hours. The solvent was removed by rotary evaporation and the residue purified by silica gel flash chromatography using methylene chloride as eluent to provide the title compound as a colorless oil (682 mg, 94%).

Example 93B

5-Hydroxy-indole-1-carboxylic acid tert-butyl ester

A solution of the product of Example 93A (680 mg, 2.103 mmol) in ethanol (20 mL) was treated with 10% palladium-on-carbon (68 mg) and ammonium formate (265 mg, 4.205 mmol), and stirred at room temperature under a nitrogen atmosphere for 1 hour. The reaction was filtered through a 0.45 μ PTFE membrane and the catalyst washed with methanol. The filtrate was concentrated by rotary evaporation under vacuum and the residue taken up in ethyl acetate (50 mL), washed with water (2×25 mL) and brine (25 mL), dried over anhydrous sodium sulfate, filtered, and concentrated under vacuum to provide the title compound as a white solid (475 mg, 96%).

Example 93C

5-[4-(4-Bromo-phenylcarbamoyl)-2-nitro-phenoxy]-indole-1-carboxylic acid tert-butyl ester The products of Example 10A (406.5 mg, 1.145 mmol) and Example 93B (267 mg, 1.145 mmol) were dissolved in anhydrous N,N-dimethylformamide (8 mL), treated with potassium carbonate (316 mg, 2.289 mmol), and heated at 800 under a nitrogen atmosphere for 3 hours. The reaction was cooled to room temperature and the solvent removed by rotary evaporation under vacuum. The residue was taken up in water (50 mL) and extracted with ethyl acetate (2×50 mL). The combined organic extracts were washed with brine (25 mL), dried over anhydrous sodium sulfate, filtered, and concentrated by rotary evaporation under vacuum. Purification by silica gel flash chromatography using 1% ethyl acetate/methylene chloride as eluent provided the title compound as a yellow foam (519 mg, 82%).

Example 93D

5-[2-Amino-4-(4-bromo-phenylcarbamoyl)-phenoxy]-indole-1-carboxylic acid tert-butyl ester The product of Example 93C (517 mg, 0.936 mmol), iron powder (322 mg, 5.76 mmol), and ammonium chloride (328 mg, 6.13 mmol) in water (3 mL) and ethanol (6 mL) were heated at 90° for 30 minutes. The hot reaction mixture was vacuum filtered and the residue washed with methanol and ethyl acetate. The filtrate was concentrated by rotary evaporation under vacuum, the residue partitioned with water (50 mL) and ethyl acetate (100 mL), and the organic phase washed with water (2×50 mL) and brine (50 mL). The organic phase was dried over anhydrous sodium sulfate, filtered, and concentrated by rotary evaporation under vacuum to provide the title compound as an off-white foam (325 mg, 66%).

Example 93E

N-(4-Bromo-phenyl)-4-(1H-indol-5-yloxy)-3-(7-isopropyl-pyrido[2,3-d]pyrimidin-4-ylamino)-benzamide A solution of the product of Example 8E (20.7 mg, 0.0957 mmol) and the product of Example 93D (50 mg, 0.0957 mmol) in acetic acid (2 mL) was stirred in an oil bath preheated to 140° C. for 30 minutes. The reaction was cooled to room temperature, diluted with hexanes (50 mL), concentrated by rotary evaporation, and co-evaporated with methylene chloride/hexanes (4×). The residue was dried under vacuum, then purified by silica gel flash chromatography using 2% methanol/methylene chloride as eluent to afford the title compound as an off-white solid (29 mg, 51%). $^1$H NMR (300 MHz, DMSO-D6) δ ppm: 1.31 (d, J=6.99 Hz, 6 H) 3.11-3.29 (m, 1 H) 6.34-6.45 (m, 1 H) 6.81-6.90 (m, 2 H) 7.24

(d, J=2.21 Hz, 1 H) 7.35-7.44 (m, 2 H) 7.53 (d, J=8.82 Hz, 2 H) 7.58 (d, J=8.46 Hz, 1 H) 7.76 (d, J=8.82 Hz, 2 H) 7.84 (dd, J=8.46, 1.47 Hz, 1 H) 8.19 (d, J=1.47 Hz, 1 H) 8.65 (s, 1 H) 8.83 (d, J=8.46 Hz, 1 H) 10.05 (s, 1 H) 10.30 (s, 1 H) 11.16 (s, 1 H); MS (APCI+) m/z 593/595 (M+H)$^+$.

Example 94

N-(4-Bromo-phenyl)-3-(7-isopropyl-pyrido[2,3-d]
pyrimidin-4-ylamino)-4-(4-methanesulfonylamino-
phenylsulfanyl)-benzamide Example 94A N-(4-Bromo-phenyl)-4-(4-methanesulfonylamino-
phenylsulfanyl)-3-nitro-benzamide The product of Example 13A (200 mg, 0.4501 mmol) was dissolved in anhydrous pyridine (4 mL) under a nitrogen atmosphere, treated with methanesulfonyl chloride (0.084 mL, 1.080 mmol), and stirred at room temperature for 19 hours. The solvent was removed by rotary evaporation under vacuum, and the residue dissolved in methylene chloride (100 mL) and washed with 1N aqueous hydrochloric acid (2×50 mL). The organic phase was dried over anhydrous sodium sulfate, filtered, and concentrated under vacuum to afford the title compound as a yellow solid (233 mg, 99%).

Example 94B

3-Amino-N-(4-bromo-phenyl)-4-(4-methanesulfony-
lamino-phenylsulfanyl)-benzamide A suspension of the product of Example 94A was reacted using the procedure of Example 89E to provide the title product (201 mg, 92%).

Example 94C

N-(4-Bromo-phenyl)-3-(7-isopropyl-pyrido[2,3-d]
pyrimidin-4-ylamino)-4-(4-methanesulfonylamino-
phenylsulfanyl)-benzamide A solution of the product of Example 8E (21 mg, 0.098 mmol) and the product of Example 94B (48.1 mg, 0.098 mmol) in acetic acid (2 mL) was stirred in an oil bath preheated to 140° C. for 1 hour. The reaction was cooled to room temperature, diluted with hexanes (50 mL), concentrated by rotary evaporation, and co-evaporated with methylene chloride/hexanes (4×). The residue was dried under vacuum, then purified by silica gel flash chromatography using 3% methanol/methylene chloride as eluent to provide the title compound as a light yellow solid (24 mg, 37%). $^1$H NMR (300 MHz, DMSO-D6) δ ppm: 1.34 (d, J=6.62 Hz, 6 H) 3.04 (s, 3 H) 3.15-3.30 (m, 1 H) 7.11 (d, J=8.09 Hz, 1 H) 7.22 (d, J=8.82 Hz, 2 H) 7.40 (d, J=8.46 Hz, 2 H) 7.53 (d, J=8.82 Hz, 2 H) 7.64 (d, J=8.46 Hz, 1 H) 7.74 (d, J=9.19 Hz, 2 H) 7.83 (dd, J=9.01, 0.92 Hz, 1 H) 8.00 (s, 1 H) 8.59 (s, 1 H) 8.85 (d, J=8.46 Hz, 1 H) 10.03 (s, 1 H) 10.23 (s, 1 H) 10.35 (s, 1 H); MS (APCI+) m/z 663/665 (M+H)$^+$.

Example 95

{3-[4-(3-Bromo-phenylcarbamoyl)-2-(7-isopropyl-
pyrido[2,3-d]pyrimidin-4-ylamino)-phenylsulfanyl]-
phenyl}-carbamic acid tert-butyl ester Example 95A 4-(3-Amino-phenylsulfanyl)-N-(3-bromo-phenyl)-3-
nitro-benzamide A solution of N-(3-Bromo-phenyl)-4-chloro-3-nitro-benzamide (from Example 26A) (2.13 g, 6.0 mmol), 3-aminothiophenol (0.75 g, 6.0 mmol) and cesium carbonate (4.0 g, 12.0 mmol) in N,N-dimethylformamide (20 mL) was heated to 95° C. for 3 hours. After cooling to room temperature the mixture was poured into ice water (100 mL) and the resultant solution adjusted to pH 6 with 1N aqueous hydrochloric acid. The solution was then extracted with ethyl acetate (3×50 mL), the combined extracts dried over sodium sulfate, filtered and concentrated under vacuum to provide the title compound (2.87 g, 99%).

Example 95B

{3-[4-(3-Bromo-phenylcarbamoyl)-2-nitro-phenyl-
sulfanyl]-phenyl}-carbamic acid tert-butyl ester A solution of the product of Example 95A (2.8 g, 6.0 mmol) and Di-tert-butyl dicarbonate (2.8 g, 12.6 mmol) in 1,4-dioxane (75 mL) was heated to 100° C. for 16 hours, cooled and concentrated under vacuum. The residue was chromatographed on silica eluting with 3:1 hexane/ethyl acetate to provide the title compound as a yellow foam, (2.87 g, 84%).

Example 95C

{3-[2-Amino-4-(3-bromo-phenylcarbamoyl)-phenyl-
sulfanyl]-phenyl}-carbamic acid tert-butyl ester A solution of the product of Example 95B (2.87 g, 5.28 mmol), iron powder (1.5 g, 26.4 mmol) and ammonium chloride (0.43 g, 8.0 mmol) in an ethanol (75 mL), tetrahydrofuran (75 mL), and water (25 mL) solution was heated to reflux for 6 hours. The resultant mixture was diluted with ethanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over sodium sulfate, filtered and concentrated under vacuum to provide the title compound as a yellow powder (2.47 g, 91%).

Example 95D

{3-[4-(3-Bromo-phenylcarbamoyl)-2-(7-isopropyl-
pyrido[2,3-d]pyrimidin-4-ylamino)-phenylsulfanyl]-
phenyl}-carbamic acid tert-butyl ester A solution of the product of Example 95C (1.03 g, 2.0 mmol) and the product of Example 8E (0.43 mg, 2.0 mmol) in acetic acid (10 mL) was stirred in a preheated 140° C. oil bath for 20 minutes. The mixture was cooled and concentrated under vacuum. The resultant residue was purified by chromatography on silica eluting with 96:4 dichloromethane/methanol to provide the title compound (0.67 g, 49%).

Example 96

4-(3-Amino-phenylsulfanyl)-N-(3-bromo-phenyl)-3-(7-isopropyl-pyrido[2,3-d]pyrimidin-4-ylamino)-benzamide To a slurry of the product of Example 95D (0.67 g, 0.98 mmol) in dichloromethane (10 mL) was added dropwise trifluoroacetic acid (5 mL). The solution was stirred for 30 minutes and concentrated under vacuum. The resultant residue was purified by HPLC with TFA to provide the title compound as a trifluoroacetic acid salt (15 mg, 35%). 1H NMR (300 MHz, DMSO-D6) δ ppm: 1.36 (d, J=6.62 Hz, 6 H), 3.22-3.33 (m, 1 H), 6.31-6.64 (m, 3 H), 6.97 (t, J=7.91 Hz, 1 H), 7.23-7.41 (m, 3 H), 7.69-7.79 (m, 1 H), 7.83 (d, J=9.56 Hz, 1 H), 7.91 (d, J=11.03 Hz, 1 H Hz, 1 H), 7.99 (s, 1 H), 8.07 (s, 1 H), 8.79 (s, 1 H), 8.95 (d, J=7.35 Hz, 1 H), 10.41 (s, 1 H), 11.40 (s, 1 H).

Example 97

Pyrrolidine-2-carboxylic acid {3-[4-(3-bromo-phenylcarbamoyl)-2-(7-isopropyl-pyrido[2,3-d]pyrimidin-4-ylamino)-phenylsulfanyl]-phenyl}-amide

Example 97A

2-{3-[4-(3-Bromo-phenylcarbamoyl)-2-(7-isopropyl-pyrido[2,3-d]pyrimidin-4-ylamino)-phenylsulfanyl]-phenylcarbamoyl}-pyrrolidine-1-carboxylic acid tert-butyl ester A mixture of the product of Example 96 (0.080 g, 0.1 mmol), L-Boc-proline (0.028 g, 0.13 mmol), N-(3-Dimethylaminopropyl)-N'-ethylcarbodiimide hydrochloride (0.025 g, 0.13 mmol), 1-Hydroxybenzotriazole hydrate (0.018 g, 0.13 mmol) and N,N-diisopropylethylamine (0.039 g, 0.3 mmol) in N,N-dimethylformamide (2 mL) was stirred for 16 hours, poured into water and extracted with ethyl acetate (3×15 mL). The combined extracts were dried over sodium sulfate, filtered and concentrated under vacuum to provide the title compound which was used without purification.

Example 97B

Pyrrolidine-2-carboxylic acid {3-[4-(3-bromo-phenylcarbamoyl)-2-(7-isopropyl-pyrido[2,3-d]pyrimidin-4-ylamino)-phenylsulfanyl]-phenyl}-amide The product from Example 97A was treated with trifluoroacetic acid following the procedure of Example 96. The crude residue was purified by HPLC with TFA to provide the title compound as a trifluoroacetic acid salt (21 mg, 23% for two steps). 1H NMR (300 MHz, DMSO-D6) δ ppm: 1.35 (d, J=6.99 Hz, 6 H), 1.90-2.04 (m, 3 H), 2.30-2.42 (m, 1 H), 3.19-3.35 (m, 3 H), 4.20-4.35 (m, 1 H), 7.16 (d, J=8.09 Hz, 1 H), 7.29-7.37 (m, 4 H), 7.49 (d, J=9.19 Hz, 1 H), 7.68-7.81 (m, 3 H), 7.90 (d, J=8.46 Hz, 1 H), 8.04 (s, 1 H), 8.08 (s, 1 H), 8.69 (d, J=22.06 Hz, 2 H), 8.90 (d, J=7.35 Hz, 1 H), 9.32 (s, 1 H), 10.45 (s, 1 H), 10.63 (s, 1 H).

Example 98

N-(3-Bromo-phenyl)-3-(7-isopropyl-pyrido[2,3-d]pyrimidin-4-ylamino)-4-[3-(7-isopropyl-pyrido[2,3-d]pyrimidin-4-ylamino)-phenylsulfanyl]-benzamide A solution of the product of Example 96 (0.029 g, 0.05 mmol) and the product from Example 8E (0.01 1 mg, 0.05 mmol) in acetic acid (1.0 mL) was stirred in a preheated 140° C. oil bath for 20 minutes. The mixture was cooled and concentrated under vacuum. The resultant residue was purified by HPLC with TFA to provide the title compound as a trifluoroacetic acid salt (22 mg, 45%).

Example 99

4-[3-(2-Amino-acetylamino)-phenylsulfanyl]-N-(3-bromo-phenyl)-3-(7-isopropyl-pyrido[2,3-d]pyrimidin-4-ylamino)-benzamide The title compound was prepared from the product of Example 96 according to the procedures used in Example 97A substituting tert-Butoxycarbonylamino-acetic acid for L-Boc-proline and Example 97B. The crude product was purified by HPLC with TFA to provide the title compound as a trifluoroacetic acid salt (9 mg, 10% for 2 steps). 1H NMR (300 MHz, DMSO-D6) δ ppm: 1.35 (d, J=6.99 Hz, 6 H), 3.19-3.35 (m, J=23.16 Hz, 1 H), 3.75 (d, J=5.52 Hz, 2 H), 7.14 (d, J=7.35 Hz, 1 H), 7.29-7.38 (m, 4 H), 7.46 (d, J=7.72 Hz, 1 H), 7.70 (s, 1 H), 7.72-7.84 (m, 2 H), 7.90 (s, 1 H), 8.01-8.12 (m, 5 H), 8.75 (s, 1 H), 8.91 (s, 1 H), 10.44 (s, 1 H), 10.50 (s, 1 H).

Example 100

{4-[4-(4-Bromo-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester

Example 100A 4-(4-Amino-phenylsulfanyl)-N-(4-bromo-phenyl)-3-nitro-benzamide A solution of the product from Example 10A (3.0 g, 8.44 mmol), 4-aminothiophenol (1.06 g, 8.44 mmol) and cesium carbonate (5.5 g, 17.0 mmol) in N,N-dimethylformamide (15 mL) was heated to 90° C. for 4 hours. After cooling to room temperature the mixture was poured into ice water (100 mL) and the resultant solution acidified to pH 5 with 1N aqueous hydrochloric acid. The solution was then extracted with ethyl acetate (3×50 mL), the combined extracts dried over sodium sulfate, filtered and concentrated under vacuum to provide the title compound as an orange solid (3.6 g, 96%).

Example 100B

{4-[4-(4-Bromo-phenylcarbamoyl)-2-nitro-phenylsulfanyl]-phenyl}-carbamic acid 2,2,2-trichloro-ethyl ester To a slurry of the product of Example 100A (3.6 g, 8.1 mmol) in dichloromethane (100 mL) and pyridine (1.3 g, 16.2 mmol) was added 2,2,2-Trichloroethyl chloroformate (2.16 g, 10.2 mmol). The solution was stirred for 16 hours, washed with water, brine, dried over sodium sulfate and concentrated under vacuum. The resulting residue was triturated in 9:1 hexane/ethyl acetate to give the title compound as an orange powder (4.15 g, 83%).

Example 100C

{4-[2-Amino-4-(4-bromo-phenylcarbamoyl)-phenylsulfanyl]-phenyl}-carbamic acid 2,2,2-trichloro-ethyl ester A solution of the product of Example 100B (1.23 g, 2.0 mmol), iron powder (0.56 g, 10.0 mmol) and ammonium chloride (0.16 g, 3.0) in an ethanol (30 mL), tetrahydrofuran (30 mL), and water (10 mL) solution was heated to reflux for 6 hours. The resultant mixture was diluted with ethanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over sodium sulfate, filtered and concentrated under vacuum to provide the title compound as a yellow powder (1.12 g, 95%).

Example 100D

{4-[4-(4-Bromo-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester A solution of the product of Example 100C (1.12 g, 1.9 mmol) and the product of Example 8E (0.41 mg, 1.9 mmol) in acetic acid (10 mL) was stirred in a preheated 140° C. oil bath for 40 minutes. The mixture was cooled and concentrated under vacuum. The resultant residue was triturated in a minimal volume of methanol and collected by filtration to give the title compound (0.98 g, 68%). 1H NMR (300 MHz, DMSO-D6) δ ppm: 1.34 (d, J=6.99 Hz, 6 H), 3.19-3.27 (m, 1 H). 4.96 (s, 2 H), 7.07 (d, J=8.46 Hz, 1 H), 7.41 (d, J=8.46 Hz, 2 H), 7.50-7.69 (m, 5 H), 7.74 (d, J=8.82 Hz, 2 H), 7.81 (d, J=8.46 Hz, 1 H), 8.00 (s, 1 H), 8.59 (s, 1 H), 8.85 (d, J=8.46 Hz, 1 H), 10.24 (s, 1 H), 10.35 (s, 1 H), 10.38 (s, 1 H); MS (ESI+) m/z 761 (M+H)+.

Example 101

N-(4-Bromo-phenyl)-3-(7-isopropyl-pyrido[2,3-d]pyrimidin-4-ylamino)-4-[4-(7-isopropyl-pyrido[2,3-d]pyrimidin-4-ylamino)-phenylsulfanyl]-benzamide A solution of the product of Example 13E (0.029 g, 0.05 mmol) and the product of Example 8E (0.011 mg, 0.05 mmol) in acetic acid (1.0 mL) was stirred in a preheated 140° C. oil bath for 20 minutes. The mixture was cooled and concentrated under vacuum. The resultant residue was purified by HPLC with TFA to provide the title compound as a trifluoroacetic acid salt (24 mg, 55%). 1H NMR (300 MHz, DMSO-D6) δ ppm: 1.33 (t, J=7.35 Hz, 12 H), 3.19-3.34 (m, 2 H), 7.30 (d, J=8.09 Hz, 1 H), 7.49 (d, J=8.82 Hz, 2 H), 7.54 (d, J=8.82 Hz, 2 H), 7.68-7.88 (m, 7 H), 7.91 (d, J=8.46 Hz, 1 H), 8.02 (s, 1 H), 8.74 (s, 1 H), 8.87 (s, 1 H), 8.93 (d, J=7.72 Hz, 1 H), 8.99 (d, J=8.82 Hz, 1 H), 10.42 (s, 1 H), 10.71 (s, 1 H); MS (ESI+) m/z 756/758 (M+H)+.

Example 102

4-(4-Acetylamino-phenylsulfanyl)-N-(4-bromo-phenyl)-3-(7-isopropyl-pyrido [2,3-d]pyrimidin-4-ylamino)-benzamide A solution of the product of Example 13E (0.029 g, 0.05 mmol) and acetic anhydride (0.0068 g, 0.066 mmol) in acetic acid (0.3 mL) was stirred at 130° C. for 20 minutes. The mixture was cooled and concentrated under vacuum. The resultant residue was purified by HPLC with TFA to provide the title compound as a trifluoroacetic acid salt (20 mg, 54%). 1H NMR (300 MHz, DMSO-D6) δ ppm: 1.35 (d, J=6.99 Hz, 6 H), 2.06 (s, 3 H), 3.16-3.32 (m, 1 H), 7.09 (d, 8.09 Hz, 1 H), 7.38 (d, J=8.82 Hz, 2 H), 7.53 (d, J=8.82 Hz, 2 H), 7.62 (d, J=8.46 Hz, 2 H), 7.73 (d, J=8.82 Hz, 2 H), 7.77 (d, J=9.93 Hz, 1 H), 7.84 (d, J=8.09 Hz, 1 H), 7.96 (s, 1 H), 8.72 (s, 1 H), 8.91 (d, J=7.72 Hz, 1 H), 10.12 (s, 1 H), 10.37 (s, 1 H), 11.07 (s, 1 H); MS (ESI+) m/z 627/629 (M+H)+.

Example 103

N-(4-Bromo-phenyl)-4-(4-dimethylamino-phenylsulfanyl)-3-(7-isopropyl-pyrido[2,3-d]pyrimidin-4-ylamino)-benzamide A solution of the product of Example 13E (0.058 g, 0.1 mmol) and 37% aqueous formaldehyde (0.080 mL, 1.0 mmol) in formic acid (0.038 mL) was stirred at 105° C. for 15 minutes. The mixture was cooled and concentrated under vacuum. The resultant residue was purified by HPLC with NH4OH to provide the title compound as a yellow powder (12 mg, 20%). 1H NMR (300 MHz, DMSO-D6) δ ppm: 1.34 (d, J=6.99 Hz, 6 H), 2.94 (s, 6 H), 3.14-3.27 (m, 1 H), 1 H), 6.75 (d, J=8.82 Hz, 2 H), 6.89 (s, 1 H), 7.28 (d, J=8.82 Hz, 2 H), 7.52 (d, J=8.82 Hz, 2 H), 7.62 (s, 1 H), 7.73 (d, J=9.19 Hz, 2 H), 7.78 (s, 1 H), 7.95 (s, 1 H), 8.58 (s, 1 H), 8.86 (s, 1 H), 10.17 (s, 1 H), 10.28 (s, 1 H); MS (ESI+) m/z 613/615 (M+H)+.

Example 104

4-(4-Amino-phenylsulfanyl)-3-(7-isopropyl-pyrido[2,3-d]pyrimidin-4-ylamino)-N-p-tolyl-benzamide Example 104A

[4-(2-Amino-4-p-tolylcarbamoyl-phenylsulfanyl)-phenyl]-carbamic acid tert-butyl ester A mixture of 4-bromoaniline was reacted with 4-chloro-3-nitrobenzoyl chloride using the procedure of Example 10A to provide 4-Chloro-3-nitro-N-p-tolyl-benzamide which was reacted according to the conditions described in Examples 13A, 13B, and 13C to provide the title product.

Example 104B 4-(4-Amino-phenylsulfanyl)-3-(7-isopropyl-pyrido[2,3-d]pyrimidin-4-ylamino)-N-p-tolyl-benzamide The product of Example 104A was reacted with the product of Example 8E according to the procedure from Example 95D substituting the product of Example 104A for the product of 404C to provide {4-[2-(7-Isopropyl-pyrido[2,3-d]pyrimidin-4-ylamino)-4-p-tolylcarbamoyl-phenylsulfanyl]-phenyl}-carbamic acid tert-butyl ester which was deprotected using the conditions from Example 96 to provide the crude product which was purified by HPLC with TFA to provide the title product as a trifluoroacetic acid salt (36 mg, 23%). 1H NMR (300 MHz, DMSO-D6) δ ppm: 1.37 (d, J=6.99 Hz, 6 H), 2.27 (s, 3 H), 3.17-3.39 (m, 1 H), 6.64 (d, J=8.46 Hz, 2 H), 6.94 (d, J=8.46 Hz, 1 H), 7.15 (dd, J=8.46, 2.94 Hz, 4 H), 7.60 (d, J=8.46 Hz, 2 H), 7.86 (dd, J=8.27, 1.65 Hz, 1 H), 7.90-7.96 (m, 2 H), 8.88 (s, 1 H), 9.04 (d, J=8.82 Hz, 1 H), 10.14 (s, 1 H), 11.64 (s, 1 H); MS (ESI+) m/z 521 (M+H)+.

Example 105

4-(4-Amino-phenylsulfanyl)-N-(3-fluoro-4-methyl-phenyl)-3-(7-isopropyl-pyrido[2,3-d]pyrimidin-4-ylamino)-benzamide

Example 105A

{4-[2-Amino-4-(3-fluoro-4-methyl-phenylcarbamoyl)-phenylsulfanyl]-phenyl-carbamic acid 2,2,2-trichloro-ethyl ester A mixture of 3-Fluoro-4-methyl-phenylamine was reacted with 4-chloro-3-nitrobenzoyl chloride using the procedure of Example 10A to provide 4-Chloro-N-(3-fluoro-4-methyl-phenyl)-3-nitro-benzamide which was reacted according to the conditions described in Examples 100A, 100B, and 100C to provide the title product.

Example 105B

{4-[4-(3-Fluoro-4-methyl-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 105A was reacted with the product from Example 8E using the procedure from Example 100D substituting the product from Example 105A for the product from Example 100C to provide the crude product was purified by trituration in dichloromethane to give a sticky yellow solid which was used without purification (0.108 g, 30%).

Example 105C 4-(4-Amino-phenylsulfanyl)-N-(3-fluoro-4-methyl-phenyl)-3-(7-isopropyl-pyrido[2,3-d]pyrimidin-4-ylamino)-benzamide To a solution of the product of Example 105B (0.108 g, 0.15 mmol) in tetrahydrofuran (3 mL) and water (3 mL) was added 1 M NaOH (0.5 mL, 0.5 mmol). The solution was heated at 60° C. for 40 minutes, cooled, adjusted to pH 6 with 1N aqueous hydrochloric acid and extracted with ethyl acetate (3×20 mL). The combined extracts were dried over sodium sulfate, filtered and concentrated under vacuum. The resultant residue was purified HPLC with TFA to provide the title compound as a trifluoroacetic acid salt (20 mg, 20%). 1H NMR (300 MHz, DMSO-D6) δ ppm: 1.37 (d, J=6.99 Hz, 6 H), 2.19 (s, 3 H), 3.06-3.42 (m, 1 H), 6.64 (d, J=8.82 Hz, 2 H), 6.96 (d, J=8.46 Hz, 1 H), 7.16 (d, J=8.82 Hz, 2 H), 7.24 (t, J=8.82 Hz, 1 H), 7.41 (dd, J=8.46, 1.84 Hz, 1 H), 7.65 (dd, J=12.32, 2.02 Hz, 1 H), 7.86 (dd, J=8.27, 1.65 Hz, 1 H), 7.89-7.97 (m, 2 H), 8.90 (s, 1 H), 9.06 (d, J=8.46 Hz, 1 H), 10.32 (s, 1 H), 11.73 (s, 1 H); MS (ESI+) m/z 539 (M+H)+.

Example 106

4-[4-(3,3-Dimethyl-ureido)-phenylsulfanyl]-N-(3-fluoro-4-methyl-phenyl)-3-(7-isopropyl-pyrido[2,3-d]pyrimidin-4-ylamino)-benzamide The product of Example 105B (0.108 g, 0.15 mmol) in tetrahydrofuran (3 mL) was treated with DBU (0.023 g, 0.15 mmol) and Dimethylamine (2.0 M in THF, 0.75 mL, 1.5 mmol) and heated at 60° C. for 20 minutes in a sealed tube, cooled, and concentrated under vacuum. The resulting residue was purified by chromatography on silica eluting with 97:3 dichloromethane/methanol to provide the title compound (0.08 g, 88%). 1H NMR (300 MHz, DMSO-D6) δ ppm: 1.34 (d, J=6.99 Hz, 6 H), 2.19 (s, 3 H), 2.93 (s, 6 H), 3.15-3.29 (m, 1 H), 7.01 (d, J=8.46 Hz, 1 H), 7.23 (t, J=8.64 Hz, 1 H), 7.33 (d, J=8.46 Hz, 2 H), 7.43 (dd, J=8.27, 1.65 Hz, 1 H), 7.57 (d, J=8.82 Hz, 2 H), 7.62-7.71 (m, 2 H), 7.80 (dd, J=8.27, 1.65 Hz, 1 H), 7.99 (s, 1 H), 8.50 (s, 1 H), 8.60 (s, 1 H), 8.87 (d, J=8.46 Hz, 1 H), 10.22 (s, 1 H), 10.30 (s, 1 H); MS (ESI+) m/z 610 (M+H)+.

Example 107

{3-[4-(3-Bromo-phenylcarbamoyl)-2-(7-isopropyl-pyrido[2,3-d]pyrimidin-4-ylamino)-phenoxy]-phenyl}-carbamic acid tert-butyl ester

Example 107A 4-(3-Amino-phenoxy)-N-(3-bromo-phenyl)-3-nitro-benzamide

A solution of N-(3-Bromo-phenyl)-4-chloro-3-nitro-benzamide (from Example 16A) (0.71 g, 2.0 mmol), 3-aminophenol (0.22 g, 2.0 mmol) and powdered potassium hydroxide (0.23 g, 4.0 mmol) in Dimethyl sulfoxide (5 mL) was heated at 100° C. for 30 minutes. After cooling to room temperature the mixture was poured into ice water (100 mL) and the resultant solution adjusted to pH 5 with 1N aqueous hydrochloric acid. The solution was then extracted with ethyl acetate (3×50 mL), the combined extracts dried over sodium sulfate, filtered and concentrated under vacuum to provide the title compound (0.8 g, 93%).

Example 107B

{3-[2-Amino-4-(3-bromo-phenylcarbamoyl)-phenoxy]-phenyl}-carbamic acid tert-butyl ester The product of Example 107A was reacted according to the procedures from Examples 13B and 13C to provide the title compound.

Example 107C

{3-[4-(3-Bromo-phenylcarbamoyl)-2-(7-isopropyl-pyrido[2,3-d]pyrimidin-4-ylamino)-phenoxy]-phenyl}-carbamic acid tert-butyl ester The product of Example 107B was reacted with the product from Example 8E using the procedure from Example 95D substituting the product from Example 107B for the product from Example 95C to provide the crude product was purified by chromatography on silica eluting with 97:3 dichloromethane/methanol to provide the title compound as a tan foam (350 mg, 40%). 1H NMR (300 MHz, DMSO-D6) δ ppm: 1.32 (d, J=6.99 Hz, 6 H), 1.45 (s, 9 H), 3.13-3.25 (m, 1 H), 6.60 (d, J=7.35 Hz, 1 H), 7.05 (d, J=8.46 Hz, 1 H), 7.11-7.24 (m, 2 H), 7.27-7.38 (m, 3 H), 7.57 (d, J=8.46 Hz, 1 H), 7.74-7.81 (m, 1 H), 7.92 (dd, J=8.64, 2.02 Hz, 1 H), 8.11 (s, 1 H), 8.19 (d, J=2.21 Hz, 1 H), 8.60 (s, 1 H), 8.77 (d, J=8.46 Hz, 1 H), 9.44 (s, 1 H), 10.03 (s, 1 H), 10.38 (s, 1 H); MS (ESI+) m/z 669/671 (M+H)+.

Example 108

{3-[4-(3-Bromo-phenylcarbamoyl)-2-(7-methyl-pyrido[2,3-d]pyrimidin-4-ylamino)-phenoxy]-phenyl}-carbamic acid tert-butyl ester The product of Example 107B was reacted with the product from Example 9B using the procedure from Example 95D substituting the product from Example 107B for the product from Example 95C and substituting the product from Example 9B for the product from Example 8E to provide the crude product was purified by HPLC with NH4OH to provide the title compound (28 mg, 44%). 1H NMR (300 MHz, DMSO-D6) δ ppm: 1.45 (s, 9 H), 2.66 (s, 3 H), 6.61 (d, J=8.09 Hz, 1 H), 7.04 (d, J=8.46 Hz, 1 H), 7.11-7.23 (m, 2 H), 7.25-7.39 (m, 3 H), 7.51 (d, J=8.46 Hz, 1 H), 7.71-7.80 (m, 1 H), 7.91 (dd, J=8.46, 2.21 Hz, 1 H), 8.09-8.12 (m, 1 H), 8.20 (d, J=1.84 Hz, 1 H), 8.60 (s, 1 H), 8.73 (d, J=8.46 Hz, 1 H), 9.44 (s, 1 H), 10.02 (s, 1 H), 10.36 (s, 1 H); MS (ESI+) m/z 641/643 (M+H)+.

Example 109

4-(3-Amino-phenoxy)-N-(3-bromo-phenyl)-3-(7-isopropyl-pyrido[2,3-d]pyrimidin-4-ylamino)-benzamide The product from Example 107C was subjected to the procedure of Example 96 substituting the product of Example 107C for the product of 404D to provide a residue which was purified by trituration in dichloromethane to provide the title compound. 1H NMR (300 MHz, DMSO-D6) δ ppm: 1.35 (d, J=6.62 Hz, 6 H), 3.16-3.41 (m, 1 H), 6.29 (d, J=8.09 Hz, 1 H), 6.33 (s, 1 H), 6.42 (d, J=8.09 Hz, 1 H), 7.03 (t, J=8.09 Hz, 1 H), 7.13 (d, J=8.46 Hz, 1 H), 7.27-7.39 (m, 2 H), 7.72-7.79 (m, 1 H), 7.91 (d, J=8.46 Hz, 1 H), 8.04 (dd, J=8.64, 2.39 Hz, 1 H), 8.08-8.11 (m, 1 H), 8.14 (d, J=2.21 Hz, 1 H), 8.93 (s, 1 H), 9.00 (d, J=8.82 Hz, 1 H), 10.43 (s, 1 H), 11.72 (s, 1 H); MS (ESI+) m/z 569/571 (M+H)+.

Example 110

({3-[4-(3-Bromo-phenylcarbamoyl)-2-(7-isopropyl-pyrido[2,3-d]pyrimidin-4-ylamino)-phenoxy]-phenylcarbamoyl}-methyl)-carbamic acid tert-butyl ester A mixture of the product of Example 109 (0.068 g, 0.1 mmol), tert-Butoxycarbonylamino-acetic acid (0.023 g, 0.13 mmol), N-(3-Dimethylaminopropyl)-N'-ethylcarbodiimide hydrochloride (0.025 g, 0.13 mmol), 1-Hydroxybenzotriazole hydrate (0.015 g, 0.11 mmol) and N,N-diisopropylethylamine (0.029 g, 0.22 mmol) in N,N-dimethylformamide (2 mL) was stirred for 16 hours, poured into water and extracted with ethyl acetate (3×15 mL). The combined extracts were dried over sodium sulfate, filtered and concentrated under vacuum to provide a residue which was purified by chromatography on silica eluting with 96:4 dichloromethane/methanol to provide the title compound (50 mg, 69%). 1H NMR (300 MHz, DMSO-D6) δ ppm: 1.31 (d, J=6.62 Hz, 6 H), 1.38 (s, 9 H), 3.13-3.27 (m, 1 H), 3.68 (d, J=5.88 Hz, 2 H), 6.63-6.71 (m, 1 H), 7.04 (t, J=6.43 Hz, 1 H), 7.08 (d, J=8.46 Hz, 1 H), 7.24 (d, J=4.78 Hz, 2 H), 7.26-7.37 (m, 2 H), 7.49 (s, 1 H), 7.58 (d, J=8.46 Hz, 1 H), 7.72-7.79 (m, 1 H), 7.92 (dd, J=8.64, 2.02 Hz, 1 H), 8.11 (s, 1 H), 8.19 (d, J=1.47 Hz, 1), 8.59 (s, 1 H), 8.76 (d, J=8.46 Hz, 1 H), 10.00 (s, 1 H), 10.05 (s, 1 H), 10.39 (s, 1 H).

Example 111

4-[3-(2-Amino-acetylamino)-phenoxy]-N-(3-bromo-phenyl)-3-(7-isopropyl-pyrido[2,3-d]pyrimidin-4-ylamino)-benzamide The product of Example 110 (0.04 g, 0.055 mmol) was treated with trifluoroacetic acid as in the procedure for Example 96. The crude product was purified by trituration in dichloromethane to provide the title compound as a trifluoroacetic acid salt (0.046 g, 98%). 1H NMR (300 MHz, DMSO-D6) δ ppm: 1.33 (d, J=6.99 Hz, 6 H), 3.21-3.32 (m, 1 H), 3.75 (d, J=5.52 Hz, 2 H), 6.81 (d, J=9.19 Hz, 1 H), 7.14 (d, J=8.82 Hz, 1 H), 7.24-7.38 (m, 3 H), 7.45 (s, 1 H), 7.72-7.78 (m, 1 H), 7.81 (d, J=8.46 Hz, 1 H), 8.02 (dd, J=8.82, 2.21 Hz, 1 H), 8.10 (s, 3 H), 8.18 (d, J=1.84 Hz, 1 H), 8.80 (s, 1 H), 8.92 (d, J=8.46 Hz, 1 H), 10.45 (s, 1 H), 11.26 (s, 1 H).

Example 112

4-(3-Amino-phenoxy)-N-(3-bromo-phenyl)-3-(7-methyl-pyrido[2,3-d]pyrimidin-4-ylamino)-benzamide The product of Example 108 (0.028 g, 0.044 mmol) was treated with trifluoroacetic acid as in the procedure for Example 96. The crude product was purified by trituration in dichloromethane to give the title compound as a trifluoroacetic acid salt (0.025 g, 87%). 1H NMR (300 MHz, DMSO-D6) δ ppm: 2.75 (s, 3 H), 6.24 (d, J=8.09 Hz, 1 H), 6.30 (s, 1 H), 6.39 (d, J=7.72 Hz, 1 H), 7.01 (t, J=7.91 Hz, 1 H), 7.12 (d, J=8.82 Hz, 1 H), 7.25-7.40 (m, 2 H), 7.69-7.78 (m, 1 H, 7.82 (d, J=8.82 Hz, 1 H), 8.03 (dd, J=8.64, 2.39 Hz, 1 H), 8.12 (dd, J=17.46, 2.02 Hz, 2 H), 8.88-9.00 (m, 2 H), 10.41 (s, 1 H), 11.60 (s, 1 H); MS (ESI+) m/z 541/543 (M+H)+.

Example 113

4-(4-Amino-phenylsulfanyl)-3-(7-isopropyl-pyrido[2,3-d]pyrimidin-4-ylamino)-benzoic acid N'-(4-bromo-phenyl)-hydrazide

Example 113A (4-{2-Amino-4-[N'-(4-bromo-phenyl)-hydrazinocarbonyl]-phenylsulfanyl}-phenyl)-carbamic acid 2,2,2-trichloro-ethyl ester A mixture of 4-chloro-3-nitrobenzoyl chloride was reacted with (4-Bromo-phenyl)-hydrazine to produce 4-Chloro-3-nitro-benzoic acid N'-(4-bromo-phenyl)-hydrazide according to the procedure of Example 10A, which was treated sequentially using the procedures from Examples 100A, 100B and 100C to provide the title product.

Example 113B 4-(4-Amino-phenylsulfanyl)-3-(7-isopropyl-pyrido[2,3-d]pyrimidin-4-ylamino)-benzoic acid N'-(4-bromo-phenyl)-hydrazide The product of Example 113A was reacted with the product of Example 8E according to the procedure from Example 100D substituting the product of Example 11 3A for the product of 409C to provide 4-[4-[N'-(4-Bromo-phenyl)-hydrazinocarbonyl]-2-(7-isopropyl-pyrido[2,3-d]pyrimidin-4-ylamino)-phenylsulfanyl]-phenyl}-carbamic acid 2,2,2- trichloro-ethyl ester which was deprotected using the conditions from Example 105C to provide the crude product which was purified by HPLC with NH4OH to provide the title compound (10 mg, 13%). 1H NMR (300 MHz, DMSO-D6) δ ppm: 1.33 (d, J=6.62 Hz, 6 H), 3.14-3.27 (m, 1 H), 5.60 (s, 2 H), 6.63 (d, J=8.82 Hz, 2 H), 6.70 (d, J=8.82 Hz, 2 H), 6.84 (d, J=7.35 Hz, 1 H), 7.14 (d, J=8.46 Hz, 2 H), 7.29 (d, J=8.82 Hz 2 H), 6.70 (d, J=8.82 Hz, 1 H), 7.74 (d, J=8.46 Hz, 1 H), 7.85 (s, 1 H), 8.11 (s, 1 H), 8.58 (s, 1 H), 8.87 (d, J=9.56 Hz, 1 H), 10.13 (s, 1 H), 10.36 (s, 1 H); MS (ESI+) m/z 600/602 (M+H)+.

Example 114

N-[4-(4-Hydroxy-phenylsulfanyl)-3-(7-methyl-pyrido[2,3-d]pyrimidin-4-ylamino)-phenyl]-3-trifluoromethyl-benzamide Example 114A N-(4-Fluoro-3-nitro-phenyl)-3-trifluoromethyl-benzamide A solution of 4-Fluoro-3-nitro-aniline (2.00 g, 12.8 mmol), 3-Trifluoromethyl-benzoyl chloride (1.895 mL, 12.8 mmol), Hunig's base (4.463 mL, 25.6 mmol) in tetrahydrofuran (50 ml) was stirred at room temperature for 1 hour. Afterwards water (450 mL) was added to the solution and the resultant solid was collected by filtration and dried in a vacuum oven to provide the title compound (3.311 g, 97%).

Example 114B

N-[4-(4-Hydroxy-phenylsulfanyl)-3-nitro-phenyl]-3-trifluoromethyl-benzamide

A solution of the product of Example 114A (2.00 g, 5.80 mmol), 4-hydroxythiophenol (0.732 g, 5.80 mmol) and potassium carbonate (1.604 g, 11.6 mmol) in N,N-dimethylformamide (40 mL) was heated to 80° C. for 2 hours. After cooling to room temperature the mixture was poured into ice water (100 mL). The solution was then extracted with ethyl acetate (3×150 mL), the combined extracts dried over magnesium sulfate, filtered and concentrated under vacuum to provide the title compound (2.52 g, 100%).

Example 114C

N-[3-Amino-4-(4-hydroxy-phenylsulfanyl)-phenyl]-3-trifluoromethyl-benzamide

A solution of the product of Example 114B (0.660 g, 1.52 mmol), iron powder (0.339 g, 6.07 mmol) and ammonium chloride (0.099 g, 1.82 mmol), tetrahydrofuran (18 mL), and water (6 mL) solution was heated to reflux for 3 hours. The resultant mixture was diluted with methanol (50 mL) and filtered through a pad of celite. The filtrate was diluted with water (50 mL) and extracted with dichloromethane (2×100 mL). The combined extracts were dried over magnesium sulfate, filtered and concentrated under vacuum to provide the title compound (0.60 g, 97%).

Example 114D

N-[4-(4-Hydroxy-phenylsulfanyl)-3-(7-methyl-pyrido[2,3-d]pyrimidin-4-ylamino)-phenyl]-3-trifluoromethyl-benzamide A solution of the product from Example 9B (40.0 mg, 0.212 mmol), and the product from Example 114C (86.0 mg, 0.212 mmol) in acetic acid (1 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (11 mg, 10%). $^1$H NMR (300 MHz, DMSO-D6) δ ppm: 2.74 (s, 3 H), 6.70 (d, J=8.82 Hz, 2 H), 7.18 (d, J=8.46 Hz, 3 H), 7.64 (dd, J=8.46, 2.21 Hz, 1 H), 7.79 (t, J=7.72 Hz, 2 H), 7.93-8.07 (m, J=6.62 Hz, 2 H), 8.21-8.30 (m, 2 H), 8.78 (s, 1 H), 8.92 (d, J=7.72 Hz, 1 H), 9.79 (s, 1 H), 10.67 (s, 1 H), 11.17-11.50 (m, 1 H) MS (ESI+) m/z 548.2(M+H)+, (ESI−) m/z 546.2 (M−H)−.

Example 115

N-[4-(4-Hydroxy-phenylsulfanyl)-3-(7-isopropyl-pyrido[2,3-d]pyrimidin-4-ylamino)-phenyl]-3-trifluoromethyl-benzamide A solution of the product from Example 8E (40.0 mg, 0.212 mmol), and the product from Example 114C (75.0 mg, 0.185 mmol) in acetic acid (1 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (3.2 mg, 4%). 1HNMR (300 MHz, DMSO-D6) δ ppm: 1.36 (d, J=6.99 Hz, 6 H), 6.71 (d, J=8.82 Hz, 2 H), 7.19 (d, J=8.82 Hz, 3H), 7.65 (d, J=9.19 Hz, 1 H), 7.75-7.89 (m, 2 H), 7.98 (d, J=7.72 Hz, 2 H), 8.23-8.33 (m, 3 H), 8.76 (s, 1 H), 8.95 (d, J=8.09 Hz, 1 H), 9.78 (s, 1 H), 10.66 (s, 1 H) MS (ESI+) m/z 576.2(M+H)+, (ESI−) m/z 574.3 (M−H)−.

Example 116

4-Bromo-N-[4-(4-hydroxy-phenylsulfanyl)-3-(pyrido[2,3-d]pyrimidin-4-ylamino)-phenyl]-benzamide Example 116A 4-Bromo-N-(4-fluoro-3-nitro-phenyl)-benzamide The title compound was prepared according to the procedure of Example 114A substituting 4-bromo-benzoyl chloride for 3-trifluoromethyl-benzoyl chloride to provide the title compound (1.125 g, 90%).

Example 116B

4-Bromo-N-[4-(4-hydroxy-phenylsulfanyl)-3-nitro-phenyl]-benzamide

The title compound was prepared according to the procedure of Example 114B substituting the product from Example 116A for the product from Example 114A to provide the title compound (0.75 g, 50%).

Example 116C

N-[3-Amino-4-(4-hydroxy-phenylsulfanyl)-phenyl]-4-bromo-benzamide

The title compound was prepared according to the procedure of Example 114C substituting the product from Example 116B for the product from Example 114B to provide the title compound (0.5 g, 80%).

Example 116D

4-Bromo-N-[4-(4-hydroxy-phenylsulfanyl)-3-(pyrido[2,3-d]pyrimidin-4-ylamino)-phenyl]-benzamide

A solution of the product from Example 29A (40.0 mg, 0.212 mmol), and the product from Example 116C (87.0 mg, 0.212 mmol) in acetic acid (1 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (37.2 mg, 25%). 1H NMR (300 MHz, DMSO-D6) δ ppm: 6.70 (d, J=8.82 Hz, 2 H), 7.10-7.22 (m, 3 H), 7.62 (dd, J=8.64, 2.02 Hz, 1 H), 7.73-7.83 (m, 3 H), 7.85-7.93 (m, 2 H), 8.00 (s, 1 H), 8.73 (s, 1 H), 9.00 (d, J=8.09 Hz, 1 H), 9.13 (d, J=3.31 Hz, 1 H), 9.77 (s, 1 H), 10.50 (s, 1 H); MS (ESI+) m/z 544 (M+H)+, (ESI–) m/z 542 (M–H)–.

Example 117

4-Bromo-N-[3-(pyrido[2,3-d]pyrimidin-4-ylamino)-phenyl]-benzamide

Example 117A

4-Bromo-N-(3-nitro-phenyl)-benzamide

The title compound was prepared according to the procedure of Example 114A substituting 3-nitro-phenylamine for 4-Fluoro-3-nitro-aniline and substituting 4-bromo-benzoyl chloride for 3-Trifluoromethyl-benzoyl chloride to provide the title product (3.373 g, 90%).

Example 117B

4-Bromo-N-(3-amino-phenyl)-benzamide

The title compound was prepared according to the procedure of Example 114B substituting the product from Example 117A for the product from Example 114A to provide the title product (1.8 g, 80%).

Example 117C

4-Bromo-N-[3-(pyrido[2,3-d]pyrimidin-4-ylamino)-phenyl]-benzamide

A solution of the product from Example 29A (40.0 mg, 0.212 mmol), and the product of Example 117B (61.0 mg, 0.212 mmol) in acetic acid (1 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (25.0 mg, 30%). 1H NMR (300 MHz, DMSO-D6) δ ppm: 7.45 (t, J=8.09 Hz, 1 H), 7.52-7.61 (m, 2 H), 7.74-7.86 (m, 3 H), 7.94 (d, J=8.82 Hz, 2 H), 8.33 (t, J=1.84 Hz, 1 H), 8.88 (s, 1 H), 9.09-9.17 (m, 2 H), 10.48 (s, 1 H), 10.94 (s, 1 H); MS (ESI+) m/z 20 (M+H)+, (ESI–) m/z 417 (M–H)–.

Example 118

4-Chloro-N-[3-(pyrido[2,3-d]pyrimidin-4-ylamino)-phenyl]-benzamide

Example 118A

N-(3-Amino-phenyl)-4-chloro-benzamide

The title compound was prepared according to the procedure of Example 117A substituting 4-chloro-benzoyl chloride for 4-bromo-benzoyl chloride followed by reduction of the nitro group using the procedure from Example 114B to provide the title product.

Example 118B

4-Chloro-N-[3-(pyrido[2,3-d]pyrimidin-4-ylamino)-phenyl]-benzamide

The product from Example 118A was reacted with the product from Example 29A using the procedure from Example 117C substituting the product from Example 118A for the product from Example 117B to provide the crude product which was purified by HPLC with TFA to provide the title compound as a trifluoroacetic acid salt (21 mg, 26%). 1H NMR (300 MHz, DMSO-D6) δ ppm: 7.43-7.50 (m, J=8.09, 8.09 Hz, 1 H), 7.52-7.61 (m, J=12.69, 8.27 Hz, 2 H), 7.63 (d, J=8.82 Hz, 2 H), 7.81-7.90 (m, 1 H), 8.01 (d, J=8.46 Hz, 2 H), 8.32 (t, J=1.84 Hz, 1 H), 8.91 (s, 1 H), 9.10-9.19 (m, 2 H), 10.49 (s, 1 H), 11.15 (s, 1 H); MS ESI+m/z 376 (M+H)+, ESI– m/z 374 (M–H)–.

Example 119

4-Methoxy-N-[3-(pyrido[2,3-d]pyrimidin-4-ylamino)-phenyl]-benzamide

Example 119A

N-(3-Amino-phenyl)-4-methoxy-benzamide

The title compound was prepared according to the procedure of Example 117A substituting 4-Methoxy-benzoyl chloride for 4-bromo-benzoyl chloride followed by reduction of the nitro group using the procedure from Example 114B to provide the title product.

Example 119B

4-Methoxy-N-[3-(pyrido[2,3-d]pyrimidin-4-ylamino)-phenyl]-benzamide

The product from Example 119A was reacted with the product from Example 29A using the procedure from Example 117C substituting the product from Example 119A for the product from Example 117B to provide the crude product which was purified by HPLC with TFA to provide the title compound as a trifluoroacetic acid salt (15 mg, 19%). 1H NMR (300 MHz, DMSO-D6) δ ppm: 3.85 (s, 3 H), 7.08 (d, J=8.82 Hz, 2 H), 7.44 (t, J=7.91 Hz, 1 H), 7.50-7.61 (m, 2 H), 7.81-7.88 (m, 1 H), 7.98 (d, J=9.19 Hz, 2 H), 8.32 (t, J=1.84

Hz, 1 H), 8.91 (s, 1 H), 9.14 (d, J=5.88 Hz, 2 H), 10.26 (s, 1 H), 11.11 (s, 1 H); MS ESI+ m/z 372 (M+H)+, ESI− m/z 370 (M−H)−.

Example 120

3-Chloro-N-[3-(pyrido[2,3-d]pyrimidin-4-ylamino)-phenyl]-benzamide

Example 120A

N-(3-Amino-phenyl)-3-chloro-benzamide

The title compound was prepared according to the procedure of Example 117A substituting 3-chloro-benzoyl chloride for 4-bromo-benzoyl chloride followed by reduction of the nitro group using the procedure from Example 114B to provide the title product.

Example 120B

3-Chloro-N-[3-(pyrido[2,3-d]pyrimidin-4-ylamino)-phenyl]-benzamide

The product from Example 120A was reacted with the product from Example 29A using the procedure from Example 117C substituting the product from Example 120A for the product from Example 117B to provide the crude product which was purified by HPLC with TFA to provide the title compound as a trifluoroacetic acid salt (29 mg, 35%). 1H NMR (300 MHz, DMSO-D6) δ ppm: 7.46 (t, J=7.91 Hz, 1 H), 7.54-7.62 (m, 3 H), 7.65-7.72 (m, 1 H), 7.84 (dt, J=5.52, 3.68 Hz, 1 H), 7.91-7.96 (m, J=7.72 Hz, 1 H), 8.03 (t, J=1.84 Hz, 1 H), 8.33 (t, J=1.84 Hz, 1), 8.91 (s, 1 H), 9.11-9.18 (m, 2 H), 10.52 (s, 1 H), 11.09 (s, 1 H); ESI+ m/z 376 (M+H)+, ESI− m/z 373 (M−H)−.

Example 121

3-Bromo-N-[3-(pyrido[2,3-d]pyrimidin-4-ylamino)-phenyl]-benzamide

Example 121A

N-(3-Amino-phenyl)-3-bromo-benzamide

The title compound was prepared according to the procedure of Example 117A substituting 3-bromo-benzoyl chloride for 4-bromo-benzoyl chloride followed by reduction of the nitro group using the procedure from Example 114B to provide the title product.

Example 121B

3-Bromo-N-[3-(pyrido[2,3-d]pyrimidin-4-ylamino)-phenyl]-benzamide

The product from Example 121A was reacted with the product from Example 29A using the procedure from Example 117C substituting the product from Example 121A for the product from Example 117B to provide the crude product which was purified by HPLC with TFA to provide the title compound as a trifluoroacetic acid salt (24 mg, 27%). 1H NMR (300 MHz, DMSO-D6) δ ppm: 7.47-7.62 (m, 4 H), 7.80-7.91 (m, 2 H), 7.98 (d, J=7.72 Hz, 1 H), 8.16 (t, J=1.65 Hz, 1 H), 8.32 (t, J=1.84 Hz, 1 H), 8.95 (s, 1 H), 9.12-9.20 (m, 2 H), 10.54 (s, 1 H), 11.33 (s, 1 H); MS ESI+ m/z 420 (M+H)+, ESI− m/z 418 (M−H)−.

Example 122

2-Chloro-N-[3-(pyrido[2,3-d]pyrimidin-4-ylamino)-phenyl]-benzamide

Example 122A

N-(3-Amino-phenyl)-2-chloro-benzamide

The title compound was prepared according to the procedure of Example 117A substituting 2-chloro-benzoyl chloride for 4-bromo-benzoyl chloride followed by reduction of the nitro group using the procedure from Example 114B to provide the title product.

Example 122B

2-Chloro-N-[3-(pyrido[2,3-d]pyrimidin-4-ylamino)-phenyl]-benzamide

The product from Example 122A was reacted with the product from Example 29A using the procedure from Example 117C substituting the product from Example 122A for the product from Example 117B to provide the crude product which was purified by HPLC with TFA to provide the title compound as a trifluoroacetic acid salt (18 mg, 22%). 1H NMR (300 MHz, DMSO-D6) δ ppm: 7.45-7.54 (m, 4 H), 7.56-7.62 (m, 3 H), 7.83-7.90 (m, 1 H), 8.25-8.29 (m, 1 H), 8.93 (s, 1 H), 9.12-9.18 (m, 2 H), 10.70 (s, 1 H), 11.23 (s, 1 H); MS ESI+ m/z 376 (M+H)+, ESI− m/z 374 (M−H)−.

Example 123

2-Bromo-N-[3-(pyrido[2,3-d]pyrimidin-4-ylamino)-phenyl]-benzamide

Example 123A

N-(3-Amino-phenyl)-2-bromo-benzamide

The title compound was prepared according to the procedure of Example 117A substituting 2-bromo-benzoyl chloride for 4-bromo-benzoyl chloride followed by reduction of the nitro group using the procedure from Example 114B to provide the title product.

Example 123B

2-Bromo-N-[3-(pyrido[2,3-d]pyrimidin-4-ylamino)-phenyl]-benzamide

The product from Example 123A was reacted with the product from Example 29A using the procedure from Example 117C substituting the product from Example 123A for the product from Example 117B to provide the crude product which was purified by HPLC with TFA to provide the title compound as a trifluoroacetic acid salt (18 mg, 22%). 1H NMR (300 MHz, DMSO-D6) δ ppm: 7.44-7.54 (m, 4 H), 7.56-7.60 (m, 2 H), 7.74 (dd, J=7.91, 0.92 Hz, 1 H), 7.82-7.89 (m, 1 H), 8.27 (s, 1 H), 8.92 (s, 1 H), 9.11-9.19 (m, 2 H), 10.68 (s, 1 H), 11.20 (s, 1 H); MS ESI+ m/z 420 (M+H)+, ESI− m/z 418 (M−H)−.

Example 124

2-Methoxy-N-[3-(pyrido[2,3-d]pyrimidin-4-ylamino)-phenyl]-benzamide

Example 124A

N-(3-Amino-phenyl)-2-methoxy-benzamide

The title compound was prepared according to the procedure of Example 117A substituting 2-methoxy-benzoyl chloride for 4-bromo-benzoyl chloride followed by reduction of the nitro group using the procedure from Example 114B to provide the title product.

Example 124B

2-Methoxy-N-[3-(pyrido[2,3-d]pyrimidin-4-ylamino)-phenyl]-benzamide

The product from Example 124A was reacted with the product from Example 29A using the procedure from Example 117C substituting the product from Example 124A for the product from Example 117B to provide the crude product which was purified by HPLC with TFA to provide the title compound as a trifluoroacetic acid salt (26 mg, 33%). 1H NMR (300 MHz, DMSO-D6) δ ppm: 3.90 (s, 3 H), 7.08 (t, J=6.99 Hz, 1 H), 7.20 (d, J=8.46 Hz, 1 H), 7.41-7.56 (m, 4 H), 7.62 (dd, J=7.54, 1.65 Hz, 1 H), 7.88 (dt, 1 H), 8.28 (s, 1 H), 8.94 (s, 1 H), 9.12-9.19 (m, 2 H), 10.30 (s, 1 H), 11.30 (s, 1 H); MS ESI+ m/z 372 (M+H)+, ESI– m/z 370 (M–H)–.

Example 125

3-Methoxy-N-[3-(pyrido[2,3-d]pyrimidin-4-ylamino)-phenyl]-benzamide

Example 125A

N-(3-Amino-phenyl)-3-methoxy-benzamide

The title compound was prepared according to the procedure of Example 117A substituting 3-methoxy-benzoyl chloride for 4-bromo-benzoyl chloride followed by reduction of the nitro group using the procedure from Example 114B to provide the title product.

Example 125B

3-Methoxy-N-[3-(pyrido[2,3-d]pyrimidin-4-ylamino)-phenyl]-benzamide

The product from Example 125A was reacted with the product from Example 29A using the procedure from Example 117C substituting the product from Example 125A for the product from Example 117B to provide the crude product which was purified by HPLC with TFA to provide the title compound as a trifluoroacetic acid salt (35 mg, 45%). 1H NMR (300 MHz, DMSO-D6) δ ppm: 3.85 (s, 3 H), 7.18 (dd, J=7.54, 2.02 Hz, 1 H), 7.42-7.51 (m, 3 H), 7.53-7.61 (m, 3 H), 7.82 (dd, J=7.72, 5.15 Hz, 1 H), 8.32 (t, J=1.84 Hz, 1 H), 8.89 (s, 1 H), 9.09-9.17 (m, 2 H), 10.38 (s, 1 H), 10.99 (s, 1 H); MS ESI+ m/z 372 (M+H)+, ESI– m/z 370 (M+H)–.

Example 126

3-Fluoro-N-[3-(pyrido[2,3-d]pyrimidin-4-ylamino)-phenyl]-benzamide

Example 126A

N-(3-Amino-phenyl)-3-fluoro-benzamide

The title compound was prepared according to the procedure of Example 117A substituting 3-fluoro-benzoyl chloride for 4-bromo-benzoyl chloride followed by reduction of the nitro group using the procedure from Example 114B to provide the title product.

Example 126B

3-Fluoro-N-[3-(pyrido[2,3-d]pyrimidin-4-ylamino)-phenyl]-benzamide

The product from Example 126A was reacted with the product from Example 29A using the procedure from Example 117C substituting the product from Example 126A for the product from Example 117B to provide the crude product which was purified by HPLC with TFA to provide the title compound as a trifluoroacetic acid salt (21 mg, 28%). 1H NMR (300 MHz, DMSO-D6) δ ppm: 7.41-7.53 (m, 2 H), 7.54-7.65 (m, 3 H), 7.77-7.86 (m, 3 H), 8.33 (s, 1 H), 8.89 (s, 1 H), 9.10-9.16 (m, 2 H), 10.48 (s, 1 H), 10.97 (s, 1 H); MS ESI+ m/z 360 (M+H)+, ESI– m/z 358 (M–H)–.

Example 127

3-Bromo-N-[4-(4-hydroxy-phenylsulfanyl)-3-(pyrido[2,3-d]pyrimidin-4-ylamino)-phenyl]-benzamide

Example 127A

N-[3-Amino-4-(4-hydroxy-phenylsulfanyl)-phenyl]-3-bromo-benzamide

The title compound was prepared according to the procedure of Example 114A substituting 3-bromo-benzoyl chloride for 3-Trifluoromethyl-benzoyl chloride followed by reacting the material according to the procedures from Examples 114B and 114C to provide the title product.

Example 127B

3-Bromo-N-[4-(4-hydroxy-phenylsulfanyl)-3-(pyrido[2,3-d]pyrimidin-4-ylamino)-phenyl]-benzamide The product from Example 127A was reacted with the product from Example 29A using the procedure from Example 117C substituting the product from Example 127A for the product from Example 117B to provide the crude product which was purified by HPLC with TFA to provide the title compound as a trifluoroacetic acid salt (41 mg, 27%). 1H NMR (300 MHz, DMSO-D6) δ ppm: 6.70 (d, J=8.46 Hz, 2 H), 7.13-7.21 (m, 3 H), 7.51 (t, J=7.91 Hz, 1 H), 7.63 (dd, J=8.46, 2.21 Hz, 1 H), 7.78-7.88 (m, 2 H), 7.94 (d, J=8.09 Hz, 1 H), 8.01 (s, 1 H), 8.13 (s, 1 H), 8.78 (s, 1 H), 9.03 (d, J=8.09

Hz, 1 H), 9.15 (d, J=3.31 Hz, 1 H), 9.79 (s, 1 H), 10.55 (s, 1 H); MS ESI+ m/z 549 (M+H)+, ESI+ m/z 470 (M-73)+, ESI- m/z 544 (M-H)-.

Example 128

4-Chloro-N-[4-(4-hydroxy-phenylsulfanyl)-3-(pyrido[2,3-d]pyrimidin-4-ylamino)-phenyl]-benzamide

Example 128A

N-[3-Amino-4-(4-hydroxy-phenylsulfanyl)-phenyl]-4-chloro-benzamide

The title compound was prepared according to the procedure of Example 114A substituting 4-chloro-benzoyl chloride for 3-Trifluoromethyl-benzoyl chloride followed by reacting the material according to the procedures from Examples 114B and 114C to provide the title product.

Example 128B

4-Chloro-N-[4-(4-hydroxy-phenylsulfanyl)-3-(pyrido[2,3-d]pyrimidin-4-ylamino)-phenyl]-benzamide The product from Example 128A was reacted with the product from Example 29A using the procedure from Example 117C substituting the product from Example 128A for the product from Example 117B to provide the crude product which was purified by HPLC with TFA to provide the title compound as a trifluoroacetic acid salt (24 mg, 17%). 1H NMR (300 MHz, DMSO-D6) δ ppm: 6.70 (d, J=8.82 Hz, 2 H), 7.12-7.23 (m, 3 H), 7.56-7.68 (m, 3 H), 7.85 (dd, J=8.27, 4.60 Hz, 1 H), 7.93-8.05 (m, 3 H), 8.78 (s, 1 H), 9.03 (d, J=7.72 Hz, 1 H), 9.15 (d, J=2.94 Hz, 1 H), 9.79 (s, 1 H), 10.53 (s, 1 H); MS ESI+ m/z 500 (M+H)+, ESI+ m/z 426 (M-73)+, ESI- m/z 498 (M-H)-.

Example 129

N-[4-(4-Hydroxy-phenylsulfanyl)-3-(pyrido[2,3-d]pyrimidin-4-ylamino)-phenyl]-4-methoxy-benzamide

Example 129A

N-[3-Amino-4-(4-hydroxy-phenylsulfanyl)-phenyl]-4-methoxy-benzamide

The title compound was prepared according to the procedure of Example 114A substituting 4-Methoxy-benzoyl chloride for 3-Trifluoromethyl-benzoyl chloride followed by reacting the material according to the procedures from Examples 114B and 114C to provide the title product.

Example 129B

N-[4-(4-Hydroxy-phenylsulfanyl)-3-(pyrido[2,3-d]pyrimidin-4-ylamino)-phenyl]-4-methoxy-benzamide The product from Example 129A was reacted with the product from Example 29A using the procedure from Example 117C substituting the product from Example 129A for the product from Example 117B to provide the crude product which was purified by HPLC with TFA to provide the title compound as a trifluoroacetic acid salt (1 mg, 2%). 1H NMR (300 MHz, DMSO-D6) δ ppm: 3.83 (s, 3 H), 6.65-6.73 (m, 2 H), 7.00-7.10 (m, 2 H), 7.12-7.22 (m, 3 H), 7.64 (dd, J=8.82, 2.21 Hz, 1 H), 7.87 (dd, J=8.64, 3.86 Hz, 1 H), 7.93 (t, J=8.09 Hz, 2 H), 8.03 (d, J=1.47 Hz, 1 H), 8.79 (s, 1 H), 9.04 (d, J=7.72 Hz, 1 H), 9.15 (d, J=2.94 Hz, 1 H), 9.76 (s, 1 H), 10.30 (s, 1 H), 11.42 (s, 1 H; MS ESI+ m/z 496 (M+H)+, ESI- m/z 494 (M-H)-.

Example 130

N-[4-(4-Hydroxy-phenylsulfanyl)-3-(7-methyl-pyrido[2,3-d]pyrimidin-4-ylamino)-phenyl]-benzamide A solution of 2-Chloro-5-nitroaniline (3 g, 17.4 mmole), 4-hydroxythiophenol (2.4 g, 19.0 mmol), cesium carbonate (12.35 g, 38 mmol) in dimethylformamide (35 ml) was heated at 100° C. for 16 hours. Afterwards ice water (200 mL) was added to the solution and to the resultant slurry was added ethyl acetate (200 ml). The layers were separated and the organic layer was washed with 10% sodium bicarbonate and 10% sodium chloride, dried over anhydrous sodium sulfate. The drying agent was filtered and solvent was removed under vacuum leaving a yellow oil. The oil was purified by silica gel chromatography eluting with methylene chloride/methanol (97:3), to provide a yellow solid (4-(2-Amino-4-nitro-phenylsulfanyl)-phenol) (2.1g, 46%).

A solution of the product from Example 9B (340 mg, 1.80 mmol), and 4-(2-Amino-4-nitro-phenylsulfanyl)-phenol (480 mg, 1.80 mmol) in acetic acid (10 mL) was stirred in an oil bath preheated to 130° C. for 30 minutes. The mixture was then cooled to room temperature, the acetic acid removed under vacuum leaving a brown oil (4-[2-(7-Methyl-pyrido[2,3-d]pyrimidin-4-ylamino)-4-nitro-phenylsulfanyl]-phenol) (0.65 g, 89%).

A slurry of 4-[2-(7-Methyl-pyrido[2,3-d]pyrimidin-4-ylamino)-4-nitro-phenylsulfanyl]-phenol (0.19 g, 0.469 mmol) and 10% Pd/C (0.025 g) in acetic acid (3 ml) was placed under a hydrogen atmosphere with stirring for 2 hr at room temperature. The slurry was filtered and the solvent removed under vacuum leaving a brown solid as an acetate salt of 4-[4-Amino-2-(7-methyl-pyrido[2,3-d]pyrimidin-4-ylamino)-phenylsulfanyl]-phenol (0.21 g, 91%).

A solution containing 4-[4-Amino-2-(7-methyl-pyrido[2,3-d]pyrimidin-4-ylamino)-phenylsulfanyl]-phenol (50 mg, 0.133 mmole), benzoyl chloride (40 mg, 0.284 mmole) in 1 ml pyridine was stirred 18 hr at room temperature. The solvent was evaporated under vacuum and the residue was stirred 18 hours with 2N NaOH (1 ml). The reaction mixture was concentrated under vacuum and the resultant residue purified by HPLC with TFA to provide the title compound as a trifluoroacetic acid salt (27 mg, 42%). 1H NMR (300 MHz, DMSO-D6) δ ppm: 2.72 (s, 3 H), 6.65-6.76 (m, 2 H), 7.07-7.24 (m, 3 H), 7.44-7.76 (m, 6 H), 7.94 (d, J=6.62 Hz, 2 H), 8.02 (s, 1 H), 8.69 (s, 1 H), 8.86 (d, J=8.46 Hz, 1 H), 9.76 (s, 1 H), 10.43 (s, 1 H).

Example 131

Furan-2-carboxylic acid [4-(4-hydroxy-phenylsulfanyl)-3-(7-methyl-pyrido[2,3-d]pyrimidin-4-ylamino)-phenyl]-amide A solution of 4-[4-Amino-2-(7-methyl-pyrido[2,3-d]pyrimidin-4-ylamino)-phenylsulfanyl]-phenol and 2-furoyl chloride were reacted according to the procedure from Example 130 substituting 2-furoyl chloride for benzoyl chloride to provide the crude product which was purified by HPLC with TFA to provide the title compound as a trifluoroacetic acid salt (17 mg, 28%). 1H NMR (300 MHz, DMSO-D6) δ ppm: 2.75 (s, 3 H), 6.59-6.83 (m, 3 H), 7.16 (d, J=8.46 Hz, 3 H), 7.26-7.36 (m, 1 H), 7.63 (dd, J=8.64, 2.39 Hz, 1 H), 7.81 (d, J=8.82 Hz, 1 H), 7.91-8.04 (m, 2 H), 8.81 (s, 1 H), 8.93 (d, J=8.46 Hz, 1 H), 9.78 (s, 1 H), 10.42 (s, 1 H), 11.52 (s, 1 H).

Example 132

N-[4-(4-Hydroxy-phenylsulfanyl)-3-(7-isopropyl-pyrido[2,3-d]pyrimidin-4-ylamino)-phenyl]-benzenesulfonamide A solution of the product from Example 9B (340 mg, 2.31 mmol), and 4-(2-Amino-4-nitro-phenylsulfanyl)-phenol (610 mg, 2.30 mmol) in acetic acid (10 mL) was stirred in an oil bath preheated to 130° C. for 10 minutes. The mixture was then cooled to room temperature, the acetic acid removed under vacuum providing a brown oil (4-[2-(7-Isopropyl-pyrido[2,3-d]pyrimidin-4-ylamino)-4-nitro-phenylsulfanyl]-phenol) (0.92 g, 92%).

A slurry of 4-[2-(7-Isopropyl-pyrido[2,3-d]pyrimidin-4-ylamino)-4-nitro-phenylsulfanyl]-phenol (0.7 g, 1.73 mmol) and 10% Pd/C (100 mg) in acetic acid (10 ml) and methanol (10 mL) was placed under a hydrogen balloon atmosphere with stirring for 20 hours at room temperature. The slurry was filtered and the solvent removed under vacuum to provide 4-[4-Amino-2-(7-isopropyl-pyrido[2,3-d]pyrimidin-4-ylamino)-phenylsulfanyl]-phenol as an acetic acid salt A solution containing 4-[4-Amino-2-(7-isopropyl-pyrido[2,3-d]pyrimidin-4-ylamino)-phenylsulfanyl]-phenol (100 mg, 0.200 mmol), benzenesulfonyl chloride (43 mg, 0.250 mmol) in 1 ml pyridine was stirred 18 hr at room temperature. The solvent was evaporated under vacuum and the resultant residue purified by HPLC with TFA to provide the title compound as a trifluoroacetic acid salt (23 mg, 18%). 1H NMR (300 MHz, DMSO-D6) δ ppm: 1.35 (d, J=6.99 Hz, 6 H), 3.21-3.37 (m, 1 H), 6.57-6.77 (m, 2 H), 6.94-7.06 (m, 2 H), 7.04-7.21 (m, 2 H), 7.21 (d, J=1.47 Hz, 1 H). 7.51-7.71 (m, 3 H), 7.80 (d, J=6.99 Hz, 2 H), 7.88 (d, J=8.46 Hz, 1 H), 8.79 (s, 1 H), 8.92 (d, J=8.46 Hz, 1 H), 9.80 (s, 1 H), 10.59 (s, 1 H), 11.50 (s, 1 H).

Example 133

[4-(4-Hydroxy-phenylsulfanyl)-3-(7-isopropyl-pyrido[2,3-d]pyrimidin-4-ylamino)-phenyl]-carbamic acid methyl ester A solution containing 4-[4-Amino-2-(7-isopropyl-pyrido[2,3-d]pyrimidin-4-ylamino)-phenylsulfanyl]-phenol (100 mg, 0.200 mmol), methoxycarbonyl chloride (25 mg, 0.250 mmol) in 1 ml pyridine was stirred 18 hr at room temperature. The solvent was evaporated under vacuum and the resultant residue was purified by HPLC with TFA to provide the title compound as a trifluoroacetic acid salt (15 mg, 13%). 1H NMR (300 MHz, DMSO-D6) δ ppm: 1.35 (d, J=6.99 Hz, 6 H), 3.23-3.32 (m, 1 H), 3.66 (s, 3 H), 6.54-6.74 (m, 2 H), 7.01-7.24 (m, 3 H), 7.37 (dd, J=8.82, 2.21 Hz, 1 H), 7.61 (s, 1 H), 7.86 (d, J=8.46 Hz, 1 H), 8.78 (s, 1 H), 8.95 (s, 1 H), 9.72 (s, 1 H), 9.92 (s, 1 H), 11.41 (bs,1H).

Example 134

[4-(4-Hydroxy-phenylsulfanyl)-3-(7-isopropyl-pyrido[2,3-d]pyrimidin-4-ylamino)-phenyl]-carbamic acid benzyl ester A solution containing 4-[4-Amino-2-(7-isopropyl-pyrido[2,3-d]pyrimidin-4-ylamino)-phenylsulfanyl]-phenol and bezyloxycarbonyl chloride was reacted according to the procedure from Example 133 substituting bezyloxycarbonyl chloride for methoxycarbonyl chloride which was purified by HPLC with TFA to provide the title compound as a trifluoroacetic acid salt (27 mg, 21%). 1H NMR (300 MHz, DMSO-D6) δ ppm: 1.36 (d, J=6.62 Hz, 6 H), 3.18-3.40 (m, 1 H), 5.15 (s, 2 H), 6.47-6.74 (m, 2 H), 7.10 (d, J=8.46 Hz, 2 H), 7.18 (d, J=8.46 Hz, 1 H), 7.30-7.47 (m, 6 H), 7.65 (d, J=1.84 Hz, 1 H), 7.91 (d, J=8.46 Hz, 1 H), 8.82 (s, 1 H), 8.97 (d, J=8.46 Hz, 1 H), 9.73 (s, 1 H), 10.07 (s, 1 H), 11.68 (s, 1 H).

Example 135

4-(4-Amino-phenylsulfanyl)-N-(4-bromo-phenyl)-3-(7-tert-butyl-pyrido[2,3-d]pyrimidin-4-ylamino)-benzamide 3,3-Dimethyl-2-butanone was reacted according to the procedures described in Examples 8A-8E to provide N'-(6-tert-Butyl-3-cyano-pyridin-2-yl)-N,N-dimethyl-formamidine.

The product of Example 13C was reacted with N'-(6-tert-Butyl-3-cyano-pyridin-2-yl)-N,N-dimethyl-formamidine using the procedure of Example 13D substituting N'-(6-tert-Butyl-3-cyano-pyridin-2-yl)-N,N-dimethyl-formamidine for the product of Example 8E to provide {4-[4-(4-Bromo-phenylcarbamoyl)-2-(7-tert-butyl-pyrido[2,3-d]pyrimidin-4-ylamino)-phenylsulfanyl]-phenyl}-carbamic acid tert-butyl ester which was reacted using the procedure of Example 13E to provide the crude title compound which was purified by HPLC using TFA to provide the title product as a trifluoroacetic acid salt (15 mg, 7%). 1H NMR (300 MHz, DMSO-D6) δ ppm: 1.45 (s, 9H), 6.64 (d, J=8.5 Hz, 2H), 6.95 (d, J=8.5 Hz, 1H), 7.16 (d, J=8.8 Hz, 2H), 7.54 (d, J=9.2 Hz, 2H), 7.72 (d, J=8.8 Hz, 2H), 7.86 (m, 1H), 7.93 (s, 1H), 8.09 (m, 1H), 8.86 (m, 1H), 9.05 (m, 1H), 10.34 (s, 1H), 11.61 (bs, 1H); MS (ESI)+ m/z 598/600 (M+H)+.

Example 136

3-(7-Isopropyl-pyrido[2,3-d]pyrimidin-4-ylamino)-4-(4-methoxy-phenylsulfanyl)-benzoic acid methyl ester Example 136A 4-(4-Methoxy-phenylsulfanyl)-3-nitro-benzoic acid methyl ester To a solution of 4-methoxy thiophenol (5 mL, 40.7 mmol) and methyl-3-nitro-4-chlorobenzoate (10.52 g, 48.8 mmol) in DMF (40 mL) was added $CsCO_3$ (26.5 g, 81.4 mmol) and the reaction mixture heated at 80° C. for 3 hours. After cooling, the solution was poured into water and extracted with ethyl acetate (3×100 mL). The combined organic layers were dried over $MgSO_4$, filtered, and concentrated under vacuum to afford the title compound after chromatography on silica gel using ethyl acetate/hexanes as eluent (10.93 g, 80%).

Example 136B

3-Amino-4-(4-methoxy-phenylsulfanyl)-benzoic acid methyl ester

To a solution of the product from Example 136A, iron powder and ammonium chloride in a methanol, tetrahydrofuran, and water solution was heated to reflux. The resultant mixture was filtered, and the filtrate was concentrated. Then ethyl acetate was added, stirred, filtered and concentrated under vacuum to provide the title compound (7.16 g, 90%).

Example 136C 3-(7-Isopropyl-pyrido[2,3-d]pyrimidin-4-ylamino)-4-(4-methoxy-phenylsulfanyl)-benzoic acid methyl ester The product from Example 136B (1.58 g, 5.5 mmol) and the product from Example 8E (1.18 g, 5.5 mmol) in acetic acid (10 mL) was heated at 140° C. for 1 hour. The reaction mixture was then cooled to room temperature and then concentrated under vacuum. The residue was then purified by silica gel chromatography using 4% methanol in dichloromethane as eluent to provide the title compound as a white solid (1.16 g, 46%). 1H NMR (300 MHz, DMSO-D6) δ ppm: 1.33 (d, J=6.99 Hz, 6H), 3.13-3.29 (m, 1H), 3.79 (s, 3H), 3.83 (s, 3H), 6.89-6.98 (m, 1H), 7.02 (d, J=8.46 Hz, 2H), 7.42 (d, J=8.82 Hz, 2H), 7.57-7.67 (m, 1H), 7.72-7.82 (m, 1H), 7.85-7.98 (m, 1H), 8.58 (s, 1H), 8.84 (s, 1H), 10.17 (s, 1H); MS (ESI)+ m/z 461 (M+H)+.

Example 137

N-(3-Hydroxy-4-methyl-phenyl)-3-(7-isopropyl-pyrido[2,3-d]pyrimidin-4-ylamino)-4-(4-methoxy-phenylsulfanyl)-benzamide

Example 137A 3-(7-Isopropyl-pyrido[2,3-d]pyrimidin-4-ylamino)-4-(4-methoxy-phenylsulfanyl)-benzoic acid To the product from Example 136C (1.56 g, 3.4 mmol) in tetrahydrofuran (20 mL) was added 1N aqueous sodium hydroxide (10 mL, 10 mmol) and the reaction mixture heated at 50° C. for 3 hours. After cooling the reaction mixture to room temperature, the pH was adjusted to 6.5 with 1N aqueous hydrochloric acid and the resulting precipitate was removed by vacuum filtration. The product was dried under high vacuum overnight to provide the title compound as an off white solid (643 mg, 42%).

Example 137B 3-(7-Isopropyl-pyrido[2,3-d]pyrimidin-4-ylamino)-4-(4-methoxy-phenylsulfanyl)-benzoyl chloride The product from Example 137A (500 mg, 1.120 mmol) in dichloromethane (10 mL) was treated with oxalyl chloride (0.115 mL, 1.344 mmol) and 1 drop of DMF. The resulting reaction mixture was stirred at room temperature for 1 hour and then concentrated under vacuum to provide the title compound as a brown solid that was used without further manipulation.

Example 137C

N-(3-Hydroxy-4-methyl-phenyl)-3-(7-isopropyl-pyrido[2,3-d]pyrimidin-4-ylamino)-4-(4-methoxy-phenylsulfanyl)-benzamide A solution of 5-amino-o-cresol (20.4 mg, 0.1655 mmol) and the product from Example 137B (70mg, 0.1655 mmol) in dichloromethane (4 mL) was treated with triethylamine (0.025 mL, 0.1806 mmol) at room temperature. The resulting solution was stirred for 18 hours. The reaction mixture was then washed with water and brine, and the combined organic layers were dried over $MgSO_4$, the concentrated under vacuum to give a residue which was purified by silica gel chromatography using methanol and dichloromethane as eluent to provide the title compound (55 mg, 65%). 1H NMR (300 MHz, DMSO-D6) δ ppm: 1.34 (d, J=6.99 Hz, 6H), 2.07 (s, 3H), 3.17-3.28 (m, 1H), 3.77 (s, 3H), 6.86-7.10 (m, 5H), 7.30-7.46 (m, 3H), 7.64 (d, J=7.35 Hz, 1H), 7.72-7.86 (m, 1H), 7.95 (s, 1H), 8.43-8.68 (m, 1H), 8.77-8.97 (m, 1H), 9.27-9.46 (m, 1H), 10.02 (s, 1H), 10.21-10.40 (m, 1H); MS (APCI) m/z 552 (M+H)+.

Example 138

3-(7-Isopropyl-pyrido[2,3-d]pyrimidin-4-ylamino)-4-(4-methoxy-phenylsulfanyl)-N-p-tolyl-benzamide To the product from Example 137B (70 mg, 0.1505 mmol) was treated with p-toluidine (16 mg, 0.1505 mmol), triethylamine (0.025 mL, 0.1806 mmol) and dichloromethane (4 mL) following the procedure from Example 137C to provide the title compound as an off white solid after chromatography (64 mg, 80%). 1H NMR (300 MHz, DMSO-D6) δ ppm: 1.34 (d, J=6.62 Hz, 6 H) 2.27 (s, 3 H) 3.17-3.30 (m, 1 H) 3.78 (s, 3 H) 7.00 (d, J=8.82 Hz, 2 H) 7.14 (d, J=8.09 Hz, 2 H) 7.40 (d, J=8.82 Hz, 2 H) 7.62 (d, J=8.46 Hz, 1 H) 7.80 (d, J=8.09 Hz, 1 H) 7.99 (s, 1 H) 8.59 (s, 1 H) 8.86 (d, J=8.46 Hz, 1 H) 10.13 (s, 1 H) 10.20 (s, 1 H); MS (APCI) m/z 536 (M+H)+.

Example 139

N-(4-Bromo-phenyl)-3-(7-isopropyl-pyrido[2,3-d]pyrimidin-4-ylamino)-4-(4-methoxy-phenylsulfanyl)-benzamide The product from Example 137B was reacted with 4-bromoaniline according to the procedure from Example 137C substituting 4-bromoaniline for 5-amino-o-cresol to provide the title compound as an off white solid after silica gel chromatography (109 mg, 85%).

Example 140

N-(3-Bromo-phenyl)-3-(7-isopropyl-pyrido[2,3-d]pyrimidin-4-ylamino)-4-(4-methoxy-phenylsulfanyl)-benzamide The product from Example 137B was reacted with 3-bromoaniline according to the procedure from Example 137C substituting 3-bromoaniline for 5-amino-o-cresol to provide the title compound as an off white solid after silica gel chromatography (50 mg, 38%). 1H NMR (300 MHz, DMSO-D6) δ ppm: 1.34 (d, J=6.99 Hz, 6H), 3.16-3.30 (m, 1H), 3.77 (s, 3H), 7.00 (d, J=8.82 Hz, 2H), 7.40 (d, J=8.82 Hz, 2H), 7.53 (d, J=8.82 Hz, 2H), 7.64 (d, J=8.82 Hz, 1), 7.74 (d, J=8.82 Hz, 2H), 7.81 (dd, J=8.46, 1.84 Hz, 1H), 7.99 (d, J=1.47 Hz, 1H), 8.59 (s, 1H), 8.86 (d, J=8.82 Hz, 1H), 10.21 (s, 1H), 10.33 (s, 1H); MS (APCI) m/z 602 (M+H)+.

Example 141

3-(7-Isopropyl-pyrido[2,3-d]pyrimidin-4-ylamino)-4-(4-methoxy-phenylsulfanyl)-N-m-tolyl-benzamide The product from Example 137B was reacted with m-toluidine according to the procedure from Example 137C substituting m-toluidine for 5-amino-o-cresol to provide the title compound as an off white solid after silica gel chromatography (56 mg, 70%). 1H NMR (300 MHz, DMSO-D6) δ ppm: 1.34 (d, J=6.99 Hz, 6H), 2.21 (s, 3H), 3.15-3.29 (m, 1H), 3.78 (s, 3H), 7.00 (d, J=8.82 Hz, 2H), 7.12-7.37 (m, 4H), 7.40 (d, J=8.82 Hz, 2H), 7.64 (d, J=8.46 Hz, 1H), 7.84 (d, J=11.40 Hz, 1H), 7.99 (s, 1H), 8.59 (s, 1H), 8.86 (d, J=8.46 Hz, 1H), 9.87 (s, 1H), 10.21 (s, 1H); MS (APCI) m/z 536 (M+H)+.

Example 142

3-(7-Isopropyl-pyrido[2,3-d]pyrimidin-4-ylamino)-N-(3-methoxy-phenyl)-4-(4-methoxy-phenylsulfanyl)-benzamide The product from Example 137B was reacted with m-anisidine according to the procedure from Example 137C substituting m-anisidine for 5-amino-o-cresol to provide the title compound as an off white solid after silica gel chromatography (60 mg, 85%). 1H NMR (300 MHz, DMSO-D6) δ ppm: 1.34 (d, J=6.99 Hz, 6H), 3.17-3.29 (m, 1H), 3.74 (s, 3H), 3.77 (s, 3H), 6.68 (dd, J=8.09, 1.84 Hz, 1H), 6.92-6.98 (m, 1H), 6.99 (d, J=8.82 Hz, 2H), 7.24 (t, J=8.09 Hz, 1H), 7.31-7.50 (m, 5H), 7.68 (d, J=8.09 Hz, 1H), 7.79 (d, J=7.35 Hz, 1H), 7.96 (s, 1H), 8.61 (s, 1H), 8.89 (d, J=8.09 Hz, 1H), 10.18 (s, 1H); MS (APCI) m/z 552 (M+H)+.

Example 143

3-(7-Isopropyl-pyrido[2,3-d]pyrimidin-4-ylamino)-N-(2-methoxy-phenyl)-4-(4-methoxy-phenylsulfanyl)-benzamide The product from Example 137B was reacted with o-anisidine according to the procedure from Example 137C substituting o-anisidine for 5-amino-o-cresol to provide the title compound as an off white solid after silica gel chromatography (120 mg, 67%). 1H NMR (300 MHz, DMSO-D6) δ ppm: 1.34 (d, J=6.99 Hz, 6H), 3.12-3.28 (m, 1H), 3.78 (s, 3H), 3.81 (s, 3H), 6.92-7.05 (m, 4H), 7.05-7.12 (m, 1H), 7.13-7.23 (m, 1H), 7.40 (d, J=8.82 Hz, 2H), 7.64 (d, J=8.46 Hz, 1H), 7.71 (d, J=7.72 Hz, 1H), 7.81 (d, J=8.82 Hz, 1H), 7.99 (s, 1H), 8.59 (s, 1H), 8.86 (d, J=8.46 Hz, 1H), 9.44 (s, 1H), 9.44 (s, 1H); MS (APCI) m/z 553 (M+H)+.

Example 144

3-(7-Isopropyl-pyrido[2,3-d]pyrimidin-4-ylamino)-4-(4-methoxy-phenylsulfanyl)-N-o-tolyl-benzamide The product from Example 137B was reacted with o-toluidine according to the procedure from Example 137C substituting o-toluidine for 5-amino-o-cresol to provide the title compound as an off white solid after silica gel chromatography (74 mg, 92%). 1H NMR (300 MHz, DMSO-D6) δ ppm: 1.34 (d, J=6.99 Hz, 6H), 2.34 (s, 3H), 3.18-3.29 (m, 1H), 3.78 (s, 3H), 6.91 (d, J=7.35 Hz, 1H), 7.00 (d, J=8.09 Hz, 2H), 7.22 (t, J=7.72 Hz, 1H), 7.40 (d, J=8.46 Hz, 2H), 7.50-7.72 (m, 4H), 7.81 (d, J=8.09 Hz, 1H), 8.00 (s, 1H), 8.59 (s, 1H), 8.87 (d, J=8.46 Hz, 1H), 10.13 (s, 1H), 10.21 (s, 1H); MS (APCI) m/z 536 (M+H)+.

Example 145

3-(7-Ethyl-pyrido[2,3-d]pyrimidin-4-ylamino)-4-(4-hydroxy-phenylsulfanyl)-N-m-tolyl-benzamide The product from Example 141 was reacted according to the procedure from Example 150 substituting the product from Example 141 for the product from Example 138 to provide a residue which was purified by HPLC with TFA to provide the title compound as a trifluoroacetic acid salt (24 mg, 50%). 1H NMR (300 MHz, DMSO-D6) δ ppm: 1.36 (d, J=6.99 Hz, 6H), 2.21 (s, 3H), 3.22-3.41 (m, 1H), 6.84 (d, J=8.46 Hz, 2H), 7.00 (d, J=8.09 Hz, 1H), 7.11-7.28 (m, 2H), 7.31 (d, J=8.46 Hz, 2H), 7.88 (t, J=9.01 Hz, 2H), 7.96 (s, 1H), 8.82 (s, 1H), 8.99 (d, J=8.09 Hz, 1H), 9.89 (s, 1H), 10.00 (s, 1H); MS (APCI) m/z 522 (M+H)+.

Example 146

N-(2-Hydroxy-phenyl)-4-(4-hydroxy-phenylsulfanyl)-3-(7-isopropyl-pyrido[2,3-d]pyrimidin-4-ylamino)-benzamide The product from Example 143 was reacted according to the procedure from Example 150 substituting the product from Example 143 for the product from Example 138 to provide a residue which was purified by trituration with methanol and diethyl ether to provide the title compound (26 mg, 55%). 1H NMR (300 MHz, DMSO-D6) δ ppm: 1.37 (d, J=6.99 Hz, 6H), 3.21-3.43 (m, 1H), 6.83 (s, 1H), 6.84 (d, J=8.82 Hz, 2H), 6.92 (d, J=8.09 Hz, 1H), 7.02 (d, J=8.09 Hz, 2H), 7.32 (d, J=8.46 Hz, 2H), 7.63 (d, J=8.09 Hz, 1H), 7.93 (dd, J=8.46, 1.84 Hz, 1H), 7.99 (s, 1H), 8.94 (s, 1H), 9.08 (d, J=8.46 Hz, 1H), 9.51 (s, 1H), 9.74 (s, 1H), 10.02 (s, 1H); MS (APCI) m/z 524 (M+H)+.

Example 147

4-(4-Hydroxy-phenylsulfanyl)-3-(7-isopropyl-pyrido[2,3-d]pyrimidin-4-ylamino)-N-o-tolyl-benzamide The product from Example 144 was reacted according to the procedure from Example 150 substituting the product from Example 144 for the product from Example 138 to provide a residue which was purified by HPLC with TFA to provide the title compound as a trifluoroacetic acid salt (24 mg, 50%). 1H NMR (300 MHz, DMSO-D6) δ ppm: 1.35 (d, J=6.62 Hz, 6H), 2.11 (s, 3H), 3.21-3.43 (m, 1H), 6.72 (d, J=7.72 Hz, 1H), 6.79-6.92 (m, 3H), 7.00 (d, J=8.09 Hz, 1H), 7.24 (d, J=8.46 Hz, 2H), 7.34 (d, J=6.62 Hz, 1H), 7.52 (d, J=7.72 Hz, 1H), 7.63 (d, J=7.72 Hz, 1H), 7.81 (d, J=8.46 Hz, 1H), 7.92 (s, 1H), 8.66 (s, 1H), 8.91 (d, J=8.09 Hz, 1H), 10.04 (s, 1H); MS (APCI) m/z 522 (M+H)+.

Example 148

4-(4-Methoxy-phenylsulfanyl)-3-(7-methyl-pyrido[2,3-d]pyrimidin-4-ylamino)-N-o-tolyl-benzamide Example 148A 4-(4-Methoxy-phenylsulfanyl)-3-(7-methyl-pyrido[2,3-d]pyrimidin-4-ylamino)-benzoic acid methyl ester The product from Example 136B (2.67 g, 9.23 mmol) and the product from Example 9B (1.72 g, 9.23 mmol) were reacted according to the procedure from Example 136C substituting the product from Example 9B for the product from Example 8E to give a residue which was purified by silica gel chromatography using 4% methanol in dichloromethane as eluent to provide the title compound as a white solid (1.79 g, 45%).

Example 148B

4-(4-Methoxy-phenylsulfanyl)-3-(7-methyl-pyrido[2, 3-d]pyrimidin-4-ylamino)-N-o-tolyl-benzamide

To a solution of o-toluidine (0.208 mL, 1.94 mmol) in toluene (10 mL) was added AlMe$_3$ (0.97 mL, 1.94 mmol) and the reaction mixture stirred for 30 minutes at room temperature. Then, the product from Example 148A (140 mg, 0.324 mmol) was added in one portion and the reaction mixture refluxed for 3 hours. The reaction mixture was cooled to room temperature and poured into a rapidly stirring solution of Rochelle's salt. After stirring the solution overnight at room temperature, the reaction was extracted with ethyl acetate (3×50 mL). The combined organic layers were dried over MgSO$_4$, and concentrated under vacuum to a residue that was purified by silica gel chromatography using methanol in dichloromethane as eluent to provide the title compound (106 mg, 65%). 1H NMR (300 MHz, DMSO-D6) δ ppm: 2.21 (s, 3H), 2.69 (s, 3H), 3.78 (s, 3H), 7.00 (d, J=8.82 Hz, 2H), 7.11-7.35 (m, 5H), 7.40 (d, J=8.82 Hz, 2H), 7.57 (d, J=8.46 Hz, 1H), 7.84 (d, J=6.99 Hz, 1H), 8.00 (s, 1H), 8.59 (s, 1H), 8.81 (d, J=8.09 Hz, 1H), 9.87 (s, 1H), 10.20 (s, 1H); MS (APCI) m/z 508 (M+H)+.

Example 149

4-(4-Methoxy-phenylsulfanyl)-3-(pyrido[2,3-d]pyrimidin-4-ylamino)-N-o-tolyl-benzamide

The product from Example 148B was reacted according to the procedure from Example 150 substituting the product from Example 148B for the product from Example 138 to provide a residue which was purified by HPLC with TFA to provide the title compound as a trifluoroacetic acid salt (26 mg, 55%). 1H NMR (300 MHz, DMSO-D6) δ ppm: 2.21 (s, 3H), 2.69 (s, 3H), 6.85 (d, J=8.46 Hz, 2H), 6.94 (d, J=8.09 Hz, 1H), 7.07-7.26 (m, 4H), 7.31 (d, J=8.82 Hz, 2H), 7.57 (d, J=8.46 Hz, 1H), 7.83 (d, J=8.46 Hz, 1H), 7.98 (s, 1H), 8.59 (s, 1H), 8.82 (d, J=8.46 Hz, 1H), 9.85 (s, 1H), 9.96 (s, 1H), 10.19 (s, 1H); MS (APCI) m/z 494 (M+H)+.

Example 150

4-(4-Hydroxy-phenylsulfanyl)-3-(7-isopropyl-pyrido [2,3-d]pyrimidin-4-ylamino)-N-p-tolyl-benzamide

The compound from Example 138 (50 mg, 0.0933 mmol) was combined with BBr$_3$ (0.4 mL, 0.4 mmol) and dichloromethane (4 mL) for 30 minutes at room temperature. The reaction was quenched by the addition of methanol (5 mL) and then concentrated under vacuum to afford an oil. The resultant residue was purified by HPLC with TFA to provide the title compound as a trifluoroacetic acid salt (20 mg, 41%). 1H NMR (300 MHz, DMSO-D6) δ ppm: 1.34 (d, J=6.62 Hz, 6H), 2.27 (s, 3H), 3.17-3.30 (m, 1H), 3.78 (s, 3H), 7.00 (d, J=8.82 Hz, 2H), 7.14 (d, J=8.09 Hz, 2H), 7.40 (d, J=8.82 Hz, 2H), 7.62 (d, J=8.46 Hz, 1H), 7.80 (d, J=8.09 Hz, 1H), 7.99 (s, 1H), 8.59 (s, 1H), 8.86 (d, J=8.46 Hz, 1H), 10.13 (s, 1H), 10.20 (s, 1H); MS (APCI) m/z 536 (M+H)+.

Example 151

4-(4-Amino-phenylsulfanyl)-N-(4-bromo-phenyl)-3-(7-isopropyl-1-methyl-1H-pyrido[2,3-d]pyrimidin-4-ylideneamino)-benzamide

The product from Example 100 (114 mg, 0.15 mmol), methyl iodide (9 μL, 0.15 mmol) and cesium carbonate (48 mg, 0.15 mmol) in DMF (3 mL) were stirred at room temperature for 16 hours. The mixture was added into water, adjusted pH to 3 by 1M HCl, extracted with ethyl acetate, dried with magnesium sulfate, filtered and evaporated. The residue was added into tetrahydrofuran (5 mL) and water (5 mL), and then sodium hydroxide (0.6 mL, 1N) was added to the solution. The mixture was heated at 60° C. for 1 hour, cooled down, adjusted pH to 3 by 1M HCl, extracted with ethyl acetate, dried with magnesium sulfate, filtered and evaporated. The residue was purified with silica gel eluting with 1% methanol in dichloromethane to 2% methanol in dichloromethane to give title compound (50 mg, 56%). $^1$H NMR (500 MHz, DMSO-d$_6$) δ ppm: 1.31 (d, J=6.84 Hz, 6 H) 3.14 (m, 1 H) 3.64 (s, 3 H) 5.49 (s, 2 H) 6.64 (m, 3 H) 7.15 (d, J=8.30 Hz, 2 H) 7.39 (dd, J=8.30, 1.95 Hz, 1 H) 7.44 (d, J=8.30 Hz, 1 H) 7.50 (m, 2 H) 7.60 (d, J=1.95 Hz, 1 H) 7.73 (m, 2 H) 8.15 (s, 1 H) 8.56 (d, J=7.81 Hz, 1 H) 10.12 (s, 1 H); MS (ESI+) m/z 599 601 (M+H)+.

Example 152

Benzenesulfonic acid 4-[4-phenylsulfonyloxy-2-(pyrido[2,3-d]pyrimidin-4-ylamino)-cyclohexa-1,3-dienylsulfanyl]-phenyl ester

The product of Example 153C (65 mg, 0.180 mmol) was reacted with Benzene sulfonyl chloride (0.046 mL, 0.36 mmol), and triethylamine (0.066 mL, 0.468 mmol) in N,N-dimethylformamide (1 mL) at room temperature for 2 hours. Afterwards, the mixture was poured into water (10 mL) and the resultant solution extracted with ethyl acetate (3×10 mL), the combined extracts dried over magnesium sulfate, filtered and concentrated under vacuum the purified by HPLC with TFA to provide the title compound as a trifluoroacetic acid salt (19 mg, 14%). $^1$H NMR (300 MHz, DMSO-d$_6$) δ ppm: 6.92 (m, 4H), 7.19 (m, 4H), 7.62 (m, 6H), 7.81 (m, 5H), 7.92 (m, 2H), 9.01 (bs, 1H); MS (ESI+) m/z 643 (M+H)+.

Example 153

Carbonic acid 4-(4-tert-butoxycarbonyloxy-phenylsulfanyl)-3-(pyrido[2,3-d]pyrimidin-4-ylamino)-phenyl ester tert-butyl ester

Example 153A

4-(4-Hydroxy-phenylsulfanyl)-3-nitro-phenol

A solution of 4-Chloro-3-nitro-phenol (2.0 g, 11.52 mmol), 4-hydroxythiophenol (1.45 g, 11.52 mmol) and cesium carbonate (11.26 g, 34.56 mmol) in N,N-dimethylformamide (25 mL) was heated to 100° C. for 4 hours. After cooling to room temperature, 1N aqueous Hydrochloric acid (150 mL) was added and the resultant solution extracted with ethyl acetate (2×100 mL), the combined extracts dried over magnesium sulfate, filtered and concentrated under vacuum to provide the crude title compound which was purified by chromatography on silica gel using hexanes/ethyl acetate as eluent to obtain the title product as a bright orange solid (1.35 g, 45%).

Example 153B

3-Amino-4-(4-hydroxy-phenylsulfanyl)-phenol

The product from Example 153A (1.34 g, 5.09 mmol) was reacted with iron (1.42 g, 25.48 mmol) and ammonium chloride (409 mg, 1.5 mmol) in 20 mL EtOH/20 mL THF/6 mL water following the procedure from Example 9E to provide the title compound (1.168 g, 97%).

Example 153C 4-(4-Hydroxy-phenylsulfanyl)-3-(pyrido[2,3-d]pyrimidin-4-ylamino)-phenol The product of Example 153B (380 mg, 1.63 mmol) was reacted with the product of Example 29A (284 mg, 1.63 mmol) using the procedure of Example 29E substituting the product of Example 153B for the product of Example 29D to provide a solid which was triturated with methanol to provide the title compound (209 mg, 35%).

Example 153D

Carbonic acid 4-(4-tert-butoxycarbonyloxy-phenylsulfanyl)-3-(pyrido[2,3-d]pyrimidin-4-ylamino)-phenyl ester tert-butyl ester The product of Example 153C (195 mg, 0.539 mmol) was reacted with Di-tert-butyl dicarbonate (234 mg, 1.078 mmol), triethyl amine (0.165 mL, 1.19 mmol), and 4-dimethylaminopryidine (2 mg) in dichloromethane (5 mL), tetrahydrofuran (3 mL) and dimethyl foramide (1 mL) at room temperature for 16 hours. Afterwards, the mixture was poured into water (10 mL) and the resultant solution extracted with ethyl acetate (3×10 mL), the combined extracts dried over magnesium sulfate, filtered and concentrated under vacuum to provide the title compound (256 mg, 84%). $^1$H NMR (300 MHz, DMSO-$d_6$) δ ppm: 1.47 (s, 9H), 1.49 (s, 9H), 7.13 (d, J=8.8 Hz, 2H), 7.20 (m, 1H), 7.29 (d, J=8.8 Hz, 2H), 7.35 (m, 1H), 7.46 (m, 1H), 7.63 (m, 1H), 8.61 (m, 1H), 8.82 (m, 1H), 9.08 (m, 1H), 10.27 (s, 1H); MS (ESI+) m/z 563 (M+H)+.

Example 154

4-(4-Amino-phenylsulfanyl)-3-(7-isopropyl-pyrido[2,3-d]pyrimidin-4-ylamino)-N-(5-trifluoromethyl-[1,3,4]thiadiazol-2-yl)-benzamide

Example 154A

{4-[2-Nitro-4-(5-trifluoromethyl-[1,3,4]thiadiazol-2-ylcarbamoyl)-phenylsulfanyl]-phenyl}-carbamic acid 9H-fluoren-9-ylmethyl ester A solution of the product of Example 19C (290 mg, 0.546 mmol) in anhydrous tetrahydrofuran (5 mL) was treated with 2-amino-5-trifluoromethyl-1,3,4-thiadiazole (102 mg, 0.601 mmol) and diisopropylethylamine (0.143 mL, 0.819 mmol), and stirred at room temperature under a nitrogen atmosphere for 16 hours. The reaction was diluted with ethyl acetate (100 mL) and washed with saturated aqueous sodium bicarbonate (25 mL), water (2×25 mL), and brine (25 mL). The organic phase was dried over anhydrous sodium sulfate, filtered, and concentrated in vacuo. Trituration with methylene chloride provided the title compound (308 mg, 85%).

Example 154B

{4-[2-Amino-4-(5-trifluoromethyl-[1,3,4]thiadiazol-2-ylcarbamoyl)-phenylsulfanyl]-phenyl}-carbamic acid 9H-fluoren-9-ylmethyl ester The product of Example 154A (307 mg, 0.463 mmol), ammonium chloride (162 mg, 3.03 mmol), and iron powder (159 mg, 2.845 mmol) in a mixture of water (3 mL), ethanol (6 mL) and tetrahydrofuran (6 mL) was heated at 90° C. under a nitrogen atmosphere for 1 hour. The reaction was cooled to room temperature, diluted with ethyl acetate (100 mL), and washed with water (3×50 mL) and brine (50 mL). The organic phase was dried over anhydrous sodium sulfate, filtered, and concentrated by rotary evaporation in vacuo to give the product as a light yellow solid (224 mg, 76

Example 154C

{4-[2-(7-Isopropyl-pyrido[2,3-d]pyrimidin-4-ylamino)-4-(5-trifluoromethyl-[1,3,4]thiadiazol-2-ylcarbamoyl)-phenylsulfanyl]-phenyl}-carbamic acid 9H-fluoren-9-ylmethyl ester A solution of the product of Example 8E (75.8 mg, 0.3503 mmol) and the product of Example 154B (222 mg, 0.3503 mmol) in acetic acid (8 mL) was stirred in an oil bath preheated to 140° C. for 1.5 hour. The reaction was cooled to room temperature, diluted with hexanes (100 mL), concentrated by rotary evaporation, and co-evaporated with methylene chloride/hexanes (4 times). The residue was dried on hi-vacuum, then purified by silica gel flash chromatography with 30% ethyl acetate/methylene chloride, followed by 3% methanol/methylene chloride to afford the title compound as a yellow solid (116 mg, 41%).

Example 154D 4-(4-Amino-phenylsulfanyl)-3-(7-isopropyl-pyrido[2,3-d]pyrimidin-4-ylamino)-N-(5-trifluoromethyl-[1,3,4]thiadiazol-2-yl)-benzamide A solution of the product of Example 154C (114 mg, 0.1416 mmol) in 1,4-dioxane (4 mL) was treated with a solution of lithium hydroxide monohydrate (11.9 mg, 0.2833 mmol) in water (2 mL) at ambient temperature, then heated at 65° for 30 minutes. The reaction was cooled to room temperature, diluted with ethyl acetate (100 mL) and water (50 mL), adjusted the aqueous pH to 5-6 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Trituration of the residue with 3% methanol/methylene chloride afforded the title compound as a light yellow solid (57 mg, 69%). $^1$H NMR (300 MHz, DMSO-$d_6$/TFA) δ ppm: 1.35 (d, J=6.62 Hz, 6 H) 3.08-3.51 (m, 1 H) 7.25 (d, J=8.46 Hz, 1 H) 7.39 (d, J=8.46 Hz, 2 H) 7.55 (d, J=8.82 Hz, 2 H) 7.94 (d, J=8.82 Hz, 1 H) 8.18 (dd, J=8.46, 2.21 Hz, 1 H) 8.27 (d, J=1.84 Hz, 1 H) 8.99 (s, 1 H) 9.10 (d, J=8.82 Hz, 1 H); MS (ESI+) m/z 583 (M+H)$^+$, (ESI−) m/z 581 (M−H)−.

Example 155

4-(4-Amino-phenylsulfanyl)-3-(7-isopropyl-pyrido[2,3-d]pyrimidin-4-ylamino)-N-(5-trifluoromethyl-[1,3,4]thiadiazol-2-yl)-benzamide

Example 155A

{4-[4-Cyclopentylcarbamoyl-2-(7-isopropyl-pyrido[2,3-d]pyrimidin-4-ylamino)-phenylsulfanyl]-phenyl}-carbamic acid 2,2,2-trichloro-ethyl ester The product of Example 162b (50 mg, 0.0824 mmol) was dissolved in anhydrous N,N-dimethylformamide (1 mL)

under a nitrogen atmosphere, and treated with cyclopentylamine (8.4 mg, 0.0989 mmol), 3-(diethoxyphosphoryloxy)-1,2,3-benzotriazin-4(3H)-one (49.3 mg, 0.1648 mmol), and triethylamine (0.034 mL, 0.2472 mmol). The reaction was stirred at room temperature for 16 hours and the solvent removed by rotary evaporation in vacuo. Purification of the residue by silica gel flash chromatography with 4% methanol/methylene chloride afforded the title compound as a light yellow solid (41 mg, 74%).

Example 155B 4-(4-Amino-phenylsulfanyl)-N-cyclopentyl-3-(7-isopropyl-pyrido[2,3-d]pyrimidin-4-ylamino)-benzamide A solution of the product of Example 155A (39.9 mg, 0.0592 mmol) in 1,4-dioxane (2 mL) was treated with a solution of sodium hydroxide (5.9 mg, 0.148 mmol) in water (1 mL), then heated at 60° C. for 1 hour. The reaction was then cooled to room temperature and diluted with ethyl acetate (50 mL) and water (25 mL). The aqueous pH was adjusted to 5 with 1N aqueous hydrochloric acid, the layers were separated, and the organic phase washed with water (2×25 mL) and brine (25 mL). The organic extract was dried over anhydrous sodium sulfate, filtered, and concentrated by rotary evaporation in vacuo. Purification of the residue by silica gel flash chromatography with 4% methanol/methylene chloride provided the title compound as a white solid (19 mg, 64%). $^1$H NMR (300 MHz, DMSO-$d_6$) δ ppm: 1.34 (d, J=6.62 Hz, 6 H) 1.43-1.58 (m, 4 H) 1.59-1.75 (m, 2 H) 1.78-1.96 (m, 2 H) 3.12-3.32 (m, 1 H) 4.11-4.26 (m, 1 H) 5.57 (s, 2 H) 6.61 (d, J=8.46 Hz, 2 H), 6.81 (d, J=8.82 Hz, 1 H) 7.11 (d, J=8.46 Hz, 2 H) 7.64 (t, J=9.01 Hz, 1 H) 7.83 (s, 1 H) 8.21 (d, J=6.62 Hz, 1 H) 8.56 (s, 1 H) 8.86 (d, J=8.82 Hz, 1 H) 10.10 (s, 1 H); MS (ESI+) m/z 499 (M+)$^+$, (ESI−) m/z 497 (M−H)$^−$.

Example 156

{4-[4-(4-Bromo-phenylcarbamoyl)-2-(7-isopropyl-pyrido[2,3-d]pyrimidin-4-ylamino)-phenylsulfanyl]-phenyl}-carbamic acid 2-dimethylamino-ethyl ester The product from Example 100 (76 mg, 0.1 mmol), 2-dimethylamino-ethanol (50 µL, 0.5 mmol) and 1,8-diazabicyclo[5.4.0]undec-7-ene (15 µL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (48 mg, 52%). $^1$H NMR (300 MHz, DMSO-$d_6$) δ ppm: 1.36 (d, J=6.99 Hz, 6 H) 2.88 (s, 6 H) 3.28 (m, 1 H) 3.43 (m, 2 H) 4.43 (t, J=4.95 Hz, 2 H) 7.08 (d, J=8.09 Hz, 1 H) 7.40 (d, J=8.82 Hz, 2 H) 7.53 (m, 4 H) 7.73 (d, J=8.82 Hz, 2 H) 7.84 (m, 2 H) 7.98 (s, 1 H) 8.78 (s, 1 H) 8.95 (s, 1 H) 9.62 (s, 1 H) 9.99 (s, 1 H) 10.38 (s, 1 H) 11.28 (s, 1 H); MS (ESI+) m/z 700 702 (M+H)+.

Example 157

{4-[4-(4-Bromo-phenylcarbamoyl)-2-(7-isopropyl-pyrido[2,3-d]pyrimidin-4-ylamino)-phenylsulfanyl]-phenyl}-carbamic acid 2-morpholin-4-yl-ethyl ester The product from Example 100 (76 mg, 0.1 mmol), 2-morpholin-4-yl-ethanol (60 µL, 0.5 mmol) and 1,8-diazabicyclo[5.4.0]undec-7-ene (15 µL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (30 mg, 35%). $^1$H NMR (300 MHz, DMSO-$d_6$) δ ppm: 1.35 (d, J=6.62 Hz, 6 H) 3.46 (m, 11 H) 4.45 (t, J=4.95 Hz, 2 H) 7.07 (d, J=8.46 Hz, 1 H) 7.41 (d, J=8.82 Hz, 2 H) 7.54 (m, 4 H) 7.73 (d, J=8.82 Hz, 2 H) 7.83 (m, 2 H) 7.98 (s, 1 H) 8.78 (s, 1 H) 8.97 (d, J=8.46 Hz, 1 H) 10.02 (s, 1 H) 10.38 (s, 1 H) 11.34 (s, 1 H); MS (ESI+) m/z 742 744 (M+H)+.

Example 158

{4-[4-(4-Bromo-phenylcarbamoyl)-2-(7-isopropyl-pyrido[2,3-d]pyrimidin-4-ylamino)-phenylsulfanyl]-phenyl}-carbamic acid 2-(1-methyl-pyrrolidin-2-yl)-ethyl ester The product from Example 100 (76 mg, 0.1 mmol), 2-(1-methyl-pyrrolidin-2-yl)-ethanol (68 µL, 0.5 mmol) and 1,8-diazabicyclo[5.4.0]undec-7-ene (15 µL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (26 mg, 27%). $^1$H NMR (300 MHz, DMSO-$d_6$) δ ppm: 1.36 (d, J=6.99 Hz, 6 H) 1.70 (m, 1 H) 1.90 (m, 3 H) 2.28 (m, 2 H) 2.86 (d, J=4.41 Hz, 3 H) 3.10 (m, 1 H) 3.30 (m, 2 H) 3.56 (m, 1 H) 4.19 (t, J=6.43 Hz, 2 H) 7.07 (d, J=8.09 Hz, 1 H) 7.40 (d, J=8.82 Hz, 2 H) 7.54 (m, 4 H) 7.73 (d, J=8.82 Hz, 2 H) 7.86 (m, 2 H) 7.98 (s, 1 H) 8.81 (s, 1 H) 8.96 (d, J=8.46 Hz, 1 H) 9.55 (s, 1 H) 9.93 (s, 1 H) 10.39 (s, 1 H) 11.45 (s, 1 H); MS (ESI+) m/z 740 742 (M+H)+.

Example 159

{4-[4-(4-Bromo-phenylcarbamoyl)-2-(7-isopropyl-pyrido[2,3-d]pyrimidin-4-ylamino)-phenylsulfanyl]-phenyl}-carbamic acid 1-methyl-piperidin-3-ylmethyl ester The product from Example 100 (76 mg, 0.1 mmol), (1-methyl-piperidin-3-yl)-methanol (65 mg, 0.5 mmol) and 1,8-diazabicyclo[5.4.0]undec-7-ene (15 µL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (36 mg, 37%). $^1$H NMR (300 MHz, DMSO-$d_6$) δ ppm: 1.20 (m, 1 H) 1.36 (d, J=6.99 Hz, 6 H) 1.78 (m, 3 H) 2.14 (m, 1 H) 2.79 (d, J=4.04 Hz, 3 H) 3.28 (m, 1 H) 3.44 (m, 4 H) 4.02 (m, 2 H) 7.07 (d, J=8.09 Hz, 1 H) 7.40 (d, J=8.82 Hz, 2 H) 7.54 (m, 4 H) 7.73 (d, J=8.82 Hz, 2 H) 7.85 (m, 2 H) 7.98 (s, 1 H) 8.79 (s, 1 H) 8.95 (d, J=8.46 Hz, 1 H) 9.46 (s, 1 H) 9.96 (s, 1 H) 10.38 (s, 1 H) 11.38 (s, 1 H); MS (ESI+) m/z 740 742 (M+H)+.

Example 160

{4-[4-(4-Bromo-phenylcarbamoyl)-2-(7-isopropyl-pyrido[2,3-d]pyrimidin-4-ylamino)-phenylsulfanyl]-phenyl}-carbamic acid 3-dimethylamino-propyl ester The product from Example 100 (76 mg, 0.1 mmol), 3-dimethylamino-propan-1-ol (59 µL, 0.5 mmol) and 1,8-diazabicyclo[5.4.0]undec-7-ene (15 µL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (31 mg, 33%). $^1$H NMR (300 MHz, DMSO-d$_6$) δ ppm: 1.35 (d, J=6.99 Hz, 6 H) 2.01 (m, 2 H) 2.81 (d, J=4.41 Hz, 6 H) 3.16 (m, 2 H) 3.28 (m, 1 H) 4.16 (t, J=6.25 Hz, 2 H) 7.06 (d, J=8.46 Hz, 1 H) 7.40 (d, J=8.82 Hz, 2 H) 7.52 (m, 4 H) 7.73 (d, J=8.82 Hz, 2 H) 7.84 (m, 2 H) 7.98 (s, 1 H) 8.77 (s, 1 H) 8.94 (d, J=8.46 Hz, 1 H) 9.47 (s, 1 H) 9.93 (s, 1 H) 10.38 (s, 1 H) 11.30 (s, 1 H); MS (ESI+) m/z 714 716 (M+H)+.

Example 161

4-(4-Amino-phenylsulfanyl)-N-(5-tert-butyl-thiazol-2-yl)-3-(7-isopropyl-pyrido[2,3-d]pyrimidin-4-ylamino)-benzamide

Example 161A

N-(5-tert-Butyl-thiazol-2-yl)-4-chloro-3-nitro-benzamide

A solution of 4-chloro-3-nitrobenzoyl chloride (1.336 g, 6.681 mmol) in anhydrous pyridine (30 mL) was treated with 2-amino-5-tert-butylthiazole (1.044 g, 6.681 mmol) and the reaction stirred at room temperature under a nitrogen atmosphere. The solvent was removed by rotary evaporation in vacuo and the residue dried on a vacuum pump. The residue was taken up in ethyl acetate (100 mL) and washed with water (4×50 mL) and brine (50 mL). The organic phase was dried over anhydrous sodium sulfate, filtered, and concentrated in vacuo. Purification by silica gel chromatography eluting with 5% ethyl acetate/methylene chloride provided the title compound (1.76 g, 78%).

Example 161B 4-(4-Amino-phenylsulfanyl)-N-(5-tert-butyl-thiazol-2-yl)-3-nitro-benzamide A mixture of the product of Example 161A (500 mg, 1.472 mmol), 4-aminothiophenol (350 mg, 2.796 mmol) and anhydrous sodium acetate (604 mg, 7.36 mmol) in anhydrous ethanol (15 mL) was heated at reflux under a nitrogen atmosphere for 3 hours. The reaction was cooled to room temperature and the ethanol removed by rotary evaporation. The residue was partitioned with water (50 mL) and ethyl acetate (100 mL), and the organic phase washed with water (2×50 mL) and brine (50 mL). The organic extract was dried over anhydrous sodium sulfate, filtered, and concentrated in vacuo. Trituration of the solid with 4% ethyl acetate/methylene chloride (25 mL) afforded the title compound (452 mg, 72%).

Example 161C

{4-[4-(5-tert-Butyl-thiazol-2-ylcarbamoyl)-2-nitro-phenylsulfanyl]-phenyl-carbamic acid 9H-fluoren-9-ylmethyl ester A suspension of the product of Example 161B (226 mg, 0.5274 mmol) in anhydrous methylene chloride (5 mL) was treated with 9-fluorenylmethoxycarbonyl chloride (164 mg, 0.6329 mmol) and dry pyridine (0.085 mL, 1.055 mmol), and the resulting yellow solution stirred under a nitrogen atmosphere at ambient temperature for 3 hours. The reaction was diluted with ethyl acetate (100 mL) and washed with water (2×50 mL) and brine (50 mL). The organic was dried over anhydrous sodium sulfate, filtered, and concentrated by rotary evaporation in vacuo to provide the title compound as a yellow solid (338 mg, 98%).

Example 161D

{4-[2-Amino-4-(5-tert-butyl-thiazol-2-ylcarbamoyl)-phenylsulfanyl]-phenyl}-carbamic acid 9H-fluoren-9-ylmethyl ester The product of Example 161C (336 mg, 0.516 mmol), ammonium chloride (181 mg, 3.382 mmol), and iron powder (177 mg, 3.175 mmol) in a mixture of water (3 mL), ethanol (6 mL) and tetrahydrofuran (6 mL) was heated at 90° C. under a nitrogen atmosphere for 1 hour. The reaction was cooled to room temperature, diluted with ethyl acetate (100 mL), and washed with water (3×50 mL) and brine (50 mL). The organic was dried over anhydrous sodium sulfate, filtered, and concentrated by rotary evaporation in vacuo to give the product as a light yellow solid (290 mg, 90%).

Example 161E

{4-[4-(5-tert-Butyl-thiazol-2-ylcarbamoyl)-2-(7-isopropyl-pyrido[2,3-d]pyrimidin-4-ylamino)-phenylsulfanyl]-phenyl}-carbamic acid 9H-fluoren-9-ylmethyl ester A solution of the product of Example 8E (100.4 mg, 0.4643 mmol) and the product of Example 161D (288.2 mg, 0.4643 mmol) in acetic acid (6 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4 times). The residue was dried on hi-vacuum, then purified by silica gel flash chromatography with 20% ethyl acetate/methylene chloride, followed by 50% ethyl acetate/methylene chloride to afford the title compound (125 mg, 34%).

Example 161F 4-(4-Amino-phenylsulfanyl)-N-(5-tert-butyl-thiazol-2-yl)-3-(7-isopropyl-pyrido[2,3-d]pyrimidin-4-ylamino)-benzamide A solution of the product of Example 161E (123.4 mg, 0.1558 mmol) in 1,4-dioxane (4 mL) was treated with a solution of lithium hydroxide monohydrate (13 mg, 0.3 116 mmol) in water (2 mL) at ambient temperature, then heated at 65° C. for 1 hour. The reaction was cooled to room temperature, diluted with ethyl acetate (100 mL) and water (30 mL), adjusted the aqueous pH to 6 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel flash chromatography with 4% methanol/methylene chloride afforded the title compound (58 mg, 65%). $^1$H NMR (300 MHz, DMSO-d$_6$) δ ppm: 1.28 (s, 9 H) 1.34 (d, J=6.99 Hz, 6 H) 3.17-3.34 (m, 1 H) 5.64 (s, 2 H) 6.65 (d, J=8.46 Hz, 2 H) 6.80 (s, 1 H) 6.82 (d, J=8.46 Hz, 1 H) 7.16 (d, J=8.46 Hz, 2 H)

7.65 (d, J=8.46 Hz, 1 H) 7.88-7.98 (dd, 1 H) 8.11 (s, 1 H) 8.58 (s, 1 H) 8.89 (d, J=8.46 Hz, 1 H) 10.13 (s, 1 H) 12.47 (s, 1 H); MS (ESI+) m/z 570 (M+H)$^+$, (ESI−) m/z 568 (M−H)$^-$.

Example 162

4-(4-Amino-phenylsulfanyl)-N-(3-fluoro-phenyl)-3-(7-isopropyl-pyrido[2,3-d]pyrimidin-4-ylamino)-N-methyl-benzamide

Example 162a

3-Nitro-4-[4-(2,2,2-trichloro-ethoxycarbonylamino)-phenylsulfanyl]-benzoic acid

To a solution of 4-(4-Amino-phenylsulfanyl)-3-nitro-benzoic acid (4.0 g, 13.8 mmol) in 75 mL of $CH_2Cl_2$ was added dropwise at room temperature Bis(trimethylsilyl)acetamide (6.73 mL, 27.6 mmol) over 10 minutes. The reaction mixture was stirred at room temperature for 1 hour. Pyridine (2.23 mL, 27.6 mmol) was added to the reaction mixture followed by the dropwise addition of TROC-chloroformate (2.04 mL, 15.2 mmol). After stirring for 2 hours the reaction mixture was concentrated under vacuum, diluted with 200 mL of water and the pH adjusted to 3.0 with 1N HCl. Decant off the aqueous solution and take the residue up in $CH_2Cl_2$ and filter off the resulting yellow precipitate providing the title compound (5.14 g, 80%).

Example 162b

[4-(4-Chlorocarbonyl-2-nitro-phenylsulfanyl)-phenyl]-carbamic acid 2,2,2-trichloro-ethyl ester The product from Example 162a (2.0 g, 42.9 mmol) in thionyl chloride (10 mL) containing 1 drop of dimethylformamide and was heated to reflux for 3 hours. Cooled and concentrated under vacuum and dried under high vacuum overnight. The title compound was used without further purification.

Example 162c (4-{4-[(3-Fluoro-phenyl)-methyl-carbamoyl]-2-nitro-phenylsulfanyl}-phenyl)-carbamic acid 2,2,2-trichloro-ethyl ester The product from Example 162b (0.25 g, 0.516 mmol) and (4-Fluoro-phenyl)-methyl-amine (71 mg, 0.568 mmol) in toluene (20 mL) was heated to reflux for 3 hours. After cooling the solution, the reaction mixture was concentrated under vacuum to afford the title compound (295 mg, 99% yield) as pale yellow solid.

Example 162d (4-{2-Amino-4-[(4-fluoro-phenyl)-methyl-carbamoyl]-phenylsulfanyl}-phenyl)-carbamic acid 2,2,2-trichloro-ethyl ester The product from Example 162c (295 mg, 0.516 mmol) was reduced with Fe and $NH_4Cl$ following the procedure from Example 9E providing the title compound was isolated as a white solid (205 mg, 73% yield).

Example 162e

{4-[4-[(4-Fluoro-phenyl)-methyl-carbamoyl]-2-(7-isopropyl-pyrido[2,3-d]pyrimidin-4-ylamino)-phenylsulfanyl]-phenyl}-carbamic acid 2,2,2-trichloro-ethyl ester The product from Example 162d (205.2 mg, 0.3780 mmol) and the product from Example 8E (81.8 mg, 0.3780 mmol) in 10 mL of acetic acid was heated at 140° C. for 1 hour. The reaction mixture was cooled to room temperature and then concentrated under vacuum giving the crude title compound that was purified by silica gel chromatography eluting with 4% methanol in dichloromethane to provide the title compound was isolated as a white solid (175 mg, 65% yield).

Example 162f 4-(4-Amino-phenylsulfanyl)-N-(4-fluoro-phenyl)-3-(7-isopropyl-pyrido[2,3-d]pyrimidin-4-ylamino)-N-methyl-benzamide The product from Example 162d (70 mg, 0.0980 mmol) in THF (10 mL) was reacted with 1N NaOH (1 mL, 1.00 mmol) and reaction mixture heated at 55° C. for 1 hour. The reaction mixture was cooled and concentrated under vacuum to remove the THF. The pH was adjusted to 6.0 with 1N HCl and the resulting precipitate was removed by vacuum filtration and dried under high vacuum providing the title compound as a pale yellow solid (45 mg, 85% yield). $^1$H NMR (300 MHz, DMSO-$d_6$) δ ppm: 1.32 (d, J=6.99 Hz, 6 H) 3.12-3.25 (m, 1 H) 3.34 (s, 3 H) 6.52-6.67 (m, 3 H) 6.94-7.11 (m, 5 H) 7.10-7.20 (m, 2 H) 7.20-7.41 (m, 2 H) 7.61 (d, J=8.46 Hz, 1 H) 8.51 (s, 1 H) 8.80 (d, J=8.09 Hz, 1 H) 10.10 (s, 1 H); MS (ESI) m/z 539 (M+H)+.

Example 163

4-(4-Amino-phenylsulfanyl)-3-(7-isopropyl-pyrido[2,3-d]pyrimidin-4-ylamino)-N-(5-methyl-thiazol-2-yl)-benzamide The title compound is produced by the procedures of Example 162 substituting 2-amino-5-methyl-thiazole for (4-Fluoro-phenyl)-methyl-amine in Example 162c.

Example 164

4-(4-Amino-phenylsulfanyl)-3-(7-isopropyl-pyrido[2,3-d]pyrimidin-4-ylamino)-N-(4-methyl-thiazol-2-yl)-benzamide The title compound is produced by the procedures of Example 162 substituting 2-amino-4-methyl-thiazole for (4-Fluoro-phenyl)-methyl-amine in Example 162c.

Example 165

4-(4-Amino-phenylsulfanyl)-N-(4-fluoro-phenyl)-3-(7-isopropyl-pyrido[2,3-d]pyrimidin-4-ylamino)-N-methyl-benzamide

Example 165A (4-{4-[(4-Fluoro-phenyl)-methyl-carbamoyl]-2-nitro-phenylsulfanyl}-phenyl)-carbamic acid 2,2,2-trichloro-ethyl ester The compound from Example 162b (250 mg, 0.516 mmol) and 4-Fluoro-phenylamine (71 mg, 0.568 mmol) were reacted following the procedure from Example 162c to yield the title compound that was used without further manipulation.

Example 165B (4-{2-Amino-4-[(4-fluoro-phenyl)-methyl-carbamoyl]-phenylsulfanyl}-phenyl)-carbamic acid 2,2,2-trichloro-ethyl ester The product from Example 165A (295 mg, 0.516 mmol) was reduced with Fe and $NH_4Cl$ following the procedure from Example 9E to yield the title compound (205 mg, 73% yield)

Example 165C

{4-[4-[(4-Fluoro-phenyl)-methyl-carbamoyl]-2-(7-isopropyl-pyrido[2,3-d]pyrimidin-4-ylamino-phenylsulfanyl]-phenyl}-carbamic acid 2,2,2-trichloro-ethyl ester The product from Example 8E (48 mg, 0.221 mmol) and Example 165B (120 mg, 0.221 mmol) were combined in acetic acid (6 mL) and reacted as in 614E to yield the title compound as a light yellow solid (83 mg, 54%).

Example 165D 4-(4-Amino-phenylsulfanyl)-N-(4-fluoro-phenyl)-3-(7-isopropyl-pyrido[2,3-d]pyrimidin-4-ylamino)-N-methyl-benzamide The product or Example 165C (83 mg, 0.1162 mmol) was reacted with NaOH as in Example 162f to give the title compound 617D (46 mg, 74%) as a yellow solid. 1H NMR (300 MHz, DMSO-D6) δ ppm: 1.32 (d, J=6.99 Hz, 6 H) 3.12-3.25 (m, 1 H) 3.34 (s, 3 H) 6.52-6.67 (m, 3 H) 6.94-7.11 (m, 5 H) 7.10-7.20 (m, 2 H) 7.20-7.41 (m, 2 H) 7.61 (d, J=8.46 Hz, 1 H) 8.51 (s, 1 H) 8.80 (d, J=8.09 Hz, 1 H) 10.10 (s, 1 H); MS (ESI) m/z 539 (m+H)+.

Example 166

{4-[2-Amino-4-([1,3,4]thiadiazol-2-ylcarbamoyl)-phenylsulfanyl]-phenyl}-carbamic acid 2,2,2-trichloro-ethyl ester

Example 166A

{4-[2-Nitro-4-([1,3,4]thiadiazol-2-ylcarbamoyl)-phenylsulfanyl]-phenyl}-carbamic acid 2,2,2-trichloro-ethyl ester The product of Example 162b (300 mg, 0.6197 mmol) and [1,3,4]Thiadiazol-2-ylamine (62 mg, 0.6197 mmol) in toluene (10 mL) were reacted as in Example 162c to yield the title compound (340 mg, 100% yield).

Example 166B

{4-[2-Amino-4-([1,3,4]thiadiazol-2-ylcarbamoyl)-phenylsulfanyl]-phenyl}-carbamic acid 2,2,2-trichloro-ethyl ester The product of Example 166A (340 mg, 0.6197 mmol) was reduced with Fe and $NH_4Cl$ following the procedure in Example 9E to yield the title compound (231 mg, 72% yield) as a white solid. 1H NMR (300 MHz, DMSO-D6) δ ppm: 4.94 (s, 2 H) 5.59 (s, 2 H) 7.14-7.35 (m, 4 H) 7.42 (s, 1 H) 7.50 (d, J=8.46 Hz, 2 H) 9.22 (s, 1 H) 10.26 (s, 1 H); MS (ESI) m/z 520 (M+H)+.

Example 167

4-(4-Amino-phenylsulfanyl)-3-(7-isopropyl-pyrido[2,3-d]pyrimidin-4-ylamino)-N-(3-methyl-isothiazol-5-yl)-benzamide

Example 167A

{4-[4-(3-Methyl-isothiazol-5-ylcarbamoyl)-2-nitrophenylsulfanyl]-phenyl-carbamic acid 9H-fluoren-9-ylmethyl ester A solution of the product of Example 19C (290 mg, 0.546 mmol) in anhydrous tetrahydrofuran (5 mL) was treated with 5-amino-3-methylisothiazole hydrochloride (90.5 mg, 0.6008 mmol) and diisopropylethylamine (0.238 mL, 1.365 mmol), and stirred at room temperature under a nitrogen atmosphere for 18 hours. The reaction was diluted with ethyl acetate (100 mL) and washed with saturated aqueous sodium bicarbonate (25 mL), water (2×25 mL), and brine (25 mL). The organic phase was dried over anhydrous sodium sulfate, filtered, and concentrated in vacuo to provide the title compound (202 mg, 61%).

Example 167B

{4-[2-Amino-4-(3-methyl-isothiazol-5-ylcarbamoyl)-phenylsulfanyl]-phenyl}-carbamic acid 9H-fluoren-9-ylmethyl ester The product of Example 167A (200 mg, 0.328 mmol), ammonium chloride (115 mg, 2.152 mmol), and iron powder (113 mg, 2.021 mmol) in a mixture of water (2 mL), ethanol (4 mL) and tetrahydrofuran (4 mL) was heated at 90° C. under a nitrogen atmosphere for 1 hour. The reaction was cooled to room temperature, diluted with ethyl acetate (50 mL), and washed with water (3×50 mL) and brine (50 mL). The organic was dried over anhydrous sodium sulfate, filtered, and concentrated by rotary evaporation in vacuo. Purification by silica gel chromatography eluting with 5% methanol/methylene chloride afforded the product as a gold-colored solid (114 mg, 60%).

Example 167C

{4-[2-(7-Isopropyl-pyrido[2,3-d]pyrimidin-4-ylamino)-4-(3-methyl-isothiazol-5-ylcarbamoyl)-phenylsulfanyl]-phenyl}-carbamic acid 9H-fluoren-9-ylmethyl ester A solution of the product of Example 8E (42 mg, 0.1939 mmol) and the product of Example 167B (112.2 mg, 0.1939 mmol) in acetic acid (4 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4 times). The residue was dried on hi-vacuum, then purified by silica gel chromatography eluting with 30% ethyl acetate/methylene chloride, followed by 4% methanol/methylene chloride to afford the title compound (119 mg, 82%).

Example 167D 4-(4-Amino-phenylsulfanyl)-3-(7-isopropyl-pyrido [2,3-d]pyrimidin-4-ylamino)-N-(3-methyl-isothiazol-5-yl)-benzamide A solution of the product of Example 167C (117 mg, 0.156 mmol) in 1,4-dioxane (4 mL) was treated with a solution of lithium hydroxide monohydrate (13.1 mg, 0.312 mmol) in water (2 mL) at ambient temperature, then heated at 70° C. for 1 hour. The reaction was cooled to room temperature, diluted with ethyl acetate (50 mL) and water (25 mL), adjusted the aqueous pH to 5 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel chromatography eluting with 5% methanol/methylene chloride afforded the title compound as a light yellow solid (58.5 mg, 71%). $^1$H NMR (300 MHz, DMSO-$d_6$) δ ppm: 1.34 (d, J=6.99 Hz, 6 H) 2.33 (s, 3 H) 3.14-3.30 (m, 1 H) 5.63 (s, 2 H) 6.65 (d, J=8.46 Hz, 2 H) 6.87 (s, 1 H) 6.91 (d, J=8.82 Hz, 1 H) 7.15 (d, J=8.46 Hz, 2 H) 7.65 (d, J=8.09 Hz, 1 H) 7.86 (d, J=7.72 Hz, 1 H) 8.03 (s, 1 H) 8.59 (s, 1 H) 8.89 (d, J=8.09 Hz, 1 H) 10.19 (s, 1 H) 12.17 (s, 1 H); MS (ESI+) m/z 528 (M+H)$^+$, (ESI−) m/z 526 (M−H)$^−$.

Example 168

4-[4-[1-(3-Bromo-phenyl)-ethoxy]-2-(pyrido[2,3-d] pyrimidin-4-ylamino)-phenylsulfanyl]-phenol

Example 168a 1-(1-Bromo-ethyl)-4-fluoro-benzene

To a solution of 1-(3-Bromo-phenyl)-ethanol (7.0 g, 34.0 mmol) in dichloromethane (40 mL) was added drop wise phosphorus tribromide (77 g, 34.0 mmol). The mixture was stirred at room temperature for 16 h. The reaction was poured onto ice/water. The aqueous phase was made basic with sodium bicarbonate. The aqueous phase was extracted with dichloromethane. The organic phase was washed with water, brine, and dried over sodium sulfate, filtered and concentrated under vacuum giving the title compound (7.8 g, 80%).

Example 168b

4-[1-(3-Bromo-phenyl)-ethoxy]-1-chloro-2-nitrobenzene

To Example 168a (7.8 g, 30 mmol) in DMF (50 mL) was added 4-chloro-3-nitro-phenol (5.14 g, 30.0 mmol), and K$_2$CO$_3$ (8.18 g, 60 mmol). The mixture was heated at 80° C. for 16 reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate 90:10) to give the title compound (7.0 g, 66%).

Example 168c

4-{4-[1-(3-Bromo-phenyl)-ethoxy]-2-nitro-phenylsulfanyl}-phenol

To Example 168b (5.0 g, 14.0 mmol) in DMF (50 mL) was added 4-mercaptophenol (1.7 g, 14.0 mmol), and K$_2$CO$_3$ (3.8 g, 28 mmol). The mixture was heated at 80° C. for 16 hr. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate/methanol 75:15:5) to give the title compound (5.2 g, 83%).

Example 168d

4-{2-Amino-4-[1-(3-bromo-phenyl)-ethoxy]-phenylsulfanyl}-phenol

The product from Example 168c (5.4 g, 12.2 mmol) was reacted with Fe and NH$_4$Cl as described in Example 9E to give the title compound (3.6 g, 76%).

Example 168e

4-[4-[1-(3-Bromo-phenyl)-ethoxy]-2-(pyrido[2,3-d] pyrimidin-4-ylamino)-phenylsulfanyl]-phenol The product from Example 29A (125 mg, 0.72 mmol) was reacted with Example 168d 298 mg, 0.72 mmol) in acetic acid (10 mL) at 125° C. in a sealed tube for 5 minute giving the crude title compound which was purified by HPLC with TFA providing the product as the trifluoroacetic acid (120 mg, 31%). $^1$H NMR (300 MHz, DMSO-$d_6$) δ ppm: 1.54 (d, J=6.25 Hz, 3 H) 5.52 (q, J=6.25 Hz, 1 H) 6.66 (d, J=8.82 Hz, 2 H) 6.85 (s, 1 H) 7.07-7.12 (m, 3 H) 7.19 (s, 1 H) 7.32 (t, J=7.72 Hz, 1 H) 7.39-7.49 (m, 2 H) 7.61 (s, 2 H) 8.57 (s, 1H) 8.80 (s, 1 H) 9.06 (s, 1H) 9.65 (s, 1 H); MS (ESI−) m/z 545 (M−H)−.

Example 169

{4-[4-(5-Fluoro-pyridin-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 174A was reacted with the product from Example 8E using the procedure from Example 100D substituting the product from Example 174A for the product from Example 100C to provide the crude product which was purified by silica gel chromatography eluting with 2% methanol in dichloromethane to provide the title compound (127 mg, 55%). $^1$H NMR (300 MHz, DMSO-$d_6$) δ ppm: 1.34 (d, J=6.99 Hz, 6 H) 3.13-3.28 (m, 1 H) 4.97 (s, 2 H) 7.00 (d, J=8.09 Hz, 1 H) 7.43 (d, J=8.82 Hz, 2 H) 7.63 (d, J=8.82 Hz, 1 H) 7.60 (d, J=8.46 Hz, 2 H) 7.79 (dt, J=8.73, 3.13 Hz, 1 H) 7.89 (d, J=8.82 Hz, 1 H) 8.10 (s, 1 H) 8.20 (dd, J=8.82, 3.68 Hz, 1 H) 8.39 (d, J=2.94 Hz, 1 H) 8.59 (s, 1 H) 8.86 (d, J=8.46 Hz, 1 H) 10.21 (s, 1 H) 10.40 (s, 1 H) 10.91 (s, 1 H).

Example 170

{4-[2-(7-Isopropyl-pyrido[2,3-d]pyrimidin-4-ylamino)-4-(5-trifluoromethyl-pyridin-2-ylcarbamoyl)-phenylsulfanyl]-phenyl}-carbamic acid 2,2,2-trichloro-ethyl ester The product from Example 175A was reacted with the product from Example 8E using the procedure from Example 100D substituting the product from Example 175A for the product from Example 100C to provide the crude product was purified by silica gel chromatography eluting with 2% methanol in dichloromethane to provide the title compound. $^1$H NMR (300 MHz, DMSO-d$_6$) δ ppm: 1.34 (d, J=6.62 Hz, 6 H) 3.08-3.29 (m, 1 H) 4.97 (s, 2 H) 7.00 (d, J=8.46 Hz, 1 H) 7.44 (d, J=8.82 Hz, 2 H) 7.51-7.70 (m, 3 H) 7.92 (d, J=9.56 Hz, 1 H) 8.12 (s, 1 H) 8.23 (dd, J=9.01, 2.02 Hz, 1 H) 8.39 (d, J=9.19 Hz, 1 H) 8.59 (s, 1 H) 8.77 (s, 1 H) 8.86 (d, J=8.46 Hz, 1 H) 10.22 (s, 1 H) 10.41 (s, 1 H) 11.26 (s, 1 H).

Example 171

{4-[2-(7-Isopropyl-pyrido[2,3-d]pyrimidin-4-ylamino)-4-(5-methyl-pyridin-2-ylcarbamoyl)-phenylsulfanyl]-phenyl}-carbamic acid 2,2,2-trichloro-ethyl ester The product from Example 173A was reacted with the product from Example 8E using the procedure from Example 100D substituting the product from Example 173A for the product from Example 100C to provide the crude product was purified by silica gel chromatography eluting with 2% methanol in dichloromethane to provide the title compound. $^1$H NMR (300 MHz, DMSO-d$_6$) δ ppm: 1.34 (d, J=6.99 Hz, 6 H) 2.27 (s, 3 H) 3.14-3.29 (m, J=9.19 Hz, 1 H) 4.97 (s, 2 H) 6.99 (d, J=8.46 Hz, 1 H) 7.43 (d, J=8.46 Hz, 2 H) 7.53-7.78 (m, J=8.09, 2.21 Hz, 2 H) 7.59 (d, J=8.46 Hz. 2 H) 7.90 (d, J=7.72 Hz, 1 H) 8.06 (d, J=8.46 Hz, 1 H) 8.10 (s, 1 H) 8.20 (d, J=2.21 Hz, 1 H) 8.59 (s, 1 H) 8.86 (d, J=8.46 Hz, 1 H) 10.20 (s, 1 H) 10.40 (s, 1 H) 10.69 (s, 1 H).

Example 172

4-(4-Amino-phenoxy)-3-(7-isopropyl-pyrido[2,3-d]pyrimidin-4-ylamino)-N-(4-trifluoromethyl-phenyl)-benzamide

Example 172a

4-Fluoro-3-nitro-benzoyl chloride

The title compound was prepared from 4-Fluoro-3-nitro-benzoic acid (1.00 g, 5.40 mmol) dissolved in dichloroethane (25 mL) to which was added SOCl$_2$ (6.427 g, 54.02 mmol). This mixture was heated to 80° C. for 12 h at which point all the solvent was removed on under vacuum and the crude oil was taken forward without purification (1.10 g, 100%).

Example 172b

4-Fluoro-3-nitro-N-(4-trifluoromethyl-phenyl)-benzamide

The title compound was prepared by dissolving 4-Trifluoromethyl-phenylamine (475 mg, 2.95 mmol) in THF (20 ml) at room temperature. To this solution was added Hunig's base (762 mg, 5.86 mmol) and then a solution of the product from Example 172a (600 mg, 2.95 mmol) in THF (10 mL) was added drop wise over 5 minutes. After complete addition the reaction mixture was allowed to stir at room temperature for 1 hr and was poured into water and the title compound collected by filtration (900 mg, 93%).

Example 172c

{4-[2-Nitro-4-(4-trifluoromethyl-phenylcarbamoyl)-phenoxy]-phenyl}-carbamic acid tert-butyl ester The product from Example 172b (215 mg, 0.655 mmol) was dissolved in DMSO (30 ml) to which KOH (75 mg, 1.31 mmol) and (4-Hydroxy-phenyl)-carbamic acid tert-butyl ester (137 mg, 0.655 mmol) were added. The reaction mixture was then heated to 80° C. for 2 h reaction mixture was then cooled to room temperature and diluted with water and the title compound collected by filtration (240 mg, 78%).

Example 172d

{4-[2-Amino-4-(4-trifluoromethyl-phenylcarbamoyl)-phenoxy]-phenyl}-carbamic acid tert-butyl ester The product from Example 172c was reacted with Fe and NH$_4$Cl following the procedure of Example 9E to give the title compound (204 mg, 90%).

Example 172e

{4-[2-(7-Isopropyl-pyrido[2,3-d]pyrimidin-4-ylamino)-4-(4-trifluoromethyl-phenylcarbamoyl)-phenoxy]-phenyl}-carbamic acid tert-butyl ester The product from Example 8E (100 mg, 0.462 mmol) and the product from Example 172d (204 mg, 0.462 mmol) were dissolved in HOAc and placed in a preheated 120° C. oil bath for 10 minutes. The solvent was removed under a stream of N$_2$ and the crude oil was taken forward without purification.

Example 172f 4-(4-Amino-phenoxy)-3-(7-isopropyl-pyrido[2,3-d]pyrimidin-4-ylamino)-N-(4-trifluoromethyl-phenyl)-benzamide The product from Example 172e was dissolved in a 1:1 mixture of TFA in DCM and stirred at room temperature for 2 hrs. The solvent was removed under vacuum and the crude oil was purified by HPLC with TFA providing the product as a trifluoroacetic acid salt (85 mg, 36%). $^1$H NMR (300 MHz, DMSO-d$_6$) δ ppm: 1.75 (d, J=6.99 Hz, 6 H), 7.21 (d, J=8.09 Hz, 2 H), 7.29-7.35 (m, 2 H), 7.38 (d, J=8.82 Hz, 1 H), 8.14 (d, J=8.82 Hz, 2 H), 8.25 (d, J=8.46 Hz, 1 H), 8.40 (d, J=8.46 Hz, 3 H), 8.56 (d, J=1.84 Hz, 1 H), 9.26 (s, 1 H), 9.37 (d, J=8.82 Hz, 1 H), 10.98 (s, 1 H); MS (ESI+) m/z 559 (M+TFA+H)+; (ESI−) m/z 557 (M+TFA−H)−.

Example 173

4-(4-Amino-phenylsulfanyl)-3-(7-isopropyl-pyrido[2,3-d]pyrimidin-4-ylamino)-N-(5-methyl-pyridin-2-yl)-benzamide

Example 173A

{4-[2-Amino-4-(5-methyl-pyridin-2-ylcarbamoyl)-phenylsulfanyl]-phenyl}-carbamic acid 2,2,2-trichloro-ethyl ester A mixture of 2-amino-5-methylpyridine was reacted with the product of Example 162e using the procedure of Example 10A to provide {4-[4-(5-Methyl-pyridin-2-ylcarbamoyl)-2-nitro-phenylsulfanyl]-phenyl}-carbamic acid 2,2,2-trichloro-ethyl ester which was reacted according to the conditions described in Example 100C to provide the title product.

Example 173B

{4-[2-(7-Isopropyl-pyrido[2,3-d]pyrimidin-4-ylamino)-4-(5-methyl-pyridin-2-ylcarbamoyl)-phenylsulfanyl]-phenyl}-carbamic acid 2,2,2-trichloro-ethyl ester The product from Example 173A was reacted with the product from Example 8E using the procedure from Example 100D substituting the product from Example 173A for the product from Example 100C to provide the crude product was purified by silica gel chromatography eluting with 2% methanol in dichloromethane to provide the title compound.

Example 173C 4-(4-Amino-phenylsulfanyl)-3-(7-isopropyl-pyrido[2,3-d]pyrimidin-4-ylamino)-N-(5-methyl-pyridin-2-yl)-benzamide To a solution of the product of Example 173B in tetrahydrofuran and water (1:1) was added 1 M NaOH (5 equiv). The solution was heated at 60° C. for 40 minutes, cooled, adjusted to pH 6 with 1N aqueous hydrochloric acid and extracted with ethyl acetate. The combined extracts were dried over magnesium sulfate, filtered and concentrated under vacuum. The crude product was purified by silica gel chromatography eluting with 4% methanol in dichloromethane to provide the title compound. $^1$H NMR (300 MHz, DMSO-$d_6$) δ ppm: 1.34 (d, J=6.99 Hz, 6 H) 2.27 (s, 3 H) 3.14-3.29 (m, 1 H) 5.62 (s, 2 H) 6.64 (d, J=8.09 Hz, 2 H) 6.82 (d, J=8.46 Hz, 1 H) 7.15 (d, J=8.09 Hz, 2 H) 7.64 (d, J=8.46 Hz, 2 H) 7.87 (dd, J=8.27, 1.29 Hz, 1 H) 7.97-8.11 (m, 2 H) 8.19 (s, 1 H) 8.32 (s, 1 H) 8.50-8.61 (m, 1 H) 8.89 (d, J=8.82 Hz, 1 H) 10.12 (s, 1 H) 10.63 (s, 1 H).

Example 174

4-(4-Amino-phenylsulfanyl)-N-(5-fluoro-pyridin-2-yl)-3-(7-isopropyl-pyrido[2,3-d]pyrimidin-4-ylamino)-benzamide

Example 174A

{4-[2-Amino-4-(5-fluoro-pyridin-2-ylcarbamoyl)-phenylsulfanyl]-phenyl}-carbamic acid 2,2,2-trichloro-ethyl ester A mixture of 2-amino-5-fluoropyridine was reacted with the product of Example 162e using the procedure of Example 10A to provide {4-[4-(5-Fluoro-pyridin-2-ylcarbamoyl)-2-nitro-phenylsulfanyl]-phenyl}-carbamic acid 2,2,2-trichloro-ethyl ester which was reacted according to the conditions described in Example 100C to provide the title product.

Example 174B

{4-[4-(5-Fluoro-pyridin-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 174A was reacted with the product from Example 8E using the procedure from Example 100D substituting the product from Example 174A for the product from Example 100C to provide the crude product which was purified by silica gel chromatography eluting with 2% methanol in dichloromethane to provide the title compound (127 mg, 55%).

Example 174C 4-(4-Amino-phenylsulfanyl)-N-(5-fluoro-pyridin-2-yl)-3-(7-isopropyl-pyrido[2,3-d]pyrimidin-4-ylamino)-benzamide To a solution of the product of Example 174B in tetrahydrofuran and water (1:1) was added 1 M NaOH (5 equiv). The solution was heated at 60° C. for 40 minutes, cooled, adjusted to pH 6 with 1N aqueous hydrochloric acid and extracted with ethyl acetate. The combined extracts were dried over magnesium sulfate, filtered and concentrated under vacuum. The resultant residue was purified by silica gel chromatography eluting with 2% methanol in dichloromethane to provide the title compound. $^1$H NMR (300 MHz, DMSO-$d_6$) δ ppm: 1.34 (d, J=6.99 Hz, 6 H) 3.15-3.29 (m, J=6.89, 6.89, 6.89, 6.89 Hz, 1 H) 5.62 (s, 2 H) 6.65 (d, J=8.46 Hz, 2 H) 6.83 (d, J=8.46 Hz, 1 H) 7.15 (d, J=8.46 Hz, 2 H) 7.64 (d, J=8.46 Hz, 1 H) 7.79 (dt, J=8.64, 2.94 Hz, 1 H) 7.87 (dd, J=8.46, 1.84 Hz, 1 H) 8.04 (d, J=1.84 Hz, 1 H) 8.20 (dd, J=9.19, 4.04 Hz, 1 H) 8.38 (d, J=2.94 Hz, 1 H) 8.58 (s, 1 H) 8.89 (d, J=8.46 Hz, 1 H) 10.13 (s, 1 H) 10.85 (s, 1 H).

Example 175

4-(4-Amino-phenylsulfanyl)-3-(7-isopropyl-pyrido[2,3-d]pyrimidin-4-ylamino)-N-(5-trifluoromethyl-pyridin-2-yl)-benzamide

Example 175A

{4-[2-Amino-4-(5-trifluoromethyl-pyridin-2-ylcarbamoyl)-phenylsulfanyl]-phenyl}-carbamic acid 2,2,2-trichloro-ethyl ester A mixture of 2-amino-5-trifluoromethylpyridine was reacted with the product of Example 162e using the procedure of Example 10A to provide {4-[2-Nitro-4-(5-trifluoromethyl-pyridin-2-ylcarbamoyl)-phenylsulfanyl]-phenyl}-carbamic acid 2,2,2-trichloro-ethyl ester which was reacted according to the conditions described in Example 100C to provide the title product.

Example 175B

{4-[2-(7-Isopropyl-pyrido[2,3-d]pyrimidin-4-ylamino)-4-(5-trifluoromethyl-pyridin-2-ylcarbamoyl)-phenylsulfanyl]-phenyl}-carbamic acid 2,2,2-trichloro-ethyl ester The product from Example 175A was reacted with the product from Example 8E using the procedure from Example 100D substituting the product from Example 175A for the product from Example 100C to provide the crude product was purified by silica gel chromatography eluting with 2% methanol in dichloromethane to provide the title compound.

Example 175C

4-(4-Amino-phenylsulfanyl)-3-(7-isopropyl-pyrido[2,3-d]pyrimidin-4-ylamino)-N-(5-trifluoromethyl-pyridin-2-yl)-benzamide To a solution of the product of Example 175B in tetrahydrofuran and water (1:1) was added 1 M NaOH (5 equiv). The solution was heated at 60° C. for 40 minutes, cooled, adjusted to pH 6 with 1N aqueous hydrochloric acid and extracted with ethyl acetate. The combined extracts were dried over magnesium sulfate, filtered and concentrated under vacuum. The crude product was purified by silica gel chromatography eluting with 2% methanol in dichloromethane to provide the title compound. $^1$H NMR (300 MHz, DMSO-$d_6$) δ ppm: 1.34 (d, J=6.62 Hz, 6 H) 3.15-3.29 (m, 1 H) 5.63 (s, 2 H) 6.65 (d, J=8.46 Hz, 2 H) 6.84 (d, J=8.46 Hz, 1 H) 7.16 (d, J=8.46 Hz, 2 H) 7.64 (d, J=8.46 Hz, 1 H) 7.90 (d, J=6.99 Hz, 1 H) 8.06 (s, 1 H) 8.23 (dd, J=8.82, 1.47 Hz, 1 H) 8.39 (d, J=8.82 Hz, 1 H) 8.59 (s, 1 H) 8.76 (s, 1 H) 8.89 (d, J=8.46 Hz, 1 H) 10.14 (s, 1 H) 11.20 (s, 1 H).

Example 176

4-(4-Amino-phenylsulfanyl)-3-(7-isopropyl-pyrido[2,3-d]pyrimidin-4-ylamino)-N-(4-methoxy-phenyl)-benzamide The title compound was prepared according to the procedures of Example 174 substituting in Example 174a 4-methoxyaniline for 2-amino-5-fluoropyridine.

Example 177

4-(4-Amino-phenylsulfanyl)-N-cyclohexyl-3-(7-isopropyl-pyrido[2,3-d]pyrimidin-4-ylamino)-benzamide

Example 177A

{4-[4-Cyclohexylcarbamoyl-2-(7-isopropyl-pyrido[2,3-d pyrimidin-4-ylamino)-phenylsulfanyl]-phenyl}-carbamic acid 2,2,2-trichloro-ethyl ester The product of Example 162b (50 mg, 0.0824 mmol) was dissolved in anhydrous N,N-dimethylformamide (1.5 mL) under a nitrogen atmosphere, and treated with cyclohexylamine (8.2 mg, 0.0824 mmol), 3-(diethoxyphosphoryloxy)-1,2,3-benzotriazin-4(3H)-one (49.3 mg, 0.1648 mmol), and triethylamine (0.034 mL, 0.2472 mmol). The reaction was stirred at room temperature for 16 hours and the solvent removed by rotary evaporation in vacuo. The reaction was diluted with ethyl acetate (50 mL) and washed with 10% aqueous sodium carbonate (2×25 mL), water (25 mL), and brine (25 mL). The organic layer was dried over anhydrous sodium sulfate, filtered, and concentrated by rotary evaporation in vacuo. Purification of the residue by silica gel chromatography eluting with 4% methanol/methylene chloride afforded the title compound (45 mg, 79%).

Example 177B 4-(4-Amino-phenylsulfanyl)-N-cyclohexyl-3-(7-isopropyl-pyrido[2,3-d]pyrimidin-4-ylamino)-benzamide A solution of the product of Example 177A (43 mg, 0.0625 mmol) in 1,4-dioxane (2 mL) was treated with a solution of sodium hydroxide (6.2 mg, 0.156 mmol) in water (1 mL), and heated at 60° C. for 30 minutes. The reaction was then cooled to room temperature and diluted with ethyl acetate (50 mL) and water (25 mL). The aqueous pH was adjusted to 5 with 1N aqueous hydrochloric acid, the layers were separated, and the organic phase washed with water (2×25 mL) and brine (25 mL). The organic extract was dried over anhydrous sodium sulfate, filtered, and concentrated by rotary evaporation in vacuo. Purification of the residue by silica gel chromatography eluting with 4% methanol/methylene chloride provided the title compound as a white solid (16 mg, 50%). $^1$H NMR (300 MHz, DMSO-$d_6$) δ ppm: 1.00-1.37 (m, 5 H) 1.34 (d, J=6.99 Hz, 6 H) 1.50-1.65 (m, 1 H) 1.65-1.89 (m, 4 H) 3.15-3.31 (m, 1 H) 3.64-3.81 (m, 1 H) 5.57 (s, 2 H) 6.61 (d, J=8.46 Hz, 2 H) 6.82 (d, J=8.46 Hz, 1 H) 7.11 (d, J=8.46 Hz, 2 H) 7.59-7.71 (m, 2 H) 7.82 (d, J=1.84 Hz, 1 H) 8.13 (d, J=7.72 Hz, 1 H) 8.56 (s, 1 H) 8.86 (d, J=8.46 Hz, 1 H) 10.11 (s, 1 H); MS (ESI+) m/z 513(M+H)$^+$, (ESI−) m/z 511 (M−H)−.

Example 178

4-(4-Amino-3-fluoro-phenoxy)-N-(4-bromo-phenyl)-3-(7-isopropyl-pyrido[2,3-d]pyrimidin-4-ylamino)-benzamide The title compound was prepared following the Troc procedure from Example 100 A-C substituting 4-amino-3-fluorophenol for 4-aminophenol. The crude product was purified by chromatography on silica (3% methanol in dichloromethane) to give the title compound (0.11 g, 65%). $^1$H NMR (300 MHz, DMSO-$d_6$) δ ppm: 1.32 (d, J=6.62 Hz, 6 H), 3.14-3.27 (m, 1 H), 5.04 (s, 2 H), 6.45-6.86 (m, 3 H), 6.94 (d, J=8.82 Hz, 1 H), 7.53 (d, J=8.82 Hz, 2 H), 7.60 (d, J=8.46 Hz, 1 H), 7.76 (d, J=8.82 Hz, 2 H), 7.88 (dd, J=8.64, 2.02 Hz, 1 H), 8.16 (d, J=1.84 Hz, 1 H), 8.61 (s, 1 H), 8.81 (d, J=8.46 Hz, 1 H), 10.01 (s, 1 H), 10.32 (s, 1 H); MS (ESI+) m/z 587 (M+H)$^+$·

Example 179

[4-(4-Amino-phenylsulfanyl)-3-(7-isopropyl-pyrido[2,3-d]pyrimidin-4-ylamino)-phenyl]-(2,6-dimethyl-morpholin-4-yl)-methanone

Example 179A

{4-[4-(2,6-Dimethyl-morpholine-4-carbonyl)-2-(7-isopropyl-pyrido[2,3-d]pyrimidin-4-ylamino)-phenylsulfanyl]-phenyl}-carbamic acid 2,2,2-trichloro-ethyl ester The product of Example 162b (75 mg, 0.1236 mmol) was dissolved in anhydrous N,N-dimethylformamide (2 mL) under a nitrogen atmosphere, and treated with cis-2,6-dimethylmorpholine (16.1 mg, 0.1359 mmol), 3-(diethoxyphosphoryloxy)-1,2,3-benzotriazin-4(3H)-one (74 mg, 0.2472 mmol), and triethylamine (0.052 mL, 0.3707 mmol). The reaction was stirred at room temperature for 16 hours, then diluted with ethyl acetate (50 mL) and washed with 10% aqueous sodium carbonate (2×25 mL), water (25 mL), and brine (25 mL). The organic phase was dried over anhydrous sodium sulfate, filtered, and concentrated by rotary evaporation in vacuo. Purification of the residue by silica gel chromatography eluting with 3% methanol/methylene chloride afforded the title compound as a light yellow solid (58 mg, 67%).

Example 179B

[4-(4-Amino-phenylsulfanyl)-3-(7-isopropyl-pyrido[2,3-d]pyrimidin-4-ylamino)-phenyl]-(2,6-dimethyl-morpholin-4-yl)-methanone A solution of the product of Example 179A (56 mg, 0.0795 mmol) in 1,4-dioxane (2 mL) was treated with a solution of sodium hydroxide (8 mg, 0.1988 mmol) in water (1 mL), and heated at 60° C. for 30 minutes. The reaction was then cooled to room temperature and diluted with ethyl acetate (50 mL) and water (25 mL). The aqueous pH was adjusted to 5 with 1N aqueous hydrochloric acid, the layers were separated, and the organic phase washed with water (2×25 mL) and brine (25 mL). The organic extract was dried over anhydrous sodium sulfate, filtered, and concentrated by rotary evaporation in vacuo. Purification of the residue by silica gel flash chromatography with 5% methanol/methylene chloride provided the title compound as an off-white solid (18 mg, 43%). $^1$H NMR (300 MHz, DMSO-$d_6$/TFA) δ ppm: 0.91-1.25 (m, 6 H) 1.37 (d, J=6.99 Hz, 6 H) 2.70-2.97 (m, 1 H) 3.25-3.40 (m, 1 H) 3.45-3.64 (m, 4 H) 4.20-4.52 (m, 1 H) 5.72 (s, 2 H) 7.29 (d, J=8.09 Hz, 1 H) 7.35 (d, J=8.46 Hz, 2 H) 7.48 (dd, J=7.91, 2.02 Hz, 1 H) 7.50 (d, J=8.45 Hz, 2 H) 7.60 (d, J=1.84 Hz, 1 H) 7.96 (d, J=8.82 Hz, 1 H) 8.97 (s, 1 H) 9.07 (d, J=8.82 Hz, 1 H); MS (ESI+) m/z 529 (M+H)$^+$, (ESI−) m/z 527 (M−H)$^-$.

Example 180

{4-[4-(5-tert-Butyl-[1,3,4]thiadiazol-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 181A was reacted with the product from Example 8E using the procedure from Example 100D substituting the product from Example 181A for the product from Example 100C to provide the crude product which was purified silica gel chromatography eluting with 2% methanol in dichloromethane to provide the title compound (160 mg, 50%). $^1$H NMR (300 MHz, DMSO-$d_6$) δ ppm: 1.34 (d, J=6.99 Hz, 6 H) 1.41 (s, 9 H) 4.97 (s, 2 H) 7.00 (d, J=8.46 Hz, 1 H) 7.44 (d, J=8.46 Hz, 2 H) 7.55-7.71 (m, J=11.40, 8.46 Hz, 3 H) 7.96 (dd, J=8.09, 2.21 Hz, 1 H) 8.15 (d, J=1.10 Hz, 1 H) 8.59 (s, 1 H) 8.86 (d, J=8.46 Hz, 1 H) 10.23 (s, 1 H) 10.42 (s, 1 H) 12.89 (s, 1 H).

Example 181

4-(4-Amino-phenylsulfanyl)-N-(5-tert-butyl-[1,3,4]thiadiazol-2-yl)-3-(7-isopropyl-pyrido[2,3-d]pyrimidin-4-ylamino)-benzamide

Example 181A

{4-[2-Amino-4-(5-tert-butyl-[1,3,4]thiadiazol-2-ylcarbamoyl)-phenylsulfanyl]-phenyl}-carbamic acid 2,2,2-trichloro-ethyl ester A mixture of 5-tert-Butyl-[1,3,4]thiadiazol-2-ylamine was reacted with the product of Example 162e using the procedure of Example 10A to provide {4-[4-(5-tert-Butyl-[1,3,4]thiadiazol-2-ylcarbamoyl)-2-nitro-phenylsulfanyl]-phenyl}-carbamic acid 2,2,2-trichloro-ethyl ester which was reacted according to the conditions described in Example 100C to provide the title product.

Example 181B

{4-[4-(5-tert-Butyl-[1,3,4]thiadiazol-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 181A was reacted with the product from Example 8E using the procedure from Example 100D substituting the product from Example 181A for the product from Example 100C to provide the crude product which was purified silica gel chromatography eluting with 2% methanol in dichloromethane to provide the title compound (160 mg, 50%).

Example 181C 4-(4-Amino-phenylsulfanyl)-N-(5-tert-butyl-[1,3,4]thiadiazol-2-yl)-3-(7-isopropyl-pyrido[2,3-d]pyrimidin-4-ylamino)-benzamide To a solution of the product of Example 181B in tetrahydrofuran and water (1:1) was added 1 M NaOH (5 equiv). The solution was heated at 60° C. for 40 minutes, cooled, adjusted to pH 6 with 1N aqueous hydrochloric acid and extracted with ethyl acetate. The combined extracts were dried over magnesium sulfate, filtered and concentrated under vacuum. The resultant residue was purified by silica gel chromatography eluting with 4% methanol in dichloromethane to provide the title compound. $^1$H NMR (300 MHz, DMSO-$d_6$) δ ppm: 1.34 (d, J=6.62 Hz, 6 H) 1.41 (s, 9 H) 3.16-3.30 (m, 1 H) 5.64 (s, 1 H) 6.65 (d, J=8.46 Hz, 2 H) 6.85 (d, J=8.46 Hz, 1 H) 7.15 (d, J=8.46 Hz, 2 H) 7.65 (d, J=8.46 Hz, 1 H) 7.94 (dd, J=8.46, 1.84 Hz, 1 H) 8.10 (d, J=1.47 Hz, 1 H) 8.59 (s, 1 H) 8.89 (d, J=8.82 Hz, 1 H) 10.15 (s, 1 H) 12.85 (s, 1 H).

Example 182

{4-[2-(7-Isopropyl-pyrido[2,3-d]pyrimidin-4-ylamino)-4-phenethylcarbamoyl-phenylsulfanyl]-phenyl}-carbamic acid 2,2,2-trichloro-ethyl ester To the product of Example 162a (60 mg, 0.1 mmol), N-(3-Dimethylaminopropyl)-N'-ethylcarbodiimide hydrochloride (19 mg, 0.1 mmol), 1-Hydroxybenzotriazole hydrate (13.5 mg, 0.1 mmol), and 4-Dimethylaminopyridine (12 mg, 0.1 mmol) in 3 mL anhydrous DMF was added phenethylamine (36 mg, 0.3 mmol). After 18 hours at room temperature the reaction was diluted with water, neutralized with 1 N HCl, and extracted into ethyl acetate. The ethyl acetate was dried with MgSO$_4$, filtered and concentrated under vacuum. The crude product was purified by silica gel chromatography eluting with 4% methanol in dichloromethane to provide the title compound. $^1$H NMR (300 MHz, DMSO-$d_6$) δ ppm: 1.33 (d, J=6.99 Hz, 6 H) 2.82 (t, J=7.35 Hz, 2 H) 3.15-3.28 (m, 1 H) 3.41-3.53 (m, 2 H) 4.96 (s, 2 H) 7.01 (d, J=8.46 Hz, 1 H) 7.15-7.33 (m, 6 H) 7.38 (d, J=8.46 Hz, 2 H) 7.56 (d, J=8.46 Hz, 2 H) 7.65 (dd, J=15.81, 8.82 Hz, 1 H) 7.86 (s, 1 H) 8.58 (s, 2 H) 8.83 (d, J=8.46 Hz, 1 H) 10.18 (s, 1 H) 10.37 (s, 1 H).

Example 183

{4-[4-(4-Bromo-phenylcarbamoyl)-2-(7-isopropyl-pyrido[2,3-d]pyrimidin-4-ylamino)-phenylsulfanyl]-phenyl}-carbamic acid 3-dimethylamino-2-hydroxy-propyl ester The product from Example 100 (76 mg, 0.1 mmol), 3-dimethylamino-propane-1,2-diol (59 μL, 0.5 mmol) and 1,8-diazabicyclo[5.4.0]undec-7-ene (15 μL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (42 mg, 43%). $^1$H NMR (300 MHz, DMSO-$d_6$) δ ppm: 1.36 (d, J=6.99 Hz, 6 H) 2.80 (d, J=4.41 Hz, 3 H) 2.84 (d, J=4.41 Hz, 3 H) 3.15 (m, 2 H) 3.28 (m, 1 H) 4.10 (m, 3 H) 7.08 (d, J=8.09 Hz, 1 H) 7.41 (d, J=8.82 Hz, 2 H) 7.54 (m, 4 H) 7.72 (d, J=8.82 Hz, 2 H) 7.89 (m, 2 H) 7.99 (s, 1 H) 8.87 (s, 1 H) 9.00 (d, J=8.46 Hz, 1 H) 9.33 (s, 1 H) 10.01 (s, 1 H) 10.40 (s, 1 H) 11.70 (s, 1 H); MS (ESI+) m/z 730 732 (M+H)+.

Example 184

{4-[4-(4-Bromo-phenylcarbamoyl)-2-(7-isopropyl-pyrido[2,3-d]pyrimidin-4-ylamino)-phenylsulfanyl]-phenyl}-carbamic acid 3-amino-propyl ester The product from Example 100 (76 mg, 0.1 mmol), (3-hydroxy-propyl)-carbamic acid tert-butyl ester (85 μL, 0.5 mmol) and 1,8-diazabicyclo[5.4.0]undec-7-ene (15 μL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was added dichloromethane (2 mL) and trifluoroacetic acid (2 mL) and stirred at room temperature for 1 hour. The solvent was evaporated and the residue was purified by reverse phase preparative HPLC with TFA method to give the title compound as a trifluoroacetic acid salt (56 mg, 61%). $^1$H NMR (300 MHz, DMSO-$d_6$) δ ppm: 1.35 (d, J=6.99 Hz, 6 H) 1.90 (m, 2 H) 2.91 (m, 2 H) 3.27 (m, 1 H) 4.16 (t, J=6.43 Hz, 2 H) 7.06 (d, J=8.46 Hz, 1 H) 7.40 (d, J=8.82 Hz, 2 H) 7.52 (m, 4 H) 7.77 (m, 7 H) 7.98 (s, 1 H) 8.76 (s, 1 H) 8.93 (d, J=8.46 Hz, 1 H) 9.90 (s, 1 H) 10.38 (s, 1 H) 11.28 (s, 1 H); MS (ESI+) m/z 686 688 (M+H)+.

Example 185

4-(4-Amino-phenylsulfanyl)-N-(4-chloro-2,6-dimethyl-phenyl)-3-(7-isopropyl-pyrido[2,3-d]pyrimidin-4-ylamino)-benzamide Example 185A {4-[4-(4-Chloro-2,6-dimethyl-phenylcarbamoyl)-2-nitro-phenylsulfanyl]-phenyl}-carbamic acid 2,2,2-trichloro-ethyl ester The product of Example 162b (300 mg, 0.6197 mmol) and 4-Chloro-2,6-dimethyl-phenylamine (119 mg, 0.6197 mmol) were combined in toluene (10 mL) and reacted as in Example 162c to give the title compound that was used without further manipulation.

Example 185B

{4-[2-Amino-4-(4-chloro-2,6-dimethyl-phenylcarbamoyl)-phenylsulfanyl]-phenyl-carbamic acid 2,2,2-trichloro-ethyl ester The product in Example 185A was reduced with Fe and NH$_4$Cl following the procedure from Example 9E to yield the title compound (253 mg, 71% yield over steps 640A and 640B) as an off white solid.

Example 185C

{4-[4-(4-Chloro-2,6-dimethyl-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 8E (67 mg, 0.3097 mmol) and Example 185B (166 mg, 0.3097 mmol) were combined in acetic acid (10 mL) and were reacted as in Example 162e to yield the title compound (126 mg, 55% yield).

Example 185D 4-(4-Amino-phenylsulfanyl)-N-(4-chloro-2,6-dimethyl-phenyl)-3-(7-isopropyl-pyrido[2,3-d]pyrimidin-4-ylamino)-benzamide The product in Example 185C (126 mg, 0.309 mmol) was deprotected with NaOH following the procedure described in Example 162f to yield the title compound (119 mg, 68%) as an off white solid. $^1$H NMR (300 MHz, DMSO-$d_6$) δ ppm: 1.34 (d, J=6.99 Hz, 6 H) 2.15 (s, 6 H) 3.09-3.32 (m, 1 H) 6.63 (d, J=8.82 Hz, 2 H) 6.89 (d, J=8.46 Hz, 1 H) 7.14 (d, J=8.82 Hz, 2 H) 7.18-7.34 (m, 3 H) 7.57-7.76 (m, 1 H) 7.84 (d, J=7.35 Hz, 1 H) 7.92 (s, 1 H) 8.51-8.75 (m, 1 H) 8.91 (d, J=7.72 Hz, 1 H) 9.77 (s, 1 H) 10.62 (s, 1 H); MS (ESI) m/z 570 (M+H)+.

Example 186

4-(4-Amino-phenylsulfanyl)-3-(7-isopropyl-pyrido[2,3-d]pyrimidin-4-ylamino)-N-(5-methyl-[1,3,4]thiadiazol-2-yl)-benzamide Example 186A {4-[4-(5-Methyl-[1,3,4]thiadiazol-2-ylcarbamoyl)-2-nitro-phenylsulfanyl]-phenyl}-carbamic acid 2,2,2-trichloro-ethyl ester A solution of Example 162b (300 mg, 0.6197 mmol) and 5-Methyl-[1,3,4]thiadiazol-2-ylamine (71 mg, 0.6197 mmol) in toluene (10 mL) was reacted as in Example 162c to give the title compound as a yellow powder.

Example 186B

{4-[2-Amino-4-(5-methyl-[1,3,4]thiadiazol-2-ylcarbamoyl)-phenylsulfanyl]-phenyl}-carbamic acid 2,2,2-trichloro-ethyl ester The product in Example 186A (0.6197 mmol) was reduced with Fe and NH$_4$Cl following the procedure from Example 9E to yield the title compound (254 mg, 77%) as a solid.

Example 186C

{4-[2-(7-Isopropyl-pyrido[2,3-d]pyrimidin-4-ylamino)-4-(5-methyl-[1,3,4]thiadiazol-2-ylcarbamoyl-phenylsulfanyl]-phenyl}-carbamic acid 2,2,2-trichloro-ethyl ester The product from Example 8E (67 mg, 0.3097 mmol) and Example 186B (150 mg, 0.2815 mmol) were combined in acetic acid (5 mL) and were reacted as in Example 162e to yield the title compound (134 mg, 68%).

Example 187

4-(4-Amino-phenylsulfanyl)-3-(7-isopropyl-pyrido[2,3-d]pyrimidin-4-ylamino)-N-[1,3,4]thiadiazol-2-yl-benzamide

Example 187A

{4-[2-(7-Isopropyl-pyrido[2,3-d]pyrimidin-4-ylamino)-4-([1,3,4]thiadiazol-2-ylcarbamoyl-phenylsulfanyl]-phenyl}-carbamic acid 2,2,2-trichloro-ethyl ester The product from Example 8E (68 mg, 0.3180 mmol) and Example 166B (150 mg, 0.2891 mmol) were combined in acetic acid (10 mL) and were reacted as in Example 162e to yield the title compound (52 mg, 26%).

Example 187B 4-(4-Amino-phenylsulfanyl)-3-(7-isopropyl-pyrido[2,3-d]pyrimidin-4-ylamino)-N-[1,3,4]thiadiazol-2-yl-benzamide The product in Example 187A (52 mg, 0.0750 mmol) was deprotected with NaOH following the procedure described in Example 162f to yield the title compound (28 mg, 72% yield) as an off white solid. 1H NMR (300 MHz, DMSO-D6) δ ppm: 1.34 (d, J=6.62 Hz, 6 H) 3.17-3.30 (m, 1 H) 5.66 (s, 1 H) 6.66 (d, J=8.46 Hz, 2 H) 6.86 (d, J=8.82 Hz, 1 H) 7.16 (d, J=8.46 Hz, 2 H) 7.65 (d, J=7.72 Hz, 1 H) 7.96 (d, J=6.99 Hz, 1 H) 8.08-8.20 (m, 1 H) 8.48-8.69 (m, 1 H) 8.80-9.01 (m, 1 H) 9.21 (s, 1 H) 10.05-10.30 (m, 1 H) 12.92-13.12 (m, 1 H); MS (ESI) m/z 515 (M+H)+.

Example 188

{4-[2-(7-Isopropyl-pyrido[2,3-d]pyrimidin-4-ylamino)-4-([1,3,4]thiadiazol-2-ylcarbamoyl)-phenylsulfanyl]-phenyl}-carbamic acid 2,2,2-trichloro-ethyl ester The product from Example 8E (68 mg, 0.3180 mmol) and Example 166B (150 mg, 0.2891 mmol) were combined in acetic acid (10 mL) and were reacted as in Example 162e to yield the title compound (52 mg, 26%). $^1$H NMR (300 MHz, DMSO-d$_6$) δ ppm: 1.34 (d, J=6.99 Hz, 6 H) 3.09-3.29 (m, 1 H) 4.97 (s, 2 H) 7.01 (d, J=8.46 Hz, 1 H) 7.45 (d, J=8.46 Hz, 2 H) 7.55-7.77 (m, 3 H) 7.99 (d, J=8.46 Hz, 1 H) 8.19 (s, 1 H) 8.60 (s, 1 H) 8.87 (d, J=8.46 Hz, 1 H) 9.21 (s, 1 H) 10.24 (s, 1 H) 10.43 (s, 1 H) 12.88-13.25 (m, 1 H); MS (ESI) m/z 691 (M+H)+.

Example 189

{4-[2-(7-Isopropyl-pyrido[2,3-d]pyrimidin-4-ylamino)-4-(5-methyl-[1,3,4]thiadiazol-2-ylcarbamoyl)-phenylsulfanyl]-phenyl}-carbamic acid 2,2,2-trichloro-ethyl ester The product from Example 8E (67 mg, 0.3097 mmol) and Example 186B (150 mg, 0.2815 mmol) were combined in acetic acid (5 mL) and were reacted as in Example 162e to yield the title compound (134 mg, 68%). $^1$H NMR (300 MHz, DMSO-d$_6$) δ ppm: 1.33 (d, J=6.62 Hz, 6 H) 2.61 (s, 3 H) 3.15-3.29 (m, 1 H) 4.97 (s, 2 H) 6.88-7.10 (m, 1 H) 7.44 (d, J=8.46 Hz, 2 H) 7.60 (d, J=8.46 Hz, 2 H) 7.88-8.05 (m, 1 H) 8.10-8.23 (m, 1 H) 8.52-8.64 (m, 1 H) 8.79-8.93 (m, 1 H) 10.15-10.29 (m, 1 H) 10.41 (s, 1 H); MS (ESI) m/z 705, 703 (M+H)+.

Example 190

N-[4-(4-Amino-phenylsulfanyl)-3-(7-methyl-pyrido[2,3-d]pyrimidin-4-ylamino)-phenyl]-3-trifluoromethyl-benzamide The title compound was prepared following the Troc procedure from Examples 100 A-C and reacting with the methyl amidine from Example 9B substituting 3-trifluoromethyl-benzoyl chloride for 4-bromobenzoyl chloride. The crude product was purified by trituration in 1:1 ethyl acetate/hexane to give the title compound (0.12 g, 69%) as a tan solid. $^1$H NMR (300 MHz, DMSO-d$_6$) δ ppm: 2.68 (s, 3 H), 5.47 (s, 2 H), 6.56 (d, J=8.46 Hz, 2 H), 6.95 (d, J=8.46 Hz, 1 H), 7.08 (d, J=8.46 Hz, 2 H), 7.48-7.68 (m, 2 H), 7.78 (t, J=7.54 Hz, 1 H), 7.91 (s, 1 H), 7.97 (d, J=7.35 Hz, 1 H), 8.21-8.37 (m, 2 H), 8.57 (s, 1 H), 8.81 (d, J=8.46 Hz, 1 H), 10.06 (s, 1 H), 10.56 (s, 1 H); MS (ESI+) m/z 547 (M+H)$^{+\cdot}$

Example 191

N-[4-(4-Amino-phenylsulfanyl)-3-(7-isopropyl-pyrido[2,3-d]pyrimidin-4-ylamino)-phenyl]-3-trifluoromethyl-benzamide The title compound was prepared following the Troc procedure from Example 100 A-C and reacting with the methyl amidine from Example 9B substituting 3-trifluoromethyl-benzoyl chloride for 4-bromobenzoyl chloride. The crude product was purified by trituration in 1:1 ethyl acetate/hexane to give the title compound (0.15 g, 79%) as a tan solid. $^1$H NMR (300 MHz, DMSO-d$_6$) δ ppm: 1.34 (d, J=6.99 Hz, 6 H), 3.15-3.28 (m, 1 H), 5.46 (s, 2 H), 6.56 (d, J=8.46 Hz, 2 H), 6.95 (d, J=8.82 Hz, 1 H), 7.09 (d, J=8.46 Hz, 2 H), 7.56-7.67 (m, 2 H), 7.78 (t, J=7.72 Hz, 1 H), 7.90 (d, J=2.21 Hz, 1 H), 7.97 (d, J=7.72 Hz, 1 H), 8.22-8.32 (m, 2 H), 8.57 (s, 1 H), 8.86 (d, J=8.82 Hz, 1 H), 10.07 (s, 1 H), 10.56 (s, 1 H); MS (ESI+) m/z 575 (M+H)$^+$.

Example 192

4-(4-Amino-2-chloro-phenoxy)-N-(4-bromo-phenyl)-3-(7-isopropyl-pyrido[2,3-d]pyrimidin-4-ylamino)-benzamide The title compound was prepared following the Troc procedure from Example 100 A-C and reacting with the methyl amidine from Example 9B substituting 4-amino-2-chlorophenol for 4-aminophenol. The crude product was purified by chromatography on silica gel (3% methanol in dichloromethane) to give the title compound (0.09 g, 51%). $^1$H NMR (300 MHz, DMSO-d$_6$) δ ppm: 1.32 (d, J=6.99 Hz, 6 H), 3.16-3.28 (m, 1 H), 5.37 (s, 2 H), 6.55 (dd, J=8.82, 2.57 Hz, 1 H), 6.68 (d, J=2.21 Hz, 1 H), 6.72 (d, J=8.82 Hz, 1 H), 6.94 (d, J=8.82 Hz, 1 H), 7.53 (d, J=8.82 Hz, 2 H), 7.61 (d, J=8.46 Hz, 1 H), 7.75 (d, J=9.19 Hz, 2 H), 7.85 (dd, J=8.64, 2.02 Hz, 1 H), 8.16 (d, J=1.84 Hz, 1 H), 8.63 (s, 1 H), 8.86 (d, J=8.46 Hz, 1 H), 10.03 (s, 1 H), 10.31 (s, 1 H); MS (ESI+) m/z 603 (M+H)+.

Example 193

3-Fluoro-N-[4-(4-hydroxy-phenylsulfanyl)-3-(7-isopropyl-pyrido[2,3-d]pyrimidin-4-ylamino)-phenyl]-benzamide

Example 193a

3-Fluoro-N-[4-(4-hydroxy-phenylsulfanyl)-3-nitro-phenyl]-benzamide

The title compound was prepared according to the procedures described in Example 115 substituting 3-trifluoromethyl benzoyl chloride with 3-fluoro benzoyl chloride to provide the title compound (0.48 g, 57%).

Example 193b

3-Fluoro-N-[4-(4-hydroxy-phenylsulfanyl)-3-(7-isopropyl-pyrido[2,3-d]pyrimidin-4-ylamino)-phenyl]-benzamide A solution of the product of Example 8E (60.6 mg, 0.28 mmol), and the product of Example 193a (99 mg, 0.28 mmol) in acetic acid (1 mL) was stirred in an oil bath preheated to 130° C. for 10 minutes. The mixture was then cooled to room temperature, the acetic acid removed under vacuum, and the resultant residue purified by HPLC with TFA to provide the title compound as a trifluoroacetic acid salt (35 mg, 24%). $^1$H NMR (300 MHz, DMSO-$d_6$) δ ppm: 1.36 (d, J=6.62 Hz, 6 H) 3.17-3.34 (m, 1 H) 6.69 (t, J=9.19 Hz, 2 H) 7.08-7.26 (m, 3 H) 7.39-7.51 (m, 1 H) 7.54-7.69 (m, 2 H) 7.70-7.91 (m, 3 H) 8.01 (s, 1 H) 8.78 (s, 1 H) 8.96 (d, J=8.46 Hz, 1 H) 9.78 (s, 1 H) 10.52 (s, 1 H) 11.35 (s, 1 H); MS (ESI+) m/z 526 (M+H)+, (ESI−) m/z 524 (M−H)−.

Example 194

3-Bromo-N-[4-(4-hydroxy-phenylsulfanyl)-3-(7-isopropyl-pyrido[2,3-d]pyrimidin-4-ylamino)-phenyl]-benzamide

Example 194a

N-[3-Amino-4-(4-hydroxy-phenylsulfanyl)-phenyl]-3-bromo-benzamide

The title compound was prepared according to the procedures described in Example 115 substituting 3-trifluoromethyl benzoyl chloride with 3-bromo benzoyl chloride (0.34 g, 65%).

Example 194b

3-Bromo-N-[4-(4-hydroxy-phenylsulfanyl)-3-(7-isopropyl-pyrido[2,3-d]pyrimidin-4-ylamino)-phenyl]-benzamide A solution of the product of Example 8E (54.4 mg, 0.25 mmol), and the product of Example 194a (100 mg, 0.25 mmol) in acetic acid (1 mL) was stirred in an oil bath preheated to 130° C. for 10 minutes. The mixture was then cooled to room temperature, the acetic acid removed under vacuum, and the resultant residue purified by HPLC with TFA to provide the title compound as a trifluoroacetic acid salt (32 mg, 22%). $^1$H NMR (300 MHz, DMSO-$d_6$) δ ppm: 1.25-1.40 (m, 6 H) 3.23-3.35 (m, 1 H) 6.70 (d, J=8.82 Hz, 2 H) 7.09-7.25 (m, 3 H) 7.41-7.59 (m, 1 H) 7.56-7.69 (m, 1 H) 7.73-7.87 (m, 2 H) 7.88-8.06 (m, 2 H) 8.08-8.17 (m, 1 H) 8.77 (s, 1 H) 8.96 (d, J=8.82 Hz, 1 H) 9.78 (s, 1 H) 10.49-10.60 (m, 1 H) 11.34 (s, 1 H); MS (ESI+) m/z 586 (M+H)+, (ESI−) m/z 584 (M−H)−.

Example 195

N-[4-(4-Hydroxy-phenylsulfanyl)-3-(7-isopropyl-pyrido[2,3-d]pyrimidin-4-ylamino)-phenyl]-4-trifluoromethyl-benzamide

Example 195a

N-[3-Amino-4-(4-hydroxy-phenylsulfanyl)-phenyl]-4-trifluoromethyl-benzamide

The title compound was prepared according to the procedures described in Example 115 substituting 3-trifluoromethyl benzoyl chloride with 4-trifluoro benzoyl chloride to provide the title compound (0.48 g, 53%).

Example 195b

N-[4-(4-Hydroxy-phenylsulfanyl)-3-(7-isopropyl-pyrido[2,3-d]pyrimidin-4-ylamino)-phenyl]-4-trifluoromethyl-benzamide A solution of the product of Example 8E (45 mg, 0.208 mmol), and the product of Example 195a (84.1 mg, 0.208 mmol) in acetic acid (1 mL) was stirred in an oil bath preheated to 130 ° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (39 mg, 32%). $^1$H NMR (300 MHz, DMSO-$d_6$) δ ppm: 1.24-1.41 (m, 6 H) 3.23 (dd, J=12.50, 5.88 Hz, 1 H) 6.74 (d, J=8.82 Hz, 2 H) 7.08 (d, J=8.82 Hz, 1 H) 7.19 (d, J=8.82 Hz, 2 H) 7.53-7.66 (m, 2 H) 7.84-8.01 (m, 3 H) 8.14 (d, J=8.46 Hz, 2 H) 8.56 (s, 1 H) 8.83 (d, J=8.09 Hz, 1 H) 9.75 (s, 1 H) 10.10 (s, 1 H) 10.60 (s, 1 H); MS (ESI+) m/z 576 (M+H)+, (ESI−) m/z 574 (M−H)−.

Example 196

4-Bromo-N-[4-(4-hydroxy-phenylsulfanyl)-3-(7-isopropyl-pyrido[2,3-d]pyrimidin-4-ylamino)-phenyl]-benzamide

Example 196a

N-[3-Amino-4-(4-hydroxy-phenylsulfanyl)-phenyl]-4-bromo-benzamide

The title compound was prepared according to the procedures described in Example 115 substituting 3-trifluoromethyl benzoyl chloride with 4-bromo benzoyl chloride to provide the title compound (0.32 g, 56%).

Example 196b

4-Bromo-N-[4-(4-hydroxy-phenylsulfanyl)-3-(7-isopropyl-pyrido[2,3-d]pyrimidin-4-ylamino)-phenyl]-benzamide A solution of the product of Example 8E (41 mg, 0.187 mmol), and the product of Example 196a (77.8 mg, 0.187 mmol) in acetic acid (1 mL) was stirred in an oil bath preheated to 130 ° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound. (56 mg, 51%). $^1$H NMR (300 MHz, DMSO-$d_6$) δ ppm: 1.24-1.38 (m, 6 H) 3.26 (s, 1 H) 6.74 (t, J=8.27 Hz, 2 H) 7.05 (s, 1 H) 7.18 (d, J=8.46 Hz, 2 H) 7.61 (d, J=8.82 Hz, 2 H) 7.75 (d, J=8.46 Hz, 2 H) 7.90 (d, J=8.46 Hz, 3 H) 8.56 (s, 1 H) 8.83 (d, J=7.72 Hz, 1 H) 9.74 (s, 1 H) 10.09 (s, 1 H) 10.45 (s, 1 H); MS (ESI+) m/z 588 (M+H)+, (ESI−) m/z 586 (M−H)−.

Example 197

4-Fluoro-N-[4-(4-hydroxy-phenylsulfanyl)-3-(7-isopropyl-pyrido[2,3-d]pyrimidin-4-ylamino)-phenyl]-benzamide

Example 197a

N-[3-Amino-4-(4-hydroxy-phenylsulfanyl)-phenyl]-4-fluoro-benzamide

The title compound was prepared according to the procedures described in Example 115 substituting 3-trifluoromethyl benzoyl chloride with 4-fluoro benzoyl chloride to give the title compound (0.43 g, 59%).

Example 197b

4-Fluoro-N-[4-(4-hydroxy-phenylsulfanyl)-3-(7-isopropyl-pyrido[2,3-d]pyrimidin-4-ylamino)-phenyl]-benzamide A solution of the product of Example 8E (79 mg, 0.367 mmol), and the product of Example 197a (130 mg, 0.367 mmol) in acetic acid (1 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (69 mg, 36%). $^1$H NMR (300 MHz, DMSO-$d_6$) δ ppm: 1.32 (t, J=7.54 Hz, 6 H) 3.16-3.30 (m, 1 H) 6.73 (d, J=8.46 Hz, 2 H) 7.07 (d, J=8.46 Hz, 1 H) 7.18 (d, J=8.46 Hz, 2 H) 7.37 (t, J=8.82 Hz, 2 H) 7.61 (d, J=8.46 Hz, 2 H) 7.89-8.09 (m, 3 H) 8.56 (s, 1 H) 8.83 (d, J=8.46 Hz, 1 H) 9.73 (s, 1 H) 10.08 (s, 1 H) 10.40 (s, 1 H); MS (ESI+) m/z 526 (M+H)+, (ESI−) m/z 524 (M−H)−.

Example 198

3-Chloro-N-[4-(4-hydroxy-phenylsulfanyl)-3-(7-isopropyl-pyrido[2,3-d]pyrimidin-4-ylamino)-phenyl]-benzamide

Example 198a

N-[3-Amino-4-(4-hydroxy-phenylsulfanyl)-phenyl]-3-chloro-benzamide

The title compound was prepared according to the procedures described in Example 115 substituting 3-trifluoromethyl benzoyl chloride with 3-chloro benzoyl chloride to give the title compound (0.49 g, 45%).

Example 198b

3-Chloro-N-[4-(4-hydroxy-phenylsulfanyl)-3-(7-isopropyl-pyrido[2,3-d]pyrimidin-4-ylamino)-phenyl]-benzamide A solution of the product of Example 8E (65 mg, 0.302 mmol), and the product of Example 198a (112 mg, 0.302 mmol) in acetic acid (1 mL) was stirred in an oil bath preheated to 130 ° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (45 mg, 28%). $^1$H NMR (300 MHz, DMSO-$d_6$) δ ppm: 1.28-1.38 (m, 6 H) 3.16-3.28 (m, 1 H) 6.73 (d, J=8.46 Hz, 2 H) 7.07 (d, J=8.82 Hz, 1 H) 7.19 (d, J=8.82 Hz, 2 H) 7.52-7.75 (m, 4 H) 7.85-8.07 (m, 3 H) 8.56 (s, 1 H) 8.83 (d, J=8.09 Hz, 1 H) 9.74 (s, 1 H) 10.09 (s, 1 H) 10.48 (s, 1 H); MS (ESI+) m/z 542 (M+H)+, (ESI−) m/z 540 (M−H)−.

Example 199

4-(4-Amino-phenoxy)-N-(5-chloro-pyridin-2-yl)-3-(7-isopropyl-pyrido[2,3-d]pyrimidin-4-ylamino)-benzamide

Example 199A

4-Chloro-N-(5-chloro-pyridin-2-yl)-3-nitro-benzamide

A solution of 4-chloro-3-nitrobenzoyl chloride (1.00 g, 4.99 mmol) in dry methylene chloride (20 mL) under a nitrogen atmosphere was treated with 2-amino-5-chloropyridine (643 mg, 4.99 mmol) and N,N-diisopropylethylamine (1.05 mL, 6.00 mmol), and the resulting mixture stirred at room temperature for 18 hours. The solvent was removed by rotary evaporation in vacuo, the residue taken up in ethyl acetate (100 mL), and washed with saturated aqueous sodium bicarbonate (50 mL), water (2×50 mL), and brine (50 mL). The organic extract was dried over anhydrous sodium sulfate, filtered, and concentrated in vacuo. Trituration with 5% ethyl acetate/methylene chloride afforded the title compound as a dark yellow solid (660 mg, 42%).

Example 199B

{4-[4-(5-Chloro-pyridin-2-ylcarbamoyl)-2-nitro-phenoxy]-phenyl}-carbamic acid tert-butyl ester A solution of the product of Example 199A (300 mg, 0.9612 mmol) in anhydrous N,N-dimethylformamide (5 mL) was treated with N-Boc-4-hydroxyaniline (201 mg, 0.9612 mmol) and potassium carbonate (266 mg, 1.922 mmol) at room temperature, then heated at 80° C. under a nitrogen atmosphere for 5 hours. The reaction was cooled to room temperature and the solvent removed by rotary evaporation in vacuo. The residue was taken up in ethyl acetate (100 mL) and washed with water (4×50 mL) and brine (50 mL). The organic layer was dried over anhydrous sodium sulfate, filtered, and concentrated by rotary evaporation in vacuo. Trituration with 5% ethyl acetate gave the title compound (284 mg, 61%).

Example 199C

{4-[2-Amino-4-(5-chloro-pyridin-2-ylcarbamoyl)-phenoxy]-phenyl}-carbamic acid tert-butyl ester A suspension of the product of Example 199B (282 mg, 0.5816 mmol), iron powder (200 mg, 3.577 mmol), and ammonium chloride (204 mg, 3.809 mmol) in ethanol (8 mL) and water (4 mL) was heated at 80° C. for 45 minutes. After cooling to room temperature, the mixture was diluted with ethyl acetate (100 mL) and washed with water (2×50 mL) and brine (50 mL). The organic phase was dried over sodium sulfate, filtered and concentrated under vacuum to provide the title compound as a beige solid (250 mg, 94%).

Example 199D

{4-[4-(5-Chloro-pyridin-2-ylcarbamoyl)-2-(7-isopropyl-pyrido[2,3-d]pyrimidin-4-ylamino)-phenoxy]-phenyl}-carbamic acid tert-butyl ester A solution of the product of Example 8E (118 mg, 0.5452 mmol) and the product of Example 199C (248 mg, 0.5452 mmol) in acetic acid (5 mL) was stirred in an oil bath preheated to 140° C. for 20 minutes. The reaction was cooled to room temperature, diluted with hexanes (100 mL), concentrated by rotary evaporation, and co-evaporated with methylene chloride/hexanes (4 times). The residue was dried on hi-vacuum overnight, then purified by silica gel flash chromatography with 2% MeOH/methylene chloride to give the title compound as a yellow solid (164 mg, 48%).

Example 199E 4-(4-Amino-phenoxy)-N-(5-chloro-pyridin-2-yl)-3-(7-isopropyl-pyrido[2,3-d]pyrimidin-4-ylamino)-benzamide The product of Example 199D (162.2 g, 0.2591 mmol) was treated with trifluoroacetic acid (2 mL) in methylene chloride (2 mL) at room temperature for 30 minutes. The solvents were removed by rotary evaporation and the residual oil taken up in ethyl acetate (75 mL) and washed with saturated aqueous sodium bicarbonate (30 mL), water (2×30 mL), and brine (30 mL). The organic phase was dried over anhydrous sodium sulfate, filtered, and concentrated in vacuo. Purification by silica gel chromatography eluting with 4% methanol/methylene chloride afforded the title compound (104 mg, 76%). $^1$H NMR (300 MHz, DMSO-$d_6$) δ ppm: 1.32 (d, J=6.99 Hz, 6 H) 3.09-3.30 (m, 1 H) 5.04 (s, 2 H) 6.57 (d, J=8.82 Hz, 2 H) 6.78 (d, J=8.83 Hz, 1 H) 6.79 (d, J=8.82 Hz, 2 H) 7.60 (d, J=8.46 Hz, 1 H) 7.94-7.98 (m, 2 H) 8.20-8.27 (m, 2 H) 8.43 (d, J=2.94 Hz, 1 H) 8.62 (s, 1 H) 8.85 (d, J=8.46 Hz, 1 H) 9.97 (s, 1 H) 10.91 (s, 1 H); MS (ESI+) m/z 526/528 (M+H)$^+$.

Example 200

{4-[4-(4-Bromo-phenylcarbamoyl)-2-(7-isopropyl-pyrido[2,3-d]pyrimidin-4-ylamino)-phenoxy]-phenyl}-carbamic acid tert-butyl ester The title compound was prepared following the procedures form Examples 10A-C. The product was then coupled with the product From Example 8E. $^1$H NMR (300 MHz, DMSO-$d_6$) δ ppm: 1.32 (d, J=6.99 Hz, 6 H) 1.46 (s, 9 H) 3.12-3.29 (m, 1 H) 6.94 (d, J=8.45 Hz, 1H) 6.96 (d, J=8.82 Hz, 2 H) 7.43 (d, J=8.82 Hz, 2 H) 7.53 (d, J=8.82 Hz, 2 H) 7.58 (d, J=8.82 Hz, 1 H) 7.76 (d, J=8.82 Hz, 2 H) 7.89 (dd, J=8.64, 2.02 Hz, 1 H) 8.17 (d, J=2.21 Hz, 1 H) 8.60 (s, 1 H) 8.79 (d, J=8.46 Hz, 1 H) 9.35 (s, 1 H) 10.03 (s, 1 H) 10.34 (s, 1 H); MS (ESI+) m/z 669/671 (M+H).

Example 201

4-(4-Amino-phenylsulfanyl)-3-(7-isopropyl-pyrido[2,3-d]pyrimidin-4-ylamino)-N-(6-methoxy-pyridin-3-yl)-benzamide

Example 201A

{4-[4-(6-Methoxy-pyridin-3-ylcarbamoyl)-2-nitro-phenylsulfanyl]-phenyl}-carbamic acid 9H-fluoren-9-ylmethyl ester A solution of the product of Example 19C (290 mg, 0.546 mmol) in anhydrous tetrahydrofuran (5 mL) was treated with 5-amino-2-methoxypyridine (78.5 mg, 0.601 mmol) and diisopropylethylamine (0.143 mL, 0.819 mmol), and stirred at room temperature under a nitrogen atmosphere for 18 hours. The reaction was diluted with ethyl acetate (100 mL) and washed with saturated aqueous sodium bicarbonate (25 mL), water (2×25 mL), and brine (25 mL). The organic phase was dried over anhydrous sodium sulfate, filtered, and concentrated in vacuo. Trituration with 3% methanol/methylene chloride provided the title compound as a dark yellow solid (202 mg, 60%).

Example 201B

{4-[2-Amino-4-(6-methoxy-pyridin-3-ylcarbamoyl)-phenylsulfanyl]-phenyl}-carbamic acid 9H-fluoren-9-ylmethyl ester The product of Example 201A (200 mg, 0.3233 mmol), ammonium chloride (113 mg, 2.118 mmol), and iron powder (111 mg, 1.988 mmol) in a mixture of water (3 mL), ethanol (6 mL) and tetrahydrofuran (6 mL) was heated at 80° C. under a nitrogen atmosphere for 75 minutes. The reaction was cooled to room temperature, diluted with ethyl acetate (100 mL), and washed with water (2×50 mL) and brine (50 mL). The organic was dried over anhydrous sodium sulfate, filtered, and concentrated by rotary evaporation in vacuo to give the product as a light beige solid (175 mg, 92%).

Example 201C

{4-[2-(7-Isopropyl-pyrido[2,3-d]pyrimidin-4-ylamino)-4-(6-methoxy-pyridin-3-ylcarbamoyl)-phenylsulfanyl]-phenyl}-carbamic acid 9H-fluoren-9-ylmethyl ester A solution of the product of Example 8E (64 mg, 0.2934 mmol) and the product of Example 201B (173 mg, 0.294 mmol) in acetic acid (4 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4 times). The residue was dried on hi-vacuum, then purified by silica gel flash chromatography with 4% methanol/methylene chloride to afford the title compound as a light yellow solid (123 mg, 55%).

Example 201D 4-(4-Amino-phenylsulfanyl)-3-(7-isopropyl-pyrido[2,3-d]pyrimidin-4-ylamino)-N-(6-methoxy-pyridin-3-yl)-benzamide A solution of the product of Example 201C (121.8 mg, 0.1603 mmol) in 1,4-dioxane (3 mL) was treated with a solution of lithium hydroxide monohydrate (13.5 mg, 0.3206 mmol) in water (1.5 mL) at ambient temperature, then heated at 70° C. for 30 minutes. The reaction was cooled to room temperature, diluted with ethyl acetate (75 mL) and water (30 mL), adjusted the aqueous pH to 6 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel flash chromatography with 6% methanol/methylene chloride afforded the title compound as a light yellow solid (66 mg, 77%). $^1$H NMR (300 MHz, DMSO-$d_6$) δ ppm: 1.34 (d, J=6.99 Hz, 6 H) 3.05-3.39 (m, 1 H) 3.83 (s, 3 H) 5.59 (s, 2 H) 6.64 (d, J=8.46 Hz, 2 H) 6.82 (d, J=8.82 Hz, 1 H) 6.88 (dd, J=7.35, 1.84 Hz, 1 H) 7.14 (d, J=8.46 Hz, 2 H) 7.57-7.69 (m, 1 H) 7.73-7.85 (m, 1 H) 7.89-7.99 (m, 1 H) 8.01 (dd, J=9.01, 2.76 Hz, 1 H) 8.48 (d, J=2.57 Hz, 1 H) 8.52-8.66 (m, 1 H) 8.83-8.98 (m, 1 H) 10.16 (s, 1 H) 10.20 (s, 1 H); MS (ESI+) m/z 538 (M+H)$^+$, 560 (M+Na)$^+$, (ESI−) m/z 536 (M−H)$^-$.

Example 202

N-(5-Bromo-thiazol-2-yl)-4-(4-hydroxy-phenylsulfanyl)-3-(7-isopropyl-pyrido[2,3-d]pyrimidin-4-ylamino)-benzamide

Example 202A

N-(5-Bromo-thiazol-2-yl)-4-chloro-3-nitro-benzamide

A solution of 4-chloro-3-nitrobenzoyl chloride (1.539 g, 7.694 mmol) in anhydrous pyridine (40 mL) was treated with 2-amino-5-bromothiazole monohydrobromide (2.00 g, 7.694 mmol), and the reaction stirred under a nitrogen atmosphere at room temperature for 18 hours. The solvent was removed by rotary evaporation in vacuo and the oil dried on hi-vacuum. The residue was taken up in ethyl acetate (150 mL) and washed with water (4×50 mL) and brine (50 mL), then dried the organic phase over anhydrous sodium sulfate, filtered, and concentrated in vacuo. Trituration with 6% ethyl acetate/methylene chloride afforded the title compound as a pinkish-tan solid (1.92 g, 69%).

Example 202B

N-(5-Bromo-thiazol-2-yl)-4-(4-hydroxy-phenylsulfanyl)-3-nitro-benzamide

A solution of the product of Example 202A (300 mg, 0.8274 mmol) in anhydrous N,N-dimethylformamide (8 mL) was treated with 4-mercaptophenol (104.4 mg, 0.8274 mmol) and cesium carbonate (539 mg, 1.655 mmol) at room temperature, then heated at 100° C. under a nitrogen atmosphere for 2 hours. The reaction was cooled to room temperature and the solvent removed by rotary evaporation in vacuo. The residue was taken up in water (50 mL) and the pH adjusted to 3 with 1N aqueous HCl. The aqueous was extracted with ethyl acetate (100 mL), and the organic extract washed with water (2×25 mL) and brine (25 mL). The organic layer was dried over anhydrous sodium sulfate, filtered, and concentrated by rotary evaporation to give the product as a golden-brown solid (416 mg, 111%).

Example 202C

3-Amino-N-(5-bromo-thiazol-2-yl)-4-(4-hydroxy-phenylsulfanyl)-benzamide

A suspension of the product of Example 202B (414 mg, 0.9153 mmol) and iron powder (204.5 mg, 3.66 mmol) in acetic acid (7 mL) and ethanol (7 mL) was heated at reflux under a nitrogen atmosphere for 1 hour. The reaction was cooled to room temperature, and the mixture was diluted with water (50 mL) and ethyl acetate (100 mL). The aqueous pH was adjusted to 5 with solid sodium carbonate, the layers were separated, and the organic phase washed with water (2×50 mL) and brine (50 mL). The organic extract was dried over sodium sulfate, filtered, and concentrated under vacuum to provide the title compound as a yellow solid (315 mg, 90%).

Example 202D

N-(5-Bromo-thiazol-2-yl)-4-(4-hydroxy-phenylsulfanyl)-3-(7-isopropyl-pyrido[2,3-d]pyrimidin-4-ylamino)-benzamide A solution of the product of Example 8E (92 mg, 0.4262 mmol) and the product of Example 202C (180 mg, 0.4262 mmol) in acetic acid (4 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4 times). The residue was dried on hi-vacuum, then purified by silica gel chromatography eluting with 5% methanol/methylene chloride to afford the title compound as a light yellow solid (151 mg, 60%). $^1$H NMR (300 MHz, DMSO-$d_6$) δ ppm: 1.34 (d, J=6.99 Hz, 6 H) 3.14-3.32 (m, 1 H) 6.82-6.93 (m, 3 H) 7.33 (d, J=8.46 Hz, 2 H) 7.60-7.70 (m, 2 H) 7.93 (dd, J=8.46, 1.84 Hz, 1 H) 8.13 (d, J=1.47 Hz, 1 H) 8.59 (s, 1 H) 8.88 (d, J=8.82 Hz, 1 H) 10.02 (s, 1 H) 10.19 (s, 1 H) 12.87 (s, 1 H); MS (ESI+) m/z 593/595 (M+H)$^+$.

Example 203

N-[4-(4-Amino-phenylsulfanyl)-3-(7-isopropyl-pyrido[2,3-d]pyrimidin-4-ylamino)-phenyl]-4-bromo-benzamide The product from Example 13A was reacted following the Troc procedure from Example 100b. The product of which was reacted with the product from Example 8E. The crude product was purified by reverse phase preparative HPLC with TFA method to give the title compound as a trifluoroacetic acid salt (81 mg, 23%). $^1$H NMR (300 MHz, DMSO-$d_6$) δ ppm: 1.37 (d, J=6.62 Hz, 6 H) 3.32 (m, 1 H) 6.56 (d, J=8.82 Hz, 2 H) 7.06 (m, 3 H) 7.60 (dd, J=8.64, 2.21 Hz, 1 H) 7.76 (m, 2 H) H); MS (ESI+) m/z 585 587 (M+H)+.

Example 204

N-[4-(4-Amino-phenylsulfanyl)-3-(7-isopropyl-pyrido[2,3-d]pyrimidin-4-ylamino)-phenyl]-3-bromo-benzamide The product from Example 66 was reacted following the Troc procedure described in Example 100b. The product of which was reacted with the product from Example 8E substituting 3-bromobenzoyl chloride for 4-bromobenzoyl chloride. The crude product was purified by reverse phase preparative HPLC with TFA method to give the title compound as a trifluoroacetic acid salt (57 mg, 18%). $^1$H NMR (300 MHz, DMSO-$d_6$) δ ppm: 1.37 (d, J=6.99 Hz, 6 H) 3.30 (m, 1 H) 6.57 (d, J=8.46 Hz, 2 H) 7.08 (m, 3 H) 7.51 (m, 1 H) 7.61 (dd, J=8.64, 2.21 Hz, 1 H) 7.81 (d, J=6.99 Hz, 1 H) 7.93 (m, 2 H) 8.00 (d, J=2.21 Hz, 1 H) 8.12 (m, 1 H) 8.88 (s, 1 H) 9.03 (d, J=8.46 Hz, 1 H) 10.55 (s, 1 H) 11.76 (s, 1 H); MS (ESI+) m/z 585 587 (M+H)+.

Example 205

N-[4-(4-Amino-phenylsulfanyl)-3-(7-methyl-pyrido[2,3-d]pyrimidin-4-ylamino)-phenyl]-4-bromo-benzamide The product from Example 13 was reacted following the Troc procedure described in Example 100. The product of which was reacted with the product from Example 9B. The crude product was purified by trituration in 1:1 ethyl acetate/hexane to give the title compound (86 mg, 39%). $^1$H NMR (300 MHz, DMSO-$d_6$) δ ppm: 2.68 (s, 3 H) 5.45 (s, 2 H) 6.55 (d, J=8.46 Hz, 2 H) 6.94 (d, J=8.46 Hz, 1 H) 7.07 (d, J=8.46 Hz, 2 H) 7.56 (m, 2 H) 7.74 (d, J=8.46 Hz, 2 H) 7.90 (m, 3 H) 8.56 (s, 1 H) 8.80 (d, J=8.46 Hz, 1 H) 10.04 (s, 1 H) 10.40 (s, 1 H); MS (ESI+) m/z 557 559 (M+H)+.

Example 206

N-[4-(4-Amino-phenylsulfanyl)-3-(7-methyl-pyrido[2,3-d]pyrimidin-4-ylamino)-phenyl]-3-bromo-benzamide The product from Example 66 was reacted following the Troc procedure described in Example 100. The product of which was reacted with the product from Example 9B substituting 3-bromobenzoyl chloride for 4-bromobenzoyl chloride. The crude product was purified by trituration in 1:1 ethyl acetate/hexane to give the title compound (71 mg, 33%). $^1$H NMR (300 MHz, DMSO-$d_6$) δ ppm: 2.68 (s, 3 H) 5.45 (s, 2 H) 6.55 (d, J=8.46 Hz, 2 H) 6.94 (d, J=8.46 Hz, 1 H) 7.07 (d, J=8.46 Hz, 2 H) 7.53 (m, 3 H) 7.80 (m, 1 H) 7.93 (m, 2 H) 8.13 (m, 1 H) 8.56 (s, 1 H) 8.80 (d, J=8.46 Hz, 1 H) 10.04 (s, 1 H) 10.43 (s, 1 H); MS (ESI+) m/z 557 559 (M+H)+.

Example 207

4-(4-Amino-phenylsulfanyl)-N-(4-bromo-2,6-dimethyl-phenyl)-3-(7-isopropyl-pyrido[2,3-d]pyrimidin-4-ylamino)-benzamide

Example 207A

{4-[4-(4-Bromo-2,6-dimethyl-phenylcarbamoyl)-2-nitro-phenylsulfanyl]-phenyl}-carbamic acid 2,2,2-trichloro-ethyl ester A solution of the product in Example 162b (300 mg, 0.6197 mmol) and 4-Bromo-2,6-dimethyl-phenylamine (123 mg, 0.6197 mmol) was heated in toluene (10 mL) as in Example 162c to yield the title compound that was used without further manipulation.

Example 207B

{4-[2-Amino-4-(4-bromo-2,6-dimethyl-phenylcarbamoyl)-phenylsulfanyl]-phenyl}-carbamic acid 2,2,2-trichloro-ethyl ester The product from Example 207A (0.6197 mmol) was reduced with Fe and NH$_4$Cl following the procedure from Example 9E to yield the title compound (239 mg, 62% yield) as a white solid.

Example 207C

{4-[4-(4-Bromo-2,6-dimethyl-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester The product from Example 8E (62 mg, 0.2881 mmol) and Example 207B (178 mg, 0.2881 mmol) were combined in acetic acid (10 mL) and reacted as in 614E to yield the title compound (146 mg, 65% yield) as a light colored solid.

Example 207D 4-(4-Amino-phenylsulfanyl)-N-(4-bromo-2,6-dimethyl-phenyl)-3-(7-isopropyl-pyrido[2,3-d]pyrimidin-4-ylamino)-benzamide The product or Example 207C (120 mg, 0.1521 mmol) was reacted with NaOH as in Example 162f to give the title compound (65 mg, 70%) as an off white solid. $^1$H NMR (300 MHz, DMSO-$d_6$) δ ppm: 1.34 (d, J=6.99 Hz, 6 H) 2.15 (s, 6 H) 3.09-3.32 (m, 1 H) 6.63 (d, J=8.82 Hz, 2 H) 6.89 (d, J=8.46 Hz, 1 H) 7.14 (d, J=8.82 Hz, 2 H) 7.18-7.34 (m, 3 H) 7.57-7.76 (m, 1 H) 7.84 (d, J=7.35 Hz, 1 H) 7.92 (s, 1 H) 8.51-8.75

(m, 1 H) 8.91 (d, J=7.72 Hz, 1 H) 9.77 (s, 1 H) 10.62 (s, 1 H); MS (ESI) m/z 613, 615 (M+H)+.

Example 208

4-(4-Amino-phenylsulfanyl)-N-(4-bromo-phenyl)-N-isopropyl-3-(7-isopropyl-pyrido[2,3-d]pyrimidin-4-ylamino)-benzamide

Example 208A (4-{4-[(4-Bromo-phenyl)-isopropyl-carbamoyl]-2-nitro-phenylsulfanyl}-phenyl)-carbamic acid 2,2,2-trichloro-ethyl ester A solution of the product in Example 162b (311 mg, 0.6428 mmol) and (4-Bromo-phenyl)-isopropyl-amine (137 mg, 0.6428 mmol) was heated in toluene (10 mL) as in Example 162c to yield the title compound that was used without further manipulation.

Example 208B (4-{2-Amino-4-[(4-bromo-phenyl)-isopropyl-carbamoyl]-phenylsulfanyl}-phenyl)-carbamic acid 2,2,2-trichloro-ethyl ester The product from Example 208A (0.6428 mmol) was reduced with Fe and NH$_4$Cl following the procedure from Example 9E to yield the title compound (218 mg, 53% yield) as an off white solid.

Example 208C

{4-[4-[(4-Bromo-phenyl)-isopropyl-carbamoyl]-2-(7-isopropyl-pyrido[2,3-d]pyrimidin-4-ylamino)-phenylsulfanyl]-phenyl}-carbamic acid 2,2,2-trichloro-ethyl ester The product from Example 8E (53 mg, 0.2469 mmol) and Example 208B (156 mg, 0.2881 mmol) were combined in acetic acid (10 mL) and reacted as in 614E to yield the title compound (68 mg, 34% yield) as a light colored solid.

Example 208D 4-(4-Amino-phenylsulfanyl)-N-(4-bromo-phenyl)-N-isopropyl-3-(7-isopropyl-pyrido[2,3-d]pyrimidin-4-ylamino)-benzamide The product or Example 208C (68 mg, 0.0847 mmol) was reacted with NaOH as in Example 162f to give the title compound (65 mg, 79%) as an off white solid. $^1$H NMR (300 MHz, DMSO-d$_6$) δ ppm: 1.07 (d, J=6.62 Hz, 6 H) 1.33 (dd, J=6.99 Hz, 6 H) 3.10-3.29 (m, 1 H) 4.70-4.92 (m, 1 H) 5.55 (s, 1 H) 6.59 (d, J=8.46 Hz, 2 H) 6.50-6.57 (m, 1 H) 6.99-7.05 (m, 1 H) 7.08 (dd, J=16.73, 8.64 Hz, 4 H) 7.16-7.24 (m, 1 H) 7.49 (d, J=8.46 Hz, 2 H) 7.56 (d, J=8.09 Hz, 1 H) 8.48 (s, 1 H) 8.77 (d, J=8.46 Hz, 1 H) 9.80-10.05 (m, 1 H); MS (ESI) m/z 629 (M+H)+.

Example 209

{4-[2-Amino-4-(4-bromo-phenylcarbamoyl)-phenylsulfanyl]-phenyl}-carbamic acid 2,2,2-trichloro-ethyl ester The compound was prepared following the procedures from Examples 100A, 100B and 100C to give the title compound.

Example 210

{4-[2-(7-Isopropyl-pyrido[2,3-d]pyrimidin-4-ylamino)-4-(1-phenyl-ethylcarbamoyl)-phenylsulfanyl]-phenyl}-carbamic acid 2,2,2-trichloro-ethyl ester A mixture of the product of Example 162a (60 mg, 0.1 mmol) was reacted with methylbenzylamine (36 mg, 0.33 mmol) using the procedure of Example 182 to provide the title product. $^1$H NMR (300 MHz, DMSO-d$_6$) δ ppm: 1.33 (d, J=6.99 Hz, 6 H) 1.45 (d, J=6.99 Hz, 3 H) 3.15-3.28 (m, 1 H) 4.95 (s, 2 H) 5.08-5.25 (m, 1 H) 7.04 (d, J=8.46 Hz, 1 H) 7.22 (d, J=6.99 Hz, 1 H) 7.26-7.41 (m, 6 H) 7.55 (d, J=8.82 Hz, 2 H) 7.62 (d, J=8.46 Hz, 1 H) 7.75 (dd, J=8.27, 1.65 Hz, 1 H) 7.94 (d, J=1.84 Hz, 1 H) 8.57 (s, 1 H) 8.82 (dd, J=8.46, 3.68 Hz, 2 H) 10.20 (s, 1 H) 10.36 (s, 1 H).

Example 211

{4-[4-[1-(4-Bromo-phenyl)-ethylcarbamoyl]-2-(7-isopropyl-pyrido[2,3-d]pyrimidin-phenylsulfanyl]-phenyl}-carbamic acid 2,2,2-trichloro-ethyl ester A mixture of the product of Example 162a (60 mg, 0.1 mmol) was reacted with methyl-4-bromo-benzylamine (60 mg, 0.33 mmol) using the procedure of Example 182 to provide the title product. $^1$H NMR (300 MHz, DMSO-d$_6$) δ ppm: 1.33 (d, J=6.99 Hz, 6 H) 1.44 (d, J=6.99 Hz, 3 H) 3.16-3.27 (m, 1 H) 4.95 (s, 2 H) 5.06-5.17 (m, 1 H) 7.04 (d, J=8.46 Hz, 1 H) 7.22-7.41 (m, 4 H) 7.45-7.58 (m, 3 H) 7.63 (d, J=8.46 Hz, 1 H) 7.74 (dd, J=8.64, 1.29 Hz, 1 H) 7.93 (d, J=1.10 Hz, 1 H) 8.02 (s, 1 H) 8.58 (s, 1 H) 8.82 (d, J=2.21 Hz, 1 H) 8.84 (s, 1 H) 10.21 (s, 1 H) 10.36 (s, 1 H).

Example 212

N-[4-(4-Amino-phenoxy)-3-(7-isopropyl-pyrido[2,3-d]pyrimidin-4-ylamino)-phenyl]-3-trifluoromethyl-benzamide The title compound was prepared according to the Boc procedure from Examples 10A-C after coupling with the product from Example 8E. The crude product was purified by HPLC with TFA to provide the title compound as a trifluoroacetic acid salt (0.18 g, 53%). $^1$H NMR (300 MHz, DMSO-d$_6$) δ ppm: 1.33 (d, J=6.99 Hz, 6 H), 3.14-3.37 (m, 1 H), 6.92 (s, 4 H), 7.03 (d, J=9.19 Hz, 1 H), 7.69 (dd, J=9.19, 2.57 Hz, 1 H), 7.81 (t, J=8.64 Hz, 2 H), 7.99 (d, J=7.72 Hz, 1 H), 8.09 (d, J=2.57 Hz, 1 H), 8.23-8.33 (m, 2 H), 8.83 (s, 1 H), 8.92 (d, J=8.46 Hz, 1 H), 10.65 (s, 1 H), 11.32 (s, 1 H); MS (ESI+) m/z 559 (M+H)+.

Example 213

N-[4-(4-Amino-phenoxy)-3-(7-methyl-pyrido[2,3-d]pyrimidin-4-ylamino)-phenyl]-3-trifluoromethyl-benzamide The title compound was prepared according to the Boc procedure from Examples 10A-C using 3-trifluoromethylaniline in place of 4-bromoaniline in the first step after which the product was coupled with the product from Example 9B. The crude product was purified by HPLC with TFA to provide the title compound as a trifluoroacetic acid salt (0.191 g, 59%). $^1$H NMR (300 MHz, DMSO-$d_6$) δ ppm: 2.72 (s, 3 H), 6.90 (s, 4 H), 7.04 (d, J=8.82 Hz, 1 H), 7.68 (dd, J=8.82, 2.57 Hz, 1 H), 7.74 (d, J=8.46 Hz, 1 H), 7.81 (t, J=7.91 Hz, 2 H), 7.99 (d, J=7.72 Hz, 1 H), 8.10 (d, J=2.57 Hz, 1 H), 8.23-8.33 (m, 2 H), 8.83 (s, 1 H), 8.86 (d, J=8.46 Hz, 1 H), 10.64 (s, 1 H), 11.26-11.34 (m, 1 H); MS (ESI+) m/z 531 (M+H)+.

Example 214

N-[4-(4-Hydroxy-phenylsulfanyl)-3-(7-isopropyl-pyrido[2,3-d]pyrimidin-4-ylamino)-phenyl]-3-trifluoromethoxy-benzamide

Example 214a

N-[3-Amino-4-(4-hydroxy-phenylsulfanyl)-phenyl]-3-trifluoromethoxy-benzamide

The title compound was prepared according to the procedures described in Example 115 substituting 3-trifluoromethyl benzoyl chloride with 3-trifluoromethoxy benzoyl chloride to give the tile compound (0.35 g, 41%).

Example 214b

N-[4-(4-Hydroxy-phenylsulfanyl)-3-(7-isopropyl-pyrido[2,3-d]pyrimidin-4-ylamino)-phenyl]-3-trifluoromethoxy-benzamide A solution of the product of Example 8E (64 mg, 0.294 mmol), and the product of Example 214a (124 mg, 0.294 mmol) in acetic acid (1 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (28 mg, 16%). $^1$H NMR (300 MHz, DMSO-$d_6$) δ ppm: 1.34 (d, J=6.62 Hz, 6 H) 3.14-3.29 (m, 1 H) 6.74 (d, J=8.82 Hz, 1 H) 7.07 (d, J=8.82 Hz, 1 H) 7.19 (d, J=8.82 Hz, 2 H) 7.56-7.70 (m, 4 H) 7.62-7.73 (m, 2 H) 7.83-8.00 (m, 1 H) 8.01 (d, J=7.72 Hz, 1 H) 8.56 (s, 1 H) 8.83 (d, J=8.46 Hz, 1 H) 9.75 (s, 1 H) 10.09 (s, 1 H) 10.51 (s, 1 H); MS (ESI+) m/z 592 (M+H)+, (ESI−) m/z 590 (M−H)−.

Example 215

N-[4-(4-Amino-phenoxy)-3-(7-isopropyl-pyrido[2,3-d]pyrimidin-4-ylamino)-phenyl]-4-bromo-benzamide The title compound was obtained following the procedures of Example 252 substituting 4-bromo-N-(4-fluoro-3-nitrophenyl)benzamide for N-(4-fluoro-3-nitrophenyl)benzamide in Example 252a. The final deprotected crude product was purified by reverse phase preparative HPLC with TFA method to give the title compound (126 mg, 32%) as a trifluoroacetic acid salt. $^1$H NMR (300 MHz, DMSO-$d_6$) δ ppm: 1.33 (d, J=6.99 Hz, 6 H) 3.26 (m, 1 H) 6.92 (m, 4 H) 7.02 (d, J=8.82 Hz, 1 H) 7.68 (dd, J=9.19, 2.57 Hz, 1 H) 7.77 (d, J=8.46 Hz, 2 H) 7.82 (d, J=8.82 Hz, 1 H) 7.92 (d, J=8.46 Hz, 2 H) 8.08 (d, J=2.57 Hz, 1 H) 8.82 (s, 1 H) 8.91 (d, J=8.82 Hz, 1 H) 10.50 (s, 1 H) 11.32 (s, 1 H); MS (ESI+) m/z 569, 571 (M+H)+.

Example 216

N-[4-(4-Amino-phenoxy)-3-(7-isopropyl-pyrido[2,3-d]pyrimidin-4-ylamino)-phenyl]-3-bromo-benzamide The title compound was obtained following the procedures of Example 252 substituting 3-bromo-N-(4-fluoro-3-nitrophenyl)benzamide for N-(4-fluoro-3-nitrophenyl)benzamide in Example 252a. The final deprotected crude product was purified by reverse phase preparative HPLC with TFA method to give the title compound as a trifluoroacetic acid salt (90 mg, 23%). $^1$H NMR (300 MHz, DMSO-$d_6$) δ ppm: 1.33 (d, J=6.62 Hz, 6 H) 3.26 (m, 1 H) 6.90 (m, 4 H) 7.03 (d,J=8.82 Hz, 1 H) 7.52 (t, J=7.91 Hz, 1 H) 7.68 (dd, J=9.19, 2.57 Hz, 1 H) 7.82 (d, J=8.82 Hz, 2 H) 7.96 (d, J=8.46 Hz, 1 H) 8.08 (d, J=2.57 Hz, 1 H) 8.15 (m, 1 H) 8.83 (s, 1 H) 8.92 (d, J=8.46 Hz, 1 H) 10.53 (s, 1 H) 11.38 (s, 1 H); MS (ESI+) m/z 569 571 (M+H)+.

Example 217

N-[4-(4-Amino-phenoxy)-3-(7-methyl-pyrido[2,3-d]pyrimidin-4-ylamino)-phenyl]-4-bromo-benzamide The title compound was obtained following the procedures of Example 252 substituting 4-bromo-N-(4-fluoro-3-nitrophenyl)benzamide for N-(4-fluoro-3-nitrophenyl)benzamide in Example 252a and substituting the product of Example 9B for the product of Example 8E in Example 252c. The final deprotected crude product was purified by reverse phase preparative HPLC with TFA method to give the title compound as a trifluoroacetic acid salt (137 mg, 36%). $^1$H NMR (300 MHz, DMSO-$d_6$) δ ppm: 2.72 (s, 3 H) 6.94 (m, 4 H) 7.06 (d, J=8.82 Hz, 1 H) 7.69 (dd, 8.82, 2.57 Hz, 1 H) 7.78 (m, 3 H) 7.92 (d, J=8.46 Hz, 2 H) 8.11 (d, J=2.57 Hz, 1 H) 8.84 (m, 2 ) 10.32 (s, 1 H) 11.46 (s, 1 H); MS (ESI+) m/z 541 543 (M+H)+.

Example 218

N-[4-(4-Amino-phenoxy)-3-(7-methyl-pyrido[2,3-d]pyrimidin-4-ylamino)-phenyl]-3-bromo-benzamide The title compound was obtained following the procedure for Example 252 substituting 3-bromo-N-(4-fluoro-3-nitrophenyl)benzamide for N-(4-fluoro-3-nitrophenyl)benzamide in Example 252a and substituting the product of Example 9B for the product of Example 8E in Example 252c. The crude product was purified by reverse phase preparative HPLC with TFA method to give the title compound as a trifluoroacetic acid salt (103 mg, 27%). $^1$H NMR (300 MHz, DMSO-$d_6$) δ ppm: 2.73 (s, 3 H) 6.96 (m, 4 H) 7.06 (d, J=8.82 Hz, 1 H) 7.52 (t, J=7.91 Hz, 1 H) 7.68 (dd, J=8.82, 2.57 Hz, 1 H) 7.76 (d, J=8.46 Hz, 1 H) 7.82 (m, 1 H) 7.96 (d, J=7.72 Hz, 1 H) 8.11

(d, J=2.21 Hz, 1 H) 8.14 (m, 1 H) 8.82 (m, 2 H) 10.54 (s, 1 H) 11.42 (s, 1 H); MS (ESI+) m/z 541 543 (M+H)+.

Example 219

4-(4-Amino-phenylsulfanyl)-N-(5-bromo-pyridin-2-yl)-3-(7-ethyl-pyrido[2,3-d]pyrimidin-4-ylamino)-benzamide A solution of the product from Example 9B (0.942 g, 5.0 mmol) in anhydrous tetrahydrofuran (50 mL) was cooled to −78° C. under a nitrogen atmosphere. To this solution was added slowly dropwise a solution of lithium diisopropylamide (3.0 mL of a 2.0 M solution in toluene/hexane/heptane, 6.0 mmol, 1.2 eq). After the addition was complete the reaction mixture was stirred at −78° C. for 1 h, and then methyl iodide (1.42 g, 10.0 mmol, 2.0 eq) was added dropwise. The reaction mixture was stirred for an additional 1.5 h at −78° C., during which time all solids dissolved. The reaction flask was then removed from the cooling bath and saturated aqueous ammonium chloride (25 mL) and water (25 mL) was added. The reaction mixture was extracted with ethyl acetate (3×100 mL) and the combined organic layers were washed with brine, dried over anhydrous magnesium sulfate, filtered, and evaporated under vacuum. The residue was purified by chromatography on silica gel, eluting with a 3/2 hexane:ethyl acetate to provide N'-(3-Cyano-6-ethyl-pyridin-2-yl)-N,N-dimethyl-formamidine (0.87 g, 86% yield) which was reacted according to the procedure of Example 17E substituting N'-(3-Cyano-6-ethyl-pyridin-2-yl)-N,N-dimethyl-formamidine for the product of Example 8E.

Example 220

N-[4-(4-Hydroxy-phenylsulfanyl)-3-(7-isopropyl-pyrido[2,3-d]pyrimidin-4-ylamino)-phenyl]-benzamide

Example 220a

N-(4-Fluoro-3-nitrophenyl)benzamide

To a solution of 4-fluoro-3-nitroaniline (2.00 g, 12.8 mmol) and Et$_3$N (1.98 mL, 14.1 mmol) in THF (40 mL) was added benzoyl chloride (1.58 ml, 13.5 mmol) dropwise at 5° C. The mixture was stirred at 5° C. for 1 hour, warmed to room temperature, and then evaporated. The residue was suspended in H$_2$O (100 ml), adjusted to pH 2, and then extracted with EtOAc. The extract was washed with H$_2$O, 10% NaHCO$_3$ and brine, dried over MgSO$_4$, and concentrated under vacuum to give the crude product, which was purified by washing with i-Pr$_2$O to give the title compound as pale brown crystal (2.70 g, 81%).

Example 220b

N-[4-(4-Hydroxyphenylsulfanyl)-3-nitrophenyl]benzamide

A mixture of the product from Example 220a (0.50 g, 1.9 mmol), 4-mercaptphenol (0.28 g, 2.0 mmol) and K$_2$CO$_3$ (0.32 g, 2.3 mmol) in DMF (10 mL) was heated at 90° C. for 1 hour, and then poured into H$_2$O (100 ml) under stirring. The resulting oily crystal was extracted with EtOAc. The extract was washed with H$_2$O (3 times) and brine, dried over MgSO$_4$, filtered and concentrated under vacuum giving the crude title compound, which was purified by washing with i-Pr$_2$O to give the desired product as yellow crystals (0.68 g, 96%).

Example 220c

N-[3-Amino-4-(4-hydroxyphenylsulfanyl)phenyl]benzamide

A suspension of the product from Example 220b (0.67 g, 1.8 mmol) and Fe powder (0.31 g, 5.5 mmol) in a mixture of EtOH (6.7 mL) and HOAc (6.7 mL) was gradually heated to 80° C. and heated at 80° C. for 3 hours. The reaction mixture was evaporated. The residue was portioned between EtOAc and 10% NaHCO$_3$ and then filtered (through celite). The organic layer was washed with brine, dried over MgSO$_4$, filtered and concentrated under vacuum giving the crude title compound, which was purified by washing with i-Pr$_2$O to give the desired compound as pale brown crystals (0.53 g, 86%).

Example 220d

N-[4-(4-Hydroxy-phenylsulfanyl)-3-(7-isopropyl-pyrido[2,3-d]pyrimidin-4-ylamino)-phenyl]-benzamide The product from Example 8E (75 mg, 0.35 mmol) was reacted with the product from Example 220c (117 mg, 0.35 mmol) in 2 mL of glacial acetic acid for 5 min. Cooled to room temperature and the acetic acid was removed under vacuum giving the crude product which was purified by trituration with EtOAc to give the title compound as a solid (70 mg, 40%). $^1$H NMR (300 MHz, DMSO-d$_6$) δ ppm: 1.34 (d, J=7.0 Hz, 6H), 3.22 (septet, J=7.0 Hz, 1H), 6.73 (d, J=8.5 Hz, 2H), 7.08 (d, J=8.5 Hz, 1H), 7.18 (d, J=8.5 Hz, 2H), 7.48-7.60 (m, 3H), 7.62 (d, J=8.5 Hz, 1H), 7.64 (dd, J=8.5, 2.2 Hz, 1H), 7.90-7.99 (m, 2H), 7.98 (d, J=2.2 Hz, 1H), 8.56 (s, 1H), 8.84 (d, J=8.5 Hz, 1H), 9.73 (s, 1H), 10.09 (s, 1H), 10.39 (s, 1H); MS (ESI+) m/z 508 (M+H)+, (ESI−) m/z 506 (M−H)−.

Example 221

Pyrazine-2-carboxylic acid [4-(4-hydroxy-phenylsulfanyl)-3-(7-isopropyl-pyrido[2,3-d]pyrimidin-4-ylamino)-phenyl]-amide

Example 221a

Pyrazine-2-carboxylic acid (4-fluoro-3-nitrophenyl)amide

To a solution of pyrazine-2-carboxylic acid (2.00 g, 16.1 mmol) and Et$_3$N (2.50 ml, 17.7 mmol) in THF (40 mL) was added ethyl chloroformate (1.74 mL, 17.7 mmol) dropwise at 5° C. and the mixture was stirred at 5° C. for 1 hour. 4-Fluoro-3-nitroaniline (2.80 g, 17.7 mmol) was added to the mixture at 5° C. The mixture was warmed to room temperature, stirred at room temperature for 4 hours, and then evaporated. The residue was suspended in a mixture of H$_2$O (100 ml) and i-Pr$_2$O (100 ml) and stirred at room temperature for 30 minutes. The resulting crystal was collected by filtration and washed with H$_2$O and i-Pr$_2$O to give the desired product as pale brown crystals (2.91 g, 69%).

Example 221b

Pyrazine-2-carboxylic acid
[4-(4-hydroxy-phenylsulfanyl)-3-nitrophenyl]amide

The product from Example 221a was obtained by following the procedure in Example 220 to provide the title compound as yellow crystals, (83%).

Example 221c

Pyrazine-2-carboxylic acid
[3-amino-4-(4-hydroxy-phenylsulfanyl)phenyl]amide

The product from Example 221b was reacted following the procedure in Example 220c providing the title compound as pale brown crystals (65%).

Example 221d

Pyrazine-2-carboxylic acid [4-(4-hydroxy-phenylsulfanyl)-3-(7-isopropyl-pyrido[2,3-d]pyrimidin-4-ylamino)-phenyl]-amide The product from Example 8E (75 mg, 0.35 mmol) was reacted with the product from Example 221c (117 mg, 0.35 mmol) in 2 mL of glacial acetic acid for 6 min. Cooled to room temperature and the acetic acid was removed under vacuum giving the crude product which was purified by trituration with EtOAc to give the title compound as a solid (83 mg, 47%). $^1$H NMR (300 MHz, DMSO-$d_6$) δ ppm: 1.34 (d, J=7.0 Hz, 6H), 3.23 (septet, J=7.0 Hz, 1H), 6.75 (d, J=8.5 Hz, 2H), 7.04 (d, J=8.4 Hz, 1H), 7.21 (d, J=8.5 Hz, 2H), 7.62 (d, J=8.1 Hz, 1H), 7.74 (br-d, J=8.4 Hz, 1H), 8.10 (d, J=1.1 Hz, 1H), 8.56 (s, 1H), 8.82 (dd, J=2.2, 1.1 Hz, 1H), 8.85 (d, J=8.1 Hz, 1H), 8.93 (d, J=2.2 Hz, 1H), 9.28 (d, J=1.1 Hz, 1H), 9.77 (s, 1H), 10.11 (s, 1H), 10.89 (s, 1H); MS (ESI+) m/z 510 (M+H)+, (ESI−) m/z 508 (M−H)−.

Example 222

Pyridine-2-carboxylic acid [4-(4-hydroxy-phenylsulfanyl)-3-(7-isopropyl-pyrido[2,3-d]pyrimidin-4-ylamino)-phenyl]-amide

Example 222a

Pyridine-2-carboxylic acid
(4-fluoro-3-nitrophenyl)amide

The title compound was prepared following the procedure for Example 221 substituting pyridine-2-carboxylic acid for pyrazine-2-carboxylic acid providing the title compound as pale brown crystals (88%).

Example 222b

Pyridine-2-carboxylic acid
[4-(4-hydroxy-phenylsulfanyl)-3-nitrophenyl]amide

The product from Example 222a was obtained following the procedure in Example 220 to provide the title compound as yellow crystals (95%).

Example 222c

Pyridine-2-carboxylic acid
[3-amino-4-(4-hydroxy-phenylsulfanyl)phenyl]amide

The product from Example 222b was used to prepare the title compound as pale brown crystals (84%).

Example 222d

Pyridine-2-carboxylic acid [4-(4-hydroxy-phenylsulfanyl)-3-(7-isopropyl-pyrido[2,3-d]pyrimidin-4-ylamino)-phenyl]-amide The product from Example 8E (75 mg, 0.35 mmol) was reacted with the product from Example 222c (117 mg, 0.35 mmol) in 2 mL of glacial acetic acid for 5 min. Cooled to room temperature and the acetic acid was removed under vacuum giving the crude product which was purified by trituration with EtOAc to give the title compound as a solid (110 mg, 60%). $^1$H NMR (300 MHz, DMSO-$d_6$) δ ppm: 1.34 (d, J=7.0 Hz, 6H), 3.23 (septet, J=7.0 Hz, 1H), 6.75 (d, J=8.4 Hz, 2H), 7.04 (d, J=8.4 Hz, 1H), 7.20 (d, J=8.4 Hz, 2H), 7.62 (d, J=8.4 Hz, 1H), 7.69 (ddd, J=7.7, 4.8, 1.5 Hz, 1H), 7.74 (dd, J=8.4, 2.2 Hz, 1H), 8.07 (td, J=7.7, 1.5 Hz, 1H), 8.12-8.18 (m, 2H), 8.56 (s, 1H), 8.73 (br-d, J=4.8 Hz, 1H), 8.85 (d, J=8.4 Hz, 1H), 9.76 (s, 1H), 10.11 (s, 1H), 10.79 (s, 1H); MS (ESI+) m/z 509 (M+H)+, (ESI−) m/z 507 (M−H)−.

Example 223

4-[4-(2-Amino-acetylamino)-phenoxy]-N-(4-bromo-phenyl)-3-(7-isopropyl-pyrido[2,3-d]pyrimidin-4-ylamino)-benzamide

Example 223A (4-[4-(4-Bromo-phenylcarbamoyl)-2-(7-isopropyl-pyrido[2,3-d]pyrimidin-4-ylamino)-phenoxy]-phenylcarbamoyl}-methyl)-carbamic acid tert-butyl ester A solution of the product of Example 100 (50 mg, 0.0878 mmol) in anhydrous tetrahydrofuran (2 mL) was treated with N-(tert-butoxycarbonyl)glycine (18.5 mg, 0.1054 mmol) and N,N'-dicyclohexylcarbodiimide (21.7 mg, 0.1054 mmol), and stirred at room temperature for 2.5 days. The solvent was removed by rotary evaporation in vacuo and the residue purified by silica gel chromatography eluting with 7% methanol/methylene chloride to afford the title compound (49.5 mg, 78%).

Example 223B

4-[4-(2-Amino-acetylamino)-phenoxy]-N-(4-bromo-phenyl)-3-(7-isopropyl-pyrido[2,3-d]pyrimidin-4-ylamino)-benzamide The product of Example 223A (48.5 mg, 0.668 mmol) was treated with trifluoroacetic acid (1 mL) in methylene chloride (1 mL) at room temperature for 40 minutes. The solvents were removed by rotary evaporation and the residual oil taken up in ethyl acetate (60 mL) and washed with saturated aqueous sodium bicarbonate (50 mL), water (2×50 mL), and brine (50 mL). The organic phase was dried over anhydrous sodium sulfate, filtered, and concentrated in vacuo. Purification by HPLC with AA provided the title compound as a white solid (12 mg, 29%). $^1$H NMR (300 MHz, DMSO-$d_6$) δ ppm: 1.31 (d, J=6.99 Hz, 6 H) 3.12-3.28 (m, 1 H) 3.25 (s, 2 H) 6.98 (d, J=8.83 Hz, 1 H) 7.00 (d, J=9.19 Hz, 2 H) 7.54 (d, J=8.82 Hz, 2 H) 7.58 (d, J=8.82 Hz, 1 H) 7.62 (d, J=9.19 Hz, 2 H) 7.76 (d, J=8.82 Hz, 2 H) 7.89 (dd, J=8.82, 1.10 Hz, 1 H) 8.17 (s, 1 H) 8.58 (s, 1 H) 8.71-8.83 (m, 1 H) 10.35 (s, 1 H); MS (ESI+) m/z 626/628 (M+H)$^+$.

Example 224

4-(4-Amino-phenylsulfanyl)-N-(5-fluoro-pyridin-3-yl)-3-(7-isopropyl-pyrido[2,3-d]pyrimidin-4-ylamino)-benzamide Example 224A 5-Fluoro-nicotinic acid A mixture of 2,6-dichloro-5-fluoro-3-pyridinecarboxylic acid (3.00 g, 0.0143 mol), anhydrous sodium acetate (3.516 g, 0.0429 mol), and 10% palladium-on-carbon (0.300 g) in methanol (50 mL) was hydrogenated at 1 atmosphere hydrogen pressure (balloon) for 18 hours. The reaction was vacuum filtered through a 0.45µ PTFE membrane and the catalyst thoroughly washed with methanol (25 mL). The filtrate was concentrated by rotary evaporation in vacuo. The residue was taken up in ethyl acetate (100 mL) and water (30 mL), the aqueous pH adjusted to 3 with 6N aqueous hydrochloric acid, and the layers separated. The organic phase was washed with water (2×30 mL) and brine (30 mL), then dried over anhydrous sodium sulfate, filtered, and concentrated in vacuo. This afforded the title compound as a white solid (1.293 g, 64%).

Example 224B (5-Fluoro-pyridin-3-yl)-carbamic acid benzyl ester

The product of Example 224A (1.00 g, 7.087 mmol) and N-methylmorpholine (0.86 mL, 7.796 mmol) in anhydrous 1,2-dichloroethane (30 mL) was stirred under a nitrogen atmosphere for 10 minutes at room temperature. Diphenyl phosphoryl azide (1.68 mL, 7.796 mmol) was then added dropwise and the reaction stirred for 30 minutes at the same temperature. The reaction was then slowly heated to 75° C. over a 20-minute period and was maintained at this temperature for 1 hour. Benzyl alcohol (1.10 mL, 10.63 mmol) and cuprous chloride (20 mg) were added and the reaction was refluxed for 3 hours. The reaction was then cooled to room temperature and the solvent removed by rotary evaporation in vacuo. Purification by silica gel chromatography eluting with 20% ethyl acetate/methylene chloride afforded the title compound as an off-white solid (718 mg, 41%).

Example 224C

5-Fluoro-pyridin-3-ylamine

A solution of the product of Example 224B (716 mg, 2.908 mmol) in methanol (17 mL) was degassed by a vacuum/nitrogen purge sequence (repeated three times), treated with 10% palladium-on-carbon (72 mg) and ammonium formate (917 mg, 14.54 mmol), and heated at reflux under a nitrogen atmosphere for 1.5 hour. The reaction was cooled to room temperature, diluted with ethyl acetate (80 mL), and vacuum filtered through a 50 mL bed of silica gel (230-400 mesh) in a glass fritted disc funnel, washing with ethyl acetate (75 mL). Concentration of the filtrate by rotary evaporation in vacuo afforded the title compound as a white crystalline solid (283 mg, 87%).

Example 224D

{4-[4-(5-Fluoro-pyridin-3-ylcarbamoyl)-2-nitro-phenylsulfanyl]-phenyl}-carbamic acid 9H-fluoren-9-ylmethyl ester A solution of the product of Example 19C (259 mg, 0.488 mmol) in anhydrous tetrahydrofuran (5 mL) was treated with the product of Example 224C (60.2 mg, 0.537 mmol) and diisopropylethylamine (0.128 mL, 0.732 mmol), and stirred at room temperature under a nitrogen atmosphere for 15 hours. The solvent was removed by rotary evaporation in vacuo, and the residue was taken up in ethyl acetate (100 mL) and washed with saturated aqueous sodium bicarbonate (25 mL), water (2×25 mL), and brine (25 mL). The organic phase was dried over anhydrous sodium sulfate, filtered, and concentrated in vacuo. Trituration with 3% methanol/methylene chloride provided the title compound as a yellow solid (176 mg, 60%).

Example 224E

{4-[2-Amino-4-(5-fluoro-pyridin-3-ylcarbamoyl)-phenylsulfanyl]-phenyl}-carbamic acid 9H-fluoren-9-ylmethyl ester The product of Example 224D (174 mg, 0.2868 mmol), ammonium chloride (100.5 mg, 1.879 mmol), and iron powder (98.5 mg, 1.764 mmol) in a mixture of water (3 mL), ethanol (6 mL) and tetrahydrofuran (6 mL) was heated at 80° C. under a nitrogen atmosphere for 1 hour. The reaction was cooled to room temperature, diluted with ethyl acetate (100 mL), and washed with water (2×25 mL) and brine (25 mL). The organic was dried over anhydrous sodium sulfate, filtered, and concentrated by rotary evaporation in vacuo to give the product as a yellow solid (160 mg, 97%).

Example 224F

{4-[4-(5-Fluoro-pyridin-3-ylcarbamoyl)-2-(7-isopropyl-pyrido[2,3-d]pyrimidin-4-ylamino)-phenylsulfanyl]-phenyl}-carbamic acid 9H-fluoren-9-ylmethyl ester A solution of the product of Example 8E (60 mg, 0.2743 mmol) and the product of Example 224E (158.2 mg, 0.2743 mmol) in acetic acid (4 mL) was stirred in an oil bath preheated to 140° C. for 1 hour. Cooled to room temperature, diluted with hexanes (100 mL), and concentrated under vacuum The reaction was dried on hi-vacuum, then purified by silica gel chromatography eluting with a gradient of 2% to 4% methanol/methylene chloride to afford the title compound as an off-white solid (120 mg, 59%).

Example 224G 4-(4-Amino-phenylsulfanyl)-N-(5-fluoro-pyridin-3-yl)-3-(7-isopropyl-pyrido[2,3-d]pyrimidin-4-ylamino)-benzamide A solution of the product of Example 224F (118.9 mg, 0.159 mmol) in 1,4-dioxane (3 mL) was treated with a solution of lithium hydroxide monohydrate (13.3 mg, 0.318 mmol) in water (1.5 mL) at ambient temperature, then heated at 70° C. for 45 minutes. The reaction was cooled to room temperature, diluted with ethyl acetate (100 mL) and water (30 mL), adjusted the aqueous pH to 6 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel chromatography eluting with 5% methanol/methylene chloride afforded the title compound as a yellow solid (51 mg, 61%). $^1$H NMR (300 MHz, DMSO-$d_6$) δ ppm: 1.34 (d, J=6.99 Hz, 6 H) 3.10-3.34 (m, 1 H) 5.61 (s, 2 H) 6.64 (d, J=8.46 Hz, 2 H) 6.90 (d, J=8.09 Hz, 1 H) 7.15 (d, J=8.46 Hz, 2 H) 7.65 (d, J=8.09 Hz, 1 H) 7.81 (dd, J=7.17, 1.65 Hz, 1 H) 7.97 (s, 1 H) 8.13-8.23 (m, 1 H) 8.32 (d, J=2.57 Hz, 1 H) 8.59 (s, 1 H) 8.76 (d, J=1.47 Hz, 1 H) 8.89 (d, J=8.09 Hz, 1 H) 10.18 (s, 1 H) 10.59 (s, 1 H); MS (ESI+) m/z 526 (M+H)$^+$, (ESI−) m/z 524 (M−H)$^−$.

Example 225

4-(4-Amino-phenoxy)-N-(5-tert-butyl-[1,3,4]thiadiazol-2-yl)-3-(7-isopropyl-pyrido[2,3-d]pyrimidin-4-ylamino)-benzamide Example 225a N-(5-tert-Butyl-[1,3,4]thiadiazol-2-yl)-4-fluoro-3-nitro-benzamide The title compound was synthesized using 5-tert-Butyl-[1,3,4]thiadiazol-2-ylamine (232 mg, 1.474 mmol) and following the procedure from Example 172b to provide the title compound as a solid (400 mg, 84%).

Example 225b

{4-[4-(5-tert-Butyl-[1,3,4]thiadiazol-2-ylcarbamoyl)-2-nitro-phenoxy]-phenyl}-carbamic acid tert-butyl ester The title compound was prepared by treating the product of Example 225a under the conditions of Example 172c providing the title compound (600 mg, 72%).

Example 225c

{4-[2-Amino-4-(5-tert-butyl-[1,3,4]thiadiazol-2-ylcarbamoyl)-phenoxy]-phenyl}-carbamic acid tert-butyl ester The title compound was prepared from the product of Example 225b using the conditions of Example 9E to provide the title compound (157 mg, 33%).

Example 225d

{4-[4-(5-tert-Butyl-[1,3,4]thiadiazol-2-ylcarbamoyl)-2-(7-isopropyl-pyrido[2,3-d]pyrimidin-4-ylamino)-phenoxy]-phenyl}-carbamic acid tert-butyl ester The products from Example 225c (157 mg, 0.323 mmol) and Example 8E (70 mg, 0.323 mmol) were dissolved in HOAc and placed in preheated 120° C. oil bath for 10 minutes. The solvent was removed under vacuum and the crude oil taken forward without purification (212 mg, 99%).

Example 225e 4-(4-Amino-phenoxy)-N-(5-tert-butyl-[1,3,4]thiadiazol-2-yl)-3-(7-isopropyl-pyrido[2,3-d]pyrimidin-4-ylamino)-benzamide The product from Example 225d (212 mg, 0.323 mmol) was dissolved in a 1:1 mixture of TFA in $CH_2Cl_2$ and stirred at room temperature for 2 hrs. The solvent was removed under vacuum and the crude oil was purified by HPLC with TFA providing the product as a trifluoroacetic acid salt (9 mg, 5%). $^1$H NMR (300 MHz, DMSO-$d_6$) δ ppm: 1.34 (d, J=6.99 Hz, 6 H), 1.42 (s, 9 H), 3.21-3.36 (m, 1 H), 6.79-6.87 (m, 2 H), 6.94 (d, J=8.82 Hz, 3 H), 7.86 (d, J=8.46 Hz, 1 H), 8.15 (dd, J=8.82, 2.21 Hz, 1 H), 8.28 (d, J=2.21 Hz, 1 H), 8.88 (s, 1 H), 8.99 (d, J=8.46 Hz, 1 H); MS (ESI+) m/z 555 (M+TFA+H)+; (ESI−) m/z 553 (M+TFA−H)−.

Example 226

4-(4-Amino-phenoxy)-N-(5-fluoro-pyridin-2-yl)-3-(7-isopropyl-pyrido[2,3-d]pyrimidin-4-ylamino)-benzamide Example 226a 4-Fluoro-N-(5-fluoro-pyridin-2-yl)-3-nitro-benzamide The product from Example 172a was reacted with 5-Fluoro-pyridin-2-ylamine (165 mg, 1.474 mmol) according to the procedure from Example 172a to provide the title compound (404 mg, 98%).

Example 226b

{4-[4-(5-Fluoro-pyridin-2-ylcarbamoyl)-2-nitro-phenoxy]-phenyl}-carbamic acid tert-butyl ester The title compound was prepared by treating the product of Example 226a under the conditions of Example 172c to provide the title compound (568 mg, 83%).

Example 226c

{4-[2-Amino-4-(5-fluoro-pyridin-2-ylcarbamoyl)-phenoxy]-phenyl}-carbamic acid tert-butyl ester The title compound was prepared from the product of Example 226b using the conditions from Example 9E to provide the title compound (203 mg, 38%).

Example 226d

{4-[4-(5-Fluoro-pyridin-2-ylcarbamoyl)-2-(7-isopropyl-pyrido[2,3-d]pyrimidin-4-ylamino)-phenoxy]-phenyl}-carbamic acid tert-butyl ester The product form Example 8E (100 mg, 0.462 mmol) and the product of Example 226c (203 mg, 0.462 mmol) were dissolved in HOAc and placed in a preheated 120° C. oil bath for 10 minutes. Reaction mixture was then cooled to room temperature and the solvent removed under vacuum to provide the title compound (282 mg, 100%).

Example 226e

4-(4-Amino-phenoxy)-N-(5-fluoro-pyridin-2-yl)-3-(7-isopropyl-pyrido[2,3-d]pyrimidin-4-ylamino)-benzamide The product from Example 226d (282 mg, 0.462 mmol) was dissolved in a 1:1 mixture of TFA in $CH_2Cl_2$ and stirred at room temperature for 2 hrs. The solvent was removed under vacuum and the crude oil was purified by HPLC with TFA providing the product as a trifluoroacetic acid salt. $^1$H NMR (300 MHz, DMSO-$d_6$) δ ppm: 1.33 (t, J=6.99 Hz, 6 H), 3.22-3.36 (m, 1 H), 6.84-7.00 (m, 6 H), 7.76-7.91 (m, 2 H), 8.09 (dd, J=8.82, 2.21 Hz, 1 H), 8.14-8.27 (m, 2 H), 8.40 (d, J=2.94 Hz, 1 H), 8.90 (s, 1 H), 9.00 (d, J=8.82 Hz, 1 H), 10.93 (s, 1 H); MS (ESI+) m/z 510 (M+TFA+H)+; (ESI−) m/z 508 (M+TFA−H)−.

Example 227

4-(4-Amino-phenoxy)-3-(7-isopropyl-pyrido[2,3-d]pyrimidin-4-ylamino)-N-(5-trifluoromethyl-pyridin-2-yl)-benzamide

Example 227a

4-Fluoro-3-nitro-N-(5-trifluoromethyl-pyridin-2-yl)-benzamide

The product from Example 172a was reacted with 5-trifluoromethyl-pyridin-2-ylamine (239 mg, 1.474 mmol) according to the procedure from Example 172b to provide the title compound (485 mg, 100%).

Example 227b

{4-[2-Nitro-4-(5-trifluoromethyl-pyridin-2-ylcarbamoyl)-phenoxy]-phenyl}-carbamic acid tert-butyl ester The product from Example 227a was prepared by following the procedures from Example 172c to give the title compound (333 mg, 44%).

Example 227c

{4-[2-Amino-4-(5-trifluoromethyl-pyridin-2-ylcarbamoyl)-phenoxy]-phenyl}-carbamic acid tert-butyl ester The product from Example 227b was reduced with Fe and $NH_4Cl$ following the procedure from Example 9E to give the title compound (271 mg, 86%).

Example 227d

{4-[2-(7-Isopropyl-pyrido[2,3-d]pyrimidin-4-ylamino)-4-(5-trifluoromethyl-pyridin-2-ylcarbamoyl)-phenoxy]-phenyl}-carbamic acid tert-butyl ester The product of Example 8E (120 mg, 0.555 mmol) and of Example 227c (271 mg, 0.555 mmol) were dissolved in HOAc and placed in a preheated 120° C. oil bath for 10 minutes. Reaction mixture was then cooled to room temperature and the solvent removed under vacuum providing the title compound (366 mg, 100%).

Example 227e

4-(4-Amino-phenoxy)-3-(7-isopropyl-pyrido[2,3-d]pyrimidin-4-ylamino)-N-(5-trifluoromethyl-pyridin-2-yl)-benzamide The product from Example 227d (366 mg, 0.555 mmol) was dissolved in a 1:1 mixture of TFA in $CH_2Cl_2$ and stirred at room temperature for 2 hrs. The solvent was removed under vacuum and the crude oil was purified by HPLC with TFA providing the product as a trifluoroacetic acid salt (47 mg, 15%). $^1$H NMR (300 MHz, DMSO-$d_6$) δ ppm: 1.35 (d, J=6.99 Hz, 6 H), 3.29 (dt, J=13.70, 6.94 Hz, 1 H), 6.86-7.00 (m, 5 H), 7.88 (d, J=8.46 Hz, 1 H), 8.11 (dd, J=8.64, 2.39 Hz, 1 H), 8.21-8.30 (m, 2 H), 8.40 (d, J=8.82 Hz, 1 H), 8.79 (s, 1 H), 8.90 (s, 1 H), 9.00 (d, J=8.46 Hz, 1 H), 11.28 (s, 1 H); MS (ESI+) m/z 560 (M+TFA+H)+; (ESI−) m/z 558 (M+TFA−H)−.

Example 228

4-(4-Amino-phenoxy)-3-(7-isopropyl-pyrido[2,3-d]pyrimidin-4-ylamino)-N-[1,3,4]thiadiazol-2-yl-benzamide

Example 228a

4-Fluoro-3-nitro-N-[1,3,4]thiadiazol-2-yl-benzamide

The product from Example 172a was reacted with [1,3,4]Thiadiazol-2-ylamine (149 mg, 1.474 mmol) according to the procedure from Example 172b to provide the title compound (272 mg, 67%).

Example 228b

{4-[2-Nitro-4-([1,3,4]thiadiazol-2-ylcarbamoyl)-phenoxy]-phenyl}-carbamic acid tert-butyl ester The product from Example 228a was prepared by following the conditions of Example 172c (272 mg, 59%).

Example 228c

{4-[2-Amino-4-([1,3,4]thiadiazol-2-ylcarbamoyl)-phenoxy]-phenyl}-carbamic acid tert-butyl ester The product from Example 228b was reduced with Fe and $NH_4Cl$ using the conditions from Example 9E to provide the title compound (217 mg, 82%).

Example 228d

{4-[2-(7-Isopropyl-pyrido[2,3-d]pyrimidin-4-ylamino)-4-([1,3,4]thiadiazol-2-ylcarbamoyl)-phenoxy]-phenyl}-carbamic acid tert-butyl ester The product of Example 8E (110 mg, 0.509 mmol) and the product of Example 228c (217 mg, 0.509 mmol) were dissolved in HOAc and placed in a preheated 120° C. oil bath for 10 minutes. Reaction mixture was then cooled to room temperature and the solvent removed under vacuum giving the title compound (304 mg, 100%).

Example 228e 4-(4-Amino-phenoxy)-3-(7-isopropyl-pyrido[2,3-d]pyrimidin-4-ylamino)-N-[1,3,4]thiadiazol-2-yl-benzamide The product from Example 227d (304 mg, 0.509 mmol) was dissolved in a 1:1 mixture of TFA in $CH_2Cl_2$ and stirred at room temperature for 2 hrs. The solvent was removed under vacuum and the crude oil was purified by HPLC with TFA providing the product as a trifluoroacetic acid salt (47 mg, 15%). $^1H$ NMR (300 MHz, DMSO-$d_6$) δ ppm: 1.35 (d, J=6.99 Hz, 6 H), 3.29 (dt, J=13.70, 6.94 Hz, 1 H), 6.82-6.98 (m, 5 H), 7.87 (d, J=8.82 Hz, 1 H), 8.18 (dd, J=8.82, 2.21 Hz, 1 H), 8.31 (d, J=2.21 Hz, 1 H), 8.89 (s, 1 H), 9.00 (d, J=8.46 Hz, 1 H), 9.23 (s, 1 H), 13.09 (s, 1 H); MS (ESI+) m/z 499 (M+TFA+H)+; (ESI−) m/z 497 (M+TFA−H)−.

Example 229

N-[4-(4-Hydroxy-phenylsulfanyl)-3-(7-isopropyl-pyrido[2,3-d]pyrimidin-4-ylamino)-phenyl]-2-trifluoromethyl-benzamide

Example 229a

N-[3-Amino-4-(4-hydroxy-phenylsulfanyl)-phenyl]-2-trifluoromethyl-benzamide

The title compound was prepared according to the procedures described in Example 115 substituting 3-trifluoromethyl benzoyl chloride with 2-trifluoromethyl benzoyl chloride giving the title compound (0.63 g, 74%).

Example 229b

N-[4-(4-Hydroxy-phenylsulfanyl)-3-(7-isopropyl-pyrido[2,3-d]pyrimidin-4-ylamino)-phenyl]-2-trifluoromethyl-benzamide A solution of the product of Example 8E (79 mg, 0.367 mmol), and the product of Example 229a (148 mg, 0.367 mmol) in acetic acid (1 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (50 mg, 24%). $^1H$ NMR (300 MHz, DMSO-$d_6$) δ ppm: 1.24-1.37 (m, 6 H) 3.16-3.29 (m, 1 H) 6.63-6.78 (m, 2 H) 7.08 (d, J=8.46 Hz, 1 H) 7.17 (d, J=8.46 Hz, 2 H) 7.42-7.52 (m, 1 H) 7.61 (d, J=8.46 Hz, 1 H) 7.71 (t, J=6.62 Hz, 2 H) 7.82 (dd, J=18.02, 7.35 Hz, 2 H) 7.81-7.96 (m, 1 H) 8.56 (s, 1 H) 8.81 (d, J=8.46 Hz, 1 H) 9.73 (s, 1 H) 10.12 (s, 1 H) 10.72 (s, 1 H); MS (ESI+) m/z 576 (M+H)+, (ESI−) m/z 574 (M−H)−.

Example 230

4-Chloro-N-[4-(4-hydroxy-phenylsulfanyl)-3-(7-isopropyl-pyrido[2,3-d]pyrimidin-4-ylamino)-phenyl]-benzamide

Example 230a

N-[3-Amino-4-(4-hydroxy-phenylsulfanyl)-phenyl]-4-chloro-benzamide

The title compound was prepared according to the procedures described in Example 115 substituting 3-trifluoromethylbenzoyl chloride with 4-chlorobenzoyl chloride. Providing the tile compound (0.19 g, 100%).

Example 230b

4-Chloro-N-[4-(4-hydroxy-phenylsulfanyl)-3-(7-isopropyl-pyrido[2,3-d]pyrimidin-4-ylamino)-phenyl]-benzamide A solution of the product of Example 8E (54 mg, 0.248 mmol), and the product of Example 230a (91.9 mg, 0.248 mmol) in acetic acid (1 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (120 mg, 89%). $^1H$ NMR (300 MHz, DMSO-$d_6$) δ ppm: 1.33 (d, J=6.99 Hz, 6 H) 3.13-3.28 (m, 1 H) 6.73 (d, J=8.46 Hz, 2 H) 7.07 (d, J=8.82 Hz, 1 H) 7.18 (d, J=8.46 Hz, 2 H) 7.53-7.66 (m, 3 H) 7.90-8.02 (m, 4 H) 8.56 (s, 1 H) 8.83 (d, J=8.46 Hz, 1 H) 9.74 (s, 1 H) 10.09 (s, 1 H) 10.45 (s, 1 H); MS (ESI+) m/z 542 (M+H)+. (ESI−) m/z 540 (M−H)−.

Example 231

4-(4-Amino-phenylsulfanyl)-N-(5-bromo-pyridin-3-yl)-3-(7-isopropyl-pyrido[2,3-d]pyrimidin-4-ylamino)-benzamide

Example 231A (5-Bromo-pyridin-3-yl)-carbamic acid benzyl ester

A mixture of 5-bromonicotinic acid (1.00 g, 4.95 mmol) and N-methylmorpholine (0.60 mL, 5.445 mmol) in anhydrous 1,2-dichloroethane (20 mL) was stirred under a nitrogen atmosphere for 10 minutes at room temperature. Diphenyl phosphoryl azide (1.17 mL, 5.445 mmol) was then added dropwise and the reaction stirred for 30 minutes at the same temperature. The reaction was then slowly heated to 75° C. over a 20-minute period and was maintained at this temperature for 1 hour. Benzyl alcohol (0.77 mL, 7.434 mmol) and cuprous chloride (15 mg) were added and the reaction was refluxed for 3 hours. The reaction was then cooled to room temperature and the solvent removed by rotary evaporation in vacuo. Purification by silica gel chromatography eluting with a gradient of 12% and 20% ethyl acetate/methylene chloride afforded the title compound as a white solid (524 mg, 34%).

Example 231B

5-Bromo-pyridin-3-ylamine dihydrobromide

A suspension of the product of Example 231A (200 mg, 0.6512 mmol) in a hydrogen bromide solution (33 weight % HBr in acetic acid, 3 mL) was stirred at room temperature for 4 hours. The solvent was removed by rotary evaporation in vacuo and the residue azeotroped with dry toluene (10 mL) to afford the title compound as a light peach colored solid (205 mg, 94%).

Example 231C

{4-[4-(5-Bromo-pyridin-3-ylcarbamoyl)-2-nitro-phenylsulfanyl]-phenyl}-carbamic acid 9H-fluoren-9-ylmethyl ester A solution of the product of Example 19C (259 mg, 0.488 mmol) in anhydrous tetrahydrofuran (5 mL) was treated with the product of Example 231B (180 mg, 0.5366 mmol) and diisopropylethylamine (0.34 mL, 1.951 mmol), and stirred at room temperature under a nitrogen atmosphere for 16 hours. The reaction was diluted with ethyl acetate (150 mL) and washed with saturated aqueous sodium bicarbonate (25 mL), water (2×25 mL), and brine (25 mL). The organic phase was dried over anhydrous sodium sulfate, filtered, and concentrated in vacuo. Trituration with 2% methanol/methylene chloride provided the title compound as a yellow solid (148 mg, 45%).

Example 231 D

{4-[2-Amino-4-(5-bromo-pyridin-3-ylcarbamoyl)-phenylsulfanyl]-phenyl}-carbamic acid 9H-fluoren-9-ylmethyl ester The product of Example 231C (146.5 mg, 0.2195 mmol), ammonium chloride (77 mg, 1.438 mmol), and iron powder (75.4 mg, 1.35 mmol) in a mixture of water (3 mL), ethanol (6 mL) and tetrahydrofuran (6 mL) was heated at 80° C. under a nitrogen atmosphere for 1 hour. The reaction was cooled to room temperature, diluted with ethyl acetate (100 mL), and washed with water (3×50 mL) and brine (50 mL). The organic was dried over anhydrous sodium sulfate, filtered, and concentrated by rotary evaporation in vacuo. Purification by silica gel chromatography eluting with 4% methanol/methylene chloride afforded the title compound as a yellow solid (103 mg, 74%).

Example 231E

{4-[4-(5-Bromo-pyridin-3-ylcarbamoyl)-2-(7-isopropyl-pyrido[2,3-d]pyrimidin-4-ylamino)-phenylsulfanyl]-phenyl}-carbamic acid 9H-fluoren-9-ylmethyl ester A solution of the product of Example 8E (34.4 mg, 0.1592 mmol) and the product of Example 231D (101.5 mg, 0.1592 mmol) in acetic acid (5 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4 times). The residue was dried on hi-vacuum, then purified by silica gel chromatography eluting with a gradient of 2% to 4% methanol/methylene chloride to afford the title compound (98 mg, 76%).

Example 231F 4-(4-Amino-phenylsulfanyl)-N-(5-bromo-pyridin-3-yl)-3-(7-isopropyl-pyrido[2,3-d]pyrimidin-4-ylamino)-benzamide A solution of the product of Example 231E (96 mg, 0.1187 mmol) in 1,4-dioxane (2 mL) was treated with a solution of lithium hydroxide monohydrate (10.0 mg, 0.2374 mmol) in water (1 mL) at ambient temperature, then heated at 70° C. for 30 minutes. The reaction was cooled to room temperature, diluted with ethyl acetate (50 mL) and water (30 mL), adjusted the aqueous pH to 5 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel chromatography eluting with 5% methanol/methylene chloride afforded the title compound as a light yellow solid (36 mg, 2%). $^1$H NMR (300 MHz, DMSO-$d_6$) δ ppm: 1.34 (d, J=6.62 Hz, 6 H) 3.12-3.30 (m, 1 H) 5.61 (s, 2 H) 6.64 (d, J=8.09 Hz, 2 H) 6.90 (dd, J=6.43, 1.29 Hz, 1 H) 7.15 (d, J=8.46 Hz, 2 H) 7.65 (dd, J=8.09, 1.84 Hz, 1 H) 7.81 (dd, J=7.91, 2.39 Hz, 1 H) 7.97 (s, 1 H) 8.43 (d, J=1.84 Hz, 1 H) 8.48-8.51 (m, 2 H) 8.59 (s, 1 H) 8.88 (d, J=1.84 Hz, 1 H) 10.18 (s, 1 H) 10.51 (s, 1 H); MS (ESI+) m/z 586/588 (M+H)$^+$.

Example 232

4-(4-Amino-phenylsulfanyl)-N-(4-bromo-phenyl)-3-(7-ethyl-pyrido[2,3-d]pyrimidin-4-ylamino)-benzamide Example 233

3-Dimethylamino-N-[4-(4-hydroxy-phenylsulfanyl)-3-(7-isopropyl-pyrido[2,3-d]pyrimidin-4-ylamino)-phenyl]-benzamide Example 233a N-[3-Amino-4-(4-hydroxy-phenylsulfanyl)-phenyl]-3-dimethylamino-benzamide The title compound was prepared according to the procedures described in Example 115 substituting 3-trifluoromethylbenzoyl chloride with 3-N,N-dimethylbenzoyl chloride hydrochloride to provide the title compound (0.35 g, 40%).

Example 233b

3-Dimethylamino-N-[4-(4-hydroxy-phenylsulfanyl)-3-(7-isopropyl-pyrido[2,3-d]pyrimidin-4-ylamino)-phenyl]-benzamide A solution of the product of Example 8E (64 mg, 0.295 mmol), and the product of Example 233a (112 mg, 0.295 mmol) in acetic acid (1 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a tan solid as the title compound (18 mg, 12%). $^1$H NMR (300 MHz, DMSO-$d_6$) δ ppm: 1.28-1.39 (m, 6 H) 2.95 (s, 6 H) 3.19-3.28 (m, 1 H) 6.72 (d, J=8.46 Hz, 2 H) 6.88-6.97 (m, 1 H) 7.07 (d, J=8.82 Hz, 1 H) 7.19 (t, J=8.82 Hz, 4 H) 7.31 (t, J=8.09 Hz, 1 H) 7.57-7.72 (m, 2 H) 7.94 (d, J=1.84 Hz, 1 H) 8.56 (s, 1 H) 8.83 (d, J=8.46 Hz, 1 H) 9.72 (s, 1 H) 10.08 (s, 1 H) 10.26 (s, 1 H); MS (ESI+) m/z 551 (M+H)+, (ESI−) m/z 549 (M−H)−.

Example 234

4-(4-Amino-2,3-dimethyl-phenoxy)-N-(4-bromo-phenyl)-3-(7-isopropyl-pyrido[2,3-d]pyrimidin-4-ylamino)-benzamide The title compound was prepared according to the Boc procedure from Examples 10A-C substituting 4-amino-2,3-dimethylphenol for 4-aminophenol in step 320C. The product was then reacted with the product from Example 8E. The crude product was purified by HPLC with TFA to provide the title compound as a trifluoroacetic acid salt (0.06 g, 50%). $^1$H NMR (300 MHz, DMSO-$d_6$) δ ppm: 1.35 (d, J=6.62 Hz, 6 H), 2.00 (s, 3 H), 2.08 (s, 3 H), 3.13-3.36 (m, 1 H), 6.72 (d, J=8.46 Hz, 1 H), 6.79 (d, J=8.46 Hz, 1 H), 6.89 (d, J=8.46 Hz, 1 H), 7.55 (d, J=8.82 Hz, 2 H), 7.74 (d, J=9.19 Hz, 2 H), 7.87 (d, J=8.46 Hz, 1 H), 7.94 (dd, J=8.64, 2.39 Hz, 1 H), 8.12 (d, J=2.21 Hz, 1 H), 8.89 (s, 1 H), 8.99 (d, J=8.46 Hz, 1 H), 10.36 (s, 1 H), 11.44 (s, 1 H); MS (ESI+) m/z 597 (M+H)$^+$.

Example 235

N-[4-(4-Amino-phenylsulfanyl)-3-(7-ethyl-pyrido[2,3-d]pyrimidin-4-ylamino)-phenyl]-4-bromo-benzamide The product from Example 100 was prepared according to the Troc procedure described in Example 100 and the product was coupled with N′-(3-Cyano-6-ethyl-pyridin-2-yl)-N,N-dimethyl-formamidine. The crude product was purified by trituration in 1:1 ethyl acetate/hexane to give the title compound (30 mg, 78%). $^1$H NMR (300 MHz, DMSO-$d_6$) δ ppm: 1.33 (t, J=7.54 Hz, 3 H) 2.96 (q, J=7.35 Hz, 2 H) 5.45 (s, 2 H) 6.55 (m, 2 H) 6.94 (d, J=8.46 Hz, 1 H) 7.06 (m, 2 H) 7.57 (m, 2 H) 7.74 (m, 2 H) 7.90 (m, 3 H) 8.57 (s, 1 H) 8.83 (d, J=8.82 Hz, 1 H) 10.05 (s, 1 H) 10.41 (s, 1 H); MS (ESI+) m/z 571 573 (M+H)+.

Example 236

4-Bromo-N-[4-(4-dimethylamino-phenylsulfanyl)-3-(7-isopropyl-pyrido[2,3-d]pyrimidin-4-ylamino)-phenyl]-benzamide The product from Example 203 (200 mg, 0.34 mmol), formaldehyde (1 mL, 37%) and formic acid were mixed and heated at 110° C. for 15 minutes. The solvent was evaporated and the residue was purified by reverse phase preparative HPLC with TFA method to give the title compound as a trifluoroacetic acid salt (44 mg, 15%). $^1$H NMR (300 MHz, DMSO-$d_6$) δ ppm: 1.37 (d, J=6.99 Hz, 6 H) 2.84 (s, 6 H) 3.30 (m, 1 H) 6.50 (m, 2 H) 7.13 (m, 2 H) 7.20 (d, J=8.46 Hz, 1 H) 7.63 (dd, J=8.64, 2.39 Hz, 1 H) 7.76 (m, 2 H) 7.90 (m, 3 H) 7.99 (d, J=2.21 Hz, 1 H) 8.80 (s, 1 H) 9.00 (d, J=8.46 Hz, 1 H) 10.53 (s, 1 H) 11.67 (s, 1 H); MS (ESI+) m/z 613 615 (M+H)+.

Example 237

4-(4-Amino-phenylsulfanyl)-3-(7-isopropyl-pyrido[2,3-d]pyrimidin-4-ylamino)-N-phenethyl-benzamide To a solution of the product of Example 182 in tetrahydrofuran and water (1:1) was added 1 M NaOH (5 equiv). The solution was heated at 60° C. for 40 minutes, cooled, adjusted to pH 6 with 1N aqueous hydrochloric acid and extracted with ethyl acetate. The combined extracts were dried over magnesium sulfate, filtered and concentrated under vacuum. The crude product was purified by silica gel chromatography eluting with 4% methanol in dichloromethane to provide the title compound. $^1$H NMR (300 MHz, DMSO-$d_6$) δ ppm: 1.34 (d, J=6.62 Hz, 6 H) 2.82 (t, J=7.17 Hz, 2 H) 3.16-3.28 (m, 1 H) 3.45 (dt, 2 H) 5.58 (s, 2 H) 6.62 (d, J=8.46 Hz, 2 H) 6.81 (d, J=8.46 Hz, 1 H) 7.12 (d, J=8.46 Hz, 2 H) 7.16-7.33 (m, 5 H) 7.58-7.68 (m, 2 H) 7.80 (d, J=1.47 Hz, 1 H) 8.51 (t, J=5.15 Hz, 1 H) 8.57 (s, 1 H) 8.86 (d, J=8.46 Hz, 1 H) 10.10 (s, 1 H).

Example 238

N-[4-(4-Amino-phenylsulfanyl)-3-(7-isopropyl-pyrido[2,3-d]pyrimidin-4-ylamino)-phenyl]-4-fluoro-benzamide Example 238a 4-Fluoro-benzoyl chloride To a solution of 4-fluorobenzoic acid (5.0 g. 35.7 mmol) in dichloroethane (50 mL) was added oxalyl chloride (5.6 g, 44.6 mmol) drop wise. The reaction was stirred for 16 h. The excess oxalyl chloride and solvent were removed under reduced pressure. The residue was chased with benzene to give the desired product (5.4 g, 96%).

Example 238b

N-(4-Chloro-3-nitro-phenyl)-4-fluoro-benzamide

To a solution of 4-chloro-3-nitro-phenylamine (3.0 g, 17.4 mmol) in dichloromethane (60 mL) was added diisopropyl-ethylamine (4.5 g, 34.8 mmol). The solution was cooled to 0° C. and Example 238a (2.75 g, 17.4 mmol) was added. The ice bath was removed and the reaction was allowed to warm to room temperature over 16 h. The reaction was poured into water and extracted with ethyl acetate (2×). The combined organic phases were washed with water, brine, and dried over sodium sulfate, filtered and concentrated under vacuum giving the crude title compound. The residue was purified by silica gel chromatography eluting with hexanes/ethyl acetate/methanol (80:25:5) to give the desired product (3.5 g, 63%).

Example 238c

N-[4-(4-Amino-phenylsulfanyl)-3-nitro-phenyl]-4-fluoro-benzamide

To a solution of Example 238b (2.5 g, 8.5 mmol) in DMF (50 mL) was added $CsCO_3$ (5.5 g, 17.0 mmol), and 4-aminothiophenol (1.0 g, 8.5 mmol). The mixture was heated at 80° C. for 16 h. The reaction was cooled and poured into water. The aqueous phase was extracted with ethyl acetate (2×). The combined organic phases were washed with water, brine, and dried over sodium sulfate, filtered and concentrated under vacuum giving the title compound. The residue was purified by silica gel chromatography eluting with hexanes/ethyl acetate/methanol (60:30:10) to give the desired product (1.5 g, 46%).

Example 238d

{4-[4-(4-Fluoro-benzoylamino)-2-nitro-phenylsulfanyl]-phenyl}-carbamic acid 2,2,2-trichloro-ethyl ester To a solution of Example 238c (0.85 g, 2.2 mmol) in dichloromethane (40 mL) was added pyridine (0.35 g, 4.4 mmol) and 2,2,2-trichloroethyl chloroformate (0.58 g, 2.7 mmol). The mixture was stirred at room temperature for 16 h. The reaction was poured into water. The aqueous phase was extracted with ethyl acetate (2×). The combined organic phases were washed with water, 5% HCl, brine, and dried over sodium sulfate, filtered and concentrated under vacuum giving the title compound. The residue was purified by silica gel chromatography eluting with chloroform/methanol (90:10) to give the desired product (0.90 g, 75%).

Example 238e

{4-[2-Amino-4-(4-fluoro-benzoylamino)-phenylsulfanyl]-phenyl}-carbamic acid 2,2,2-trichloro-ethyl ester The product from Example 238d (0.88 g, 1.6 mmol) was reacted with Fe and $NH_4Cl$ as described for Example 9E to give the desired product (0.50 g, 60%).

Example 238f

N-[4-(4-Amino-phenylsulfanyl)-3-(7-isopropyl-pyrido[2,3-d]pyrimidin-4-ylamino)-phenyl]-4-fluoro-benzamide The product from Example 8E (80 mg, 0.37 mmol) was reacted with Example 238e (195 mg, 0.37 mmol) in acetic acid (10 mL) at 125° C. in a sealed tube for 5 minute giving the crude title compound which was purified by HPLC with TFA providing the product as the trifluoroacetic acid (15 mg, 7.8%). $^1H$ NMR (300 MHz, DMSO-$d_6$) δ ppm: 1.34 (d, J=6.99 Hz, 6 H) 3.28 (q, 1 H) 7.00 (dd, J=8.46, 2.21 Hz, 1 H) 7.16 (d, J=8.46 Hz, 2 H) 7.30-7.40 (m, 4 H) 7.45 (d, J=1.84 Hz, 1 H) 7.61 (d, J=8.82 Hz, 2 H) 7.86 (d, J=8.82 Hz, 1 H) 8.02 (dd, J=8.82, 5.52 Hz, 2 H) 8.88 (s, 1 H) 9.01 (d, J=8.82 Hz, 1 H) 10.22 (s, 1H); MS (ESI+) m/z 525 (M+H)+.

Example 239

{4-[4-(3-Dimethylamino-benzoylamino)-2-(7-methyl-pyrido[2,3-d]pyrimidin-4-ylamino)-phenylsulfanyl]-phenyl}-carbamic acid 2,2-dichloro-ethyl ester

Example 239a

3-Dimethylamino-benzoyl chloride hydrochloride salt

To a solution of 3-(dimethylamino) benzoic acid (5.0 g. 30.0 mmol) in dichloroethane (50 mL) was added oxalyl chloride (5.6 g, 44.6 mmol) drop wise followed by catalytic amount of DMF. The reaction was stirred for 16 h. The excess oxalyl chloride and solvent were removed under reduced pressure. The residue was chased with benzene to give the desired product (6.1 g, 92%).

Example 239b

N-(4-Chloro-3-nitro-phenyl)-3-dimethylamino-benzamide

To a solution of 4-chloro-3-nitro-phenylamine (5.0 g, 28.0 mmol) in dichloromethane (60 mL) was added diisopropylethylamine (7.2 g, 56.0 mmol). The solution was cooled to 0° C. and Example 239a (5.0 g, 28.0 mmol) was added. The ice bath was removed and the reaction was allowed to warm to room temperature over 16 h. The reaction was poured into water and extracted with ethyl acetate (2×). The combined organic phases were washed with water, brine, and dried over sodium sulfate filtered and concentrated under vacuum giving the title compound. The residue was purified by silica gel chromatography eluting with hexanes/ethyl acetate/methanol (80:15:5) to give the desired product (5.0 g, 53%).

Example 239c

N-[4-(4-Amino-phenylsulfanyl)-3-nitro-phenyl]-3-dimethylamino-benzamide

To a solution of Example 239b (5.0 g, 15.6 mmol) in DMF (50 mL) was added $K_2CO_3$ (4.3 g, 17.0 mmol) and 4-aminothiophenol (1.9 g, 8.5 mmol). The mixture was heated at 65° C. for 16 h. The reaction was cooled and poured into water. The aqueous phase was extracted with ethyl acetate (2×). The combined organic phases were washed with water, brine, and dried over sodium sulfate, filtered and concentrated under vacuum giving the title compound. The residue was purified by silica gel chromatography eluting with hexanes/ethyl acetate/methanol (50:40:10) to give the desired product (3.4 g, 53%).

Example 239d

{4-[4-(3-Dimethylamino-benzoylamino)-2-nitro-phenylsulfanyl]-phenyl}-carbamic acid 2,2-dichloro-ethyl ester To a solution of Example 239c (2.8 g, 6.8 mmol) in dichloromethane (40 mL) was added pyridine (1.1 g, 13.7 mmol) and 2,2,2-trichloroethyl chloroformate (1.7 g, 2.8 mmol). The mixture was stirred at room temperature for 72 h. The reaction was poured into water. The aqueous phase was extracted with ethyl acetate (2×). The combined organic phases were washed with water, brine, and dried over sodium sulfate, filtered and concentrated under vacuum giving the title compound. The residue was purified by silica gel chromatography eluting with hexane/ethyl acetate/methanol (80:15:5) to give the desired product (2.0 g, 53%).

Example 239e

{4-[2-Amino-4-(3-dimethylamino-benzoylamino)-phenylsulfanyl]-phenyl}-carbamic acid 2,2-dichloro-ethyl ester The product from Example 239d (2.0 g, 3.6 mmol) was reacted with Fe and $NH_4Cl$ as described for Example 9E to give the desired product (1.1 g, 58%).

Example 239f

{4-[4-(3-Dimethylamino-benzoylamino)-2-(7-methyl-pyrido[2,3-d]pyrimidin-4-ylamino)-phenylsulfanyl]-phenyl}-carbamic acid 2,2-dichloro-ethyl ester The product from Example 9B (90 mg, 0.48 mmol) was reacted with Example 239e (248 mg, 0.48 mmol) in acetic acid (10 mL) at 125° C. in a sealed tube for 5 minute giving the crude title compound which was purified by HPLC with TFA providing the product as the trifluoroacetic acid (40 mg, 13%). $^1$H NMR (300 MHz, DMSO-d$_6$) δ ppm: 2.72 (s, 3 H) 2.96 (s, 6 H) 4.54 (d, J=5.15 Hz, 2 H) 6.51 (t, J=5.15 Hz, 1 H) 6.95 (dd, J=7.35, 1.84 Hz, 1 H) 7.18-7.24 (m, 4 H) 7.30-7.40 (m, 4 H) 7.71 (dd, J=8.64, 2.39 Hz, 1 H) 7.85 (d, J=8.82 Hz, 1 H) 8.09 (d, J=2.57 Hz, 1 H) 8.87 (s, 1 H) 8.93 (d, J=8.46 Hz, 1 H) 10.05 (s, 1 H) 10.43 (s, 1 H); MS (ESI+) m/z 662 (M+H)+.

Example 240

Thiophene-2-carboxylic acid [4-(4-hydroxy-phenylsulfanyl)-3-(7-isopropyl-pyrido[2,3-d]pyrimidin-4-ylamino)-phenyl]-amide

Example 240a

Thiophene-2-carboxylic acid (4-fluoro-3-nitro-phenyl)-amide

The title compound was synthesized from 4-fluoro-3-nitro-phenylamine (2.00 g, 12.81 mmol) dissolved in THF (25 ml) and Hunig's base (3.312 g, 25.62 mmol) to which was added thiophene-2-carbonyl chloride (1.878 g, 12.81 mmol) drop wise over 10 minutes. Reaction mixture was stirred at room temperature for 1 hr at which time water was added and the title compound was collected by filtration providing the title compound (3.25 g, 95%).

Example 240b

Thiophene-2-carboxylic acid [4-(4-hydroxy-phenylsulfanyl)-3-nitro-phenyl]-amide

The product of Example 240a (1.50 g, 5.63 mmol) was dissolved in DMF to which K$_2$CO$_3$ (1.55 g, 11.27 mmol), and 4-mercapto-phenol (711 mg, 5.634 mmol) were added. The reaction mixture was then heated to 80° C. for 2 hrs. At this point the reaction mixture was cooled to room temperature and diluted with water which was then extracted with ethyl acetate to isolate the desired compound (1.66 g, 79%).

Example 240c

Thiophene-2-carboxylic acid [3-amino-4-(4-hydroxy-phenylsulfanyl)-phenyl]-amide

The product from Example 240b was reduced with Fe and NH4Cl following the procedure from Example 9E to provide the title compound (800 mg, 52%).

Example 240d

Thiophene-2-carboxylic acid [4-(4-hydroxy-phenylsulfanyl)-3-(7-isopropyl-pyrido[2,3-d]pyrimidin-4-ylamino)-phenyl]-amide The product of Example 8E (100 mg, 0.462 mmol) and of Example 240c (158 mg, 0.462 mmol) were dissolved in HOAc and placed in a preheated 120° C. oil bath for 10 minutes. Reaction mixture was then cooled to room temperature; the solvent removed under vacuum and the crude oil was purified by HPLC with TFA providing the product as a trifluoroacetic acid salt (32 mg, 13%). $^1$H NMR (300 MHz, DMSO-d$_6$) δ ppm: 1.36 (d, J=6.99 Hz, 6 H), 6.70 (ddd, J=9.19, 2.94, 2.57 Hz, 2 H), 7.13-7.20 (m, 3 H), 7.20-7.25 (m, 1 H), 7.61 (dd, J=8.64, 2.39 Hz, 1 H), 7.82-7.90 (m, 2 H), 7.94 (s, 1 H), 8.02 (d, J=2.57 Hz, 1 H), 8.78 (s, 1 H), 8.96 (d, J=8.82 Hz, 1 H), 9.78 (s, 2 H), 10.43 (s, 1 H);

MS (ESI+) m/z 514 (M+TFA+H)+; (ESI−) m/z 512 (M+TFA−H)−.

Example 241

5-Bromo-thiophene-2-carboxylic acid [4-(4-hydroxy-phenylsulfanyl)-3-(7-isopropyl-pyrido[2,3-d]pyrimidin-4-ylamino)-phenyl]-amide

Example 241a

5-Bromo-thiophene-2-carbonyl chloride

5-Bromo-thiophene-2-carboxylic acid (2.00 g, 10.47 mmol) was dissolved in DCM (10 mL) to which was added oxalyl chloride (1.99 g, 15.71 mmol) and a catalytic amount of DMF (100 μL). This reaction mixture was stirred at room temperature for 1 hr at which time the solvent was removed under vacuum and taken forward immediately.

Example 241b

5-Bromo-thiophene-2-carboxylic acid (4-fluoro-3-nitro-phenyl)-amide

The product from Example 241a (2.178 g, 10.25 mmol) was reacted with 4-fluoro-3-nitro-phenylamine (1.60 g, 10.25 mmol) dissolved in THF (25 mL) and Hunig's base (2.484 g, 19.22 mmol). Reaction mixture was stirred at room temperature for 1 hr at which time water was added and the title compound was collected by filtration (2.00 g, 78%).

Example 241c

5-Bromo-thiophene-2-carboxylic acid [4-(4-hydroxy-phenylsulfanyl)-3-nitro-phenyl]-amide The product of Example 241b (1.50 g, 4.34 mmol) was dissolved in DMF to which K$_2$CO$_3$ (1.20 g, 8.69 mmol), and 4-mercapto-phenol (548 mg, 4.34 mmol) were added. The reaction mixture was then heated to 80° C. for 2 hrs. At this point the reaction mixture was cooled to room temperature and diluted with water which was then extracted with ethyl acetate to isolate the desired compound (1.54 g, 78%).

Example 241d

5-Bromo-thiophene-2-carboxylic acid [3-amino-4-(4-hydroxy-phenylsulfanyl)-phenyl]-amide The product from Example 241 c was reduced with Fe and NH4Cl following the procedure from Example 9E to provide the title compound (550 mg, 27%).

Example 241e

5-Bromo-thiophene-2-carboxylic acid [4-(4-hydroxy-phenylsulfanyl)-3-(7-isopropyl-pyrido[2,3-d]pyrimidin-4-ylamino)-phenyl]-amide The product of Example 8E (100 mg, 0.462 mmol) and of Example 241d (195 mg, 0.462 mmol) were dissolved in HOAc and placed in a preheated 120° C. oil bath for 10 minutes. Reaction mixture was then cooled to room temperature, the solvent removed under vacuum and the crude oil was purified by HPLC with TFA providing the product as a trifluoroacetic acid salt (35 mg, 14%). $^1$H NMR (300 MHz, DMSO-$d_6$) δ ppm: 1.35 (d, J=6.99 Hz, 6 H), 6.65-6.73 (m, 2 H), 7.08-7.20 (m, 3 H), 7.38 (d, J=4.04 Hz, 1 H), 7.57 (dd, J=8.64, 2.39 Hz, 1 H), 7.79-7.87 (m, 2 H), 7.90 (s, 1 H), 8.75 (s, 1 H), 8.94 (d, J=8.46 Hz, 1 H), 9.79 (s, 1 H), 10.48 (s, 1 H); MS (ESI+) m/z 592 (M+TFA+H)+; (ESI−) m/z 590 (M+TFA−H)−.

Example 242

N-[4-(4-tert-Butyl-phenylsulfanyl)-3-(7-isopropyl-pyrido[2,3-d]pyrimidin-4-ylamino)-phenyl]-3-trifluoromethyl-benzamide

Example 242a

N-(4-Fluoro-3-nitro-phenyl)-3-trifluoromethyl-benzamide

The title compound was synthesized from 4-fluoro-3-nitro-phenylamine (2.00 g, 12.81 mmol) dissolved in THF (25 ml) and Hunig's base (3.312 g, 25.62 mmol) to which was added 3-trifluoromethyl-benzoyl chloride (2.672 g, 12.81 mmol) drop wise over 10 minutes. Reaction mixture was stirred at room temperature for 1 hr at which time water was added and the title compound was collected by filtration (3.11 g, 97%).

Example 242b

N-[4-(4-tert-Butyl-phenylsulfanyl)-3-nitro-phenyl]-3-trifluoromethyl-benzamide

The product from Example 242a (600 mg, 1.828 mmol) was dissolved in DMF (20 ml) to which $K_2CO_3$ (505 mg, 3.656 mmol), and 4-tert-Butyl-benzenethiol (304 mg, 1.828 mmol) were added. This reaction mixture was then heated to 80° C. for 1 hr. At this time the reaction mixture was cooled to room temperature, diluted with water, and the title compound collected by filtration (311 mg, 35%)

Example 242c

N-[3-Amino-4-(4-tert-butyl-phenylsulfanyl)-phenyl]-3-trifluoromethyl-benzamide

The product from Example 242b was reduced with Fe and $NH_4Cl$ following the procedure from Example 9E to give the title compound (206 mg, 70%).

Example 242d

N-[4-(4-tert-Butyl-phenylsulfanyl)-3-(7-isopropyl-pyrido[2,3-d]pyrimidin-4-ylamino)-phenyl]-3-trifluoromethyl-benzamide The product of Example 8E (100 mg, 0.462 mmol) and of Example 242c (206 mg, 0.462 mmol) were dissolved in HOAc and placed in a preheated 120° C. oil bath for 10 minutes. Reaction mixture was then cooled to room temperature and the solvent removed under vacuum. The crude oil was purified by HPLC with TFA providing the product as a trifluoroacetic acid salt (20 mg, 14%). $^1$H NMR (300 MHz, DMSO-$d_6$) δ ppm: 1.09-1.17 (m, 9 H), 1.34 (d, J=6.99 Hz, 6 H), 7.08-7.18 (m, 4 H), 7.54 (d, J=8.46 Hz, 1 H), 7.73-7.85 (m, 3 H), 8.00 (d, J=7.72 Hz, 1 H), 8.08 (s, 1 H), 8.24-8.32 (m, 2 H), 8.72 (s, 1 H), 8.87 (d, J=8.46 Hz, 1 H), 10.75 (s, 1 H); MS (ESI+) m/z 616 (M+TFA+H)+; (ESI−) m/z 614 (M+TFA−H)−.

Example 243

N-[3-(7-Isopropyl-pyrido[2,3-d]pyrimidin-4-ylamino)-4-p-tolylsulfanyl-phenyl]-3-trifluoromethyl-benzamide

Example 243a

N-(3-Nitro-4-p-tolylsulfanyl-phenyl)-3-trifluoromethyl-benzamide

The product from Example 242b (600 mg, 1.828 mmol) was dissolved in DMF (20 mL) to which $K_2CO_3$ (505 mg, 3.656 mmol), and 4-methyl-benzenethiol (227 mg, 1.828 mmol) were added. This reaction mixture was then heated to 80° C. for 1 hr. At this time the reaction mixture was cooled to room temperature, diluted with water, and the title compound collected by filtration (611 mg, 77

Example 243b

N-(3-Amino-4-p-tolylsulfanyl-phenyl)-3-trifluoromethyl-benzamide

The product from Example 243a was reduced with Fe and $NH_4Cl$ following the procedure from Example 9E to give the title compound (420 mg, 73%).

Example 243c

N-[3-(7-Isopropyl-pyrido[2,3-d]pyrimidin-4-ylamino)-4-p-tolylsulfanyl-phenyl]-3-trifluoromethyl-benzamide The product of Example 8E (100 mg, 0.462 mmol) and of Example 243b (186 mg, 0.462 mmol) were dissolved in HOAc and placed in a preheated 120° C. oil bath for 10 minutes. Reaction mixture was then cooled to room temperature and the solvent removed under vacuum. The crude oil was purified by HPLC with TFA providing the product as a trifluoroacetic acid salt (10 mg, 3%). $^1$H NMR (300 MHz, DMSO-$d_6$) δ ppm: 1.35 (d, J=6.99 Hz, 6 H), 2.16-2.20 (m, 3 H), 6.96-7.02 (m, 2 H), 7.10 (d, J=8.46 Hz, 2 H), 7.42 (d, J=8.46 Hz, 1 H), 7.72 (dd, J=8.46, 2.21 Hz, 1 H), 7.80 (t, J=7.91 Hz, 2 H), 7.99 (d, J=8.09 Hz, 1 H), 8.08 (s, 1 H), 8.22-8.30 (m, 2 H), 8.72 (s, 1 H), 8.89 (d, J=9.56 Hz, 1 H), 10.73 (s, 1 H); MS (ESI+) m/z 574 (M+TFA+H)+; (ESI−) m/z 572 (M+TFA−H)−.

Example 244

4-(4-Amino-3-methyl-phenoxy)-N-(4-bromo-phenyl)-3-(7-isopropyl-pyrido[2,3-d]pyrimidin-4-ylamino)-benzamide The title compound was prepared according to the Boc procedure from Examples 10A-C and the product was coupled with the product form Example 100. The crude product was purified by HPLC with TFA to provide the title compound as a trifluoroacetic acid salt (0.09 g, 44%). $^1$H NMR (300 MHz, DMSO-d$_6$) δ ppm: 1.34 (d, J=6.62 Hz, 6 H), 2.09 (s, 3 H), 3.12-3.39 (m, 1 H), 6.72-6.90 (m, 3 H), 6.99 (d, J=8.46 Hz, 1 H), 7.49-7.60 (m, 2 H), 7.71-7.78 (m, 2 H), 7.86 (d, J=8.46 Hz, 1 H), 7.98 (dd, J=8.46, 2.21 Hz, 1 H), 8.12 (d, J=1.84 Hz, 1 H), 8.88 (s, 1 H), 8.96 (d, J=8.46 Hz, 1 H), 10.37 (s, 1 H), 11.42 (s, 1 H); MS (ESI+) m/z 583 (M+H)+.

Example 245

{4-[4-(3-Dimethylamino-benzoylamino)-2-(7-isopropyl-pyrido[2,3-d]pyrimidin-4-ylamino)-phenylsulfanyl]-phenyl}-carbamic acid 2,2-dichloro-ethyl ester The product from Example 8E (80 mg, 0.37 mmol) was reacted with the product from Example 100 using 3-dimethylaminobenzoic acid in place of 3-bromobenzoic acid in a sealed tube for 5 minute giving the crude title compound which was purified by HPLC with TFA providing the product as the trifluoroacetic acid (30 mg, 10%). $^1$H NMR (300 MHz, DMSO-d$_6$) δ ppm: 1.35 (d, J=6.99 Hz, 6 H) 2.96 (s, 6 H) 3.26 (q, 1 H) 4.53 (d, J=5.15 Hz, 2 H) 6.50 (t, J=5.15 Hz, 1 H) 6.94 (dd, J=7.54, 2.02 Hz, 1 H) 7.18-7.23 (m, 4 H) 7.29-7.40 (m, 4 H) 7.70 (dd, J=8.64, 2.39 Hz, 1 H) 7.82 (d, J=8.46 Hz, 1 H) 8.06 (s, 1 H) 8.77 (s, 1 H) 8.91 (d, J=8.46 Hz, 1 H) 10.05 (s, 1 H) 10.39 (s, 1 H); MS (ESI+) m/z 690 (M+H)+.

Example 246

4-(4-Amino-2-methyl-phenoxy)-N-(4-bromo-phenyl)-3-(7-isopropyl-pyrido[2,3-d]pyrimidin-4-ylamino)-benzamide The title compounds was prepared according to the Boc procedure from Examples 10A-C substituting 4-amino-2-methylphenol for 4-aminophenol in step 320C. The product was then reacted with the product from Example 8E. The crude product was purified by HPLC with TFA to provide the title compound as a trifluoroacetic acid salt (0.09 g, 44%). $^1$H NMR (300 MHz, DMSO-d$_6$) δ ppm: 1.35 (d, J=6.62 Hz, 6 H), 2.00 (s, 3 H), 3.15-3.39 (m, 1 H), 6.60-6.73 (m, 2 H), 6.76 (d, J=8.82 Hz, 1 H), 6.85 (d, J=8.46 Hz, 1 H), 7.44-7.65 (m, 2 H), 7.69-7.80 (m, 2 H), 7.87 (d, J=8.46 Hz, 1 H), 7.95 (dd, J=8.46, 2.21 Hz, 1 H), 8.12 (d, J=2.21 Hz, 1 H), 8.88 (s, 1 H), 9.00 (d, J=8.82 Hz, 1 H), 10.36 (s, 1 H), 11.41 (s, 1 H); MS (ESI+) m/z 583 (M+H)$^+$.

Example 247

N-[4-(4-Benzyloxy-phenoxy)-3-(7-isopropyl-pyrido [2,3-d]pyrimidin-4-ylamino)-phenyl]-4-bromo-benzamide Example 247a 4-Bromo-N-(4-fluoro-3-nitro-phenyl)-benzamide A mixture of 4-Fluoro-3-nitro aniline (0.5 g, 3.2 mmol), 4-bromobenzoyl chloride (0.702 g, 3.2 mmol), diisopropylethylamine (0.56 ml, 3.2 mmol) in dichloromethane (10 mL) was stirred at room temperature for 2 hr. The mixture was diluted with dichloromethane (50 mL) and washed with 10% sodium bicarbonate and 10% sodium chloride, then dried over anhydrous sodium sulfate, filtered and concentrated under vacuum giving the title compound as a yellow solid (0.89 g, 82%).

Example 247b

N-[4-(4-Benzyloxy-phenoxy)-3-nitro-phenyl]-4-bromo-benzamide

The product from Example 247a (0.89 g, 2.63 mmol) was mixed with cesium carbonate (0.85 g, 2.63 mmol) and 4-benzyloxyphenol (0.53 g, 2.63 mmol) in DMF (10 mL) and stirred at room temperature a total of sixty hours. The reaction mixture was diluted with ethyl acetate (100 ml) and treated with 2N HCl (20 ml). The organic layer was separated and washed with 2N NaOH, 2, 10% sodium chloride and dried over anhydrous sodium sulfate. The drying agent was filtered and the solvent was evaporated under vacuum leaving the title compound as a yellow solid (118 g, 86%).

Example 247c

N-[3-Amino-4-(4-benzyloxy-phenoxy)-phenyl]-4-bromo-benzamide

The product from Example 247b (1.18 g, 2.27 mmol), iron powder (0.51 g, 9.1 mmol) and ammonium chloride (0.14 g, 2.5 mmol) in a methanol (10 ml), THF (10 ml) and water (5 mL) solution was heated at reflux for 1.5 hr. The resultant mixture was filtered, rinsed with hot methanol (50 ml) and concentrated under vacuum to an oily residue. The residue was diluted with ethyl acetate (100 ml) and washed with water and 10% sodium chloride, then dried over anhydrous sodium sulfate. The drying agent was filtered and the organic solvent was removed under vacuum providing the title compound (0.81 g, 73%).

Example 247d

N-[4-(4-Benzyloxy-phenylsulfanyl)-3-(7-isopropyl-pyrido[2,3-d]pyrimidin-4-ylamino)-phenyl]-4-bromo-benzamide A solution of the product of Example 8E (73.5 mg, 0.339 mmol), and the product of Example 247c (166 mg, 0.339 mmol) in acetic acid (2 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 CH$_2$Cl$_2$/MeOH to 97:3 CH$_2$Cl$_2$/MeOH. The fractions containing product were pooled, concentrated under vacuum to give the title compound as a tan solid (160 mg, 69%). $^1$H NMR (300 MHz, DMSO-d$_6$) δ ppm: 1.24-1.36 (m, 6 H) 3.13-3.24 (m, 1 H) 4.98 (s, 2 H) 6.89 (s, 4 H) 6.96 (d, J=9.19 Hz, 1 H) 7.30-7.45 (m, 5 H) 7.54 (d, J=8.82 Hz, 1 H) 7.65 dd, J=9.01, 2.02 Hz, 1 H) 7.76 (d, J=8.46 Hz, 2 H) 7.92 (d, J=8.46 Hz, 2 H) 8.04 (d, J=1.84 Hz, 1 H) 8.56 (s, 1 H) 8.74 (d, J=8.46 Hz, 1 H) 9.89 (s, 1 H) 10.41 (s, 1 H); MS (ESI+) m/z 661 (M+H)+, (ESI−) m/z 659 (M−H)−.

Example 248

N-[4-(4-Benzyloxy-phenoxy)-3-(7-isopropyl-pyrido[2,3-d]pyrimidin-4-ylamino)-phenyl]-3-bromo-benzamide

Example 248a

N-[3-Amino-4-(4-benzyloxy-phenoxy)-phenyl]-3-bromo-benzamide

The title compound was prepared according to the procedures described in Examples 247a, 247b, 247c substituting 4-bromo benzoyl chloride with 3-bromobenzoyl chloride to provide the title compound (0.62 g, 66%).

Example 248b

N-[4-(4-Benzyloxy-phenylsulfanyl)-3-(7-isopropyl-pyrido[2,3-d]pyrimidin-4-ylamino)-phenyl]-3-bromo-benzamide A solution of the product of Example 8E (63.8 mg, 0.294 mmol), and the product of Example 248a (144 mg, 0.294 mmol) in acetic acid (2 mL) was stirred in an oil bath preheated to 130° C. for 10 minutes. The mixture was then cooled to room temperature, the acetic acid removed under vacuum, and the resultant residue purified by silica gel chromatography eluting with a gradient beginning with 99:1 $CH_2Cl_2$/MeOH to 97:3 $CH_2Cl_2$/MeOH. The fractions containing product were pooled, concentrated under vacuum to a yellow solid as the title compound (150 mg, 75%). $^1$H NMR (300 MHz, DMSO-$d_6$) δ ppm: 1.30 (d, J=6.99 Hz, 6 H) 3.11-3.26 (m, 1 H) 4.98 (s, 2 H) 6.89 (s, 4 H) 6.96 (d, J=8.82 Hz, 1 H) 7.28-7.46 (m, 6 H) 7.46-7.60 (m, 2 H) 7.65 (dd, J=8.82, 2.57 Hz, 1 H) 7.81 (d, J=6.99 Hz, 1 H) 7.97 (d, J=8.09 Hz, 1 H) 8.04 (d, J=2.57 Hz, 1 H) 8.16 (s, 1 H) 8.56 (s, 1 H) 8.74 (d, J=8.82 Hz, 1 H) 9.89 (s, 1 H) 10.44 (s, 1 H); MS (ESI+) m/z 661 (M+H)+, (ESI−) m/z 659 (M−H)−.

Example 249

N-(4-Bromo-phenyl)-3-(7-isopropyl-pyrido[2,3-d]pyrimidin-4-ylamino)-4-(4-propylamino-phenoxy)-benzamide The product from Example 10 (57 mg, 0.07 mmol) and sodium triacetoxyborohydride (32 mg, 0.15 mmol) in dichloromethane/methanol (2 mL, 9:1) was added propionaldehyde (7.3 μL, 0.1 mmol). The mixture was stirred at room temperature for 2 hours and evaporated. The residue was purified by reverse phase preparative HPLC with AA method to give the title compound (10 mg, 23%). $^1$H NMR (300 MHz, DMSO-$d_6$) δ ppm: 0.93 (t, J=7.35 Hz, 3 H) 1.32 (d, J=6.62 Hz, 6 H) 1.54 (m, 2 H) 2.92 (m, 2 H) 3.21 (m, 1 H) 5.55 (t, J=5.52 Hz, 1 H) 6.55 (m, 2 H) 6.84 (m, 3 H) 7.52 (m, 2 H) 7.60 (d, J=8.82 Hz, 1 H) 7.76 (m, 2 H) 7.85 (dd, J=8.82, 2.21 Hz, 1 H) 8.16 (d, J=2.21 Hz, 1 H) 8.62 (s, 1 H) 8.83 (d, J=8.46 Hz, 1 H) 10.00 (s, 1 H) 10.29 (s, 1 H); MS (ESI+) m/z 611 613 (M+H)+.

Example 250

N-(4-Bromo-phenyl)-4-(4-dipropylamino-phenoxy)-3-(7-isopropyl-pyrido[2,3-d]pyrimidin-4-ylamino)-benzamide The title compound (6 mg, 13%) was obtained during the purification of the mixture from Example 249. $^1$H NMR (300 MHz, DMSO-$d_6$) δ ppm: 0.86 (t, J=7.35 Hz, 6 H) 1.32 (d, J=6.99 Hz, 6 H) 1.48 (m, 4 H) 3.16 (m, 5 H) 6.60 (d, J=9.19 Hz, 2 H) 6.89 (m, 3 H) 7.53 (m, 2 H) 7.58 (d, J=8.46 Hz, 1 H) 7.76 (m, 2 H) 7.86 (dd, J=8.46, 2.21 Hz, 1 H) 8.16 (d, J=1.84 Hz, 1 H) 8.61 (s, 1 H) 8.80 (d, J=8.46 Hz, 1 H) 9.98 (s, 1 H) 10.30 (s, 1 H); MS (ESI+) m/z 653 655 (M+H)+.

Example 251

N-(4-Bromo-phenyl)-3-(7-isopropyl-pyrido[2,3-d]pyrimidin-4-ylamino)-4-[4-(7-isopropyl-pyrido[2,3-d]pyrimidin-4-ylamino)-2-methyl-phenoxy]-benzamide The title compound was prepared from the product of Example 246 and the product from Example 8E as in Example 101. The crude product was purified by HPLC with TFA to provide the title compound as a trifluoroacetic acid salt (0.02 g, 7%). $^1$H NMR (300 MHz, DMSO-$d_6$) δ ppm: 1.33 (d, J=6.99 Hz, 6 H), 1.35 (d, J=6.99 Hz, 6 H), 2.16 (s, 3 H), 3.19-3.36 (m, 2 H), 6.93 (d, J=8.82 Hz, 1 H), 7.12 (d, J=8.46 Hz, 1 H), 7.50-7.60 (m, 2 H), 7.61-7.69 (m, 2 H), 7.72-7.80 (m, 2 H), 7.81-7.92 (m, 2 H), 8.01 (dd, J=8.46, 2.21 Hz, 1 H), 8.17 (d, J=1.84 Hz, 1 H), 8.85-8.91 (m, 2 H), 8.97 (d, J=8.82 Hz, 1 H), 9.01 (d, J=8.82 Hz, 1 H), 10.40 (s, 1 H), 11.07 (s, 1 H), 11.25 (s, 1 H); MS (ESI+) m/z 754 (M+H)+.

Example 252

N-[4-(4-Amino-phenoxy)-3-(7-isopropyl-pyrido[2,3-d]pyrimidin-4-ylamino)-phenyl]-benzamide

Example 252a

[4-(4-Benzoylamino-2-nitrophenoxy)-phenyl]carbamic acid tert-butyl ester

A mixture of N-(4-fluoro-3-nitrophenyl)benzamide (1.00 g, 3.8 mmol), N-Boc-4-hydroxyaniline (0.83 g, 3.8 mmol) and 85% KOH (0.51 g, 7.7 mmol) in DMSO (20 mL) was heated at 80° C. for 1 hour, and then poured into $H_2O$ (100 ml) under stirring. The resulting oily crystal was extracted with EtOAc. The extract was washed with $H_2O$ (3 times) and brine, dried over $MgSO_4$, filtered and concentrated under vacuum giving the crude title compound, which was purified by washing with i-$Pr_2O$ to give the desired compound as yellow crystals (1.59 g, 92%).

Example 252b

[4-(2-Amino-4-benzoylaminophenoxy)phenyl]carbamic acid tert-butyl ester

The product from Example 252a (1.50 g, 3.3 mmol), Fe powder (0.78 g, 13.4 mmol) and $NH_4Cl$ (0.71 g, 13.4 mmol) in a mixture of THF (7.5 mL) and $H_2O$ (3 mL) was gradually heated to reflux and refluxed for 19 hours. The reaction mixture was portioned between EtOAc and 10% $NaHCO_3$ and then filtered (through celite). The organic layer was washed with brine, dried over $MgSO_4$, filtered and concentrated under vacuum giving the crude title compound which was purified by column chromatography on silica gel eluting with 1:1 n-hexane/EtOAc to give the title compound as a yellow foam (1.32 g, 94%).

Example 252c

[4-[4-Benzoylamino-2-(7-isopropylpyrido[2,3-d] pyrimidin-4-ylamino)phenoxy]phenyl]carbamic acid tert-butyl ester The product from Example 252b (0.15 g, 0.7 mmol) and the product of Example 8E (0.7 mmol) in HOAc (3 mL) was heated at 120° C. for 5 minutes under $N_2$. The reaction mixture was portioned between i-$Pr_2O$ and 10% $NaHCO_3$ under stirring. The resulting crystal was collected by filtration, washed with $H_2O$ and i-$Pr_2O$, and dried in vacuum to give the title compound as slightly brown crystals (0.50 g, 100%).

Example 252d

N-[4-(4-Amino-phenoxy)-3-(7-isopropyl-pyrido[2,3-d]pyrimidin-4-ylamino)-phenyl]-benzamide The title compound was produced by the procedure of Example 10E substituting the product of Example 252c for the product of Example 10D.

Example 253

Pyridine-2-carboxylic acid [4-(4-amino-phenoxy)-3-(7-isopropyl-pyrido[2,3-d]pyrimidin-4-ylamino)-phenyl]-amide

Example 253a

[4-[2-Nitro-4-[(pyridine-2-carbonyl)amino]phenoxy] phenyl]carbamic acid tert-butyl ester The title compound was obtained following the procedure for Example 252a substituting pyridine-2-carboxylic acid (4-fluoro-3-nitro-phenyl)-amide for N-(4-fluoro-3-nitrophenyl)benzamide to provide the title compound as pale yellow crystals (94%).

Example 253b

[4-[2-Amino-4-[(pyridine-2-carbonyl)amino]phenoxy]phenyl]carbamic acid tert-butyl ester The product form Example 253a was reacted following the procedure in Example 252b to provide the title compound as slightly brown crystals (76%).

Example 253c

[4-[2-(7-Isopropyl-pyrido[2,3-d]pyrimidin-4-ylamino)-4-[(pyridine-2-carbonyl)amino]phenoxy] phenyl]carbamic acid tert-butyl ester The product from Example 253b was reacted following the procedure in Example 252c to provide the title compound as slightly brown crystals (88%).

Example 253d

Pyridine-2-carboxylic acid [4-(4-amino-phenoxy)-3-(7-isopropyl-pyrido[2,3-d]pyrimidin-4-ylamino)-phenyl]-amide The product from Example 253c (350 mg, 0.59 mmol) was reacted with 4M HCl/1,4-dioxane for 1 hour at room temperature. The solvent was removed under vacuum and the crude product was washed with EtOAc providing the title compound (150 mg, 50%). $^1$H NMR (300 MHz, DMSO-$d_6$) δ ppm: 1.32 (d, J=6.7 Hz, 6H), 3.20 (septet, J=6.7 Hz, 1H), 4.91 (br-s, 2H), 6.50 (d, J=8.1 Hz, 2H), 6.71 (d, J=8.1 Hz, 2H), 6.81 (d, J=8.9 Hz, 1H), 7.57 (d, J=8.4 Hz, 1H), 7.62-7.77 (m, 2H), 8.01-8.22 (m, 3H), 8.59 (s, 1H), 8.75 (d, J=3.7 Hz, 1H), 8.82 (d, J=8.8 Hz, 1H), 9.90 (s, 1H), 10.69 (s, 1H); MS (ESI−) m/z 490 (M−H)−, (ESI+) m/z 492 (M+H)+.

Example 254

N-[4-(4-Amino-phenoxy)-3-(7-isopropyl-pyrido[2,3-d]pyrimidin-4-ylamino)-phenyl]-3,5-dichloro-benzamide

Example 254a 3,5-Dichloro-N-(4-fluoro-3-nitro-phenyl)-benzamide

To a solution of 4-fluoro-3-nitro-phenylamine (3.0 g, 20 mmol) in dichloromethane (60 mL) was added pyridine (3.2 g, 40.0 mmol). The solution was cooled to 0° C. and 3,5-dichlorobenzoyl chloride (4.0 g, 20.0 mmol) was added. The ice bath was removed and the reaction was allowed to warm to room temperature over 18 h. The reaction was poured into water and a precipitate formed. The solid was collected and washed with excess water. This solid was than dried under vacuum at 50° C. for 18h. This solid was taken up in ethyl acetate. The ethyl acetate was washed with 5% HCl, water, brine, and dried over sodium sulfate, filtered and concentrated under vacuum giving the title compound (5.8 g, 92%).

Example 254b

{4-[4-(3,5-Dichloro-benzoylamino)-2-nitro-phenoxy]-phenyl}-carbamic acid tert-butyl ester To a solution of Example 254a (2.0 g, 6.1 mmol) in DMSO (50 mL) was added KOH (1.4 g, 24.3 mmol) and N-Boc-4-aminophenol (1.3 g, 6.1 mmol). The mixture was heated at 80° C. for 4 h. The reaction was cooled and poured into water. The aqueous phase was extracted with ethyl acetate (2×). The combined organic phases were washed with water, brine, and dried over sodium sulfate, filtered and concentrated under vacuum giving the title compound. The residue was purified by silica gel chromatography eluting with hexanes/ethyl acetate/methanol (80:10:10) to give the desired product (1.6 g, 51%).

Example 254c

{4-[2-Amino-4-(3,5-dichloro-benzoylamino)-phenoxy]-phenyl}-carbamic acid tert-butyl ester The product from Example 254b (1.1 g, 2.1 mmol) was reacted with Fe and $NH_4Cl$ as described for Example 9E to give the desired product (0.6 g, 58.8%).

Example 254d

N-[4-(4-Amino-phenoxy)-3-(7-isopropyl-pyrido[2,3-d]pyrimidin-4-ylamino)-phenyl]-3,5-dichloro-benzamide The product from Example 8E (70 mg, 0.32 mmol) was reacted with Example 254c (162 mg, 0.32 mmol) in acetic acid (10 mL) at 125° C. in a sealed tube for 5 minute giving the crude title compound which was purified by HPLC with TFA providing the product as the trifluoroacetic acid (60 mg, 27%). $^1$H NMR (300 MHz, DMSO-$d_6$) δ ppm: 1.33 (d, J=6.99 Hz, 6 H) 3.27 (q, 1 H) 6.96 (d, 2 H) 7.01-7.09 (m, 3 H) 7.69 (dd, J=9.19, 2.57 Hz, 1 H) 7.81-7.92 (m, 3 H) 7.99 (d, J=1.84 Hz, 2 H) 8.85 (s, 1 H) 8.93 (d, J=8.82 Hz, 1 H) 10.64 (s, 1 H); MS (ESI+) m/z 559 (M+H)+.

Example 255

Furan-2-carboxylic acid [4-(4-hydroxy-phenylsulfanyl)-3-(7-isopropyl-pyrido[2,3-d]pyrimidin-4-ylamino)-phenyl]-amide

Example 255a

Furan-2-carboxylic acid (4-fluoro-3-nitro-phenyl)-amide

The title compound was synthesized from 4-fluoro-3-nitro-phenylamine (2.00 g, 12.81 mmol) dissolved in THF (25 ml) and Hunig's base (3.312 g, 25.62 mmol) to which was added furan-2-carbonyl chloride (1.672 g, 12.81 mmol) drop wise over 10 minutes. Reaction mixture was stirred at room temperature for 1 hr at which time water was added and the title compound was collected by filtration providing the title compound (2.90 g, 90%).

Example 255b

Furan-2-carboxylic acid [4-(4-hydroxy-phenylsulfanyl)-3-nitro-phenyl]-amide

The product of Example 255a (1.00 g, 2.89 mmol) was dissolved in DMF to which $K_2CO_3$ (801 mg, 5.79 mmol), and 4-mercapto-phenol (366 mg, 2.89 mmol) were added. The reaction mixture was then heated to 80° C. for 2 hrs. At this point the reaction mixture was cooled to room temperature and diluted with water which was then extracted with ethyl acetate to isolate the desired compound (1.00 g, 99%).

Example 255c

Furan-2-carboxylic acid [3-amino-4-(4-hydroxy-phenylsulfanyl)-phenyl]-amide

The product from Example 255b was reduced with Fe and $NH_4Cl$ following the procedure from Example 9E to provide the title compound (980 mg, 90%).

Example 255d

Furan-2-carboxylic acid [4-(4-hydroxy-phenylsulfanyl)-3-(7-isopropyl-pyrido[2,3-d]pyrimidin-4-ylamino)-phenyl]-amide The product of Example 8E (100 mg, 0.462 mmol) and of Example 255c (151 mg, 0.462 mmol) were dissolved in HOAc and placed in a preheated 120° C. oil bath for 10 minutes. Reaction mixture was then cooled to room temperature, the solvent removed under vacuum and the crude oil was purified by HPLC with TFA providing the product as a trifluoroacetic acid salt (93 mg, 45%). $^1$H NMR (300 MHz, DMSO-$d_6$) δ ppm: 1.36 (d, J=6.62 Hz, 6 H), 6.64-6.73 (m, 3 H), 7.09-7.20 (m, 3 H), 7.34 (d, J=3.31 Hz, 1 H), 7.63 (dd, J=8.64, 2.39 Hz, 1 H), 7.79-7.89 (m, 1 H), 7.93-8.00 (m, 2 H), 8.74-8.80 (m, 1 H), 8.95 (d, J=8.82 Hz, 1 H), 9.77 (s, 1 H), 10.40 (s, 1 H); MS (ESI+) m/z 498 (M+TFA+H)+; (ESI−) m/z 496 (M+TFA−H)−.

Example 256

Thiophene-2-carboxylic acid [4-(4-amino-phenoxy)-3-(7-isopropyl-pyrido[2,3-d]pyrimidin-4-ylamino)-phenyl]-amide

Example 256a

Thiophene-2-carboxylic acid (4-fluoro-3-nitro-phenyl)-amide

The title compound was synthesized from 4-fluoro-3-nitro-phenylamine (2.00 g, 12.81 mmol) dissolved in THF (25 mL) and Hunig's base (3.312 g, 25.62 mmol) to which was added thiophene-2-carbonyl chloride (1.878 g, 12.81 mmol) drop wise over 10 minutes. Reaction mixture was stirred at room temperature for 1 hr at which time water was added and the title compound was collected by filtration (3.25 g, 95%).

Example 256b (4-{2-Nitro-4-[(thiophene-2-carbonyl)-amino]-phenoxy}-phenyl)-carbamic acid tert-butyl ester The product from Example 256a was reacted following the procedure from Example 172c to provide the title compound (2.053 g, 79%).

Example 256c (4-{2-Amino-4-[(thiophene-2-carbonyl)-amino]-phenoxy}-phenyl)-carbamic acid tert-butyl ester The product from Example 256b was reduced with Fe and $NH_4Cl$ using the conditions of Example 9E to provide the title compound (1.25 g, 65%).

Example 256d (4-{2-(7-Isopropyl-pyrido[2,3-d]pyrimidin-4-ylamino)-4-[(thiophene-2-carbonyl)-amino]-phenoxy}-phenyl)-carbamic acid tert-butyl ester The product of Example 8E (100 mg, 0.462 mmol) and of Example 255c (197 mg, 0.462 mmol) were dissolved in HOAc and placed in a preheated 120° C. oil bath for 10 minutes. Reaction mixture was then cooled to room temperature and the solvent removed under vacuum to provide the title compound (276 mg, 100%).

Example 256e

Thiophene-2-carboxylic acid [4-(4-amino-phenoxy)-3-(7-isopropyl-pyrido[2,3-d]pyrimidin-4-ylamino)-phenyl]-amide The product from Example 256d (276 mg, 0.462 mmol) was dissolved in a 1:1 mixture of TFA in $CH_2Cl_2$ and stirred at room temperature for 2 hrs. The solvent was removed under vacuum and the crude oil was purified by HPLC with TFA providing the product as a trifluoroacetic acid salt (33 mg, 12%). $^1$H NMR (300 MHz, DMSO-$d_6$) δ ppm: 1.27-1.35 (m, 6 H), 6.80-6.91 (m, 5 H), 6.99 (d, J=9.19 Hz, 1 H), 7.21-7.25

(m, 1 H), 7.63 (dd, J=8.82, 2.57 Hz, 1 H), 7.81 (d, J=8.46 Hz, 1 H), 7.87 (d, J=4.04 Hz, 1 H), 8.01-8.03 (m, 2 H), 8.82 (s, 1 H), 8.91 (d, J=8.46 Hz, 1 H), 10.39 (s, 1 H) MS (ESI+) m/z 497 (M+TFA+H)+; (ESI−) m/z 495 (M+TFA−H)−.

Example 257

5-Bromo-thiophene-2-carboxylic acid [4-(4-amino-phenoxy)-3-(7-isopropyl-pyrido[2,3-d]pyrimidin-4-ylamino)-phenyl]-amide

Example 257a (4-{4-[(5-Bromo-thiophene-2-carbonyl)-amino]-2-nitro-phenoxy}-phenyl)-carbamic acid tert-butyl ester The product of Example 241b (1.50 g, 4.34 mmol) was dissolved in DMF to which KOH (469 mg, 8.69 mmol), and (4-Hydroxy-phenyl)-carbamic acid tert-butyl ester (909 mg, 4.34 mmol) were added. The reaction mixture was then heated to 80° C. for 2 hrs. At this point the reaction mixture was cooled to room temperature and diluted with water that was then extracted with ethyl acetate. Dried over $Na_2SO_4$, filtered and concentrated under vacuum giving the title compound to provide the title compound (2.11 g, 90%).

Example 257b (4-{2-Amino-4-[(5-bromo-thiophene-2-carbonyl)-amino]-phenoxy}-phenyl)-carbamic acid tert-butyl ester The product from Example 257a was reduced with Fe and $NH_4Cl$ following the procedure from Example 9E to provide the title compound (922 mg, 50%).

Example 257c

{4-[4-[(5-Bromo-thiophene-2-carbonyl)-amino]-2-(7-isopropyl-pyrido[2,3-d]pyrimidin-4-ylamino)-phenoxy]-phenyl}-carbamic acid tert-butyl ester The product of Example 8E (100 mg, 0.462 mmol) and of Example 257b (233 mg, 0.462 mmol) were dissolved in HOAc and placed in a preheated 120° C. oil bath for 10 minutes. Reaction mixture was then cooled to room temperature and the solvent removed under vacuum to provide the title compound (312 mg, 100%).

Example 257d

5-Bromo-thiophene-2-carboxylic acid [4-(4-amino-phenoxy)-3-(7-isopropyl-pyrido[2,3-d]pyrimidin-4-ylamino)-phenyl]-amide The product from Example 257c (mg, 0.462 mmol) was dissolved in a 1:1 mixture of TFA in $CH_2Cl_2$ and stirred at room temperature for 2 hrs. The solvent was removed under vacuum and the crude oil was purified by HPLC with TFA providing the product as a trifluoroacetic acid salt (16 mg, 6%). $^1H$ NMR (300 MHz, DMSO-$d_6$) δ ppm: 1.32 (t, J=6.99 Hz, 6 H), 3.18-3.33 (m, 1 H), 6.82-6.91 (m, 4 H), 6.99 (d, J=9.19 Hz, 1 H), 7.39 (d, J=4.04 Hz, 1 H), 7.61 (dd, J=8.82, 2.57 Hz, 1 H), 7.81 (d, J=8.46 Hz, 1 H), 7.86 (d, J=4.04 Hz, 1 H), 7.99 (d, J=2.57 Hz, 1 H), 8.81 (s, 1 H), 8.91 (d, J=8.09 Hz, 1 H), 10.45 (s, 1 H); MS (ESI+) m/z 575 (M+TFA+H)+; (ESI−) m/z 573 (M+TFA−H)−.

Example 258

2-{4-[4-(4-Hydroxy-phenylsulfanyl)-3-(7-isopropyl-pyrido[2,3-d]pyrimidin-4-ylamino)-benzoylamino]-phenyl}-acetimidic acid methyl ester N-(4-Cyanomethyl-phenyl)-3-(7-isopropyl-pyrido[2,3-d]pyrimidin-4-ylamino)-4-(4-methoxy-phenylsulfanyl)-benzamide was reacted according to the procedure from Example 150 to provide a residue which was purified by trituration from methanol to provide the title compound as an off white solid (15.9 mg, 51%). 1H NMR (300 MHz, DMSO-D6) δ ppm: 10.13-10.29 (m, J=1.84 Hz, 2 H), 9.95 (s, 1 H), 8.87 (d, J=8.46 Hz, 1 H), 8.59 (s, 1 H), 7.98 (s, 1 H), 7.80 (d, J=8.09 Hz, 1 H), 7.61-7.73 (m, J=8.46 Hz, 3 H), 7.31 (d, J=8.46 Hz, 2 H), 7.22 (d, J=8.46 Hz, 2 H), 6.93 (d, J=9.19 Hz, 1 H), 6.85 (d, J=8.46 Hz, 2 H), 3.64 (s, 2 H), 3.61 (s, 3 H), 3.17-3.28 (m, 1 H), 1.34 (d, J=6.99 Hz, 6 H); MS (ESI$^+$) m/z 580.2 (M+H)$^+$, (ESI$^-$) m/z 578.2 (M−H)$^-$.

Example 259

N-(4-Cyano-phenyl)-3-(7-isopropyl-pyrido[2,3-d]pyrimidin-4-ylamino)-4-(4-methoxy-phenylsulfanyl)-benzamide The product from Example 137B was reacted with 4-aminobenzonitrile according to the procedure from Example 137C substituting 4-aminobenzyonitrile for 5-amino-o-cresol to provide the title compound as an off white solid after trituration of the reaction product from methanol (20 mg, 23%). 1H NMR (300 MHz, DMSO-D6) δ ppm: 10.63 (s, 1 H), 8.92 (s, 1 H), 8.69 (s, 1 H), 7.96 (d, J=8.82 Hz, 2 H), 7.66-7.90 (m, 4 H), 7.35-7.46 (m, 3 H), 6.95-7.11 (m, 3 H), 6.55-6.64 (m, 1 H), 3.77 (s, 3 H), 3.18-3.30 (m, 1 H), 1.35 (d, J=6.99 Hz, 6 H); MS (ESI$^+$) m/z 547.3 (M+H)$^+$, (ESI$^-$) m/z 545.3 (M−H)$^-$.

Example 260

4-(4-Hydroxy-phenylsulfanyl)-3-(pyrido[2,3-d]pyrimidin-4-ylamino)-N-(3-trifluoromethyl-phenyl)-benzamide

Example 260A 4-(4-Methoxy-phenylsulfanyl)-3-(pyrido[2,3-d]pyrimidin-4-ylamino)-benzoic acid methyl ester The product from Example 136B and the product from Example 29A were reacted according to the procedure from Example 136C substituting the product from Example 29A for the product from Example 8E to provide the title compound.

Example 260B 4-(4-Methoxy-phenylsulfanyl)-3-(pyrido[2,3-d]pyrimidin-4-ylamino)-benzoyl chloride The product from Example 260A was reacted according to the procedure from Examples 137A and 137B to provide the title compound.

Example 260C 4-(4-Methoxy-phenylsulfanyl)-3-(pyrido[2,3-d]pyrimidin-4-ylamino)-N-(3-trifluoromethyl-phenyl)-benzamide The product from Example 260B was reacted with 3-(trifluoromethyl)aniline according to the procedure from Example 137C substituting 3-(trifluoromethyl)aniline for 5-amino-o-cresol and substituting the product from Example 260B for the product from Example 137B to provide the title compound as an off white solid after trituration of the reaction product from methanol (43 mg, 47%).

Example 260D 4-(4-Hydroxy-phenylsulfanyl)-3-(pyrido[2,3-d]pyrimidin-4-ylamino)-N-(3-trifluoromethyl-phenyl)-benzamide The product from Example 260C was reacted according to the procedure from Example 150 substituting the product from Example 260C for the product from Example 138 to provide a residue which was purified by trituration from methanol to provide the title compound as an off white solid (33.3 mg, 90%). 1H NMR (300 MHz, DMSO-D6) δ ppm: 11.74 (s, 1 H), 10.54 (s, 1 H), 10.01 (s, 1 H), 9.19 (s, 1 H), 9.11 (d, J=7.35 Hz, 1 H), 8.90 (s, 1 H), 8.19 (s, 1 H), 7.86-8.08 (m, 4 H), 7.60 (t, J=7.91 Hz, 1 H), 7.46 (d, J=7.72 Hz, 1 H), 7.24-7.38 (m, 2 H), 7.03 (d, J=8.46 Hz, 1 H), 6.73-6.91 (m, 2 H); MS (ESI$^+$) m/z 534.1 (M+H)$^+$, (ESI$^-$) m/z 532.2 (M–H)$^-$.

Example 261

N-(4-Fluoro-3-methyl-phenyl)-4-(4-hydroxy-phenylsulfanyl)-3-(pyrido[2,3-d]pyrimidin-4-ylamino)-benzamide

Example 261A

N-(4-Fluoro-3-methyl-phenyl)-4-(4-methoxy-phenylsulfanyl)-3-(pyrido[2,3-d]pyrimidin-4-ylamino)-benzamide The product from Example 260B was reacted with 4-fluoro-3-methylaniline according to the procedure from Example 260C substituting 4-fluoro-3-methylaniline for 3-(trifluoromethyl)aniline to provide the title compound as an off white solid after trituration of the reaction product from methanol (44 mg, 52%).

Example 261B

N-(4-Fluoro-3-methyl-phenyl)-4-(4-hydroxy-phenylsulfanyl)-3-(pyrido[2,3-d]pyrimidin-4-ylamino)-benzamide The product from Example 261A was reacted according to the procedure from Example 150 substituting the product from Example 261A for the product from Example 138 to provide a residue which was purified by trituration from methanol to provide the title compound as an off white solid (30.4 mg, 82%). 1H NMR (300 MHz, DMSO-D6) δ ppm: 10.22 (s, 1 H), 10.01 (s, 1 H), 9.20 (d, J=3.68 Hz, 1 H), 9.12 (d, J=8.82 Hz, 1 H), 8.92 (s, 1 H), 7.83-8.00 (m, 4 H), 7.64 (dd, J=7.17, 2.39 Hz, 1 H), 7.50-7.60 (m, 1 H), 7.29-7.34 (m, 2 H), 7.12 (t, J=9.19 Hz, 1 H), 7.02 (d, J=8.46 Hz, 1 H), 6.80-6.85 (m, 2 H), 2.23 (d, J=1.84 Hz, 3 H); MS (ESI$^+$) m/z 498.1 (M+H)$^+$, (ESI$^-$) m/z 496.1 (M–H)$^-$.

Example 262

N-(4-Cyanomethyl-phenyl)-4-(4-methoxy-phenylsulfanyl)-3-(pyrido[2,3-d]pyrimidin-4-ylamino)-benzamide The product from Example 260B was reacted with 4-aminobenzyl cyanide according to the procedure from Example 137C substituting 4-aminobenzyl cyanide for 5-amino-o-cresol and substituting the product from Example 260B for the product from Example 137B to provide the title compound as an off white solid after trituration of the reaction product from methanol (54.7 mg, 64%). 1H NMR (300 MHz, DMSO-D6) δ ppm: 10.60 (s, 1 H), 10.26 (s, 1 H), 9.09 (s, 1 H), 8.95 (s, 1 H), 8.65 (s, 1 H), 7.98 (s, 1 H), 7.64-7.89 (m, J=8.46 Hz, 4 H), 7.36-7.47 (m, 2 H), 7.31 (d, J=8.82 Hz, 2 H), 6.91-7.07 (m, 3 H), 3.99 (s, 2 H), 3.78 (s, 3 H); MS (ESI$^+$) m/z 519.4 (M+H)$^+$, (ESI$^-$) m/z 517.1 (M–H)$^-$.

Example 263

N-(4-Cyano-phenyl)-4-(4-methoxy-phenylsulfanyl)-3-(pyrido[2,3-d]pyrimidin-4-ylamino)-benzamide The product from Example 260B was reacted with 4-aminobenzonitrile according to the procedure from Example 137C substituting 4-aminobenzonitrile for 5-amino-o-cresol and substituting the product from Example 260B for the product from Example 137B to provide the title compound as an off white solid after trituration of the reaction product from methanol (51.5 mg, 62%). 1H NMR (300 MHz, DMSO-D6) δ ppm: 11.11 (s, 1 H), 10.62 (s, 1 H), 9.11 (s, 1 H), 9.00 (d, J=5.51 Hz, 1 H), 8.57-8.80 (m, 1 H), 7.97 (d, J=8.82 Hz, 2 H), 7.68-7.90 (m, J=8.82 Hz, 3 H), 7.38-7.52 (m, 2 H), 6.88-7.12 (m, 3 H), 6.45-6.71 (m, 1 H), 3.77 (s, 3 H).

Example 264

N-(3-Dimethylamino-phenyl)-4-(4-methoxy-phenylsulfanyl)-3-(pyrido[2,3-d]pyrimidin-4-ylamino)-benzamide The product from Example 260B was reacted with N,N-dimethyl-1,3-phenylenediamine according to the procedure from Example 137C substituting N,N-dimethyl-1,3-phenylenediamine for 5-amino-o-cresol and substituting the product from Example 260B for the product from Example 137B to provide the title compound as an off white solid after trituration of the reaction product from methanol (45 mg, 52%). 1H NMR (300 MHz, DMSO-D6) δ ppm: 10.33 (s, 1 H), 9.99 (s, 1 H), 9.11 (dd, J=4.41, 1.84 Hz, 1 H), 8.96 (dd, J=8.46, 1.84 Hz, 1 H), 8.63 (s, 1 H), 8.01 (d, J=1.84 Hz, 1 H), 7.82 (dd, J=8.46, 1.84 Hz, 1 H), 7.70 (dd, J=8.09, 4.41 Hz, 1 H), 7.36-7.43 (m, 2 H), 7.10-7.20 (m, 3 H), 6.97-7.04 (m, 3 H), 6.48 (td, J=4.50, 2.39 Hz, 1 H), 3.77 (s, 3 H), 2.88 (s, 6 H); MS (ESI$^+$) m/z 523.5 (M+H)$^-$, (ESI$^-$) m/z 521.2 (M–H)$^-$.

Example 265

N-[5-(4-Hydroxy-phenylsulfanyl)-4-(7-isopropyl-pyrido[2,3-d]pyrimidin-4-ylamino)-2-methyl-phenyl]-2-phenyl-acetamide

Example 265A

N-(5-Chloro-2-methyl-4-nitro-phenyl)-2-phenyl-acetamide

A mixture of 5-chloro-2-methyl-4-nitrophenylamine (0.475 g, 2.55 mmol) and phenylacetyl chloride (0.394 g, 2.55 mmol) in toluene (10 mL) was heated under reflux for 4 h, then cooled to room temperature. A solid crystallized from the reaction mixture upon cooling, and was isolated by vacuum filtration and dried to provide the title compound as a yellow solid (0.330 g, 43%).

Example 265B

N-[5-(4-Hydroxy-phenylsulfanyl)-2-methyl-4-nitro-phenyl]-2-phenyl-acetamide

The product from Example 265A (0.305 g, 1.0 mmol), 4-mercaptophenol (0.151 g, 1.2 mmol, 1.2 eq) and cesium carbonate (0.782 g, 2.4 mmol, 2.4 eq) in dimethyl formamide (10 mL) was heated at 110° C. for 2 h, cooled to room temperature, and poured over ice water (100 mL). This mixture was extracted with ethyl acetate (3×150 mL) and the combined organic phases were washed with saturated aqueous sodium chloride, dried over anhydrous magnesium sulfate, filtered, and evaporated. The residue was purified by chromatography on silica gel eluting with 1:1 hexane/ethyl acetate to provide the title compound as a yellow solid (0.282 g, 72%).

Example 265C

N-[4-Amino-5-(4-hydroxy-phenylsulfanyl)-2-methyl-phenyl]-2-phenyl-acetamide

The product of Example 265B (0.282 g, 0.715 mmol), iron powder (0.160 g, 2.86 mmol, 4.0 eq), and ammonium chloride (0.0469 g, 0.858 mmol, 1.2 eq) in tetrahydrofuran (6 mL), methanol (6 mL) and water (2 mL) was heated under reflux for 1.5 h and then cooled to room temperature. The reaction mixture was then filtered through Celite and the Celite pad rinsed with methanol (50 mL). The filtrate was evaporated under reduced pressure and the residue partitioned between ethyl acetate and water. The organic phase was dried over anhydrous magnesium sulfate, filtered, and evaporated to provide an orange oil that was triturated with dichloromethane to provide the title compound as a yellow powder (0.246 g, 94%).

Example 265D

N-[5-(4-Hydroxy-phenylsulfanyl)-4-(7-isopropyl-pyrido[2,3-d]pyrimidin-4-ylamino)-2-methyl-phenyl]-2-phenyl-acetamide A mixture of the product of Example 265C (0.071 g, 0.19 mmol) and the product from Example 8E (0.0463 g, 0.21 mmol) in glacial acetic acid (1 mL) was heated in a 135° C. oil bath for 15 min. The solvent was then evaporated under a stream of nitrogen gas and the residue purified by chromatography on silica gel, eluting with a methanol/dichloromethane gradient (0-5% MeOH) to provide the title compound as a beige solid (0.0502 g, 48%). 1H NMR (300 MHz, DMSO-D6) δ ppm: 9.95 (s, 1 H), 9.77 (s, 1 H), 9.51 (s, 1 H), 8.81 (d, J=8.46 Hz, 1 H), 8.52 (s, 1 H), 7.59 (d, J=8.46 Hz, 1 H), 7.20-7.39 (m, 6 H), 7.13-7.20 (m, 2 H), 7.05 (s, 1 H), 6.73 (d, J=8.82 Hz, 2 H), 3.61 (s, 2 H), 3.14-3.27 (m, 1 H), 2.11 (s, 3 H), 1.32 (d, J=6.62 Hz, 6 H); MS (ESI$^+$) m/z 536.2 (M+H)$^+$, (ESI$^-$) m/z 534.2 (M−H)$^-$.

Example 266

3-Bromo-N-[5-(4-hydroxy-phenylsulfanyl)-4-(7-isopropyl-pyrido[2,3-d]pyrimidin-4-ylamino)-2-methyl-phenyl]-benzamide

Example 266A

3-Bromo-N-(5-chloro-2-methyl-4-nitro-phenyl)-benzamide

A mixture of 5-chloro-2-methyl-4-nitrophenylamine (0.373 g, 2.00 mmol) and 4-bromobenzoyl chloride (0.439 g, 2.00 mmol) in toluene (10 mL) was heated under reflux for 1.5 h, and cooled to room temperature. A solid crystallized from the reaction mixture upon cooling, and was isolated by vacuum filtration and dried to provide the title compound as a gray solid (0.241 g, 33%).

Example 266B

3-Bromo-N-[5-(4-hydroxy-phenylsulfanyl)-2-methyl-4-nitro-phenyl]-benzamide

The product from Example 266A was reacted according to the procedure from Example 265B substituting the product from Example 266A for the product from Example 265A to provide a residue which was purified by silica gel chromatography, eluting with a methanol/dichloromethane gradient (0-5% methanol) to provide the title compound as a yellow solid (0.204 g, 71%).

Example 266C

N-[4-Amino-5-(4-hydroxy-phenylsulfanyl)-2-methyl-phenyl]-3-bromo-benzamide

The product from Example 266B was reacted according to the procedure from Example 265C substituting the product from Example 266B for the product from Example 265B to provide the title compound as a brown solid (0.164 g, 86%). This material was utilized without purification by silica gel chromatography.

Example 266D

3-Bromo-N-[5-(4-hydroxy-phenylsulfanyl)-4-(7-isopropyl-pyrido[2,3-d]pyrimidin-4-ylamino)-2-methyl-phenyl]-benzamide The product from Example 266C was reacted according to the procedure from Example 265D substituting the product from Example 266C for the product from Example 265C to provide a residue which was purified by silica gel chromatography, eluting with a methanol/dichloromethane gradient (0-5% methanol) to provide the title compound as a yellow solid (0.0356 g, 52%). 1H NMR (300 MHz, DMSO-D6) δ ppm: 10.03 (s, 1 H), 10.01 (s, 1 H), 9.76 (s, 1 H), 8.84 (d, J=8.46 Hz, 1 H), 8.56 (s, 1 H), 8.10 (s, 1 H), 7.93 (d, J=8.09 Hz, 1 H), 7.80 (dd, J=8.09, 1.10 Hz, 1 H), 7.61 (d, J=8.82 Hz, 1 H), 7.48 (t, J=7.91 Hz, 1 H), 7.33 (s, 1 H), 7.17-7.24 (m, 2 H), 6.97 (s, 1 H), 6.70-6.76 (m, J=8.46 Hz, 2 H), 3.17-3.28 (m, 1 H), 2.19 (s, 3 H), 1.34 (d, J=6.62 Hz, 6 H); MS (ESI$^+$) m/z 600.2 (M+H)$^+$, 602.2 (M+H)$^+$, (ESI$^-$) m/z 598.1 (M−H)$^-$ 600.1 (M−H)$^-$.

Example 267

N-[5-(4-Hydroxy-phenylsulfanyl)-4-(7-isopropyl-pyrido[2,3-d]pyrimidin-4-ylamino)-2-methyl-phenyl]-benzamide

Example 267A

N-(5-Chloro-2-methyl-4-nitro-phenyl)-benzamide

A mixture of 5-chloro-2-methyl-4-nitrophenylamine (0.560 g, 3.00 mmol) and benzoyl chloride (0.422 g, 3.00 mmol) in toluene (15 mL) was heated under reflux for 1.5 h, and cooled to room temperature. A solid crystallized from the reaction mixture upon cooling, and was isolated by vacuum filtration and dried to provide the title compound as a gray solid (0.276 g, 32%).

Example 267B

N-[5-(4-Hydroxy-phenylsulfanyl)-2-methyl-4-nitro-phenyl]-benzamide

The product from Example 267A was reacted according to the procedure from Example 265B substituting the product from Example 267A for the product from Example 265A to provide a residue which was purified by silica gel chromatography, eluting with a ethyl acetate/hexane gradient (0-50% ethyl acetate) to provide the title compound as a yellow solid (0.120 g, 37%).

Example 267C

N-[4-Amino-5-(4-hydroxy-phenylsulfanyl)-2-methyl-phenyl]-benzamide

The product from Example 267B was reacted according to the procedure from Example 265C substituting the product from Example 267B for the product from Example 265B to provide the title compound as a brown solid (0.11 g, 100%). This material was utilized without purification by silica gel chromatography.

Example 267D

N-[5-(4-Hydroxy-phenylsulfanyl)-4-(7-isopropyl-pyrido[2,3-d]pyrimidin-4-ylamino)-2-methyl-phenyl]-benzamide The product from Example 267C was reacted according to the procedure from Example 265D substituting the product from Example 267C for the product from Example 265C to provide a residue which was purified by silica gel chromatography, eluting with a methanol/dichloromethane gradient (0-5% methanol) to provide the title compound as a yellow solid (0.0212 g, 33%). 1H NMR (300 MHz, DMSO-D6) δ ppm: 10.02 (s, 1 H), 9.90 (s, 1 H), 9.77 (s, 1 H), 8.84 (d, J=8.46 Hz, 1 H), 8.56 (s, 1 H), 7.93 (d, J=6.99 Hz, 2 H), 7.55-7.65 (m, 2 H), 7.51 (t, J=7.35 Hz, 2 H), 7.33 (s, 1 H), 7.15-7.25 (m, 2 H), 6.99 (s, 1 H), 6.65-6.79 (m, 2 H), 3.14-3.27 (m, 1 H), 2.20 (s, 3 H), 1.33 (d, J=6.62 Hz, 6 H); MS (ESI$^+$) m/z 522.2 (M+H)$^+$, (ESI$^-$) m/z 520.2 (M−H)$^-$.

Example 268

Morpholine-4-carboxylic acid {4-[4-(4-bromo-phenylcarbamoyl)-2-(7-isopropyl-pyrido[2,3-d]pyrimidin-4-ylamino)-phenoxy]-phenyl}-amide

Example 268A 4-(4-Amino-phenoxy)-N-(4-bromo-phenyl)-3-nitro-benzamide

A mixture of the product from Example 10A (3.55g, 10 mmol), 4-aminophenol (1.09 g, 10 mmol), and potassium hydroxide (1.12 g, 20 mmol) were dissolved in dimethyl sulfoxide (15 mL) and heated at 100° C. in a CEM Discover microwave for 25 minutes. The mixture was then cooled to room temperature, poured into water (300 mL), the pH of the solution adjusted to 6 with 1N aqueous hydrochloric acid, the resultant solution stirred for 30 minutes and the resultant solid collected and dried to provide the title compound as a yellow solid (4.2 g, 98%).

Example 268B

{4-[4-(4-Bromo-phenylcarbamoyl)-2-nitro-phenoxy]-phenyl}-carbamic acid 2,2,2-trichloro-ethyl ester To the product from Example 268A (4.2 g, 9.8 mmol) dissolved in dichloromethane (100 mL) was added pyridine (1.62 mL, 20 mmol) followed by the dropwise addition of 2,2,2-trichloroethyl chloroformate (2.29 g, 10.8 mmol). The resultant solution was stirred for 4 hours and then concentrated under vacuum. The mixture was then poured into water (200 mL), the pH of the solution adjusted to 5 with 1N aqueous hydrochloric acid, the resultant solution stirred for 30 minutes and the resultant solid collected and dried to provide the title compound (6.0 g, 100%).

Example 268C

{4-[2-Amino-4-(4-bromo-phenylcarbamoyl)-phenoxy]-phenyl}-carbamic acid 2,2,2-trichloro-ethyl ester The product from Example 268B (6.0 g, 10 mmol), iron powder (2.8 g, 50 mmol) and ammonium chloride (0.81 g, 15 mmol) in a mixture of ethanol (60 mL), tetrahydrofuran (60 mL), and water (20 mL) was heated under reflux for 5 hours and then cooled to room temperature. The reaction mixture was filtered through Celite and the filter pad was rinsed with ethanol (100 mL). The filtrate was evaporated under reduced pressure to leave a residue which was triturated with hexanes/ethyl acetate 4/1 to provide the title product (2.39 g, 42%) as a tan solid.

Example 268D

{4-[4-(4-Bromo-phenylcarbamoyl)-2-(7-isopropyl-pyrido[2,3-d]pyrimidin-4-ylamino)-phenoxy]-phenyl}-carbamic acid 2,2,2-trichloro-ethyl ester A mixture of the product from Example 268C (2.39 g, 4.2 mmol) and the product from Example 8E (0.91 g, 4.2 mmol)

in glacial acetic acid (10 mL) was heated in a 130° C. oil bath for 15 min. The reaction mixture was then cooled to room temperature and the solvent evaporated under reduced pressure to provide the title product as a brown powder.

Example 268E

Morpholine-4-carboxylic acid {4-[4-(4-bromo-phenylcarbamoyl)-2-(7-isopropyl-pyrido[2,3-d]pyrimidin-4-ylamino)-phenoxy]-phenyl}-amide A mixture of the product from Example 268D (74 mg, 0.1 mmol), 1,8-diazabicyclo[5.4.0]undec-7-ene (30 mg, 0.2 mmol), and morpholine (87 mg, 1.0 mmol) in tetrahydrofuran (2 ml) was heated at 65° C. in a sealed tube for 1 hour. The mixture was then cooled to room temperature, concentrated under vacuum and the resultant residue purified by HPLC with TFA to provide the title compound as a trifluoroacetic acid salt (50 mg, 63%). 1H NMR (300 MHz, DMSO-D6) δ ppm: 1.34 (d, J=6.99 Hz, 6 H), 3.19-3.32 (m, 1 H), 3.35-3.44 (m, 4 H), 3.57-3.63 (m, 4 H), 6.95-7.03 (m, 3 H), 7.47 (d, J=9.19 Hz, 2 H), 7.54 (d, J=8.82 Hz, 2 H), 7.75 (d, J=8.82 Hz, 2 H), 7.82 (d, J=8.46 Hz, 1 H), 7.98 (dd, J=8.64, 2.02 Hz, 1 H), 8.14 (d, J=1.84 Hz, 1 H), 8.56 (s, 1 H), 8.85 (s, 1 H), 8.94 (d, J=8.46 Hz, 1 H), 10.38 (s, 1 H); MS (ESI+) m/z 682/684 (M+H)+.

Example 269

N-(4-Bromo-phenyl)-3-(7-isopropyl-pyrido[2,3-d]pyrimidin-4-ylamino)-4-[4-(3-methyl-ureido)-phenoxy]-benzamide The product from Example 268D was reacted using the procedure from Example 268E substituting methylamine for morpholine to provide the crude material which was purified by HPLC with TFA to provide the title compound as a trifluoroacetic acid salt. 1H NMR (300 MHz, DMSO-D6) δ ppm: 1.34 (d, J=6.99 Hz, 6 H), 2.63 (d, J=4.41 Hz, 3 H), 3.14-3.32 (m, 1 H), 5.99 (q, J=4.78 Hz, 1 H), 6.91-7.04 (m, 3 H), 7.40 (d, J=9.19 Hz, 2 H), 7.54 (d, J=8.82 Hz, 2 H), 7.75 (d, J=8.82 Hz, 2 H), 7.82 (d, J=8.82 Hz, 1 H), 7.97 (dd, J=8.64, 2.02 Hz, 1 H), 8.14 (d, J=1.84 Hz, 1 H), 8.54 (s, 1 H), 8.85 (s, 1 H), 8.94 (d, J=8.82 Hz, 1 H), 10.37 (s, 1 H), 11.21 (s, 1 H); MS (ESI+) m/z 626/628 (M+H)+.

Example 270

N-(4-Bromo-phenyl)-4-[4-(3,3-dimethyl-ureido)-phenoxy]-3-(7-isopropyl-pyrido[2,3-d]pyrimidin-4-ylamino)-benzamide The product from Example 268D was reacted using the procedure from Example 268E substituting dimethylamine for morpholine to provide the crude material which was purified by HPLC with TFA to provide the title compound as a trifluoroacetic acid salt. 1H NMR (300 MHz, DMSO-D6) δ ppm: 1.34 (d, J=6.99 Hz, 6 H), 2.91 (s, 6 H), 3.12-3.35 (m, 1 H), 6.93-7.02 (m, 3 H), 7.47 (d, J=9.19 Hz, 2 H), 7.53-7.56 (m, 2 H), 7.73-7.78 (m, 2 H), 7.82 (d, J=8.82 Hz, 1 H), 7.98 (dd, J=8.82, 2.21 Hz, 1 H), 8.14 (d, J=2.21 Hz, 1 H), 8.31 (s, 1 H), 8.85 (s, 1 H), 8.94 (d, J=8.46 Hz, 1 H), 10.38 (s, 1 H), 11.23 (s, 1 H); MS (ESI+) m/z 640/642 (M+H)+.

Example 271

N-(4-Bromo-phenyl)-4-[4-(3-ethyl-ureido)-phenoxy]-3-(7-isopropyl-pyrido[2,3-d]pyrimidin-4-ylamino)-benzamide The product from Example 268D was reacted using the procedure from Example 268E substituting ethylamine for morpholine to provide the crude material which was purified by HPLC with TFA to provide the title compound as a trifluoroacetic acid salt. 1H NMR (300 MHz, DMSO-D6) δ ppm: 1.04 (t, J=7.17 Hz, 3 H), 1.34 (d, J=6.62 Hz, 6 H), 3.01-3.17 (m, 2 H), 3.21-3.32 (m, 1 H), 6.09 (t, J=5.52 Hz, 1 H), 6.93-7.05 (m, J=9.01, 3.49 Hz, 3 H), 7.40 (d, J=8.82 Hz, 2 H), 7.54 (d, J=9.19 Hz, 2 H), 7.75 (d, J=9.19 Hz, 2 H), 7.81 (d, J=8.82 Hz, 1 H), 7.96 (dd, J=8.46, 2.21 Hz, 1 H), 8.14 (d, J=2.21 Hz, 1 H), 8.47 (s, 1 H), 8.84 (s, 1 H), 8.94 (d, J=8.82 Hz, 1 H), 10.37 (s, 1 H), 11.19 (s, 1 H); MS (ESI+) m/z 640/642 (M+H)+.

Example 272

Piperidine-1-carboxylic acid {4-[4-(4-bromo-phenylcarbamoyl)-2-(7-isopropyl-pyrido[2,3-d]pyrimidin-4-ylamino)-phenoxy]-phenyl}-amide The product from Example 268D was reacted using the procedure from Example 268E substituting piperidine for morpholine to provide the crude material which was purified by HPLC with TFA to provide the title compound as a trifluoroacetic acid salt. 1H NMR (300 MHz, DMSO-D6) δ ppm: 1.34 (d, J=6.62 Hz, 6 H), 1.42-1.66 (m, 6 H), 3.22-3.32 (m, 1 H), 3.36-3.43 (m, 4 H), 6.98 (t, J=9.01 Hz, 3 H), 7.47 (d, J=9.19 Hz, 2 H), 7.54 (d, J=8.82 Hz, 2 H), 7.75 (d, J=8.82 Hz, 2 H), 7.83 (d, J=8.46 Hz, 1 H), 7.98 (dd, J=8.46, 2.21 Hz, 1 H), 8.14 (d, J=2.21 Hz, 1 H), 8.47 (s, 1 H), 8.86 (s, 1 H), 8.95 (d, J=8.46 Hz, 1 H), 10.38 (s, 1 H), 11.30 (s, 1 H); MS (ESI+) m/z 680/682 (M+H)+.

Example 273

N-(4-Bromo-phenyl)-4-[4-(3-cyclopentyl-ureido)-phenoxy]-3-(7-isopropyl-pyrido[2,3-d]pyrimidin-4-ylamino)-benzamide The product from Example 268D was reacted using the procedure from Example 268E substituting cyclopentylamine for morpholine to provide the crude material which was purified by HPLC with TFA to provide the title compound as a trifluoroacetic acid salt. 1H NMR (300 MHz, DMSO-D6) δ ppm: 1.34 (d, J=6.99 Hz, 6 H), 1.34-1.43 (m, 2 H), 1.46-1.71 (m, 4 H), 1.74-1.92 (m, 2 H), 3.12-3.31 (m, 1 H), 3.78-4.00 (m, 1 H), 6.14 (d, J=7.35 Hz, 1 H), 6.93-7.02 (m, J=9.01, 2.76 Hz, 3 H), 7.38 (d, J=9.19 Hz, 2 H), 7.54 (d, J=8.82 Hz, 2 H), 7.75 (d, J=9.19 Hz, 2 H), 7.81 (d, J=8.46 Hz, 1 H), 7.96 (dd, J=8.82, 2.21 Hz, 1 H), 8.14 (d, J=2.21 Hz, 1 H), 8.31 (s, 1 H), 8.84 (s, 1 H), 8.94 (d, J=8.82 Hz, 1 H), 10.37 (s, 1 H), 11.18 (s, 1 H); MS (ESI+) m/z 680/682 (M+H)+.

Example 274

N-(4-Bromo-phenyl)-4-[4-(3-cyclopropyl-ureido)-phenoxy]-3-(7-isopropyl-pyrido[2,3-d]pyrimidin-4-ylamino)-benzamide The product from Example 268D was reacted using the procedure from Example 268E substituting cyclopropylamine for morpholine to provide the crude material which was purified by HPLC with TFA to provide the title compound as a trifluoroacetic acid salt. 1H NMR (300 MHz, DMSO-D6) δ ppm: 0.30-0.45 (m, 2 H), 0.57-0.68 (m, 2 H), 1.34 (d, J=6.99 Hz, 6 H), 3.15-3.37 (m, 2 H), 6.37 (d, J=2.21 Hz, 1 H), 6.97 (dd, J=9.01, 2.02 Hz, 3 H), 7.41 (d, J=9.19 Hz, 2 H), 7.54 (d, J=8.82 Hz, 2 H), 7.75 (d, J=8.82 Hz, 2 H), 7.79 (d, J=8.82 Hz, 1 H), 7.96 (d, J=10.66 Hz, 1 H), 8.14 (s, 1 H), 8.33 (s, 1 H), 8.83 (s, 1 H), 8.93 (d, J=9.56 Hz, 1 H), 10.36 (s, 1 H), 11.08 (s, 1 H); MS (ESI+) m/z 652/654 (M+H)+.

Example 275

N-(4-Bromo-phenyl)-4-[4-(3-butyl-3-methyl-ureido)-phenoxy]-3-(7-isopropyl-pyrido[2,3-d]pyrimidin-4-ylamino)-benzamide The product from Example 268D was reacted using the procedure from Example 268E substituting N-butylmethylamine for morpholine to provide the crude material which was purified by HPLC with TFA to provide the title compound as a trifluoroacetic acid salt. 1H NMR (300 MHz, DMSO-D6) δ ppm: 0.90 (t, J=7.35 Hz, 3 H), 1.10-1.31 (m, 2 H), 1.33 (d, J=6.62 Hz, 6 H), 1.40-1.53 (m, 3 H), 2.91 (s, 3 H), 3.17-3.32 (m, 3 H), 6.91-7.03 (m, 3 H), 7.47 (d, J=9.19 Hz, 2 H), 7.54 (d, J=8.82 Hz, 2 H), 7.73-7.83 (m, 3 H), 7.96 (dd, J=8.46, 2.21 Hz, 1 H), 8.14 (d, J=1.84 Hz, 1 H), 8.23 (s, 1 H), 8.82 (s, 1 H), 8.93 (d, J=8.46 Hz, 1 H), 10.37 (s, 1 H); MS (ESI+) m/z 682/684 (M+H)+.

Example 276

N-(4-Bromo-phenyl)-3-(7-isopropyl-pyrido[2,3-d]pyrimidin-4-ylamino)-4-[4-(3-pentyl-ureido-phenoxy]-benzamide The product from Example 268D was reacted using the procedure from Example 268E substituting 1-aminopentane for morpholine to provide the crude material which was purified by HPLC with TFA to provide the title compound as a trifluoroacetic acid salt. 1H NMR (300 MHz, DMSO-D6) δ ppm: 0.85-0.90 (m, 3 H), 1.23-1.31 (m, 4 H), 1.33 (d, J=6.99 Hz, 6 H), 1.38-1.47 (m, 2 H), 2.99-3.10 (m, 2 H), 3.19-3.29 (m, 1 H), 6.09 (t, J=5.52 Hz, 1 H), 6.96 (dd, J=9.01, 3.13 Hz, 3 H), 7.39 (d, J=8.82 Hz, 2 H), 7.54 (d, J=8.82 Hz, 2 H), 7.75 (d, J=9.19 Hz, 2 H), 7.79 (d, J=8.82 Hz, 1 H), 7.96 (dd, J=8.82, 1.84 Hz, 1 H), 8.13 (s, 1 H), 8.43 (s, 1 H), 8.82 (s, 1 H), 8.92 (d, J=8.46 Hz, 1 H), 10.36 (s, 1 H), 11.08 (s, 1 H); MS (ESI+) m/z 682/684 (M+H)+.

Example 277

N-(4-Bromo-phenyl)-3-(7-isopropyl-pyrido[2,3-d]pyrimidin-4-ylamino)-4-{4-[3-(2-methoxy-ethyl)-ureido]-phenoxy}-benzamide The product from Example 268D was reacted using the procedure from Example 268E substituting 2-methoxyethylamine for morpholine to provide the crude material which was purified by HPLC with TFA to provide the title compound as a trifluoroacetic acid salt. 1H NMR (300 MHz, DMSO-D6) δ ppm: 1.34 (d, J=6.99 Hz, 6 H), 3.20-3.31 (m, 5 H), 3.27 (s, 3 H), 6.17 (t, J=5.88 Hz, 1 H H), 6.92-7.01 (m, 3 H), 7.38 (d, J=8.82 Hz, 2 H), 7.54 (d, J=8.82 Hz, 2 H), 7.75 (d, J=8.82 Hz, 2 H), 7.80 (d, J=9.19 Hz, 1 H), 7.96 (dd, J=8.64, 2.02 Hz, 1 H), 8.14 (d, J=1.47 Hz, 1 H), 8.56 (s, 1 H), 8.83 (s, 1 H), 8.93 (d, J=9.93 Hz, 1 H), 10.36 (s, 1 H), 11.13 (s, 1 H); MS (ESI+) m/z 670/672 (M+H)+.

Example 278

N-(4-Bromo-phenyl)-4-{4-[3-(2-ethoxy-ethyl)-ureido]-phenoxy}-3-(7-isopropyl-pyrido[2,3-d]pyrimidin-4-ylamino)-benzamide The product from Example 268D was reacted using the procedure from Example 268E substituting 2-ethoxyethylamine for morpholine to provide the crude material which was purified by HPLC with TFA to provide the title compound as a trifluoroacetic acid salt. 1H NMR (300 MHz, DMSO-D6) δ ppm: 1.13 (t, J=6.99 Hz, 3 H), 1.33 (d, J=6.99 Hz, 6 H), 3.17-3.27 (m, 3 H), 3.40-3.54 (m, 4 H), 6.15 (t, J=5.70 Hz, 1 H), 6.94-7.03 (m, 3 H), 7.38 (d, J=9.19 Hz, 2 H), 7.54 (d, J=8.82 Hz, 2 H), 7.71-7.83 (m, 3 H), 7.95 (dd, J=8.64, 2.02 Hz, 1 H), 8.14 (d, J=1.47 Hz, 1 H), 8.59 (s, 1 H), 8.80 (s, 1 H), 8.91 (d, J=8.46 Hz, 1 H), 10.36 (s, 1 H), 11.01 (s, 1 H); MS (ESI+) m/z 684/686 (M+H)+.

Example 279

4-[4-(3-Benzyl-3-methyl-ureido)-phenoxy]-N-(4-bromo-phenyl)-3-(7-isopropyl-pyrido[2,3-d]pyrimidin-4-ylamino)-benzamide The product from Example 268D was reacted using the procedure from Example 268E substituting N-benzylmethylamine for morpholine to provide the crude material which was purified by HPLC with TFA to provide the title compound as a trifluoroacetic acid salt. 1H NMR (300 MHz, DMSO-D6) δ ppm: 1.34 (d, J=6.62 Hz, 6 H), 2.91 (s, 3 H), 3.22-3.31 (m, 1 H), 4.54 (s, 2 H), 7.00 (dd, J=9.01, 4.23 Hz, 3 H), 7.20-7.40 (m, 4 H), 7.47-7.61 (m, 4 H), 7.72-7.84 (m, 3 H), 7.97 (dd, J=8.64, 2.02 Hz, 1 H), 8.14 (d, J=2.21 Hz, 1 H), 8.46 (s, 1 H), 8.84 (s, 1 H), 8.94 (d, J=8.82 Hz, 1 H), 10.38 (s, 1 H), 11.19 (s, 1 H); MS (ESI+) m/z 716/718 (M+H)+.

Example 280

4-[4-(3-Benzyl-ureido)-phenoxy]-N-(4-bromo-phenyl)-3-(7-isopropyl-pyrido[2,3-d]pyrimidin-4-ylamino)-benzamide The product from Example 268D was reacted using the procedure from Example 268E substituting benzylamine for morpholine to provide the crude material which was purified by HPLC with TFA to provide the title compound as a trifluoroacetic acid salt. 1H NMR (300 MHz, DMSO-D6) δ ppm: 1.34 (d, J=6.99 Hz, 6 H), 3.18-3.35 (m, 1 H), 4.29 (d, J=5.88 Hz, 2 H), 6.61 (t, J=6.07 Hz, 1 H), 6.98 (d, J=8.82 Hz, 3 H), 7.17-7.38 (m, 5 H), 7.42 (d, J=8.82 Hz, 2 H), 7.52-7.56 (m, 2 H), 7.75 (d, J=8.82 Hz, 2 H), 7.81 (d, J=8.46 Hz, 1 H), 7.97 (dd, J=8.82, 2.21 Hz, 1 H), 8.14 (d, J=2.21 Hz, 1 H), 8.62 (s, 1 H), 8.84 (s, 1 H), 8.94 (d, J=8.82 Hz, 1 H), 10.37 (s, 1 H), 11.21 (s, 1 H); MS (ESI+) m/z 702/704 (M+H)+.

Example 281

N-(4-Bromo-phenyl)-4-[4-(3,3-diisopropyl-ureido)-phenoxy]-3-(7-isopropyl-pyrido[2,3-d]pyrimidin-4-ylamino)-benzamide The product from Example 268D was reacted using the procedure from Example 268E substituting diisopropylamine for morpholine to provide the crude material which was purified by HPLC with TFA to provide the title compound as a trifluoroacetic acid salt. 1H NMR (300 MHz, DMSO-D6) δ ppm: 1.24 (d, J=6.62 Hz, 12 H), 1.34 (d, J=6.99 Hz, 6 H), 3.22-3.34 (m, 1 H), 3.76-3.87 (m, 2 H), 6.92-7.02 (m, 3 H), 7.46 (d, J=9.19 Hz, 2 H), 7.54 (d, J=8.82 Hz, 2 H), 7.75 (d, J=8.82 Hz, 2 H), 7.83 (d, J=8.46 Hz, 1 H), 7.98 (dd, J=8.82, 2.21 Hz, 1 H), 8.07 (s, 1 H), 8.14 (d, J=2.21 Hz, 1 H), 8.86 (s, 1 H), 8.96 (d, J=8.46 Hz, 1 H), 10.38 (s, 1 H), 11.28 (s, 1 H); MS (ESI+) m/z 696/698 (M+H)+.

Example 282

N-(4-Bromo-phenyl)-3-(7-isopropyl-pyrido[2,3-d]pyrimidin-4-ylamino)-4-{4-[3-(1-phenyl-ethyl)-ureido]-phenoxy}-benzamide The product from Example 268D was reacted using the procedure from Example 268E substituting (R)-(+)-α-methylbenzylamine for morpholine to provide the crude material which was purified by HPLC with TFA to provide the title compound as a trifluoroacetic acid salt. 1H NMR (300 MHz, DMSO-D6) δ ppm: 1.33 (d, J=6.99 Hz, 6 H), 1.38 (d, J=6.99 Hz, 3 H), 3.12-3.30 (m, 1 H), 4.73-4.89 (m, 1 H), 6.61 (d, J=8.09 Hz, 1 H), 6.96 (d, J=9.19 Hz, 3 H), 7.19-7.29 (m, 1 H), 7.31-7.40 (m, 5 H), 7.54 (d, J=8.82 Hz, 2 H), 7.74 (d, J=8.82 Hz, 2 H), 7.80 (d, J=8.09 Hz, 1 H), 7.95 (dd, J=8.64, 2.02 Hz, 1 H), 8.13 (d, J=1.84 Hz, 1 H), 8.44 (s, 1 H), 8.83 (s, 1 H), 8.93 (d, J=8.09 Hz, 1 H), 10.36 (s, 1 H), 11.17 (s, 1 H); MS (ESI+) m/z 716/718 (M+H)+.

Example 283

N-(4-Bromo-phenyl)-3-(7-isopropyl-pyrido[2,3-d]pyrimidin-4-ylamino)-4-{4-[3-(1-phenyl-ethyl)-ureido]-phenoxy}-benzamide The product from Example 268D was reacted using the procedure from Example 268E substituting (S)-(−)-α-methylbenzylamine for morpholine to provide the crude material which was purified by HPLC with TFA to provide the title compound as a trifluoroacetic acid salt. 1H NMR (300 MHz, DMSO-D6) d ppm 1.33 (d, J=6.99 Hz, 6 H), 1.38 (d, J=6.99 Hz, 3 H), 3.12-3.30 (m, 1 H), 4.73-4.89 (m, 1 H), 6.61 (d, J=8.09 Hz, 1 H), 6.96 (d, J=9.19 Hz, 3 H), 7.19-7.29 (m, 1 H), 7.31-7.40 (m, 5 H), 7.54 (d, J=8.82 Hz, 2 H), 7.74 (d, J=8.82 Hz, 2 H), 7.80 (d, J=8.09 Hz, 1 H), 7.95 (dd, J=8.64, 2.02 Hz, 1 H), 8.13 (d, J=1.84 Hz, 1 H), 8.44 (s, 1 H), 8.83 (s, 1 H), 8.93 (d, J=8.09 Hz, 1 H), 10.36 (s, 1 H), 11.17 (s, 1 H); MS (ESI+) m/z 716/718 (M+H)+.

Example 284

N-(4-Bromo-phenyl)-4-(4-ethylamino-phenoxy)-3-(7-isopropyl-pyrido[2,3-d]pyrimidin-4-ylamino)-benzamide To the product from Example 10 and sodium triacetoxyborohydride in 9/1 dichloromethane/methanol was added acetaldehyde. The mixture was stirred at room temperature for 2 hours and evaporated. The residue was purified by reverse phase preparative HPLC with the AA method to provide the title compound. $^1$H NMR (300 MHz, DMSO-d$_6$) δ ppm: 1.14 (t, J=7.17 Hz, 3 H) 1.32 (d, J=6.62 Hz, 6 H) 2.98 (m, 2 H) 3.21 (m, 1 H) 5.50 (t, J=5.15 Hz, 1 H) 6.55 (d, J=8.82 Hz, 2 H) 6.84 (m, 3 H) 7.53 (d, J=8.82 Hz, 2 H) 7.60 (d, J=8.82 Hz, 1 H) 7.75 (d, J=9.19 Hz, 2 H), 7.85 (dd, J=8.46, 1.84 Hz, 1 H) 8.16 (d, J=1.84 Hz, 1 H) 8.62 (s, 1 H) 8.83 (d, J=8.46 Hz, 1 H) 9.99 (s, 1 H) 10.29 (s, 1 H); MS (ESI+) m/z 597/599 (M+H)+.

Example 285

N-(4-Bromo-phenyl)-4-(4-diethylamino-phenoxy)-3-(7-isopropyl-pyrido[2,3-d]pyrimidin-4-ylamino)-benzamide The title compound was obtained during the purification of the mixture from Example 284. 1H NMR (300 MHz, DMSO-D6) δ ppm: 1.04 (t, J=6.99 Hz, 6 H) 1.32 (d, J=6.99 Hz, 6 H), 3.26 (m, 5 H) 6.63 (m, 2 H) 6.89 (m, 3 H) 7.54 (m, 2 H) 7.58 (d, J=8.46 Hz, 1 H) 7.76 (m, 2 H) 7.86 (m, 1 H) 8.16 (s, 1 H) 8.61 (s, 1 H) 8.80 (d, J=8.46 Hz, 1 H) 9.99 (s, 1 H) 10.30 (s, 1 H); MS (ESI+) m/z 625/627 (M+H)+.

Example 286

N-(4-Bromo-phenyl)-4-[4-(2,2-dimethyl-propylamino)-phenoxy]-3-(7-isopropyl-pyrido[2,3-d]pyrimidin-4-ylamino)-benzamide To the product from Example 10 and sodium triacetoxyborohydride in 9/1 dichloromethane/methanol was added trimethylacetaldehyde. The mixture was stirred at room temperature for 2 hours and evaporated. The residue was purified by reverse phase preparative HPLC with the AA method to provide the title compound. 1H NMR (300 MHz, DMSO-D6) δ ppm: 0.94 (s, 9 H) 1.32 (d, J=6.99 Hz, 6 H) 2.77 (d, J=5.88 Hz, 2 H) 3.20 (m, 1 H) 5.41 (t, J=5.88 Hz, 1 H) 6.63 (d, J=9.19 Hz, 2 H) 6.84 (m, 3 H) 7.53 (d, J=8.82 Hz, 2 H) 7.60 (d, J=8.82 Hz, 1 H) 7.75 (d, J=8.82 Hz, 2 H) 7.86 (m, 1 H) 8.16 (d, J=1.84 Hz, 1 H) 8.62 (s, 1 H) 8.83 (d, J=8.46 Hz, 1 H) 9.99 (s, 1 H) 10.29 (s, 1 H); MS (ESI+) m/z 639/641 (M+H)+.

Example 287

N-(4-Bromo-phenyl)-4-[4-(cyclopropylmethyl-amino)-phenoxy]-3-(7-isopropyl-pyrido[2,3-d]pyrimidin-4-ylamino)-benzamide To the product from Example 10 and sodium triacetoxyborohydride in 9/1 dichloromethane/methanol was added cyclopropanecarboxaldehyde. The mixture was stirred at room temperature for 2 hours and evaporated. The residue was purified by reverse phase preparative HPLC with the AA method to provide the title compound. 1H NMR (300 MHz, DMSO-D6) δ ppm: 0.20 (m, 2 H) 0.45 (m, 2 H) 1.01 (m, 1 H) 1.32 (d, J=6.62 Hz, 6 H) 2.84 (t, J=6.07 Hz, 2 H) 3.21 (m, 1 H) 5.63 (t, J=5.85 Hz, 1 H) 6.57 (d, J=8.82 Hz, 2 H) 6.84 (m, 3 H) 7.53 (d, J=8.82 Hz, 2 H) 7.60 (d, J=8.82 Hz, 1 H) 7.75 (d, J=8.82 Hz, 2 H) 7.84 (m, 1 H) 8.16 (d, J=1.47 Hz, 1 H) 8.61 (s, 1 H) 8.83 (d, J=8.46 Hz, 1 H) 10.00 (s, 1 H) 10.29 (s, 1 H); MS (ESI+) m/z 623/625 (M+H)+.

Example 288

N-(4-Bromo-phenyl)-4-(4-dimethylamino-phenoxy)-3-(7-isopropyl-pyrido[2,3-d]pyrimidin-4-ylamino)-benzamide To the product from Example 10 and sodium triacetoxyborohydride in 9/1 dichloromethane/methanol was added excess formaldehyde (37% wt in water). The mixture was stirred at room temperature for 2 hours and evaporated. The residue was purified by reverse phase preparative HPLC with the AA method to provide the title compound. 1H NMR (300 MHz, DMSO-D6) δ ppm: 1.32 (d, J=6.62 Hz, 6 H) 2.84 (s, 6 H) 3.20 (m, 1 H) 6.70 (d, J=9.19 Hz, 2 H) 6.88 (d, J=8.46 Hz, 1 H) 6.92 (d, J=9.19 Hz, 2 H) 7.53 (d, J=8.82 Hz, 2 H) 7.59 (d, J=8.46 Hz, 1 H) 7.75 (d, J=9.19 Hz, 2 H) 7.86 (dd, J=8.82, 2.21 Hz, 1 H) 8.16 (d, J=2.21 Hz, 1 H) 8.61 (s, 1 H) 8.81 (d, J=8.46 Hz, 1 H) 10.01 (s, 1 H) 10.30 (s, 1 H); MS (ESI+) m/z 597/599 (M+H)+.

Example 289

N-(4-Bromo-phenyl)-3-(7-isopropyl-pyrido[2,3-d] pyrimidin-4-ylamino)-4-(4-piperidin-1-yl-phenoxy)-benzamide To the product from Example 10 and sodium triacetoxyborohydride in 9/1 dichloromethane/methanol was added glutaraldehyde. The mixture was stirred at room temperature for 2 hours and evaporated. The residue was purified by HPLC with TFA to provide the title compound. 1H NMR (300 MHz, DMSO-D6) δ ppm: 1.34 (d, J=6.99 Hz, 6 H) 1.52 (m, 2 H) 1.57 (m, 4 H) 3.07 (m, 4 H) 3.26 (m, 1 H) 6.96 (s, 4 H) 7.05 (d, J=8.46 Hz, 1 H) 7.55 (d, J=8.82 Hz, 2 H), 7.75 (d, J=8.82 Hz, 2 H) 7.83 (d, J=8.82 Hz, 1 H) 7.99 (d, J=8.82 Hz, 1 H) 8.12 (s, 1 H) 8.85 (s, 1 H) 8.92 (d, J=8.46 Hz, 1 H) 10.38 (s, 1 H) 11.29 (s, 1 H); MS (ESI+) m/z 637/639 (M+H)+.

Example 290

N-(5-Bromo-pyridin-2-yl)-3-(7-isopropyl-pyrido[2,3-d]pyrimidin-4-ylamino)-4-(4-propylamino-phenylsulfanyl)-benzamide To the product from Example 17 and sodium triacetoxyborohydride in 9/1 dichloromethane/methanol was added propionaldehyde. The mixture was stirred at room temperature for 2 hours and evaporated. The residue was purified by reverse phase preparative HPLC with the AA method to provide the title compound. 1H NMR (300 MHz, DMSO-D6) δ ppm: 0.95 (t, J=7.35 Hz, 3 H) 1.34 (d, J=6.99 Hz, 6 H) 1.57 (m, 2 H) 2.99 (m, 2 H) 3.24 (m, 1 H) 6.16 (t, J=5.16 Hz, 1 H) 6.64 (d, J=8.82 Hz, 2 H) 6.83 (d, J=8.46 Hz, 1 H) 7.20 (d, J=8.82 Hz, 2 H) 7.63 (d, J=8.46 Hz, 1 H) 7.86 (d, J=8.46 Hz, 1 H) 8.04 (d, J=2.57 Hz, 1 H) 8.07 (d, J=2.57 Hz, 1 H) 8.16 (m, 1 H) 8.49 (d, J=2.57 Hz, 1 H) 8.58 (s, 1 H) 8.87 (d, J=8.46 Hz, 1 H) 10.13 (s, 1 H) 10.91 (s, 1 H); MS (ESI+) m/z 628/630 (M+H)+.

Example 291

N-(5-Bromo-pyridin-2-yl)-3-(7-isopropyl-pyrido[2,3-d]pyrimidin-4-ylamino)-4-[4-(methyl-propyl-amino)-phenylsulfanyl]-benzamide To the product from Example 290 and sodium triacetoxyborohydride in 9/1 dichloromethane/methanol was added excess formaldehyde (37% in water). The mixture was stirred at room temperature for 2 hours and evaporated. The residue was purified by reverse phase preparative HPLC with the AA method to provide the title compound. 1H NMR (300 MHz, DMSO-D6) δ ppm: 0.88 (t, J=7.35 Hz, 3 H) 1.34 (d, J=6.99 Hz, 6 H) 1.54 (m, 2 H) 2.93 (s, 3 H) 3.25 (m, 3 H) 6.75 (d, J=9.19 Hz, 2 H) 6.85 (d, J=7.72 Hz, 1 H) 7.27 (d, J=8.82 Hz, 2 H) 7.63 (d, J=8.46 Hz, 1 H) 7.87 (d, J=8.46 Hz, 1 H) 8.04 (d, J=2.57 Hz, 1 H) 8.07 (d, J=2.21 Hz, 1 H) 8.17 (m, 1 H) 8.49 (d, J=2.21 Hz, 1 H) 8.58 (s, 1 H) 8.88 (d, J=8.82 Hz, 1 H) 10.13 (s, 1 H) 10.91 (s, 1 H); MS (ESI+) m/z 642/644 (M+H)+.

Example 292

N-(5-Bromo-pyridin-2-yl)-4-[4-(ethyl-propyl-amino)-phenylsulfanyl]-3-(7-isopropyl-pyrido[2,3-d]pyrimidin-4-ylamino)-benzamide To the product from Example 290 and sodium triacetoxyborohydride in 9/1 dichloromethane/methanol was added excess acetaldehyde. The mixture was stirred at room temperature for 2 hours and evaporated. The residue was purified by reverse phase preparative HPLC with the AA method to provide the title compound. 1H NMR (300 MHz, DMSO-D6) δ ppm: 0.90 (t, J=7.35 Hz, 3 H) 1.09 (t, J=6.99 Hz, 3 H) 1.34 (d, J=6.99 Hz, 6 H) 1.55 (m, 2 H) 3.24 (m, 3 H) 3.38 (q, J=6.99 Hz, 2 H) 6.71 (d, J=8.82 Hz, 2 H) 6.87 (d, J=8.82 Hz, 1 H) 7.26 (d, J=8.82 Hz, 2 H) 7.63 (d, J=8.46 Hz, 1 H) 7.88 (d, J=8.46 Hz, 1 H) 8.04 (d, J=2.57 Hz, 1 H) 8.07 (d, J=2.21 Hz, 1 H) 8.17 (m, 1 H) 8.49 (d, J=1.84 Hz, 1 H) 8.58 (s, 1 H) 8.89 (d, J=8.46 Hz, 1 H) 10.13 (s, 1 H) 10.91 (s, 1 H); MS (ESI+) m/z 656/658 (M+H)+.

Example 293

N-(5-Bromo-pyridin-2-yl)-4-(4-dipropylamino-phenylsulfanyl)-3-(7-isopropyl-pyrido[2,3-d]pyrimidin-4-ylamino)-benzamide To the product from Example 17 and sodium triacetoxyborohydride in 9/1 dichloromethane/methanol was added excess propionaldehyde. The mixture was stirred at room temperature for 2 hours and evaporated. The residue was purified by reverse phase preparative HPLC with the AA method to provide the title compound. 1H NMR (300 MHz, DMSO-D6) δ ppm: 0.89 (t, J=7.35 Hz, 6 H), 1.34 (d, J=6.99 Hz, 6 H), 1.45-1.69 (m, 4 H), 3.11-3.30 (m, 5 H), 6.70 (d, J=8.82 Hz, 2 H), 6.87 (d, J=8.46 Hz, 1 H), 7.25 (d, J=8.82 Hz, 2 H), 7.64 (d, J=8.82 Hz, 1 H), 7.87 (dd, J=8.46, 1.84 Hz, 1 H), 8.00-8.09 (m, 2 H), 8.12-8.20 (m, 1 H), 8.49 (d, J=2.57 Hz, 1 H), 8.58 (s, 1 H), 8.88 (d, J=8.46 Hz, 1 H), 10.12 (s, 1 H), 10.91 (s, 1 H); MS (ESI+) m/z 670/672 (M+H)+.

Example 294

4-(4-Amino-phenoxy)-N-(3-fluoro-phenyl)-3-(7-isopropyl-pyrido[2,3-d]pyrimidin-4-ylamino)-benzamide Example 294A {4-[2-Amino-4-(3-fluoro-phenylcarbamoyl)-phenoxy]-phenyl}-carbamic acid tert-butyl ester The product from Example 172a was reacted with 3-fluoroaniline according to the procedure from Example 172b substituting 3-fluoroaniline for 4-Trifluoromethyl-phenylamine followed by reaction according to the procedures from Examples 172c and 172d to provide the title product.

Example 294B 4-(4-Amino-phenoxy)-N-(3-fluoro-phenyl)-3-(7-isopropyl-pyrido[2,3-d]pyrimidin-4-ylamino)-benzamide The product from Example 294A was reacted with the product from Example 8E according to the procedure from Example 172e substituting the product from Example 294A for the product from Example 172d which was deprotected according to the procedure from Example 172f to provide the crude material which was purified by HPLC with TFA to provide the title product as a trifluoroacetic acid salt. 1H NMR (300 MHz, DMSO-D6) δ ppm: 1.34 (d, J=6.62 Hz, 6 H) 3.16-3.37 (m, 1 H) 6.84-7.04 (m, 6 H) 7.34-7.47 (m, 1 H) 7.55 (d, J=8.46 Hz, 1 H) 7.74 (d, J=11.77 Hz, 1 H) 7.87 (d, J=8.46 Hz, 1 H) 8.00 (dd, J=8.82, 2.21 Hz, 1 H) 8.14 (d, J=1.84 Hz, 1 H) 8.88 (s, 1 H) 8.98 (d, J=8.46 Hz, 1 H) 10.45 (s, 1 H); MS (ESI+) m/z 509.3 (M+H)+.

Example 295

4-(4-Amino-phenoxy)-N-(4-bromo-3-fluoro-phenyl)-3-(7-isopropyl-pyrido[2,3-d]pyrimidin-4-ylamino)-benzamide Example 295A {4-[2-Amino-4-(4-bromo-3-fluoro-phenylcarbamoyl)-phenoxy]-phenyl}-carbamic acid tert-butyl ester The product from Example 172a was reacted with 4-bromo-3-fluoroaniline according to the procedure from Example 172b substituting 4-bromo-3-fluoroaniline for 4-Trifluoromethyl-phenylamine followed by reaction according to the procedures from Examples 172c and 172d to provide the title product.

Example 295B 4-(4-Amino-phenoxy)-N-(4-bromo-3-fluoro-phenyl)-3-(7-isopropyl-pyrido[2,3-d]pyrimidin-4-ylamino)-benzamide The product from Example 295A was reacted with the product from Example 8E according to the procedure from Example 172e substituting the product from Example 295A for the product from Example 172d which was deprotected according to the procedure from Example 172f to provide the crude material which was purified by HPLC with TFA to provide the title product as a trifluoroacetic acid salt. 1H NMR (300 MHz, DMSO-D6) δ ppm: 1.34 (d, J=6.99 Hz, 6 H) 3.20-3.35 (m, 1 H) 6.83-7.02 (m, 5 H) 7.54 (dd, J=8.82, 2.21 Hz, 1 H) 7.69 (t, J=8.46 Hz, 1 H) 7.86 (d, J=8.46 Hz, 1 H) 7.91 (dd, J=11.58, 2.39 Hz, 1 H) 7.99 (dd, J=8.82, 2.21 Hz, 1 H) 8.14 (d, J=2.21 Hz, 1 H) 8.87 (s, 1 H) 8.98 (d, J=8.46 Hz, 1 H) 10.55 (s, 1 H); MS (ESI+) m/z 589.2 (M+H)+.

Example 296

4-(4-Amino-phenoxy)-N-(3-bromo-phenyl)-3-(7-isopropyl-pyrido[2,3-d]pyrimidin-4-ylamino)-benzamide Example 296A {4-[2-Amino-4-(3-bromo-phenylcarbamoyl)-phenoxy]-phenyl}-carbamic acid tert-butyl ester The product from Example 172a was reacted with 3-bromoaniline according to the procedure from Example 172b substituting 3-bromoaniline for 4-Trifluoromethyl-phenylamine followed by reaction according to the procedures from Examples 172c and 172d to provide the title product.

Example 296B 4-(4-Amino-phenoxy)-N-(3-bromo-phenyl)-3-(7-isopropyl-pyrido[2,3-d]pyrimidin-4-ylamino)-benzamide The product from Example 296A was reacted with the product from Example 8E according to the procedure from Example 172e substituting the product from Example 296A for the product from Example 172d which was deprotected according to the procedure from Example 172f to provide the crude material which was purified by HPLC with TFA to provide the title product as a trifluoroacetic acid salt. 1H NMR (300 MHz, DMSO-D6) δ ppm: 1.34 (d, J=6.62 Hz, 6 H) 3.22-3.36 (m, 1 H) 6.82-7.02 (m, 5 H) 7.27-7.37 (m, 2 H) 7.72-7.78 (m, 1 H) 7.86 (d, J=8.82 Hz, 1 H) 7.99 (dd, J=8.46, 2.21 Hz, 1 H) 8.09 (s, 1 H) 8.14 (d, J=1.84 Hz, 1 H) 8.87 (s, 1 H) 8.97 (d, J=8.82 Hz, 1 H) 10.39 (s, 1 H); MS (ESI+) m/z 569.2 (M+H)+.

Example 297

{4-[2-(7-Methyl-pyrido[2,3-d]pyrimidin-4-ylamino)-4-(5-methyl-thiazol-2-ylcarbamoyl)-phenoxy]-phenyl}-carbamic acid tert-butyl ester Example 297A {4-[2-Amino-4-(5-methyl-thiazol-2-ylcarbamoyl)-phenoxy]-phenyl}-carbamic acid tert-butyl ester The product from Example 172a was reacted with 5-methyl-thiazol-2-ylamine according to the procedure from Example 172b substituting 5-methyl-thiazol-2-ylamine for 4-Trifluoromethyl-phenylamine followed by reaction according to the procedures from Examples 172c and 172d to provide the title product.

Example 297B

{4-[2-(7-Methyl-pyrido[2,3-d]pyrimidin-4-ylamino)-4-(5-methyl-thiazol-2-ylcarbamoyl)-phenoxy]-phenyl}-carbamic acid tert-butyl ester The product from Example 297A was reacted with the product from Example 9B according to the procedure from Example 172e substituting the product from Example 297A for the product from Example 172d and substituting the product from Example 9B for the product from Example 8E to provide the crude material which was purified by HPLC with TFA to provide the title product as a trifluoroacetic acid salt. 1H NMR (300 MHz, DMSO-D6) δ ppm: 1.47 (s, 9 H) 2.37 (s, 3 H) 2.66 (s, 3 H) 6.89 (d, J=8.46 Hz, 1 H) 6.99 (d, J=9.19 Hz, 2 H) 7.21 (d, J=1.10 Hz, 1 H) 7.45 (d, J=9.19 Hz, 2 H) 7.53 (d, J=8.46 Hz, 1 H) 8.01 (dd, J=8.46, 2.21 Hz, 1 H) 8.34 (d, J=2.21 Hz, 1 H) 8.62 (s, 1 H) 8.77 (d, J=8.46 Hz, 1 H) 9.37 (s, 1 H) 10.00 (s, 1 H) 12.40 (s, 1 H).

Example 298

{4-[2-(7-Isopropyl-pyrido[2,3-d]pyrimidin-4-ylamino)-4-(5-methyl-thiazol-2-ylcarbamoyl)-phenoxy]-phenyl}-carbamic acid tert-butyl ester The product from Example 297A was reacted with the product from Example 9B according to the procedure from Example 172e substituting the product from Example 297A for the product from Example 172d to provide the crude material which was purified by HPLC with TFA to provide the title product as a trifluoroacetic acid salt. 1H NMR (300 MHz, DMSO-D6) δ ppm: 1.32 (d, J=6.99 Hz, 6 H) 1.47 (s, 9 H) 2.37 (s, 3 H) 3.09-3.28 (m, 1 H) 6.89 (d, J=8.46 Hz, 1 H) 6.99 (d, J=8.82 Hz, 2 H) 7.21 (s, 1 H) 7.44 (d, J=8.82 Hz, 2 H) 7.59 (d, J=8.46 Hz, 1 H) 8.02 (dd, J=8.82, 1.84 Hz, 1 H) 8.32 (s, 1 H) 8.62 (s, 1 H) 8.81 (d, J=8.46 Hz, 1 H) 9.37 (s, 1 H) 10.02 (s, 1 H) 12.40 (s, 1 H).

Example 299

4-(4-Amino-phenoxy)-N-(5-tert-butyl-thiazol-2-yl)-3-(7-methyl-pyrido[2,3-d]pyrimidin-4-ylamino)-benzamide Example 299A {4-[2-Amino-4-(5-tert-butyl-thiazol-2-ylcarbamoyl)-phenoxy]-phenyl}-carbamic acid tert-butyl ester The product from Example 172a was reacted with 5-tert-Butyl-thiazol-2-ylamine according to the procedure from Example 172b substituting 5-tert-Butyl-thiazol-2-ylamine for 4-Trifluoromethyl-phenylamine followed by reaction according to the procedures from Examples 172c and 172d to provide the title product.

Example 299B 4-(4-Amino-phenoxy)-N-(5-tert-butyl-thiazol-2-yl)-3-(7-methyl-pyrido[2,3-d]pyrimidin-4-ylamino)-benzamide The product from Example 299A was reacted with the product from Example 9B according to the procedure from Example 172e substituting the product from Example 299A for the product from Example 172d and substituting the product from Example 9B for the product from Example 8E which was deprotected according to the procedure from Example 172f to provide the crude material which was purified by HPLC with TFA to provide the title product as a trifluoroacetic acid salt. 1H NMR (300 MHz, DMSO-D6) δ ppm: 1.29 (s, 9 H) 2.75 (s, 3 H) 4.85 (s, 2 H) 6.81 (s, 1 H) 6.97 (d, J=8.82 Hz, 1 H) 7.03 (s, 4 H) 7.83 (d, J=8.82 Hz, 1 H) 8.18 (dd, J=8.46, 2.21 Hz, 1 H) 8.30 (d, J=2.21 Hz, 1 H) 8.94 (s, 1 H) 8.97 (d, J=8.46 Hz, 1 H) 11.66 (s, 1 H) 12.57 (s, 1 H).

Example 300

4-(4-Amino-phenoxy)-N-(5-tert-butyl-thiazol-2-yl)-3-(7-isopropyl-pyrido[2,3-d]pyrimidin-4-ylamino)-benzamide The product from Example 299A was reacted with the product from Example 8E according to the procedure from Example 172e substituting the product from Example 299A for the product from Example 172d which was deprotected according to the procedure from Example 172f to provide the crude material which was purified by HPLC with TFA to provide the title product as a trifluoroacetic acid salt. 1H NMR (300 MHz, DMSO-D6) δ ppm: 1.29 (s, 9 H) 1.32 (d, J=6.99 Hz, 6 H) 3.12-3.28 (m, 1 H) 5.06 (s, 2 H) 6.58 (d, J=8.82 Hz, 2 H) 6.73-6.87 (m, 3 H) 7.61 (d, J=8.46 Hz, 1 H) 8.02 (dd, J=8.82, 2.21 Hz, 1 H) 8.33 (d, J=2.21 Hz, 1 H) 8.64 (s, 1 H) 8.86 (d, J=8.46 Hz, 1 H) 9.97 (s, 1 H) 12.43 (s, 1 H).

Example 301

2,3-Difluoro-N-[4-(4-hydroxy-phenylsulfanyl)-3-(7-isopropyl-pyrido[2,3-d]pyrimidin-4-ylamino)-phenyl]-benzamide Example 301A N-[3-Amino-4-(4-hydroxy-phenylsulfanyl)-phenyl]-2,3-difluoro-benzamide The title compound was synthesized by reacting 4-fluoro-3-nitro-phenylamine with 2,3-difluorobenzoyl chloride according to the procedure from Example 255a substituting 2,3-difluorobenzoyl chloride for furan-2-carbonyl chloride followed by reaction of the resultant material according to the procedure from Examples 255b and 255c to provide the title product.

Example 301B 2,3-Difluoro-N-[4-(4-hydroxy-phenylsulfanyl)-3-(7-isopropyl-pyrido[2,3-d]pyrimidin-4-ylamino)-phenyl]-benzamide The product from Example 301A was reacted with the product from Example 8E according to the procedure from Example 255d substituting the product from Example 301A for the product from Example 255c to provide the crude product which was purified by HPLC with TFA to provide the title product as a trifluoroacetic acid salt. 1H NMR (300 MHz, DMSO-d6) δ ppm: 1.33 (d, J=7.0 Hz, 6H), 3.22 (seven, J=7.0 Hz, 1H), 6.74 (d, J=8.8 Hz, 2H), 7.08 (d, J=8.5 Hz, 1H), 7.18 (d, J=8.8 Hz, 2H), 7.30-7.39 (m, 1H), 7.44-7.68, (m, 4H), 7.91 (br-s, 1H), 8.75 (s, 1H), 8.83 (d, J=8.5 Hz, 1H), 9.75 (s, 1H), 10.10 (s, 1H), 10.70 (s, 1H); MS (ESI+) m/z 544 (M+H)+.

Example 302

2,4-Difluoro-N-[4-(4-hydroxy-phenylsulfanyl)-3-(7-isopropyl-pyrido[2,3-d]pyrimidin-4-ylamino)-phenyl]-benzamide Example 302A N-[3-Amino-4-(4-hydroxy-phenylsulfanyl)-phenyl]-2,4-difluoro-benzamide The title compound was synthesized by reacting 4-fluoro-3-nitro-phenylamine with 2,4-difluorobenzoyl chloride according to the procedure from Example 255a substituting 2,4-difluorobenzoyl chloride for furan-2-carbonyl chloride followed by reaction of the resultant material according to the procedure from Examples 255b and 255c to provide the title product.

Example 302B 2,4-Difluoro-N-[4-(4-hydroxy-phenylsulfanyl)-3-(7-isopropyl-pyrido[2,3-d]pyrimidin-4-ylamino)-phenyl]-benzamide The product from Example 302A was reacted with the product from Example 8E according to the procedure from Example 255d substituting the product from Example 302A for the product from Example 255c to provide the crude product which was purified by HPLC with TFA to provide the title product as a trifluoroacetic acid salt. 1H NMR (300 MHz, DMSO-d6) δ ppm: 1.33 (d, J=7.0 Hz, 6H), 3.22 (seven, J=7.0 Hz, 1H), 6.73 (d, J=8.8 Hz, 2H), 7.08 (d, J=8.5 Hz, 1H), 7.18 (d, J=8.8 Hz, 2H), 7.24 (dd, J=8.5, 2.2 Hz, 1H), 7.43 (td, J=10.0, 2.3 Hz, 1H), 7.53 (br-d, J=8.1 Hz, 1H), 7.62 (d, J=8.5 Hz, 1H), 7.54 (dd, J=15.1, 8.5 Hz, 1H), 7.90 (br-s, 1H), 8.56 (s, 1H), 8.82 (d, J=8.5 Hz, 1H), 9.73 (s, 1H), 10.09 (s, 1H), 10.56 (s, 1H); MS (ESI+) m/z 544 (M+H)+.

Example 303

3,5-Difluoro-N-[4-(4-hydroxy-phenylsulfanyl)-3-(7-isopropyl-pyrido[2,3-d]pyrimidin-4-ylamino)-phenyl]-benzamide Example 303A N-[3-Amino-4-(4-hydroxy-phenylsulfanyl)-phenyl]-3,5-difluoro-benzamide The title compound was synthesized by reacting 4-fluoro-3-nitro-phenylamine with 3,5-difluorobenzoyl chloride according to the procedure from Example 255a substituting 3,5-difluorobenzoyl chloride for furan-2-carbonyl chloride followed by reaction of the resultant material according to the procedure from Examples 255b and 255c to provide the title product.

Example 303B 3,5-Difluoro-N-[4-(4-hydroxy-phenylsulfanyl)-3-(7-isopropyl-pyrido[2,3-d]pyrimidin-4-ylamino)-phenyl]-benzamide The product from Example 303A was reacted with the product from Example 8E according to the procedure from Example 255d substituting the product from Example 303A for the product from Example 255c to provide the crude product which was purified by HPLC with TFA to provide the title product as a trifluoroacetic acid salt. 1H NMR (300 MHz, DMSO-d6) δ ppm: 1.33 (d, J=7.0 Hz, 6H), 3.22 (seven, J=7.0 Hz, 1H), 6.74 (d, J=8.5 Hz, 2H), 7.07 (br-d, J=8.8 Hz, 1H), 7.20 (d, J=8.5 Hz, 2H), 7.47-7.74 (m, 5H), 7.94 (br-s, 1H), 8.56 (s, 1H), 8.83 (br-d, J=8.1 Hz, 1H), 9.75 (s, 1H), 10.09 (s, 1H), 10.48 (s, 1H); MS (ESI+) m/z 544 (M+H)+.

Example 304

3-Fluoro-N-[4-(4-hydroxy-phenylsulfanyl)-3-(7-isopropyl-pyrido[2,3-d]pyrimidin-4-ylamino)-phenyl]-4-methoxy-benzamide Example 304A N-[3-Amino-4-(4-hydroxy-phenylsulfanyl)-phenyl]-3-fluoro-4-methoxy-benzamide The title compound was synthesized by reacting 4-fluoro-3-nitro-phenylamine with 3-fluoro-4-methoxybenzoyl chloride according to the procedure from Example 255a substituting 3-fluoro-4-methoxybenzoyl chloride for furan-2-carbonyl chloride followed by reaction of the resultant material according to the procedure from Examples 255b and 255c to provide the title product.

Example 304B

3-Fluoro-N-[4-(4-hydroxy-phenylsulfanyl)-3-(7-isopropyl-pyrido[2,3-d]pyrimidin-4-ylamino)-phenyl]-4-methoxy-benzamide The product from Example 304A was reacted with the product from Example 8E according to the procedure from Example 255d substituting the product from Example 304A for the product from Example 255c to provide the crude product which was purified by HPLC with TFA to provide the title product as a trifluoroacetic acid salt. 1H NMR (300 MHz, DMSO-D6) δ ppm: 1.35 (d, J=6.99 Hz, 6 H) 3.20-3.33 (m, 1H) 3.92 (s, 3 H) 6.71 (d, 2 H) 7.13 (d, 1 H) 7.17 (d, 2H) 7.32 (t, J=8.64 Hz, 1 H) 7.62 (dd, J=8.64, 2.02 Hz, 1 H) 7.77 (d, 1 H) 7.83 (d, 2H) 7.98 (s, 1 H) 8.71 (s, 1 H) 8.92 (d, J=8.46 Hz, 1 H) 9.77 (s, 1 H) 10.33 (s, 1 H); (ESI+) m/z 556 (M+H)+.

Example 305

3,4-Dichloro-N-[4-(4-hydroxy-phenylsulfanyl)-3-(7-isopropyl-pyrido[2,3-d]pyrimidin-4-ylamino)-phenyl]-benzamide Example 305A N-[3-Amino-4-(4-hydroxy-phenylsulfanyl)-phenyl]-3,4-dichloro-benzamide The title compound was synthesized by reacting 4-fluoro-3-nitro-phenylamine with 3,4-dichlorobenzoyl chloride according to the procedure from Example 255a substituting 3,4-dichlorobenzoyl chloride for furan-2-carbonyl chloride followed by reaction of the resultant material according to the procedure from Examples 255b and 255c to provide the title product.

Example 305B 3,4-Dichloro-N-[4-(4-hydroxy-phenylsulfanyl)-3-(7-isopropyl-pyrido[2,3-d]pyrimidin-4-ylamino)-phenyl]-benzamide The product from Example 305A was reacted with the product from Example 8E according to the procedure from Example 255d substituting the product from Example 305A for the product from Example 255c to provide the crude product which was purified by HPLC with TFA to provide the title product as a trifluoroacetic acid salt. 1H NMR (300 MHz, DMSO-D6) δ ppm: 1.34 (d, J=6.62 Hz, 6 H) 3.20-3.33 (m, 1 H) 6.71 (d, 2 H) 7.08-7.21 (m, 3 H) 7.61 (dd, J=8.46 Hz, 1 H) 7.80 (d, J=9.19 Hz, 2 H) 7.94 (dd, 1 H) 7.97 (s, 1 H) 8.20 (s, 1 H) 8.72 (s, 1 H) 8.92 (d, J=8.46 Hz, 1 H) 9.78 (s, 1 H) 10.58 (s, 1 H); MS (ESI+) m/z 576 (M+H)+.

Example 306

2,5-Difluoro-N-[4-(4-hydroxy-phenylsulfanyl)-3-(7-isopropyl-pyrido[2,3-d]pyrimidin-4-ylamino)-phenyl]-benzamide Example 306A N-[3-Amino-4-(4-hydroxy-phenylsulfanyl)-phenyl]-2,5-difluoro-benzamide The title compound was synthesized by reacting 4-fluoro-3-nitro-phenylamine with 2,5-difluorobenzoyl chloride according to the procedure from Example 255a substituting 2,5-difluorobenzoyl chloride for furan-2-carbonyl chloride followed by reaction of the resultant material according to the procedure from Examples 255b and 255c to provide the title product.

Example 306B 2,5-Difluoro-N-[4-(4-hydroxy-phenylsulfanyl)-3-(7-isopropyl-pyrido[2,3-d]pyrimidin-4-ylamino)-phenyl]-benzamide The product from Example 306A was reacted with the product from Example 8E according to the procedure from Example 255d substituting the product from Example 306A for the product from Example 255c to provide the crude product which was purified by HPLC with TFA followed by neutralization and addition of aqueous hydrochloric acid to provide the title product as a hydrochloric acid salt. 1H NMR (300 MHz, DMSO-d6) δ ppm: 1.37 (d, J=7.0 Hz, 6H), 3.31 (septet, J=7.0 Hz, 1H), 6.70 (d, J=8.5 Hz, 2H), 7.17 (d, J=8.5 Hz, 2H), 7.20 (d, J=8.5 Hz, 1H), 7.38-7.60 (m, 4H), 7.96 (d, J=8.8 Hz, 1H), 7.98 (d, J=2.2 Hz, 1H), 8.89 (s, 1H), 9.16 (d, J=8.8 Hz, 1H), 9.83 (br-s, 1H), 10.79 (s, 1H), 12.12 (br-s, 1H); MS (ESI+) m/z 544 (M+H)+.

Example 307

2-Fluoro-N-[4-(4-hydroxy-phenylsulfanyl)-3-(7-isopropyl-pyrido[2,3-d]pyrimidin-4-ylamino)-phenyl]-benzamide

Example 307A

N-[3-Amino-4-(4-hydroxy-phenylsulfanyl)-phenyl]-2-fluoro-benzamide

The title compound was synthesized by reacting 4-fluoro-3-nitro-phenylamine with 2-fluorobenzoyl chloride according to the procedure from Example 255a substituting 2-fluorobenzoyl chloride for furan-2-carbonyl chloride followed by reaction of the resultant material according to the procedure from Examples 255b and 255c to provide the title product.

Example 307B

2-Fluoro-N-[4-(4-hydroxy-phenylsulfanyl)-3-(7-isopropyl-pyrido[2,3-d]pyrimidin-4-ylamino)-phenyl]-benzamide The product from Example 307A was reacted with the product from Example 8E according to the procedure from Example 255d substituting the product from Example 307A for the product from Example 255c to provide the crude product which was purified by HPLC with TFA to provide the title product as a trifluoroacetic acid salt. 1H NMR (300 MHz, DMSO-d6) δ ppm: 1.33 (d, J=7.0 Hz, 6H), 3.22 (septet, J=7.0 Hz, 1H), 6.73 (d, J=8.8 Hz, 2H), 7.08 (d, J=8.5 Hz, 1H), 7.18 (d, J=8.8 Hz, 2H), 7.28-7.40 (m, 2H), 7.48-7.70 (m, 4H), 7.92 (s, 1H), 8.56 (s, 1H), 8.82 (d, J=8.5 Hz, 1H), 9.73 (s, 1H), 10.12 (s, 1H), 10.57 (s, 1H); MS (ESI+) m/z 526 (M+H)+.

Example 308

1H-Pyrrole-2-carboxylic acid [4-(4-hydroxy-phenylsulfanyl)-3-(7-isopropyl-pyrido[2,3-d]pyrimidin-4-ylamino)-phenyl]-amide

Example 308A

1H-Pyrrole-2-carboxylic acid [3-amino-4-(4-hydroxy-phenylsulfanyl)-phenyl]-amide The title compound was synthesized by reacting 4-fluoro-3-nitro-phenylamine with 1H-pyrrole-2-carbonyl chloride according to the procedure from Example 255a substituting 1H-pyrrole-2-carbonyl chloride for furan-2-carbonyl chloride followed by reaction of the resultant material according to the procedure from Examples 255b and 255c to provide the title product.

Example 308B

1H-Pyrrole-2-carboxylic acid [4-(4-hydroxy-phenylsulfanyl)-3-(7-isopropyl-pyrido[2,3-d]pyrimidin-4-ylamino)-phenyl]-amide The product from Example 308A was reacted with the product from Example 8E according to the procedure from Example 255d substituting the product from Example 308A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.62 Hz, 6 H), 6.09-6.19 (m, 1 H), 6.68 (d, J=8.82 Hz, 2 H), 6.97 (s, 1H), 7.06 (s, 1 H), 7.11-7.19 (m, 3 H), 7.61-7.67 (m, 1 H), 7.86 (d, J=8.46 Hz, 1 H), 7.95 (s, 1 H), 8.79 (s, 1 H), 8.96 (d, J=9.56 Hz, 1 H), 9.74 (s, 1 H), 9.95 (s, 1 H), 11.65 (d, J=1.47 Hz, 1 H); MS (ESI+) m/z 497 (M+H)+.

Example 309

4-Hydroxy-N-[4-(4-hydroxy-phenylsulfanyl)-3-(7-isopropyl-pyrido[2,3-d]pyrimidin-4-ylamino)-phenyl]-benzamide

Example 309A

N-[3-Amino-4-(4-hydroxy-phenylsulfanyl)-phenyl]-4-hydroxy-benzamide

The title compound was synthesized by reacting 4-fluoro-3-nitro-phenylamine with 4-hydroxybenzoyl chloride according to the procedure from Example 255a substituting 4-hydroxybenzoyl chloride for furan-2-carbonyl chloride followed by reaction of the resultant material according to the procedure from Examples 255b and 255c to provide the title product.

Example 309B

4-Hydroxy-N-[4-(4-hydroxy-phenylsulfanyl)-3-(7-isopropyl-pyrido[2,3-d]pyrimidin-4-ylamino)-phenyl]-benzamide The product from Example 309A was reacted with the product from Example 8E according to the procedure from Example 255d substituting the product from Example 309A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.99 Hz, 6 H) 3.27-3.34 (m, 1 H) 6.68 (d, 2 H) 6.85 (d, 2 H) 7.18 (m, 3H) 7.63 (dd, J=8.64, 2.39 Hz, 1 H) 7.84 (m, 3 H) 8.02 (s, 1 H) 8.79 (s, 1 H) 8.98 (d, 1 H) 9.76 (s, 1 H, ) 10.15 (s, 1H), 10.21 (s, 1H); MS (ESI+) m/z 524 (M+H)+.

Example 310

N-[4-(4-Hydroxy-phenylsulfanyl)-3-(7-isopropyl-pyrido[2,3-d]pyrimidin-4-ylamino)-phenyl]-2-methoxy-benzamide Example 310A N-[3-Amino-4-(4-hydroxy-phenylsulfanyl)-phenyl]-2-methoxy-benzamide The title compound was synthesized by reacting 4-fluoro-3-nitro-phenylamine with 2-methoxybenzoyl chloride according to the procedure from Example 255a substituting 2-methoxybenzoyl chloride for furan-2-carbonyl chloride followed by reaction of the resultant material according to the procedure from Examples 255b and 255c to provide the title product.

Example 310B

N-[4-(4-Hydroxy-phenylsulfanyl)-3-(7-isopropyl-pyrido[2,3-d]pyrimidin-4-ylamino)-phenyl]-2-methoxy-benzamide The product from Example 310A was reacted with the product from Example 8E according to the procedure from Example 255d substituting the product from Example 310A for the product from Example 255c to provide the title product as an acetic acid salt. 1H NMR (300 MHz, DMSO-D6) δ ppm: 1.33 (d, J=6.99 Hz, 6 H), 3.23 (dd, J=12.87, 6.62 Hz, 1 H), 3.87 (s, 3 H), 6.72 (d, J=8.46 Hz, 2 H), 7.05 (t, J=7.91 Hz, 2 H), 7.16 (dd, J=8.64, 2.39 Hz, 3 H), 7.47-7.62 (m, 4 H), 7.93 (s, 1 H), 8.55 (s, 1 H), 8.82 (d, J=8.09 Hz, 1 H), 9.71 (s, 1 H), 10.09 (s, 1 H), 10.25 (s, 1 H).

Example 311

3-Hydroxy-N-[4-(4-hydroxy-phenylsulfanyl)-3-(7-isopropyl-pyrido[2,3-d]pyrimidin-4-ylamino)-phenyl]-benzamide Example 311A N-[3-Amino-4-(4-hydroxy-phenylsulfanyl)-phenyl]-3-hydroxy-benzamide The title compound was synthesized by reacting 4-fluoro-3-nitro-phenylamine with 3-hydroxybenzoyl chloride according to the procedure from Example 255a substituting 3-hydroxybenzoyl chloride for furan-2-carbonyl chloride followed by reaction of the resultant material according to the procedure from Examples 255b and 255c to provide the title product.

Example 311B

3-Hydroxy-N-[4-(4-hydroxy-phenylsulfanyl)-3-(7-isopropyl-pyrido[2,3-d]pyrimidin-4-ylamino)-phenyl]-benzamide The product from Example 311A was reacted with the product from Example 8E according to the procedure from Example 255d substituting the product from Example 311A for the product from Example 255c to provide the crude product which was purified by HPLC with TFA followed by neutralization and addition of aqueous hydrobromic acid to provide the title product as a hydrobromic acid salt. 1H NMR (300 MHz, DMSO-D6) δ ppm: 1.39 (d, J=6.62 Hz, 6 H), 3.29-3.38 (m, 1 H), 6.69 (d, J=8.46 Hz, 2 H), 6.96-7.04 (m, 1 H), 7.17 (d, J=8.46 Hz, 2 H), 7.25 (d, J=8.82 Hz, 1 H), 7.29-7.41 (m, 3 H), 7.70 (dd, J=8.82, 2.57 Hz, 1 H), 7.96 (d, J=8.82 Hz, 1 H), 8.05-8.15 (m, 1 H), 8.93 (s, 1 H), 9.09 (d, J=8.46 Hz, 1 H); MS (ESI+) m/z 524 (M+H)+.

Example 312

4-Acetylamino-N-[4-(4-hydroxy-phenylsulfanyl)-3-(7-isopropyl-pyrido[2,3-d]pyrimidin-4-ylamino)-phenyl]-benzamide Example 312A 4-Acetylamino-N-[3-amino-4-(4-hydroxy-phenylsulfanyl)-phenyl]-benzamide The title compound was synthesized by reacting 4-fluoro-3-nitro-phenylamine with 4-acetylaminobenzoyl chloride according to the procedure from Example 255a substituting 4-acetylaminobenzoyl chloride for furan-2-carbonyl chloride followed by reaction of the resultant material according to the procedure from Examples 255b and 255c to provide the title product.

Example 312B

4-Acetylamino-N-[4-(4-hydroxy-phenylsulfanyl)-3-(7-isopropyl-pyrido[2,3-d]pyrimidin-4-ylamino)-phenyl]-benzamide The product from Example 312A was reacted with the product from Example 8E according to the procedure from Example 255d substituting the product from Example 312A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.99 Hz, 6 H) 2.08 (s, 3 H) 3.24-3.34 (m, 1 H) 6.67 (d, 2 H) 7.18 (m, 3 H) 7.63 (dd, J=8.64, 2.39 Hz, 1 H) 7.71 (d, J=9.19 Hz, 2 H) 7.91 (m, 3 H) 8.02 (s,1H) 8.80 (s, 1 H) 8.98 (d, 1 H) 9.97 (s, 1 H) 10.23 (s, 1H), 10.34 (s, 1H); MS (ESI+) m/z 556 (M+H)+.

Example 313

2-Chloro-N-[4-(4-hydroxy-phenylsulfanyl)-3-(7-isopropyl-pyrido[2,3-d]pyrimidin-4-ylamino)-phenyl]-4-trifluoromethyl-benzamide

Example 313A

N-[3-Amino-4-(4-hydroxy-phenylsulfanyl)-phenyl]-2-chloro-4-trifluoromethyl-benzamide The title compound was synthesized by reacting 4-fluoro-3-nitro-phenylamine with 2-chloro-4-trifluoromethylbenzoyl chloride according to the procedure from Example 255a substituting 2-chloro-4-trifluoromethylbenzoyl chloride for furan-2-carbonyl chloride followed by reaction of the resultant material according to the procedure from Examples 255b and 255c to provide the title product.

Example 313B

2-Chloro-N-[4-(4-hydroxy-phenylsulfanyl)-3-(7-isopropyl-pyrido[2,3-d]pyrimidin-4-ylamino)-phenyl]-4-trifluoromethyl-benzamide The product from Example 313A was reacted with the product from Example 8E according to the procedure from Example 255d substituting the product from Example 313A for the product from Example 255c to provide the crude product which was purified by HPLC with TFA to provide the title product as a trifluoroacetic acid salt. 1H NMR (300 MHz, DMSO-D6) δ ppm: 1.35 (d, J=6.99 Hz, 6 H) 3.20-3.33 (m, 1H) 6.70 (d, 2 H) 7.18 (m, 3 H) 7.53 (dd, J=8.64, 2.02 Hz, 1 H) 7.82-7.91 (m, 3 H) 7.98 (s, 1H) 8.04 (s, 1 H) 8.84 (s, 1 H) 8.92 (d, J=8.46 Hz, 1 H) 9.80 (s, 1 H) 10.89 (s, 1 H); MS (ESI+) m/z 610 (M+H)+.

Example 314

N-[4-(4-Hydroxy-phenylsulfanyl)-3-(7-isopropyl-pyrido[2,3-d]pyrimidin-4-ylamino)-phenyl]-4-methoxy-benzamide

Example 314A

N-[3-Amino-4-(4-hydroxy-phenylsulfanyl)-phenyl]-4-methoxy-benzamide

The title compound was synthesized by reacting 4-fluoro-3-nitro-phenylamine with 4-methoxybenzoyl chloride according to the procedure from Example 255a substituting 4-methoxybenzoyl chloride for furan-2-carbonyl chloride followed by reaction of the resultant material according to the procedure from Examples 255b and 255c to provide the title product.

Example 314B

N-[4-(4-Hydroxy-phenylsulfanyl)-3-(7-isopropyl-pyrido[2,3-d]pyrimidin-4-ylamino)-phenyl]-4-methoxy-benzamide The product from Example 314A was reacted with the product from Example 8E according to the procedure from Example 255d substituting the product from Example 314A for the product from Example 255c to provide the crude product which was purified by HPLC with TFA to provide the title product as a trifluoroacetic acid salt. 1H NMR (300 MHz, DMSO-D6) δ ppm: 1.16 (d, J=6.99 Hz, 6 H) 1.36 (d, J=6.99 Hz, 6 H) 2.76-2.89 (m, 1 H) 3.22-3.37 (m, 1 H) 3.83 (s, 3 H) 6.55 (d, J=7.72 Hz, 1 H) 6.68 (d, J=8.82 Hz, 2 H) 7.06 (d, J=9.19 Hz, 2 H) 7.16 (d, J=8.82 Hz, 2 H) 7.20 (s, 1 H) 7.65 (dd, J=8.64, 2.39 Hz, 1 H) 7.77 (d, J=7.72 Hz, 1 H) 7.90 (s, 1 H) 7.95 (d, J=9.19 Hz, 2 H) 8.04 (d, J=2.21 Hz, 1 H) 8.84 (s, 1 H) 9.00 (d, J=8.46 Hz, 1 H) 9.78 (s, 1 H) 10.33 (s, 1 H) 11.70 (s, 1 H); MS (ESI+) m/z 538 (M+H)+.

Example 315

N-[4-(4-Hydroxy-phenylsulfanyl)-3-(7-methyl-pyrido[2,3-d]pyrimidin-4-ylamino)-phenyl]-4-methoxy-benzamide The product from Example 314A was reacted with the product from Example 9B according to the procedure from Example 255d substituting the product from Example 314A for the product from Example 255c and substituting the product from Example 9B for the product from Example 8E to provide the crude product which was purified by HPLC with TFA to provide the title product as a trifluoroacetic acid salt. 1H NMR (300 MHz, DMSO-D6) δ ppm: 2.73 (s, 3 H) 3.83 (s, 3 H) 6.69 (d, J=8.82 Hz, 2 H) 7.06 (d, J=9.19 Hz, 2 H) 7.16 (d, J=8.82 Hz, 2 H) 7.63 (dd, J=8.64, 2.39 Hz, 1 H) 7.74 (d, J=8.46 Hz, 1 H) 7.94 (d, J=8.82 Hz, 2 H) 8.02 (d, J=1.47 Hz, 1 H) 8.73 (s, 1 H) 8.89 (d, J=8.46 Hz, 1 H) 9.75 (s, 1 H) 10.28 (s, 1 H) 11.13 (s, 1 H); MS (ESI+) m/z 510 (M+H)+.

Example 316

N-[4-(3-Hydroxy-phenylsulfanyl)-3-(7-isopropyl-pyrido[2,3-d]pyrimidin-4-ylamino)-phenyl]-4-methoxy-benzamide

Example 316A

N-[3-Amino-4-(3-hydroxy-phenylsulfanyl)-phenyl]-4-methoxy-benzamide

The title compound was synthesized by reacting 4-fluoro-3-nitro-phenylamine with 4-methoxybenzoyl chloride according to the procedure from Example 255a substituting 4-methoxybenzoyl chloride for furan-2-carbonyl chloride followed by reaction of the resultant material according to the procedure from Example 255b substituting 3-mercapto-phenol for 4-mercapto-phenol and Example 255c to provide the title product.

Example 316B

N-[4-(3-Hydroxy-phenylsulfanyl)-3-(7-isopropyl-pyrido[2,3-d]pyrimidin-4-ylamino)-phenyl]-4-methoxy-benzamide The product from Example 316A was reacted with the product from Example 8E according to the procedure from Example 255d substituting the product from Example 316A for the product from Example 255c to provide the crude product which was purified by HPLC with TFA to provide the title product as a trifluoroacetic acid salt. 1H NMR (300 MHz, DMSO-D6) δ ppm: 1.35 (d, J=6.99 Hz, 6 H) 3.22-3.35 (m, 1 H) 3.84 (s, 3 H) 6.45-6.60 (m, 3 H) 6.94 (t, J=7.91 Hz, 1 H) 7.08 (d, J=8.82 Hz, 2 H) 7.52 (d, J=8.46 Hz, 1 H) 7.76 (dd, J=8.64, 2.39 Hz, 1 H) 7.85 (d, J=8.82 Hz, 1 H) 7.97 (d, J=9.19

Hz, 2 H) 8.14 (d, J=2.21 Hz, 1 H) 8.77 (s, 1 H) 8.92 (d, J=8.46 Hz, 1 H) 9.51 (s, 1 H) 10.42 (s, 1 H) 11.55 (s, 1 H); MS (ESI+) m/z 538 (M+H)+.

Example 317

N-[4-(3-Hydroxy-phenylsulfanyl)-3-(pyrido[2,3-d]pyrimidin-4-ylamino)-phenyl]-4-methoxy-benzamide The product from Example 316A was reacted with the product from Example 29A according to the procedure from Example 255d substituting the product from Example 316A for the product from Example 255c and substituting the product from Example 29A for the product from Example 8E to provide the crude product which was purified by HPLC with TFA to provide the title product as a trifluoroacetic acid salt. 1H NMR (300 MHz, DMSO-D6) δ ppm: 3.84 (s, 3 H) 6.42-6.64 (m, 3 H) 6.95 (t, J=7.91 Hz, 1 H) 7.08 (d, J=8.82 Hz, 2 H) 7.52 (d, J=8.46 Hz, 1 H) 7.75 (dd, J=8.64, 2.39 Hz, 1 H) 7.84 (dd, J=8.27, 4.60 Hz, 1 H) 7.97 (d, J=8.82 Hz, 2 H) 8.15 (d, J=1.84 Hz, 1 H) 8.77 (s, 1 H) 8.98 (dd, J=8.27, 1.29 Hz, 1 H) 9.14 (dd, J=4.41, 1.47 Hz, 1 H) 9.52 (s, 1 H) 10.41 (s, 1 H) 11.47 (s, 1 H); MS (ESI+) m/z 496 (M+H)+.

Example 318

N-[4-(4-Hydroxy-phenylsulfanyl)-3-(7-isopropyl-pyrido[2,3-d]pyrimidin-4-ylamino)-phenyl]-3-methoxy-benzamide Example 318A N-[3-Amino-4-(4-hydroxy-phenylsulfanyl)-phenyl]-3-methoxy-benzamide The title compound was synthesized by reacting 4-fluoro-3-nitro-phenylamine with 3-methoxybenzoyl chloride according to the procedure from Example 255a substituting 3-methoxybenzoyl chloride for furan-2-carbonyl chloride followed by reaction of the resultant material according to the procedure from Examples 255b and 255c to provide the title product.

Example 318B

N-[4-(4-Hydroxy-phenylsulfanyl)-3-(7-isopropyl-pyrido[2,3-d]pyrimidin-4-ylamino)-phenyl]-3-methoxy-benzamide The product from Example 318A was reacted with the product from Example 8E according to the procedure from Example 255d substituting the product from Example 318A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.62 Hz, 6 H) 3.22-3.36 (m, 1 H) 3.83 (s, 3 H) 6.70 (d, J=8.82 Hz, 2 H) 7.12-7.21 (m, 4 H) 7.40-7.55 (m, 3 H) 7.64 (dd, J=8.64, 2.39 Hz, 1 H) 7.84 (d, J=8.46 Hz, 1 H) 8.01 (d, J=2.21 Hz, 1 H) 8.77 (s, 1 H) 8.96 (d, J=8.46 Hz, 1 H) 9.78 (s, 1 H) 10.43 (s, 1 H) 11.35 (s, 1 H); MS (ESI+) m/z 538 (M+H)+.

Example 319

N-[4-(4-Hydroxy-phenylsulfanyl)-3-(7-methyl-pyrido[2,3-d]pyrimidin-4-ylamino)-phenyl]-3-methoxy-benzamide The product from Example 318A was reacted with the product from Example 9B according to the procedure from Example 255d substituting the product from Example 318A for the product from Example 255c and substituting the product from Example 9B for the product from Example 8E to provide the crude product which was purified by HPLC with TFA to provide the title product as a trifluoroacetic acid salt. 1H NMR (300 MHz, DMSO-D6) δ ppm: 2.75 (s, 3 H) 3.83 (s, 3 H) 6.69 (d, J=8.46 Hz, 2 H) 7.12-7.21 (m, 4 H) 7.41-7.54 (m, 3 H) 7.64 (dd, J=8.46, 2.21 Hz, 1 H) 7.80 (d, J=8.46 Hz, 1 H) 8.03 (d, J=1.84 Hz, 1 H) 8.80 (s, 1 H) 8.93 (d, J=8.09 Hz, 1 H) 9.77 (s, 1 H) 10.43 (s, 1 H) 11.45 (s, 1 H); MS (ESI+) m/z 510 (M+H)+.

Example 320

N-[4-(3-Hydroxy-phenylsulfanyl)-3-(7-isopropyl-pyrido[2,3-d]pyrimidin-4-ylamino)-phenyl]-3-methoxy-benzamide Example 320A N-[3-Amino-4-(3-hydroxy-phenylsulfanyl)-phenyl]-3-methoxy-benzamide The title compound was synthesized by reacting 4-fluoro-3-nitro-phenylamine with 3-methoxybenzoyl chloride according to the procedure from Example 255a substituting 3-methoxybenzoyl chloride for furan-2-carbonyl chloride followed by reaction of the resultant material according to the procedure from Example 255b substituting 3-mercapto-phenol for 4-mercapto-phenol and Example 255c to provide the title product.

Example 320B

N-[4-(3-Hydroxy-phenylsulfanyl)-3-(7-isopropyl-pyrido[2,3-d]pyrimidin-4-ylamino)-phenyl]-3-methoxy-benzamide The product from Example 320A was reacted with the product from Example 8E according to the procedure from Example 255d substituting the product from Example 320A for the product from Example 255c to provide the crude product which was purified by HPLC with TFA to provide the title product as a trifluoroacetic acid salt. 1H NMR (300 MHz, DMSO-D6) δ ppm: 1.16 (d, J=6.99 Hz, 2 H) 1.35 (d, J=6.62 Hz, 4 H) 2.75-2.87 (m, 1 H) 3.22-3.36 (m, 1 H) 3.84 (s, 3 H) 6.46-6.61 (m, 3 H) 6.95 (t, J=7.91 Hz, 1 H) 7.16-7.23 (m, 1 H) 7.42-7.57 (m, 3 H) 7.74-7.80 (m, 1 H) 7.87 (d, J=8.46 Hz, 1 H) 8.14 (d, J=2.21 Hz, 1 H) 8.80 (s, 1 H) 8.94 (d, J=8.46 Hz, 1 H) 10.56 (s, 1 H) 11.65 (s, 1 H); MS (ESI+) m/z 538 (M+H)+.

Example 321

5-Chloro-N-[4-(4-hydroxy-phenylsulfanyl)-3-(7-isopropyl-pyrido[2,3-d]pyrimidin-4-ylamino)-phenyl]-2-methoxy-benzamide Example 321A N-[3-Amino-4-(4-hydroxy-phenylsulfanyl)-phenyl]-5-chloro-2-methoxy-benzamide The title compound was synthesized by reacting 4-fluoro-3-nitro-phenylamine with 5-chloro-2-methoxybenzoyl chloride according to the procedure from Example 255a substituting 5-chloro-2-methoxybenzoyl chloride for furan-2-carbonyl chloride followed by reaction of the resultant material according to the procedure from Examples 255b and 255c to provide the title product.

Example 321B

5-Chloro-N-[4-(4-hydroxy-phenylsulfanyl)-3-(7-isopropyl-pyrido[2,3-d]pyrimidin-4-ylamino)-phenyl]-2-methoxy-benzamide The product from Example 321A was reacted with the product from Example 8E according to the procedure from Example 255d substituting the product from Example 321A for the product from Example 255c to provide the crude product which was purified by HPLC with TFA to provide the title product as a trifluoroacetic acid salt. 1H NMR (300 MHz, DMSO-D6) δ ppm: 1.35 (t, J=6.07 Hz, 6 H) 3.20-3.35 (m, 1 H) 3.86 (s, 3 H) 6.65-6.72 (m, 2 H) 7.07-7.29 (m, 4 H) 7.51-7.59 (m, 3 H) 7.85 (d, J=8.82 Hz, 1 H) 7.97 (s, 1 H) 8.78 (s, 1 H) 8.96 (d, J=8.46 Hz, 1 H) 9.77 (s, 1 H) 10.41 (s, 1 H); MS (ESI+) m/z 572 (M+H)+.

Example 322

3-Hydroxy-pyridine-2-carboxylic acid [4-(4-hydroxy-phenylsulfanyl)-3-(7-isopropyl-pyrido[2,3-d]pyrimidin-4-ylamino)-phenyl]-amide Example 322A 3-Hydroxy-pyridine-2-carboxylic acid [3-amino-4-(4-hydroxy-phenylsulfanyl)-phenyl]-amide The title compound was synthesized by reacting 4-fluoro-3-nitro-phenylamine with 3-hydroxy-pyridine-2-carbonyl chloride according to the procedure from Example 255a substituting 3-hydroxy-pyridine-2-carbonyl chloride for furan-2-carbonyl chloride followed by reaction of the resultant material according to the procedure from Examples 255b and 255c to provide the title product.

Example 322B

3-Hydroxy-pyridine-2-carboxylic acid [4-(4-hydroxy-phenylsulfanyl)-3-(7-isopropyl-pyrido[2,3-d]pyrimidin-4-ylamino)-phenyl]-amide The product from Example 322A was reacted with the product from Example 8E according to the procedure from Example 255d substituting the product from Example 322A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.62 Hz, 6 H) 3.23-3.34 (m, 1 H) 6.73 (d, J=8.46 Hz, 2 H) 7.11 (d, J=8.82 Hz, 1 H) 7.21 (d, J=8.82 Hz, 2 H) 7.49 (dd, J=8.46, 1.47 Hz, 1 H) 7.59 (d, J=4.41 Hz, 1 H) 7.62 (d, J=4.41 Hz, 1 H) 7.73 (dd, J=8.82, 2.21 Hz, 1 H) 7.86 (d, J=8.46 Hz, 1 H) 8.05 (s, 1 H) 8.26 (d, J=3.31 Hz, 1 H) 8.79 (s, 1 H) 8.97 (d, J=8.46 Hz, 1 H) 9.83 (s, 1 H) 11.10 (s, 1 H); MS (ESI+) m/z 525 (M+H)+.

Example 323

2-Hydroxy-N-[4-(4-hydroxy-phenylsulfanyl)-3-(7-isopropyl-pyrido[2,3-d]pyrimidin-4-ylamino)-phenyl]-nicotinamide Example 323A N-[3-Amino-4-(4-hydroxy-phenylsulfanyl)-phenyl]-2-hydroxy-nicotinamide The title compound was synthesized by reacting 4-fluoro-3-nitro-phenylamine with 2-hydroxy-nicotinoyl chloride according to the procedure from Example 255a substituting 2-hydroxy-nicotinyl chloride for furan-2-carbonyl chloride followed by reaction of the resultant material according to the procedure from Examples 255b and 255c to provide the title product.

Example 323B

2-Hydroxy-N-[4-(4-hydroxy-phenylsulfanyl)-3-(7-isopropyl-pyrido[2,3-d]pyrimidin-4-ylamino)-phenyl]-nicotinamide The product from Example 323A was reacted with the product from Example 8E according to the procedure from Example 255d substituting the product from Example 323A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.62 Hz, 6 H) 3.23-3.40 (m, 1 H) 6.58 (t, J=6.25 Hz, 1 H) 6.66-6.74 (m, 2 H) 7.14-7.22 (m, 3 H) 7.56 (dd, J=8.64, 2.39 Hz, 1 H) 7.79-7.86 (m, 1 H) 7.92 (d, J=8.46 Hz, 1 H) 7.97 (d, J=2.21 Hz, 1 H) 8.43 (dd, J=6.99, 2.21 Hz, 1 H) 8.85 (s, 1 H) 9.00 (d, J=8.46 Hz, 1 H) 9.80 (d, 1 H) 11.71 (d, 1 H) 12.34 (s, 1 H) 12.79 (d, J=6.62 Hz, 1 H); MS (ESI+) m/z 525 (M+H)+.

Example 324

N-[4-(4-Hydroxy-phenylsulfanyl)-3-(7-isopropyl-pyrido[2,3-d]pyrimidin-4-ylamino)-phenyl]-3-methyl-benzamide Example 324A N-[3-Amino-4-(4-hydroxy-phenylsulfanyl)-phenyl]-3-methyl-benzamide The title compound was synthesized by reacting 4-fluoro-3-nitro-phenylamine with 3-methylbenzoyl chloride according to the procedure from Example 255a substituting 3-methylbenzoyl chloride for furan-2-carbonyl chloride followed by reaction of the resultant material according to the procedure from Examples 255b and 255c to provide the title product.

Example 324B

N-[4-(4-Hydroxy-phenylsulfanyl)-3-(7-isopropyl-pyrido[2,3-d]pyrimidin-4-ylamino)-phenyl]-3-methyl-benzamide The product from Example 324A was reacted with the product from Example 8E according to the procedure from Example 255d substituting the product from Example 324A for the product from Example 255c to provide the crude product which was purified by HPLC with TFA to provide the title product as a trifluoroacetic acid salt. MS (ESI+) m/z 522 (M+H)+.

Example 325

4-Dimethylamino-N-[4-(4-hydroxy-phenylsulfanyl)-3-(7-isopropyl-pyrido[2,3-d]pyrimidin-4-ylamino)-phenyl]-benzamide Example 325A N-[3-Amino-4-(4-hydroxy-phenylsulfanyl)-phenyl]-4-dimethylamino-benzamide The title compound was synthesized by reacting 4-fluoro-3-nitro-phenylamine with 4-dimethylamino-benzoyl chloride according to the procedure from Example 255a substituting 4-dimethylamino-benzoyl chloride for furan-2-carbonyl chloride followed by reaction of the resultant material according to the procedure from Examples 255b and 255c to provide the title product.

Example 325B

4-Dimethylamino-N-[4-(4-hydroxy-phenylsulfanyl)-3-(7-isopropyl-pyrido[2,3-d]pyrimidin-4-ylamino)-phenyl]-benzamide The product from Example 325A was reacted with the product from Example 8E according to the procedure from Example 255d substituting the product from Example 325A for the product from Example 255c to provide the crude product which was purified by HPLC with TFA to provide the title product as a trifluoroacetic acid salt. 1H NMR (300 MHz, DMSO-D6) δ ppm: 1.36 (d, J=6.99 Hz, 6 H) 3.00 (s, 6 H) 3.24-3.37 (m, 1 H) 6.67 (d, 2 H) 6.75 (d, J=9.19 Hz, 2 H) 7.13 (d, 2 H) 7.21 (d, J=8.46 Hz, 1 H) 7.65 (dd, J=8.64, 2.39 Hz, 1 H) 7.85 (d, J=9.19 Hz, 2 H) 7.91 (d, J=8.46 Hz, 1 H) 8.05 (d, J=2.21 Hz, 1 H) 8.83 (s, 1 H) 9.01 (d, J=8.82 Hz, 1 H) 10.10 (s, 1 H). (ESI+) m/z 551 (M+H)+.

Example 326

4-Dimethylamino-N-[4-(4-hydroxy-phenylsulfanyl)-3-(7-methyl-pyrido[2,3-d]pyrimidin-4-ylamino)-phenyl]-benzamide The product from Example 325A was reacted with the product from Example 9B according to the procedure from Example 255d substituting the product from Example 325A for the product from Example 255c and substituting the product from Example 9B for the product from Example 8E to provide the crude product which was purified by HPLC with TFA to provide the title product as a trifluoroacetic acid salt. 1H NMR (300 MHz, DMSO-D6) δ ppm: 2.73 (s, 3 H) 2.94 (s, 6 H) 6.61 (d, J=8.82 Hz, 2 H) 6.70 (d, J=9.19 Hz, 2 H) 7.08 (d, J=8.46 Hz, 2 H) 7.16 (d, J=8.82 Hz, 1 H) 7.60 (dd, J=8.46, 2.21 Hz, 1 H) 7.79 (m, 4 H) 8.01 (d, J=1.84 Hz, 1 H) 8.78 (s, 1 H) 8.91 (d, J=8.46 Hz, 1 H) 10.06 (s, 1H); MS (ESI−) m/z 522 (M−H)−.

Example 327

3,4-Dichloro-N-[4-(4-hydroxy-phenylsulfanyl)-3-(pyrido[2,3-d]pyrimidin-4-ylamino)-phenyl]-benzamide The product from Example 305A was reacted with the product from Example 29A according to the procedure from Example 255d substituting the product from Example 305A for the product from Example 255c and substituting the product from Example 29A for the product from Example 8E to provide the crude product which was purified by HPLC with TFA to provide the title product as a trifluoroacetic acid salt. 1H NMR (300 MHz, DMSO-D6) δ ppm: 6.69 (d, 2 H) 7.16-7.20 (m, 3 H) 7.62 (dd, J=8.46, 2.21 Hz, 1 H) 7.82 (d, 1 H) 7.89-7.94 (m, J=8.36, 1.88, 1.88 Hz, 2H) 8.03 (s, 1 H) 8.21(s, 1 H) 8.84 (s, 1 H) 9.05 (d, 1 H) 9.17 (d, 1 H) 10.61 (s, 1 H). ); MS (ESI+) m/z 535 (M+H)+.

Example 328

4-Bromo-N-[4-(4-hydroxy-phenoxy)-3-(7-isopropyl-pyrido[2,3-d]pyrimidin-4-ylamino)-phenyl]-benzamide The product from Example 247d was reacted with pentamethylbenzene in trifluoroacetic acid according to the procedure from Example 43F substituting the product from Example 247d for the product from Example 43F to provide the crude material which was purified by column chromatography on silica gel using methanol/dichloromethane as eluent to provide the title product. 1H NMR (300 MHz, DMSO-D6) δ ppm: 1.24-1.40 (m, 6 H) 3.17-3.28 (m, 1 H) 6.60-6.72 (m, 2 H) 6.75-6.88 (m, 2 H) 6.91 (d, J=8.82 Hz, 1 H) 7.62 (dd, J=9.19, 2.57 Hz, 1 H) 7.71-7.83 (m, 3 H) 7.91 (d, J=8.46 Hz, 2 H) 8.05 (d, J=2.21 Hz, 1 H) 8.77 (s, 1 H) 8.89 (d, J=8.46 Hz, 1 H) 9.26 (s, 1 H) 10.44 (s, 1 H), 10.94 (bs, 1H); MS (ESI+) m/z 570/572 (M+H)+.

Example 329

3-Bromo-N-[4-(4-hydroxy-phenoxy)-3-(7-isopropyl-pyrido[2,3-d]pyrimidin-4-ylamino)-phenyl]-benzamide The product from Example 248b was reacted with pentamethylbenzene in trifluoroacetic acid according to the procedure from Example 43F substituting the product from Example 248b for the product from Example 43F to provide the crude material which was purified by column chromatography on silica gel using methanol/dichloromethane as eluent to provide the title product. 1H NMR (300 MHz, DMSO-D6) δ ppm: 1.31 (d, J=6.99 Hz, 6 H) 3.14-3.26 (m, 1 H) 6.59-6.74 (m, 2 H) 6.75-6.85 (m, 2 H) 6.83-6.94 (m, 1 H) 7.51 (t, J=7.91 Hz, 1 H) 7.57-7.69 (m, 2 H) 7.79 (s, 1 H) 7.96 (d, J=8.09 Hz, 1 H) 8.03 (s, 1 H) 8.15 (s, 1 H) 8.61 (s, 1 H) 8.79 (d, J=8.82 Hz, 1 H) 9.21 (s, 1 H) 10.07 (s, 1 H) 10.42 (s, 1 H); MS (ESI+) m/z 570/572 (M+H)+.

Example 330

N-[4-(4-Hydroxy-phenoxy)-3-(7-isopropyl-pyrido[2,3-d]pyrimidin-4-ylamino)-phenyl]-3-trifluoromethyl-benzamide Example 330A N-[3-Amino-4-(4-hydroxy-phenoxy)-phenyl]-3-trifluoromethyl-benzamide A solution of hydroquinone was heated under a nitrogen atmosphere. A solution of the product from Example 114A was added dropwise. The mixture was then stirred, cooled, poured into water, and adjusted the pH. The mixture was extracted, washed, and concentrated to provide N-[4-(4-Hydroxy-phenoxy)-3-nitro-phenyl]-3-trifluoromethyl-benzamide which was reduced to provide the title product.

Example 330B

N-[4-(4-Hydroxy-phenoxy)-3-(7-isopropyl-pyrido[2,3-d]pyrimidin-4-ylamino)-phenyl]-3-trifluoromethyl-benzamide The product from Example 330A was reacted with the product from Example 8E according to the procedure from Example 255d substituting the product from Example 330A for the product from Example 255c to provide the crude product which was purified by HPLC with TFA to provide the title product as a trifluoroacetic acid salt. 1H NMR (300 MHz, DMSO-D6) δ ppm: 1.34 (d, J=6.99 Hz, 6 H), 3.28 (dt, J=13.70, 6.94 Hz, 1 H), 6.66-6.74 (m, 2 H), 6.82-6.86 (m, 2 H), 6.95 (d, J=8.82 Hz, 1 H), 7.65 (dd, J=8.82, 2.57 Hz, 1 H), 7.77-7.89 (m, 2 H), 7.99 (d, J=7.72 Hz, 1 H), 8.08 (d, J=2.57 Hz, 1 H), 8.24-8.31 (m, 2 H), 8.89 (s, 1 H), 8.96 (d, J=8.46 Hz, 1 H), 9.32 (s, 1 H), 10.63 (s, 1 H), 11.47 (s, 1 H); MS (ESI+) m/z 560 (M+H)+.

Example 331

N-[4-(4-Hydroxy-phenoxy)-3-(7-isopropyl-pyrido[2,3-d]pyrimidin-4-ylamino)-phenyl]-4-methoxy-benzamide

Example 331A

N-[3-Amino-4-(4-hydroxy-phenoxy)-phenyl]-4-methoxy-benzamide

N-(4-Fluoro-3-nitro-phenyl)-4-methoxy-benzamide (from Example 314A) was reacted with hydroquinone according to the procedure from Example 330A to provide N-[4-(4-Hydroxy-phenoxy)-3-nitro-phenyl]-4-methoxy-benzamide which was reduced to provide the title product.

Example 331B

N-[4-(4-Hydroxy-phenoxy)-3-(7-isopropyl-pyrido[2,3-d]pyrimidin-4-ylamino)-phenyl]-4-methoxy-benzamide The product from Example 331A was reacted with the product from Example 8E according to the procedure from Example 255d substituting the product from Example 331A for the product from Example 255c to provide the crude product which was purified by HPLC with TFA to provide the title product as a trifluoroacetic acid salt. 1H NMR (300 MHz, DMSO-D6) δ ppm: 1.33 (d, J=6.99 Hz, 6 H) 3.21-3.34 (m, 1 H) 3.84 (s, 3 H) 6.67 (d, J=9.19 Hz, 2 H) 6.82 (d, J=9.19 Hz, 2 H) 6.92 (d, J=8.82 Hz, 1 H) 7.07 (d, J=8.82 Hz, 2 H) 7.63 (dd, J=8.82, 2.57 Hz, 1 H) 7.81 (d, J=8.82 Hz, 1 H) 7.96 (d, J=8.82 Hz, 2 H) 8.06 (d, J=2.57 Hz, 1 H) 8.83 (s, 1 H) 8.92 (d, J=8.46 Hz, 1 H) 9.27 (s, 1 H) 10.23 (s, 1 H) 11.23 (s, 1 H); MS (ESI+) m/z 522 (M+H)+.

Example 332

The product from Example 17B was reacted with bis-(carbamic acid tert-butyl ester)-thiourea, mercury chloride, and triethylamine in dimethylformamide to provide the crude product which was purified by silica gel flash chromatography using methylene chloride/ethyl acetate as eluent to provide the title product. 1H NMR (300 MHz, DMSO-D6) δ ppm: 1.34 (d, J=6.99 Hz, 6 H) 1.41 (s, 9 H) 1.51 (s, 9 H) 3.16-3.29 (m, 1 H) 7.10 (d, J=8.46 Hz, 1 H) 7.41 (d, J=8.82 Hz, 2 H) 7.63 (d, J=8.82 Hz, 3 H) 7.92 (dd, J=8.46, 1.84 Hz, 1 H) 8.02-8.10 (m, 1 H) 8.12 (d, J=1.84 Hz, 1 H) 8.15-8.22 (m, 1 H) 8.50 (d, J=2.57 Hz, 1 H) 8.59 (s, 1 H) 8.85 (d, J=8.46 Hz, 1 H) 10.06 (s, 1 H) 10.23 (s, 1 H) 11.00 (s, 1 H) 11.30 (s, 1 H).

Example 333

N-(5-Bromo-pyridin-2-yl)-4-(4-guanidino-phenylsulfanyl)-3-(7-isopropyl-pyrido[2,3-d]pyrimidin-4-ylamino)-benzamide The product from Example 332 was reacted with a 50% solution of trifluoroacetic acid in dichloromethane for 2 hours at room temperature. After removal of the solution under vacuum, the residue was purified by silica gel flash chromatography using methanol/chloroform as eluent to provide the title product. 1H NMR (300 MHz, DMSO-D6) δ ppm: 1.34 (d, J=6.99 Hz, 6 H) 3.18-3.30 (m, 1 H) 7.20 (d, J=8.46 Hz, 1 H) 7.26 (d, J=8.46 Hz, 2 H) 7.46 (d, J=8.46 Hz, 2 H) 7.58 (s, 4 H) 7.65 (d, J=8.46 Hz, 1 H) 7.92 (dd, J=8.46, 1.10 Hz, 1 H) 8.07 (dd, 1 H) 8.13-8.24 (m, 2 H) 8.51 (d, J=2.21 Hz, 1 H) 8.59 (s, 1 H) 8.86 (d, J=8.46 Hz, 1 H) 9.91 (s, 1 H) 10.27 (s, 1 H) 11.02 (s, 1 H); MS (ESI+) m/z 628 (M+H)+.

Example 334

N-[4-(4-Amino-phenoxy)-3-(7-isopropyl-pyrido[2,3-d]pyrimidin-4-ylamino)-phenyl]-3-methyl-benzamide

Example 334A

{4-[2-Amino-4-(3-methyl-benzoylamino)-phenoxy]-phenyl}-carbamic acid tert-butyl ester 4-Fluoro-3-nitro-phenylamine was reacted with 3-methylbenzoyl chloride according to the procedure of Example 256a substituting 3-methylbenzoyl chloride for thiophene-2-carbonyl chloride to provide N-(4-Fluoro-3-nitro-phenyl)-3-methyl-benzamide which was then reacted according to the procedures of Examples 256b and 256c to provide the title product.

Example 334B

N-[4-(4-Amino-phenoxy)-3-(7-isopropyl-pyrido[2,3-d]pyrimidin-4-ylamino)-phenyl]-3-methyl-benzamide The product from Example 334A was reacted with the product from Example 8E according to the procedure from Example 256d substituting the product from Example 334A for the product from Example 256c to provide {4-[2-(7-Isopropyl-pyrido[2,3-d]pyrimidin-4-ylamino)-4-(3-methyl-benzoylamino)-phenoxy]-phenyl}-carbamic acid tert-butyl ester which was deprotected according to the procedure from Example 256e to provide the crude product which was purified by HPLC with TFA to provide the title product as a trifluoroacetic acid salt. 1H NMR (300 MHz, DMSO-D6) δ ppm: 1.33 (d, J=6.99 Hz, 6 H), 2.40 (s, 3 H), 3.19-3.34 (m, 1 H), 6.89-6.99 (m, 4 H), 7.03 (d, J=8.82 Hz, 1 H), 7.42 (d, J=5.52 Hz, 2 H), 7.67-7.78 (m, 3 H), 7.83 (d, J=8.46 Hz, 1 H), 8.10 (d, J=2.57 Hz, 1 H), 8.83 (s, 1 H), 8.92 (d, J=8.46 Hz, 1 H), 10.40 (s, 1 H); MS (ESI+) m/z 505 (M+H)+.

Example 335

N-[4-(4-Amino-phenoxy)-3-(7-isopropyl-pyrido[2,3-d]pyrimidin-4-ylamino)-phenyl]-4-methoxy-benzamide Example 335A {4-[2-Amino-4-(4-methoxy-benzoylamino)-phenoxy]-phenyl}-carbamic acid tert-butyl ester 4-Fluoro-3-nitro-phenylamine was reacted with 4-methoxybenzoyl chloride according to the procedure of Example 256a substituting 4-methoxybenzoyl chloride for thiophene-2-carbonyl chloride to provide N-(4-Fluoro-3-nitro-phenyl)-4-methoxy-benzamide which was then reacted according to the procedures of Examples 256b and 256c to provide the title product.

Example 335B

N-[4-(4-Amino-phenoxy)-3-(7-isopropyl-pyrido[2,3-d]pyrimidin-4-ylamino)-phenyl]-4-methoxy-benzamide The product from Example 335A was reacted with the product from Example 8E according to the procedure from Example 256d substituting the product from Example 335A for the product from Example 256c to provide {4-[2-(7-Isopropyl-pyrido[2,3-d]pyrimidin-4-ylamino)-4-(4-methoxy-benzoylamino)-phenoxy]-phenyl}-carbamic acid tert-butyl ester which was deprotected according to the procedure from Example 256e to provide the crude product which was purified by HPLC with TFA to provide the title product as a trifluoroacetic acid salt. 1H NMR (300 MHz, DMSO-D6) δ ppm: 1.33 (d, J=6.99 Hz, 6 H) 3.20-3.33 (m, 1 H) 3.84 (s, 3 H) 6.91-6.97 (m, 2 H) 7.02 (d, J=7.35 Hz, 1 H) 7.08 (d, J=9.19 Hz, 2 H) 7.70 (dd, J=8.82, 2.57 Hz, 1 H) 7.84 (d, J=8.46 Hz, 1 H) 7.97 (d, J=9.19 Hz, 2 H) 8.10 (d, J=2.57 Hz, 1 H) 8.85 (s, 1 H) 8.92 (d, J=8.46 Hz, 1 H) 10.30 (s, 1 H); MS (ESI+) m/z 521 (M+H)+.

Example 336

N-[4-(4-Amino-phenoxy)-3-(7-isopropyl-pyrido[2,3-d]pyrimidin-4-ylamino)-phenyl]-3-methoxy-benzamide Example 336A {4-[2-Amino-4-(3-methoxy-benzoylamino)-phenoxy]-phenyl}-carbamic acid tert-butyl ester 4-Fluoro-3-nitro-phenylamine was reacted with 3-methoxybenzoyl chloride according to the procedure of Example 256a substituting 3-methoxybenzoyl chloride for thiophene-2-carbonyl chloride to provide N-(4-Fluoro-3-nitro-phenyl)-3-methoxy-benzamide which was then reacted according to the procedures of Examples 256b and 256c to provide the title product.

Example 336B

N-[4-(4-Amino-phenoxy)-3-(7-isopropyl-pyrido[2,3-d]pyrimidin-4-ylamino)-phenyl]-3-methoxy-benzamide The product from Example 336A was reacted with the product from Example 8E according to the procedure from Example 256d substituting the product from Example 336A for the product from Example 256c to provide {4-[2-(7-Isopropyl-pyrido[2,3-d]pyrimidin-4-ylamino)-4-(3-methoxy-benzoylamino)-phenoxy]-phenyl}-carbamic acid tert-butyl ester which was deprotected according to the procedure from Example 256e to provide the crude product which was purified by HPLC with TFA to provide the title product as a trifluoroacetic acid salt. 1H NMR (300 MHz, DMSO-D6) δ ppm: 1.33 (d, J=6.99 Hz, 6 H) 3.21-3.34 (m, 1 H) 3.84 (s, 3 H) 6.90-7.22 (m, 6 H) 7.38-7.58 (m, 4 H) 7.70 (dd, J=8.82, 2.57 Hz, 1 H) 7.84 (d, J=8.46 Hz, 1 H) 8.09 (d, J=2.57 Hz, 1 H) 8.24 (dd, J=21.69, 2.57 Hz, 1 H) 8.84 (s, 1 H) 8.92 (d, J=8.46 Hz, 1 H) 10.41 (s, 1 H) 11.44 (s, 1 H); MS (ESI+) m/z 521 (M+H)+.

Example 337

N-[4-(4-Amino-phenoxy)-3-(7-isopropyl-pyrido[2,3-d]pyrimidin-4-ylamino)-phenyl]-2,5-difluoro-benzamide Example 337A {4-[2-Amino-4-(2,5-difluoro-benzoylamino)-phenoxy]-phenyl}-carbamic acid tert-butyl ester 4-Fluoro-3-nitro-phenylamine was reacted with 2,5-difluorobenzoyl chloride according to the procedure of Example 256a substituting 2,5-difluorobenzoyl chloride for thiophene-2-carbonyl chloride to provide 2,5-Difluoro-N-(4-fluoro-3-nitro-phenyl)-benzamide which was then reacted according to the procedures of Examples 256b and 256c to provide the title product.

Example 337B

N-[4-(4-Amino-phenoxy)-3-(7-isopropyl-pyrido[2,3-d]pyrimidin-4-ylamino)-phenyl]-2,5-difluoro-benzamide The product from Example 337A was reacted with the product from Example 8E according to the procedure from Example 256d substituting the product from Example 337A for the product from Example 256c to provide {4-[2-(7-Isopropyl-pyrido[2,3-d]pyrimidin-4-ylamino)-4-(2,5-difluoro-benzoylamino)-phenoxy]-phenyl}-carbamic acid tert-butyl ester which was deprotected according to the procedure from Example 256e to provide the crude product which was purified by silica gel chromatography to provide the title product as a hydrochloride salt. 1H NMR (300 MHz, DMSO-d6) δ ppm: 1.34 (d, J=7.0 Hz, 6H), 3.28 (septet, J=7.0 Hz, 1H), 7.05 (d, J=8.8 Hz, 2H), 7.12 (d, J=8.8 Hz, 1H), 7.26 (d, J=8.8 Hz, 2H), 7.41-7.50 (m, 2H), 7.52-7.61 (m, 1H), 7.69 (dd, J=8.8, 2.6 Hz, 1H), 7.88 (d, J=8.8 Hz, 1H), 8.03 (d, J=2.6 Hz, 1H), 8.88 (s, 1H), 9.19 (d, J=8.8 Hz, 1H), 10.80 (s, 1H), 12.16 (br-s, 1H); MS (ESI+) m/z 527 (M+H)+.

Example 338

N-[4-(4-Amino-phenoxy)-3-(7-isopropyl-pyrido[2,3-d]pyrimidin-4-ylamino)-phenyl]-2-fluoro-benzamide

Example 338A

{4-[2-Amino-4-(2-fluoro-benzoylamino)-phenoxy]-phenyl}-carbamic acid tert-butyl ester 4-Fluoro-3-nitro-phenylamine was reacted with 2-fluorobenzoyl chloride according to the procedure of Example 256a substituting 2-fluorobenzoyl chloride for thiophene-2-carbonyl chloride to provide 2-fluoro-N-(4-fluoro-3-nitro-phenyl)-benzamide which was then reacted according to the procedures of Examples 256b and 256c to provide the title product.

Example 338B

N-[4-(4-Amino-phenoxy)-3-(7-isopropyl-pyrido[2,3-d]pyrimidin-4-ylamino)-phenyl]-2-fluoro-benzamide The product from Example 338A was reacted with the product from Example 8E according to the procedure from Example 256d substituting the product from Example 338A for the product from Example 256c to provide {4-[2-(7-Isopropyl-pyrido[2,3-d]pyrimidin-4-ylamino)-4-(2-fluoro-benzoylamino)-phenoxy]-phenyl}-carbamic acid tert-butyl ester which was deprotected according to the procedure from Example 256e to provide the crude product which was purified by silica gel chromatography to provide the title product as a hydrochloride salt. 1H NMR (300 MHz, DMSO-d6) δ ppm: 1.34 (d, J=7.0 Hz, 6H), 3.27 (septet, J=7.0 Hz, 1H), 7.03 (d, J=8.8 Hz, 2H), 7.11 (d, J=9.2 Hz, 1H), 7.20 (d, J=8.8 Hz, 2H), 7.31-7.42 (m, 2H), 7.55-7.73 (m, 3H), 7.87 (d, J=8.5 Hz, 1H), 8.05 (d, J=2.5 Hz, 1H), 8.87 (s, 1H), 9.11 (d, J=8.5 Hz, 1H), 10.69 (s, 1H), 11.97 (br-s, 1H); MS (ESI+) m/z 509 (M+H)+.

Example 339

N-[4-(4-Amino-phenoxy)-3-(7-isopropyl-pyrido[2,3-d]pyrimidin-4-ylamino)-phenyl]-3,5-bis-trifluoromethyl-benzamide

Example 339A

{4-[2-Amino-4-(3,5-bis-trifluoromethyl-benzoylamino)-phenoxy]-phenyl}-carbamic acid tert-butyl ester 4-Fluoro-3-nitro-phenylamine was reacted with 3,5-bis-trifluoromethyl-benzoyl chloride according to the procedure of Example 256a substituting 3,5-bis-trifluoromethyl-benzoyl chloride for thiophene-2-carbonyl chloride to provide N-(4-Fluoro-3-nitro-phenyl)-3,5-bis-trifluoromethyl-benzamide which was then reacted according to the procedures of Examples 256b and 256c to provide the title product.

Example 339B

N-[4-(4-Amino-phenoxy)-3-(7-isopropyl-pyrido[2,3-d]pyrimidin-4-ylamino)-phenyl]-3,5-bis-trifluoromethyl-benzamide The product from Example 339A was reacted with the product from Example 8E according to the procedure from Example 256d substituting the product from Example 339A for the product from Example 256c to provide {4-[4-(3,5-Bis-trifluoromethyl-benzoylamino)-2-(7-isopropyl-pyrido[2,3-d]pyrimidin-4-ylamino)-phenoxy]-phenyl}-carbamic acid tert-butyl ester which was deprotected according to the procedure from Example 256e to provide the crude product which was purified by silica gel chromatography to provide the title product. 1H NMR (300 MHz, DMSO-d6) δ ppm: 1.32 (d, J=7.0 Hz, 6H), 3.20 (septet, J=7.0 Hz, 1H), 4.91 (s, 2H), 6.52 (d, J=8.8 Hz, 2H), 6.74 (d, J=8.8 Hz, 2H), 6.86 (d, J=9.2 Hz, 1H), 7.58 (d, J=8.5 Hz, 1H), 7.60 (dd, J=9.2, 2.6 Hz, 1H), 8.04 (d, J=2.6 Hz, 1H), 8.38 (br-s, 1H), 8.60 (s, 1H), 8.62 (br-s, 2H), 8.82 (d, J=8.5 Hz, 1H), 9.88 (s, 1H), 10.70 (s, 1H); MS (ESI+) m/z 627 (M+H)+.

Example 340

N-[4-(4-Amino-phenoxy)-3-(7-isopropyl-pyrido[2,3-d]pyrimidin-4-ylamino)-phenyl]-3-fluoro-5-trifluoromethyl-benzamide

Example 340A

{4-[2-Amino-4-(3-fluoro-5-trifluoromethyl-benzoylamino)-phenoxy]-phenyl}-carbamic acid tert-butyl ester 4-Fluoro-3-nitro-phenylamine was reacted with 3-fluoro-5-trifluoromethyl-benzoyl chloride according to the procedure of Example 256a substituting 3-fluoro-5-trifluoromethyl-benzoyl chloride for thiophene-2-carbonyl chloride to provide N-(4-Fluoro-3-nitro-phenyl)-3-fluoro-5-trifluoromethyl-benzamide which was then reacted according to the procedures of Examples 256b and 256c to provide the title product.

Example 340B

N-[4-(4-Amino-phenoxy)-3-(7-isopropyl-pyrido[2,3-d]pyrimidin-4-ylamino)-phenyl]-3-fluoro-5-trifluoromethyl-benzamide The product from Example 340A was reacted with the product from Example 8E according to the procedure from Example 256d substituting the product from Example 340A for the product from Example 256c to provide {4-[4-(3-fluoro-5-trifluoromethyl-benzoylamino)-2-(7-isopropyl-pyrido[2,3-d]pyrimidin-4-ylamino)-phenoxy]-phenyl}-carbamic acid tert-butyl ester which was deprotected according to the procedure from Example 256e to provide the crude product which was purified by silica gel chromatography to provide the title product. 1H NMR (300 MHz, DMSO-d6) δ ppm: 1.32 (d, J=7.0 Hz, 6H), 3.20 (septet, J=7.0 Hz, 1H), 4.90 (s, 2H), 6.51 (d, J=8.8 Hz, 2H), 6.73 (d, J=8.8 Hz, 2H), 6.84 (d, J=8.8 Hz, 1H), 7.58 (d, J=8.5 Hz, 7.59 (dd, J=8.8, 2.6 Hz, 1H), 7.98 (br-d, J=8.4 Hz, 1H), 8.03 (d, J=2.6 Hz, 1H), 8.13 (br-d, J=8.8 Hz, 1H), 8.18 (s, 1H), 8.60 (s, 1H), 8.82 (d, J=8.5 Hz, 1H), 9.88 (s, 1H), 10.55 (s, 1H); MS (ESI+) m/z 577 (M+H)+.

Example 341

4,4'-(4,4'-carbonylbis(azanediyl)bis(4,1-phenylene) bis(sulfanediyl))bis(N-(5-bromopyridin-2-yl)-3-(7-isopropylpyrido[2,3-d]pyrimidin-4-ylamino)benzamide)

The product from Example 17B (1 equiv.) was heated to 60° C. with triphosgene [bis(trichloromethyl) carbonate, 0.33 equiv] in THF for 3 hours. The solvent was then removed under vacuum to provide the resultant crude isocyanate which was dissolved in THF and the product from Example 17B (1 equiv.) added. The resultant solution was heated at 60° C. for 3 hours followed by removal of the solvent under vacuum. The residue was then purified by HPLC with TFA to provide the title product as a trifluoroacetic acid salt. 1H NMR (300 MHz, DMSO-D6) δ ppm: 1.35 (d, J=6.99 Hz, 12 H), 3.19-3.34 (m, J=6.99 Hz, 2 H), 7.03 (d, J=7.72 Hz, 2 H), 7.42 (d, J=8.46 Hz, 4 H), 7.52-7.59 (m, 4 H), 7.83 (d, J=8.09 Hz, 2 H), 7.95 (d, J=7.72 Hz, 2 H), 8.04-8.10 (m, 4 H), 8.12-8.21 (m, 2 H), 8.51 (d, J=2.57 Hz, 2 H), 8.79 (s, 2 H), 8.97 (d, J=5.88 Hz, 2 H), 9.12 (s, 2 H), 10.99 (s, 2 H), 11.29 (s, 2 H); MS (ESI+) m/z 1199 (M+H)+.

Example 342

Piperidine-1-carboxylic acid {4-[4-(5-bromo-pyridin-2-ylcarbamoyl)-2-(7-isopropyl-pyrido[2,3-d]pyrimidin-4-ylamino)-phenylsulfanyl]-phenyl}-amide

Example 342A

{4-[2-Amino-4-(5-bromo-pyridin-2-ylcarbamoyl)-phenylsulfanyl]-phenyl}-carbamic acid 2,2,2-trichloro-ethyl ester A mixture of 4-chloro-3-nitrobenzoyl chloride was reacted with 5-Bromo-pyridin-2-ylamine to produce N-(4-Bromo-phenyl)-4-chloro-3-nitro-benzamide according to the procedure of Example 10A, which was treated sequentially using the procedures from Examples 13A, 268B and 268C to provide the title product.

Example 342B

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester A mixture of the product from Example 342A and the product from Example 8E in glacial acetic acid was heated in a 130° C. oil bath for 15 min. The reaction mixture was then cooled to room temperature and the solvent evaporated under vacuum to provide the title product.

Example 342C

Piperidine-1-carboxylic acid {4-[4-(5-bromo-pyridin-2-ylcarbamoyl)-2-(7-isopropyl-pyrido[2,4-d]pyrimidin-4-ylamino)-phenylsulfanyl]-phenyl}-amide A mixture of the product from Example 342B (1 equiv.), 1,8-diazabicyclo[5.4.0]undec-7-ene (2 equiv.), and piperidine (10 equiv.) in tetrahydrofuran (2 ml) was heated at 65° C. in a sealed tube for 2 hours. The mixture was then cooled to room temperature, concentrated under vacuum and the resultant residue purified by HPLC with TFA to provide the title compound as a trifluoroacetic acid salt. 1H NMR (300 MHz, DMSO-D6) δ ppm: 1.35 (d, J=6.99 Hz, 6 H), 1.43-1.64 (m, 6 H), 3.22-3.37 (m, 5 H), 6.97 (d, J=8.46 Hz, 1 H), 7.35 (d, J=8.82 Hz, 2 H), 7.56 (d, J=8.82 Hz, 2 H), 7.82 (d, J=9.56 Hz, 1 H), 7.93 (d, J=9.19 Hz, 1 H), 8.07 (dd, J=8.82, 2.57 Hz, 2 H), 8.14-8.18 (m, 1 H), 8.50 (d, J=2.21 Hz, 1 H), 8.68 (s, 1 H), 8.78 (s, 1 H), 8.96 (d, J=8.82 Hz, 1 H), 10.98 (s, 1 H), 11.24 (s, 1 H); MS (ESI+) m/z 697 (M+H)+.

Example 343

-[4-(3-Benzyl-ureido)-phenylsulfanyl]-N-(5-bromo-pyridin-2-yl)-3-(7-isopropyl-pyrido[2,3-d]pyrimidin-4-ylamino)-benzamide The product from Example 342B was reacted according to the procedure of Example 342C substituting benzylamine for piperidine to provide the crude product which was purified by HPLC with TFA to provide the title compound as a trifluoroacetic acid salt. 1H NMR (300 MHz, DMSO-D6) δ ppm: 1.36 (d, J=6.62 Hz, 6 H), 3.18-3.38 (m, 1 H), 4.31 (d, J=5.88 Hz, 2 H), 6.75 (t, J=5.88 Hz, 1 H), 6.96 (d, J=8.09 Hz, 1 H), 7.20-7.40 (m, 7 H), 7.52 (d, J=8.82 Hz, 2 H), 7.84 (d, J=8.46 Hz, 1 H), 7.93 (d, J=8.82 Hz, 1 H), 8.05 (d, J=2.57 Hz, 1 H), 8.08 (d, J=2.57 Hz, 1 H), 8.14-8.20 (m, 1 H), 8.50 (d, J=2.57 Hz, 1 H), 8.79 (s, 1 H), 8.88 (s, 1 H), 8.97 (d, J=9.19 Hz, 1 H), 10.99 (s, 1 H), 11.36 (s, 1 H); MS (ESI+) m/z 719/721 (M+H)+.

Example 344

N-(5-Bromo-pyridin-2-yl)-3-(7-isopropyl-pyrido[2,3-d]pyrimidin-4-ylamino)-4-[4-(3-pentyl-ureido)-phenylsulfanyl]-benzamide The product from Example 342B was reacted according to the procedure of Example 342C substituting 1-aminopentane for piperidine to provide the crude product which was purified by HPLC with TFA to provide the title compound as a trifluoroacetic acid salt. 1H NMR (300 MHz, DMSO-D6) δ ppm: 0.83-0.92 (m, 3 H), 1.21-1.32 (m, 4 H), 1.35 (d, J=6.62 Hz, 6 H), 1.39-1.51 (m, 2 H), 3.08 (q, J=6.62 Hz, 2 H), 3.20-3.35 (m, 1 H), 6.24 (t, J=5.70 Hz, 1 H), 6.95 (d, J=8.46 Hz, 1 H), 7.35 (d, J=8.82 Hz, 2 H), 7.47-7.52 (m, 2 H), 7.82 (d, J=8.09 Hz, 1 H), 7.93 (d, J=8.82 Hz, 1 H), 8.06 (dd, J=9.01, 2.39 Hz, 2 H), 8.13-8.19 (m, 1 H), 8.50 (d, J=2.57 Hz, 1 H), 8.70 (s, 1 H), 8.77 (s, 1 H), 8.96 (d, J=9.19 Hz, 1 H), 10.98 (s, 1 H), 11.25 (s, 1 H); MS (ESI+) m/z 699/701 (M+H)+.

Example 345

N-[4-(4-Dimethylamino-phenylsulfanyl)-3-(7-isopropyl-pyrido[2,3-d]pyrimidin-4-ylamino)-phenyl]-3-trifluoromethyl-benzamide

Example 345A

N-[3-Amino-4-(4-dimethylamino-phenylsulfanyl)-phenyl]-3-trifluoromethyl-benzamide The product from Example 114A was reacted according to the procedure from Example 114B substituting 4-dimethylamino-benzenethiol for 4-hydroxythiophenol followed by reduction of the nitro group according to the procedure from Example 114C to provide the title product.

Example 345B

N-[4-(4-Dimethylamino-phenylsulfanyl)-3-(7-isopropyl-pyrido[2,3-d]pyrimidin-4-ylamino)-phenyl]-3-trifluoromethyl-benzamide A mixture of the product from Example 345A and the product from Example 8E in glacial acetic acid was heated in a 130° C. oil bath for 15 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 1.34 (d, J=6.99 Hz, 6 H), 2.88 (s, 6 H), 3.17-3.28 (m, 1 H), 6.65 (d, J=8.82 Hz, 2 H), 7.02 (d, J=8.82 Hz, 1 H), 7.20 (d, J=8.82 Hz, 2 H), 7.61 (d, J=8.82 Hz, 2 H), 7.78 (t, J=7.72 Hz, 1 H), 7.91 (d, J=2.21 Hz, 1 H), 7.97 (d, J=6.99 Hz, 1 H), 8.18-8.33 (m, 2 H), 8.55 (s, 1 H), 8.84 (d, J=8.46 Hz, 1 H), 10.05 (s, 1 H), 10.57 (s, 1 H); MS (ESI+) m/z 699/701 (M+H)+.

Example 346

N-(5-Bromo-pyridin-2-yl)-4-(4-dimethylamino-phenylsulfanyl)-3-(7-isopropyl-pyrido[2,3-d]pyrimidin-4-ylamino)-benzamide

Example 346A

3-Amino-N-(5-bromo-pyridin-2-yl)-4-(4-dimethylamino-phenylsulfanyl)-benzamide

A mixture of 4-chloro-3-nitrobenzoyl chloride was reacted with 5-Bromo-pyridin-2-ylamine to produce N-(4-Bromophenyl)-4-chloro-3-nitro-benzamide according to the procedure of Example 10A, followed by reaction according to the procedure from Example 114B substituting 4-dimethylamino-benzenethiol for 4-hydroxythiophenol followed by reduction of the nitro group according to the procedure from Example 114C to provide the title product.

Example 346B

N-(5-Bromo-pyridin-2-yl)-4-(4-dimethylamino-phenylsulfanyl)-3-(7-isopropyl-pyrido[2,3-d]pyrimidin-4-ylamino)-benzamide A mixture of the product from Example 346A and the product from Example 8E in glacial acetic acid was heated in a 130° C. oil bath for 15 min. The reaction mixture was then cooled to room temperature and the solvent evaporated under vacuum to provide a residue, which was purified by column chromatography on silica gel to provide the title product. 1H NMR (300 MHz, DMSO-D6) δ ppm: 1.34 (d, J=6.99 Hz, 6 H) 2.95 (s, 6 H) 3.24 (m, 1 H) 6.77 (d, J=9.19 Hz, 2 H) 6.85 (d, J=8.82 Hz,1 H) 7.29 (d, J=8.82 Hz, 2 H) 7.65 (d, J=8.82 Hz, 1 H) 7.88 (d, J=8.82 Hz, 1 H) 8.10 (m, 3 H) 8.49 (d, J=2.57 Hz, 1 H) 8.54 (s, 1 H) 8.89 (d, J=8.82 Hz, 1 H) 10.13 (s, 1 H) 10.92 (s, 1 H); MS (ESI+) m/z 614/616 (M+H)+.

Example 347

N-(5-Bromo-pyridin-2-yl)-3-(7-isopropyl-pyrido[2,3-d]pyrimidin-4-ylamino)-4-[4-(7-isopropyl-pyrido[2,3-d]pyrimidin-4-ylamino)-phenylsulfanyl]-benzamide A mixture of the product from Example 17B and the product from Example 8E in glacial acetic acid was heated in a 130° C. oil bath for 15 min. The reaction mixture was then cooled to room temperature and the solvent evaporated under vacuum to provide a residue, which was purified by column chromatography on silica gel to provide the title product. 1H NMR (300 MHz, DMSO-D6) δ ppm: 1.33 (d, J=6.26 Hz, 6 H) 1.34 (d, J=6.98 Hz, 6 H) 3.10-3.32 (m, 2 H) 7.02-7.15 (m, 1 H) 7.37-7.44 (m, 1 H) 7.51 (d, J=8.46 Hz, 2 H) 7.66 (d, J=8.46 Hz, 2 H) 7.93 (dd, J=7.17, 1.65 Hz, 1 H) 8.01 (d, J=8.82 Hz, 2 H) 8.06 (dd, J=9.19, 2.20 Hz, 1 H) 8.12 (s, 1 H) 8.18 (d, J=8.82 Hz, 2 H) 8.50 (d, J=2.21 Hz, 1 H) 8.54-8.66 (m, 1 H) 8.76 (s, 1 H) 8.83-8.91 (m, 1 H) 8.94 (d, J=8.46 Hz, 1 H) 10.07 (s, 1 H) 10.24 (s, 1 H) 10.99 (s, 1 H); MS (ESI+) m/z 757/759 (M+H)+.

Example 348

N-(5-Bromo-pyridin-2-yl)-3-(7-isopropyl-pyrido[2,3-d]pyrimidin-4-ylamino)-4-(4-pyrrol-1-yl-phenylsulfanyl)-benzamide A mixture of the product from Example 17B (1 equiv.) and succinic dialdehyde (40% in water)(3 equiv.) in toluene/methanol 1/1 mix was added 4a molecular sieves and acetic acid (0.05 equiv.). The mixture was heated at 75° C. for 30 hours followed by removal of the 4a molecular sieves and solvent under vacuum to provide a residue, which was purified by HPLC with TFA to provide the title compound as a trifluoroacetic acid salt. 1H NMR (300 MHz, DMSO-D6) δ ppm: 1.34 (d, J=6.6 Hz, 6H), 3.24 (m, 1H), 6.29 (t, J=2.2 Hz, 2H), 7.25 (d, J=8.1 Hz, 1H), 7.36 (t, J=2.2 Hz, 2H), 7.49 (d, J=8.5 Hz, 2H), 7.60 (d, J=8.9 Hz, 2H), 7.85 (d, J=8.5 Hz, 1H), 8.01 (m, 1H), 8.09 (m, 2H), 8.18 (d, J=8.8 Hz, 1H), 8.51 (m, 1H), 8.80 (bs, 1H), 8.96 (d, J=7.5 Hz, 1H), 11.04 (s, 1H); MS (ESI+) m/z 636/638 (M+H)+.

Example 349

4-[6-(7-Isopropyl-pyrido[2,3-d]pyrimidin-4-ylamino)-2-thiazol-2-yl-benzooxazol-5-ylsulfanyl]-phenol

Example 349A

5-Chloro-6-nitro-2-thiazol-2-yl-benzooxazole

To a flask equipped with a vigreux column was added 2-amino-4-chloro-5-nitro-phenol, thiazole-2-carbaldehyde, Darco KB and xylenes. The mixture was then refluxed overnight and the mixture was cooled, filtered and the solvent removed under vacuum. The resultant solid was recrystallized from Et₂O to yield 4.76 g (63%) of a yellow colored solid.

Example 349B

4-(6-Amino-2-thiazol-2-yl-benzooxazol-5-ylsulfanyl)-phenol

To a flask equipped with a magnetic stir bar and vigreux column was added the product from Example 349A, 4-mercaptophenol, potassium carbonate, and ethanol. The mixture was refluxed for 2 hours followed by addition of tin dichloride while the mixture was maintained at 70° C. After heating overnight the mixture was then cooled and filtered through silica, eluting with 10% $CH_3OH/CHCl_3$. The organic layer was then concentrated under vacuum and subjected to purification via Reverse phase (C-18) column chromatography (3% to 100% $CH_3CN/H_2O$ with 0.1% TFA) to provide the title product.

Example 349C

4-[6-(7-Isopropyl-pyrido[2,3-d]pyrimidin-4-ylamino)-2-thiazol-2-yl-benzooxazol-5-ylsulfanyl]-phenol A mixture of the product from Example 349B and the product from Example 8E in glacial acetic acid was heated in a 130° C. oil bath for 5 min. The reaction mixture was then cooled to room temperature and the solvent evaporated under vacuum to provide a residue, which was purified by HPLC with TFA to provide the title compound as a trifluoroacetic acid salt. $^1H$ NMR (300 MHz, DMSO-$D_6$) δ ppm: 1.18 (d, J=6.99 Hz, 6 H) 2.79-2.91 (m, 1 H) 6.58 (d, J=7.72 Hz, 2 H) 6.79 (d, J=8.82 Hz, 1 H) 7.29 (d, J=8.82 Hz, 1 H) 7.47 (s, 1 H) 7.80 (d, J=8.09 Hz, 2 H) 7.99 (d, J=8.82 Hz, 1 H) 8.07 (s, 1 H) 8.22 (s, 1 H) 8.90 (s, 1 H) 9.09 (d, J=8.46 Hz, 1 H); MS (ESI+) m/z 513 (M+H)+.

Example 350

4-[6-(7-Isopropyl-pyrido[2,3-d]pyrimidin-4-ylamino)-2-phenyl-benzooxazol-5-ylsulfanyl]-phenol

Example 350A

4-(6-Amino-2-phenyl-benzooxazol-5-ylsulfanyl)-phenol

To a flask equipped with a vigreux column was added 2-amino-4-chloro-5-nitro-phenol, benzaldehyde, Darco KB and xylenes. The mixture was then refluxed overnight and the mixture was cooled, filtered and the solvent removed under vacuum. The resultant solid was recrystallized from $Et_2O$ to yield 5-chloro-6-nitro-2-phenyl-benzooxazole which was subjected to the procedure from Example 349B substituting 5-chloro-6-nitro-2-phenyl-benzooxazole for the product from Example 349A to provide the title product.

Example 350B

4-[6-(7-Isopropyl-pyrido[2,3-d]pyrimidin-4-ylamino)-2-phenyl-benzooxazol-5-ylsulfanyl]-phenol A mixture of the product from Example 350A and the product from Example 8E in glacial acetic acid was heated in a 130° C. oil bath for 5 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 1.35 (d, J=6.99 Hz, 6 H) 3.20-3.30 (m, 1 H) 6.80 (d, J=8.82 Hz, 2 H) 7.28 (d, J=8.46 Hz, 2 H) 7.58-7.68 (m, 5 H) 7.75 (d, J=7.35 Hz, 1 H) 7.95 (s, 1 H) 8.18 (dd, J=7.72, 1.84 Hz, 2 H) 8.66 (s, 1 H) 8.91 (s, 1 H) 9.89 (s, 1 H); MS (ESI+) m/z 506 (M+H)+.

Example 351

5-(4-Hydroxy-phenylsulfanyl)-4-(7-isopropyl-pyrido[2,3-d]pyrimidin-4-ylamino)-thiophene-2-carboxylic acid (3-bromo-phenyl)-amide

Example 351A

5-Chloro-4-nitro-thiophene-2-carboxylic acid ethyl ester

A solution of fuming nitric acid (75 mL) was cooled to 10° C. followed by the addition of 5-chloro-thiophene-2-carboxylic acid ethyl ester (15 g, 78.7 mmol). The resulting mixture was stirred for 30 minutes at 10° C. followed by the addition of ice water. The solution was then extracted with ethyl acetate and dried, then concentrated under vacuum and purified by column chromatography using silica gel to provide 10.29 g (55%) of the title product.

Example 351B

5-(4-Hydroxy-phenylsulfanyl)-4-nitro-thiophene-2-carboxylic acid ethyl ester The product from Example 351A (1 equiv) and 4-mercaptophenol (1 equiv) were dissolved in dimethylformamide and cesium carbonate (5 equiv) added. The resultant mixture was stirred at 80° C. for 2.5 hours, cooled to room temperature and water added. The solution was extracted with ethyl acetate, the organic extracts dried and concentrated under vacuum to provide the title product.

Example 351C

5-(4-Hydroxy-phenylsulfanyl)-4-nitro-thiophene-2-carboxylic acid

The product from Example 351B (1 equiv) was dissolved in a methanol/water 3/1 mixture followed by the addition of lithium hydroxide (5 equiv). The resultant solution was stirred at room temperature for 24 hours followed by the addition of 1N aqueous hydrochloric acid until the solution was a pH of 2. The mixture was then extracted with ethyl acetate, the organic extracts dried and concentrated under vacuum to provide the title product.

Example 351D

5-(4-Hydroxy-phenylsulfanyl)-4-nitro-thiophene-2-carboxylic acid (3-bromo-phenyl)-amide The product from Example 351C was dissolved in dichloromethane followed by the addition of a solution of oxalyl chloride and a catalytic amount of dimethylformamide. The solution was stirred at room temperature for 3 hours followed by the addition of 3-bromoaniline and pyridine. The resultant solution was stirred at room temperature for 20 hours followed by the addition of water and extraction of the solution with ethyl acetate, the organic extracts dried and concentrated under vacuum to provide the crude product, which was purified by silica gel chromatograpy to provide the title product.

Example 351E

4-Amino-5-(4-hydroxy-phenylsulfanyl)-thiophene-2-carboxylic acid (3-bromo-phenyl)-amide To a solution of the product from Example 351D (1 equiv), iron powder (5 equiv) and ammonium chloride (3 equiv) in a mixture of tetrahydrofuran, water and ethanol was heated to reflux for 3 hours. The mixture was cooled to room temperature, filtered through a pad of celite, which was washed with ethanol and the resultant filtrate concentrated under vacuum. The material was then dissolved in water and extracted with ethyl acetate, the organic layer dried and concentrated under vacuum to provide the title product.

Example 351F 5-(4-Hydroxy-phenylsulfanyl)-4-(7-isopropyl-pyrido[2,3-d]pyrimidin-4-ylamino)-thiophene-2-carboxylic acid (3-bromo-phenyl)-amide A mixture of the product from Example 351E and the product from Example 8E in glacial acetic acid was heated in a preheated 130° C. oil bath for 20 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 1.36 (d, J=6.99 Hz, 6 H) 3.28 (qq, 1 H) 6.75 (d, J=8.82 Hz, 2 H) 7.23-7.42 (m, 4 H) 7.61-7.72 (m, J=2.94 Hz, 1 H) 7.84 (d, J=8.46 Hz, 1 H) 7.96-8.01 (m, 1 H) 8.10 (s, 1 H) 8.85 (s, 1 H) 8.94 (d, J=8.46 Hz, 1 H) 9.93 (s, 1 H) 10.42 (s, 1 H) 11.13 (s, 1 H); MS (ESI+) m/z 594 (M+H)+.

Example 352

5-(4-Hydroxy-phenylsulfanyl)-4-(7-methyl-pyrido[2,3-d]pyrimidin-4-ylamino)-thiophene-2-carboxylic acid (3-bromo-phenyl)-amide A mixture of the product from Example 351E and the product from Example 9B in glacial acetic acid was heated in a preheated 130° C. oil bath for 20 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 2.72 (s, 3 H) 6.75 (d, J=8.82 Hz, 2 H) 7.25-7.37 (m, 4 H) 7.62-7.76 (m, 2 H) 8.00 (s, 1 H) 8.12 (s, 1 H) 8.78 (s, 1 H) 8.86 (d, J=8.09 Hz, 1 H) 9.91 (s, 1 H) 10.38 (s, 1 H) 10.82 (s, 1 H); MS (ESI+) m/z 565 (M+H)+.

Example 353

5-(4-Hydroxy-phenylsulfanyl)-4-(7-isopropyl-pyrido[2,3-d]pyrimidin-4-ylamino)-thiophene-2-carboxylic acid phenylamide Example 353A 4-Amino-5-(4-hydroxy-phenylsulfanyl)-thiophene-2-carboxylic acid phenylamide The product from Example 351C was reacted with aniline according to the procedure of Example 351D substituting aniline for 3-bromoaniline followed by reduction of the nitro group according to the procedure from Example 351E to provide the title product.

Example 353B 5-(4-Hydroxy-phenylsulfanyl)-4-(7-isopropyl-pyrido[2,3-d]pyrimidin-4-ylamino)-thiophene-2-carboxylic acid phenylamide A mixture of the product from Example 353A and the product from Example 8E in glacial acetic acid was heated in a preheated 130° C. oil bath for 20 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 1.36 (d, J=6.99 Hz, 6 H) 3.28 (qq, 1 H) 6.75 (d, J=8.82 Hz, 2 H) 7.23-7.42 (m, 4 H) 7.61-7.72 (m, J=2.94 Hz, 1 H) 7.84 (d, J=8.46 Hz, 1 H) 7.96-8.01 (m, 1 H) 8.10 (s, 1 H) 8.85 (s, 1 H) 8.94 (d, J=8.46 Hz, 1 H) 9.93 (s, 1 H) 10.42 (s, 1 H) 11.13 (s, 1 H); MS (ESI+) m/z 514 (M+H)+.

Example 354

4-[7-(1-Hydroxy-1-methyl-ethyl)-pyrido[2,3-d]pyrimidin-4-ylamino]-5-(4-hydroxy-phenylsulfanyl)-thiophene-2-carboxylic acid phenylamide A mixture of the product from Example 353A and the product from Example 8E in glacial acetic acid was heated slowly (over 20 minutes) from room temperature to 130° C. oil bath, then kept at this temperature for 20 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 1.56 (s, 6 H) 6.75 (d, J=8.46 Hz, 2 H) 7.11 (t, J=7.35 Hz, 1 H) 7.26-7.44 (m, 4 H) 7.68 (d, J=7.72 Hz, 2 H) 8.10 (s, 1 H) 8.15 (d, J=8.46 Hz, 1 H) 8.88 (s, 1 H) 9.02 (d, J=8.82 Hz, 1 H) 9.93 (s, 1 H) 10.30 (s, 1 H) 11.26 (s, 1 H); MS (ESI+) m/z 530 (M+H)+.

Example 355

5-(3-Hydroxy-phenylsulfanyl)-4-(7-isopropyl-pyrido[2,3-d]pyrimidin-4-ylamino)-thiophene-2-carboxylic acid (3-bromo-phenyl)-amide Example 355A 4-Amino-5-(3-hydroxy-phenylsulfanyl)-thiophene-2-carboxylic acid (3-bromo-phenyl)-amide The product from Example 351B was reacted with 3-mercaptophenol according to the procedure of Example 351C substituting 3-mercaptophenol for 4-mercaptophenol followed by reaction according to the procedures from Example 351D and 828E to provide the title product.

Example 355B 5-(3-Hydroxy-phenylsulfanyl)-4-(7-isopropyl-pyrido[2,3-d]pyrimidin-4-ylamino)-thiophene-2-carboxylic acid (3-bromo-phenyl)-amide A mixture of the product from Example 355A and the product from Example 8E in glacial acetic acid was heated in a preheated 130° C. oil bath for 20 min. The reaction mixture was then cooled to room temperature and the solvent evaporated under vacuum to provide a residue, which was purified by HPLC with TFA to provide the title compound as a trifluoroacetic acid salt. 1H NMR (300 MHz, DMSO-D6) δ ppm: 1.34 (d, J=6.99 Hz, 6 H) 3.26 (m, 1 H) 6.66 (m, 3 H) 7.08 (t, J=7.91 Hz, 1 H) 7.32 (m, 2 H) 7.72 (m, 2 H) 8.02 (s, 1 H) 8.24 (s, 1 H) 8.76 (s, 1 H) 8.85 (d, j=8.46 Hz, 1 H) 9.67 (s, 1 H) 10.50 (s, 1 H) 10.82 (s, 1 H); MS (ESI+) m/z 592/594 (M+H)+.

Example 356

{4-[5-(3-Bromo-phenylcarbamoyl)-3-(7-isopropyl-pyrido[2,3-d]pyrimidin-4-ylamino)-thiophen-2-ylsulfanyl]-phenyl}-carbamic acid 2,2,2-trichloro-ethyl ester Example 356A 5-Chloro-4-nitro-thiophene-2-carboxylic acid The product from Example 351A (1 equiv) was dissolved in a methanol/water 3/1 mixture followed by the addition of lithium hydroxide (5 equiv). The resultant solution was stirred at room temperature for 24 hours followed by the addition of 1N aqueous hydrochloric acid until the solution was a pH of 2. The mixture was then extracted with ethyl acetate, the organic extracts dried and concentrated under vacuum to provide the title product.

Example 356B

5-Chloro-4-nitro-thiophene-2-carboxylic acid (3-bromo-phenyl)-amide

The product from Example 356A was dissolved in dichloromethane followed by the addition of a solution of thionyl chloride and a catalytic amount of dimethylformamide. The solution was stirred at room temperature for 3 hours followed by removal of the solvent under vacuum. The residue was then dissolved in toluene and 3-bromoaniline was added. The resultant solution was heated at reflux for 2 hours followed by the addition of hexanes and filtration through filter paper followed by concentration of the filtrate under vacuum to provide the title product.

Example 356C 5-(4-Amino-phenylsulfanyl)-4-nitro-thiophene-2-carboxylic acid (3-bromo-phenyl)-amide The product from Example 356B was dissolved in dimethylformamide and 4-aminophenol was added followed by cesium carbonate. The resultant solution was stirred for 3 hours followed by dilution of the solution with water followed by addition of 1N aqueous hydrochloric acid until the pH of the solution was 3. The solid that formed was collected by filtration and dried in a vacuum oven to provide the title product.

Example 356D

{4-[3-Amino-5-(3-bromo-phenylcarbamoyl)-thiophen-2-ylsulfanyl]-phenyl}-carbamic acid 2,2,2-trichloro-ethyl ester To the product from Example 356C dissolved in dichloromethane was added pyridine followed by the dropwise addition of 2,2,2-trichloroethyl chloroformate. The resultant solution was stirred for 4 hours and then concentrated under vacuum. The mixture was then poured into water, the pH of the solution adjusted to 5 with 1N aqueous hydrochloric acid, the resultant solution stirred for 30 minutes and the resultant solid collected and dried followed by reduction of the nitro group according to the procedure described in Example 356E to provide the title product.

Example 356E

{4-[5-(3-Bromo-phenylcarbamoyl)-3-(7-isopropyl-pyrido[2,3-d]pyrimidin-4-ylamino)-thiophen-2-ylsulfanyl]-phenyl}-carbamic acid 2,2,2-trichloro-ethyl ester A mixture of the product from Example 356D and the product from Example 8E in glacial acetic acid was heated in a preheated 130° C. oil bath for 20 min. The reaction mixture was then cooled to room temperature and the solvent evaporated under vacuum to provide the title compound as an acetic acid salt. 1H NMR (300 MHz, DMSO-D6) δ ppm: 1.33 (d, J=6.62 Hz, 6 H) 3.13-3.28 (m, 1 H) 4.93 (s, 2 H) 7.35 (d, J=8.82 Hz, 2 H) 7.32 (d, J=6.25 Hz, 2 H) 7.47 (d, 2 H) 7.63 (d, J=8.46 Hz, 1 H) 7.70 (dt, J=4.50, 2.39 Hz, 1 H) 8.02 (s, 1 H) 8.23 (s, 1 H) 8.67 (s, 1 H) 8.83 (d, J=8.46 Hz, 1 H) 10.12 (s, 1 H) 10.28 (s, 1 H) 10.42 (s, 1 H) 11.96 (s, 2 H).

Example 357

5-(4-Amino-phenylsulfanyl)-4-(7-isopropyl-pyrido[2,3-d]pyrimidin-4-ylamino)-thiophene-2-carboxylic acid (3-bromo-phenyl)-amide The product from Example 356E (1 equiv) was dissolved in THF/water followed by the addition of 1N aqueous sodium hydroxide (3 equiv), the mixture was heated to 60° C. for 2 hours followed by the addition of water and extraction with ethyl acetate. The organic extracts were dried and concentrated under vacuum to provide a residue which was purified by HPLC with TFA to provide the title compound as a trifluoroacetic acid salt. 1H NMR (300 MHz, DMSO-D6) δ ppm: 1.36 (d, J=6.62 Hz, 6 H) 3.30 (dq, J=6.89 Hz, 1 H) 6.57 (d, J=8.82 Hz, 2 H) 7.20 (d, J=8.46 Hz, 2 H) 7.25-7.37 (m, 2 H) 7.67 (dt, J=4.32, 2.39 Hz, 1 H) 7.90 (d, J=8.46 Hz, 1 H) 7.99 (s, 1 H) 8.05 (s, 1 H) 8.92 (s, 1 H) 8.99 (d, J=8.82 Hz, 1 H) 10.39 (s, 1 H) 11.39 (s, 1 H).

Example 358

N-(5-Bromo-pyridin-2-yl)-3-(7-isopropyl-pyrido[2,3-d]pyrimidin-4-ylamino)-4-{4-[4-(3,7,12-trihydroxy-10,13-dimethyl-hexadecahydro-cyclopenta[a]phenanthren-17-yl)-pentanoylamino]-phenylsulfanyl}-benzamide Example 358A 4-(3,7,12-Triformyloxy-10,13-dimethyl-hexadecahydro-cyclopenta[a]phenanthren-17-yl)-pentanoic acid Prepared according to the procedure of *JACS* 57 1393 (1935). A solution of cholic acid (5.00 g, 12.24 mmol) in 96% formic acid (10 mL) was heated at 55° C. for 5 hours, then evaporated to dryness by rotary evaporation at 55°. The white foam was taken up in boiling 95% ethanol (50 mL) and treated with water (60 mL) at such a rate that a solution was maintained. The solution was stirred magnetically as it was allowed to cool to room temperature, then let the mixture stand overnight. The white solid was collected by vacuum filtration and washed with a mixture of 95% ethanol (10 mL) and water (8.3 mL); the washing was repeated one time. Drying in a vacuum oven at 80° for 2 hours afforded the title compound (4.683 g, 9.51 mmol, 78%).

Example 358B

Formic acid 17-(3-{4-[4-(5-bromo-pyridin-2-ylcarbamoyl)-2-(7-isopropyl-pyrido[2,3-d]pyrimidin-4-ylamino)-phenylsulfanyl]-phenylcarbamoyl}-1-methyl-propyl)-3,7-diformyloxy-10,13-dimethyl-hexadecahydro-cyclopenta[a]phenanthren-12-yl ester A solution of the product of Example 358A (200 mg, 0.406 mmol) in anhydrous benzene (4 mL) under a nitrogen atmosphere was treated with oxalyl chloride (0.40 mL, 4.588 mmol) dropwise, and the reaction was stirred at room temperature for two hours. The solvent was removed by rotary evaporation, co-evaporated with methylene chloride, and dried under vacuum to a white foam. A solution of the acid chloride in anhydrous tetrahydrofuran (2.5 mL) was added to a suspension of the product of Example 17B (158.7 mg, 0.2706 mmol) and pyridine (0.20 mL, 2.47 mmol) in tetrahydrofuran (2.5 mL). The solution was stirred under nitrogen at room temperature for three hours, then evaporated by rotary evaporation. Purification by silica gel flash chromatography with a gradient of 3% to 4% methanol/methylene chloride afforded the title compound as a yellow solid (167 mg, 0.157 mmol, 58%).

Example 358C

N-(5-Bromo-pyridin-2-yl)-3-(7-isopropyl-pyrido[2,3-d]pyrimidin-4-ylamino)-4-{4-[4-(3,7,12-trihydroxy-10,13-dimethyl-hexadecahydro-cyclopenta[a]phenanthren-17-yl)-pentanoylamino]-phenylsulfanyl}-benzamide The product of Example 358B (162 mg, 0.1527 mmol) was suspended in methanol (2 mL) and treated with 10% sodium hydroxide in methanol (2 mL), sonicated briefly to achieve dissolution, and stirred at room temperature for one hour. The solvent was removed by rotary evaporation in vacuo and the residue taken up in ethyl acetate (150 mL) and water (50 mL). The aqueous pH was adjusted to 5 with 1N aqueous hydrochloric acid and the layers separated. The organic phase was washed with water (50 mL) and brine (50 mL), then dried over anhydrous sodium sulfate, filtered, and concentrated by rotary evaporation. Purification by silica gel flash chromatography with a gradient of 8% to 10% methanol/methylene chloride afforded the title compound (137 mg, 0.140 mmol, 92%). $^1$H NMR (300 MHz, DMSO-D6) δ ppm: 0.60 (s, 3 H) 0.81 (s, 3 H) 0.98 (d, J=5.88 Hz, 3 H) 1.12-2.52 (m, 24 H) 1.33 (d, J=6.99 Hz, 6 H) 3.12-3.31 (m, 2 H) 3.55-3.69 (m, 1 H) 3.75-3.87 (m, 1 H) 4.02 (d, J=3.31 Hz, 1 H) 4.13 (d, J=3.68 Hz, 1 H) 4.32 (d, J=4.41 Hz, 1 H) 6.89-7.05 (m, 1 H) 7.40 (d, J=8.46 Hz, 2 H) 7.57-7.66 (m, 1 H) 7.68 (d, J=8.46 Hz, 2 H) 7.81-7.95 (m, 1 H) 8.01-8.12 (m, 2 H) 8.16 (d, J=8.82 Hz, 1 H) 8.50 (d, J=2.57 Hz, 1 H) 8.53-8.67 (m, 1 H) 8.76-8.96 (m, 1 H) 10.09 (s, 1 H) 10.21 (br s, 1 H) 10.97 (br s, 1 H); MS (ESI+) m/z 977/979 (M+H)$^+$.

Example 359

4-(3-{4-[-(5-Bromo-pyridin-2-ylcarbamoyl)-2-(7-isopropyl-pyrido[2,3-d]pyrimidin-4-ylamino)-phenylsulfanyl]-phenylcarbamoyloxy}-7,12-dihydroxy-10,13-dimethyl-hexadecahydro-cyclopenta[a]phenanthren-17-yl)-pentanoic acid methyl ester A suspension of the product of Example 17B (100 mg, 0.1705 mmol) in anhydrous tetrahydrofuran (2.5 mL) under a nitrogen atmosphere was treated with anhydrous pyridine (0.041 mL, 0.512 mmol) and a solution of 7α,12α-dihydroxy-3α-chlorocarbonyloxy-5α-cholanoic acid-(24)-methyl ester (124 mg, 0.256 mmol, prepared according to the procedure in *JACS* 119(4) 640 (1997)), in tetrahydrofuran (0.5 mL). The reaction was stirred at room temperature for 16 hours and the solvent was removed by rotary evaporation in vacuo. Purification by silica gel flash chromatography with a gradient of 3% to 4% methanol/methylene chloride provided the title compound as a yellow solid (108 mg, 0.104 mmol, 61%). $^1$H NMR (300 MHz, DMSO-D6) δ ppm: 0.60 (s, 3 H) 0.86 (s, 3 H) 0.92 (d, J=6.25 Hz, 3 H) 0.96-2.64 (m, 24 H) 1.34 (d, J=6.62 Hz, 6 H) 3.15-3.32 (m, 1 H) 3.57 (s, 3 H) 3.61-3.68 (m, 1 H) 3.76-3.88 (m, 1 H) 4.12 (d, J=3.31 Hz, 1 H) 4.16 (d, J=3.31 Hz, 1 H) 4.35-4.55 (m, 1 H) 6.94 (d, J=8.09 Hz, 1 H) 7.34-7.44 (m, 2 H) 7.54 (d, J=8.82 Hz, 2 H) 7.64 (d, J=8.46 Hz, 1 H) 7.88 (dd, J=7.72, 1.47 Hz, 1 H) 8.02-8.11 (m, 2 H) 8.13-8.22 (m, 1 H) 8.49 (d, J=2.21 Hz, 1 H) 8.59 (s, 1 H) 8.86 (d, J=8.46 Hz, 1 H) 9.82 (s, 1 H) 10.20 (s, 1 H) 10.97 (s, 1 H); MS (ESI+) m/z 1035/1037 (M+H)$^+$.

Example 360

4-Trifluoromethyl-cyclohexanecarboxylic acid [4-(4-hydroxy-phenylsulfanyl)-3-(7-isopropyl-pyrido[2,3-d]pyrimidin-4-ylamino)-phenyl]-amide

Example 360A

4-Trifluoromethyl-cyclohexanecarboxylic acid [3-amino-4-(4-hydroxy-phenylsulfanyl)-phenyl]-amide The title compound was synthesized by reacting 4-fluoro-3-nitro-phenylamine with 4-trifluoromethyl-cyclohexanecarbonyl chloride according to the procedure from Example 255a substituting 4-trifluoromethyl-cyclohexanecarbonyl chloride for furan-2-carbonyl chloride followed by reaction of the resultant material according to the procedure from Examples 255b and 255c to provide the title product.

Example 360B

4-Trifluoromethyl-cyclohexanecarboxylic acid [4-(4-hydroxy-phenylsulfanyl)-3-(7-isopropyl-pyrido[2,3-d]pyrimidin-4-ylamino)-phenyl]-amide The product from Example 360A was reacted with the product from Example 8E according to the procedure from Example 255d substituting the product from Example 360A for the product from Example 255c to provide the crude product which was purified by column chromatography on silica gel to provide the title product. 1H NMR (300 MHz, DMSO-d6) δ ppm: 1.33 (d, J=7.0 Hz, 6H), 1.51-1.80 (m, 6H), 1.90-2.04 (m, 2H), 2.20-2.41 (m, 1H), 2.64 (br-t, J=4.0 Hz, 1H), 3.21 (septet, J=7.0 Hz, 1H), 6.70 (d, J=8.8 Hz, 2H), 7.05 (d, J=8.5 Hz, 1H), 7.14 (d, J=8.8 Hz, 2H), 7.41 (dd, J=8.5, 1.8

Hz, 1H), 7.60 (d, J=8.4 Hz, 1H), 7.83 (d, J=1.8 Hz, 1H), 8.54 (s, 1H), 8.80 (d, J=8.4 Hz, 1H), 9.69 (s, 1H), 9.97 (s, 1H), 10.04 (s, 1H); MS (ESI+) m/z 582 (M+H)+.

Example 361

Piperidine-1-carboxylic acid {4-[4-(4-bromo-phenyl-carbamoyl)-2-(7-isopropyl-pyrido[2,3-d]pyrimidin-4-ylamino)-phenoxy]-phenyl}-amide Example 361C 4-(4-Amino-phenoxy)-N-(4-bromo-phenyl)-3-nitrobenzamide A mixture of 4-(4-aminophenoxy)-N-(4-bromophenyl)-3-nitrobenzamide (3.55 g, 0.01 mol), 4-aminophenol (1.09 g, 0.01 mol), potassium hydroxide (1.12 g, 0.02 mol) and 10 mL of DMSO in a sealed microwave tube was heated by microwave at 100° C. for 25 minutes. The reaction mixture was then allowed to cool, poured into 300 mL of water and the pH was adjusted to 6 by addition of 1M HCl. The mixture was stirred for 30 minutes, filtered, and the collected solid was dried in vacuo to give the title compound (4.2 g, 98%).

Example 361D

{4-[4-(4-Bromo-phenylcarbamoyl)-2-nitro-phenoxy]-phenyl}-carbamic acid 2,2,2-trichloro-ethyl ester To a mixture of the product of Example 361C (4.2 g, 9.8 mmol) and pyridine (1.6 g, 1.62 mL, 20 mmol) in dichloromethane (100 mL) was added dropwise 2,2,2-trichloroethyl chloroformate (2.29 g, 10.8 mmol) over 30 minutes. The reaction mixture was stirred for 4 hours, concentrated and the residue was poured into 200 mL of water adjusting the pH to 5 with 1 M HCl. The mixture was stirred for 30 minutes, filtered, and the collected solid was dried in vacuo to give the title compound (6.0 g, 98%).

Example 361E

{4-[2-Amino-4-(4-bromo-phenylcarbamoyl)-phenoxy]-phenyl}-carbamic acid 2,2,2-trichloro-ethyl ester A mixture of the product of Example 361D (6.0 g, 10.0 mmol), iron powder (2.8 g, 50 mmol, 5 equiv, from Acros, electrolytically reduced, reagent, powder), and ammonium chloride (0.81 g, 15.0 mmol, 1.5 equiv) in tetrahydrofuran/ethanol/water (60/60/20 mL) was heated under reflux for 5 hours. The reaction mixture was cooled to room temperature and filtered through Celite, rinsing the Celite pad with 50 mL of ethanol. The resulting filtrate was evaporated under reduced pressure and the residue was partitioned between ethyl acetate (100 mL) and water (100 mL). The aqueous phase was extracted with ethyl acetate (2×100 mL). The combined organic phases were washed with brine (50 mL), dried over anhydrous magnesium sulfate, filtered, and evaporated under reduced pressure to give the title compound (4.71 g, 83%) as a tan solid.

Example 361F

{4-[4-(4-Bromo-phenylcarbamoyl)-2-(7-isopropyl-pyrido[2,3-d]pyrimidin-4-ylamino)-phenoxy]-phenyl}-carbamic acid 2,2,2-trichloro-ethyl ester A mixture of the products of Example 361E (2.39 g, 4.2 mmol) and Example 8E (N'-(3-cyano-6-isopropyl-pyridin-2-yl)-N,N-dimethyl-formamidine) (0.91 g, 4.2 mmol) in 10 mL of glacial acetic acid was heated in a 140° C. preheated oil bath for 45 minutes. The reaction mixture was cooled, evaporated in vacuo and the residue partitioned between ethyl acetate (250 mL) and water (100 mL). The organic phase was then washed with saturated aqueous sodium bicarbonate and then brine, dried over anhydrous magnesium sulfate, filtered, and evaporated under reduced pressure. The resulting residue was triturated with methanol, filtered, and dried in vacuo to provide the title compound (2.0 g, 64%) as a beige solid. MS (ESI+) m/z 743/745 (M+H)$^+$; $^1$H NMR (300 MHz, DMSO-$d_6$) δ ppm: 1.31 (d, J=6.62 Hz, 6 H), 3.10-3.27 (m, 1 H), 4.93 (s, 2 H), 6.93-7.05 (m, 3 H), 7.39-7.62 (m, 5 H), 7.77 (d, J=8.82 Hz, 2 H), 8.17 (s, 1 H), 8.60 (s, 1 H), 8.78 (d, J=8.09 Hz, 1 H), 10.08 (s, 1 H), 10.16 (s, 1 H), 10.35 (s, 2 H).

Example 361G

Piperidine-1-carboxylic acid {4-[4-(4-bromo-phenylcarbamoyl)-2-(7-isopropyl-pyrido[2,3-d]pyrimidin-4-ylamino)-phenoxy]-phenyl}-amide The product of Example 361F (74 mg, 0.1 mmol) in tetrahydrofuran (1 mL) was treated with 1,8-diazobicyclo[5.4.0]undec-7-ene (30 µL, 0.2 mmol) and piperidine (85 mg, 1.0 mmol) and heated at 60° C. for 1 hour in a sealed tube. The reaction mixture was cooled, concentrated and the crude product was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title compound as a trifluoroacetic acid salt (0.04 g, 59%). $^1$H NMR (300 MHz, DMSO-$D_6$) δ ppm: 1.34 (d, J=6.62 Hz, 6 H), 1.42-1.66 (m, 6 H), 3.22-3.32 (m, 1 H), 3.36-3.43 (m, 4 H), 6.98 (t, J=9.01 Hz, 3 H), 7.47 (d, J=9.19 Hz, 2 H), 7.54 (d, J=8.82 Hz, 2 H), 7.75 (d, J=8.82 Hz, 2 H), 7.83 (d, J=8.46 Hz, 1 H), 7.98 (dd, J=8.46, 2.21 Hz, 1 H), 8.14 (d, J=2.21 Hz, 1 H), 8.47 (s, 1 H), 8.86 (s, 1 H), 8.95 (d, J=8.46 Hz, 1 H), 10.38 (s, 1 H), 11.30 (s, 1 H); (ESI+) m/z 680/682 (M+H)+.

Example 362

N-(4-Bromo-phenyl)-4-[4-(3-cyclopentyl-ureido)-phenoxy]-3-(7-isopropyl-pyrido[2,3-d]pyrimidin-4-ylamino)-benzamide The title compound was prepared as in Example 361G substituting cyclopentylamine (85 mg, 1.0 mmol) for piperidine to give a trifluoroacetic acid salt (42 mg, 62%). (ESI+) m/z 680/682 (M+H)+; 1H NMR (300 MHz, DMSO-D6) δ ppm: 1.34 (d, J=6.99 Hz, 6 H), 1.34-1.43 (m, 2 H), 1.46-1.71 (m, 4 H), 1.74-1.92 (m, 2 H), 3.12-3.31 (m, 1 H), 3.78-4.00 (m, 1 H), 6.14 (d, J=7.35 Hz, 1 H), 6.93-7.02 (m, J=9.01, 2.76 Hz, 3 H), 7.38 (d, J=9.19 Hz, 2 H), 7.54 (d, J=8.82 Hz, 2 H), 7.75 (d, J=9.19 Hz, 2 H), 7.81 (d, J=8.46 Hz, 1 H), 7.96 (dd, J=8.82, 2.21 Hz, 1 H), 8.14 (d, J=2.21 Hz, 1 H), 8.31 (s, 1 H), 8.84 (s, 1 H), 8.94 (d, J=8.82 Hz, 1 H), 10.37 (s, 1 H), 11.18 (s, 1 H).

Example 363

4-[4-(3-Benzyl-ureido)-phenoxy]-N-(4-bromo-phenyl)-3-(7-isopropyl-pyrido[2,3-d]pyrimidin-4-ylamino)-benzamide

The title compound was prepared as in Example 361G substituting benzylamine (107 mg, 1.0 mmol) for piperidine to give a trifluoroacetic acid salt (45 mg, 64%). (ESI+) m/z 702/704 (M+H)+; $^1$H NMR (300 MHz, DMSO-D6) δ ppm: 1.34 (d, J=6.99 Hz, 6 H), 3.18-3.35 (m, 1 H), 4.29 (d, J=5.88 Hz, 2 H), 6.61 (t, J=6.07 Hz, 1 H), 6.98 (d, J=8.82 Hz, 3 H), 7.17-7.38 (m, 5 H), 7.42 (d, J=8.82 Hz, 2 H), 7.52-7.56 (m, 2 H), 7.75 (d, J=8.82 Hz, 2 H), 7.81 (d, J=8.46 Hz, 1 H), 7.97 (dd, J=8.82, 2.21 Hz, 1 H), 8.14 (d, J=2.21 Hz, 1 H), 8.62 (s, 1 H), 8.84 (s, 1 H), 8.94 (d, J=8.82 Hz, 1 H), 10.37 (s, 1 H), 11.21 (s, 1 H).

Example 364

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester

Example 364A

N-(5-Bromo-pyridin-2-yl)-4-chloro-3-nitro-benzamide

A mixture of 4-chloro-3-nitrobenzoyl chloride (22.0 g, 0.1 mol) and 2-amino-5-bromopyridine (17.3 g, 0.1 mol) in toluene (250 mL) was refluxed for 4 hours, allowing gaseous HCl to escape the reaction vessel through an open, water cooled condenser. The reaction mixture was cooled to room temperature, diluted with hexanes (200 mL) and filtered to give the title compound (33.9 g, 95%).

Example 364B

4-(4-Amino-phenylsulfanyl)-N-(5-bromo-pyridin-2-yl)-3-nitro-benzamide

A mixture of the product of Example 364A (24.2 g, 0.0678 mol), 4-amino-benzenethiol (12.7 g, 0.102 mol, 1.5 equiv.), and sodium acetate trihydrate (46.1 g, 0.339 mol, 5.0 equiv.) in 500 mL of ethanol was heated under reflux under nitrogen with stirring for 2 hours. The reaction mixture was then allowed to cool to room temperature and 200 mL of water added. The mixture was stirred for 30 minutes, filtered, and dried in vacuo to give the title compound (29.8 g, 99%).

Example 364C

{4-[4-(5-Bromo-pyridin-2-ylcarbamoyl)-2-nitrophenylsulfanyl]-phenyl}-carbamic acid 2,2,2-trichloro-ethyl ester

A mixture of the product of Example 364B (27.5 g, 0.0618 mol) and pyridine (7.73 g, 7.50 mL, 0.0927 mol, 1.5 equiv.) in dichloromethane (500 mL) was stirred at room temperature. To this mixture was added slowly, dropwise 2,2,2-trichloro-ethyl chloroformate (17.0 g, 10.8 mL, 0.0803 mol, 1.3 equiv.) over 30 minutes. The reaction mixture was stirred at room temperature for 2 hours, during which time the product precipitated as a yellow solid. The mixture was filtered and the filter cake was rinsed with dichloromethane (100 mL) and dried in vacuo to give the title compound (35.3 g, 92%) as a yellow solid.

Example 364D

{4-[2-Amino-4-(5-bromo-pyridin-2-ylcarbamoyl)-phenylsulfanyl]-phenyl}-carbamic acid 2,2,2-trichloro-ethyl ester

A mixture of the product of Example 364C (1.63 g, 2.63 mmol), iron powder (0.737 g, 13.1 mmol, 5 equiv., from Acros, electrolytically reduced, reagent, powder), and ammonium chloride (0.211 g, 3.94 mmol, 1.5 equiv.) in tetrahydrofuran/ethanol/water (30/30/10 mL) was heated under reflux for 2.5 hours. The reaction mixture was cooled to room temperature and filtered through Celite, rinsing the Celite pad with 50 mL of ethanol. The resulting filtrate was evaporated under reduced pressure and the residue was partitioned between ethyl acetate (100 mL) and water (100 mL). The aqueous phase was washed with ethyl acetate (2×100 mL). The combined organic phases were washed with brine (50 mL), dried over anhydrous magnesium sulfate, filtered, and evaporated under reduced pressure to give the title compound (1.48 g, 95%) as a faintly yellow solid.

Example 364E

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid 2,2,2-trichloro-ethyl ester

A mixture of the products of Example 364D (3.05 g, 5.16 mmol) and Example 8E (N'-(3-cyano-6-isopropyl-pyridin-2-yl)-N,N-dimethyl-formamidine) (1.34 g, 6.20 mmol, 1.2 equiv.) in 25 mL of glacial acetic acid was heated in a 140° C. preheated oil bath for 45 minutes. The reaction mixture was cooled, evaporated in vacuo and the residue partitioned between ethyl acetate (250 mL) and water (100 mL). The organic phase was then washed with saturated aqueous sodium bicarbonate and then brine, dried over anhydrous magnesium sulfate, filtered, and evaporated under reduced pressure. The resulting residue was triturated with methanol, filtered, and dried in vacuo to provide the title compound (3.10 g, 79%) as a beige solid. MS (ESI+) m/z 762/764 (M+H)$^+$; $^1$H NMR (300 MHz, DMSO-d$_6$) δ ppm: 1.33 (d, J=6.99 Hz, 6 H), 3.16-3.26 (m, 1 H), 4.97 (s, 2 H), 6.96 (s, 1 H), 7.43 (d, J=8.82 Hz, 2 H), 7.59 (s, 2 H), 7.86 (s, 1 H), 8.01-8.10 (m, 3 H), 8.15-8.20 (m, 1 H), 8.50 (d, J=2.57 Hz, 1 H), 8.57 (s, 1 H), 8.84 (s, 1 H), 10.23 (s, 1 H), 10.40 (s, 1 H), 10.94 (s, 1 H).

Example 365

N-(5-Bromo-pyridin-2-yl)-3-(7-isopropyl-pyrido[2,3-d]pyrimidin-4-ylamino)-4-{4-[3-((R)-1-phenyl-ethyl)-ureido]-phenylsulfanyl}-benzamide

The product of Example 364E (152 mg, 0.2 mmol) in tetrahydrofuran (2 mL) was treated with 1,8-diazabicyclo[5.4.0]undec-7-ene (60 µL, 0.4 mm01) and (R)-(+)-α-methylbenzylamine (121 mg, 1.0 mmol) and heated at 60° C. for 1 hour in a sealed tube. The reaction mixture was cooled, concentrated and the residue was purified by preparative HPLC on a Waters Symmetry C8 column (40 mm×100 mm, 7 um particle size) using a gradient of 10% to 100% acetonitrile:

aqueous ammonium acetate (10 mM) over 12 min (15 min run time) at a flow rate of 70 mL/min to give the title compound (21 mg, 14%). $^1$H NMR (300 MHz, DMSO-D$_6$) δ ppm: 1.33 (d, J=6.99 Hz, 6 H) 1.40 (d, J=6.62 Hz, 3 H) 3.22 (m, 1 H) 4.82 (m, 1 H) 6.73 (d, J=8.09 Hz, 1 H) 6.90 (s, br, 1 H) 7.24 (m, 1 H) 7.35 (m, 6 H) 7.48 (m, 2 H) 7.63 (s, br, 1 H) 7.86 (s, br, 1 H) 8.04 (d, J=2.57 Hz, 1 H) 8.07 (d, J=2.57 Hz, 1 H) 8.17 (m, 1 H) 8.49 (d, J=2.57 Hz, 1 H) 8.60 (s, 1 H) 8.66 (s, 1 H) 8.86 (s, br, 1 H) 10.28 (s, 1 H) 10.95 (s, 1 H); (ESI+) m/z 733 735 (M+H)+.

Example 366

N-(5-Bromo-pyridin-2-yl)-3-(7-isopropyl-pyrido[2,3-d]pyrimidin-4-ylamino)-4-{4-[3-((S)-1-phenyl-ethyl)-ureido]-phenylsulfanyl}-benzamide The title compound was prepared as in Example 365 substituting (S)-(−)-α-methylbenzylamine (121 mg, 1.0 mmol) for (R)-(+)-α-methylbenzylamine to give a yellow solid (29 mg, 20%). $^1$H NMR (300 MHz, DMSO-D$_6$) δ ppm: 1.34 (d, J=6.99 Hz, 6 H) 1.40 (d, J=6.99 Hz, 3 H) 3.22 (m, 1 H) 4.82 (m, 1 H) 6.72 (d, J=7.72 Hz, 1 H) 6.90 (d, J=8.46 Hz, 1 H) 7.25 (m, 1 H) 7.34 (m, 1 H) 7.34 (m, 6 H) 7.48 (d, J=8.82 Hz, 2 H) 7.64 (d, J=8.46 Hz, 1 H) 7.86 (d, J=8.46 Hz, 1 H) 8.04 (d, J=2.57 Hz, 1 H) 8.07 (d, J=2.57 Hz, 1 H) 8.16 (m, 1 H) 8.49 (d, J=2.21 Hz, 1 H) 8.59 (s, 1 H) 8.66 (s, 1 H) 8.87 (d, J=8.09 Hz, 1 H) 10.20 (s, 1 H) 10.95 (s, 1 H); (ESI+) m/z 733, 735 (M+H)+.

Example 367

N-(5-Bromo-pyridin-2-yl)-3-(7-isopropyl-pyrido[2,3-d]pyrimidin-4-ylamino)-4-[4-(3-thiophen-2-ylmethyl-ureido)-phenylsulfanyl]-benzamide The title compound was prepared as in Example 365 substituting 2-thiophenemethylamine (113 mg, 1.0 mmol) for (R)-(+)-α-methylbenzylamine to give a yellow solid (57 mg, 39%). $^1$H NMR (300 MHz, DMSO-D$_6$) δ ppm: 1.34 (d, J=6.62 Hz, 6 H) 3.21 (m, 1 H) 4.47 (d, J=5.88 Hz, 2 H) 6.78 (t, J=6.07 Hz, 1 H) 6.95 (m, 3 H) 7.37 (m, 3 H) 7.52 (d, J=8.82 Hz, 2 H) 7.64 (d, J=7.35 Hz, 1 H) 7.87 (d, J=8.82 Hz, 1 H) 8.04 (d, J=2.57 Hz, 1 H) 8.07 (d, J=2.57 Hz, 1 H) 8.17 (m, 1 H) 8.49 (d, J=2.21 Hz, 1 H) 8.59 (s, 1 H) 8.86 (m, 2 H) 10.19 (s, 1 H) 10.96 (s, 1 H); (ESI+) m/z 725, 727 (M+H)+.

Example 368

N-(5-Bromo-pyridin-2-yl)-3-(7-isopropyl-pyrido[2,3-d]pyrimidin-4-ylamino)-4-[4-(3-thiophen-3-ylmethyl-ureido)-phenylsulfanyl]-benzamide The title compound was prepared as in Example 365 substituting 3-thiophenemethylamine (113 mg, 1.0 mmol) for (R)-(+)-α-methylbenzylamine to give a yellow solid (31 mg, 21%). $^1$H NMR (300 MHz, DMSO-D$_6$) δ ppm: 1.33 (d, J=6.99 Hz, 6 H) 3.22 (m, 1 H) 4.29 (d, J=5.52 Hz, 2 H) 6.66 (t, J=5.70 Hz, 1 H) 6.93 (d, J=8.82 Hz, 1 H) 7.07 (dd, J=4.80 Hz, 1.47 Hz, 1 H) 7.35 (m, 3 H) 7.50 (m, 3 H) 7.63 (d, J=8.82 Hz, 1 H) 7.87 (d, J=8.82 Hz, 1 H) 8.04 (d, J=2.57 Hz, 1 H) 8.07 (d, J=2.57 Hz, 1 H) 8.17 (m, 1 H) 8.49 (d, J=2.21 Hz, 1 H) 8.59 (s, 1 H) 8.80 (s, 1 H) 8.88 (d, J=8.46 Hz, 1 H) 10.19 (s, 1 H) 10.96 (s, 1 H); (ESI+) m/z 725 727 (M+H)+.

Example 369

N-(5-Bromo-pyridin-2-yl)-4-[4-(3-furan-2-ylmethyl-ureido)-phenylsulfanyl]-3-(7-isopropyl-pyrido[2,3-d]pyrimidin-4-ylamino)-benzamide The title compound was prepared as in Example 365 substituting 2-furfurylamine (97 mg, 1.0 mmol) for (R)-(+)-α-methylbenzylamine to give a yellow solid (19 mg, 13%). $^1$H NMR (300 MHz, DMSO-D$_6$) δ ppm: 1.34 (d, J=6.99 Hz, 6 H) 3.22 (m, 1 H) 4.30 (d, J=5.52 Hz, 2 H) 6.26 (d, J=2.57 Hz, 1 H) 6.40 (dd, J=3.31, 1.84 Hz, 1 H) 6.65 (t, J=5.70 Hz, 1 H) 6.93 (d, J=8.46 Hz, 1 H) 7.36 (d, J=8.82 Hz, 2 H) 7.50 (d, J=8.82 Hz, 2 H) 7.59 (dd, J=1.84 Hz, 0.99 Hz, 1 H) 7.64 (d, J=8.46 Hz, 1 H) 7.89 (d, J=8.46 Hz, 1 H) 8.04 (d, J=2.21 Hz, 1 H) 8.07 (d, J=2.57 Hz, 1 H) 8.16 (m, 1 H) 8.49 (d, J=2.21 Hz, 1 H) 8.59 (s, 1 H) 8.80 (s, 1 H) 8.87 (d, J=8.46 Hz, 1 H) 10.19 (s, 1 H) 10.96 (s, 1 H); (ESI+) m/z 709, 711 (M+H)+.

Example 370

N-(5-Bromo-pyridin-2-yl)-4-[4-(3-furan-3-ylmethyl-ureido)-phenylsulfanyl]-3-(7-isopropyl-pyrido[2,3-d]pyrimidin-4-ylamino)-benzamide The title compound was prepared as in Example 365 substituting 3-furfurylamine (97 mg, 1.0 mmol) for (R)-(+)-α-methylbenzylamine to give a yellow solid (58 mg, 41%). $^1$H NMR (300 MHz, DMSO-D$_6$) δ . ppm 1.33 (d, J=6.99 Hz, 6 H) 3.22 (m, 1 H) 4.13 (d, J=5.52 Hz, 2 H) 6.46 (m, 1 H) 6.52 (t, J=5.88 Hz, 1 H) 6.90 (d, J=8.46 Hz, 1 H) 7.36 (d, J=8.82 Hz, 2 H) 7.51 (d, J=8.82 Hz, 2 H) 7.61 (m, 3 H) 7.87 (d, J=8.46 Hz, 1 H) 8.04 (d, J=2.57 Hz, 1 H) 8.07 (d, J=2.57 Hz, 1 H) 8.17 (m, 1 H) 8.49 (d, J=2.57 Hz, 1 H) 8.58 (s, 1 H) 8.76 (s, 1 H) 8.87 (d, J=8.46 Hz, 1 H) 10.19 (s, 1 H) 10.96 (s, 1 H); (ESI+) m/z 709, 711 (M+H)+.

Example 371

N-(5-Bromo-pyridin-2-yl)-4-{4-[3-(2-ethoxy-ethyl)-ureido]-phenylsulfanyl}-3-(7-isopropyl-pyrido[2,3-d]pyrimidin-4-ylamino)-benzamide The title compound was prepared as in Example 365 substituting 2-ethoxy-ethylamine (89 mg, 1.0 mmol) for (R)-(+)-α-methylbenzylamine. The crude product was purified by reverse phase preparative HPLC on a Waters Symmetry C8 column (25 mm×100 mm, 7 μm particle size) using a gradient of 10% to 100% acetonitrile/0.1% aqueous trifluoroacetic acid over 8 minutes (10 minutes run time) at a flow rate of 40 mL/min to provide the title compound as a trifluoroacetic acid salt (60 mg, 37%). $^1$H NMR (300 MHz, DMSO-D$_6$) δ ppm: 1.14 (t, J=6.99 Hz, 3 H) 1.36 (d, J=6.99 Hz, 6 H) 3.26 (m, 3 H) 3.46 (m, 4 H) 6.29 (t, J=5.52 Hz, 1 H) 6.96 (d, 8.46 Hz, 1 H) 7.35 (d, J=8.82 Hz, 2 H) 7.48 (d, J=8.82 Hz, 2 H) 7.84 (d, J=8.46 Hz, 1 H) 7.93 (d, J=8.46 Hz, 1 H) 8.05 (d, J=2.57 Hz, 1 H) 8.08 (d, J=2.21 Hz, 1 H) 8.17 (m, 1 H) 8.50 (d, J=2.57 Hz, 1 H) 8.78 (s, 1 H) 8.84 (s, 1 H) 8.97 (d, J=8.82 Hz, 1 H) 10.99 (s, 1 H) 11.34 (s, 1 H); (ESI+) m/z 701, 703 (M+H)+.

Example 372

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid benzyl ester The title compound was prepared as in Example 365 substituting benzyl alcohol (108 mg, 1.0 mmol) for (R)-(+)-α- methylbenzylamine. The crude product was purified by reverse phase preparative HPLC on a Waters Symmetry C8 column (25 mm×100 mm, 7 µm particle size) using a gradient of 10% to 100% acetonitrile/0.1% aqueous trifluoroacetic acid over 8 minutes (10 minutes run time) at a flow rate of 40 mL/min to provide the title compound as a trifluoroacetic acid salt (26 mg, 16%). $^1$H NMR (300 MHz, DMSO-D$_6$) δ ppm: 1.35 (d, J=6.99 Hz, 6 H) 3.26 (m, 1 H) 5.17 (s, 2 H) 6.99 (d, J=8.46 Hz, 1 H) 7.40 (m, 7 H) 7.54 (m, 2 H) 7.79 (d, J=8.46 Hz, 1 H) 7.93 (d, J=8.46 Hz, 1 H) 8.05 (d, J=2.57 Hz, 1 H) 8.08 (d, J=2.21 Hz, 1 H) 8.16 (m, 1 H) 8.50 (d, J=1.84 Hz, 1 H) 8.74 (s, 1 H) 8.92 (d, J=8.46 Hz, 1 H) 10.04 (s, 1 H) 10.98 (s, 1 H) 11.16 (s, 1 H); (ESI+) m/z 720, 722 (M+H)+.

Example 373

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid thiophen-2-ylmethyl ester The title compound was prepared as in Example 365 substituting 2-thiophene methanol (114 mg, 1.0 mmol) for (R)-(+)-α-methylbenzylamine. The crude product was purified by reverse phase preparative HPLC on a Waters Symmetry C8 column (25 mm×100 mm, 7 µm particle size) using a gradient of 10% to 100% acetonitrile/0.1% aqueous trifluoroacetic acid over 8 minutes (10 minutes run time) at a flow rate of 40 mL/min to provide the title compound as a trifluoroacetic acid salt (33 mg, 20%). $^1$H NMR (300 MHz, DMSO-D$_6$) δ ppm: 1.36 (d, J=6.99 Hz, 6 H) 3.28 (m, 1 H) 5.34 (s, 2 H) 7.04 (m, 2 H) 7.22 (m, 1 H) 7.41 (d, J=8.82 Hz, 2 H) 7.53 (d, J=8.82 Hz, 2 H) 7.58 (dd, J=5.13, 1.83 Hz, 1 H) 7.74 (d, J=8.46 Hz, 1 H) 7.93 (d, J=8.46 Hz, 1 H) 8.05 (d, J=2.57 Hz, 1 H) 8.08 (d, J=2.57 Hz, 1 H) 8.16 (m, 1 H) 8.51 (d, J=2.57 Hz, 1 H) 8.83 (s, 1 H) 8.96 (d, J=8.46 Hz, 1 H) 10.03 (s, 1 H) 11.01 (s, 1 H) 11.50 (s, 1 H); (ESI+) m/z 726, 728 (M+H)+.

Example 374

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid butyl ester The title compound was prepared as in Example 365 substituting 1-butanol (74 mg, 1.0 mmol) for (R)-(+)-α-methylbenzylamine. The crude product was purified by reverse phase preparative HPLC on a Waters Symmetry C8 column (25 mm×100 mm, 7 µm particle size) using a gradient of 10% to 100% acetonitrile/0.1% aqueous trifluoroacetic acid over 8 minutes (10 minutes run time) at a flow rate of 40 mL/min to provide the title compound as a trifluoroacetic acid salt (42 mg, 26%). $^1$H NMR (300 MHz, DMSO-D$_6$) δ ppm: 0.92 (t, J=7.35 Hz, 3 H) 1.37 (m, 8 H) 1.61 (m, 2 H) 3.26 (m, 1 H) 4.10 (t, J=6.62 Hz, 2 H) 7.00 (d, J=8.09 Hz, 1 H) 7.40 (d, J=8.46 Hz, 2 H) 7.54 (d, J=8.46 Hz, 2 H) 7.81 (d, J=8.46 Hz, 1 H) 7.92 (d, J=8.46 Hz, 1 H) 8.05 (d, J=2.21 Hz, 1 H) 8.08 (d, J=2.57 Hz, 1 H) 8.16 (m, 1 H) 8.50 (d, J=2.57 Hz, 1 H) 8.74 (s, 1 H) 8.93 (d, J=8.46 Hz, 1 H) 9.87 (s, 1 H) 10.99 (s, 1 H) 11.20 (s, 1 H); (ESI+) m/z 686, 688 (M+H)+.

Example 375

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid tetrahydro-furan-2-ylmethyl ester The title compound was prepared as in Example 365 substituting tetrahydrofuran-2-yl-methanol (101 mg, 1.0 mmol) for (R)-(+)-α-methylbenzylamine. The crude product was purified by reverse phase preparative HPLC on a Waters Symmetry C8 column (25 mm×100 mm, 7 µm particle size) using a gradient of 10% to 100% acetonitrile/0.1% aqueous trifluoroacetic acid over 8 minutes (10 minutes run time) at a flow rate of 40 mL/min to provide the title compound as a trifluoroacetic acid salt (89 mg, 52%). $^1$H NMR (300 MHz, DMSO-D$_6$) δ ppm: 1.35 (d, J=6.99 Hz, 6 H) 1.60 (m, 1 H) 1.82 (m, 1 H) 1.94 (m, 1 H) 3.26 (m, 1 H) 3.66 (m, 1 H) 3.77 (m, 1 H) 4.05 (m, 3 H) 6.99 (d, J=8.09 Hz, 1 H) 7.40 (d, J=8.46 Hz, 2 H) 7.54 (d, J=8.46 Hz, 2 H) 7.78 (d, J=8.82 Hz, 1 H) 7.90 (d, J=8.82 Hz, 1 H) 8.05 (d, J=2.21 Hz, 1 H) 8.08 (d, J=2.57 Hz, 1 H) 8.16 (m, 1 H) 8.50 (d, J=2.57 Hz, 1 H) 8.72 (s, 1 H) 8.91 (d, J=8.46 Hz, 1 H) 9.98 (s, 1 H) 10.98 (s, 1 H); (ESI+) m/z 714, 716 (M+H)+.

Example 376

{4-[4-(5-Bromo-pyridin-2-ylcarbamoyl)-2-(7-isopropyl-pyrido[2,3-d]pyrimidin-4-ylamino)-phenylsulfanyl]-phenyl}-carbamic acid 2-(2-methoxy-ethoxy)-ethyl ester The title compound was prepared as in Example 365 substituting 2-(2-methoxy-ethoxy)-ethanol (72 mg, 0.6 mmol) for (R)-(+)-α-methylbenzylamine. The crude product was purified by reverse phase preparative HPLC on a Waters Symmetry C8 column (25 mm×100 mm, 7 µm particle size) using a gradient of 10% to 100% acetonitrile/0.1% aqueous trifluoroacetic acid over 8 minutes (10 minutes run time) at a flow rate of 40 mL/min to provide the title compound as a trifluoroacetic acid salt (38 mg, 45% yield).+; $^1$H NMR (300 MHz, DMSO-D$_6$) δ ppm: 1.34 (d, J=6.62 Hz, 6 H), 3.13-3.27 (m, 1 H), 3.25 (s, 3 H), 3.42-3.48 (m, 2 H), 3.53-3.59 (m, 2 H), 3.62-3.68 (m, 2 H), 4.19-4.24 (m, 2 H), 6.94 (d, J=8.09 Hz, 1 H), 7.40 (d, J=8.82 Hz, 2 H), 7.56 (d, J=8.82 Hz, 2 H), 7.67 (d, J=8.46 Hz, 1 H), 7.87 (d, J=6.25 Hz, 1 H), 8.06 (dd, J=9.19, 2.57 Hz, 2 H), 8.12-8.20 (m, 1 H), 8.50 (d, J=1.84 Hz, 1 H), 8.61 (s, 1 H), 8.86 (d, J=7.72 Hz, 1 H), 10.02 (s, 1 H), 10.56 (s, 1 H), 10.96 (s, 1 H); MS (ESI+) m/z 732, 734 (M+H).

Example 377

4,4'-(4,4'-carbonylbis(azanediyl)bis(4,1-phenylene) bis(sulfanediyl))bis(N-(5-bromopyridin-2-yl)-3-(7-isopropylpyrido[2,3-d]pyrimidin-4-ylamino)benzamide)

The title compound was prepared as in Example 365 substituting the product of Example 17 (120 mg, 0.2 mmol) for (R)-(+)-α-methylbenzylamine. The crude product was purified by reverse phase preparative HPLC on a Waters Symmetry C8 column (25 mm×100 mm, 7 µm particle size) using a gradient of 10% to 100% acetonitrile/0.1% aqueous trifluoroacetic acid over 8 minutes (10 minutes run time) at a flow rate of 40 mL/min to provide the title compound as a bis-trifluoroacetic acid salt (30 mg, 45% yield). $^1$H NMR (300 MHz, DMSO-D$_6$) δ ppm: 1.35 (d, J=6.99 Hz, 12 H), 3.19-3.34 (m, J=6.99 Hz, 2 H), 7.03 (d, J=7.72 Hz, 2 H), 7.42 (d, J=8.46 Hz, 4 H), 7.52-7.59 (m, 4 H), 7.83 (d, J=8.09 Hz, 2 H), 7.95 (d, J=7.72 Hz, 2 H), 8.04-8.10 (m, 4 H), 8.12-8.21 (m, 2 H), 8.51 (d, J=2.57 Hz, 2 H), 8.79 (s, 2 H), 8.97 (d, J=5.88 Hz, 2 H), 9.12 (s, 2 H), 10.99 (s, 2 H), 11.29 (s, 2 H); MS (ESI+) m/z 1199 (M+H).

Example 378

N-(5-Bromo-pyridin-2-yl)-3-(7-isopropyl-pyrido[2,3-d]pyrimidin-4-ylamino)-4-(4-propylamino-phenylsulfanyl)-benzamide To the product of Example 17B (586 mg, 1.0 mmol) and sodium triacetoxyborohydride (844 mg, 4.0 mmol) in dichloromethane/methanol (50 mL, 9:1) was added propionaldehyde (218 μL, 3.0 mmol). The reaction mixture was stirred at room temperature for 2 days and evaporated. The residue was partitioned between saturated sodium carbonate solution and ethyl acetate. The organic layer was washed with water, dried with magnesium sulfate, filtered and evaporated. The residue was purified by silica gel chromatography eluting with dichloromethane/methanol (99:1) to give the title compound (207 mg, 33%). $^1$H NMR (300 MHz, DMSO-D$_6$) δ ppm: 0.95 (t, J=7.35 Hz, 3 H) 1.34 (d, J=6.99 Hz, 6 H) 1.57 (m, 2 H) 2.99 (m, 2 H) 3.24 (m, 1 H) 6.16 (t, J=5.16 Hz, 1 H) 6.64 (d, J=8.82 Hz, 2 H) 6.83 (d, J=8.46 Hz, 1 H) 7.20 (d, J=8.82 Hz, 2 H) 7.63 (d, J=8.46 Hz, 1 H) 7.86 (d, J=8.46 Hz, 1 H) 8.04 (d, J=2.57 Hz, 1 H) 8.07 (d, J=2.57 Hz, 1 H) 8.16 (m, 1 H) 8.49 (d, J=2.57 Hz, 1 H) 8.58 (s, 1 H) 8.87 (d, J=8.46 Hz, 1 H) 10.13 (s, 1 H) 10.91 (s, 1 H); (ESI+) m/z 628, 630 (M+H)+.

Example 379

N-(5-Bromo-pyridin-2-yl)-3-(7-isopropyl-pyrido[2,3-d]pyrimidin-4-ylamino)-4-[4-(ethyl-propyl-amino)-phenylsulfanyl]-benzamide To the product of Example 378 (31 mg, 0.05 mmol) and sodium triacetoxyborohydride (414 mg, 2.0 mmol) in dichloromethane/methanol (5 mL, 9:1) was added acetaldehyde (112 μL, 2.0 mmol). The mixture was stirred at room temperature for 16 hours and evaporated. The residue was partitioned between saturated sodium carbonate solution and ethyl acetate. The organic layer was washed with water, dried with magnesium sulfate, filtered and evaporated. The residue was purified by silica gel chromatography eluting with dichloromethane/methanol (99:1) to give the title compound (25 mg, 77%). $^1$H NMR (300 MHz, DMSO-D$_6$) δ ppm: 0.90 (t, J=7.35 Hz, 3 H) 1.09 (t, J=6.99 Hz, 3 H) 1.34 (d, J=6.99 Hz, 6 H) 1.55 (m, 2 H) 3.24 (m, 3 H) 3.38 (q, J=6.99 Hz, 2 H) 6.71 (d, J=8.82 Hz, 2 H) 6.87 (d, J=8.82 Hz, 1 H) 7.26 (d, J=8.82 Hz, 2 H) 7.63 (d, J=8.46 Hz, 1 H) 7.88 (d, J=8.46 Hz, 1 H) 8.04 (d, J=2.57 Hz, 1 H) 8.07 (d, J=2.21 Hz, 1 H) 8.17 (m, 1 H) 8.49 (d, J=1.84 Hz, 1 H) 8.58 (s, 1 H) 8.89 (d, J=8.46 Hz, 1 H) 10.13 (s, 1 H) 10.91 (s, 1 H); (ESI+) m/z 656, 658 (M+H)+.

Example 380

4-[4-Benzoylamino-phenylsulfanyl]-N-(5-bromo-pyridin-2-yl)-3-(7-isopropyl-pyrido[2,3-d]pyrimidin-4-ylamino)-benzamide To a solution of the product from Example 17B (117 mg, 0.2 mmol) and benzoic acid (28 mg, 0.22 mmol) in tetrahydrofuran (4 ml) was added 3-(diethoxyphosphoryloxy)-1,2,3-benzo-triazin-4(3H)-one (72 mg, 0.22 mmol) and triethylamine (0.14 ml, 1.0 mmol). The mixture was stirred at room temperature for 16 hours then poured into saturated sodium carbonate solution and extracted with ethyl acetate. The organic layer was dried with magnesium sulfate, filtered and evaporated. The residue was purified by chromatography on a Waters Symmetry C8 column eluting with 0.1% trifluoroacetic acid in water/methanol (90/10) to 0.1% trifluoroacetic in water/methanol (5/95) to give the title compound as a trifluoroacetic acid salt (24 mg, 15%). $^1$H NMR (300 MHz, DMSO-D$_6$) δ ppm: 1.35 (d, J=6.62 Hz, 6 H) 3.29 (m, 1 H) 7.16 (d, J=8.09 Hz, 1 H) 7.46 (d, J=8.82 Hz, 2 H) 7.57 (m, 3 H) 7.84 (d, J=8.82 Hz, 2 H) 7.94 (m, 3 H) 8.01 (dd, J=8.46, 1.84 Hz, 1 H) 8.06 (d, J=2.57 Hz, 1 H) 8.09 (d, J=2.21 Hz, 1 H) 8.17 (m, 1 H) 8.51 (d, J=2.21 Hz, 1 H) 8.89 (s, 1 H) 9.01 (d, J=8.46 Hz, 1 H) 10.41 (s, 1 H) 11.04 (s, 1 H) 11.74 (s, 1 H); ESI+) m/z 690, 692 (M+H)+.

Example 381

N-(5-bromo-pyridin-2-yl)-4-[4-(2-ethoxy-acetylamino)-phenylsulfanyl]-3-(7-isopropyl-pyrido[2,3-d]pyrimidin-4-ylamino)-benzamide The title compound was prepared as in Example 380 substituting ethoxyacetic acid (23 mg, 0.22 mmol) for benzoic acid to give a trifluoroacetic acid salt (40 mg, 25%). $^1$H NMR (300 MHz, DMSO-D$_6$) δ ppm: 1.19 (t, J=6.99 Hz, 3 H) 1.35 (d, J=6.99 Hz, 6 H) 3.28 (m, 1 H) 3.57 (q, J=6.99 Hz, 2 H) 4.04 (s, 2 H) 7.04 (d, J=8.09 Hz, 1 H) 7.42 (d, J=8.82 Hz, 2 H) 7.73 (d, J=8.82 Hz, 2 H) 7.82 (d, J=8.46 Hz, 1 H) 7.94 (d, J=8.46 Hz, 1 H) 8.06 (m, 2 H) 8.16 (m, 1 H) 8.51 (d, J=2.21 Hz, 1 H) 8.76 (s, 1 H) 8.95 (d, J=8.46 Hz, 1 H) 9.92 (s, 1 H) 11.00 (s, 1 H) 11.25 (s, 1 H); (ESI+) m/z 672, 674 (M+H)+.

Example 382

N-(5-bromo-pyridin-2-yl)-4-{4-[2-(2,4-dimethoxyphenyl)-acetylamino]-phenylsulfanyl}-3-(7-isopropyl-pyrido[2,3-d]pyrimidin-4-ylamino)-benzamide The title compound was prepared as in Example 380 substituting 2,4-dimethoxyphenylacetic acid (43 mg, 0.22 mmol) for benzoic acid to give a trifluoroacetic acid salt (21 mg, 12%). $^1$H NMR (300 MHz, DMSO-D$_6$) δ ppm: 1.35 (d, J=6.62 Hz, 6 H) 3.26 (m, 1 H) 3.56 (s, 2 H) 3.75 (s, 3 H) 3.76 (s, 3 H) 6.49 (dd, J=8.09, 2.57 Hz, 1 H) 6.55 (d, J=2.21 Hz, 1 H) 7.00 (d, J=8.46 Hz, 1 H) 7.11 (d, J=8.09 Hz, 1 H) 7.41 (d, J=8.82 Hz, 2 H) 7.69 (d, J=8.82 Hz, 2 H) 7.77 (d, J=8.46 Hz, 1 H) 7.90 (d, J=8.46 Hz, 1 H) 8.05 (d, J=2.57 Hz, 1 H) 8.08 (d, J=2.21 Hz, 1 H) 8.18 (m, 1 H) 8.50 (d, J=1.84 Hz, 1 H) 8.71 (s, 1 H) 8.93 (d, J=8.46 Hz, 1 H) 10.21 (s, 1 H) 10.98 (s, 1 H); (ESI+) m/z 764 766 (M+H)+.

Example 383

N-(5-bromo-pyridin-2-yl)-4-{4-[2-(4-hydroxymethyl-phenyl)-acetylamino]-phenylsulfanyl}-3-(7-isopropyl-pyrido[2,3-d]pyrimidin-4-ylamino)-benzamide The title compound was prepared as in Example 380 substituting substituting 4-hydroxymethylphenylacetic acid (37 mg, 0.22 mmol) for benzoic acid to give the title compound as a trifluoroacetic acid salt (19 mg, 11%). $^1$H NMR (300 MHz, DMSO-D$_6$) δ ppm: 1.35 (d, J=6.99 Hz, 6 H) 3.26 (m, 1 H) 3.63 (s, 2 H) 4.47 (s, 2 H) 7.01 (d, J=8.46 Hz, 1 H) 7.28 (m, 4 H) 7.41 (d, J=8.82 Hz, 2 H) 7.68 (d, J=8.46 Hz, 2 H) 7.79 (d, J=8.46 Hz, 1 H) 7.90 (d, J=8.46 Hz, 1 H) 8.05 (d, J=2.57 Hz, 1 H) 8.08 (d, J=2.57 Hz, 1 H) 8.16 (m, 1 H) 8.50 (d, J=2.57 Hz, 1 H) 8.75 (s, 1 H) 8.92 (d, J=8.46 Hz, 1 H) 10.36 (s, 1 H) 10.99 (s, 1 H); (ESI+) m/z 734, 736 (M+H)+.

Example 384

5-Bromo-pyridine-2-carboxylic acid [4-(4-amino-phenylsulfanyl)-3-(7-isopropyl-pyrido[2,3-d]pyrimidin-4-ylamino)-phenyl]-amide

Example 384A

5-Bromo-pyridine-2-carbonyl chloride

To a solution of 5-bromo-pyridine-2-carboxylic acid (1.5 g, 7.42 mmol) in THF (20 mL) was added cat. DMF (2 drops) and oxalyl chloride (0.64 mL, 8.16 mmol). The reaction mixture was stirred for 0.5 hr and than refluxed for 0.5 hr. The reaction was cooled and the solvent removed under reduced pressure to give the acid chloride hydrochloride salt (1.85 g, 97%). This acid chloride hydrochloride salt was used with out further purification.

Example 384B

5-Bromo-pyridine-2-carboxylic acid (4-fluoro-3-nitro-phenyl)-amide

To a solution of 4-fluoro-3-nitro-phenylamine (0.82 g, 5.23 mmol) and N,N-diisopropylethylamine (1.5 g, 12.0 mmol) in DMF (25 mL) was added the product from Example 384A (1.0 g, 5.23 mmol) in one portion. The solution was stirred at 40° C. overnight. The reaction was poured into water and the yellow precipitate was collected by filtration. The precipitate was washed with water (2x) and dried under vacuum at 60° C. overnight to give the desired product (1.0, 68%)

Example 384C (4-{4-[(5-Bromo-pyridine-2-carbonyl)-amino]-2-nitro-phenylsulfanyl}-phenyl)-carbamic acid 9H-fluoren-9-ylmethyl ester The product from the previous Example 384B (0.42 gm, 0.95 mmol) in a round bottom flask was suspended in THF (12 ml) at room temperature to which was added pyridine (0.24 mL, 2.85 mmol). To this was added 9-fluorenyl-methoxycarbonyl chloride (0.304 gm, 1.17 mmol) in one portion and the flask caped with a rubber septum. The reaction mixture was allowed to stir at room temperature overnight. The product was isolated by dilution with diethyl ether (50 mL) and vacuum filtration. The cake was rinsed with additional ether then dried in vacuo to give the title compound (0.526 gm, 82%).

Example 384D (4-{2-Amino-4-[(5-bromo-pyridine-2-carbonyl)-amino]-phenylsulfanyl}-phenyl)-carbamic acid 9H-fluoren-9-ylmethyl ester The product from Example 384C (0.20 gm, 0.30 mmol) was suspended in a 4/1 v-v mixture of glacial acetic acid and ethanol (8 ml). To this vigorously stirred suspension was added, in one portion, iron powder (0.215 gm, 3.85 mmol) and the resulting mixture heated under nitrogen in an oil bath at 100° C. After 19.5 hours the reaction mixture was cooled then concentrated under vacuum to a paste which was suspended in water and the solid product collected by vacuum filtration. The cake was washed with water then dried in vacuo at room temperature (0.204 gm, quant.).

Example 384E

{4-[4-[(5-Bromo-pyridine-2-carbonyl)-amino]-2-(7-isopropyl-pyrido[2,3-d]pyrimidin-4-ylamino)-phenylsulfanyl]-phenyl}-carbamic acid 9H-fluoren-9-ylmethyl ester The product from Example 384D (0.10 gm, 0.157 mmol) was combined with the product from Example 8E (0.045 gm, 0.21 mmol) in glacial acetic acid (2 ml) and the mixture heated in a sealed tube in an oil bath at 120° C. for thirty five minutes. A second aliquot of amidine (0.055 gm, 0.25 mmol) was added and heating resumed for 22 minutes upon which time it was determined that the amine starting material was consumed. The reaction mixture was allowed to cool then combined with two similar scale reactions and the lot concentrated in vacuo. The residue was partitioned with water and dichloromethane and the resulting aqueous phase extracted repeatedly with dichloromethane (100 ml total). The combined organics were dried with $MgSO_4$ then concentrated in vacuo to give a green foam. The crude product was dissolved in dichloromethane and applied in portions to a Biotage KPSil samplet (25 mm) drying in a vacuum oven at room temperature between sample applications. The samplet was coupled with a 25 mm column and eluted with ethyl acetate-hexane (1/10-1/1 v-v) followed by dichloromethane-methanol (95/5 v-v) to elute the product (0.15 gm, 47%).

Example 384F

5-Bromo-pyridine-2-carboxylic acid [4-(4-amino-phenylsulfanyl)-3-(7-isopropyl-pyrido[2,3-d]pyrimidin-4-ylamino)-phenyl]-amide The product described in Example 384E (0.179 gm, 0.22 mmol) was dissolved in THF (12 ml) at room temperature. To this solution was added tetra n-butyl ammonium fluoride as a 1.0M solution in THF (0.225 ml, 0.225 mmol) dropwise via syringe. The mixture was allowed to stir thirty minutes then partitioned with ethyl acetate and water. The organic phase was water washed (3x) then concentrated to a small volume and dried by azeotroping with benzene. The volatiles were subsequently removed and the residue suspended in ether and the resulting solid collected by vacuum filtration. 1H NMR suggested the presence of a quaternary ammonium species so the cake was re-dissolved in minimum THF, diluted with ethyl acetate and water washed eight times (total volume of washings 140 ml). The resulting organic phase was concentrated, dried and the product isolated as noted above (0.077 gm, 60%) pale yellow solid. $^1$H NMR (300 MHz, DMSO-$d_6$) δ ppm: 1.34 (d, J=6.99 Hz, 6 H) 3.15-3.29 (m, 1 H) 5.46 (s, 2 H) 6.56 (d, J=8.46 Hz, 2 H) 6.90 (d, J=8.82 Hz, 1 H) 7.08 (d, J=8.46 Hz, 2 H) 7.62 (d, J=8.46 Hz, 1 H) 7.68 (dd, J=8.82, 2.21 Hz, 1 H) 8.00-8.11 (m, 2 H) 8.32 (dd, J=8.46, 2.21 Hz, 1 H) 8.56 (s, 1 H) 8.81-8.91 (m, 2 H) 10.07 (s, 1 H).

Example 385

(S)-4-(4-Amino-phenylsulfanyl)-3-(7-isopropyl-pyrido[2,3-d]pyrimidin-4-ylamino)-N-(1-phenyl-ethyl)-benzamide

Example 385A 4-(4-Amino-phenylsulfanyl)-3-nitro-benzoic acid methyl ester

A mixture of 4-chloro-3-nitrobenzoic acid methyl ester (15.0 g, 68 mmol), 4-aminothiophenol (8.8 g, 68 mmol) and K2CO3 (11.8 g, 85 mmol) in DMF (150 mL) was heated at 90° C. for 1.5 hours, cooled to room temperature, and then poured into H2O (450 mL) under stirring. The aqueous mixture was extracted with AcOEt (400 mL). The extract was washed with H2O (3 times) and brine, dried over MgSO4, and evaporated to give the crude product as orange crystal. The crude product was suspended in 150 mL of i-Pr2O and stirred at room temperature for 1 hour. The crystal was collected by filtration, washed with i-Pr2O and dried at 60° C. for 3 days under reduced pressure to give purified title compound as orange crystal (18.6 g, 90%).

Example 385B 4-(4-tert-Butoxycarbonylamino-phenylsulfanyl)-3-nitro-benzoic acid methyl ester A solution of 4-(4-amino-phenylsulfanyl)-3-nitro-benzoic acid methyl ester (18.5 g, 61 mmol) and Boc2O (26.8 g, 122 mmol) in p-dioxane (280 mL) was heated at 90° C. for 3 hours. An additional Boc2O (26.8 g, 122 mmol) was added and the mixture was heated at 90° C. for 3 hours. A second additional Boc2O (13.4 g, 61 mmol) was added and the mixture was heated at 90° C. for 4 hours. The reaction mixture was cooled to room temperature, and then evaporated. The residue was diluted with i-Pr2O (250 mL) and the mixture was stirred at room temperature for 1 hour. The resulting crystal was collected by filtration, washed with i-Pr2O and dried at 60° C. overnight under reduced pressure to give the title compound as yellow crystal (22.8 g, 93%).

Example 385C

3-Amino-4-(4-tert-butoxycarbonylamino-phenylsulfanyl)-benzoic acid methyl ester

A suspension of 4-(4-tert-butoxycarbonylamino-phenylsulfanyl)-3-nitro-benzoic acid methyl ester (22.8 g, 56 mmol), Fe powder (16.4 g, 282 mmol) and NH4Cl (15.1 g, 282 mmol) in aqueous EtOH [prepared from EtOH (228 mL) and H2O (228 mL)] was gradually heated to reflux and gently refluxed for 2 hours. The reaction mixture was cooled to room temperature and filtered through celite pad. The filtrate was evaporated. The aqueous residue was portioned between AcOEt and H2O, made basic to pH 9 with K2CO3, and then filtered through celite pad. The organic layer was separated, washed with H2O and brine, dried over MgSO4 and evaporated. The oily residue was crystallized in the treatment with i-Pr2O (200 mL) and stirred at room temperature for 30 minutes. The resulting crystal was collected by filtration, washed with i-Pr2O and dried at 60° C. overnight under reduced pressure to give the title compound as colorless crystal (13.9 g, 66%).

Example 385D 4-(4-tert-Butoxycarbonylamino-phenylsulfanyl)-3-(7-isopropyl-pyrido[2,3-d]pyrimidin-4-ylamino)-benzoic acid methyl ester A suspension of N'-(3-cyano-6-isopropyl-pyridin-2-yl)-N,N-dimethyl-formamidine (2.00 g, 9.3 mmol) and 3-amino-4-(4-tert-butoxycarbonylamino-phenylsulfanyl)-benzoic acid methyl ester (3.46 g, 9.3 mmol) in AcOH (40 mL) was heated at 120° C. for 20 minutes under N2. After cooling to room temperature, the reaction mixture was portioned between AcOEt (150 mL) and H2O (200 mL), and then made basic to pH 9 with K2CO3 under stirring. The organic layer was separated, washed with 10% NaHCO3, H2O and brine, dried over MgSO4, and evaporated to give pale brown oil. The oily residue was separated by silica gel column chromatography (AcOEt/n-hexane=5/1) to give yellow crystal. Further purification by washing with cold AcOEt (15 mL) gave the title compound as slightly yellow crystal (3.27 g, 65%).

Example 385E 4-(4-tert-Butoxycarbonylamino-phenylsulfanyl)-3-(7-isopropyl-pyrido[2,3-d]pyrimidin-4-ylamino)-benzoic acid To a solution of 4-(4-tert-butoxycarbonylamino-phenylsulfanyl)-3-(7-isopropyl-pyrido[2,3-d]pyrimidin-4-ylamino)-benzoic acid methyl ester (3.25 g, 6.0 mmol) in THF (32.5 mL) was added aqueous LiOH [prepared from LiOH monohydrate (1.02 g, 24 mmol) and H2O (10 mL)] dropwise at room temperature. The mixture was stirred at room temperature for 26 hours, and then evaporated. The aqueous mixture was diluted with 100 mL of H2O, washed with AcOEt (50 mL), and then carefully acidified to pH 4-5 with 10% HCl at 5° C. under stirring. The resulting solid was collected by filtration, washed with H2O, and dried at 60° C. overnight under reduced pressure to give the title compound as pale yellow crystal (3.09 g, 98%). $^1$H-NMR (300 MHz, DMSO-d6) δ ppm: 1.34 (d, J=7.0 Hz, 6H), 1.48 (s, 9H), 3.22 (septet, J=7.0 Hz, 1H), 6.93 (d, J=8.5 Hz, 1H), 7.36 (d, J=8.8 Hz, 2H), 7.54 (d, J=8.8 Hz, 2H), 7.63 (d, J=8.5 Hz, 1H), 7.75 (dd, J=8.5, 1.8 Hz, 1H), 7.89 (d,J=1.8 Hz, 1H), 8.58 (s, 1H), 8.84 (d,J=8.5 Hz, 1H), 9.61 (s, 1H), 10.16 (s, 1H), 12.98 (br-s, 1H)

Example 385F (S)-{4-[2-(7-Isopropyl-pyrido[2,3-d]pyrimidin-4-ylamino)-4-(1-phenyl-ethylcarbamoyl)-phenylsulfanyl]-phenyl}-carbamic acid tert-butyl ester To a suspension of 4-(4-tert-butoxycarbonylamino-phenylsulfanyl)-3-(7-isopropyl-pyrido[2,3-d]pyrimidin-4-ylamino)-benzoic acid (100 mg, 0.19 mmol) and O-benzotriazol-1-yl-N,N,N',N'-tetramethyluronium tetrafluoroborate [TBTU] (68 mg, 0.21 mmol) in DMSO (1 mL) was added S-(−)-α-methylbenzylamine (25 μL, 0.19 mmol) and N,N-diisopropylethylamine (67 μL, 0.38 mmol) dropwise at room temperature under N2. The mixture was stirred at room temperature for 1 hour under N2, and then poured into H2O (20 mL) under stirring. The resulting precipitate was extracted with AcOEt (20 mL). The organic layer was washed with H2O (3 times) and 10% NaHCO3, dried over MgSO4, and evaporated to give yellow amorphous. The oily residue was separated by silica gel column chromatography (AcOEt/n-hexane=10/1) to give pale yellow amorphous, which was solidified by the treatment of i-Pr2O. The resulting solid was collected by filtration, washed with i-Pr2O, and dried at 40° C. for 3 days under reduced pressure to give the title compound as pale yellow crystal (92 mg, 77%). 1H-NMR (300 MHz, DMSO-d6) δ ppm: 1.33 (d, J=7.0 Hz, 6H), 1.45 (d, J=7.3 Hz, 3H), 1.47 (s, 9H), 3.22 (septet, J=7.0 Hz, 1H), 5.16 (quintet, J=7.3 Hz, 1H), 6.97 (d, J=8.4 Hz, 1H), 7.17-7.25 (m, 1H), 7.26-7.40 (m, 4H), 7.32 (d, J=8.8 Hz, 2H), 7.51 (d, J=8.8 Hz, 2H), 7.63 (d, J=8.5 Hz, 1H), 7.74 (br-d, J=8.4 Hz, 1H), 7.93 (br-s, 1H), 8.57 (s, 1H), 8.81 (d, J=7.3 Hz, 1H), 8.84 (d, J=8.5 Hz, 1H), 9.58 (s, 1H), 10.19 (s, 1H) MS ESI+ m/z: 635 (M+H)

Example 385G (S)-4-(4-Amino-phenylsulfanyl)-3-(7-isopropyl-pyrido[2,3-d]pyrimidin-4-ylamino)-N-(1-phenyl-ethyl)-benzamide To a solution of (S)-{4-[2-(7-isopropyl-pyrido[2,3-d]pyrimidin-4-ylamino)-4-(1-phenyl-ethylcarbamoyl)-phenylsulfanyl]-phenyl}-carbamic acid tert-butyl ester (80 mg) in dichloromethane (1.6 mL) was added trifluoroacetic acid [TFA] (0.40 mL) dropwise at room temperature and the mixture was stirred at room temperature for 1 hour. The reaction mixture was portioned between AcOEt and aqueous K2CO3. The organic layer was separated, washed with H2O and brine, dried over MgSO4, and evaporated to pale yellow amorphous, which was solidified by trituration in i-Pr2O. The resulting solid was collected by filtration, washed with i-Pr2O, and dried at 40° C. overnight under reduced pressure to give the title compound as yellow crystal (57 mg, 85%). 1H-NMR (300 MHz, DMSO-d6) δ ppm: 1.34 (d, J=7.0 Hz, 6H), 1.45 (d, J=7.3 Hz, 3H), 3.23 (septet, J=7.0 Hz, 1H), 5.15 (quintet, J=7.3 Hz, 1H), 5.58 (s, 2H), 6.62 (d, J=8.4 Hz, 2H), 6.84 (d, J=8.5 Hz, 1H), 7.12 (d, J=8.4 Hz, 2H), 7.16-7.25 (m, 1H), 7.25-7.40 (m, 4H), 7.63 (d, J=8.4 Hz, 1H), 7.71 (dd, J=8.5, 1.8 Hz, 1H), 7.88 (d, J=1.8 Hz, 1H), 8.57 (s, 1H), 8.75 (d, J=7.3 Hz, 1H), 8.87 (d, J=8.5 Hz, 1H), 10.12 (s, 1H) MS ESI+ m/z: 535 (M+H)

Example 386

(R)-4-(4-Amino-phenylsulfanyl)-3-(7-isopropyl-pyrido[2,3-d]pyrimidin-4-ylamino)-N-(1-phenyl-ethyl)-benzamide

Example 386A (R)-{4-[2-(7-Isopropyl-pyrido[2,3-d]pyrimidin-4-ylamino)-4-(1-phenyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and R-(+)-α-methylbenzylamine: yield 72%.

Example 386B (R)-4-(4-Amino-phenylsulfanyl)-3-(7-isopropyl-pyrido[2,3-d]pyrimidin-4-ylamino)-N-(1-phenyl-ethyl)-benzamide According to the procedure in Example 385G, the title compound was prepared from (R)-{4-[2-(7-isopropyl-pyrido[2,3-d]pyrimidin-4-ylamino)-4-(1-phenyl-ethylcarbamoyl)-phenylsulfanyl]-phenyl}-carbamic acid tert-butyl ester (prepared in Example 386A): yield 81%. 1H-NMR (300 MHz, DMSO-d6) δ ppm: 1.34 (d, J=7.0 Hz, 6H), 1.45 (d, J=7.0 Hz, 3H), 3.23 (septet, J=7.0 Hz, 1H), 5.15 (quintet, J=7.0 Hz, 1H), 5.58 (s, 2H), 6.62 (d, J=8.5 Hz, 2H), 6.84 (d, J=8.5 Hz, 1H), 7.12 (d, J=8.5 Hz, 2H), 7.17-7.25 (m, 1H), 7.26-7.39 (m, 4H), 7.63 (d, J=8.5 Hz, 1H), 7.71 (dd, J=8.5, 1.8 Hz, 1H), 7.88 (d, J=1.8 Hz, 1H), 8.57 (s, 1H), 8.75 (d, J=7.3 Hz, 1H), 8.87 (d, J=8.5 Hz, 1H), 10.12 (s, 1H) MS ESI+ m/z: 535 (M+H) ESI- m/z: 533 (M-H)

Example 387

(S)-4-(4-Amino-phenylsulfanyl)-N-[1-(4-fluoro-phenyl)-ethyl]-3-(7-isopropyl-pyrido[2,3-d]pyrimidin-4-ylamino)-benzamide

Example 387A (S)-{4-[4-[1-(4-Fluoro-phenyl)-ethylcarbamoyl]-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(4-fluorophenyl)ethylamine: yield 95%.

Example 387B (S)-4-(4-Amino-phenylsulfanyl)-N-[1-(4-fluoro-phenyl)-ethyl]-3-(7-isopropyl-pyrido[2,3-d]pyrimidin-4-ylamino)-benzamide According to the procedure in Example 385G, the title compound was prepared from (S)-{4-[4-[1-(4-fluoro-phenyl)-ethylcarbamoyl]-2-(7-isopropyl-pyrido[2,3-d]pyrimidin-4-ylamino)-phenylsulfanyl]-phenyl}-carbamic acid tert-butyl ester (prepared in Example 387A): yield 87%. 1H-NMR (300 MHz, DMSO-d6) δ ppm: 1.34 (d, J=6.62 Hz, 6H) 1.44 (d, J=7.35 Hz, 3H) 3.15-3.28 (m, 1H) 5.09-5.21 (m, 1H) 5.58 (s, 2H) 6.61 (d, J=8.46 Hz, 2H) 6.83 (d, J=8.46 Hz, 1H) 7.07-7.18 (m, 4H) 7.34-7.44 (m, 2H) 7.63 (d, J=8.46 Hz, 1H) 7.70 (dd, J=8.46, 1.84 Hz, 1H) 7.87 (d, J=1.84 Hz, 1H) 8.57 (s, 1H) 8.74 (d, J=7.72 Hz, 1H) 8.86 (d, J=8.46 Hz, 1H) 10.12 (s, 1H) MS ESI+ m/z: 553 (M+H)

Example 388

(S)-4-(4-Amino-phenylsulfanyl)-N-[1-(4-chloro-phenyl)-ethyl]-3-(7-isopropyl-pyrido[2,3-d]pyrimidin-4-ylamino)-benzamide

Example 388A (S)-{4-[4-[1-(4-Chloro-phenyl)-ethylcarbamoyl]-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(4-chlorophenyl)ethylamine: yield 76%.

Example 388B (S)-4-(4-Amino-phenylsulfanyl)-N-[1-(4-chloro-phenyl)-ethyl]-3-(7-isopropyl-pyrido[2,3-d]pyrimidin-4-ylamino)-benzamide According to the procedure in Example 385G, the title compound was prepared from (S)-{4-[4-[1-(4-chloro-phenyl)-ethylcarbamoyl]-2-(7-isopropyl-pyrido[2,3-d]pyrimidin-4-ylamino)-phenylsulfanyl]-phenyl}-carbamic acid tert-

Example 389

(S)-4-(4-Amino-phenylsulfanyl)-N-[1-(4-bromo-phenyl)-ethyl]-3-(7-isopropyl-pyrido[2,3-d]pyrimidin-4-ylamino)-benzamide

Example 389A (S)-{4-[4-[1-(4-Bromo-phenyl)-ethylcarbamoyl]-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(4-bromophenyl)ethylamine: yield 95%.

Example 389B (S)-4-(4-Amino-phenylsulfanyl)-N-[1-(4-bromo-phenyl)-ethyl]-3-(7-isopropyl-pyrido[2,3-d]pyrimidin-4-ylamino)-benzamide According to the procedure in Example 385G, the title compound was prepared from (S)-{4-[4-[1-(4-bromo-phenyl)-ethylcarbamoyl]-2-(7-isopropyl-pyrido[2,3-d]pyrimidin-4-ylamino)-phenylsulfanyl]-phenyl}-carbamic acid tert-butyl ester (prepared in Example 389A): yield 93%. 1H-NMR (300 MHz, DMSO-d6) δ ppm: 1.34 (d, J=6.62 Hz, 6 H) 1.43 (d, J=6.99 Hz, 3 H) 3.16-3.28 (m, 1 H) 5.04-5.15 (m, 1 H) 5.58 (s, 2 H) 6.61 (d, J=8.46 Hz, 2 H) 6.83 (d, J=8.46 Hz, 1 H) 7.11 (d, J=8.46 Hz, 2 H) 7.31 (d, J=8.09 Hz, 2 H) 7.50 (d, J=8.46 Hz, 2 H) 7.63 (d, J=8.82 Hz, 1 H) 7.70 (dd, J=8.27, 1.65 Hz, 1 H) 7.86 (d, J=1.80 Hz, 1 H) 8.57 (s, 1 H) 8.77 (d, J=7.72 Hz, 1 H) 8.86 (d, J=8.46 Hz, 1 H) 10.13 (s, 1 H) MS ESI+ m/z: 613, 615 (M+H)

Example 390

(S)-4-(4-Amino-phenylsulfanyl)-3-(7-isopropyl-pyrido[2,3-d]pyrimidin-4-ylamino)-N-(1-p-tolyl-ethyl)-benzamide

Example 390A (S)-{4-[2-(7-Isopropyl-pyrido[2,3-d]pyrimidin-4-ylamino)-4-(1-p-tolyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-α,4-dimethylbenzylamine: yield 84%. butyl ester (prepared in Example 388A): yield 85%. 1H-NMR (300 MHz, DMSO-d6) δ ppm: 1.33 (d, J=6.99 Hz, 6 H) 1.43 (d, J=6.99 Hz, 3 H) 3.18-3.27 (m, 1 H) 5.06-5.18 (m, 1 H) 5.58 (s, 2 H) 6.61 (d, J=8.82 Hz, 2 H) 6.83 (d, J=8.46 Hz, 1 H) 7.11 (d, J=8.46 Hz, 2 H) 7.32-7.41 (m, 4 H) 7.64 (d, J=8.46 Hz, 1 H) 7.70 (d, J=8.46 Hz, 1 H) 7.87 (s, 1 H) 8.58 (s, 1 H) 8.75 (d, J=8.82 Hz, 1 H) 8.87 (d, J=8.82 Hz, 1 H) 10.17 (s, 1 H) MS ESI+ m/z: 569 (M+H)

Example 390B (S)-4-(4-Amino-phenylsulfanyl)-3-(7-isopropyl-pyrido[2,3-d]pyrimidin-4-ylamino)-N-(1-p-tolyl-ethyl)-benzamide According to the procedure in Example 385G, the title compound was prepared from (S)-{4-[2-(7-isopropyl-pyrido[2,3-d]pyrimidin-4-ylamino)-4-(1-p-tolyl-ethylcarbamoyl)-phenylsulfanyl]-phenyl}-carbamic acid tert-butyl ester (prepared in Example 390A): yield 89%. 1H-NMR (300 MHz, DMSO-d6) δ ppm: 1.34 (d, J=7.0 Hz, 6H), 1.42 (d, J=7.0 Hz, 3H), 2.25 (s, 3H), 3.23 (septet, J=6.6 Hz, 1H), 5.11 (dq, J=8.1, 7.0 Hz, 1H), 5.58 (s, 2H), 6.62 (d, J=8.5 Hz, 2H), 6.83 (d, J=8.5 Hz, 1H), 7.11 (d, J=8.1 Hz, 2H), 7.12 (d, J=8.5 Hz, 2H), 7.24 (d, J=8.1 Hz, 2H), 7.63 (d, J=8.5 Hz, 1H), 7.70 (dd, J=8.5, 1.9 Hz, 1H), 7.87 (d, J=1.9 Hz, 1H), 8.57 (s, 1H), 8.69 (d, J=8.1 Hz, 1H), 8.87 (d, J=8.5 Hz, 1H), 10.12 (s, 1H) MS ESI+ m/z: 549 (M+H) ESI− m/z: 547 (M−H)

Example 391

(S)-4-(4-Amino-phenylsulfanyl)-3-(7-isopropyl-pyrido[2,3-d]pyrimidin-4-ylamino)-N-[1-(3-methoxy-phenyl)-ethyl]-benzamide

Example 391A (S)-(4-{2-(7-Isopropyl-pyrido[2,3-]pyrimidin-4-ylamino)-4-[1-(4-methoxy-phenyl)-ethylcarbamoyl]-phenylsulfanyl}-phenyl)-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(4-methoxyphenyl)ethylamine: yield 96%.

Example 391B (S)-4-(4-Amino-phenylsulfanyl)-3-(7-isopropyl-pyrido[2,3-d]pyrimidin-4-ylamino)-N-[1-(4-methoxy-phenyl)-ethyl]-benzamide According to the procedure in Example 385G, the title compound was prepared from (S)-(4-{2-(7-isopropyl-pyrido[2,3-d]pyrimidin-4-ylamino)-4-[1-(4-methoxy-phenyl)-ethylcarbamoyl]-phenylsulfanyl}-phenyl)-carbamic acid tert-butyl ester (prepared in Example 391A): yield 52%. 1H-NMR (300 MHz, DMSO-d6) δ ppm: 1.34 (d, J=7.0 Hz, 6H), 1.42 (d, J=7.0 Hz, 3H), 3.23 (septet, J=7.0 Hz, 1H), 3.71 (s, 3H), 5.03-5.18 (m, 1H), 5.58 (s, 2H), 6.62 (d, J=8.5 Hz, 2H), 6.83 (d, J=8.5 Hz, 1H), 6.87 (d, J=8.5 Hz, 2H), 7.12 (d, J=8.5 Hz, 2H), 7.28 (d, J=8.5 Hz, 2H), 7.63 (d, J=8.5 Hz, 1H), 7.70 (dd, J=8.5, 1.8 Hz, 1H), 7.86 (d, J=1.8 Hz, 1H), 8.57 (s, 1H), 8.67 (d, J=8.1 Hz, 1H), 8.87 (d, J=8.5 Hz, 1H), 10.12 (s, 1H) MS ESI+ m/z: 565 (M+H) ESI− m/z: 565 (M−H).

Example 392

(S)-4-(4-Amino-phenylsulfanyl)-3-(7-isopropyl-pyrido[2,3-d]pyrimidin-4-ylamino)-N-[1-(3-trifluoromethyl-phenyl)-ethyl]-benzamide

Example 392A (S)-(4-{2-(7-Isopropyl-pyrido[2,3-d]pyrimidin-4-ylamino)-4-[1-(3-trifluoromethyl-phenyl)-ethylcarbamoyl]-phenylsulfanyl}-phenyl)-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(3-trifluoromethylphenyl)ethylamine: yield 85%.

Example 392B (S)-4-(4-Amino-phenylsulfanyl)-3-(7-isopropyl-pyrido[2,3-d]pyrimidin-4-ylamino)-N-[(3-trifluoromethyl-phenyl)-ethyl]-benzamide According to the procedure in Example 385G, the title compound was prepared from (S)-(4-{2-(7-isopropyl-pyrido[2,3-d]pyrimidin-4-ylamino)-4-[1-(3-trifluoromethyl-phenyl)-ethylcarbamoyl]-phenylsulfanyl}-phenyl)-carbamic acid tert-butyl ester (prepared in Example 392A): yield 96%. 1H-NMR (300 MHz, DMSO-d6) δ ppm: 1.34 (d, J=7.0 Hz, 6H), 1.48 (d, J=7.3 Hz, 3H), 3.22 (septet, J=7.0 Hz, 1H), 5.22 (quintet, J=7.3 Hz, 1H), 5.58 (s, 2H), 6.62 (d, J=8.8 Hz, 2H), 6.85 (d, J=8.4 Hz, 1H), 7.12 (d, J=8.8 Hz, 2H), 7.52-7.75 (m, 5H), 7.64 (d, J=8.5 Hz, 1H), 7.88 (d, J=1.8 Hz, 1H), 8.57 (s, 1H), 8.86 (d, J=7.3 Hz, 1H), 8.87 (d, J=8.5 Hz, 1H), 10.13 (s, 1H) MS ESI+ m/z: 603 (M+H) ESI− m/z: 601 (M−H).

Example 393

(S)-4-(4-Amino-phenylsulfanyl)-3-(7-isopropyl-pyrido[2,3-d]pyrimidin-4-ylamino)-N-[1-(3-methoxyphenyl)-ethyl]-benzamide

Example 393A (S)-(4-{2-(7-Isopropyl-pyrido[2,3-d]pyrimidin-4-ylamino)-4-[1-(3-methoxy-phenyl)-ethylcarbamoyl]-phenylsulfanyl}-phenyl)-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(3-methoxyphenyl)ethylamine: yield 85%.

Example 393B (S)-4-(4-Amino-phenylsulfanyl)-3-(7-isopropyl-pyrido[2,3-d]pyrimidin-4-ylamino)-N-[1-(3-methoxyphenyl)-ethyl]-benzamide According to the procedure in Example 385G, the title compound was prepared from (S)-(4-{2-(7-isopropyl-pyrido[2,3-d]pyrimidin-4-ylamino)-4-[1-(3-methoxy-phenyl)-ethylcarbamoyl]-phenylsulfanyl}-phenyl)-carbamic acid tert-butyl ester (prepared in Example 393A): yield 85%. 1H-NMR (300 MHz, DMSO-d6) δ ppm: 1.34 (d, J=7.0 Hz, 6H), 1.43 (d, J=7.0 Hz, 3H), 3.23 (septet, J=7.0 Hz, 1H), 3.72 (s, 3H), 5.02-5.21 (m, 1H), 5.58 (s, 2H), 6.62 (d, J=8.5 Hz, 2H), 6.78 (dd, J=8.1, 1.8 Hz, 1H), 6.84 (d, J=8.5 Hz, 1H), 6.88-6.96 (m, 2H), 7.12 (d, J=8.5 Hz, 2H), 7.22 (t, J=8.1 Hz, 1H), 7.64 (d, J=8.5 Hz, 1H), 7.71 (dd, J=8.5, 1.8 Hz, 1H), 7.88 (br-s, 1H), 8.57 (s, 1H), 8.72 (d, J=8.1 Hz, 1H), 8.87 (d, J=8.5 Hz, 1H), 10.13 (s, 1H) MS ESI+ m/z: 565 (M+H) ESI− m/z: 563 (M−H).

Example 394

(S)-4-(4-Amino-phenylsulfanyl)-N-[1-(2-bromo-phenyl)-ethyl]-3-(7-isopropyl-pyrido[2,3-d]pyrimidin-4-ylamino)-benzamide

Example 394A (S)-1-(1-Azidoethyl)-2-bromobenzene

To a solution of (R)-(+)-2-bromo-α-methylbenzyl alcohol (402 mg, 2.0 mmol) and diphenylphosphoryl azide (0.692 ml, 3.2 mmol) in THF (10 mL) was added 1,8-diazabicyclo[5.4.0]undec-7-ene (0.466 ml, 3.2 mmol). The mixture was heated at 50° C. for overnight, partitioned with H2O and AcOEt, and then adjusted to pH 7 by adding 1M HCl. The organic layer was dried with MgSO4, filtered and evaporated. The residue was purified by silica gel column chromatography [eluting with n-hexane/AcOEt=95/5] to give the title compound (381 mg, 84%).

Example 394B (S)-(−)-1-(2-Bromophenyl)ethylamine

To a solution of (S)-1-(1-azidoethyl)-2-bromobenzene (45 mg, 0.2 mmol) in EtOH/H2O (5 mL/5 mL) was added in NH4Cl (108 mg, 2.0 mmol) and indium (91 mg, 0.8 mmol). The mixture was refluxed overnight. The reaction mixture was filtered, washed with EtOH and evaporated. The residue was triturated with AcOEt and filtered. The filtrate was evaporated to give the title compound (35 mg, 88%).

Example 394C (S)-{4-[4-[1-(2-Bromo-phenyl)-ethylcarbamoyl]-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(2-bromophenyl)ethylamine (prepared in Example 394B): yield 30%.

Example 394D (S)-4-(4-Amino-phenylsulfanyl)-N-[1-(2-bromo-phenyl)-ethyl]-3-(7-isopropyl-pyrido[2,3-d]pyrimidin-4-ylamino)-benzamide According to the procedure in Example 385G, the title compound was prepared from (S)-{4-[4-[1-(2-bromo-phenyl)-ethylcarbamoyl]-2-(7-isopropyl-pyrido[2,3-d]pyrimidin-4-ylamino)-phenylsulfanyl]-phenyl}-carbamic acid tert-butyl ester (prepared in Example 394C): yield 89%. 1H-NMR (300 MHz, DMSO-d6) δ ppm: 1.34 (d, J=6.99 Hz, 6 H) 1.41 (d, J=6.99 Hz, 3 H) 3.16-3.28 (m, 1 H) 5.31-5.41 (m, 1 H) 5.58 (s, 2 H) 6.62 (d, J=8.82 Hz, 2 H) 6.84 (d, J=8.46 Hz, 1 H) 7.08-7.20 (m, 3 H) 7.35 (t, J=7.35 Hz, 1 H) 7.48 (dd, J=7.71 Hz, 1.47 Hz, 1 H) 7.57 (d, J=8.09 Hz, 1 H) 7.64 (d, J=8.46 Hz, 1 H) 7.72 (dd, J=8.46, 1.47 Hz, 1 H) 7.90 (d, J=1.47 Hz, 1 H) 8.58 (s, 1 H) 8.78-9.00 (m, 2 H) 10.14 (s, 1 H) MS ESI+ m/z: 613,615 (M+H).

Example 395

(S)-4-(4-Amino-phenylsulfanyl)-3-(7-isopropyl-pyrido[2,3-d]pyrimidin-4-ylamino)-N-[1-(2-trifluoromethyl-phenyl)-ethyl]-benzamide Example 395A (S)-(4-{2-(7-Isopropyl-pyrido[2,3-d]pyrimidin-4-ylamino)-4-[1-(2-trifluoromethyl-phenyl)-ethylcarbamoyl]-phenylsulfanyl}-phenyl)-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-(2-trifluoromethylphenyl)ethylamine: yield 68%.

Example 395B (S)-4-(4-Amino-phenylsulfanyl)-3-(7-isopropyl-pyrido[2,3-d]pyrimidin-4-ylamino)-N-[1-(2-trifluoromethyl-phenyl)-ethyl]-benzamide According to the procedure in Example 385G, the title compound was prepared from (S)-(4-{2-(7-isopropyl-pyrido[2,3-d]pyrimidin-4-ylamino)-4-[1-(2-trifluoromethyl-phenyl)-ethylcarbamoyl]-phenylsulfanyl}-phenyl)-carbamic acid tert-butyl ester (prepared in Example 395A): yield 83%. 1H-NMR (300 MHz, DMSO-d6) δ ppm: 1.34 (d, J=6.99 Hz, 6 H) 1.44 (d, J=6.99 Hz, 3 H) 3.14-3.28 (m, 1 H) 5.38-5.49 (m, 1 H) 5.59 (s, 2 H) 6.62 (d, J=8.82 Hz, 2 H) 6.83 (d, J=8.46 Hz, 1 H) 7.12 (d, J=8.46 Hz, 2 H) 7.43 (t, J=7.54 Hz, 1 H) 7.61-7.73 (m, 4 H) 7.79 (d, J=8.09 Hz, 1 H) 7.89 (s, 1 H) 8.58 (s, 1 H) 8.77-8.99 (m, 2 H) 10.13 (s, 1 H) MS ESI+ m/z: 603 (M+H).

Example 396

(S)-4-(4-Amino-phenylsulfanyl)-3-(7-isopropyl-pyrido[2,3-d]pyrimidin-4-ylamino)-N-(1-naphthalen-2-yl-ethyl)-benzamide Example 396A (S)-{4-[2-(7-Isopropyl-pyrido[2,3-d]pyrimidin-4-ylamino)-4-(1-naphthalen-2-yl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-naphthalen-2-yl-ethylamine: yield 72%.

Example 396B (S)-4-(4-Amino-phenylsulfanyl)-3-(7-isopropyl-pyrido[2,3-d]pyrimidin-4-ylamino)-N-(1-naphthalen-2-yl-ethyl)-benzamide According to the procedure in Example 385G, the title compound was prepared from (S)-{4-[2-(7-Isopropyl-pyrido[2,3-d]pyrimidin-4-ylamino)-4-(1-naphthalen-2-yl-ethylcarbamoyl)-phenylsulfanyl]-phenyl}-carbamic acid tert-butyl ester (prepared in Example 396A): yield 64%. 1H-NMR (300 MHz, DMSO-d6) δ ppm: 1.33 (d, J=6.62 Hz, 6 H) 1.59 (d, J=6.99 Hz, 3 H) 3.12-3.30 (m, 1 H) 5.58 (s, 2 H) 5.89-6.01 (m, 1 H) 6.61 (d, J=8.46 Hz, 2 H) 6.83 (d, J=8.46 Hz, 1 H) 7.11 (d, J=8.46 Hz, 2 H) 7.43-7.65 (m, 5 H) 7.70-7.77 (dd, J=8.46, 1.47 Hz, 1 H) 7.82 (d, J=8.09 Hz, 1 H) 7.88-7.98 (m, 2 H) 8.18 (d, J=8.09 Hz, 1 H) 8.56 (s, 1 H) 8.85 (d, J=8.46 Hz, 1 H) 8.90 (d, J=7.72 Hz, 1 H) 10.12 (s, 1 H) MS ESI+ m/z: 585 (M+H).

EXAMPLE 397

(RS)-4-(4-Amino-phenylsulfanyl)-3-(7-isopropyl-pyrido[2,3-d]pyrimidin-4-ylamino)-N-(1-thiophen-2-yl-ethyl)-benzamide

EXAMPLE 397A (RS)-{4-[2-(7-Isopropyl-pyrido[2,3-d]pyrimidin-4-ylamino)-4-(1-thiophen-2-yl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-1-thiophen-2-yl-ethylamine: yield 92%.

EXAMPLE 397B (RS)-4-(4-Amino-phenylsulfanyl)-3-(7-isopropyl-pyrido[2,3-d]pyrimidin-4-ylamino)-N-(1-thiophen-2-yl-ethyl)-benzamide According to the procedure in Example 385G, the title compound was prepared from (RS)-{4-[2-(7-isopropyl-pyrido[2,3-d]pyrimidin-4-ylamino)-4-(1-thiophen-2-yl-ethylcarbamoyl)-phenylsulfanyl]-phenyl}-carbamic acid tert-butyl ester (prepared in Example 397A) as di-trifluoroacetate: yield 31%. 1H-NMR (300 MHz, DMSO-d6) δ ppm: 1.36 (d, J=6.62 Hz, 6 H) 1.56 (d, J=6.99 Hz, 3 H) 3.23-3.41 (m, 1 H) 4.03 (s, 2 H) 5.31-5.56 (m, 1 H) 6.62 (d, J=8.82 Hz, 2 H) 6.85-7.06 (m, 3 H) 7.13 (d, J=8.46 Hz, 2 H) 7.33-7.42 (m, 1 H) 7.80 (dd, J=8.46, 1.84 Hz, 1 H) 7.88 (s, 1 H) 7.93 (d, J=8.46 Hz, 1 H) 8.87-8.94 (m, 2 H) 9.03 (d, J=8.46 Hz, 1 H) 11.72 (s, 1 H) MS ESI+ m/z: 541 (M+H)

EXAMPLE 398

(RS)-4-(4-Amino-phenylsulfanyl)-3-(7-isopropyl-pyrido[2,3-d]pyrimidin-4-ylamino)-N-(1-pyridin-2-yl-ethyl)-benzamide

EXAMPLE 398A (RS)-{4-[2-(7-Isopropyl-pyrido[2,3-d]pyrimidin-4-ylamino)-4-(1-pyridin-2-yl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-1-pyridin-2-yl-ethylamine: yield 93%.

EXAMPLE 398B (RS)-4-(4-Amino-phenylsulfanyl)-3-(7-isopropyl-pyrido[2,3-d]pyrimidin-4-ylamino)-N-(1-pyridin-2-yl-ethyl)-benzamide According to the procedure in Example 385G, the title compound was prepared from (RS)-{4-[2-(7-isopropyl-pyrido[2,3-d]pyrimidin-4-ylamino)-4-(1-pyridin-2-yl-ethylcarbamoyl)-phenylsulfanyl]-phenyl}-carbamic acid tert-butyl ester (prepared in Example 398A): yield 95%. 1H-NMR (300 MHz, DMSO-d6) δ ppm: 1.34 (d, J=6.62 Hz, 6 H) 1.47 (d, J=7.35 Hz, 3 H) 3.12-3.28 (m, 1 H) 5.17 (qt, 1 H) 5.58 (s, 2 H) 6.62 (d, J=8.46 Hz, 2 H) 6.84 (d, J=8.46 Hz, 1 H) 7.12 (d, J=8.46 Hz, 2 H) 7.24 (dd, J=6.62, 4.78 Hz, 1 H) 7.37 (d, J=8.09 Hz, 1 H) 7.63 (d, J=8.09 Hz, 1 H) 7.69-7.83 (m, 2 H) 7.91 (s, 1 H) 8.50 (d, J=4.04 Hz, 1 H) 8.57 (s, 1 H) 8.78 (d, J=7.72 Hz, 1 H) 8.87 (d, J=8.82 Hz, 1 H) 10.13 (s, 1 H) MS ESI+ m/z: 536 (M+H).

EXAMPLE 399

(RS)-4-(4-Amino-phenylsulfanyl)-3-(7-isopropyl-pyrido[2,3-d]pyrimidin-4-ylamino)-N-(1-pyridin-3-yl-ethyl)-benzamide

EXAMPLE 399A (RS)-{4-[2-(7-Isopropyl-pyrido[2,3-d]pyrimidin-4-ylamino)-4-(1-pyridin-3-yl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-1-pyridin-3-yl-ethylamine: yield 79%.

EXAMPLE 399B (RS)-4-(4-Amino-phenylsulfanyl)-3-(7-isopropyl-pyrido[2,3-d]pyrimidin-4-ylamino)-N-(1-pyridin-3-yl-ethyl)-benzamide According to the procedure in Example 385G, the title compound was prepared from (RS)-{4-[2-(7-isopropyl-pyrido[2,3-d]pyrimidin-4-ylamino)-4-(1-pyridin-3-yl-ethylcarbamoyl)-phenylsulfanyl]-phenyl}-carbamic acid tert-butyl ester (prepared in Example 399A): yield 98%. 1H-NMR (300 MHz, DMSO-d6) δ ppm: 1.34 (d, J=6.99 Hz, 6 H) 1.48 (d, J=6.99 Hz, 3 H) 3.14-3.27 (m, 1 H) 5.12-5.28 (m, 1 H) 5.58 (s, 2 H) 6.61 (d, J=8.82 Hz, 2 H) 6.80-6.86 (m, J=8.46 Hz, 1 H) 7.11 (d, J=8.82 Hz, 2 H) 7.34 (dd, J=7.91, 4.23 Hz, 1 H) 7.63 (d, J=8.46 Hz, 1 H) 7.68-7.78 (m, 2 H) 7.87 (d, J=1.47 Hz, 1 H) 8.43 (dd, J=4.78, 1.47 Hz, 1 H) 8.55-8.59 (m, 2 H) 8.82 (d, J=7.72 Hz, 1 H) 8.86 (d, J=8.46 Hz, 1 H) 10.12 (s, 1 H) MS ESI+ m/z: 536 (M+H).

EXAMPLE 400

(RS)-4-(4-Amino-phenylsulfanyl)-3-(7-isopropyl-pyrido[2,3-d]pyrimidin-4-ylamino)-N-(1-pyridin-4-yl-ethyl)-benzamide

EXAMPLE 400A (RS)-{4-[2-(7-Isopropyl-pyrido[2,3-d]pyrimidin-4-ylamino)-4-(1-pyridin-4-yl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-1-pyridin-4-yl-ethylamine: yield 41%.

EXAMPLE 400B (RS)-4-(4-Amino-phenylsulfanyl)-3-(7-isopropyl-pyrido[2,3-d]pyrimidin-4-ylamino)-N-(1-pyridin-4-yl-ethyl)-benzamide According to the procedure in Example 385G, the title compound was prepared from (RS)-{4-[2-(7-isopropyl-pyrido[2,3-d]pyrimidin-4-ylamino)-4-(1-pyridin-4-yl-ethylcarbamoyl)-phenylsulfanyl]-phenyl}-carbamic acid tert-butyl ester (prepared in Example 400A): yield 83%. 1H-NMR (300 MHz, DMSO-d6) δ ppm: 1.34 (d, J=6.99 Hz, 6 H) 1.45 (d, J=6.99 Hz, 3 H) 3.13-3.27 (m, 1 H) 5.02-5.23 (m, 1 H) 5.58 (s, 2 H) 6.62 (d, J=8.82 Hz, 2 H) 6.84 (d, J=8.09 Hz, 1 H) 7.12 (d, J=8.46 Hz, 2 H) 7.34 (d, J=6.25 Hz, 2 H) 7.63 (d, J=8.46 Hz, 1 H) 7.72 (dd, J=8.27, 1.65 Hz, 1 H) 7.89 (d, J=1.47 Hz, 1 H) 8.49 (d, J=5.88 Hz, 2 H) 8.58 (s, 1 H) 8.85 (t, J=8.27 Hz, 2 H) 10.13 (s, 1 H) MS ESI+ m/z: 536 (M+H).

EXAMPLE 401

(S)-4-(4-Amino-phenylsulfanyl)-N-(1-cyclohexyl-ethyl)-3-(7-isopropyl-pyrido[2,3-d]pyrimidin-4-ylamino)-benzamide

EXAMPLE 401A (S)-{4-[4-(1-Cyclohexyl-ethylcarbamoyl)-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(+)-1-cyclohexylethylamine: yield 73%.

EXAMPLE 401B (S)-4-(4-Amino-phenylsulfanyl)-N-(1-cyclohexyl-ethyl)-3-(7-isopropyl-pyrido[2,3-d]pyrimidin-4-ylamino)-benzamide According to the procedure in Example 385G, the title compound was prepared from (S)-{4-[4-(1-cyclohexyl-ethylcarbamoyl)-2-(7-isopropyl-pyrido[2,3-d]pyrimidin-4-ylamino)-phenylsulfanyl]-phenyl}-carbamic acid tert-butyl ester (prepared in Example 401A): yield 90%. 1H-NMR (300 MHz, DMSO-d6) δ ppm: 0.86-0.97 (m, 2 H) 1.04-1.16 (m, 6 H) 1.28-1.40 (m, 7 H) 1.54-1.76 (m, 5 H) 3.16-3.28 (m, 1 H) 3.77-3.86 (m, 1 H) 5.57 (s, 2 H) 6.61 (d, J=8.46 Hz, 2 H) 6.83 (d, J=8.46 Hz, 1 H) 7.11 (d, J=8.46 Hz, 2 H) 7.57-7.72 (m, 2 H) 7.83 (d, J=1.47 Hz, 1 H) 8.05 (d, J=8.46 Hz, 1 H) 8.57 (s, 1 H) 8.86 (d, J=8.46 Hz, 1 H) 10.12 (s, 1 H) MS ESI+ m/z: 541 (M+H).

EXAMPLE 402

(S)-4-(4-Amino-phenylsulfanyl)-N-indan-1-yl-3-(7-isopropyl-pyrido[2,3-d]pyrimidin-4-ylamino)-benzamide

EXAMPLE 402A (S)-{4-[4-(Indan-1-ylcarbamoyl)-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(+)-1-aminoindane: yield 71%.

EXAMPLE 402B (S)-4-(4-Amino-phenylsulfanyl)-N-indan-1-yl-3-(7-isopropyl-pyrido[2,3-d]pyrimidin-4-ylamino)-benzamide According to the procedure in Example 385G, the title compound was prepared from (S)-{4-[4-(indan-1-ylcarbamoyl)-2-(7-isopropyl-pyrido[2,3-d]pyrimidin-4-ylamino)-phenyl]-phenyl}-carbamic acid tert-butyl ester (prepared in Example 402A): yield 92%. 1H-NMR (300 MHz, DMSO-d6) δ ppm: 1.33 (d, J=6.99 Hz, 6 H) 1.88-1.98 (m, 1 H) 2.37-2.46 (m, 1 H) 2.76-2.88 (m, 1 H) 2.90-3.02 (m, 1 H) 3.16-3.27 (m, 1 H) 5.47-5.66 (m, 3 H) 6.62 (d, J=8.46 Hz, 2 H) 6.82 (d, J=8.09 Hz, 1 H) 7.12 (d, J=8.46 Hz, 2 H) 7.16-7.28 (m, 4 H) 7.63 (d, J=8.46 Hz, 1 H) 7.74 (d, J=8.46 Hz, 1 H) 7.90 (s, 1 H) 8.57 (s, 1 H) 8.72 (d, J=8.46 Hz, 1 H) 8.86 (d, J=8.46 Hz, 1 H) 10.12 (s, 1 H) MS ESI+ m/z: 547 (M+H).

EXAMPLE 403

(S)-4-(4-Amino-phenylsulfanyl)-3-(7-isopropyl-pyrido[2,3-d]pyrimidin-4-ylamino)-N-(1-phenyl-propyl)-benzamide

EXAMPLE 403A (S)-{4-[2-(7-Isopropyl-pyrido[2,3-d]pyrimidin-4-ylamino)-4-(1-phenyl-propylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and S-(−)-1-phenylpropylamine: yield 90%.

EXAMPLE 403B (S)-4-(4-Amino-phenylsulfanyl)-3-(7-isopropyl-pyrido[2,3-d]pyrimidin-4-ylamino)-N-(1-phenyl-propyl)-benzamide According to the procedure in Example 385G, the title compound was prepared from (S)-{4-[2-(7-isopropyl-pyrido[2,3-d]pyrimidin-4-ylamino)-4-(1-phenyl-propylcarbamoyl)-phenylsulfanyl]-phenyl}-carbamic acid tert-butyl ester (prepared in Example 403A): yield 89%. 1H-NMR (300 MHz, DMSO-d6) δ ppm: 0.88 (d, J=7.3 Hz, 3H), 1.34 (d, J=7.0 Hz, 6H), 1.68-1.90 (m, 2H), 3.23 (septet, J=7.0 Hz, 1H), 4.89 (dt, J=8.1, 7.3 Hz, 1H), 5.58 (s, 2H), 6.62 (d, J=8.5 Hz, 2H), 6.84 (d, J=8.4 Hz, 1H), 7.12 (d, J=8.5 Hz, 2H), 7.21 (t, J=7.0 Hz, 1H), 7.30 (t, J=7.0 Hz, 2H), 7.36 (d, J=7.0 Hz, 2H), 7.64 (d, J=8.5 Hz, 1H), 7.71 (dd, J=8.4, 1.8 Hz, 1H), 7.88 (d, J=1.8 Hz, 1H), 8.57 (s, 1H), 8.68 (d, J=8.1 Hz, 1H), 8.87 (d, J=8.5 Hz, 1H), 10.13 (s, 1H) MS ESI+ m/z 549 (M+H) ESI− m/z: 547 (M−H).

EXAMPLE 404

(R)-4-(4-Amino-phenylsulfanyl)-3-(7-isopropyl-pyrido[2,3-d]pyrimidin-4-ylamino)-N-(1-phenyl-propyl)-benzamide

EXAMPLE 404A (R)-{4-[2-(7-Isopropyl-pyrido[2,3-d]pyrimidin-4-ylamino)-4-(1-phenyl-propylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and R-(+)-1-phenylpropylamine: yield 88%.

EXAMPLE 404B (R)-4-(4-Amino-phenylsulfanyl)-3-(7-isopropyl-pyrido[2,3-d]pyrimidin-4-ylamino)-N-(1-phenyl-propyl)-benzamide According to the procedure in Example 385G, the title compound was prepared from (R)-{4-[2-(7-isopropyl-pyrido[2,3-d]pyrimidin-4-ylamino)-4-(1-phenyl-propylcarbamoyl)-phenylsulfanyl]-phenyl}-carbamic acid tert-butyl ester (prepared in Example 404A): yield 89%. 1H-NMR (300 MHz, DMSO-d6) δ ppm: 0.88 (d, J=7.3 Hz, 3H), 1.34 (d, J=7.0 Hz, 6H), 1.67-1.92 (m, 2H), 3.23 (septet, J=7.0 Hz, 1H), 4.89 (dt, J=8.1, 7.3 Hz, 1H), 5.57 (s, 2H), 6.62 (d, J=8.5 Hz, 2H), 6.84 (d, J=8.5 Hz, 1H), 7.11 (d, J=8.5 Hz, 2H), 7.21 (t, J=7.0 Hz, 1H), 7.30 (t, J=7.0 Hz, 2H), 7.36 (d, J=7.0 Hz, 2H), 7.64 (d, J=8.5 Hz, 1H), 7.71 (dd, J=8.5, 1.8 Hz, 1H), 7.88 (d, J=1.8 Hz, 1H), 8.57 (s, 1H), 8.68 (d, J=8.1 Hz, 1H), 8.87 (d, J=8.5 Hz, 1H), 10.13 (s, 1H) MS ESI+ m/z: 549 (M+H) ESI− m/z: 547 (M−H).

EXAMPLE 405

(R)-4-(4-Amino-phenylsulfanyl)-N-(2-hydroxy-1-phenyl-ethyl)-3-(7-isopropyl-pyrido[2,3-d]pyrimidin-4-ylamino)-benzamide

EXAMPLE 405A (R)-{4-[4-(2-Hydroxy-1-phenyl-ethylcarbamoyl)-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and R-(−)-2-phenylglycinol: yield 70%.

EXAMPLE 405B (R)-4-(4-Amino-phenylsulfanyl)-N-(2-hydroxy-1-phenyl-ethyl)-3-(7-isopropyl-pyrido[2,3-d]pyrimidin-4-ylamino)-benzamide According to the procedure in Example 385G, the title compound was prepared from (R)-{4-[4-(2-hydroxy-1-phenyl-ethylcarbamoyl)-2-(7-isopropyl-pyrido[2,3-d]pyrimidin-4-ylamino)-phenylsulfanyl]-phenyl}-carbamic acid tert-butyl ester (prepared in Example 405A): yield 59%. 1H-NMR (300 MHz, DMSO-d6) δ ppm: 1.34 (d, J=7.0 Hz, 6H), 3.22 (septet, J=7.0 Hz, 1H) 3.52-3.75 (m, 2H), 4.92 (t, J=5.1 Hz, 1H), 4.98-5.13 (m, 1H), 5.64 (br-s, 2H), 6.62 (d, J=8.5 Hz, 2H), 6.83 (br-d, 1H), 7.12 (d, J=8.5 Hz, 2H), 7.21 (t, J=7.0 Hz, 1H), 7.30 (t, J=7.0 Hz, 2H), 7.36 (d, J=7.0 Hz, 2H), 7.64 (br-d, J=8.5 Hz, 1H), 7.72 (br-d, 1H), 7.90 (br-s, 1H), 8.58 (br-s, 1H), 8.65 (br-d, J=8.1 Hz, 1H), 8.87 (br-d, J=8.5 Hz, 1H), 10.19 (br-s, 1H) MS ESI+ m/z: 551 (M+H) ESI− m/z: 549 (M−H).

EXAMPLE 406

(S)-4-(4-Amino-phenylsulfanyl)-N-(3-hydroxy-1-phenyl-propyl)-3-(7-isopropyl-pyrido[2,3-d]pyrimidin-4-ylamino)-benzamide

EXAMPLE 406A (S)-{4-[4-(3-Hydroxy-1-phenyl-propylcarbamoyl)-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (S)-3-amino-3-phenylpropan-1-ol: yield 81%.

EXAMPLE 406B (S)-4-(4-Amino-phenylsulfanyl)-N-(3-hydroxy-1-phenyl-propyl)-3-(7-isopropyl-pyrido[2,3-d]pyrimidin-4-ylamino)-benzamide According to the procedure in Example 385G, the title compound was prepared from (S)-{4-[4-(3-hydroxy-1-phenyl-propylcarbamoyl)-2-(7-isopropyl-pyrido[2,3-d]pyrimidin-4-ylamino)-phenylsulfanyl]-phenyl}-carbamic acid tert-butyl ester (prepared in Example 406A): yield 80%. 1H-NMR (300 MHz, DMSO-d6) δ ppm: 1.34 (d, J=7.0 Hz, 6H), 1.78-2.08 (m, 2H), 3.23 (septet, J=7.0 Hz, 1H), 3.33-3.48 (m, 2H), 4.55 (t, J=4.8 Hz, 1H), 5.05-5.22 (m, 1H), 5.58 (s, 2H), 6.62 (d, J=8.8 Hz, 2H), 6.84 (d, J=8.5 Hz, 1H), 7.11 (d, J=8.8 Hz, 2H), 7.16-7.42 (m, 5H), 7.63 (d, J=8.5 Hz, 1H), 7.70 (dd, J=8.5, 1.8 Hz, 1H), 7.86 (d, J=1.8 Hz, 1H), 8.57 (s, 1H), 8.71 (d, J=8.1 Hz, 1H), 8.87 (d, J=8.5 Hz, 1H), 10.13 (s, 1H) MS ESI+ m/z: 565 (M+H) ESI− m/z: 563 (M−H).

EXAMPLE 407

(R)-[4-(4-Amino-phenylsulfanyl)-3-(7-isopropyl-pyrido[2,3-d]pyrimidin-4-ylamino)-benzoylamino]-phenyl-acetic acid methyl ester

EXAMPLE 407A (R)-[4-(4-tert-Butoxycarbonylamino-phenylsulfanyl)-3-(7-isopropyl-pyrido[2,3-d]pyrimidin-4-ylamino)-benzoylamino]-phenyl-acetic acid methyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and R-(−)-2-phenylglycine methyl ester (hydrochloride): yield 91%.

EXAMPLE 407B (R)-[4-(4-Amino-phenylsulfanyl)-3-(7-isopropyl-pyrido[2,3-d]pyrimidin-4-ylamino)-benzoylamino]-phenyl-acetic acid methyl ester According to the procedure in Example 385G, the title compound was prepared from (R)-[4-(4-tert-butoxycarbonylamino-phenylsulfanyl)-3-(7-isopropyl-pyrido[2,3-d]pyrimidin-4-ylamino)-benzoylamino]-phenyl-acetic acid methyl ester (prepared in Example 407A): yield 80%. 1H-NMR (300 MHz, DMSO-d6) δ ppm: 1.33 (d, J=7.0 Hz, 6H), 3.22 (septet, J=7.0 Hz, 1H), 3.64 (s, 3H), 5.59 (s, 2H), 5.65 (d, J=7.0 Hz, 1H), 6.62 (d, J=8.5 Hz, 2H), 6.82 (d, J=8.5 Hz, 1H), 7.12 (d, J=8.5 Hz, 2H), 7.30-7.49 (m, 5H), 7.63 (d, J=8.5 Hz, 1H), 7.74 (dd, J=8.5, 1.8 Hz, 1H), 7.94 (d, J=1.8 Hz, 1H), 8.56 (s, 1H), 8.86 (d, J=8.5 Hz, 1H), 9.13 (d, J=7.0 Hz, 1H), 10.12 (s, 1H) MS ESI+ m/z: 579 (M+H) ESI− m/z: 577 (M−H).

EXAMPLE 408

(S)-4-(4-Amino-phenylsulfanyl)-3-(7-isopropyl-pyrido[2,3-d]pyrimidin-4-ylamino)-N-methyl-N-(1-phenyl-ethyl)-benzamide

EXAMPLE 408A (S)-(4-{2-(7-Isopropyl-pyrido[2,3-d]pyrimidin-4-ylamino)-4-[methyl-(1-phenyl-ethyl)-carbamoyl]-phenylsulfanyl}-phenyl)-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (S)-N,α-dimethylbenzylamine: yield 54%.

EXAMPLE 408B (S)-4-(4-Amino-phenylsulfanyl)-3-(7-isopropyl-pyrido[2,3-d]pyrimidin-4-ylamino)-N-methyl-N-(1-phenyl-ethyl)-benzamide According to the procedure in Example 385G, the title compound was prepared from (S)-(4-{2-(7-isopropyl-pyrido[2,3-d]pyrimidin-4-ylamino)-4-[methyl-(1-phenyl-ethyl)-carbamoyl]-phenylsulfanyl}-phenyl)-carbamic acid tert-butyl ester (prepared in Example 408A) as di-trifluoroacetate: yield 67%. 1H-NMR (300 MHz, DMSO-d6) δ ppm: 1.36 (d, J=6.99 Hz, 6 H) 1.55 (d, J=6.99 Hz, 3 H) 2.62 (s, 3 H) 3.15-3.38 (m, 1 H) 3.20-3.80 (m, 4 H) 6.63 (d, J=8.46 Hz, 2 H) 6.91 (d, J=8.09 Hz, 1 H) 7.15 (d, J=8.46 Hz, 2 H) 7.25-7.45 (m, 5 H) 7.50 (s, 1 H) 7.93 (d, J=8.46 Hz, 1 H) 8.86 (s, 1 H) 9.03 (d, J=8.82 Hz, 1 H) MS ESI+ m/z: 549 (M+H).

EXAMPLE 409

(S)-N-Allyl-4-(4-amino-phenylsulfanyl)-3-(7-isopropyl-pyrido[2,3-d]pyrimidin-4-ylamino)-N-(1-phenyl-ethyl)-benzamide

EXAMPLE 409A (S)-{4-[4-[Allyl-(1-phenyl-ethyl)-carbamoyl]-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (S)-N-allyl-α-methylbenzylamine: yield 36%.

EXAMPLE 409B (S)-N-Allyl-4-(4-amino-phenylsulfanyl)-3-(7-isopropyl-pyrido[2,3-d]pyrimidin-4-ylamino)-N-(1-phenyl-ethyl)-benzamide According to the procedure in Example 385G, the title compound was prepared from (S)-{4-[4-[allyl-(1-phenyl-ethyl)-carbamoyl]-2-(7-isopropyl-pyrido[2,3-d]pyrimidin-4-ylamino)-phenylsulfanyl]-phenyl}-carbamic acid tert-butyl ester as prepared in Example 409A: yield 88%. 1H-NMR (300 MHz, DMSO-d6) δ ppm: 1.33 (d, J=6.99 Hz, 6 H) 1.57 (d, J=6.99 Hz, 3 H) 3.11-3.28 (m, 1 H) 3.39-3.53 (m, 1 H) 3.93-4.03 (m, 1 H) 4.85-5.15 (m, 3 H) 5.48-5.73 (m, 3 H) 6.61 (d, J=8.46 Hz, 2 H) 6.83 (d, J=8.09 Hz, 1 H) 7.13 (d, J=8.09 Hz, 2 H) 7.22-7.38 (m, 6 H) 7.47 (s, 1 H) 7.62 (d, J=8.46 Hz, 1 H) 8.52 (s, 1 H) 8.86 (d, J=8.82 Hz, 1 H) 10.04 (s, 1 H) MS ESI+ m/z: 575 (M+H)

EXAMPLE 410

(S)-4-(4-Hydroxy-phenylsulfanyl)-3-(7-isopropyl-pyrido[2,3-d]pyrimidin-4-ylamino)-N-(1-phenyl-ethyl)-benzamide

EXAMPLE 410A 4-(4-Hydroxy-phenylsulfanyl)-3-nitro-benzoic acid methyl ester

To a solution of 4-chloro-3-nitrobenzoic acid methyl ester (4.00 g, 18 mmol) and 4-mercaptophenol (2.37 g, 18 mmol) in acetone (60 mL) was added Cs2CO3 (5.93 g, 18 mmol) at room temperature, and then the mixture was refluxed for 30 minutes. After cooling to room temperature, the mixture was filtered and the filtrate was evaporated. The residue was diluted with AcOEt (30 mL), washed with H2O (3 times) and brine, dried over MgSO4, and evaporated to give brown oil. The oily residue was separated by silica gel column chromatography (n-hexane/AcOEt=4/3) to give the title compound as yellow amorphous (5.60 g).

EXAMPLE 410B

3-Amino-4-(4-hydroxy-phenylsulfanyl)-benzoic acid methyl ester

A suspension of 4-(4-hydroxy-phenylsulfanyl)-3-nitrobenzoic acid methyl ester (5.60 g, 18 mmol), Fe powder (5.34 g, 92 mmol) and NH4Cl (4.91 g, 92 mmol) in aqueous EtOH [prepared from EtOH (50 mL) and H2O (50 mL)] was gradually heated to reflux and refluxed for 45 minutes. The reaction mixture was diluted with AcOEt (50 mL) and filtered through celite pad. The filtrate was evaporated and the aqueous residue was portioned between AcOEt and 10% NaHCO3. The organic layer was separated, washed with H2O and brine, dried over MgSO4 and evaporated to give pale yellow solid. The resulting solid was washed with i-Pr2O and dried at 40° C. for 3 days under reduced pressure to give the title compound as slightly yellow crystal (4.50 g, 90% by 2 steps).

EXAMPLE 410C 4-(4-Hydroxy-phenylsulfanyl)-3-(7-isopropyl-pyrido[2,3-d]pyrimidin-4-ylamino)-benzoic acid methyl ester A suspension of N'-(3-cyano-6-isopropyl-pyridin-2-yl)-N,N-dimethyl-formamidine (0.75 g, 3.5 mmol) and 3-amino-4-(4-hydroxy-phenylsulfanyl)-benzoic acid methyl ester (0.96 g, 3.5 mmol) in AcOH (15 mL) was heated at 120° C. for 10 minutes under N2. The reaction mixture was portioned between AcOEt (10 mL) and H2O (150 mL) and made basic to pH 9 with K2CO3 under stirring. The resulting solid was collected by filtration, washed with H2O and AcOEt, and dried at 50° C. overnight under reduced pressure to give the title compound as pale brown crystal (1.27 g, 82%).

EXAMPLE 410D 4-(4-Hydroxy-phenylsulfanyl)-3-(7-isopropyl-pyrido[2,3-d]pyrimidin-4-ylamino)-benzoic acid To a suspension of 4-(4-hydroxy-phenylsulfanyl)-3-(7-isopropyl-pyrido[2,3-d]pyrimidin-4-ylamino)-benzoic acid methyl ester (0.50 g, 1.1 mmol) in THF (5 mL) was added aqueous LiOH [prepared from LiOH monohydrate (0.15 g) and H2O (1.5 mL)] dropwise at room temperature. The mixture was stirred at room temperature for 24 hours. Additional aqueous LiOH [prepared from LiOH monohydrate (0.15 g) and H2O (1.5 mL)] was added at room temperature. The mixture was mixture was stirred at room temperature for 23 hours, and then evaporated. The aqueous mixture was diluted with 50 mL of H2O, washed with AcOEt, and treated with active charcoal. The mixture was filtered and the filtrate was carefully acidified to pH 4-5 with 10% HCl under stirring. The resulting solid was collected by filtration, washed with $H_2O$, and dried at 40° C. for 3 days under reduced pressure to give the title compound as pale yellow crystal (0.35 g, 73%).

1H-NMR (300 MHz, DMSO-d6) δ ppm: 1.33 (d, J=7.0 Hz, 6H), 3.22 (septet, J=7.0 Hz, 1H), 6.81-6.90 (m, 1H), 6.85 (d, J=8.5 Hz, 2H), 7.30 (d, J=8.5 Hz, 2H), 7.63 (br-d, J=8.4 Hz, 1H), 7.73 (br-d, J=8.1 Hz, 1H), 7.85 (br-s, 1H), 8.57 (s, 1H), 8.86 (d, J=8.4 Hz, 1H), 10.14 (s, 1H).

EXAMPLE 410E (S)-4-(4-Hydroxy-phenylsulfanyl)-3-(7-isopropyl-pyrido[2,3-d]pyrimidin-4-ylamino)-N-(1-phenyl-ethyl)-benzamide According to the procedure in Example 385F, the title compound was prepared using 4-(4-hydroxy-phenylsulfanyl)-3-(7-isopropyl-pyrido[2,3-d]pyrimidin-4-ylamino)-benzoic acid (prepared in Example 410D) and S-(−)-α-methylbenzylamine: yield 39%. 1H-NMR (300 MHz, DMSO-d6) δ ppm: 1.34 (d, J=7.0 Hz, 6H), 1.45 (d, J=7.4 Hz, 3H), 3.23 (septet, J=7.0 Hz, 1H), 5.15 (quintet, J=7.4 Hz, 1H), 6.83 (d, J=8.4 Hz, 2H), 6.90 (d, J=8.1 Hz, 1H), 7.16-7.40 (m, 5H), 7.28 (d, J=8.4 Hz, 2H), 7.63 (d, J=8.4 Hz, 1H), 7.73 (br-d, J=8.1 Hz, 1H), 7.91 (br-s, 1H), 8.57 (s, 1H), 8.78 (d, J=7.3 Hz, 1H), 8.86 (d, J=8.4 Hz, 1H), 9.93 (s, 1H), 10.16 (s, 1H) MS ESI+ m/z: 536 (M+H) ESI− m/z: 534 (M−H).

EXAMPLE 411

(S)-4-(4-Amino-phenoxy)-3-(7-isopropyl-pyrido[2,3-d]pyrimidin-4-ylamino)-N-(1-phenyl-ethyl)-benzamide

EXAMPLE 411A 4-(4-tert-Butoxycarbonylamino-phenoxy)-3-nitro-benzoic acid methyl ester A mixture of 4-chloro-3-nitrobenzoic acid methyl ester (15.0 g, 68 mmol), (4-hydroxy-phenyl)-carbamic acid tert-butyl ester (14.7 g, 68 mmol) and K2CO3 (18.9 g, 136 mmol) in DMF (300 mL) was heated at 110° C. for 1 hour under N2, cooled to room temperature, and then poured into ice-H2O (1200 mL) under stirring. The aqueous mixture was extracted with AcOEt (600 mL). The extract was washed with H2O (3 times) and brine, dried over MgSO4, and evaporated to give pale brown crystal, which was purified by washing with i-Pr2O and dried at 40° C. overnight under reduced pressure to give the title compound as pale yellow crystal (18.5 g, 70%).

EXAMPLE 411B

3-Amino-4-(4-tert-butoxycarbonylamino-phenoxy)-benzoic acid methyl ester

A suspension of 4-(4-tert-butoxycarbonylamino-phenoxy)-3-nitro-benzoic acid methyl ester (18.0 g, 46 mmol), Fe powder (13.5 g, 232 mmol) and NH4Cl (12.4 g, 232 mmol) in aqueous EtOH [prepared from EtOH (180 mL) and H2O (180 mL)] was gradually heated to reflux and refluxed for 1.5 hours. The reaction mixture was filtrated through celite pad and the filtrate was evaporated. The aqueous residue was portioned between AcOEt and 5% NaHCO3 and then filtered through celite pad. The organic layer was separated, washed H2O and brine, dried over MgSO4 and evaporated to give pale brown oil, which was diluted with i-Pr2O (100 mL) and stirred at room temperature for 1 hour. The resulting crystal was collected by filtration, washed with i-Pr2O, and dried at 40° C. overnight under reduced pressure to give the title compound as colorless crystal (10.5 g, 63%).

EXAMPLE 411C 4-(4-tert-Butoxycarbonylamino-phenoxy)-3-(7-isopropyl-pyrido[2,3-]pyrimidin-4-ylamino)-benzoic acid methyl ester A suspension of N'-(3-cyano-6-isopropyl-pyridin-2-yl)-N,N-dimethyl-formamidine (2.00 g, 9.3 mmol) and 3-amino-4-(4-tert-butoxycarbonylamino-phenoxy)-benzoic acid methyl ester (3.31 g, 9.3 mmol) in AcOH (40 mL) was heated at 120° C. for 10 minutes under N2. The reaction mixture was portioned between AcOEt (30 mL) and H2O (250 mL) and made basic to pH 9 with K2CO3 under stirring. The resulting solid was collected by filtration, washed with cold AcOEt, and dried at 40° C. overnight under reduced pressure to give the title compound as slightly yellow crystal (4.31 g, 88%).

EXAMPLE 411D 4-(4-tert-Butoxycarbonylamino-phenoxy)-3-(7-isopropyl-pyrido[2,3-d]pyrimidin-4-ylamino)-benzoic acid To a suspension of 4-(4-tert-butoxycarbonylamino-phenoxy)-3-(7-isopropyl-pyrido[2,3-d]pyrimidin-4-ylamino)-benzoic acid methyl ester (4.30 g, 8.1 mmol) in THF (43 mL) was added aqueous LiOH [prepared from LiOH monohydrate (1.08 g) and H2O (11 mL)] dropwise at room temperature. The mixture was stirred at room temperature for 21 hours. Additional aqueous LiOH [prepared from LiOH monohydrate (0.70 g) and H2O (7 mL)] was added at room temperature. The mixture was mixture was stirred at 35° C. for 6 hours, and then evaporated. The aqueous mixture was diluted with 150 mL of H2O, washed with AcOEt, and treated with active charcoal. The mixture was filtered and the filtrate was carefully acidified to pH 4-5 with 1N HCl under stirring. The resulting solid was collected by filtration, washed with $H_2O$, and dried at 40° C. for 1 day under reduced pressure to give the title compound as pale yellow crystal (4.06 g, 97%).

EXAMPLE 411E (S)-{4-[2-(7-Isopropyl-pyrido[2,3-]pyrimidin-4-ylamino)-4-(1-phenyl-ethylcarbamoyl)-phenoxy]-phenyl}-carbamic acid tert-butyl ester According to the procedure in Example 385F, the title compound was prepared using 4-(4-tert-butoxycarbonylamino-phenoxy)-3-(7-isopropyl-pyrido[2,3-d]pyrimidin-4-ylamino)-benzoic acid (prepared in Example 411D) and S-(−)-α-methylbenzylamine: yield 75%.

EXAMPLE 411F (S)-4-(4-Amino-phenoxy)-3-(7-isopropyl-pyrido[2,3-d]pyrimidin-4-ylamino)-N-(1-phenyl-ethyl)-benzamide According to the procedure in Example 385G, the title compound was prepared from (S)-{4-[2-(7-isopropyl-pyrido[2,3-d]pyrimidin-4-ylamino)-4-(1-phenyl-ethylcarbamoyl)-phenoxy]-phenyl}-carbamic acid tert-butyl ester (prepared in Example 411E): yield 78%. 1H-NMR (300 MHz, DMSO-d6) δ ppm: 1.32 (d, J=7.0 Hz, 6H), 1.47 (d, J=7.3 Hz, 3H), 3.20

(septet, J=7.0 Hz, 1H), 4.99 (s, 2H), 5.17 (quintet, J=7.3 Hz, 1H), 6.55 (d, J=8.8 Hz, 2H), 6.75 (d, J=8.8 Hz, 2H), 6.78 (d, J=8.8 Hz, 1H), 7.21 (br-t, J=7.0 Hz, 1H), 7.32 (t, J=7.0 Hz, 2H), 7.38 (d, J=7.0 Hz, 2H), 7.59 (d, J=8.5 Hz, 1H), 7.78 (dd, J=8.8, 2.2 Hz, 1H), 8.07 (d, J=2.2 Hz, 1H), 8.59 (s, 1H), 8.74 (d, J=7.3 Hz, 1H), 8.82 (d, J=8.5 Hz, 1H), 9.96 (s, 1H) MS ESI+ m/z: 519 (M+H) ESI– m/z: 517 (M–H).

EXAMPLE 412

(R)-4-(4-Amino-phenoxy)-3-(7-isopropyl-pyrido[2,3-d]pyrimidin-4-ylamino)-N-(1-phenyl-ethyl)-benzamide

EXAMPLE 412A (R)-{4-[2-(7-Isopropyl-pyrido[2,3-d]pyrimidin-4-ylamino)-4-(1-phenyl-ethylcarbamoyl)-phenoxy]-phenyl}-carbamic acid tert-butyl ester According to the procedure in Example 385F, the title compound was prepared using 4-(4-tert-butoxycarbonylamino-phenoxy)-3-(7-isopropyl-pyrido[2,3-d]pyrimidin-4-ylamino)-benzoic acid (prepared in Example 411D) and R-(+)-α-methylbenzylamine: yield 84%.

EXAMPLE 412B (R)-4-(4-Amino-phenoxy)-3-(7-isopropyl-pyrido[2,3-d]pyrimidin-4-ylamino)-N-(1-phenyl-ethyl)-benzamide According to the procedure in Example 385G, the title compound was prepared from (R)-{4-[2-(7-isopropyl-pyrido[2,3-d]pyrimidin-4-ylamino)-4-(1-phenyl-ethylcarbamoyl)-phenoxy]-phenyl}-carbamic acid tert-butyl ester (prepared in Example 412A): yield 71%. 1H-NMR (300 MHz, DMSO-d6) δ ppm: 1.32 (d, J=7.0 Hz, 6H), 1.47 (d, J=7.3 Hz, 3H), 3.20 (septet, J=7.0 Hz, 1H), 5.00 (s, 2H), 5.17 (quintet, J=7.3 Hz, 1H), 6.55 (d, J=8.8 Hz, 2H), 6.75 (d, J=8.8 Hz, 2H), 6.78 (d, J=8.5 Hz, 1H), 7.22 (br-t, J=7.0 Hz, 1H), 7.32 (t, J=7.0 Hz, 2H), 7.38 (d, J=7.0 Hz, 2H), 7.59 (d, J=8.5 Hz, 1H), 7.78 (dd, J=8.5, 2.2 Hz, 1H), 8.07 (d, J=2.2 Hz, 1H), 8.59 (s, 1H), 8.75 (d, J=7.3 Hz, 1H), 8.82 (d, J=8.5 Hz, 1H), 9.96 (s, 1H).

EXAMPLE 413

(S)-4-(4-Amino-phenylsulfanyl)-3-(7-methyl-pyrido[2,3-d]pyrimidin-4-ylamino)-N-(1-phenyl-ethyl)-benzamide

EXAMPLE 413A 4-(4-tert-Butoxycarbonylamino-phenylsulfanyl)-3-(7-methyl-pyrido[2,3-d]pyrimidin-4-ylamino)-benzoic acid methyl ester A suspension of N'-(3-cyano-6-methyl-pyridin-2-yl)-N,N-dimethyl-formamidine (1.00 g, 5.3 mmol) and 3-amino-4-(4-tert-butoxycarbonylamino-phenylsulfanyl)-benzoic acid methyl ester (prepared in Example 385C) (1.99 g, 5.3 mmol) in AcOH (20 mL) was heated at 120° C. for 30 minutes under N2. After cooling to room temperature, the reaction mixture was portioned between AcOEt (250 mL) and H2O (200 mL), and then made basic to pH 9 with K2CO3 under stirring. The organic layer was separated, washed with 10% NaHCO3, H2O and brine, dried over MgSO4, and evaporated to give pale brown oil. The oily residue was separated by silica gel column chromatography (AcOEt) to yellow amorphous, which was solidified by the treatment of i-Pr2O. The resulting solid was collected by filtration, washed with i-Pr2O, and dried at 40° C. overnight under reduced pressure to give the title compound as pale yellow crystal (1.70 g, 62%).

EXAMPLE 413B 4-(4-tert-Butoxycarbonylamino-phenylsulfanyl)-3-(7-methyl-pyrido[2,3-d]pyrimidin-4-ylamino)-benzoic acid To a solution of 4-(4-tert-butoxycarbonylamino-phenylsulfanyl)-3-(7-methyl-pyrido[2,3-d]pyrimidin-4-ylamino)-benzoic acid methyl ester (1.50 g, 2.9 mmol) in THF (15 mL) was added aqueous LiOH [prepared from LiOH monohydrate (0.39 g, 9.0 mmol) and H2O (3.9 mL)] dropwise at room temperature. The mixture was stirred at room temperature for 21 hours. Additional aqueous LiOH solution [prepared from LiOH monohydrate (0.25 g) and H2O (2.5 mL)] was added at room temperature. The mixture was mixture was stirred at room temperature for 24 hours, and then evaporated. The aqueous mixture was diluted with 50 mL of H2O, washed with AcOEt, and treated with active charcoal. The mixture was filtered and the filtrate was carefully acidified to pH 4-5 with 1N HCl under stirring. The mixture (including oily precipitate) was sonicated for 1 hour and stirred at room temperature for 1 hour to give pale yellow solid. The resulting solid was collected by filtration, washed with H2O, and dried at 60° C. overnight under reduced pressure to give the title compound as pale yellow crystal (1.36 g, 93%). 1H-NMR (300 MHz, DMSO-d6) δ ppm: 1.48 (s, 9H), 2.68 (s, 3H), 6.93 (d, J=8.5 Hz, 1H), 7.37 (d, J=8.5 Hz, 2H), 7.55 (d, J=8.5 Hz, 2H), 7.57 (d, J=8.5 Hz, 1H), 7.75 (br-d, J=8.5 Hz, 1H), 7.89 (br-s, 1H), 8.58 (s, 1H), 8.80 (d, J=8.5 Hz, 1H), 9.62 (s, 1H), 10.15 (s, 1H), 12.97 (br-s, 1H)

EXAMPLE 413C (S)-{4-[2-(7-Methyl-pyrido[2,3-d]pyrimidin-4-ylamino)-4-(1-phenyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-methyl-pyrido[2,3-d]pyrimidin-4-ylamino)-benzoic acid (prepared in Example 413B) and S-(–)-α-methylbenzylamine: yield 88%.

EXAMPLE 413D (S)-4-(4-Amino-phenylsulfanyl)-3-(7-methyl-pyrido[2,3-d]pyrimidin-4-ylamino)-N-(1-phenyl-ethyl)-benzamide According to the procedure in Example 385G, the title compound was prepared from (S)-{4-[2-(7-methyl-pyrido[2,3-]pyrimidin-4-ylamino)-4-(1-phenyl-ethylcarbamoyl)-phenylsulfanyl]-phenyl}-carbamic acid tert-butyl ester (prepared in Example 413C): yield 84%. 1H-NMR (300 MHz, DMSO-d6) δ ppm: 1.45 (d, J=7.3 Hz, 3H), 2.68 (s, 3H), 5.15 (quintet, J=7.3 Hz, 1H), 5.58 (s, 2H), 6.62 (d, J=8.5 Hz, 2H), 6.84 (d, J=8.5 Hz, 1H), 7.12 (d, J=8.5 Hz, 2H), 7.16-7.25 (m, 1H), 7.26-7.39 (m, 4H), 7.57 (d, J=8.5 Hz, 1H), 7.71 (dd, J=8.5, 1.8

Hz, 1H), 7.90 (d, J=1.8 Hz, 1H), 8.57 (s, 1H), 8.74 (d, J=7.3 Hz, 1H), 8.82 (d, J=8.5 Hz, 1H), 10.11 (s, 1H) MS ESI+ m/z: 507 (M+H).

EXAMPLE 414

(S)-4-(4-Amino-phenylsulfanyl)-3-(7-tert-butyl-pyrido[2,3-d]pyrimidin-4-ylamino)-N-(1-phenyl-ethyl)-benzamide

EXAMPLE 414A 4-(4-tert-Butoxycarbonylamino-phenylsulfanyl)-3-(7-tert-butyl-pyrido[2,3-d]pyrimidin-4-ylamino)-benzoic acid methyl ester A suspension of N'-(6-tert-butyl-3-cyano-pyridin-2-yl)-N,N-dimethyl-formamidine (0.46 g, 2.0 mmol) and 3-amino-4-(4-tert-butoxycarbonylamino-phenylsulfanyl)-benzoic acid methyl ester [prepared in Example 385C] (0.75 g, 2.0 mmol) in AcOH (10 mL) was heated at 120° C. for 30 minutes under N2. After cooling to room temperature, the reaction mixture was portioned between AcOEt and H2O, and then made basic to pH 9 with K2CO3 under stirring. The organic layer was separated, washed with 10% NaHCO3, H2O and brine, dried over MgSO4, and evaporated to give pale brown oil. The oily residue was separated by silica gel column chromatography (CH2Cl2/MeOH=98/2) to give the title compound as off-white powder (0.53 g, 47%).

EXAMPLE 414B 4-(4-tert-Butoxycarbonylamino-phenylsulfanyl)-3-(7-tert-butyl-pyrido[2,3-d]pyrimidin-4-ylamino)-benzoic acid To a solution of 4-(4-tert-butoxycarbonylamino-phenylsulfanyl)-3-(7-tert-butyl-pyrido[2,3-d]pyrimidin-4-ylamino)-benzoic acid methyl ester (0.53 g, 0.1 mmol) in a mixture of THF (9 mL) and MeOH (3 mL) was added aqueous LiOH [prepared from LiOH monohydrate (0.21 g, 5.0 mmol) and H2O (3 mL)] dropwise at room temperature. The mixture was stirred at 50° C. for 4 hours, and then evaporated. The aqueous mixture was diluted with H2O, washed with AcOEt, and then carefully acidified to pH 4-5 with 10% HCl at 5° C. under stirring. The resulting solid was collected by filtration, washed with H2O, and dried at 60° C. overnight under reduced pressure to give the title compound as yellow powder (0.53 g, 99%).

EXAMPLE 414C (S)-{4-[2-(7-tert-Butyl-pyrido[2,3-]pyrimidin-4-ylamino)-4-(1-phenyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-tert-butyl-pyrido[2,3-d]pyrimidin-4-ylamino)-benzoic acid (prepared in Example 414B) and S-(−)-α-methylbenzylamine: yield 99%.

EXAMPLE 414D (S)-4-(4-Amino-phenylsulfanyl)-3-(7-tert-butyl-pyrido[2,3-d]pyrimidin-4-ylamino)-N-(1-phenyl-ethyl)-benzamide According to the procedure in Example 385G, the title compound was prepared from (S)-{4-[2-(7-tert-Butyl-pyrido[2,3-]pyrimidin-4-ylamino)-4-(1-phenyl-ethylcarbamoyl)-phenylsulfanyl]-phenyl}-carbamic acid tert-butyl ester (prepared in Example 414C): yield 88%. 1H-NMR (300 MHz, DMSO-d6) δ ppm: 1.42 (s, 9 H) 1.45 (d, J=7.35 Hz, 3 H) 5.09-5.21 (m, 1 H) 5.58 (s, 2 H) 6.62 (d, J=8.46 Hz, 2 H) 6.83 (d, J=8.09 Hz, 1 H) 7.11 (d, J=8.46 Hz, 2 H) 7.17-7.39 (m, 5 H) 7.71 (d, J=8.82 Hz, 1 H) 7.82 (d, J=8.46 Hz, 1 H) 7.88 (s, 1 H) 8.57 (s, 1 H) 8.75 (d, J=8.09 Hz, 1 H) 8.88 (d, J=8.82 Hz, 1 H) 10.13 (s, 1 H) MS ESI+ m/z: 549 (M+H).

EXAMPLE 415

4-(4-Amino-phenylsulfanyl)-N-benzyl-3-(7-isopropyl-pyrido[2,3-]pyrimidin-4-ylamino)-benzamide

EXAMPLE 415A

{4-[4-Benzylcarbamoyl-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and benzylamine: yield 79%.

EXAMPLE 415B 4-(4-Amino-phenylsulfanyl)-N-benzyl-3-(7-isopropyl-pyrido[2,3-d]pyrimidin-4-ylamino)-benzamide According to the procedure in Example 385G, the title compound was prepared from {4-[4-benzylcarbamoyl-2-(7-isopropyl-pyrido[2,3-d]pyrimidin-4-ylamino)-phenylsulfanyl]-phenyl-carbamic acid tert-butyl ester (prepared in Example 415A): yield 79%. 1H-NMR (300 MHz, DMSO-d6) δ ppm: 1.34 (d, J=7.0 Hz, 6H), 3.22 (septet, J=7.0 Hz, 1H), 4.45 (d, J=5.9 Hz, 2H), 5.59 (s, 2H), 6.62 (d, J=8.5 Hz, 2H), 6.83 (d, J=8.5 Hz, 1H), 7.13 (d, J=8.5 Hz, 2H), 7.18-7.35 (m, 5H), 7.63 (d, J=8.5 Hz, 1H), 7.72 (dd, J=8.5, 1.8 Hz, 1H), 7.87 (d, J=1.8 Hz, 1H), 8.57 (s, 1H), 8.87 (d, J=8.5 Hz, 1H), 9.00 (t, J=5.9 Hz, 1H), 10.11 (s, 1H) MS ESI+ m/z: 521 (M+H) ESI− m/z: 519 (M−H).

EXAMPLE 416

4-(4-Amino-phenylsulfanyl)-N-(2-bromo-benzyl)-3-(7-isopropyl-pyrido[2,3-d]pyrimidin-4-ylamino)-benzamide

EXAMPLE 416A

{4-[4-(2-Bromo-benzylcarbamoyl)-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and o-bromobenzylamine.

EXAMPLE 416B

4-(4-Amino-phenylsulfanyl)-N-(2-bromo-benzyl)-3-(7-isopropyl-pyrido[2,3-d]pyrimidin-4-ylamino)-benzamide According to the procedure in Example 385G, the title compound was prepared from {4-[4-(2-bromo-benzylcarbamoyl)-2-(7-isopropyl-pyrido[2,3-d]pyrimidin-4-ylamino)-phenylsulfanyl]-phenyl}-carbamic acid tert-butyl ester (prepared in Example 416A) as di-trifluoroacetate. 1H-NMR (500 MHz, DMSO-d6) δ ppm: 1.37 (d, J=6.71 Hz, 6 H) 3.27-3.38 (m, 1 H) 4.50 (s, 2 H) 6.64-6.74 (m, 2 H) 7.01 (d, J=8.54 Hz, 1 H) 7.14-7.20 (m, 2 H) 7.21-7.26 (m, 1 H) 7.29-7.34 (m, 1 H) 7.34-7.41 (m, 1 H) 7.63 (d, J=7.93 Hz, 1 H) 7.84 (dd, J=8.24, 1.83 Hz, 1 H) 7.90 (d, J=1.83 Hz, 1 H) 7.93 (d, J=8.85 Hz, 1 H) 8.86 (s, 1 H) 9.01 (d, J=8.54 Hz, 1 H) MS ESI+ m/z: 599, 601 (M+H).

EXAMPLE 417

4-(4-Amino-phenylsulfanyl)-N-(4-bromo-benzyl)-3-(7-isopropyl-pyrido[2,3-d]pyrimidin-4-ylamino)-benzamide

EXAMPLE 417A

{4-[4-(4-Bromo-benzylcarbamoyl)-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and p-bromobenzylamine.

EXAMPLE 417B

4-(4-Amino-phenylsulfanyl)-N-(4-bromo-benzyl)-3-(7-isopropyl-pyrido[2,3-d]pyrimidin-4-ylamino)-benzamide According to the procedure in Example 385G, the title compound was prepared from {4-[4-(4-bromo-benzylcarbamoyl)-2-(7-isopropyl-pyrido[2,3-d]pyrimidin-4-ylamino)-phenylsulfanyl]-phenyl}-carbamic acid tert-butyl ester (prepared in Example 417A) as di-trifluoroacetate. 1H-NMR (500 MHz, DMSO-d6) δ ppm: 1.37 (d, J=6.00 Hz, 1 H) 3.28-3.39 (m, 1 H) 4.42 (s, 2 H) 6.64-6.76 (m, 2 H) 6.99 (d, J=8.54 Hz, 1 H) 7.14-7.21 (m, 2 H) 7.27 (d, J=8.54 Hz, 2 H) 7.49-7.56 (m, 2 H) 7.80 (dd, J=8.39, 1.98 Hz, 1 H) 7.87 (d, J=1.83 Hz, 1 H) 7.93 (d, J=8.85 Hz, 1 H) 8.85 (s, 1 H) 9.01 (d, J=8.54 Hz, 1 H) MS ESI+ m/z: 599, 601 (M+H)

EXAMPLE 418

4-(4-Amino-phenylsulfanyl)-3-(7-isopropyl-pyrido[2,3-d]pyrimidin-4-ylamino)-N-(2-methyl-benzyl)-benzamide

EXAMPLE 418A

{4-[2-(7-Isopropyl-pyrido[2,3-d]pyrimidin-4-ylamino)-4-(2-methyl-benzylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and o-methylbenzylamine.

EXAMPLE 418B

4-(4-Amino-phenylsulfanyl)-3-(7-isopropyl-pyrido[2,3-d]pyrimidin-4-ylamino)-N-(2-methyl-benzyl)-benzamide According to the procedure in Example 385G, the title compound was prepared from {4-[2-(7-isopropyl-pyrido[2,3-d]pyrimidin-4-ylamino)-4-(2-methyl-benzylcarbamoyl)-phenylsulfanyl]-phenyl}-carbamic acid tert-butyl ester (prepared in Example 418A) as di-trifluoroacetate. 1H-NMR (500 MHz, DMSO-d6) δ ppm: 1.37 (d, J=7.0 Hz, 6H), 2.31 (s, 3H), 3.32 (septet, J=7.0 Hz, 1H), 4.44 (s, 2H), 6.68 (d, J=8.5 Hz, 2H), 6.99 (d, J=8.5 Hz, 1H), 7.11-7.24 (m, 4H), 7.17 (d, J=8.5 Hz, 2H), 7.82 (dd, J=8.5, 1.8 Hz, 1H), 7.89 (d, J=1.8 Hz, 1H), 7.93 (d, J=8.8 Hz, 1H), 8.85 (s, 1H), 9.01 (d, J=8.8 Hz, 1H) MS ESI+ m/z: 535 (M+H) ESI− m/z: 533 (M−H).

EXAMPLE 419

4-(4-Amino-phenylsulfanyl)-3-(7-isopropyl-pyrido[2,3-d]pyrimidin-4-ylamino)-N-(3-methyl-benzyl)-benzamide

EXAMPLE 419A

{4-[2-(7-Isopropyl-pyrido[2,3-d]pyrimidin-4-ylamino)-4-(3-methyl-benzylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and m-methylbenzylamine.

EXAMPLE 419B

4-(4-Amino-phenylsulfanyl)-3-(7-isopropyl-pyrido[2,3-d]pyrimidin-4-ylamino)-N-(3-methyl-benzyl)-benzamide According to the procedure in Example 385G, the title compound was prepared from {4-[2-(7-isopropyl-pyrido[2,3-d]pyrimidin-4-ylamino)-4-(3-methyl-benzylcarbamoyl)-phenylsulfanyl]-phenyl}-carbamic acid tert-butyl ester (prepared in Example 419A) as di-trifluoroacetate. 1H-NMR (500 MHz, DMSO-d6) δ ppm: 1.37 (d, J=7.0 Hz, 6H), 2.28 (s, 3H), 3.32 (septet, J=7.0 Hz, 1H), 4.42 (s, 2H), 6.68 (d, J=8.5 Hz, 2H), 6.99 (d, J=8.5 Hz, 1H), 7.04-7.13 (m, 3H), 7.17 (d, J=8.5 Hz, 2H), 7.21 (t, J=7.5 Hz, 1H), 7.81 (dd, J=8.5, 1.8 Hz, 1H), 7.88 (d, J=1.8 Hz, 1H), 7.93 (d, J=8.5 Hz, 1H), 8.85 (s, 1H), 9.01 (d, J=8.5 Hz, 1H) MS ESI+ m/z: 535 (M+H) ESI− m/z: 533 (M−H).

EXAMPLE 420

4-(4-Amino-phenylsulfanyl)-3-(7-isopropyl-pyrido[2,3-d]pyrimidin-4-ylamino)-N-(4-methyl-benzyl)-benzamide

EXAMPLE 420A

{4-[2-(7-Isopropyl-pyrido[2,3-d]pyrimidin-4-ylamino)-4-(4-methyl-benzylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and p-methylbenzylamine.

EXAMPLE 420B 4-(4-Amino-phenylsulfanyl)-3-(7-isopropyl-pyrido[2,3-d]pyrimidin-4-ylamino)-N-(4-methyl-benzyl)-benzamide According to the procedure in Example 385G, the title compound was prepared from {4-[2-(7-isopropyl-pyrido[2,3-d]pyrimidin-4-ylamino)-4-(4-methyl-benzylcarbamoyl)-phenylsulfanyl]-phenyl}-carbamic acid tert-butyl ester (prepared in Example 420A) as di-trifluoroacetate. 1H-NMR (500 MHz, DMSO-d6) δ ppm: 1.37 (d, J=7.0 Hz, 6H), 2.27 (s, 3H), 3.32 (septet, J=7.0 Hz, 1H), 4.41 (s, 2H), 6.68 (d, J=8.5 Hz, 2H), 6.99 (d, J=8.5 Hz, 1H), 7.13 (d, J=8.0 Hz, 2H), 7.17 (d, J=8.5 Hz, 2H), 7.19 (d, J=8.0 Hz, 2H), 7.80 (dd, J=8.5, 2.0 Hz, 1H), 7.87 (d, J=2.0 Hz, 1H), 7.93 (d, J=8.5 Hz, 1H), 8.85 (s, 1H), 9.01 (d, J=8.5 Hz, 1H) MS ESI+ m/z: 535 (M+H) ESI– m/z: 533 (M–H).

EXAMPLE 421

4-(4-Amino-phenylsulfanyl)-3-(7-isopropyl-pyrido[2,3-d]pyrimidin-4-ylamino)-N-(3-trifluoromethyl-benzyl)-benzamide

EXAMPLE 421A

{4-[2-(7-Isopropyl-pyrido[2,3-d]pyrimidin-4-ylamino)-4-(3-trifluoromethyl-benzylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (m-trifluoromethyl)benzylamine: yield 64%.

EXAMPLE 421B 4-(4-Amino-phenylsulfanyl)-3-(7-isopropyl-pyrido[2,3-d]pyrimidin-4-ylamino)-N-(3-trifluoromethyl-benzyl)-benzamide According to the procedure in Example 385G, the title compound was prepared from {4-[2-(7-isopropyl-pyrido[2,3-d]pyrimidin-4-ylamino)-4-(3-trifluoromethyl-benzylcarbamoyl)-phenylsulfanyl]-phenyl}-carbamic acid tert-butyl ester (prepared in Example 421A): yield 80%. 1H-NMR (300 MHz, DMSO-d6) δ ppm: 1.34 (d, J=7.0 Hz, 6H), 3.22 (septet, J=7.0 Hz, 1H), 4.54 (d, J=5.9 Hz, 2H), 5.59 (s, 2H), 6.63 (d, J=8.8 Hz, 2H), 6.84 (d, J=8.4 Hz, 1H), 7.13 (d, J=8.8 Hz, 2H), 7.52-7.67 (m, 5H), 7.72 (dd, J=8.4, 1.5 Hz, 1H), 7.86 (d, J=1.5 Hz, 1H), 8.57 (s, 1H), 8.87 (d, J=8.9 Hz, 1H), 9.09 (t, J=5.9 Hz, 1H), 10.12 (s, 1H) MS ESI+ m/z: 589 (M+H) ESI– m/z: 587 (M–H)

EXAMPLE 422

4-(4-Amino-phenylsulfanyl)-3-(7-isopropyl-pyrido[2,3-d]pyrimidin-4-ylamino)-N-(4-trifluoromethyl-benzyl)-benzamide

EXAMPLE 422A

{4-[2-(7-Isopropyl-pyrido[2,3-d]pyrimidin-4-ylamino)-4-(4-trifluoromethyl-benzylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (p-trifluoromethyl)benzylamine.

EXAMPLE 422B 4-(4-Amino-phenylsulfanyl)-3-(7-isopropyl-pyrido[2,3-d]pyrimidin-4-ylamino)-N-(4-trifluoromethyl-benzyl)-benzamide According to the procedure in Example 385G, the title compound was prepared from {4-[2-(7-isopropyl-pyrido[2,3-d]pyrimidin-4-ylamino)-4-(4-trifluoromethyl-benzylcarbamoyl)-phenylsulfanyl]-phenyl}-carbamic acid tert-butyl ester (prepared in Example 422A) as di-trifluoroacetate. 1H-NMR (500 MHz, DMSO-d6) δ ppm: 1.37 (d, J=7.02 Hz, 6 H) 3.25-3.39 (m, 1 H) 4.54 (s, 2 H) 6.60-6.77 (m, 2 H) 7.01 (d, J=8.24 Hz, 1 H) 7.14-7.22 (m, 2 H) 7.52 (d, J=7.93 Hz, 2 H) 7.69 (d, J=7.93 Hz, 2 H) 7.82 (dd, J=8.54, 1.83 Hz, 1 H) 7.88 (d, J=2.14 Hz, 1 H) 7.94 (d, J=8.54 Hz, 1 H) 8.82-8.89 (m, 1 H) 9.01 (d, J=8.54 Hz, 1 H) MS ESI+ m/z: 589 (M+H).

EXAMPLE 423

4-(4-Amino-phenylsulfanyl)-3-(7-isopropyl-pyrido[2,3-d]pyrimidin-4-ylamino)-N-thiophen-2-ylmethyl-benzamide

EXAMPLE 423A (4-{2-(7-Isopropyl-pyrido[2,3-d]pyrimidin-4-ylamino)-4-[(thiophen-2-ylmethyl)-carbamoyl]-phenylsulfanyl}-phenyl)-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and 2-thiophenylmethylamine.

EXAMPLE 423B 4-(4-Amino-phenylsulfanyl)-3-(7-isopropyl-pyrido[2,3-d]pyrimidin-4-ylamino)-N-thiophen-2-ylmethyl-benzamide According to the procedure in Example 385G, the title compound was prepared from (4-{2-(7-isopropyl-pyrido[2,3-d]pyrimidin-4-ylamino)-4-[(thiophen-2-ylmethyl)-carbamoyl]-phenylsulfanyl}-phenyl)-carbamic acid tert-butyl ester (prepared in Example 423A) as di-trifluoroacetate. 1H-NMR (500 MHz, DMSO-d6) δ ppm: 1.37 (d, J=6.71 Hz, 6 H) 3.27-3.39 (m, 1 H) 4.50 (s, 2 H) 6.61-6.75 (m, 2 H) 7.01 (d, J=8.54 Hz, 1 H) 7.14-7.21 (m, 2 H) 7.21-7.27 (m, 1 H) 7.29-7.33 (m, 1 H) 7.37 (t, J=7.48 Hz, 1 H) 7.63 (d, J=7.93 Hz, 1 H) 7.84 (dd, J=8.24, 1.83 Hz, 1 H) 7.90 (d, J=1.83 Hz, 1 H) 7.93 (d, J=8.85 Hz, 1 H) 8.86 (s, 1 H) 9.01 (d, J=8.54 Hz, 1 H) MS ESI+ m/z: 527 (M+H).

EXAMPLE 424

4-(4-Amino-phenylsulfanyl)-3-(7-isopropyl-pyrido[2,3-d]pyrimidin-4-ylamino)-N-(2-m-tolyl-ethyl)-benzamide

EXAMPLE 424A

{4-[2-(7-Isopropyl-pyrido[2,3-d]pyrimidin-4-ylamino)-4-(2-m-tolyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and 2-(m-tolyl)ethylamine.

EXAMPLE 424B 4-(4-Amino-phenylsulfanyl)-3-(7-isopropyl-pyrido[2,3-d]pyrimidin-4-ylamino)-N-(2-m-tolyl-ethyl)-benzamide According to the procedure in Example 385G, the title compound was prepared from {4-[2-(7-isopropyl-pyrido[2,3-d]pyrimidin-4-ylamino)-4-(2-m-tolyl-ethylcarbamoyl)-phenylsulfanyl]-phenyl}-carbamic acid tert-butyl ester (prepared in Example 424A) as di-trifluoroacetate. 1H-NMR (500 MHz, DMSO-d6) δ ppm: 1.36 (t, J=7.32 Hz, 6 H) 2.26 (s, 3H) 2.76-2.84 (m, 2 H) 3.28-3.38 (m, 1 H) 3.42-3.52 (m, 2 H) 6.62-6.76 (m, 2 H) 6.96 (d, J=8.24 Hz, 1 H) 7.00-7.08 (m, 3 H) 7.11-7.24 (m, 3 H) 7.72 (dd, J=8.54, 1.83 Hz, 1 H) 7.81 (d, J=1.83 Hz, 1 H) 7.93 (d, J=8.54 Hz, 1 H) 8.85 (s, 1 H) 9.01 (d, J=8.54 Hz, 1 H) MS ESI+ m/z: 549 (M+H).

EXAMPLE 425

4-(4-Amino-phenylsulfanyl)-3-(7-isopropyl-pyrido[2,3-d]pyrimidin-4-ylamino)-N-(2-p-tolyl-ethyl)-benzamide

EXAMPLE 425A

{4-[2-(7-Isopropyl-pyrido[2,3-d]pyrimidin-4-ylamino)-4-(2-p-tolyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and 2-(p-tolyl)ethylamine.

EXAMPLE 425B 4-(4-Amino-phenylsulfanyl)-3-(7-isopropyl-pyrido[2,3-d]pyrimidin-4-ylamino)-N-(2-p-tolyl-ethyl)-benzamide According to the procedure in Example 385G, the title compound was prepared from {4-[2-(7-isopropyl-pyrido[2,3-d]pyrimidin-4-ylamino)-4-(2-p-tolyl-ethylcarbamoyl)-phenylsulfanyl]-phenyl}-carbamic acid tert-butyl ester (prepared in Example 425A) as di-trifluoroacetate. 1H-NMR (500 MHz, DMSO-d6) δ ppm: 1.37 (d, J=6.71 Hz, 6 H) 2.25 (s, 3H) 2.74-2.83 (m, 2 H) 3.28-3.37 (m, 1 H) 3.45 (t, J=7.48 Hz, 2 H) 6.61-6.71 (m, 2 H) 6.96 (d, J=8.54 Hz, 1 H) 7.06-7.14 (m, 4 H) 7.14-7.21 (m, 2 H) 7.71 (dd, J=8.39, 1.98 Hz, 1 H) 7.81 (d, J=1.83 Hz, 1 H) 7.93 (d, J=8.54 Hz, 1 H) 8.86 (s, 1 H) 9.01 (d, J=8.54 Hz, 1 H) MS ESI+ m/z: 549 (M+H).

EXAMPLE 426

4-(4-Amino-phenylsulfanyl)-3-(7-isopropyl-pyrido[2,3-d]pyrimidin-4-ylamino)-N-(1-methyl-1-phenyl-ethyl)-benzamide

EXAMPLE 426A

{4-[2-(7-Isopropyl-pyrido[2,3-d]pyrimidin-4-ylamino)-4-(1-methyl-1-phenyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and cumylamine: yield 81%.

EXAMPLE 426B 4-(4-Amino-phenylsulfanyl)-3-(7-isopropyl-pyrido[2,3-d]pyrimidin-4-ylamino)-N-(1-methyl-1-phenyl-ethyl)-benzamide According to the procedure in Example 385G, the title compound was prepared from {4-[2-(7-isopropyl-pyrido[2,3-]pyrimidin-4-ylamino)-4-(1-methyl-1-phenyl-ethylcarbamoyl)-phenylsulfanyl]-phenyl}-carbamic acid tert-butyl ester (prepared in Example 426A): yield 26%. 1H-NMR (300 MHz, DMSO-d6) δ ppm: 1.34 (d, J=7.0 Hz, 6H), 1.64 (s, 6H), 3.22 (septet, J=7.0 Hz, 1H), 5.57 (s, 2H), 6.62 (d, J=8.8 Hz, 2H), 6.83 (d, J=8.1 Hz, 1H), 7.12 (d, J=8.8 Hz, 2H), 7.15 (t, J=7.3 Hz, 1H), 7.26 (t, J=7.3 Hz, 2H), 7.35 (d, J=7.3 Hz, 2H), 7.63 (d, J=8.5 Hz, 1H), 7.67 (dd, J=8.1, 0.7 Hz, 1H), 7.84 (d, J=0.7 Hz, 1H), 8.36 (s, 1H), 8.58 (s, 1H), 8.87 (d, J=8.5 Hz, 1H), 10.12 (s, 1H) MS ESI+ m/z: 549 (M+H) ESI− m/z: 547 (M−H)

EXAMPLE 427

(RS)-4-(4-Amino-phenylsulfanyl)-3-(7-isopropyl-pyrido[2,3-d]pyrimidin-4-ylamino)-N-(1-phenyl-ethyl)-benzamide

EXAMPLE 427A (RS)-{4-[2-(7-Isopropyl-pyrido[2,3-d]pyrimidin-4-ylamino)-4-(1-phenyl-ethylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-α-methylbenzylamine: yield 78%.

EXAMPLE 427B (RS)-4-(4-Amino-phenylsulfanyl)-3-(7-isopropyl-pyrido[2,3-d]pyrimidin-4-ylamino)-N-(1-phenyl-ethyl)-benzamide According to the procedure in Example 385G, the title compound was prepared from (RS)-{4-[2-(7-Isopropyl-pyrido[2,3-d]pyrimidin-4-ylamino)-4-(1-phenyl-ethylcarbamoyl)-phenylsulfanyl]-phenyl}-carbamic acid tert-butyl ester (prepared in Example 427A): yield 70%. 1H-NMR (300 MHz, DMSO-d6) δ ppm: 1.34 (d, J=7.0 Hz, 6H), 1.45 (d, J=7.4 Hz, 3H), 3.23 (septet, J=7.0 Hz, 1H), 5.15 (quintet, J=7.4 Hz, 1H), 5.58 (s, 2H), 6.62 (d, J=8.4 Hz, 2H), 6.84 (d, J=8.5 Hz, 1H), 7.12 (d, J=8.4 Hz, 2H), 7.16-7.25 (m, 1H), 7.25-7.40 (m, 4H), 7.63 (d, J=8.4 Hz, 1H), 7.71 (dd, J=8.5, 1.8 Hz, 1H), 7.88 (d, J=1.8 Hz, 1H), 8.57 (s, 1H), 8.75 (d, J=7.3 Hz, 1H), 8.87 (d, J=8.5 Hz, 1H), 10.12 (s, 1H) MS ESI+ m/z: 535 (M+H) ESI– m/z: 533 (M–H)

EXAMPLE 428

(RS)-4-(4-Amino-phenylsulfanyl)-3-(7-isopropyl-pyrido[2,3-d]pyrimidin-4-ylamino)-N-(1-phenyl-propyl)-benzamide

EXAMPLE 428A (RS)-{4-[2-(7-Isopropyl-pyrido[2,3-d]pyrimidin-4-ylamino)-4-(1-phenyl-propylcarbamoyl)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-1-phenylpropylamine: yield 90%.

EXAMPLE 428B (RS)-4-(4-Amino-phenylsulfanyl)-3-(7-isopropyl-pyrido[2,3-d]pyrimidin-4-ylamino)-N-(1-phenyl-propyl)-benzamide According to the procedure in Example 385G, the title compound was prepared from (RS)-{4-[2-(7-Isopropyl-pyrido[2,3-d]pyrimidin-4-ylamino)-4-(1-phenyl-propylcarbamoyl)-phenylsulfanyl]-phenyl}-carbamic acid tert-butyl ester (prepared in Example 428A): yield 88%. 1H-NMR (300 MHz, DMSO-d6) δ ppm: 0.88 (d, J=7.3 Hz, 3H), 1.34 (d, J=7.0 Hz, 6H), 1.68-1.91 (m, 2H), 3.22 (septet, J=7.0 Hz, 1H), 4.89 (dt, J=8.1, 7.3 Hz, 1H), 5.57 (s, 2H), 6.62 (d, J=8.5 Hz, 2H), 6.83 (br-d, J=8.5 Hz, 1H), 7.12 (d, J=8.5 Hz, 2H), 7.21 (t, J=7.0 Hz, 1H), 7.30 (t, J=7.0 Hz, 2H), 7.36 (d, J=7.0 Hz, 2H), 7.63 (br-d, J=8.5 Hz, 1H), 7.70 (br-d, J=8.5 Hz, 1H), 7.86 (br-s, 1H), 8.56 (br-s, 1H), 8.67 (br-d, J=8.1 Hz, 1H), 8.86 (br-d, J=8.5 Hz, 1H), 10.13 (br-s, 1H) MS ESI+ m/z: 549 (M+H) ESI– m/z: 547 (M–H).

EXAMPLE 429

(RS)-4-(4-Amino-phenylsulfanyl)-N-[1-(2-fluoro-phenyl)-ethyl]-3-(7-isopropyl-pyrido[2,3-d]pyrimidin-4-ylamino)-benzamide

EXAMPLE 429A (RS)-{4-[4-[1-(2-Fluoro-phenyl)-ethylcarbamoyl]-2-(7-isopropyl-pyrido[2,3-d]pyrimidin-4-ylamino)-phenylsulfanyl]-phenyl}-carbamic acid tert-butyl ester According to the procedure in Example 385F, the title compound was prepared using 4-(4-tert-butoxycarbonylamino-phenylsulfanyl)-3-(7-isopropyl-pyrido[2,3-d]pyrimidin-4-ylamino)-benzoic acid (prepared in Example 385E) and (RS)-1-(2-fluorophenyl)ethylamine: yield 84%.

EXAMPLE 429B (RS)-4-(4-Amino-phenylsulfanyl)-N-[1-(2-fluoro-phenyl)-ethyl]-3-(7-isopropyl-pyrido[2,3-d]pyrimidin-4-ylamino)-benzamide According to the procedure in Example 385G, the title compound was prepared from (RS)-{4-[4-[1-(2-fluoro-phenyl)-ethylcarbamoyl]-2-(7-isopropyl-pyrido[2,3-d]pyrimidin-4-ylamino)-phenylsulfanyl]-phenyl}-carbamic acid tert-butyl ester (prepared in Example 429A): yield 88%. 1H-NMR (300 MHz, DMSO-d6) δ ppm: 1.34 (d, J=6.99 Hz, 6 H) 1.44 (d, J=7.35 Hz, 3 H) 3.11-3.28 (m, 1 H) 5.37 (t, J=7.17 Hz, 1 H) 5.58 (s, 2 H) 6.62 (d, J=8.82 Hz, 2 H) 6.84 (d, J=8.46 Hz, 1 H) 7.09-7.19 (m, 4 H) 7.23-7.33 (m, 1 H) 7.36-7.46 (m, 1 H) 7.63 (d, J=8.46 Hz, 1 H) 7.71 (dd, J=8.46, 1.47 Hz, 1 H) 7.89 (d, J=1.47 Hz, 1 H) 8.57 (s, 1 H) 8.81 (d, J=7.72 Hz, 1 H) 8.86 (d, J=8.82 Hz, 1 H) 10.13 (s, 1 H) MS ESI+ m/z: 553 (M+H)

EXAMPLE 430

(S)-5-(4-aminophenylthio)-4-(7-isopropylpyrido[2,3-d]pyrimidin-4-ylamino)-N-(2-phenylpropyl)thiophene-2-carboxamide

EXAMPLE 430A

Ethyl 5-chloro-4-nitrothiophene-2-carboxylate

To fuming nitric acid (50 mL) cooled in an ice bath to 5° was added neat ethyl 5-chloro-2-thiophene-2-carboxylate (10 g, 0.0524 mol) dropwise at such a rate that the reaction temperature remained below 10°. The reaction was stirred for 30 minutes at 5-10°, then added ice (200 g) and extracted with ethyl acetate (2×100 mL). The combined organic extracts were washed with water (2×100 mL) and brine (50 mL), then dried over magnesium sulfate and filtered. The filtrate was concentrated by rotary evaporation and the residue purified by silica gel flash chromatography eluting with 10:90 ethyl acetate/hexanes to afford the title compound as a crystalline light yellow solid (7.6 g, 0.0322 mol, 62%). $^1$H NMR (300 MHz, DMSO-D6) δ ppm 1.31 (t, J=7.17 Hz, 3 H) 4.35 (q, J=7.23 Hz, 2 H) 8.17 (s, 1 H).

EXAMPLE 430B

Ethyl 5-(4-aminophenylthio)-4-nitrothiophene-2-carboxylate

The product of Example 430A (1.0 g, 4.244 mmol), 4-aminothiophenol (0.797 g, 6.366 mmol), and anhydrous sodium acetate (1.74 g, 21.22 mmol) were heated in anhydrous ethanol (40 mL) under a nitrogen atmosphere at reflux for 30 minutes. The reaction was cooled to room temperature, partitioned with ethyl acetate (100 mL) and water (50 mL), separated layers, and washed organic phase with water (2×50 mL) and brine (50 mL). The organic extract was dried over sodium sulfate, filtered, and concentrated by rotary evaporation. Trituration of the resulting solid with ethyl ether (2×30 mL) afforded the title compound as a bright yellow solid (1.167 g, 3.598 mmol, 85%). $^1$H NMR (300 MHz, DMSO-D6) δ ppm 1.24 (t, J=7.17 Hz, 3 H) 4.24 (q, J=7.23 Hz, 2 H) 5.94 (s, 2 H) 6.71 (d, J=8.82 Hz, 2 H) 7.35 (d, J=8.46 Hz, 2 H) 8.08 (s, 1 H); MS (ESI+) m/z 325 (M+H)$^+$, MS (ESI−) m/z 323 (M−H)$^-$.

EXAMPLE 430C

Ethyl 5-(4-(((9H-fluoren-9-yl)methoxy)carbonylamino)phenylthio)-4-nitrothiophene-2-carboxylate A suspension of the product of Example 430B (0.500 g, 1.541 mmol) and 9-fluorenylmethoxycarbonyl chloride (0.478 g, 1.849 mmol) in methylene chloride (10 mL) under a nitrogen atmosphere was treated with pyridine (0.25 mL, 3.083 mmol), and the resulting solution stirred for 18 hours at room temperature. The reaction was diluted with methylene chloride (50 mL) and washed with 1N aqueous HCl (50 mL) then water (50 mL). The organic was dried over magnesium sulfate, filtered, and concentrated by rotary evaporation. Purification by silica gel flash chromatography eluting with methylene chloride afforded the title compound as a bright yellow solid (0.842 g, quantitative). $^1$H NMR (300 MHz, DMSO-D6) δ ppm 1.23 (t, J=7.17 Hz, 3 H) 4.24 (q, J=7.23 Hz, 2 H) 4.35 (t, J=6.43 Hz, 1 H) 4.57 (d, J=6.25 Hz, 2 H) 7.29-7.50 (m, 4 H) 7.69 (s, 4 H) 7.77 (d, J=7.35 Hz, 2 H) 7.92 (d, J=7.35 Hz, 2 H) 8.11 (s, 1 H) 10.15 (s, 1 H); MS (ESI+) m/z 564 (M+NH$_4$)$^+$, 569 (M+Na)$^+$.

EXAMPLE 430D

Ethyl 5-(4-(((9H-fluoren-9-yl)methoxy)carbonylamino)phenylthio)-4-aminothiophene-2-carboxylate A solution of the product of Example 430C (0.918 g, 1.679 mmol) in ethanol (14 mL) and tetrahydrofuran (14 mL) was treated with iron powder (0.577 g, 10.33 mmol) and a solution of ammonium chloride (0.588 g, 10.99 mmol) in water (7 mL), then refluxed for one hour. The reaction was cooled, diluted with ethyl acetate (100 mL), and washed with water (3×25 mL) and brine (25 mL). The organic extract was dried over sodium sulfate, filtered, and concentrated by rotary evaporation to afford the title compound as a yellow solid (0.698 g, 1.351 mmol, 80%). $^1$H NMR (300 MHz, DMSO-D6) δ ppm 1.27 (t, J=6.99 Hz, 3 H) 4.19-4.36 (m, 3 H) 4.48 (d, J=6.62 Hz, 2 H) 5.56 (s, 2 H) 7.10 (d, J=8.09 Hz, 2 H) 7.28-7.55 (m, 7 H) 7.74 (d, J=7.35 Hz, 2 H) 7.90 (d, J=7.35 Hz, 2 H) 9.73 (s, 1 H); MS (ESI+) m/z 517 (M+H)$^+$, 539 (M+Na)$^+$.

EXAMPLE 430E

Ethyl 5-(4-(((9H-fluoren-9-yl)methoxy)carbonylamino)phenylthio)-4-(7-isopropylpyrido[2,3-d]pyrimidin-4-ylamino)thiophene-2-carboxylate The products of Example 8E (0.105 g, 0.484 mmol) and Example 430D (0.250 g, 0.484 mmol) in acetic acid (5 mL) were reacted under a nitrogen atmosphere in a preheated 140° oil bath for 30 minutes. The reaction was cooled and the solvent removed by rotary evaporation. The residue was co-concentrated with methylene chloride/hexanes (1:1 v/v) four times and the resulting solid dried on high vacuum. Purification by silica gel flash chromatography eluting with 3:97 methanol/methylene chloride afforded the title compound (0.247 g, 0.359 mmol, 74%). $^1$H NMR (300 MHz, DMSO-D6) δ ppm 1.27 (t, J=6.99 Hz, 3 H) 1.32 (d, J=6.99 Hz, 6 H) 3.13-3.26 (m, 1 H) 4.18-4.38 (m, 3 H) 4.50 (d, J=6.25 Hz, 2 H) 7.29-7.50 (m, 8 H) 7.62 (d, J=8.82 Hz, 1 H) 7.74 (d, J=7.35 Hz, 2 H) 7.90 (d, J=7.72 Hz, 2 H) 7.92 (d, J=2.21 Hz, 1 H) 8.65 (s, 1 H) 8.79 (d, J=8.46 Hz, 1 H) 9.85 (s, 1 H) 10.07 (s, 1 H); MS (ESI+) m/z 688 (M+H)$^+$.

EXAMPLE 430F 5-(4-Aminophenylthio)-4-(7-isopropylpyrido[2,3-d]pyrimidin-4-ylamino)thiophene-2-carboxylic acid The product of Example 430E (0.245 g, 0.356 mmol) in 1,4-dioxane (3 mL), was treated with a solution of lithium hydroxide monohydrate (0.0747 g, 1.78 mmol) in water (1.5 mL) at room temperature, the resulting mixture was heated at 60° for 25 minutes. The reaction mixture was cooled, diluted with water (10 mL), adjusted the pH to 3 with 1N aqueous HCl, and the resulting precipitate was collected by vacuum filtration. Washing of the crude product with small volumes of 1,4-dioxane afforded the title compound (0.113 g, 0.258 mmol, 72%). MS (ESI+) m/z 438 (M+H)$^+$, MS (ESI−) m/z 436 (M−H).

EXAMPLE 430G (S)-5-(4-aminophenylthio)-4-(7-isopropylpyrido[2,3-d]pyrimidin-4-ylamino)-N-(2-phenylpropyl)thiophene-2-carboxamide The product of Example 430F (62 mg, 0.142 mmol) in dimethyl sulfoxide (2 mL) under a nitrogen atmosphere was reacted with (S)-(−)-β-methylphenethylamine (23 mg, 0.170 mmol), N,N-diisopropylethylamine (0.123 mL, 0.708 mmol), and O-benzotriazol-1-yl-N,N,N',N'-tetramethyluronium tetrafluoroborate (55 mg, 0.170 mmol at room temperature for 20 hours. The reaction mixture was diluted with water (10 mL), and extracted with ethyl acetate (50 mL). The organic extract was washed sequentially with water (3×10 mL), saturated aqueous sodium hydrogencarbonate (20 mL), and brine (20 mL), dried over magnesium sulfate, filtered, and concentrated by rotary evaporation. Purification of the residue by silica gel flash chromatography eluting with 4:96 methanol/methylene chloride afforded the title compound (67 mg, 0.121 mmol, 85%). $^1$H NMR (300 MHz, DMSO-D6)

δ ppm 1.19 (d, J=6.99 Hz, 3 H) 1.33 (d, J=6.99 Hz, 6 H) 2.91-3.07 (m, 1 H) 3.14-3.29 (m, 1 H) 5.50 (s, 2 H) 6.51 (d, J=8.46 Hz, 2 H) 7.12 (d, J=8.82 Hz, 2 H) 7.16-7.34 (m, 5 H) 7.63 (d, J=8.46 Hz, 1 H) 7.77 (s, 1 H) 8.50 (t, J=5.88 Hz, 1 H) 8.62 (s, 1 H) 8.82 (d, J=8.82 Hz, 1 H) 9.97 (s, 1 H); MS (ESI+) m/z 555 (M+H)$^+$, 1109 (2M+H)$^+$, MS (ESI−) m/z 553 (M−H)$^-$.

EXAMPLE 431

(S)-4-(4-aminophenylthio)-3-(7-isopropylquinazolin-4-ylamino)-N-(1-phenylethyl)benzamide

EXAMPLE 431A

1-Bromo-4-isopropyl-2-nitrobenzene

To fuming nitric acid (5 mL) cooled to 5° was added neat 4-bromoisopropylbenzene (1.0 g, 5.023 mmol) dropwise at such a rate that the reaction temperature remained below 10°. The reaction was stirred for 2 hours at 5-10°, quenched with ice (50 g), extracted with ethyl acetate (50 mL), and the organic extract was washed with water (2×25 mL) and brine (25 mL), then dried over magnesium sulfate filtered and concentrated by rotary evaporation. The residue was purified by silica gel flash chromatography eluting with 5:95 ethyl acetate/hexanes to afford the title compound as a light yellow solid (1.03 g, 4.22 mmol, 84%). $^1$H NMR (300 MHz, CHLOROFORM-D) δ ppm 1.27 (d, J=6.99 Hz, 6 H) 2.75-3.23 (m, 1 H) 7.29 (dd, J=8.82, 2.21 Hz, 1 H) 7.63 (d, J=8.09 Hz, 1 H) 7.69 (d, J=2.21 Hz, 1 H); MS (DCI) m/z 261/263 (M+NH$_4$)$^-$.

EXAMPLE 431B

4-Isopropyl-2-nitrobenzonitrile

The product of Example 431A (0.581 g, 2.380 mmol) and copper (I) cyanide (0.426 g, 4.760 mmol) in N,N-dimethylformamide (5 mL) under a nitrogen atmosphere were heated in 160° oil bath for 1.5 hour. The reaction was cooled, treated with a solution of iron (III) chloride hexahydrate (2.48 g) in water (3.72 mL) and concentrated hydrochloric acid (0.62 mL), and then heated at 65° for 20 minutes. The cooled reaction mixture was extracted with ethyl ether (2×50 mL). The combined ethereal extracts were washed sequentially with 1N aqueous HCl (25 mL), 3N aqueous sodium hydroxide (25 mL), water (25 mL), and brine (25 mL) then dried over magnesium sulfate, filtered, and concentrated by rotary evaporation. Purification of the residue by silica gel flash chromatography eluting with 20:80 ethyl acetate/hexanes afforded the title compound as a yellow liquid (0.351 g, 1.845 mmol, 58%). $^1$H NMR (300 MHz, CHLOROFORM-D) δ ppm 1.33 (d, J=6.99 Hz, 6 H) 2.82-3.47 (m, 1 H) 7.66 (dd, J=7.91, 1.29 Hz, 1 H) 7.83 (d, J=7.72 Hz, 1 H) 8.18 (d, J=1.47 Hz, 1 H); MS (DCI) m/z 208 (M+NH$_4$)$^+$.

EXAMPLE 431C 4-isopropyl-2-nitrobenzoic acid

The product of Example 431B (1.746 g, 9.1798 mmol) dissolved in a 2:1:1 v/v/v mixture of water/acetic acid/concentrated sulfuric acid (24 mL) was heated at reflux for 3 days. The reaction was cooled, poured onto ice water (80 mL) and adjusted to pH12 with 6N aqueous sodium hydroxide. The reaction was washed with ethyl ether (3×50 mL). The aqueous phase was acidified to pH 2 with concentrated hydrochloric acid and extracted with ethyl ether (2×75 mL). The ethereal extracts were dried over magnesium sulfate, filtered, and concentrated by rotary evaporation. The residue was co-concentrated with methylene chloride (5 mL)/hexanes (100 mL) three times and dried on high vacuum to afford the title compound as an off-white solid (1.402 g, 6.702 mmol, 73%). $^1$H NMR (300 MHz, DMSO-D6) δ ppm 1.23 (d, J=6.62 Hz, 6 H) 2.88-3.23 (m, 1 H) 7.66 (dd, J=8.09, 1.84 Hz, 1 H) 7.80 (d, J=7.72 Hz, 1 H) 7.83 (d, J=1.47 Hz, 1 H) 13.70 (br s, 1 H).

EXAMPLE 431D

2-Amino-4-isopropylbenzoic acid

The product of Example 431C (0.697 g, 3.332 mmol) was hydrogenated in methanol (30 mL) with 10% palladium-on-carbon (70 mg) at 1 atmosphere hydrogen pressure (balloon) for 2 hours. The reaction was filtered through a 0.45 micron PTFE membrane and the catalyst thoroughly washed with methanol. The filtrate was concentrated by rotary evaporation to give the title compound (0.585 g, 3.264 mmol, 98%). $^1$H NMR (300 MHz, DMSO-D6) δ ppm 1.15 (d, J=6.62 Hz, 6 H) 2.61-2.92 (m, 1 H) 6.41 (dd, J=8.46, 1.47 Hz, 1 H) 6.58 (d, J=1.84 Hz, 1 H) 7.60 (d, J=8.46 Hz, 1 H) 8.46 (br s, 2 H); MS (ESI+) m/z 180 (M+H)$^+$.

EXAMPLE 431E

7-Isopropylquinazolin-4(3H)-one

The product of Example 431D (0.579 g, 3.231 mmol) was reacted with formamide (1.3 mL) under a nitrogen atmosphere in a microwave (Personal Chemistry Emrys Creator, 300 W) at 150°$^C$ for 30 minutes. The cooled reaction gave a solid mass which was recrystallized from absolute ethanol (2 mL) to afford the title compound as an off-white solid (0.208 g, 1.105 mmol, 34%). $^1$H NMR (300 MHz, DMSO-D6) δ ppm 1.26 (d, J=6.99 Hz, 6 H) 2.91-3.21 (m, 1 H) 7.44 (dd, J=8.27, 1.65 Hz, 1 H) 7.50 (d, J=1.84 Hz, 1 H) 8.02-8.07 (m, 2 H) 12.15 (s, 1 H); MS (APCI) m/z 189 (M+H)$^+$, 211 (M+Na)$^+$.

EXAMPLE 431F

4-Chloro-7-isopropylquinazoline

The product of Example 431E (100 mg, 0.5313 mmol) in phosphorous oxychloride (2 mL) was heated under a nitrogen atmosphere at reflux for one hour. The reaction was cooled and concentrated by rotary evaporation. The residue was dissolved in ethyl acetate (50 mL) and washed sequentially with saturated aqueous sodium hydrogencarbonate (2×25 mL), water (25 mL), and brine (25 mL). The organic extract was dried over sodium sulfate, filtered, and concentrated by rotary evaporation to afford the title compound as a yellow oil (107 mg, 0.5177 mmol, 97%). $^1$H NMR (300 MHz, DMSO-D6) δ ppm 1.33 (d, J=6.99 Hz, 6 H) 3.14-3.29 (m, 1 H) 7.86 (dd, J=8.64, 1.65 Hz, 1 H) 7.93 (s, 1 H) 8.22 (d, J=8.46 Hz, 1 H) 9.07 (s, 1 H).

EXAMPLE 431G (S)-tert-butyl 4-(2-(7-isopropylquinazolin-4-ylamino)-4-(1-phenylethylcarbamoyl)phenylthio)phenylcarbamate (S)-tert-butyl 4-(2-amino-4-(1-phenylethylcarbamoyl)phenylthio)-phenylcarbamate (50 mg, 0.1078 mmol) and the product of Example 431F (24.5 mg, 0.1186 mmol) were heated at reflux in anhydrous ethanol (2 mL) under a nitrogen atmosphere for one hour. The reaction was cooled and concentrated by rotary evaporation. The residue was purified by silica gel flash chromatography eluting with 3:97 methanol/methylene chloride to afford the title compound as an off-white solid (51 mg, 0.0805 mmol, 68%). $^1$H NMR (300 MHz, DMSO-D6) δ ppm 1.31 (d, J=6.99 Hz, 6 H) 1.45 (d, J=7.35 Hz, 3 H) 1.47 (s, 9 H) 3.03-3.21 (m, 1 H) 5.01-5.29 (m, 1 H) 6.96 (d, J=8.46 Hz, 1 H) 7.16-7.25 (m, 1 H) 7.26-7.43 (m, 3 H) 7.32 (d, J=8.09 Hz, 2 H) 7.51 (d, J=8.82 Hz, 2 H) 7.55-7.63 (m, 2 H) 7.72 (dd, J=8.46, 1.47 Hz, 1 H) 7.94 (d, J=1.47 Hz, 1 H) 8.41 (d, J=8.82 Hz, 1 H) 8.44 (s, 1 H) 8.80 (d, J=8.09 Hz, 1 H) 9.58 (s, 1 H) 9.95 (s, 1 H); MS (ESI+) m/z 634 (M+H)$^+$; MS (ESI−) m/z 632 (M−H)$^−$.

EXAMPLE 431H (S)-4-(4-aminophenylthio)-3-(7-isopropylquinazolin-4-ylamino)-N-(1-phenylethyl)benzamide The product of Example 431G (36 mg, 0.0568 mmol) was treated with 1:1 v/v methylene chloride/trifluoroacetic acid (3 mL) at room temperature for one hour then concentrated by rotary evaporation. The residue was dissolved in ethyl acetate (50 mL), washed with saturated aqueous sodium hydrogencarbonate (25 mL), water (25 mL), and brine (25 mL) then dried over magnesium sulfate, filtered, and concentrated by rotary evaporation. Purification by silica gel flash chromatography eluting with 3:97 methanol/methylene chloride afforded the title compound as a white solid (22 mg, 0.0412 mmol, 73%). $^1$H NMR (300 MHz, DMSO-D6) δ ppm 1.31 (d, J=6.99 Hz, 6 H) 1.45 (d, J=7.35 Hz, 3 H) 3.01-3.20 (m, 1 H) 5.07-5.26 (m, 1 H) 5.57 (s, 2 H) 6.61 (d, J=8.46 Hz, 2 H) 6.83 (d, J=8.46 Hz, 1H) 7.11 (d, J=8.82 Hz, 2 H) 7.17-7.43 (m, 5 H) 7.54-7.64 (m, 2 H) 7.69 (dd, J=8.46, 1.10 Hz, 1 H) 7.89 (d, J=1.47 Hz, 1 H) 8.43 (t, J=4.23 Hz, 2 H) 8.74 (d, J=7.72 Hz, 1 H) 9.88 (s, 1 H); MS (ESI+) m/z 534 (M+H)$^+$, 1067 (2M+H); MS (ESI−) m/z 532 (M−H)$^−$.

EXAMPLE 432

(R)-4-(4-Aminophenylthio)-N-(2,3-dihydro-1H-inden-1-yl)-3-(7-isopropylquinazolin-4-ylamino)benzamide

EXAMPLE 432A

Methyl 4-(4-aminophenylthio)-3-nitrobenzoate

A solution of methyl 4-chloro-3-nitrobenzoate (1.00 g, 4.638 mmol) in anhydrous ethanol (40 mL) was treated with 4-aminothiophenol (0.813 g, 6.494 mmol) and anhydrous sodium acetate (1.90 g, 23.19 mmol) at room temperature under a nitrogen atmosphere, at reflux for 2 hours. The reaction was cooled, diluted with ethyl acetate (100 mL), and washed with water (3×50 mL) and brine (50 mL). The organic phase was dried over magnesium sulfate, filtered, and concentrated by rotary evaporation. The resulting orange solid was triturated with ethyl ether/hexanes (1:1 v/v, 3×30 mL), and dried in vacuo to afford the title compound (1.36 g, 4.469 mmol, 96%). $^1$H NMR (300 MHz, DMSO-D6) δ ppm 3.87 (s, 3 H) 5.80 (s, 2 H) 6.70 (d, J=8.46 Hz, 2 H) 7.00 (d, J=8.46 Hz, 1 H) 7.23 (d, J=8.46 Hz, 2 H) 8.05 (dd, J=8.46, 1.84 Hz, 1 H) 8.64 (d, J=1.84 Hz, 1 H). MS (ESI+) m/z 305 (M+H)$^+$.

EXAMPLE 432B

Methyl 4-(4-tert-butoxycarbonylamino)phenylthio)-3-nitrobenzoate

The product of Example 432A (1.36 g, 4.469 mmol) in 1,4-dioxane (25 mL) under a nitrogen atmosphere was treated with a solution of di-tert-butyl dicarbonate (1.46 g, 6.703 mmol) in 1,4-dioxane (5 mL) at room temperature, then refluxed for 3.5 hours. The reaction was cooled and additional di-tert-butyl dicarbonate (1.46 g) was added, and refluxed for another 3.5 hours. Recooled the reaction, treated with di-tert-butyl dicarbonate (1.46 g), and refluxed for 16 hours. The reaction was cooled to room temperature and concentrated by rotary evaporation, then dried. The residue was triturated with ethyl acetate (30 mL) and vacuum filtered to give the title compound as a yellow solid (1.56 g, (3.857 mmol, 86%). $^1$H NMR (300 MHz, DMSO-D6) δ ppm 1.50 (s, 9 H) 3.87 (s, 3 H) 6.95 (d, J=8.46 Hz, 1 H) 7.47-7.57 (d, J=8.82 Hz , 2 H) 7.67 (d, J=8.82 Hz, 2 H) 8.05 (dd, J=8.64, 2.02 Hz, 1 H) 8.66 (d, J=1.84 Hz, 1 H) 9.77 (s, 1 H). MS (ESI+) m/z 422 (M+NH$_4$)$^+$, 427 (M+Na)$^+$.

EXAMPLE 432C

Methyl 3-amino-4-(4-tert-butoxycarbonylamino)phenylthio)benzoate

The product of Example 432B (1.56 g, 3.857 mmol) in ethanol (20 mL) and tetrahydrofuran (20 mL) was treated with iron powder (1.32 g, 23.72 mmol) and a solution of ammonium chloride (1.351 g, 25.26 mmol) in water (10 mL), then heated at 80° for three hours. The reaction was cooled, diluted with ethyl acetate (150 mL), and washed with water (3×50 mL) and brine (50 mL). The organic extract was dried over magnesium sulfate, filtered, and concentrated by rotary evaporation. Purification by silica gel flash chromatography eluting with 3:97 methanol/methylene chloride afforded the title compound as a yellow solid (0.920 g, 2.46 mmol, 64%). $^1$H NMR (300 MHz, DMSO-D6) δ ppm 1.46 (s, 9 H) 3.80 (s, 3 H) 5.53 (s, 2 H) 7.05-7.14 (m, 2 H) 7.19 (d, J=8.82 Hz, 2 H) 7.36 (d, J=1.84 Hz, 1 H) 7.44 (d, J=8.82 Hz, 2 H) 9.46 (s, 1 H). MS (ESI−) m/z 373 (M−H)$^−$.

EXAMPLE 432D methyl 4-(4-(tert-butoxycarbonylamino)phenylthio)-3-(7-isopropylquinazolin-4-ylamino)benzoate The products of Example 431F (0.572 g, 2.768 mmol) and methyl 3-amino-4-(4-(tert-butoxycarbonylamino)phenylthio)benzoate the product of Example 385C or Example 432C (0.902 g, 2.409 mmol) were reacted in anhydrous ethanol (25 mL) under a nitrogen atmosphere at reflux for 30 minutes. The reaction was cooled and concentrated by rotary evaporation. The residue was dissolved in methylene chloride (50 mL) and washed with saturated aqueous sodium hydrogencarbonate (25 mL) and water (25 mL). The organic phase was dried over magnesium sulfate, filtered, and concentrated by rotary evaporation. Purification by silica gel flash chromatography eluting with 3:97 methanol/methylene chloride afforded the title compound as a white solid (0.505 g, 0.927 mmol, 33%). $^1$H NMR (300 MHz, DMSO-D6) δ ppm 1.32 (d, J=6.99 Hz, 6 H) 1.48 (s, 9 H) 2.99-3.21 (m, 1 H) 3.83 (s, 3 H) 6.93 (d, J=8.46 Hz, 1 H) 7.37 (d, J=8.82 Hz, 2 H) 7.55 (d, J=8.82 Hz, 2 H) 7.55-7.64 (m, 2 H) 7.75 (dd, J=8.46, 1.84 Hz, 1 H) 7.91 (d, J=1.84 Hz, 1 H) 8.41 (d, J=8.46 Hz, 1 H) 8.45 (s, 1 H) 9.62 (s, 1 H) 9.92 (s, 1 H). MS (ESI+) m/z 545 (M+H)$^+$.

EXAMPLE 432E 4-(4-(tert-butoxycarbonylamino)phenylthio)-3-(7-isopropylquinazolin-4-ylamino)benzoic acid The product of Example 432D (0.505 g, 0.927 mmol) was suspended in 1,4-dioxane (6 mL), treated with a solution of lithium hydroxide monohydrate (0.078 g, 1.85 mmol) in water (3 mL) at room temperature, then heated at 50° for one hour. The reaction was diluted with water (25 mL), adjusted to pH 1 with 1N aqueous HCl, and extracted with ethyl acetate (50 mL). The organic extract was washed with water (25 mL) and brine (25 mL), dried over magnesium sulfate, filtered, and concentrated by rotary evaporation to afford the title compound as a light yellow solid (0.433 g, 0.816 mmol, 88%). $^1$H NMR (300 MHz, DMSO-D6) δ ppm 1.31 (d, J=6.99 Hz, 6 H) 1.48 (s, 9 H) 2.98-3.23 (m, 1 H) 6.92 (d, J=8.09 Hz, 1 H) 7.36 (d, J=8.46 Hz, 2 H) 7.54 (d, J=8.82 Hz, 2 H) 7.59 (d, J=11.77 Hz, 1 H) 7.73 (d, J=8.09 Hz, 1 H) 7.89 (s, 1 H) 8.34-8.49 (m, 2 H) 9.61 (s, 1 H) 9.94 (s, 1 H). MS (ESI+) m/z 531 (M+H)$^+$.

EXAMPLE 432F (R)-4-(4-Aminophenylthio)-N-(2,3-dihydro-1H-inden-1-yl)-3-(7-isopropylquinazolin-4-ylamino)benzamide The product of Example 432E (45 mg, 0.0848 mmol) was dissolved in dichloromethane (2 mL), treated with trifluoroacetic acid (2 mL), at room temperature for one hour. The reaction was concentrated by rotary evaporation and azeotroped from dichloromethane/hexanes (25 mL, 1:1 v/v) again. Drying under high vacuum afforded the deprotected compound as a yellow powder, which was dissolved in dimethyl sulfoxide (2 mL) under a nitrogen atmosphere and treated with (R)-(−)-1-aminoindane (13.6 mg, 0.102 mmol), N,N-diisopropylethylamine (0.074 mL, 0.424 mmol) and O-benzotriazol-1-yl-N,N,N',N'-tetramethyluronium tetrafluoroborate (32.7 mg, 0.102 mmol) at room temperature for 2 hours. The reaction was diluted with water (10 mL), extracted with ethyl acetate (50 mL) and the organic extract was washed with water (3×10 mL), saturated aqueous sodium hydrogencarbonate (20 mL), and brine (20 mL). The organic phase was dried over magnesium sulfate, filtered, and concentrated by rotary evaporation. Purification by silica gel flash chromatography eluting with 4:96 methanol/methylene chloride afforded the title compound as a white solid (22 mg, 0.0403 mmol, 48%). $^1$H NMR (300 MHz, DMSO-D6) δ ppm 1.31 (d, J=6.99 Hz, 6 H) 1.85-2.09 (m, 1 H) 2.35-2.47 (m, 1 H) 2.75-3.03 (m, 2 H) 3.04-3.18 (m, 1 H) 5.50-5.60 (m, 1 H) 5.57 (s, 2 H) 6.62 (d, J=8.46 Hz, 2 H) 6.82 (d, J=8.46 Hz, 1 H) 7.12 (d, J=8.46 Hz, 2 H) 7.15-7.29 (m, 4 H) 7.57 (dd, J=8.46, 1.47 Hz, 1 H) 7.60 (s, 1 H) 7.73 (dd, J=8.46, 1.84 Hz, 1 H) 7.91 (d, J=1.84 Hz, 1 H) 8.42 (t, J=4.41 Hz, 2 H) 8.72 (d, J=8.09 Hz, 1 H) 9.83 (s, 1 H). MS (ESI+) m/z 546 (M+H)$^+$, 1091 (2M+H)$^+$.

EXAMPLE 433

4-(4-Aminophenylthio)-N-(1-hydroxy-2-phenylpropan-2-yl)-3-(7-isopropylpyrido[2,3-d]pyrimidin-4-ylamino)benzamide The product of Example 454 (205 mg, 0.3104 mmol) was dissolved in dimethyl sulfoxide (4 mL) under a nitrogen atmosphere and reacted with 2-amino-2-phenylpropan-1-ol hydrochloride (70 mg, 0.3725 mmol), N,N-diisopropylethylamine (0.27 mL, 1.552 mmol) and O-benzotriazol-1-yl-N,N,N',N'-tetramethyluronium tetrafluoroborate (120 mg, 0.3725 mmol) at room temperature for 15 hours, The reaction was diluted with water (20 mL), extracted with ethyl acetate (3×50 mL), then washed with water (3×20 mL), saturated aqueous sodium hydrogencarbonate (40 mL), and brine (40 mL). The organic phase was dried over magnesium sulfate, filtered, and concentrated by rotary evaporation. Purification by silica gel flash chromatography eluting with 5:95 methanol/methylene chloride afforded the title compound as a light yellow solid (69 mg, 0.122 mmol, 39%). $^1$H NMR (300 MHz, DMSO-D6) δ ppm 1.34 (d, J=6.62 Hz, 6 H) 1.69 (s, 3 H) 3.13-3.29 (m, 1 H) 3.51 (dd, J=11.03, 6.25 Hz, 1 H) 3.73 (dd, J=10.85, 5.70 Hz, 1 H) 5.09 (t, J=6.07 Hz, 1 H) 5.57 (s, 2 H) 6.61 (d, J=8.46 Hz, 2 H) 6.85 (d, J=8.09 Hz, 1 H) 7.11 (d, J=8.46 Hz, 2 H) 7.12-7.37 (m, 5 H) 7.63 (d, J=8.82 Hz, 1 H) 7.64-7.69 (m, 1 H) 7.84 (d, J=1.47 Hz, 1 H) 8.03 (s, 1 H) 8.58 (s, 1 H) 8.87 (d, J=8.46 Hz, 1 H) 10.14 (s, 1 H). MS (ESI+) m/z 565 (M+H)$^+$ MS (ESI−) m/z 563 (M−H)$^−$.

EXAMPLE 434

4-(4-Aminophenylthio)-N-(1-(hydroxymethyl)-2,3-dihydro-1H-inden-1-yl)-3-(7-isopropylpyrido[2,3-d]pyrimidin-4-ylamino)benzamide

EXAMPLE 434A

Ethyl 1-amino-2,3-dihydro-1H-indene-1-carboxylate

Thionyl chloride (0.617 mL, 8.465 mmol) was added dropwise to anhydrous ethanol (6 mL) cooled to −30° followed by 1-amino-2,3-dihydro-1H-indene-1-carboxylic acid (0.300 g, 1.693 mmol) the reaction was then refluxed for 4 hours. The reaction was concentrated by rotary evaporation and diluted with water (5 mL) and the pH was adjusted to 9 with 6N aqueous sodium hydroxide. The solution was extracted with ethyl acetate (2×25 mL) and the organic extracts were washed with brine (25 mL), dried over sodium sulfate, filtered, and concentrated by rotary evaporation to afford the title compound as an oil (0.293 g, 1.43 mmol, 84%). $^1$H NMR (300 MHz, DMSO-D6) δ ppm 1.12 (t, J=7.17 Hz, 3 H) 1.85-2.07 (m, 1 H) 2.31 (s, 2 H) 2.51-2.66 (m, 1 H) 2.93 (t, J=6.99 Hz, 2 H) 3.90-4.21 (m, 2 H) 7.13-7.34 (m, 4 H). MS (DCI) m/z 206 (M+H)$^+$, 223 (M+NH$_4$)$^+$.

EXAMPLE 434B (1-Amino-2,3-dihydro-1H-inden-1-yl)methanol

The product of Example 434A (0.292 g, 1.423 mmol) and sodium borohydride (0.275 g, 7.113 mmol) were reacted in 1:3 v/v water/ethanol (7 mL), at reflux for 4 hours. The reaction was concentrated by rotary evaporation the partitioned between water (5 mL), ethyl ether (20 mL), 1N aqueous sodium hydroxide (0.712 mL). Solid sodium chloride was added to saturate the aqueous phase and separate the phases. The aqueous phase was extracted with ethyl ether (2×25 mL). The combined ethereal extracts were washed with brine (25 mL), dried over potassium carbonate, filtered, and concentrated by rotary evaporation to afford the title compound (0.197 g, 1.209 mmol, 85%). $^1$H NMR (300 MHz, DMSO-D6) δ ppm 1.64-1.80 (m, 1 H) 1.85 (s, 2 H) 2.16-2.31

(m, 1 H) 2.63-2.91 (m, 2 H) 3.30 (d, J=5.52 Hz, 2 H) 4.74 (t, J=5.52 Hz, 1 H) 6.80-7.63 (m, 4 H). MS (DCI) m/z 164 (M+H)+, 181 (M+NH4)+.

EXAMPLE 434C 4-(4-Aminophenylthio)-N-(1-(hydroxymethyl)-2,3-dihydro-1H-inden-1-yl)-3-(7-isopropylpyrido[2,3-d]pyrimidin-4-ylamino)benzamide The product of Example 454 (57 mg, 0.0865 mmol) was reacted with the product of Example 434B (16.9 mg, 0.104 mmol), N,N-diisopropylethylamine (0.075 mL, 0.433 mmol), and O-benzotriazol-1-yl-N,N,N',N'-tetramethyluronium tetrafluoroborate (33 mg, 0.104 mmol) in dimethyl sulfoxide (2 mL) under a nitrogen atmosphere at room temperature for 1 hour. The reaction was diluted with water (10 mL), extracted with ethyl acetate (50 mL). The organic extract was washed sequentially with water (3×10 mL), saturated aqueous sodium hydrogencarbonate (20 mL), and brine (20 mL) then dried over magnesium sulfate, filtered, and concentrated by rotary evaporation. Purification of the residue by silica gel flash chromatography eluting with 5:95 methanol/methylene chloride afforded the title compound as a light yellow solid (28 mg, 0.0486 mmol, 56%). 1H NMR (300 MHz, DMSO-D6) δ ppm 1.33 (d, J=6.99 Hz, 6 H) 2.19-2.38 (m, 1 H) 2.49-2.63 (m, 1 H) 2.76-2.90 (m, 1 H) 2.91-3.07 (m, 1 H) 3.16-3.28 (m, 1 H) 3.53 (dd, J=11.03, 5.88 Hz, 1 H) 3.73 (dd, J=11.03, 5.88 Hz, 1 H) 5.09 (t, J=6.07 Hz, 1 H) 5.57 (s, 2 H) 6.61 (d, J=8.46 Hz, 2 H) 6.81 (d, J=8.09 Hz, 1 H) 7.05-7.22 (m, 3 H) 7.10 (d, J=8.46 Hz, 2 H) 7.27 (d, J=7.35 Hz, 1 H) 7.55-7.71 (m, 2 H) 7.80 (d, J=1.84 Hz, 1 H) 7.94 (s, 1 H) 8.56 (s, 1 H) 8.86 (d, J=8.46 Hz, 1 H) 10.10 (s, 1 H). MS (ESI+) m/z 577 (M+H)+. MS (ESI−) m/z 575 (M−H)−.

EXAMPLE 435

4-(4-Aminophenylthio)-N-(1-hydroxy-2-phenylbutan-2-yl)-3-(7-isopropylpyrido[2,3-d]pyrimidin-4-ylamino)benzamide

EXAMPLE 435A

2-Amino-2-phenylbutan-1-ol

A solution of ethyl 2-amino-2-phenylbutanoate (0.162 g, 0.782 mmol) in 1:3 v/v water/ethanol (4 mL) was reacted with sodium borohydride (0.151 g, 3.908 mmol) at reflux for four hours. The reaction was concentrated and partition between water (5 mL), ethyl ether (10 mL) and 1N aqueous sodium hydroxide (0.39 mL). Solid sodium chloride was added to saturate the aqueous and separate the phases. The aqueous phase was separated and re-extracted with ethyl ether (2×20 mL). The combined ethereal extracts were washed with brine (25 mL), dried over potassium carbonate, filtered, and concentrated by rotary evaporation to afford the title compound as an oil (0.116 g, 0.702 mmol, 90%). 1H NMR (300 MHz, DMSO-D6) δ ppm 0.59 (t, J=7.54 Hz, 3 H) 1.49-1.80 (m, 4 H) 3.44 (d, J=5.15 Hz, 2 H) 4.63 (t, J=5.52 Hz, 1 H) 6.89-7.76 (m, 5 H). MS (DCI) m/z 166 (M+H)+.

EXAMPLE 435B 4-(4-Aminophenylthio)-N-(1-hydroxy-2-phenylbutan-2-yl)-3-(7-isopropylpyrido[2,3-d]pyrimidin-4-ylamino)benzamide The product of Example 454 (58 mg, 0.0884 mmol) was reacted with the product of Example 435A (17.5 mg, 0.106 mmol), N,N-diisopropylethylamine (0.077 mL, 0.442 mmol), and O-benzotriazol-1-yl-N,N,N',N'-tetramethyluronium tetrafluoroborate (34 mg, 0.106 mmol)in dimethyl sulfoxide (2 mL) under a nitrogen atmosphere at 60° for 1 hour. The reaction was diluted into water (10 mL), extracted with ethyl acetate (50 mL), and the organic extract was washed sequentially with water (2×10 mL), saturated aqueous sodium hydrogencarbonate (20 mL), and brine (20 mL), and dried over magnesium sulfate, filtered, and concentrated by rotary evaporation. Purification of the residue by silica gel flash chromatography eluting with 5:95 methanol/methylene chloride afforded the title compound (11 mg, 0.019 mmol, 22%). 1H NMR (300 MHz, DMSO-D6) δ ppm 0.74 (t, J=7.17 Hz, 3 H) 1.34 (d, J=6.99 Hz, 6 H) 1.93-2.28 (m, 2 H) 3.13-3.28 (m, 1 H) 3.71-4.03 (m, 2 H) 4.90 (t, J=5.70 Hz, 1 H) 5.57 (s, 2 H) 6.61 (d, J=8.46 Hz, 2 H) 6.85 (d, J=8.46 Hz, 1 H) 7.08-7.21 (m, 1 H) 7.11 (d, J=8.46 Hz, 2 H) 7.21-7.34 (m, 4 H) 7.63 (d, J=8.46 Hz, 1 H) 7.67 (dd, J=8.46, 1.84 Hz, 1 H) 7.81-7.90 (m, 2 H) 8.58 (s, 1 H) 8.87 (d, J=8.46 Hz, 1 H) 10.13 (s, 1 H). MS (ESI+) m/z 579 (M+H)+, 1157 (2M+H)+, 1179 (2M+Na)+. MS (ESI−) m/z 577 (M−H)−.

EXAMPLE 436

Sodium (S)-2-(4-(4-(2-(7-isopropylpyrido[2,3-d]pyrimidin-4-ylamino)-4-(1-phenylethylcarbamoyl)phenylthio)phenylthio)-2-methyl-4-oxobutan-2-yl)-3,5-dimethylphenyl phosphate

EXAMPLE 436A 4,4,5,7-tetramethylchroman-2-one 3,5-Dimethylphenol (5.00 g, 0.0409 mol) and methyl 3,3-dimethylacrylate (5.14 g, 0.045 mol) were added to methanesulfonic acid (5 mL) at room temperature followed by heating at 70° for 17 hours. The reaction was cooled, diluted with water (750 mL), extracted with ethyl acetate (2×200 mL) and the combined organic extracts were washed with saturated aqueous sodium hydrogencarbonate (2×100 mL) and brine (50 mL). The organic phase was dried over magnesium sulfate, filtered, and concentrated by rotary evaporation. Purification by silica gel flash chromatography eluting with methylene chloride afforded the title compound as a beige solid (7.73 g, 0.0378 mol, 92%). 1H NMR (300 MHz, CHLOROFORM-D) δ ppm 1.43 (s, 6 H) 2.27 (s, 3 H) 2.46 (s, 3 H) 2.59 (s, 2 H) 6.74 (s, 2 H). MS (DCI) m/z 205 (M+H)+, 222 (M+NH4)+.

EXAMPLE 436B 2-(4-Hydroxy-2-methylbutan-2-yl)-3,5-dimethylphenol

The product of Example 436A (4.00 g, 0.0196 mol) in tetrahydrofuran (75 mL) was added dropwise to a solution of lithium aluminum hydride (1.0 M in tetrahydrofuran, 20.6 mL, 0.0206 mol) in tetrahydrofuran (105 mL) at room temperature over a period of 30 minutes then stirred an additional one hour at ambient temperature. The stirred reaction was quenched by dropwise addition of saturated aqueous ammonium chloride (5 mL) after 15 minutes, the precipitate was removed by vacuum filtration. The filtrate was concentrated by rotary evaporation and the residue purified by silica gel flash chromatography eluting with 4:96 methanol/methylene chloride to afford the title compound as a white solid (2.94 g, 0.014 mol, 72%). 1H NMR (300 MHz, DMSO-D6) δ ppm 1.44 (s, 6 H) 2.00-2.07 (m, 2 H) 2.08 (s, 3 H) 2.36 (s, 3 H) 3.11-3.28 (m, 2 H) 4.09 (t, J=4.78 Hz, 1 H) 6.29 (s, 1 H) 6.42 (s, 1 H) 8.95 (s, 1 H). MS (ESI+) m/z 209 (M+H)⁻, 226 (M+NH₄)⁺.

EXAMPLE 436C

2-(4-tert-Butyldimethylsilyloxy)-2-methylbutan-2-yl)-3,5-dimethylphenol

The product of Example 436B (2.938 g, 0.0141 mol) was treated with tert-butyldimethylsilyl chloride (2.63 g, 0.0169 mol) and imidazole (2.40 g, 0.0353 mol) in N,N-dimethylformamide (30 mL) under a nitrogen atmosphere at room temperature for 2 hours. The solvent was removed by rotary evaporation and high vacuum. The residue was purified by silica gel flash chromatography eluting with 30:70 ethyl acetate/hexanes to afford the title compound as a white solid (4.295 g, 0.0133 mol, 94%). ¹H NMR (300 MHz, DMSO-D6) δ ppm −0.07 (s, 6 H) 0.80 (s, 9 H) 1.45 (s, 6 H) 2.00-2.17 (m, 5 H) 2.37 (s, 3 H) 3.34-3.44 (m, 2 H) 6.30 (s, 1 H) 6.43 (s, 1 H) 9.00 (s, 1 H). MS (DCI) m/z 323 (M+H)⁺, 340 (M+NH₄)⁺.

EXAMPLE 436D

Dibenzyl 2-(4-(tert-butyldimethylsilyloxy)-2-methylbutan-2-yl)-3,5-dimethylphenyl phosphate The product of Example 436C (1.70 g, 5.272 mmol) was treated with solid potassium tert-butoxide (0.685 g, 5.799 mmol) in tetrahydrofuran (90 mL) at 60° for 5 minutes followed by tetrabenzyl pyrophosphate (3.123 g, 5.799 mmol) for one additional hour. Upon cooling the resulting thick white reaction mixture was diluted with hexanes (125 mL), vacuum filtered and the filtrate was concentrated by rotary evaporation. Purification of the residue by silica gel flash chromatography eluting with 20:80 ethyl acetate/hexanes afforded the title compound as a colorless oil (3.07 g, 5.27 mmol, quantitative). ¹H NMR (300 MHz, CHLOROFORM-D) δ ppm −0.07 (s, 6 H) 0.82 (s, 9 H) 1.51 (s, 6 H) 2.07 (t, J=7.35 Hz 2 H) 2.16 (s, 3 H) 2.49 (s, 3 H) 3.47 (t, J=7.35 Hz, 2 H) 5.10 (d, J=8.09 Hz, 4 H) 6.70 (s, 1 H) 7.08 (s, 1 H) 7.27-7.38 (m, 10 H). MS (ESI+) m/z 583 (M+H)⁺, 605 (M+Na)⁺.

EXAMPLE 436E

3-(2-Bis(benzyloxy)phosphoryloxy)-4,6-dimethylphenyl)-3-methylbutanoic acid

The product of Example 436D (0.732 g, 1.256 mmol) was reacted with potassium fluoride (0.0803 g, 1.382 mmol) in acetone (10 mL) at 0° followed by dropwise addition of Jones reagent (1.04 mL, prepared according to *Fieser and Fieser* 1, p. 142) over 20 minutes. After 2 hours, added additional Jones reagent (0.50 mL) and then quenched after an additional 2 hours with isopropyl alcohol (1 mL) for 20 minutes. The reaction mixture was concentrated by rotary evaporation, dissolved in water (25 mL), extracted with ethyl acetate (3×50 mL), and the combined organic layers were washed with brine (25 mL) and dried over magnesium sulfate. Filtration and concentration of the filtrate by rotary evaporation afforded the title compound as an oil (0.544 g, 1.127 mmol, 90%). ¹H NMR (300 MHz, CHLOROFORM-D) δ ppm 1.61 (s, 6 H) 2.12 (s, 3 H) 2.51 (s, 3 H) 2.84 (s, 2 H) 5.11 (d, J=8.09 Hz, 4 H) 6.73 (s, 1 H) 6.97 (s, 1 H) 7.28-7.42 (m, 10 H). MS (ESI+) m/z 483 (M+H)⁺, 505 (M+Na)⁺. MS (ESI−) m/z 481 (M−H)⁻.

EXAMPLE 436F

(S)-Dibenzyl 2-(4-(2-(7-isopropylpyrido[2,3-d]pyrimidin-4-ylamino)-4-(1-phenylethylcarbamoyl)phenylthio)phenylamino)-2-methyl-4-oxobutan-2-yl)-3,5-dimethylphenyl phosphate The product of Example 436E (0.235 g, 0.4863 mmol) was treated with N-(3-dimethylaminopropyl)-N'-ethylcarbodiimide hydrochloride (0.129 g, 0.6733 mmol) and 4-dimethylaminopyridine (7 mg, 0.056 mmol) in N,N-dimethylformamide (3.7 mL) under a nitrogen atmosphere at 0° for 15 minutes, followed by the product of Example 385G (0.200 g, 0.374 mmol) at 0° to room temperature over 20 hours. The reaction was concentrated by rotary evaporation and under high vacuum. Purification by silica gel flash chromatography eluting with 3:97 methanol/methylene chloride afforded the title compound as a yellow solid (0.151 g, 0.151 mmol, 40%). ¹H NMR (300 MHz, DMSO-D6) δ ppm 1.33 (d, J=6.99 Hz, 6 H) 1.45 (d, J=6.99 Hz, 3 H) 1.56 (s, 6 H) 2.10 (s, 3 H) 2.48 (s, 3 H) 2.89 (s, 2 H) 3.14-3.27 (m, 1 H) 5.14 (d, J=8.09 Hz, 4 H) 6.73 (s, 1 H) 6.92 (s, 1 H) 6.97 (d, J=8.82 Hz, 1 H) 7.15-7.43 (m, 17 H) 7.53 (d, J=8.46 Hz, 2 H) 7.62 (d, J=8.09 Hz, 1 H) 7.71 (d, J=8.46 Hz, 1 H) 7.93 (s, 1 H) 8.58 (s, 1 H) 8.81 (t, J=8.46 Hz, 2 H) 9.89 (s, 1 H) 10.23 (s, 1 H). MS (ESI+) m/z 999 (M+H)⁺. MS (ESI−) m/z 997 (M−H)⁻.

EXAMPLE 436G

Sodium (S)-2-(4-(4-(2-(7-isopropylpyrido[2,3-d]pyrimidin-4-ylamino)-4-(1-phenylethylcarbamoyl)phenylthio)phenylthio)-2-methyl-4-oxobutan-2-yl)-3,5-dimethylphenyl phosphate A suspension of the product of Example 436F (0.149 g, 0.1491 mmol) in acetonitrile (3 mL) under a nitrogen atmosphere was treated with sodium iodide (0.0894 g, 0.5965 mmol) followed by dropwise addition of chlorotrimethylsilane (0.076 mL, 0.5965 mmol) at room temperature. After 3 hours the reaction was quenched with water (3 mL), adjusted pH to 9 with saturated aqueous sodium hydrogencarbonate, water was added until solution clouded then sufficient methanol to regain a clear solution. The solution was injected on a C₁₈ HPLC column (Biotage 40S cartridge) and eluted with water (5 minutes) followed by a gradient of 0% to 100% methanol over 25 minutes. The product containing fractions, which eluted at 21-26 minutes, were combined, concentrated by rotary evaporation, and co-evaporated with a mixture of methanol, methylene chloride, and hexanes. Drying on high vacuum overnight afforded the title compound as a yellow solid (0.055 g, 0.0637 mmol, 43%). ¹H NMR (300 MHz, DMSO-D6) δ ppm 1.28 (d, J=6.99 Hz, 6 H) 1.43 (d, J=6.99 Hz, 3 H) 1.63 (s, 6 H) 2.07 (s, 3 H) 2.33 (s, 3 H) 2.80 (s, 2 H) 2.98-3.13 (m, 1 H) 5.02-5.23 (m, 1 H) 6.36 (s, 1 H) 7.09-7.47 (m, 10 H) 7.58 (d, J=8.82 Hz, 2 H) 7.93 (s, 1 H) 8.59 (br s, 2 H) 11.70 (s, 1 H). MS (ESI+) m/z 819 (M+H)⁺, 862 (M+2Na). MS (ESI−) m/z 817 (M−H)⁻.

EXAMPLE 437

4-(4-Aminophenylthio)-N-(1-hydroxy-2-(thiophen-2-yl)-3-(7-isopropylpyrido[2,3-d]pyrimidin-4-ylamino)benzamide

EXAMPLE 437A

Ethyl 2-amino-2-(thiophen-2-yl)propanoate

Thionyl chloride (1 mL, 14.6 mmol) was added dropwise to 2-amino-2-(thiophen-2-yl)propanoic acid (0.500 g, 2.92 mmol) suspended in anhydrous ethanol (10 mL) at 0° then the reaction was heated at reflux for 22 hours. The reaction was concentrated by rotary evaporation, diluted with water (5 mL), adjusted pH to 9 with 6N aqueous sodium hydroxide, and extracted with ethyl acetate (2×25 mL). The combined organic extracts were washed with brine (25 mL), dried over sodium sulfate, filtered, and concentrated by rotary evaporation to afford the title compound as an oil (0.498 g, 2.499 mmol, 86%). $^1$H NMR (300 MHz, DMSO-D6) δ ppm 1.17 (t, J=7.17 Hz, 3 H) 1.60 (s, 3 H) 2.53 (s, 2 H) 4.11 (q, J=7.23 Hz, 2 H) 6.91-6.98 (m, 1 H) 7.00 (dd, J=3.68, 1.10 Hz, 1 H) 7.37 (dd, J=5.15, 1.10 Hz, 1 H). MS (DCI) m/z 200 (M+H)$^+$, 217 (M+NH$_4$)$^-$.

EXAMPLE 437B

2-Amino-2-(thiophen-2-yl)propan-1-ol

The product of Example 437A (0.497 g, 2.494 mmol) in 1:3 v/v water/ethanol (12 mL) was reacted with sodium borohydride (0.481 g, 12.47 mmol) at reflux for 4 hours. The reaction was concentrated by rotary evaporation partition between water (5 mL), ethyl ether (25 mL), 1N aqueous sodium hydroxide (1.25 mL). Solid sodium chloride was added to saturate separate phases. The aqueous was re-extracted with ethyl ether (25 mL). The combined ethereal extracts were washed with brine (25 mL), dried over potassium carbonate, filtered, and concentrated by rotary evaporation to afford the title compound as an oil (0.330 g, 2.099 mmol, 84%). $^1$H NMR (300 MHz, DMSO-D6) δ ppm 1.35 (s, 3 H) 1.96 (s, 2 H) 3.33-3.42 (m, 2 H) 4.91 (t, J=5.70 Hz, 1 H) 6.89-6.95 (m, 2 H) 7.28 (dd, J=3.49, 2.76 Hz, 1 H). MS (DCI) m/z 158 (M+H)$^+$.

EXAMPLE 437C 4-(4-Aminophenylthio)-N-(1-hydroxy-2-(thiophen-2-yl)-3-(7-isopropylpyrido[2,3-d]pyrimidin-4-ylamino)benzamide The product of Example 454 (1.00 g, 1.5199 mmol) was reacted with the product of Example 437B (0.287 g, 1.824 mmol), N,N-diisopropylethylamine (1.32 mL, 7.599 mmol) and O-benzotriazol-1-yl-N,N,N',N'-tetramethyluronium tetrafluoroborate (0.586 g, 1.824 mmol) in dimethyl sulfoxide (15 mL) under a nitrogen atmosphere at room temperature for 15 hours. The reaction was diluted into water (75 mL), extracted with ethyl acetate (100 mL), and the organic extract washed with water (3×50 mL), saturated aqueous sodium hydrogencarbonate (50 mL), and brine (50 mL). The organics were dried over magnesium sulfate, filtered, and concentrated by rotary evaporation. Purification by silica gel flash chromatography eluting with 6:94 methanol/methylene chloride afforded the title compound as a light yellow solid (0.464 g, 0.813 mmol, 53%). $^1$H NMR (300 MHz, DMSO-D6) δ ppm 1.34 (d, J=6.99 Hz, 6 H) 1.73 (s, 3 H) 3.12-3.27 (m, 1 H) 3.56 (dd, J=1 1.03, 6.62 Hz, 1 H) 3.86 (dd, J=11.21, 6.07 Hz, 1 H) 5.19 (t, J=6.07 Hz, 1 H) 5.57 (s, 2 H) 6.61 (d, J=8.46 Hz, 2 H) 6.84 (d, J=8.46 Hz, 1 H) 6.91 (d, J=3.31 Hz, 2 H) 7.11 (d, J=8.46 Hz, 2 H) 7.25-7.33 (m, 1 H) 7.63 (d, J=8.46 Hz, 2 H) 7.81 (s, 1 H) 8.08 (s, 1 H) 8.58 (s, 1 H) 8.87 (d, J=8.46 Hz, 1 H) 10.13 (s, 1 H). MS (ESI+) m/z 571 (M+H)$^+$, 1141 (2M+H)$^+$. MS (ESI−) m/z 569 (M−H)$^-$, 1139 (2M−H)$^-$.

EXAMPLE 438 sodium 2-(4-(4-aminophenylthio)-3-(7-isopropylpyrido[2,3-d]pyrimidin-4-ylamino)benzamido)-2-methylpropyl phosphate

EXAMPLE 438A benzyl 1-hydroxy-2-methylpropan-2-ylcarbamate

A solution of 2-amino-2-methylpropan-1-ol (1.0 g, 11.2 mmol), triethylamine (1.7 mL, 12.2 mmol) and N-(benzyloxycarbonyloxy)-succinimide (3.1 g, 12.4 mmol) in THF (100 mL) at 0° C. were reacted for 0.5 hours then at room temperature for an additional hour. The reaction was concentrated and extracted with ethyl acetate (100 mL). The organic extract was washed sequentially with water, brine, dried over MgSO4, and concentrated in vacuo. The residue was purified by chromatography on silica gel, eluting with a gradient of ethyl acetate in dichloromethane (0-20%) to give the title compound as a colorless oil (2.5 g, quantitative).

EXAMPLE 438B benzyl 1-(di-tert-butoxyphosphoryloxy)-2-methylpropan-2-ylcarbamate The product of Example 438A (0.80 g, 3.8 mmol), di-tert-butyl diethylphosphoramidite (1.07 mL, 3.8 mmol), and 1-H-tetrazole (0.63 g, 8.99 mmol) in THF (35 mL) were reacted at room temperature for 12 hours. The reaction was diluted with dichloromethane (35 mL) and cooled to −45° C., and treated with mCPBA (0.90 g, 4.0 mmol) for 0.5 hours then diluted with ethyl acetate (100 mL). The organics were washed with 10% Na2CO3 (2×), brine, dried over MgSO4, and concentrated. The residue was purified by chromatography on silica gel, eluting with a gradient of ethyl acetate in dichloromethane (0-25%) to give the title compound as a colorless oil (0.926 g, 62%).

EXAMPLE 438C 2-amino-2-methylpropyl di-tert-butyl phosphate

The product of Example 438B (0.40 g, 0.96 mmol) and 20% palladium hydroxide on carbon (0.21 g) in a ethyl acetate (10 mL) and methanol (1 mL) was stirred under a an atmosphere of hydrogen for 0.5 hours. The reaction was filtered through a bed of celite and concentrate to give the title product (0.256 g).

EXAMPLE 438D tert-butyl 4-(4-(1-(di-tert-butoxyphosphoryloxy)-2-methylpropan-2-ylcarbamoyl)-2-(7-isopropylpyrido[2,3-d]pyrimidin-4-ylamino)phenylthio)phenylcarbamate To a solution of the product of Example 385E (100 mg, 0.19 mmol), O-benzotriazol-1-yl-N,N,N',N'-tetramethyluronium tetrafluoroborate [TBTU] (72 mg, 0.22 mmol), the product of Example 438C (65 mg, 0.23 mmol) in DMSO (1 mL) was added N,N-diisopropylethylamine (0.065 mL, 0.37 mmol) dropwise at room temperature under N2. The mixture was stirred at room temperature for 12 hours under N2. The reaction was diluted with ethyl acetate and the organic layer was washed sequentially with water (3×) and brine, dried over MgSO4, and concentrated. The residue was purified by chromatography on silica gel, eluting with a gradient of ethyl acetate in dichloromethane (0-100%) to give the title compound (93 mg, 62%).

EXAMPLE 438E sodium 2-(4-(4-aminophenylthio)-3-(7-isopropylpyrido[2,3-d]pyrimidin-4-ylamino)benzamido)-2-methylpropyl phosphate The product of Example 438D (90 mg, 0.11 mmol) in dichloromethane (0.5 mL) was reacted with trifluoroacetic acid [TFA] (0.5 mL) dropwise at room temperature then stirred for 1 hour. The reaction was concentrated and re-dissolved in a mixture of methanol and water to which was added sodium hydrogencarbonate (0.10 g, 1.19 mmol). Purification of the residue on a reverse phase C18 column eluting with a gradient of methanol in water (0-100%) gave the title compound as a yellow solid (62.5 mg, 88%). 1H NMR (300 MHz, DMSO-D6) δ ppm 1.29 (d, J=6.99 Hz, 6 H) 1.32 (s, 6 H) 3.03-3.20 (m, 1 H) 3.54 (d, J=11.40 Hz, 2 H) 5.45 (s, 2 H) 6.50-6.53 (m, 1 H) 6.62 (d, J=8.46 Hz, 2 H) 7.11 (d, J=8.46 Hz, 2 H) 7.34 (s, 1 H) 7.60 (s, 1 H) 7.87 (s, 1 H) 8.29 (s, 1 H) 8.74 (s, 1 H) 9.82 (s, 1 H).

EXAMPLE 439 methyl 4-(4-(1-hydroxy-2-phenylpropan-2-ylcarbamoyl)-2-(7-isopropylpyrido[2,3-d]pyrimidin-4-ylamino)phenylthio)phenylcarbamate To a solution of the product from Example 441D (30 mg, 0.061 mmol), O-benzotriazol-1-yl-N,N,N',N'-tetramethyluronium tetrafluoroborate [TBTU] (25 mg, 0.078 mmol), and 2-amino-2-phenylpropan-1-ol (11 mg, 0.073 mmol) in DMSO (0.3 mL) was added N,N-diisopropylethylamine (0.020 mL, 0.115 mmol) dropwise at room temperature under N2. The mixture was stirred at room temperature for 0.25 hours under N2. The mixture was diluted with ethyl acetate. The organic layer was washed sequentially with water (3×) and brine, dried over MgSO4, and concentrated. The residue was purified by chromatography on silica gel, eluting with a gradient of ethyl acetate in dichloromethane (0-100%) to give the title compound (15.6 mg, 41%). 1H NMR (300 MHz, DMSO-D6) δ ppm 1.33 (d, J=6.99 Hz, 6 H) 1.70 (s, 3 H) 3.15-3.28 (m, 1 H) 3.52 (dd, J=10.66, 5.88 Hz, 1 H) 3.67 (s, 3 H) 3.70-3.78 (m, 1 H) 5.10 (t, J=6.07 Hz, 1 H) 7.02 (d, J=8.46 Hz, 1 H) 7.14-7.39 (m, 8 H) 7.50 (d, J=8.46 Hz, 2 H) 7.62 (d, J=8.46 Hz, 1 H) 7.70 (d, J=8.09 Hz, 1 H) 7.90 (s, 1 H) 8.10 (s, 1 H) 8.58 (s, 1 H) 8.84 (d, J=8.46 Hz, 1 H) 9.86 (s, 1 H) 10.20 (s, 1 H).

EXAMPLE 440

(S)-3-(7-isopropylpyrido[2,3-d]pyrimidin-4-ylamino)-4-(4-(methylsulfonamido)phenylthio)-N-(1-phenylethyl)benzamide A solution of the product of Example 385G (50 mg, 0.094 mmol) and triethylamine (0.030 mL, 0.215 mmol) in THF (1.0 mL) at 0° C. under N2 was treated with methanesulfonyl chloride (0.008 mL, 0.103 mmol) added dropwise then reacted at room temperature for 1 hour. The reaction was recooled to 0° C., followed by additional methanesulfonyl chloride (0.004 mL, 0.052 mmol) added dropwise and reaction at room temperature for 0.5 hours. The mixture was diluted with ethyl acetate (20 mL) and the organic layer was washed with saturated NaHCO3 and brine, dried over MgSO4, and concentrated. The residue was purified by chromatography on silica gel, eluting with a gradient starting with dichloromethane and ending with ethyl acetate (25 mg, 44%). 1H NMR (300 MHz, DMSO-D6) δ ppm 1.33 (d, J=6.99 Hz, 6 H) 1.46 (d, J=6.99 Hz, 3 H) 3.03 (s, 3 H) 3.15-3.28 (m, 1 H) 5.04-5.31 (m, 1 H) 7.09 (d, J=8.09 Hz, 2 H) 7.13-7.27 (m, 3 H) 7.26-7.45 (m, 7 H) 7.62 (d, J=8.46 Hz, 1 H) 7.77 (dd, J=8.27, 1.65 Hz, 1 H) 7.95 (s, 1 H) 8.57 (s, 1 H) 8.82 (d, J=8.46 Hz, 2 H) 10.00 (s, 1 H) 10.20 (s, 1 H).

EXAMPLE 441 sodium 2-(3-(7-isopropylpyrido[2,3-d]pyrimidin-4-ylamino)-4-(4-(methoxycarbonylamino)phenylthio)benzamido)-2-methylpropyl phosphate

EXAMPLE 441A methyl 4-(4-(methoxycarbonylamino)phenylthio)-3-nitrobenzoate

A solution of the product from Example 385A (5.0 g., 16.4 mmol), pyridine (2.7 ml., 32.8 mmol), and methyl chloroformate (1.3 ml., 16.4 mmol) in CH2Cl2 (130 ml.) was reacted at room temperature for 1 hr. The reaction was diluted with CH2Cl2 (500 ml.) and washed sequentially with satd. NaHCO3 (100 ml.), 1NHCl (100 ml.), and brine (100 ml.). The organic phase was dried over MgSO4 and concentrated to give the title compound (6 g., 100%).

EXAMPLE 441B methyl 3-amino-4-(4-(methoxycarbonylamino)phenylthio)benzoate

The title compound was prepared by the procedure in Example 385C substituting the product from Example 441A for the product of Example 385B. The reaction was purified by silica gel chromatography (ethyl acetate/CHCl3=1/9) to give the title compound (yield 88%).

EXAMPLE 441C 3-(7-isopropylpyrido[2,3-d]pyrimidin-4-ylamino)-4-(4-(methoxycarbonylamino)phenylthio)benzoic acid The title compound was prepared (yield 88%) by the procedure of Example 385D substituting the product of Example 441B for the product of Example 385C.

EXAMPLE 441D 3-(7-isopropylpyrido[2,3-d]pyrimidin-4-ylamino)-4-(4-(methoxycarbonylamino)phenylthio)benzoic acid The title compound was prepared (yield 92%) by the procedure of Example 385E substituting the product of Example 441C for the product of Example 385D.

EXAMPLE 441E methyl 4-(4-(1-(di-tert-butoxyphosphoryloxy)-2-methylpropan-2-ylcarbamoyl)-2-(7-isopropylpyrido[2,3-d]pyrimidin-4-ylamino)phenylthio)phenylcarbamate To a suspension of the product from Example 441D (200 mg, 0.41 mmol) and O-benzotriazol-1-yl-N,N,N',N'-tetramethyluronium tetrafluoroborate [TBTU] (187 mg, 0.57 mmol) in DMSO (2 mL) was added the product of Example 438C (178 mg, 0.57 mmol) then N,N-diisopropylethylamine (0.220 mL, 1.10 mmol) dropwise at room temperature under N2. After 2 hours the reaction was quenche with water (20 mL) and extracted with ethyl acetate (75 mL). The organic layer was washed sequentially with water (3×) and saturated aqueous NaHCO3, dried over MgSO4, and concentrated. The residue was purified by silica gel column chromatography eluting with ethyl acetate to give the title compound as a pale yellow amorphous solid (245 mg., 79%).

EXAMPLE 441F sodium 2-(3-(7-isopropylpyrido[2,3-d]pyrimidin-4-ylamino)-4-(4-(methoxycarbonylamino)phenylthio)benzamido)-2-methylpropyl phosphate The product of Example 441E (240 mg., 0.32 mmol) in CH2Cl2 (1.6 ml.) was reacted with TFA (1.6 ml.) at room temperature for 30 min. The reaction was concentrated, redissolved in water (4 mL) and treated with solid NaHCO3 (270 mg., 3.2 mmol) with stirring. The solution was purified on a C-18 column eluted with a gradient of methanol in water (0-100%). to give the title compound (202 mg., 92%). 1H NMR (300 MHz, DMSO-D6) δ ppm 1.17-1.40 (m, 12 H) 2.98-3.11 (m, 1 H) 3.66 (s, 3 H) 6.65 (s, 1 H) 7.18-7.27 (m, 1 H) 7.32 (d, J=8.09 Hz, 2 H) 7.48 (d, J=8.09 Hz, 2 H) 7.51-7.62 (m, 1 H) 7.94 (s, 1 H) 8.18-8.29 (s, 1 H) 8.77 (s, 1 H) 9.84 (s, 1 H)

EXAMPLE 442 sodium 2-(3-(7-isopropylpyrido[2,3-d]pyrimidin-4-ylamino)-4-(4-(methoxycarbonylamino)phenylthio)benzamido)-2-phenylpropyl phosphate

EXAMPLE 442A benzyl 1-hydroxy-2-phenylpropan-2-ylcarbamate

2-Amino-2-phenylpropan-1-ol hydrochloride (0.5 g, 2.7 mmol) was reacted with N-(benzyloxycarbonyloxy)-succinimide (0.73 g, 2.9 mmol) and triethylamine (0.82 mL, 5.9 mmol) in THF (25 mL) at 0° C. for 1.0 hours and then at room temperature for 1 hour. The reaction was concentrated and extracted with ethyl acetate (25 mL). The extract was washed with water (2×) and brine, dried over MgSO4, and concentrated to give the crude title compound and used without further purification.

EXAMPLE 442B benzyl 1-(di-tert-butoxyphosphoryloxy)-2-phenylpropan-2-ylcarbamate The product of Example 442A (2.7 mmol), di-tert-butyl diethylphosphoramidite (0.80 mL, 2.7 mmol), and 1-H-tetrazole (0.50 g, 6.8 mmol) in THF (25 mL) were reacted at room temperature for 12 hours. Subsequently the reaction was diluted with dichloromethane (25 mL) and cooled to −45° C. and followed by treatment with meta-chloroperoxybenzoic acid (0.66 g, 3.0 mmol) for 0.5 hours. The reaction was extracted with ethyl acetate (70 mL) and the organic extracts washed with 10% sodium carbonate (2×) and brine, dried over MgSO4, and concentrated. The residue was purified by chromatography on silica gel, eluting with a gradient of ethyl acetate in dichloromethane (0-25%) to give the title compound as a colorless oil (0.99 g, 78%).

EXAMPLE 442C 2-amino-2-phenylpropyl di-tert-butyl phosphate

The product of Example 442B (0.10 g, 0.21 mmol) and 20% palladium hydroxide on carbon (0.02 g) in ethyl acetate (1 mL) and methanol (1 mL) was stirred under an atmosphere of hydrogen or 18 hours. The reaction was filtered through a bed of celite and concentrated to give the title compound, which was used without further purification (0.073 g).

EXAMPLE 442D methyl 4-(4-(1-(di-tert-butoxyphosphoryloxy)-2-phenylpropan-2-ylcarbamoyl)-2-(7-isopropylpyrido[2,3-d]pyrimidin-4-ylamino)phenylthio)phenylcarbamate The title compound was prepared (yield 43%) by the procedure of Example 441E substituting the product of Example 442C for the product of Example 441D.

EXAMPLE 442E sodium 2-(3-(7-isopropylpyrido[2,3-d]pyrimidin-4-ylamino)-4-(4-(methoxycarbonylamino)phenylthio)benzamido)-2-phenylpropyl phosphate The title compound was prepared (yield 76%) by the procedure of Example 441F substituting the product of Example 442D for the product of Example 441E. 1H NMR (300 MHz, DMSO-D6) δ ppm 1.25 (d, J=6.99 Hz, 6 H) 1.77 (s, 3 H) 2.93-3.08 (m, 1 H) 3.68 (s, 3 H) 3.71-3.82 (m, 1 H) 6.48 (s, 1 H) 6.98-7.33 (m, 6 H) 7.39 (d, J=8.09 Hz, 2 H) 7.52 (d, J=8.09 Hz, 2 H) 7.56-7.68 (m, 1 H) 7.92-8.10 (m, 2 H) 8.56 (s, 1 H) 9.82 (s, 1 H) 10.42 (s, 1 H).

EXAMPLE 443 sodium 2-(4-(4-aminophenylthio)-3-(7-isopropylpyrido[2,3-d]pyrimidin-4-ylamino)benzamido)-2-phenylpropyl phosphate

EXAMPLE 443A tert-butyl 4-(4-(1-(di-tert-butoxyphosphoryloxy)-2-phenylpropan-2-ylcarbamoyl)-2-(7-isopropylpyrido[2,3-d]pyrimidin-4-ylamino)phenylthio)phenylcarbamate The product of Example 385E (100 mg, 0.19 mmol), O-benzotriazol-1-yl-N,N,N',N'-tetramethyluronium tetrafluoroborate [TBTU] (79 mg, 0.24 mmol) and the product of Example 442C (90 mg., 0.26 mmol) in DMSO (1.0 mL) were treated with N,N-diisopropylethylamine (100 μL, 0.57 mmol) dropwise at room temperature and stirred under N2 for 2 hours. The reaction was diluted with WATER (10 mL) with stirring. The resulting precipitate was extracted with ethyl acetate (50 mL). The organic layer was washed with WATER (3×), saturated aqueous NaHCO3, then brine, dried over MgSO4, and concentrated. The residue was purified by silica gel column chromatography (ethyl acetate:chloroform=4:1) to give the title compound as a pale yellow amorphous solid (112 mg, 69%).

EXAMPLE 443B 2-(4-(4-aminophenylthio)-3-(7-isopropylpyrido[2,3-d]pyrimidin-4-ylamino)cyclohexa-1,5-dienecarboxamido)-2-phenylpropyl phosphate The title compound was prepared (yield 74%) by the procedure of Example 441F substituting the product of Example 443A for the product of Example 441E. 1H NMR (500 MHz, DMSO-D6) δ ppm 1.26 (d, J=6.84 Hz, 6 H) 1.75 (s, 3 H) 3.00-3.11 (m, 1 H) 3.73-3.85 (m, 2 H) 5.39 (s, 2 H) 6.55-6.63 (m, 3 H) 7.00-7.34 (m, 8 H) 7.58-7.70 (m, 1 H) 7.91 (s, 1 H) 8.81 (s, 1 H).

EXAMPLE 444 ethyl 2-(4-(4-aminophenylthio)-3-(7-isopropylpyrido[2,3-d]pyrimidin-4-ylamino)benzamido)-2-phenylpropanoate

EXAMPLE 444A ethyl 2-(4-(4-(tert-butoxycarbonylamino)phenylthio)-3-(7-isopropylpyrido[2,3-d]pyrimidin-4-ylamino)benzamido)-2-phenylpropanoate The product of Example 385E (90 mg, 0.17 mmol), O-benzotriazol-1-yl-N,N,N',N'-tetramethyluronium tetrafluoroborate [TBTU] (60 mg, 0.19 mmol) and ethyl 2-amino-2-phenylpropanoate (39 mg., 0.20 mmol) in DMSO (0.9 mL) was reacted with N,N-diisopropylethylamine (0.060 mL, 0.34 mmol) dropwise at room temperature then stirred at room temperature for 18 hours under N2. The mixture was poured into water (10 mL) with stirring. The resulting precipitate was extracted with ethyl acetate (50 mL) and the organic layer was washed with water (3×), saturated aqueous NaHCO3, then brine, dried over MgSO4, and concentrated. The residue was purified by silica gel chromatography (ethyl acetate:chloroform 4:1) to give the title compound as a pale yellow amorphous solid (93 mg, 78%).

EXAMPLE 444B ethyl 2-(4-(4-aminophenylthio)-3-(7-isopropylpyrido[2,3-d]pyrimidin-4-ylamino)benzamido)-2-phenylpropanoate The product of Example 444A (93 mg.) was reacted with trifluoroacetic acid [TFA] (0.60 mL) in dichloromethane (0.60 mL) added dropwise at room temperature then stirred at room temperature for 1 hour. The reaction mixture was concentrated and partitioned between ethyl acetate and saturated aqueous NaHCO3. The organic layer was washed with brine, dried over MgSO4, and concentrated. The residue was chromatographed on a C-18 HPLC column with a gradient elution of acetonitrile in 0.1% TFA water (0-100%). The desired fractions were combined, concentrated, dissolved in ethyl acetate, washed with saturated aqueous NaHCO3 then brine, dried over MgSO4 and concentrated to give a pale yellow amorphous solid (67 mg, 84%). 1H NMR (300 MHz, DMSO-D6) δ ppm 1.07 (t, J=6.99 Hz, 3 H) 1.34 (d, J=6.62 Hz, 6 H) 1.84 (s, 3 H) 3.15-3.29 (m, 1 H) 4.03 (q, J=7.35 Hz, 2 H) 5.59 (s, 2 H) 6.62 (d, J=8.46 Hz, 2 H) 6.84 (d, J=8.46 Hz, 1 H) 7.12 (d, J=8.46 Hz, 2 H) 7.24-7.41 (m, 4 H) 7.52 (d, J=7.35 Hz, 2 H) 7.63 (d, J=8.46 Hz, 1 H) 7.73 (dd, J=8.46, 1.84 Hz, 1 H) 7.90 (d, J=1.84 Hz, 1 H) 8.57 (s, 1 H) 8.83 (s, 1 H) 8.86 (d, J=8.46 Hz, 2 H) 10.13 (s, 1 H).

EXAMPLE 445

(S)-4-(4-Aminophenylthio)-N-(1-hydroxy-2-phenyl-propan-2-yl)-3-(7-isopropylpyrido[2,3-d]pyrimidin-4-ylamino)benzamide

EXAMPLE 445A (RS)-2-Formamido-2-phenylpropanoic acid (RS)-2-amino-2-phenylpropanoic acid (20 g, 0.12 mol) in 88% formic acid (220 mL) was reacted with acetic anhydride (100 mL) at such rate as to keep the internal temperature at 60-65° C. After the final addition, the reaction was stirred until the internal temperature dropped to 35° C., and then concentrated. The solid residue was dried by azeotroping with toluene. The solid residue was dissolved in hot ethanol (70 mL), treated with active charcoal (0.5 g), and filtered. Hot water (210 mL) was added with stirring to the hot filtrate. The mixture was cooled in the refrigerator for 3 days. The resulting crystals was collected by filtration, washed with cold EtOH/water (1:3), and dried at 60° C. for 4 hours to give the title compound as colorless crystal. (17.8 g, 76%).

EXAMPLE 445B (S)-2-Formamido-2-phenylpropanoic acid

The title compound was prepared by the chiral resolution method described in *J. Chem. Soc.*, 1912, 101, 390.

EXAMPLE 445C (S)-Ethyl 2-amino-2-phenylpropanoate

The product of Example 445B (1.25g, 7.6 mmol)) in 1N HCl (12.5 mL) was refluxed for 1 hour. The reaction mixture was concentrated and dried at 40° C. under vacuum overnight to give (S)-2-amino-2-phenylpropanoic acid hydrochloride as a pale brown crystal (1.53 g). The intermediate amino acid (1.5 g. 7.5 mmol) was dissolved in EtOH (30 mL) was reacted with thionyl chloride (2.7 ml., 37.5 mmol) dropwise at room temperature then refluxed for 23 hours. The reaction was concentrated and the residue was partitioned between saturated NaHCO3 solution and ethyl acetate. The organic layer was washed with water (3×15 mL) and 10% aqueous NaHCO3 (1×15 mL), dried over MgSO4, concentrated to give the title compound (1.28 g, 90%).

EXAMPLE 445D (S)-2-Amino-2-phenylpropan-1-ol

The product of Example 445C (1.28 g, 6.6 mmol, prepared in) was reacted with sodium borohydride (1.25 g, 33 mmol) in 75% aqueous EtOH (32 mL) at reflux for 1 hour. The reaction was concentrated, diluted with water (20 mL) and extracted with ethyl acetate (3×75 mL). The organic layer was washed with 10% NaHCO3 solution (2×10 mL), dried over MgSO4, and concentrated to give the title compound as colorless viscous oil (1.09 g., 100%).

EXAMPLE 445E (S)-4-(4-aminophenylthio)-N-(1-hydroxy-2-phenyl-propan-2-yl)-3-(7-isopropylpyrido[2,3-d]pyrimidin-4-ylamino)benzamide The product of Example 454 (50mg., 0.12 mmol), O-benzotriazol-1-yl-N,N,N',N'-tetramethyluronium tetrafluoroborate [TBTU] (42 mg, 0.13 mmol) and the product of Example 445D (21 mg., 0.13 mmol) in DMSO (0.6 mL) was reacted with N,N-diisopropylethylamine (0.040 mL, 0.24 mmol) dropwise at room temperature under N2 for 2 hours then poured into water (10 mL) with stirring. The resulting precipitate was extracted with ethyl acetate (40 mL). The organic layer was washed with water (3×) and saturated aqueous NaHCO3, dried over MgSO4, and concentrated. The residue was chromatographed on a C-18 column with a gradient elution of acetonitrile in 0.1% TFA water (0-100%). The product containing fractions were combined, concentrated and redissolved in ethyl acetate, washed with saturated aqueous NaHCO3, then brine, dried over MgSO4 and concentrated to give the title compound (13 mg, 20%). 1H NMR (300 MHz, DMSO-D6) δ ppm 1.34 (d, J=6.99 Hz, 6 H) 1.69 (s, 3 H) 3.13-3.27 (m, 1 H) 3.51 (dd, J=10.85, 6.43 Hz, 1 H) 3.73 (dd, J=10.85, 6.07 Hz, 1 H) 5.10 (t, J=6.07 Hz, 1 H) 5.57 (s, 2 H) 6.62 (d, J=8.46 Hz, 2 H) 6.85 (d, J=8.46 Hz, 1 H) 7.07-7.22 (m, 3 H) 7.22-7.37 (m, 4 H) 7.57-7.72 (m, 2 H) 7.85 (d, J=1.84 Hz, 1 H) 8.04 (s, 1 H) 8.58 (s, 1 H) 8.87 (d, J=8.46 Hz, 1 H) 10.14 (s, 1 H).

EXAMPLE 446

(R)-4-(4-Aminophenylthio)-N-(2,3-dihydro-1H-inden-1-yl)-3-(7-isopropylpyrido[2,3-d]pyrimidin-4-ylamino)benzamide

EXAMPLE 446A (R)-tert-Butyl 4-(4-(2,3-dihydro-1H-inden-1-ylcarbamoyl)-2-(7-isopropylpyrido[2,3-d]pyrimidin-4-ylamino)phenylthio)phenylcarbamate The title compound was prepared (yield 84%) by the procedure of Example 385F by reacting the product of Example 385E with R-(−)-1-aminoindane. 1H-NMR (300 MHz, DMSO-d6) δ ppm: 1.33 (d, J=6.6 Hz, 6H), 1.48 (s, 9H), 1.87-2.04 (m, 1H), 2.35-2.50 (m, 1H), 2.75-3.04 (m, 2H), 3.13-3.28 (m, 1H), 5.55 (q, J=8.1 Hz, 1H), 6.96 (d, J=8.4 Hz, 1H), 7.12-7.29 (m, 4H), 7.33 (d, J=8.8 Hz, 2H), 7.52 (d, J=8.8 Hz, 2H), 7.62 (d, J=8.5 Hz, 1H), 7.77 (br-d, J=8.4 Hz, 1H), 7.95 (br-s, 1H), 8.57 (s, 1H), 8.78 (d, J=8.5 Hz, 1H), 8.83 (d, J=8.5 Hz, 1H), 9.58 (s, 1H), 10.17 (s, 1H) MS ESI+ m/z: 647 (M+H), ESI− m/z: 645 (M−H)

EXAMPLE 446B (R)-4-(4-Aminophenylthio)-N-(2,3-dihydro-1H-inden-1-yl)-3-(7-isopropylpyrido[2,3-d]pyrimidin-4-ylamino)benzamide The title compound was prepared (yield 89%) by the procedure in Example 385G substituting the product of Example 446A for the product of Example 385F. 1H-NMR (300 MHz, DMSO-d6) δ ppm: 1.33 (d, J=7.0 Hz, 6H), 1.86-2.04 (m, 1H), 2.33-2.53 (m, 1H), 2.74-3.03 (m, 2H), 3.22 (septet, J=7.0 Hz, 1H), 5.48-5.62 (m, 1H), 5.58 (s, 2H), 6.62 (d, J=8.5 Hz, 2H), 6.83 (d, J=8.1 Hz, 1H), 7.11-7.28 (m, 4H), 7.13 (d, J=8.5 Hz, 2H), 7.63 (d, J=8.5 Hz, 1H), 7.75 (dd, J=8.1, 1.5 Hz, 1H), 7.90 (d, J=1.5 Hz, 1H), 8.56 (s, 1H), 8.73 (d, J=8.1 Hz, 1H), 8.86 (d, J=8.5 Hz, 1H), 10.11 (s, 1H) MS ESI+ m/z: 547 (M+H), ESI− m/z: 545 (M−H)

EXAMPLE 447

(R)-4-(4-Aminophenylthio)-3-(7-isopropylpyrido[2,3-d]pyrimidin-4-ylamino)-N-(2,2,2-trifluoro-1-phenylethyl)benzamide

EXAMPLE 447A (R)-1-Phenyl-N-(2,2,2-trifluoro-1-phenylethylidene)ethanamine

A solution of 2,2,2-trifluoroacetophenone (7.0 g, 40 mmol), R-(+)-α-methylbenzylamine (7.75 mL, 60 mmol), and p-toluenesulfonic acid monohydrate (0.77g, 4.0 mmol) in toluene (40 mL) was refluxed for 18 hours with a Dean-Stark trap. After cooling, the reaction mixture was diluted with toluene (50 mL), washed with 5% NaOH (1×50 mL), saturated NH4Cl (4×30 mL) and brine, dried over MgSO4, concentrated and dried at room temperature in vacuum to give the title compound as pale yellow liquid (11.1 g).

EXAMPLE 447B (R)-2,2,2-Trifluoro-1-phenyl-N-((R)-1-phenylethyl)ethanamine

The product of Example 447A (11.1 g, 40 mmol) in THF (60 mL) was treated with a solution of sodium cyanoborohydride (5.3 g, 80 mmol) in THF (30 mL) dropwise at 5° C. over 15 minutes, then 5° C. for 3 hours and at room temperature for 3 days. The reaction was quenched with 1N HCl (to pH 1) and stirred at room temperature for 3 hours, adjusted to pH 11 with K2CO3, and then extracted with ethyl acetate (100 mL). The organic layer was washed with water (3×50 mL) and brine, dried over MgSO4, concentrated and dried at room temperature in vacuum to give crude product (10.2 g) as colorless liquid. The obtained crude product was diluted with i-PrOH (71 mL), treated with p-toluenesulfonic acid monohydrate (7.05g, 37 mmol), and then the mixture was heated to reflux. n-Hexane (71 mL) was added to the hot solution, and then the solution was cooled to room temperature gradually and stirred at room temperature for 2 hours. The resulting crystal was collected by filtration, washed with a mixture of i-PrOH and n-hexane (1:1), and dried at 40° C. overnight in vacuum to give the title compound as tosylate (colorless crystal, 9.3 g): yield 52% from 2,2,2-trifluoroacetophenone

EXAMPLE 447C

R-(−)-2,2,2-Trifluoro-1-phenylethanamine

A mixture of (R)-2,2,2-trifluoro-1-phenyl-N-((R)-1-phenylethyl)ethanamine tosylate (10.2 g, 23 mmol, prepared in Example 447B), cyclohexene (11.6 mL, 113 mmol) and 20% Pd(OH)2/C (0.31 g) in EtOH (204 mL) was refluxed for 8 hours. After cooling, the reaction mixture was filtered through a celite pad. The filtrate was concentrated to give a colorless solid. The residue was diluted with water (50 mL), adjusted to pH 11 with K2CO3, and extracted with CH2Cl2 (3×50 mL). The organic layer was washed with brine, dried over MgSO4, concentrated to give slightly brown liquid (3.9 g). The residue was distilled under reduced pressure to give the title compound as colorless liquid (3.2 g): yield 81%. B.p. 106-108° C./37 mmHg $[\alpha]_D^{23}$ : −23.1° (c=0.97, EtOH) 1H-NMR (300 MHz, CDCl3) δ ppm: 1.78 (br-s, 2H), 4.40 (q, J=7.4 Hz, 1H), 7.32-7.47 (m, 5H) MS ESI+ m/z: 176 (M+H).

EXAMPLE 447D (R)-tert-Butyl 4-(2-(7-isopropylpyrido[2,3-d]pyrimidin-4-ylamino)-4-(2,2,2-trifluoro-1-phenylethylcarbamoyl)phenylthio)phenylcarbamate To a suspension of 4-(4-tert-butoxycarbonylamino-phenylsulfanyl)-3-(7-isopropyl-pyrido[2,3-d]pyrimidin-4-ylamino)-benzoic acid (120 mg, 0.23 mmol, prepared in Example 385E) and O-(7-azabenzotriazol-1-yl)-N,N,N',N'-tetramethyluronium hexafluorophosphate [HATU] (97 mg, 0.25 mmol) in DMSO (1.2 mL) was added R-(−)2,2,2-trifluoro-1-phenylethanamine (42 mg, 0.24 mmol, prepared in Example 447C) and N,N-diisopropylethylamine (0.079 mL, 0.45 mmol) dropwise at room temperature under N2. The mixture was stirred at room temperature overnight under N2, and then poured into water (20 mL) under stirring. The resulting precipitate was extracted with ethyl acetate (20 mL). The organic layer was washed with water (3×15 mL) and 10% NaHCO3 (1×15 mL), dried over MgSO4, and concentrated to give yellow amorphous. The oily residue was separated by silica gel column chromatography (ethyl acetate/n-hexane=3/1) to give pale yellow amorphous, which was solidified by the treatment of i-Pr2O. The resulting solid was collected by filtration, washed with i-Pr2O, and dried at 60° C. for 5 hours in vacuum to give the title compound as yellow crystals (93 mg, 60%). 1H-NMR (300 MHz, DMSO-d6) δ ppm: 1.34 (d, J=7.0 Hz, 6H), 1.48 (s, 9H), 3.23 (septet, J=7.0 Hz, 1H), 6.05 (quintet, J=8.8 Hz, 1H), 6.99 (d, J=8.4 Hz, 1H), 7.30-7.48 (m, 3H), 7.34 (d, J=8.8 Hz, 2H), 7.52 (d, J=8.8 Hz, 2H), 7.60-7.71 (m, 2H), 7.64 (d, J=8.8 Hz, 1H), 7.77 (br-d, J=8.4 Hz, 1H), 7.98 (br-s, 1H), 8.58 (s, 1H), 8.84 (d, J=8.8 Hz, 1H), 9.49 (d, J=9.2 Hz, 1H), 9.59 (s, 1H), 10.22 (s, 1H) MS ESI+ m/z: 689 (M+H), ESI− m/z: 687 (M−H)

EXAMPLE 447E (R)-4-(4-Aminophenylthio)-3-(7-isopropylpyrido[2,3-d]pyrimidin-4-ylamino)-N-(2,2,2-trifluoro-1-phenylethyl)benzamide The title compound was prepared (yield 88%) by the procedure in Example 385G substituting the product of Example 447D for the product of Example 385F.

The title compound was prepared (yield 88%) by the procedure of Example 385G, substituting the product of Example 447D for the product of Example 385F. 1H-NMR (300 MHz, DMSO-d6) δ ppm: 1.34 (d, J=7.0 Hz, 6H), 3.23 (septet, J=7.0 Hz, 1H), 5.60 (br-s, 2H), 6.05 (quintet, J=9.2 Hz, 1H), 6.63 (d, J=8.5 Hz, 2H), 6.86 (d, J=8.4 Hz, 1H), 7.12 (d, J=8.5 Hz, 2H), 7.36-7.47 (m, 3H), 7.60-7.71 (m, 2H), 7.64 (d, J=8.5 Hz, 1H), 7.75 (br-d, J=8.4 Hz, 1H), 7.95 (br-s, 1H), 8.57 (s, 1H), 8.87 (d, J=8.5 Hz, 1H), 9.42 (d, J=9.5 Hz, 1H), 10.16 (s, 1H) MS ESI+ m/z: 589 (M+H)

EXAMPLE 448

(R)-4-(4-Aminophenylthio)-N-(2-fluoro-1-phenylethyl)-3-(7-isopropylpyrido[2,3-d]pyrimidin-4-ylamino)benzamide

EXAMPLE 448A (R)-2-Fluoro-1-phenylethanamine

The title compound was prepared by the procedures of Examples 447A-C, substituting 2-fluoroacetophenone (J. Fluorine Chem. 2001, 112, 357) for 2,2,2-trifluoroacetophenone in Example 447A. 1H-NMR (300 MHz, CDCl3) δ ppm: 1.83 (br-s, 2H), 4.22-4.61 (m, 3H), 7.24-7.42 (m, 5H) MS ESI+ m/z: 140 (M+H).

EXAMPLE 448B (R)-tert-Butyl 4-(4-(2-fluoro-1-phenylethylcarbamoyl)-2-(7-isopropylpyrido[2,3-d]pyrimidin-4-ylamino)phenylthio)phenylcarbamate The title compound was prepared (yield 63%) by the procedure of Example 447D substituting the product of Example 448A for the product of Example 447C. 1H-NMR (300 MHz, DMSO-d6) δ ppm: 1.34 (d, J=7.0 Hz, 6H), 1.48 (s, 9H), 3.23 (septet, J=7.0 Hz, 1H), 4.50-4.80 (m, 2H), 5.33-5.50 (m, 1H), 6.99 (d, J=8.1 Hz, 1H), 7.24-7.40 (m, 3H), 7.33 (d, J=8.8 Hz, 2H), 7.44 (d, J=7.0 Hz, 2H), 7.52 (d, J=8.8 Hz, 2H), 7.63 (d, J=8.4 Hz, 1H), 7.76 (br-d, J=8.1 Hz, 1H), 7.95 (br-s, 1H), 8.58 (s, 1H), 8.84 (d, J=8.4 Hz, 1H), 9.06 (d, J=8.1 Hz, 1H), 9.58 (s, 1H), 10.21 (s, 1H) MS ESI+ m/z: 653 (M+H), ESI− m/z: 651 (M+H).

EXAMPLE 448C (R)-4-(4-Aminophenylthio)-N-(2-fluoro-1-phenylethyl)-3-(7-isopropylpyrido[2,3-d]pyrimidin-4-ylamino)benzamide The title compound was prepared (yield 71%) by the procedure of Example 385G substituting the product of Example 448B for the product of Example 385F. 1H-NMR (300 MHz, DMSO-d6) δ ppm: 1.34 (d, J=7.0 Hz, 6H), 3.23 (septet, J=7.0 Hz, 1H), 4.48-4.79 (m, 2H), 5.32-5.49 (m, 1H), 6.62 (d, J=8.5 Hz, 2H), 6.86 (d, J=8.4 Hz, 1H), 7.13 (d, J=8.5 Hz, 2H), 7.28 (t, J=7.0 Hz, 1H), 7.35 (t, J=7.0 Hz, 2H), 7.43 (d, J=7.0 Hz, 2H), 7.68 (d, J=8.1 Hz, 1H), 7.73 (br-d, J=8.4 Hz, 1H), 7.88 (br-s, 1H), 8.61 (br-s, 1H), 8.89 (d, J=8.1 Hz, 1H), 9.00 (d, J=8.1 Hz, 1H), 10.45 (br-s, 1H) MS ESI+ m/z: 553 (M+H), ESI− m/z: 551 (M+H).

EXAMPLE 449

(RS)-4-(4-Amino-3-fluorophenylthio)-N-(1-hydroxy-2-phenylpropan-2-yl)-3-(7-isopropylpyrido[2,3-d]pyrimidin-4-ylamino)benzamide

EXAMPLE 449A 4-amino-3-fluorobenzenethiol hydrochloride

2-Fluoroaniline (9.8 mL, 0.1 mol) and sodium thiocyanate (24.9 g, 0.3 mol) in MeOH (55 mL) were treated with a cold solution of bromine (5.7 mL, 0.11 mol) in saturated NaBr-MeOH solution (50 mL) added dropwise at −5-0° C. over 2 hours. After the addition, the reaction mixture was poured into cold water (200 mL) with stirring, adjusted to pH 8-9 with NaHCO3 (10 g), and stirred at 5° C. for 30 minutes. The resulting crystals were collected by filtration, washed with cold water, and dried at room temperature overnight in vacuum to give crude product 2-fluoro-4-thiocyanatoaniline (14.5 g) as slightly brown crystal. A mixture of the crude 2-fluoro-4-thiocyanatoaniline (14.5 g) and concentrated hydrochloric acid (58 mL) in EtOH (15 mL) was refluxed for 8 hours. The reaction mixture was cooled and stirred at room temperature overnight. The resulting crystals were collected by filtration, washed with cold EtOH and i-Pr2O, dried at room temperature overnight in vacuum to give the title compound as its hydrochloride salt (pale yellow crystal, 10.1 g, 56%).

EXAMPLE 449B

Methyl 4-(4-amino-3-fluorophenylthio)-3-nitrobenzoate

A mixture of methyl 4-chloro-3-nitrobenzoate (3.0 g, 14 mmol), the product of Example 449A (2.8 g, 16 mmol,) and Cs2CO3 (8.9 g, 27 mmol) in DMF (30 mL) was heated at 90° C. for 3 hours. The reaction was cooled, poured into water (90 mL) with stirring and extracted with ethyl acetate (100 mL). The organic extract was washed with water (3×40 mL) and brine, dried over MgSO4, and concentrated to give the crude product as yellow crystal. The crystalline residue was suspended in 30 mL of i-Pr2O and stirred at room temperature for 30 minutes. Crystala were collected by filtration, washed with i-Pr2O, and dried at 40° C. in vacuum overnight to give the title compound as pale yellow crystal (3.6 g, 82%).

EXAMPLE 449C

Methyl 4-(3-fluoro-4-((2,2,2-trichloroethoxy)carbonylamino)phenylthio)-3-nitrobenzoate The product of Example 449B (2.0 g, 6.2 mmol) and pyridine (0.55 mL, 6.8 mmol) in CH2Cl2 (20 mL) was reacted with 2,2,2-trichloroethyl chloroformate (0.92 mL, 6.5 mmol) dropwise at 5° C. The mixture was stirred at 5° C. for 30 minutes and concentrated. The residue was diluted with water (50 mL). The resulting crystals were collected by filtration, washed with water and i-Pr2O, and dried at room temperature in vacuum overnight to give the title compound as pale yellow crystals (2.9 g, 93%).

EXAMPLE 449D

Methyl 3-amino-4-(3-fluoro-4-((2,2,2-trichloroethoxy)carbonylamino)phenylthio)benzoate The product of Example 449C (2.8 g, 5.6 mmol), Fe powder (1.6 g, 28 mmol) and NH4Cl (1.5 g, 28 mmol) in a mixture of EtOH (28 mL), THF (14 mL) and water (28 mL) was gently refluxed for 1 hour. The reaction mixture was cooled and filtered through celite pad. The filtrate was concentrated. The aqueous residue was partitioned between ethyl acetate and water, and adjusted to pH 8-9 with NaHCO3. The organic layer was separated, washed with water and brine, dried over MgSO4 and concentrated. The oily residue was separated by column chromatography (SiO2, n-hexane/ethyl acetate=3/1) to give the title compound as pale yellow crystal (1.3 g, 48%).

EXAMPLE 449E

Methyl 4-(3-fluoro-4-((2,2,2-trichloroethoxy)carbonylamino)phenylthio)-3-(7-isopropylpyrido[2,3-d]pyrimidin-4-ylamino)benzoate A suspension of the product of Example 8E (0.50 g, 2.3 mmol) and the product of Example 449D in AcOH (10 mL) were heated at 120° C. for 1 hour under N2. The reaction mixture was cooled to room temperature, partitioned between ethyl acetate (50 mL) and water (50 mL), and adjusted to pH 9-10 with K2CO3 under stirring. The organic layer was washed with water (1×30 mL) and brine, dried over MgSO4, and concentrated. The oily residue was separated by column chromatography (SiO2, n-hexane/ethyl acetate=1/3) product containing fractions solidified on treatment of i-Pr2O. The resulting solid was collected by filtration, washed with i-Pr2O, and dried at 40° C. in vacuum overnight to give the title compound as yellow crystals (1.26 g, 85%).

EXAMPLE 449F 4-(4-Amino-3-fluorophenylthio)-3-(7-isopropylpyrido[2,3-d]pyrimidin-4-ylamino)benzoic acid The product of Example 449E (1.25 g, 2.0 mmol) in THF (12.5 mL) was reacted with aqueous LiOH solution [prepared from LiOH monohydrate (0.42 g, 10 mmol) and water (8.4 mL)] dropwise at room temperature. The mixture was stirred at 40° C. for 16 hours, and then concentrated. The aqueous mixture was diluted with 50 mL of water, washed with ethyl acetate (1×40 mL), and then carefully acidified to pH 5-6 with 1N HCl under stirring. After 30 minutes, the resulting precipitate was collected by filtration, washed with cold water, and dried at 40° C. for 3 days in vacuum to give the title compound as pale brown crystal (0.77 g, 87%). 1H-NMR (300 MHz, DMSO-d6) δ ppm: 1.34 (d, J=7.0 Hz, 6H), 3.23 (septet, J=7.0 Hz, 1H), 5.67 (s, 2H), 7.15-7.30 (m, 2H), 6.81 (dd, J=9.2, 8.4 Hz, 1H), 6.91 (d, J=8.4 Hz, 1H), 7.02 (dd, J=8.4, 1.8 Hz, 1H), 7.11 (dd, J=11.4, 1.8 Hz, 1H), 7.64 (d, J=8.5 Hz, 1H), 7.76 (dd, J=8.4, 1.9 Hz, 1H), 7.86 (d, J=1.9 Hz, 1H), 8.57 (s, 1H), 8.85 (d, J=8.5 Hz, 1H), 10.12 (s, 1H). MS ESI+ m/z: 450 (M+H), ESI− m/z: 448 (M−H).

EXAMPLE 449G (RS)-Methyl 2-amino-2-phenylpropanoate

The title compound was prepared from 2-phenylglycine methyl ester hydrochloride by the procedure described in *J. Med. Chem.*, 1995, 38, 4446.

EXAMPLE 449H (RS)-2-Amino-2-phenylpropan-1-ol

The product of Example 449G (0.58 g, 3.2 mmol) and sodium borohydride (0.12 g, 3.2 mmol) in 75% aqueous EtOH (7.6 mL) were refluxed for 1.5 hours. The reaction mixture was concentrated and the residue was diluted with water (15 mL) and extracted with ethyl acetate (2×25 mL). The organic layer was washed with water (2×10 mL) and brine, dried over MgSO4, concentrated to give the title compound as colorless viscous oil, which later crystallized (0.27 g, 55%). 1H-NMR (300 MHz, CDCl3) δ ppm: 1.46 (s, 3H), 1.86 (br-s, 2H), 3.59 (d, J=10.7 Hz, 1H), 3.65 (d, J=10.7 Hz, 1H), 7.22-7.30 (m, 1H), 7.31-7.41 (m, 2H), 7.41-7.49 (m, 2H). MS ESI+ m/z: 152 (M+H).

EXAMPLE 449I (RS)-4-(4-Amino-3-fluorophenylthio)-N-(1-hydroxy-2-phenylpropan-2-yl)-3-(7-isopropylpyrido[2,3-d]pyrimidin-4-ylamino)benzamide To the product of Example 449F (150 mg, 0.31 mmol) and O-(7-azabenzotriazol-1-yl)-N,N,N',N'-tetramethyluronium hexafluorophosphate [HATU] (132 mg, 0.21 mmol) in DMSO (1.5 mL) was added the product of Example 449H (49 mg, 0.32 mmol) and N,N-diisopropylethylamine (0.11 mL, 0.61 mmol) added dropwise at room temperature under N2. The mixture was stirred at room temperature for 2 hours, then poured into water (30 mL) with stirring. The resulting precipitate was extracted with ethyl acetate (1×30 mL). The organic layer was washed with water (3×15 mL) and 10% NaHCO3 (1×15 mL), dried over MgSO4, and concentrated. The residue was purified by column chromatography (SiO2, gradient elution of ethyl acetate/MeOH=98/2 to 95/5) to give a yellow solid. Trituration of product containing fractions with ethyl acetate gave the title compound as pale yellow crystal (86 mg, 48%). 1H-NMR (300 MHz, DMSO-d6) δ ppm: 1.34 (d, J=7.0 Hz, 6H), 1.69 (s, 3H), 3.23 (septet, J=7.0 Hz, 1H), 3.52 (dd, J=11.0, 6.3 Hz, 1H), 3.74 (dd, J=11.0, 5.9 Hz, 1H), 5.09 (dd, J=6.3, 5.9 Hz, 1H), 5.61 (s, 2H), 6.79 (dd, J=9.2, 8.4 Hz, 1H), 6.95 (d, J=8.5 Hz, 1H), 6.99 (dd, J=8.4, 1.8 Hz, 1H), 7.08 (dd, J=11.4, 1.8 Hz, 1H), 7.17 (br-t, J=7.0 Hz, 1H), 7.27 (t, J=7.0 Hz, 2H), 7.33 (br-d, J=7.0 Hz, 2H), 7.64 (d, J=8.4 Hz, 1H), 7.69 (dd, J=8.5, 1.8 Hz, 1H), 7.87 (d, J=1.8 Hz, 1H), 8.07 (s, 1H), 8.58 (s, 1H), 8.86 (d, J=8.4 Hz, 1H), 10.17 (s, 1H). MS ESI+ m/z: 583 (M+H), ESI− m/z: 581 (M−H).

EXAMPLE 450

(R)-4-(4-Aminophenylthio)-N-(1-hydroxy-2-phenylpropan-2-yl)-3-(7-isopropylpyrido[2,3-d]pyrimidin-4-ylamino)benzamide

EXAMPLE 450A (R)-2-Formamido-2-phenylpropanoic acid

The title compound was prepared from the product of Example 445A by the chiral resolution method described in *J. Chem. Soc.*, 1912, 101, 390.

EXAMPLE 450B (R)-Ethyl 2-amino-2-phenylpropanoate

The title compound was prepared (1.12 g, 76%) by the procedure of Example 445C substituting the product of Example 450A for the product of Example 445B.

EXAMPLE 450C (R)-2-Amino-2-phenylpropan-1-ol

The title compound was prepared by the procedure of Example 445D substituting the product of Example 450B for the product of Example 445C to give a colorless viscous oil (0.57 g, 67%). [α]$_D^{23}$: −13.8°(c=1.05, EtOH). 1H-NMR (300 MHz, DMSO-d6) δ ppm: 1.28 (s, 3H), 1.76 (br-s, 2H), 3.39 (d, J=5.2 Hz, 2H), 4.72 (t, J=5.2 Hz, 1H), 7.12-7.20 (m, 1H), 7.22-7.32 (m, 2H), 7.44-7.54 (m, 2H). MS ESI+ m/z: 152 (M+H).

EXAMPLE 450D (R)-4-(4-Aminophenylthio)-N-(1-hydroxy-2-phenylpropan-2-yl)-3-(7-isopropylpyrido[2,3-d]pyrimidin-4-ylamino)benzamide The title compound was prepared (yield 58%) by the procedure of Example 445E substituting the product of Example 450C for the product of Example 445D. 1H-NMR (300 MHz, DMSO-d6) δ ppm 1.34 (d, J=7.0 Hz, 6H), 1.69 (s, 3H), 3.23 (septet, J=7.0 Hz, 1H), 3.51 (dd, J=11.0, 6.3 Hz, 1H), 3.73 (dd, J=11.0, 5.8 Hz, 1H), 5.09 (dd, J=6.3, 5.8 Hz, 1H), 5.57 (br-s, 2H), 6.62 (d, J=8.4 Hz, 2H), 6.85 (d, J=8.1 Hz, 1H), 7.12 (d, J=8.4 Hz, 1H), 7.17 (br-t, J=7.0 Hz, 1H), 7.27 (t, J=7.0 Hz, 2H), 7.32 (br-d, J=7.0 Hz, 2H), 7.64 (d, J=8.9 Hz, 1H), 7.67 (dd, J=8.1, 1.8 Hz, 1H), 7.85 (d, J=1.8 Hz, 1H), 8.03 (s, 1H), 8.58 (s, 1H), 8.87 (d, J=8.9 Hz, 1H), 10.13 (s, 1H). MS ESI+ m/z: 565 (M+H), ESI− m/z: 563 (M−H).

EXAMPLE 451

(RS)-4-(4-Aminophenylthio)-3-(6-fluoro-7-isopropylpyrido[2,3-d]pyrimidin-4-ylamino)-N-(1-hydroxy-2-phenylpropan-2-yl)benzamide

EXAMPLE 451A

N'-(3-Cyano-5-fluoro-6-isopropylpyridin-2-yl)-N,N-dimethylformimidamide

To a solution of N'-(3-cyano-6-isopropyl-pyridin-2-yl)-N,N-dimethyl-formamidine (3.0 g, 14 mmol) in dry CH3CN (139 mL) was added 1-(chloromethyl)-4-fluoro-1,4-diazoniabicyclo[2.2.2]octane bis(tetrafluoroborate) [SELECT-FLUOR™] (5.4 g, 15 mmol) at room temperature. The mixture was stirred at room temperature for 18 hours under N2, then concentrated. The residue was diluted with ethyl acetate (100 mL), washed with water (5×40 mL) and brine, dried over MgSO4, and concentrated. The oily residue was purified by column chromatography (SiO2, n-hexane/ethyl acetate=3/1) to give the title compound as colorless crystals (0.63 g, 19%). 1H-NMR (300 MHz, CDCl3) δ ppm: 1.26 (d, J=7.0 Hz, 6H), 3.15 (s, 3H), 3.16 (s, 3H), 3.29 (septet-d, J=7.0, 1.9 Hz, 1H), 7.41 (d, J=8.8 Hz, 1H), 8.55 (s, 1H). MS ESI+ m/z: 235 (M+H).

EXAMPLE 451B

Methyl 4-(4-(tert-butoxycarbonylamino)phenylthio)-3-(6-fluoro-7-isopropylpyrido[2,3-d]pyrimidin-4-ylamino)benzoate The title compound was prepared (yield 62%) by the procedure of Example 385D, substituting the product of Example 451A for the product of Example 8E.

EXAMPLE 451C 4-(4-(tert-Butoxycarbonylamino)phenylthio)-3-(6-fluoro-7-isopropylpyrido[2,3-d]pyrimidin-4-ylamino)benzoic acid The title compound was prepared (yield 84%) by the procedure of Example 385E, substituting the product of Example 451B for the product of Example 385D. $^1$H-NMR (300 MHz, DMSO-d6) δ ppm: 1.34 (d, J=7.0 Hz, 6H), 1.48 (s, 9H), 3.43-3.58 (m, 1H), 6.95 (d, J=8.4 Hz, 1H), 7.36 (d, J=8.8 Hz, 2H), 7.54 (d, J=8.8 Hz, 2H), 7.76 (dd, J=8.4, 1.8 Hz, 1H), 7.89 (d, J=1.8 Hz, 1H), 8.59 (s, 1H), 8.71 (d, J=10.3 Hz, 1H), 9.61 (s, 1H), 10.11 (s, 1H), 12.99 (br-s, 1H). MS ESI+ m/z: 550 (M+H) ESI– m/z: 548 (M–H).

EXAMPLE 451D 4-(4-Aminophenylthio)-3-(6-fluoro-7-isopropylpyrido[2,3-d]pyrimidin-4-ylamino)benzoic acid The product of Example 451C (0.23 g, 0.4 mmo) in CH2Cl2 (4.6 mL) was treated with trifluoroacetic acid [TFA] (1.15 mL) dropwise at room temperature then stirred for 1 hour. The reaction mixture was concentrated. The residue was diluted with water, made basic with K2CO3, stirred at room temperature overnight. The pH was adjusted to pH 5-6 with 1N HCl stirred at room temperature for 1 hour, the resulting precipitate was collected by filtration, washed with water and i-Pr2O, and dried at 40° C. in vacuum overnight to give the title compound as yellow crystal (0.13 g, 71%). $^1$H-NMR (300 MHz, DMSO-d6) δ ppm: 1.34 (d, J=7.0 Hz, 6H), 3.42-3.60 (m, 1H), 5.64 (br-s, 2H), 6.64 (d, J=8.4 Hz, 2H), 6.84 (d, J=7.7 Hz, 1H), 7.14 (d, J=8.4 Hz, 2H), 7.73 (br-d, J=7.7 Hz, 1H), 7.83 (br-s, 1H), 8.58 (s, 1H), 8.65-8.80 (m, 1H), 10.10 (s, 1H), 12.91 (br-s, 1H). MS ESI+m/z: 450 (M+H), ESI– m/z: 448 (M–H).

EXAMPLE 451E (RS)-4-(4-Aminophenylthio)-3-(6-fluoro-7-isopropylpyrido[2,3-d]pyrimidin-4-ylamino)-N-(1-hydroxy-2-phenylpropan-2-yl)benzamide The title compound was prepared (yield 30%) by the procedure of Example 449I, substituting the product of Example 451D for the product of Example 449H. $^1$H-NMR (300 MHz, DMSO-d6) δ ppm: 1.34 (d, J=7.0 Hz, 6H), 1.69 (s, 3H), 3.43-3.58 (m, 2H), 3.74 (dd, J=10.7, 5.9 Hz, 1H), 5.09 (t, J=5.9 Hz, 1H), 5.57 (br-s, 2H), 6.62 (d, J=8.5 Hz, 2H), 6.86 (d, J=8.5 Hz, 1H), 7.12 (d, J=8.5 Hz, 2H), 7.17 (br-t, J=7.0 Hz, 1H), 7.27 (t, J=7.0 Hz, 2H), 7.33 (br-d, J=7.0 Hz, 2H), 7.68 (dd, J=8.5, 1.5 Hz, 1H), 7.83 (d, J=1.5 Hz, 1H), 8.04 (s, 1H), 8.60 (s, 1H), 8.76 (d, J=10.3 Hz, 1H), 10.10 (s, 1H). MS ESI+ m/z: 583 (M+H), ESI– m/z: 581 (M–H).

EXAMPLE 452

(R)-4-(4-Amino-3-fluorophenylthio)-N-(1-hydroxy-2-phenylpropan-2-yl)-3-(7-isopropylpyrido[2,3-d]pyrimidin-4-ylamino)benzamide The title compound was prepared (yield 61%) by the procedure of Example 449I, substituting the product of Example 450C for the product of Example 449H. $^1$H-NMR (300 MHz, DMSO-d6) δ ppm: 1.34 (d, J=7.0 Hz, 6H), 1.69 (s, 3H), 3.23 (septet, J=7.0 Hz, 1H), 3.52 (dd, J=11.0, 6.2 Hz, 1H), 3.74 (dd, J=11.0, 5.5 Hz, 1H), 5.09 (dd, J=6.2, 5.5 Hz, 1H), 5.61 (s, 2H), 6.79 (dd, J=9.2, 8.4 Hz, 1H), 6.95 (d, J=8.5 Hz, 1H), 6.99 (dd, J=8.4, 1.8 Hz, 1H), 7.08 (dd, J=11.4, 1.8 Hz, 1H), 7.17 (br-t, J=7.0 Hz, 1H), 7.27 (t, J=7.0 Hz, 2H), 7.33 (br-d, J=7.0 Hz, 2H), 7.64 (d, J=8.5 Hz, 1H), 7.70 (br-d, J=8.5 Hz, 1H), 7.86 (br-s, 1H), 8.07 (br-s, 1H), 8.58 (s, 1H), 8.86 (d, J=8.5 Hz, 1H), 10.18 (s, 1H). MS ESI+ m/z: 583 (M+H), ESI– m/z: 581 (M–H).

EXAMPLE 453

(S)-4-(4-Aminophenylthio)-3-(6-fluoro-7-isopropylpyrido[2,3-d]pyrimidin-4-ylamino)-N-(1-phenylethyl)benzamide

EXAMPLE 453A (S)-tert-Butyl 4-(2-(6-fluoro-7-isopropylpyrido[2,3-d]pyrimidin-4-ylamino)-4-(1-phenylethylcarbamoyl)phenylthio)phenylcarbamate The title compound was prepared by the procedure of Example 385F, substituting the product of Example 451C for the product of Example 385E. 1H-NMR (300 MHz, DMSO-d6) δ ppm: 1.34 (d, J=7.0 Hz, 6H), 1.45 (d, J=7.3 Hz, 3H), 1.47 (s, 9H), 3.42-3.57 (m, 1H), 5.07-5.22 (m, 1H), 7.00 (d, J=8.1 Hz, 1H), 7.21 (br-t, J=7.0 Hz, 1H), 7.31 (t, J=7.0 Hz, 2H), 7.31 (d, J=8.8 Hz, 2H), 7.37 (d, J=7.0 Hz, 2H), 7.49 (d, J=8.8 Hz, 2H), 7.75 (dd, J=8.1, 1.5 Hz, 1H), 7.92 (d, J=1.5 Hz, 1H), 8.58 (s, 1H), 8.70 (d, J=10.3 Hz, 1H), 8.81 (d, J=8.1 Hz, 1H), 9.57 (s, 1H), 10.13 (s, 1H). MS ESI+ m/z: 653 (M+H), ESI– m/z: 651 (M–H).

EXAMPLE 453B

-(S)-4-(4-Aminophenylthio)-3-(6-fluoro-7-isopropylpyrido[2,3-d]pyrimidin-4-ylamino)-N-(1-phenylethyl)benzamide The title compound was prepared yield (70%) by the procedure of Example 385G, substituting the product of Example 453A for the product of Example 385F. 1H-NMR (300 MHz, DMSO-d6) δ ppm: 1.34 (d, J=7.0 Hz, 6H), 1.45 (d, J=7.0 Hz, 3H), 3.43-3.58 (m, 1H), 5.07-5.22 (m, 1H), 5.58 (s, 2H), 6.62 (d, J=8.4 Hz, 2H), 6.84 (d, J=8.5 Hz, 1H), 7.12 (d, J=8.4 Hz, 2H), 7.21 (br-t, J=7.0 Hz, 1H), 7.30 (t, J=7.0 Hz, 2H), 7.36 (br-d, J=7.0 Hz, 2H), 7.72 (dd, J=8.5, 1.8 Hz, 1H), 7.87 (d, J=1.8 Hz, 1H), 8.58 (s, 1H), 8.75 (d, J=10.0 Hz, 1H), 8.75 (d, J=7.3 Hz, 1H), 10.08 (s, 1H). MS ESI+ m/z: 553 (M+H), ESI– m/z: 551 (M–H).

EXAMPLE 454

4-(4-aminophenylthio)-3-(7-isopropylpyrido[2,3-d]pyrimidin-4-ylamino)benzoic acid bis-trifluoroacetic acid salt The product of Example 385E (808 mg, 1.52 mmol) was dissolved in dichloromethane (8 mL), treated with trifluoroacetic acid (8 mL), and stirred at room temperature for one hour. The solvents were removed by rotary evaporation and the oily residue taken up in dichloromethane/hexanes (25 mL, 1:1 v/v) and concentrated again. Drying on high vacuum afforded the title compound as a dark yellow powder (1.01 g, quantitative). $^1$H NMR (300 MHz, DMSO-D6) δ ppm 1.37 (d, J=6.62 Hz, 6 H) 3.21-3.43 (m, 1 H) 6.65 (d, J=8.46 Hz, 2 H) 6.92 (d, J=8.09 Hz, 1 H) 7.15 (d, J=8.46 Hz, 2 H) 7.83 (dd, J=8.27, 1.65 Hz, 1 H) 7.90 (d, J=1.84 Hz, 1 H) 7.95 (d, J=8.46 Hz, 1 H) 8.92 (s, 1 H) 9.05 (d, J=8.82 Hz, 1 H); MS (ESI+) m/z 432 (M+H)$^+$, MS (ESI–) m/z 430 (M–H)$^-$.

EXAMPLE 455

4-(4-aminophenylthio)-N-(1-hydroxy-2-methylpropan-2-yl)-3-(7-isopropylpyrido[2,3-d]pyrimidin-4-ylamino)benzamide To the product of Example 454 ((0.238 g, 0.55 mmol) in DMSO (4 ml) was added 2-amino-2-methylpropan-1-ol (0.059 g, 0.66 mmol) followed by N,N-diisopropylethyl amine (Hunigs Base) (0.192 ml, 1.10 mmol) and lastly, O-benzotriazol-1-yl-N,N,N',N'-tetramethyluronium tetrafluoroborate [TBTU] (0.195 g, 0.606 mmol) and the resulting mixture stirred under nitrogen at room temperature for two hours. A second aliquot of TBTU (0.184 g, 0.572 mmol) and Hunigs Base (0.190 ml, 1.10 mmol) was added and stirring continued for an additional thirty minutes at which time the reaction was partitioned between ethyl acetate and water. The aqueous phase was extracted twice with ethyl acetate and the organics combined and washed with water three times then dried with magnesium sulfate and concentrated in vacuo. The crude product was purified by flash chromatography on silica gel (ethyl acetate-hexane-methanol) then preparative ($C_{18}$) HPLC (gradient of methanol in 0.1% TFA/water). Fractions containing the product were concentrated in vacuo and diluted with 5% sodium bicarbonate solution. The resulting precipitate was isolated by vacuum filtration, water washed and dried in vacuo to give the desired product (0.0766 g, 28%) as a pale yellow solid. 1H NMR (300 MHz, DMSO-D6) δ ppm 1.28 (s, 6 H) 1.34 (d, J=6.62 Hz, 6 H) 3.16-3.29 (m, 1 H) 3.48 (d, J=5.88 Hz, 2 H) 4.88 (t, J=5.88 Hz, 1 H) 5.57 (s, 2 H) 6.61 (d, J=8.46 Hz, 2 H) 6.81 (d, J=8.46 Hz, 1 H) 7.11 (d, J=8.46 Hz, 2 H) 7.47 (s, 1 H) 7.61-7.64 (m, 2 H) 7.79 (s, 1 H) 8.57 (s, 1 H) 8.87 (d, J=8.46 Hz, 1 H) 10.10 (s, 1 H). (ESI+) m/z 503.3 (M+H)+(ESI−) m/z 501.3 (M−H)−.

EXAMPLE 456

4-(4-aminophenylthio)-3-(7-isopropylpyrido[2,3-d] pyrimidin-4-ylamino)-N-(2-methyl-1-phenoxypropan-2-yl)benzamide

EXAMPLE 456A tert-butyl 4-(2-(7-isopropylpyrido[2,3-d]pyrimidin-4-ylamino)-4-(2-methyl-1-phenoxypropan-2-ylcarbamoyl)phenylthio)phenylcarbamate The title compound was prepared (yield 100%) by the procedure of Example 385F, substituting 2-methyl-1-phenoxypropan-2-amine hydrochloride prepared as described in JACS, 73, 2584(1951) for S-(−)-α-methylbenzylamine.

EXAMPLE 456B 4-(4-aminophenylthio)-3-(7-isopropylpyrido[2,3-d] pyrimidin-4-ylamino)-N-(2-methyl-1-phenoxypropan-2-yl)benzamide The title compound was prepared (yield 100%) by the procedure of Example 385G, substituting the product of Example 456B for the product of Example 385F. 1H NMR (300 MHz, DMSO-D6) δ ppm 1.31 (d, J=6.99 Hz, 6 H) 1.43 (s, 6 H) 3.16 (s, 1 H) 4.15 (s, 5.53 (s, 2 H) 6.61 (d, J=8.46 Hz, 2 H) 6.65-6.72 (m, 1 H) 6.90 (t, J=7.35 Hz, 3 H) 7.11 (d, J=8.46 Hz, 2 H) 7.17-7.36 (m, 2 H) 7.46 (s, 2 H) 7.70 (s, 1 H) 7.82 (s, 1 H) 8.38 (s, 1 H) 8.75 (s, 1 H) 10.05-10.32 (m, 1 H). (ESI+) m/z 579.4 (M+H)+, (ESI−) m/z 577.4 (M−H)−.

EXAMPLE 457

4-(4-aminophenylthio)-N-(4-hydroxy-2-phenylbutan-2-yl)-3-(7-isopropylpyrido[2,3-d]pyrimidin-4-ylamino)benzamide

EXAMPLE 457A 4-(tert-butyldimethylsilyloxy)butan-2-one

4-Hydroxybutan-2-one (1.0 g, 11.35 mmol), imidazole (1.16 g, 17 mmol) in DMF (15 ml) was reacted with tert-butyldimethylsilyl chloride (1.7 g, 11.35 mmol) for three hours at room temperature. The reaction was partitioned with ether and water. The aqueous phase was extracted several times with ether. The combined organics were washed several times with water then dried over magnesium sulfate and concentrated in vacuo to give the title compound as a clear oil (2.16 g, 94%).

EXAMPLE 457B 4-(tert-butyldimethylsilyloxy)-2-phenylbutan-2-ol

The product of Example 457A (2.0 g, 9.88 mmol) in anhydrous THF (50ml) under at 0 C under nitrogen was reacted with phenylmagnesium bromide as a 3.0M solution in ether (5.0 ml, 15 mmol) dropwise via syringe then stirred for one hour. The reaction was quenched by the drop wise addition of a saturated solution of ammonium chloride and the reaction was partitioned with ether and water. The combined organics were dried over magnesium sulfate and concentrated in vacuo to give the desired compound as a clear oil (2.71 g, quantitative).

EXAMPLE 457C 3-phenylbutane-1,3-diol

The product of Example 457B (2.71 g, 9.66 mmol) in THF (50 ml) at room temperature was reacted with tetra-n-butylammonium fluoride (TBAF) as a 1.0M solution in THF (10.6 ml, 10.6 mmol) and stirred for 0.5 hours. The reaction was partitioned mixture with ethyl acetate and brine. The aqueous phase was extracted with ethyl acetate. The combined extracts were dried over magnesium sulfate and concentrated in vacuo. The residue was purified by flash chromatography on silica gel (ethyl acetate-hexane) to give the desired diol as a clear oil (1.38 g, 86%).

EXAMPLE 457D 2,4-dimethyl-4-phenyl-5,6-dihydro-4H-1,3-oxazine

The product of Example 457C (0.994, 5.98mmol) in acetonitrile (2.6 ml, 50 mmol) was added drop wise with rapid stirring and cooling to concentrated sulfuric acid (7 ml) under nitrogen at a rate maintaining the internal temperature at 6° C. or below. After addition, the reaction mixture was stirred at 0° additional forty five minutes then quenched by pouring onto ice. The resulting solution was extracted three times with dichloromethane. The aqueous phase was cooled with ice and made basic with solid NaOH and extracted with with ether. The combined extracts were washed one time with water, dried with magnesium sulfate and concentrated in vacuo to give the desired product as a clear oil (0.886 g, 78%).

EXAMPLE 457E 3-amino-3-phenylbutan-1-ol

The product of Example 457D (0.886 g, 4.68 mmol) in methanol (15 ml) at room temperature was reacted with 6N NaOH (15 ml) and the resulting mixture heated under nitrogen at 80° C. overnight. The methanol was evaporated in vacuo and the aqueous residue isolated by extraction with dichloromethane. The combined extracts were dried over sodium sulfate and concentrated in vacuo to give the title compound (0.717 g, 93%) as a pale yellow solid used without further purification.

EXAMPLE 457F 4-(4-aminophenylthio)-N-(4-hydroxy-2-phenylbutan-2-yl)-3-(7-isopropylpyrido[2,3-d]pyrimidin-4-ylamino)benzamide To the product of Example 454 (0.050 g, 0.117 mmol) in DMSO (800 ul) was added 3-amino-3-phenylbutan-1-ol (0.023 g, 0.140 mmol) followed by N,N-diisopropylethyl amine (Hunigs Base) (41 ul, 0.233 mmol) and lastly, O-benzotriazol-1-yl-N,N,N',N'-tetramethyluronium tetrafluoroborate [TBTU] (0.045 g, 0.142 mmol) and the resulting mixture stirred under nitrogen at room temperature for one hour. The reaction was partitioned with ethyl acetate and water. The aqueous phase was extracted twice with ethyl acetate and the organics combined and washed with water three times then dried with magnesium sulfate and concentrated in vacuo. The crude product was purified by preparative ($C_{18}$) HPLC (methanol-0.1% TFA/water). Fractions containing the product were concentrated in vacuo and diluted with 5% sodium bicarbonate solution and extracted with ethyl acetate. The combined extracts were dried with magnesium sulfate and concentrated to dryness in vacuo. The resulting yellow solid was triturated with ether and collected by vacuum filtration to give the desired product (0.0112 g, 17%).1H NMR (300 MHz, DMSO-D6) δ ppm 1.33 (d, J=6.99 Hz, 6 H) 1.77 (s, 3 H) 1.90-2.16 (m, 2 H) 3.14-3.28 (m, 1 H) 3.46-3.57 (m, J=5.88 Hz, 1 H) 4.98 (t, J=4.23 Hz, 1 H) 5.57 (s, 2 H) 6.62 (d, J=8.46 Hz, 2 H) 6.82 (d, 1 H) 7.06-7.22 (m, 3 H) 7.22-7.35 (m, 5 H) 7.56-7.67 (m, 2 H) 7.76 (s, 1 H) 8.57 (s, 1 H) 8.72 (s, 1 H) 8.85 (d, 1 H) 10.12 (s, 1 H). (ESI+) m/z 579.3 (M+H)+, (ESI−) m/z 577.3 (M−H)−.

EXAMPLE 458

4-(4-Amino-phenylsulfanyl)-N-(4-bromo-phenyl)-3-(7-isopropyl-pyrido[2,3-d]pyrimidin-4-ylamino)-benzenesulfonamide

EXAMPLE 458A

N-(4-Bromo-phenyl)-4-chloro-3-nitro-benzenesulfonamide

A solution of 4-chloro-3-nitrobenzenesulfonyl chloride (2.561 g, 10 mmol) in acetic acid (20 mL) was treated with 4-bromoaniline (1.72 g, 10 mmol) and anhydrous sodium acetate (1.23 g, 15 mmol), then heated at 100° for 30 minutes. The reaction was cooled to room temperature and the acetic acid removed by rotary evaporation under vacuum. The residue was taken up in ethyl acetate (100 mL) and washed with water (2×25 mL) and brine (25 mL). The organic phase was dried over anhydrous sodium sulfate, filtered, and concentrated under vacuum, co-evaporating the oil with methylene chloride/hexanes. Purification by silica gel chromatography using methylene chloride followed by 5% ethyl acetate/methylene chloride as eluent provided the title compound as a yellow solid (2.038 g, 52%).

EXAMPLE 458B 4-(4-Amino-phenylsulfanyl)-N-(4-bromo-phenyl)-3-nitro-benzenesulfonamide A mixture of the product of Example 458A (500 mg, 1.277 mmol), 4-aminothiophenol (240 mg, 1.915 mmol) and anhydrous sodium acetate (524 mg, 6.384 mmol) in anhydrous ethanol (9 mL) was heated at reflux under a nitrogen atmosphere for 1 hour. The reaction was cooled to room temperature and the ethanol removed by rotary evaporation under vacuum. The residue was taken up in ethyl acetate (100 mL) and washed with water (2×50 mL) and brine (50 mL). The organic phase was dried over anhydrous sodium sulfate, filtered, and concentrated under vacuum, Co-evaporating the oil with methylene chloride/hexanes to obtain the title compound as an orange foam (613 mg, 100%).

EXAMPLE 458C

{4-[4-(4-Bromo-phenylsulfamoyl)-2-nitro-phenylsulfanyl]-phenyl}-carbamic acid tert-butyl ester A solution of the product of Example 458B (613 mg, 1.277 mmol) in anhydrous 1,4-dioxane (10 mL) was treated with di-tert-butyl dicarbonate (418 mg, 1.92 mmol) at room temperature, then the reaction was heated at reflux under a nitrogen atmosphere for 3 hours. The reaction was cooled to room temperature, additional di-tert-butyl dicarbonate (500 mg) was added, and the reaction refluxed for 17 hours. The reaction was cooled to room temperature and the solvent removed by rotary evaporation under vacuum. Purification of the residue by silica gel chromatography using 3% ethyl acetate/methylene chloride as eluent provided the title compound as a yellow solid (512 mg, 69%).

EXAMPLE 458D

{4-[2-Amino-4-(4-bromo-phenylsulfamoyl)-phenylsulfanyl]-phenyl}-carbamic acid tert-butyl ester The product of Example 458C (510 mg, 0.879 mmol), iron powder (302 mg, 5.40 mmol), and ammonium chloride (308 mg, 5.76 mmol) in water (4 mL) and ethanol (8 mL) were heated at 80° for 40 minutes. The reaction was cooled to room temperature, diluted with ethyl acetate (100 mL), and washed with water (2×50 mL) and brine (50 mL). The organic phase was dried over anhydrous sodium sulfate, filtered, and concentrated by rotary evaporation under vacuum to provide the title compound as a white foam (436 mg, 90%).

EXAMPLE 458E

{4-[4-(4-Bromo-phenylsulfamoyl)-2-(7-isopropyl-pyrido[2,3-d]pyrimidin-4-ylamino)-phenylsulfanyl]-phenyl}-carbamic acid tert-butyl ester A solution of the product from Example 8E (59 mg, 0.2725 mmol) and the product from Example 458D (150 mg, 0.2725 mmol) in acetic acid (4 mL) was stirred in an oil bath preheated to 140° C. for 25 minutes. The reaction was cooled to room temperature, diluted with hexanes (100 mL), concentrated by rotary evaporation under vacuum, and co-evaporated with methylene chloride/hexanes (4×). The residue was dried under vacuum, then purified by silica gel chromatography using 4% methanol/methylene chloride as eluent to provide the title compound as a tan solid (67 mg, 34%).

EXAMPLE 458F 4-(4-Amino-phenylsulfanyl)-N-(4-bromo-phenyl)-3-(7-isopropyl-pyrido[2,3-d]pyrimidin-4-ylamino)-benzenesulfonamide The product from Example 458E (44 mg, 0.061 mmol) was treated with trifluoroacetic acid (2 mL) in methylene chloride (2 mL) at room temperature for 30 minutes. The solvents were removed by rotary evaporation under vacuum and the residual oil dried under hi-vacuum. Purification by silica gel chromatography using 5% methanol/methylene chloride as eluent provided the title compound as a trifluoroacetic acid salt (25 mg, 48%). $^1$H NMR (300 MHz, DMSO-D6) δ ppm: 1.35 (d, J=6.62 Hz, 6 H), 3.13-3.38 (m, 1 H), 6.63 (d, J=8.46 Hz, 2 H), 6.87 (d, J=7.72 Hz, 1 H), 7.01-7.09 (d, J=8.82 Hz, 2 H), 7.12 (d, J=8.46 Hz, 2 H), 7.44 (d, J=8.82 Hz, 2 H), 7.61 (dd, J=7.72, 1.47 Hz, 1 H), 7.71 (s, 1 H), 7.81 (dd, J=6.62, 1.47 Hz, 1 H), 8.66-8.80 (m, 1 H), 8.90 (d, J=6.99 Hz, 1 H), 10.55 (s, 1 H); MS (ESI+) m/z 621/623 (M+H)$^+$.

EXAMPLE 459

4-(4-Amino-phenylsulfanyl)-N-(4-bromo-phenyl)-3-(7-methyl-pyrido[2,3-d]pyrimidin-4-ylamino)-benzenesulfonamide The product from Example 458D was reacted with the product from Example 9B using the procedure described in Example 458E substituting the product from Example 9B for the product from Example 8E to provide {4-[4-(4-Bromo-phenylsulfamoyl)-2-(7-methyl-pyrido[2,3-d]pyrimidin-4-ylamino)-phenylsulfanyl]-phenyl}-carbamic acid tert-butyl ester which was deprotected according to the procedure described in Example 458F, followed by silica gel chromatography provided the title compound as a trifluoroacetic acid salt. $^1$H NMR (300 MHz, DMSO-D6) δ ppm: 2.74 (s, 3 H), 6.64 (d, J=8.46 Hz, 2 H), 6.89 (d, J=8.09 Hz, 1 H), 7.05 (d, J=9.19 Hz, 2 H), 7.12 (d, J=8.82 Hz, 2 H), 7.44 (d, J=8.82 Hz, 2 H), 7.63 (dd, J=7.72, 0.74 Hz, 1 H), 7.74 (s, 1 H), 7.79 (dd, J=7.72, 1.10 Hz, 1 H), 8.70-8.83 (m, 1 H), 8.88 (d, J=8.09 Hz, 1 H), 10.55 (s, 1 H); MS (ESI+) m/z 593/595 (M+H)+.

Biological Evaluation

Representative compounds of the invention were analyzed according to the assays described below.

The following acronyms are used herein:

| | |
|---|---|
| IC$_{50}$ | 50% inhibitory concentration |
| TC$_{50}$ | 50% toxicity concentration |
| DMEM | Dulbecco's Modified Essential Medium ™ |
| RNA | ribonucleic acid |
| RT-PCR | reverse transcriptase polymerase chain reaction |
| SEAP | secreted alkaline phosphatase |

The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in Ikeda et al., J. VIROLOGY, 76(6): 2997-3006 (2002), and Blight et al., SCIENCE, 290:1972-1974 (2000). The mechanism of RNA replication in these cell lines is considered to be identical to the replication of full length HCV RNA in infected hepatocytes. The compounds of this invention are inhibitors of HCV RNA replication in the replicon assay systems described below.

Evaluation of the HCV Inhibitors in HCV Replicon

Representative compounds of the invention were evaluated for their inhibitory effect on HCV genotype 1a and 1b replicons. They were also evaluated by MTT assay for cytotoxicity to the host cells. The cell lines were maintained according to the methods described by Yi et al., VIROLOGY, 304(2):197-210 (2002).

A. RNA Assay and SEAP Assay

The purpose of these assays was to evaluate the efficacy of the compounds in inhibiting the replication of HCV genotype 1a and 1b replicons in vitro.

Genotype 1a and/or 1b replicon cells were plated at 3-5× 10$^3$ cells per well in 96-well plate in DMEM medium containing 5% fetal calf serum. The next day, the culture medium was removed and replaced with fresh medium containing eight serial dilutions of compound. The untreated control culture was treated in an identical manner except no inhibitor was added to the medium. Plates were incubated in a CO$_2$ incubator at 37° C. On day 4, 100 μl lysis buffer (RTL) (Qiagen) was added to each well after removal of culture medium. RNA was purified according to manufacturer's recommendations (Qiagen RNAeasy) and eluted in 200 μl of water. The HCV RNA level was quantified from a portion (5 μl out of 200 μl) of the purified RNA by real-time RT-PCR method. The primers and probe were derived from specific sequence in the 5'-Untranslated Region (5'UTR). RT-PCR reaction was performed at 48° C. for 30 min, followed by 40 cycles set to 95° C., 15 s; 54° C., 30 s; and 72° C., 40 s. Alternatively, the activity of SEAP was measured in each culture supernatant after four days incubation with compound according to the manufacturer's instructions. The percentage reduction of HCV RNA or SEAP in the presence of compound was calculated and the 50% inhibitory concentration (IC$_{50}$) was calculated by non-linear regression analysis using the Prism program (version 4.0, GraphPad software, San Diego, Calif.).

When tested using the above method, representative compounds of the present invention inhibited HCV replicon replication with IC$_{50}$ values in the range of from about 0.3 nM to about 100 μM.

B. Cytotoxicity Assay

The purpose of this assay was to determine the toxicity of the compounds on viral host cells in vitro.

Cytotoxicity of the compounds was measured using a mitochondrial enzyme-based cell proliferation/viability assay in replicon cells. Briefly, HCV replicon cells were plated at 3-5×10$^3$ cells per well in 96-well plate in DMEM medium containing 5% FCS. At day 1, culture medium was removed and replaced with fresh medium containing eight serial dilutions of compound. The untreated control culture was treated in an identical manner except no inhibitor was added to the medium. Plates were incubated in a CO$_2$ incubator at 37° C. On day 4, stock solution of the tetrazolium salt, MTT (4 mg/ml in PBS, Sigma cat.# M 2128) was added to each well at 25 μl per well. Plates were further incubated for 4 hours, treated with 20% SDS plus 0.02 N HCl at 50 μl per well to lyse the cells. After an overnight incubation, optical density was measured by reading the plates at 570/650 nm wavelengths. The percent reduction of formazan blue color formed relative to control was calculated and the 50% toxicity concentration ($TC_{50}$) was calculated by non-linear regression analysis using the Prism program (version 4.0, GraphPad software, San Diego, Calif.).

When tested using the above method, the $TC_{50}$ values of representative compounds of the present invention were greater than the corresponding $IC_{50}$ values of these compounds.

Pharmaceutical Compositions and Uses

The present invention features pharmaceutical compositions comprising the compounds of the invention. As a non-limiting example, a pharmaceutical composition of the present invention comprises one or more compounds of this invention, wherein each compound is independently selected from Formulae I, I(a), I(b), I(c), I(d), I(e), I(f), I(g) or I(h). Preferably, each compound is independently selected from Examples 1-457.

The present invention also features pharmaceutical compositions comprising pharmaceutically acceptable salts, solvates, or prodrugs of the compounds of this invention. Pharmaceutically acceptable salts can be zwitterions or derived from pharmaceutically acceptable inorganic or organic acids or bases. Preferably, a pharmaceutically acceptable salt of a compound of the invention retains the biological effectiveness of the free acid or base of the compound without undue toxicity, irritation, or allergic response, has a reasonable benefit/risk ratio, and is effective for their intended use and not biologically or otherwise undesirable. Non-limiting examples of pharmaceutically acceptable salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. The basic nitrogen-containing groups can also be quaternized with such agents as loweralkyl halides (e.g., methyl, ethyl, propyl or butyl chlorides, bromides or iodides), dialkyl sulfates (e.g., dimethyl, diethyl, dibutyl or diamyl sulfates), long chain halides (e.g., decyl, lauryl, myristyl or stearyl chlorides, bromides or iodides), aralkyl halides (e.g., benzyl or phenethyl bromides). Other salts that can be used in the present invention include salts with alkali or alkaline earth metals, such as sodium, potassium, calcium or magnesium, or with organic bases. Examples of acids which can be used to form pharmaceutically acceptable acid addition salts include, but are not limited to, hydrochloric acid, sulphuric acid, phosphoric acid, oxalic acid, maleic acid, succinic acid, citric acid, or other suitable inorganic or organic acids.

The present invention further features pharmaceutical compositions comprising a compound of the invention (or a salt, solvate or prodrug thereof) and another therapeutic agent. In a non-limiting example, a pharmaceutical composition of the present invention includes 1, 2, 3 or more compounds of the invention (or salts, solvates or prodrugs thereof), and 1, 2, 3 or more other therapeutic agents. By way of illustration not limitation, these other therapeutic agents can be selected from antiviral agents (e.g., anti-HIV agents or other anti-HCV agents), immunomodulators, anti-cancer or chemotherapeutic agents, or anti-inflammation agents. Specific examples of these other therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals);

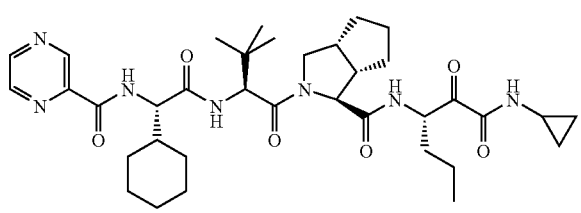

(hereinafter compound VX-950, Vertex Pharmaceuticals Inc.);

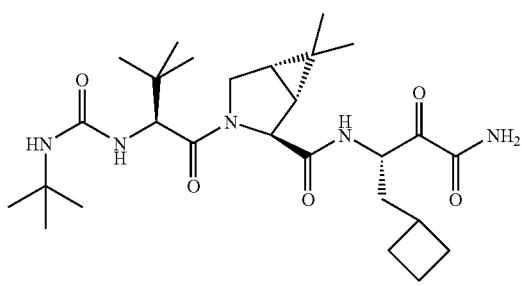

(hereinafter compound SCH503034, Schering-Plough Co.); and

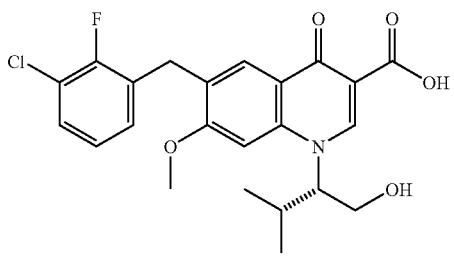

(hereinafter compound GS9137, Gilead Sciences, Inc., Foster City, Calif.). Any other desirable therapeutic agent(s) can also be included in a pharmaceutical composition of the present invention.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. In one example, each of the compounds of the present invention is independently selected from Formulae I, I(a), I(b), I(c), I(d), I(e), I(f), I(g) or I(h), or Examples 1-457, and each of the other anti-HCV agents is independently selected from HCV RNA dependent RNA polymerase inhibitors (e.g., nucleoside or non-nucleoside type polymerase inhibitors), HCV protease inhibitors, or HCV helicase inhibitors.

In a further embodiment, a pharmaceutical composition of the present invention comprises one or more compounds of the present invention (or salts, solvates or prodrugs thereof), and two or more other anti-HCV inhibitors. Preferably, each compound of the present invention is independently selected from Formulae I(a), I(b), I(c), I(d), I(e), I(f), I(g) or 1(h), or from Examples 1-457. The other anti-HCV inhibitors can be selected from the same inhibitor class (e.g., all of them are selected from HCV RNA dependent RNA polymerase inhibitors, or from HCV protease inhibitors), or selected from different inhibitor classes (e.g., one or more are selected from HCV RNA dependent RNA polymerase inhibitor and the other or others are selected from HCV protease inhibitors).

In still another embodiment, a pharmaceutical composition of the present invention comprises at least one compound of the present invention (or a salt, solvate or prodrug thereof), and at least one HCV RNA dependent RNA polymerase inhibitor. Preferably, each compound of the present invention is independently selected from Formulae I(a), I(b), I(c), I(d), I(e), I(f), I(g) or I(h), or Examples 1-457.

In another embodiment, a pharmaceutical composition of the present invention comprises at least one compound of the present invention (or a salt, solvate or prodrug thereof), and at least one HCV protease inhibitor. Preferably, the compound of the present invention is selected from Formulae I(a), I(b), I(c), I(d), I(e), I(f), I(g) or I(h), or Examples 1-457.

In yet another embodiment, a pharmaceutical composition of the present invention comprises at least one compound of the present invention (or a salt, solvate or prodrug thereof), at least one HCV RNA dependent RNA polymerase inhibitor, and at least one HCV protease inhibitor. Preferably, the compound of the present invention is selected from Formulae I(a), I(b), I(c), I(d), I(e), I(f), I(g) or I(h), or Examples 1-457.

In still yet another embodiment, a pharmaceutical composition of the present invention comprises at least one compound of the present invention (or a salt, solvate or prodrug thereof), and two or more anti-HCV agents each of which is independently selected from HCV RNA dependent RNA polymerase inhibitors or HCV protease inhibitors. Preferably, the compound of the present invention is selected from Formulae I(a), I(b), I(c), I(d), I(e), I(f), I(g) or I(h), or Examples 1-457.

In still another embodiment, a pharmaceutical composition of the present invention comprises at least one compound of the present invention (or a salt, solvate or prodrug thereof), and three or more other anti-HCV agents each of which is independently selected from HCV RNA dependent RNA polymerase inhibitors or HCV protease inhibitors. Preferably, the compound of the present invention is selected from Formulae I(a), I(b), I(c), I(d), I(e), I(f), I(g) or I(h), or Examples 1-457.

Non-limiting examples of HCV RNA dependent RNA polymerase inhibitors include those described in WO0190121(A2), U.S. Pat. No. 6,348,587B1, WO0160315, WO0132153, EP1162196A1 and WO0204425. Non-limiting examples of HCV protease inhibitors include BILN-2061, VX-950, and SCH503034.

In another embodiment, a pharmaceutical composition of the present invention comprises at least one compound of the present invention (or a salt, solvate or prodrug thereof), and one or more other antiviral agents, such as anti-HBV or anti-HIV agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, and other HIV protease, reverse transcriptase, integrase or fusion inhibitors. Other desirable antiviral agents can also be included in a pharmaceutical composition of the present invention, as appreciated by those skilled in the art.

In one embodiment, a pharmaceutical composition of the present invention comprises at least one compound of the present invention selected from Formulae I, I(a), I(b), I(c), I(d), I(e), I(f), I(g) or I(h) or from Examples 1-457, or a salt, solvate or prodrug thereof, and at least one anti-HBV agent. In another embodiment, a pharmaceutical composition of the present invention comprises at least one compound of the present invention selected from Formulae I, I(a), I(b), I(c), I(d), I(e), I(f), I(g) or I(h) or from Examples 1-457, or a salt, solvate or prodrug thereof, and at least one anti-HIV agent. In yet another embodiment, a pharmaceutical composition of the present invention comprises at least one compound of the present invention selected from Formulae I, I(a), I(b), I(c), I(d), I(e), I(f), I(g) or I(h) or from Examples 1-457, or a salt, solvate or prodrug thereof, and at least one anti-hepatitis A, anti-hepatitis D, anti-hepatitis E or anti-hepatitis G agent.

In still yet another embodiment, a pharmaceutical composition of the present invention comprises at least one compound of the present invention selected from Formulae I, I(a), I(b), I(c), I(d), I(e), I(f), I(g) or I(h) or from Examples 1-457, or a salt, solvate or prodrug thereof, and at least one agent suitable for treating liver inflammation.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention, as appreciated by those of ordinary skill in the art.

A pharmaceutical composition of the present invention can be administered to a patient in need thereof via a variety of routes, such as orally, parenterally, sublingually, rectally, topically or by inhalation spray. Topical administration may involve the use of transdermal administration such as transdermal patches or iontophoresis devices. Parenteral administration includes, but is not limited to, subcutaneous, intravenous, intramuscular or intrastemal injections, and infusion techniques.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

The present invention further features methods of using the compounds of the present invention (or salts, solvates or prodrugs thereof) to inhibit HCV replication. In one embodiment, the methods comprise contacting HCV virus with an effective amount of a compound of the present invention (or a salt, solvate or prodrug thereof), thereby inhibiting the replication of the HCV virus. In another embodiment, the methods comprise contacting cells infected with HCV virus with an effective amount of a compound of the present invention (or a salt, solvate or prodrug thereof), thereby inhibiting the replication of the HCV virus in the cells. In still another embodiment, the methods comprise contacting HCV virus or infected cells with an effective amount of two or more compounds of the present invention (or salts, solvates or prodrugs thereof), thereby inhibiting the replication of the HCV virus. As used herein, "inhibiting" means significantly reducing, or abolishing, the activity being inhibited (e.g., viral replication). In many cases, representative compounds of the present invention can reduce the replication of HCV virus (e.g., in HCV replicon assays as described above) by at least 10%, 20%, 30%, 40%, 50%, 60%, 70%, 80%, 90%, 95% or more.

The compounds of the present invention may inhibit all HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c or 3a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. These methods typically comprise administering a therapeutic effective amount of a compound of the present invention (or a salt, solvate or prodrug thereof) to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof) to an HCV patient, thereby reducing the HCV viral level in the blood or liver of the patient. Preferably, the compound(s) employed in these methods has Formulae I(a), I(b), I(c), I(d), I(e), I(f), I(g) or I(h) or is selected from Examples 1-457, or is a salt, solvate or prodrug thereof.

In another aspect, the present invention features methods of using a pharmaceutical composition of the present invention to treat HCV infection. Any pharmaceutical composition described herein can be used for this purpose. These methods typically comprise administering a therapeutic effective amount of a pharmaceutical composition of the present invention to an HCV patient, thereby reducing the HCV viral level in the blood or liver of the patient. Where the pharmaceutical composition includes other therapeutic agent(s), it may also treat other diseases, disorders or conditions in the patient.

In one embodiment, the pharmaceutical composition being administered comprises at least one compound of the present invention selected from Formulae I(a), I(b), I(c), I(d), I(e), I(f), I(g) or I(h) or from Examples 1-457, or a salt, solvate or prodrug thereof, and at least another anti-HCV agent selected from HCV RNA dependent RNA polymerase inhibitors, HCV protease inhibitors or HCV helicase inhibitors. In another embodiment, the pharmaceutical composition being administered comprises at least one compound of the present invention selected from Formulae I(a), I(b), I(c), I(d), I(e), I(f), I(g) or I(h) or from Examples 1-457, or a salt, solvate or prodrug thereof, and at least two other anti-HCV agents each of which is independently selected from HCV RNA dependent RNA polymerase inhibitors, HCV protease inhibitors or HCV helicase inhibitors. In still another embodiment, the pharmaceutical composition being administered comprises at least one compound of the present invention selected from Formulae I(a), I(b), I(c), I(d), I(e), I(f), I(g) or I(h) or from Examples 1-457, or a salt, solvate or prodrug thereof, and 1, 2 or more HCV RNA dependent RNA polymerase inhibitors (e.g., those described in WO0190121(A2), U.S. Pat. No. 6,348,587B1, WO0160315, WO0132153, EP1162196A1 and WO0204425). In yet another embodiment, the pharmaceutical composition being administered comprises at least one compound of the present invention selected from Formulae I(a), I(b), I(c), I(d), I(e), I(f), I(g) or I(h) or from Examples 1-457, or a salt, solvate or prodrug thereof, and 1, 2 or more HCV protease inhibitors (e.g., BILN-2061, VX-950, and SCH503034).

In a further embodiment, the pharmaceutical composition being administered comprises at least one compound of the present invention selected from Formulae I(a), I(b), I(c), I(d), I(e), I(f), I(g) or I(h) or from Examples 1-457, or a salt, solvate or prodrug thereof, and at least one antiviral agent selected from anti-HIV agents, anti-HBV agents, anti-hepatitis A agents, anti-hepatitis D agents, anti-hepatitis E agents, or anti-hepatitis G agents.

In yet another aspect, the present invention provides methods of using a compound(s) of the present invention and another therapeutic agent(s) to treat HCV infection. The methods comprise administering a therapeutic effective amount of a compound(s) of the present invention and another therapeutic agent(s) to an HCV patient, thereby reducing the HCV viral level in the blood or liver of the patient. Each compound of the present invention (or a salt, solvate or prodrug thereof) and the other therapeutic agent(s) can be combined in a single formulation and administered simultaneously to the patient. They can also be administered simultaneously but in different formulations. In addition, they can be administered sequentially.

In one embodiment, the compound(s) of the present invention being administered includes one or more compounds selected from Formulae I(a), I(b), I(c), I(d), I(e), I(f), I(g) or I(h) or from Examples 1-457, or salts, solvates or prodrugs thereof, and the other therapeutic agent(s) being administered includes one or more agents selected from HCV RNA dependent RNA polymerase inhibitors, HCV protease inhibitors or HCV helicase inhibitors. In another embodiment, the compound(s) of the present invention being administered includes one or more compounds selected from Formulae I(a), I(b), I(c), I(d), I(e), I(f), I(g) or I(h) or from Examples 1-457, or salts, solvates or prodrugs thereof, and the other therapeutic agent(s) being administered includes two or more agents selected from HCV RNA dependent RNA polymerase inhibitors, HCV protease inhibitors or HCV helicase inhibitors. In yet another embodiment, the compound(s) of the present invention being administered includes one or more compounds selected from Formulae I(a), I(b), I(c), I(d), I(e), I(f), I(g) or I(h) or from Examples 1-457, or salts, solvates or prodrugs thereof, and the other therapeutic agent(s) being administered includes one, two or more HCV RNA dependent RNA polymerase inhibitors (e.g., those described in WO0190121(A2), U.S. Pat. No. 6,348,587B1, WO0160315, WO0132153, EP1162196A1 and WO0204425). In still yet another embodiment, the compound(s) of the present invention being administered includes one or more compounds selected from Formulae I(a), I(b), I(c), I(d), I(e), I(f), I(g) or I(h) or from Examples 1-457, or salts, solvates or prodrugs thereof, and the other therapeutic agent(s) being administered includes one, two or more HCV protease inhibitors (e.g., BILN-2061, VX-950, and SCH503034).

A compound of the present invention (or a salt, solvate or prodrug thereof) can also be coadministered with other desired drugs, such as anti-HIV agents, anti-HBV agents, anti-hepatitis A agents, anti-hepatitis D agents, anti-hepatitis E agents, anti-hepatitis G agents, or other antiviral drugs.

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

In still another aspect, the compounds of Formulae I, I(a), I(b), I(c), I(d), I(e), I(f), I(g) or I(h), or their pharmaceutically acceptable salts, stereoisomers or tautomers, can be administered as the sole active pharmaceutical agent, or used in combination with one or more other agents, to treat infections or symptoms associated with other RNA-containing viruses.

Treatment or prevention of infection caused by RNA-containing viruses can be provided by a combination therapy comprising a therapeutically effective amount of a first antiviral agent provided by one or more compounds, or salts thereof, of Formulae I, I(a), I(b), I(c), I(d), I(e), I(f), I(g) or I(h), along with a therapeutically-effective amount of a second agent provided by one or more compounds selected from the group consisting of another anti-viral agent; a host immune modulator; interferon derivative, such as interferon-alpha, pegylated-interferon-alpha, interferon-beta, and interferon-gamma; a cytokine; a vaccine; a nucleoside analog;

inhibitors of key enzymes which result in HCV dysfunction, examples of such enzymes being HCV metalloprotease, HCV serine protease, inosine monophosphate dehydrogenase (IMPDH), and HCV helicase; inhibitors of viral particle proteins such as HCV NS4B protein, and HCV NS5a protein; and agents which inhibit HCV function, such as HCV entry, HCV assembly, and HCV egress. Also included are vaccines comprising HCV antigens or antigen adjuvant combinations directed against HCV. Further included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7.

In one embodiment, the present invention is directed to a method of treating or preventing infection caused by an RNA-containing virus comprising administering to a patient in need of such treatment a therapeutically effective amount of a compound of Formulae I, I(a), I(b), I(c), I(d), I(e), I(f), I(g) or I(h), or a pharmaceutically acceptable salt thereof.

In another embodiment, the present invention is directed to a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound of Formulae I, I(a), I(b), I(c), I(d), I(e), I(f), I(g) or I(h), or a pharmaceutically acceptable salt thereof.

In yet another embodiment, the present invention is directed to a method of treating or preventing infection caused by an RNA-containing virus comprising co-administering to a patient in need of such treatment one or more agents selected from the group consisting of interferon-alpha, pegylated-interferon-alpha, interferon-beta, interferon-gamma, a cytokine, a vaccine, and a vaccine comprising an antigen and an adjuvant, and a second antiviral agent, or a combination thereof, with a therapeutically effective amount of a compound of Formulae I, I(a), I(b), I(c), I(d), I(e), I(f), I(g) or I(h), or a pharmaceutically acceptable salt thereof.

In still another embodiment, the present invention provides a method of treating or preventing infection caused by an RNA-containing virus comprising co-administering to a patient in need of such treatment one or more agents selected from the group consisting of a host immune modulator and a second antiviral agent which inhibits replication of HCV by inhibiting host cellular functions associated with viral replication, or a combination thereof, with a therapeutically effective amount of a compound of Formulae I, I(a), I(b), I(c), I(d), I(e), I(f), I(g) or I(h), or a pharmaceutically acceptable salt thereof.

In a further embodiment, the present invention provides a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound of Formulae I, I(a), I(b), I(c), I(d), I(e), I(f), I(g) or I(h), or a pharmaceutically acceptable salt thereof.

In another embodiment, the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound of Formulae I, I(a), I(b), I(c), I(d), I(e), I(f), I(g) or I(h), or a pharmaceutically acceptable salt thereof.

In yet another embodiment, the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound of Formulae I, I(a), I(b), I(c), I(d), I(e), I(f), I(g) or I(h), or a pharmaceutically acceptable salt thereof.

The phrase "combination therapy" (or "co-therapy"), is intended to embrace administration of each agent in a sequential manner in a regimen that will provide beneficial effects of the drug combination, and is intended as well to embrace co-administration of these agents in a substantially simultaneous manner, such as by oral ingestion or a single capsule having a fixed ratio of these active agents or ingestion of multiple, separate capsules for each agent. "Combination therapy" will also include simultaneous or sequential administration by oral, intravenous, intramuscular or other parenteral routes into the body, including direct absorption through mucous membrane tissues, as found in the sinus passages. Sequential administration also includes drug combinations where the individual agents may be administered at different times and/or by different routes but which act in combination to provide a beneficial effect, for example, by co-action of pharmacokinetic or pharmacodynamic effects of each agent.

The present invention also features use of the compounds of the invention, or pharmaceutically acceptable salts, solvates or prodrugs thereof, for the manufacture of medicaments for the treatment of HCV or other viral infections. In one embodiment, the present invention features the use of a compound of the present invention selected from Formulae I, I(a), I(b), I(c), I(d), I(e), I(f), I(g) or I(h), or a salt, solvate or prodrug thereof, for the manufacture of a medicament for the treatment of HCV infection. In another embodiment, the present invention features the use of two or more compounds of the present invention (or salts, solvates or prodrugs thereof) for the manufacture of a medicament for the treatment of HCV infection, wherein each of the two or more compounds is independently selected from Formulae I, I(a), I(b), I(c), I(d), I(e), I(f), I(g) or I(h).

In still another embodiment, the present invention features the use of at least one compound of the present invention (or a salt, solvate or prodrug thereof) and at least one additional therapeutic agent for the manufacture of a medicament for the treatment of HCV infection. Preferably, the compound(s) of the present invention is selected from Formulae I(a), I(b), I(c), I(d), I(e), I(f), I(g) or I(h), and the additional therapeutic agent(s) can be selected, by way of illustration not limitation, from antiviral agents (e.g., anti-HIV agents or other anti-HCV agents), immunomodulators, anti-cancer or chemotherapeutic agents, and anti-inflammation agents. Specific examples of additional therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.; Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals); compound VX-950 (Vertex Pharmaceuticals Inc.); compound SCH503034 (Schering-Plough Co.); and compound GS9137 (Gilead Sciences, Inc., Foster City, Calif.).

In yet another embodiment, the present invention features the use of at least one compound of the present invention (or a salt, solvate or prodrug thereof) and at least one additional anti-viral agent for the manufacture of a medicament for the treatment of viral infection. Preferably, the compound(s) of the present invention is selected from Formulae I(a), I(b), I(c), I(d), I(e), I(f), I(g) or I(h), and the additional anti-viral agent(s) can be selected, without limitation, from anti-HCV or anti-HIV agents. In one example, the present invention features the use of at least one compound of the present invention selected from Formulae I(a), I(b), I(c), I(d), I(e), I(f), I(g) or I(h) (or a salt, solvate or prodrug thereof), and at least one additional anti-HCV agent for the manufacture of a medicament for the treatment of HCV infection. Non-limiting examples of anti-HCV agents include HCV RNA dependent RNA polymerase inhibitors (e.g., nucleoside or non-nucleoside type polymerase inhibitors) or HCV protease inhibitors. In another example, the present invention features the use of at least one compound of the present invention selected from Formulae I(a), I(b), I(c), I(d), I(e), I(f), I(g) or I(h) (or a salt, solvate or prodrug thereof), and at least two or more additional anti-HCV agents for the manufacture of a medicament for the treatment of HCV infection. Each of the additional anti-HCV agents can be independently selected from HCV RNA dependent RNA polymerase inhibitors or HCV protease inhibitors.

In still another embodiment, the present invention features the use of at least one compound of the present invention selected from Formulae I, I(a), I(b), I(c), I(d), I(e), I(f), I(g) or I(h) (or a salt, solvate or prodrug thereof), and at least one anti-HIV agent for the manufacture of a medicament for the treatment of HIV or HCV infection. In still yet another embodiment, the present invention features the use of at least one compound of the present invention selected from Formulae I, I(a), I(b), I(c), I(d), I(e), I(f), I(g) or I(h) (or a salt, solvate or prodrug thereof), and at least one anti-hepatitis A, anti-hepatitis B, anti-hepatitis D, anti-hepatitis E or anti-hepatitis G agent for the manufacture of a medicament for the treatment of viral hepatitis. In a further embodiment, the present invention features the use of at least one compound of the present invention selected from Formulae I, I(a), I(b), I(c), I(d), I(e), I(f), I(g) or I(h) (or a salt, solvate or prodrug thereof), and at least one agent for treating liver inflammation, for the manufacture of a medicament for the treatment of Hepatitis C.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound, a tautomer of the compound, or a pharmaceutically acceptable salt of the compound or tautomer, wherein the compound has Formula I,

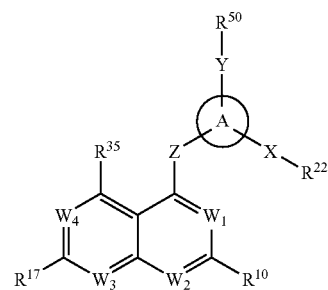

wherein:
$W_1$, $W_2$ and $W_3$ are N, and $W_4$ is $C(R^{33})$;
Z is a bond, —$CR^{41}R^{41'}$— or —$NR^{41}$—, wherein $R^{41}$ and $R^{41'}$ are each independently selected from the group consisting of hydrogen, alkyl, alkenyl and alkynyl;
A is a carbocyclyl or heterocyclyl, and is optionally substituted with one or more $R^{18}$, wherein $R^{18}$ is independently selected at each occurrence from the group consisting of halogen, hydroxy, mercapto, nitro, cyano, amino, carboxy, formyl, azido, alkyl, alkenyl, alkynyl, -$L_S$O—$R_S$, -$L_S$-S-$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S''}$, -$L_S$-S(O) $R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'}R_{S''}$), -$L_S$-N($R_{S'}$)C(=N$R_S$)$R_{S''}$, -$L_S$-

N($R_S$)C(O)N($R_S$,$R_{S''}$), -$L_S$-N($R_S$)SO$_2$$R_{S'}$, -$L_S$-SO$_2$N($R_S$$R_{S'}$), and -$L_S$-N($R_S$)SO$_2$N($R_S$,$R_{S''}$);

$R^{17}$, $R^{33}$ and $R^{35}$ are each independently selected at each occurrence from the group consisting of hydrogen, halogen, hydroxy, mercapto, nitro, cyano, amino, carboxy, formyl, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), and -$L_S$-N($R_S$)SO$_2$N($R_S$$R_{S''}$));

$R^{10}$ is hydrogen or halogen;

X is selected from the group consisting of a bond, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is carbocyclyl or heterocyclyl, and is optionally substituted with one or more $R^{26}$, wherein $R^{26}$ is independently selected at each occurrence from the group consisting of halogen, hydroxy, mercapto, nitro, cyano, amino, carboxy, formyl, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N=C(N$R_S$$R_{S'}$)(N$R_S$$R_{S'}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), -$L_E$-Q-$L_{E'}$-(C$_3$-C$_{18}$carbocyclyl) and -$L_E$-Q-$L_{E'}$-(3- to 18-membered heterocyclyl);

Y is selected from the group consisting of —C(O)N($R^{15}$)— and —N($R^{15}$)C(O)—, wherein $R^{15}$ is selected from the group consisting of hydrogen, alkyl, alkenyl and alkynyl;

$R^{50}$ is -$L^1$-$A^1$, wherein $A^1$ is selected from the group consisting of carbocyclyl and heterocyclyl, and $L^1$ is selected from the group consisting of a bond, alkylene, alkenylene and alkynylene, wherein $A^1$ is optionally substituted with one or more $R^{30}$, and $R^{30}$ is independently selected at each occurrence from the group consisting of halogen, hydroxy, mercapto, nitro, cyano, amino, carboxy, formyl, azido, alkyl, alkenyl, alkynyl, -$L_S$-O—$R_S$, -$L_S$-S—$R_S$, $L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N ($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), -$L_E$-Q-$L_{E'}$-(C$_3$-C$_{18}$carbocyclyl) and -$L_E$-Q-$L_{E'}$-(3- to 18-membered heterocyclyl), and wherein $L^1$ is optionally substituted with one or more $R^{38}$, and $R^{38}$ is independently selected at each occurrence from the group consisting of halogen, hydroxy, mercapto, nitro, cyano, amino, carboxy, formyl, azido, alkoxy, thioalkoxy, alkylcarbonyl, alkoxycarbonyl, alkylcarbonyloxy, alkylamino, alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), carbocyclyl, heterocyclyl, carbocyclylalkyl, heterocyclylalkyl, -$L_E$-Q-$L_{E'}$-(C$_3$-C$_{18}$carbocyclyl) and -$L_E$-Q-$L_{E'}$-(3 to 18-membered heterocyclyl);

$L_S$ is independently selected at each occurrence from the group consisting of a bond, alkylene, alkenylene and alkynylene;

$R_S$, $R_{S'}$ and $R_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

$L_E$ and $L_{E'}$ are each independently selected at each occurrence from the group consisting of a bond, alkylene, alkenylene and alkynylene;

Q is independently selected at each occurrence from the group consisting of a bond, alkylene, alkenylene, alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—; and each C$_3$-C$_{18}$carbocyclyl and 3- to 18-membered heterocyclyl moiety in -$L_E$-Q-$L_{E'}$-(C$_3$-C$_{18}$carbocyclyl) and -$L_E$-Q-$L_{E'}$-(3- to 18-membered heterocyclyl) is independently optionally substituted at each occurrence with at least one substituent selected from the group consisting of hydrogen, halogen, hydroxy, mercapto, nitro, cyano, amino, carboxy, formyl, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl.

2. The compound, tautomer or pharmaceutically acceptable salt of claim 1, wherein:

Z is a bond, —CR$^{41}$R$^{41'}$ or —NR$^{41}$—, wherein R$^{41}$ and R$^{41'}$ are each independently selected from the group consisting of hydrogen, C$_1$-C$_6$alkyl, C$_2$-C$_6$alkenyl and C$_2$-C$_6$alkynyl;

A is a carbocyclyl or heterocyclyl, and is optionally substituted with one or more $R^{18}$, wherein $R^{18}$ is independently selected at each occurrence from the group consisting of halogen, hydroxy, mercapto, nitro, cyano, amino, carboxy, formyl, azido, C$_1$-C$_6$alkyl, C$_2$-C$_6$alkenyl, C$_2$-C$_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), and -$L_S$-N($R_S$)SO$_2$N($R_S$$R_{S''}$);

$R^{17}$, $R^{33}$ and $R^{35}$ are each independently selected at each occurrence from the group consisting of hydrogen, halogen, hydroxy, mercapto, nitro, cyano, amino, carboxy, formyl, azido, C$_1$-C$_6$alkyl, C$_2$-C$_6$alkenyl, C$_2$-C$_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, and -$L_S$-N($R_S$)SO$_2$N($R_S$$R_{S''}$));

$R_{10}$ is hydrogen or halogen;

X is selected from the group consisting of a bond, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N $(R_{S'})$—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is carbocyclyl or heterocyclyl, and is optionally substituted with one or more $R^{26}$, wherein $R^{26}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N=C(N$R_S R_{S'}$)(N$R_S R_{S'}$), -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-(3- to 18-membered heterocyclyl);

Y is selected from the group consisting of a bond, —C(O)N($R^{15}$)—, and —N($R^{15}$)C(O)—, wherein $R^{15}$ is selected from the group consisting of hydrogen, $C_1$-$C_6$alkyl, $C_2$-$C_6$alkenyl and $C_2$-$C_6$alkynyl;

$R^{50}$ is -$L^1$-$A^1$, wherein $A^1$ is selected from the group consisting of carbocyclyl and heterocyclyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-(3- to 18-membered heterocyclyl), and wherein $L^1$ is optionally substituted with one or more $R^{38}$, and $R^{38}$ is independently selected at each occurrence from the group consisting of halogen, hydroxy, mercapto, nitro, cyano, amino, carboxy, formyl, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q -$L_{E'}$-(3- to 18-membered heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—; and each $C_3$-$C_{18}$carbocyclyl and 3- to 18-membered heterocyclyl moiety in -$L_E$-Q-$L_{E'}$-($C_3$-$C_{18}$carbocyclyl) and -$L_E$-Q-$L_{E'}$-(3- to 18-membered heterocyclyl) is independently optionally substituted at each occurrence with at least one substituent selected from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl.

3. The compound, tautomer or pharmaceutically acceptable salt of claim 2, wherein:

Z is —N$R^{41}$—;

$R^{33}$ and $R^{35}$ are each independently selected from hydrogen, halogen or $C_1$-$C_6$alkyl;

$R^{41}$ is selected from hydrogen or $C_1$-$C_6$alkyl;

$R^{10}$ is hydrogen;

$R^{17}$ is $C_1$-$C_6$alkyl;

A is a $C_5$-$C_6$carbocyclyl or 5- to 6-membered heterocyclyl, and is optionally X is —S—;

$R^{22}$ is

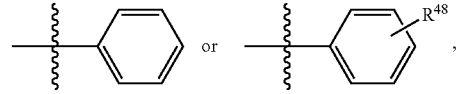

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ is optionally substituted with one or more $R^{26}$;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl; and $R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or 4- to 12-membered heterocyclyl and is optionally substituted with one or more $R^{30}$;

$L^1$ is a bond, and $A^1$ is a $C_4$-$C_{12}$carbocyclyl or 4- to 12-membered heterocyclyl and is optionally substituted with one or more $R^{30}$; or $L^1$ is a bond, and $A^1$ is a bicyclic ring having from 6 to 12 ring atoms and is optionally substituted with one or more $R^{30}$.

4. The compound, tautomer or pharmaceutically acceptable salt of claim 1, wherein the compound has a formula selected from the group consisting of Formulae I(a), I(b), I(c) and I(d),

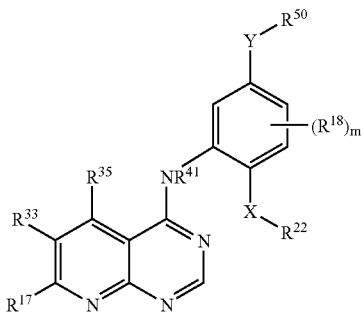

I(a)

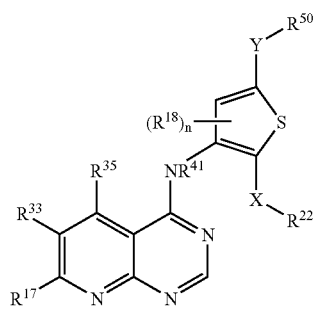

I(b)

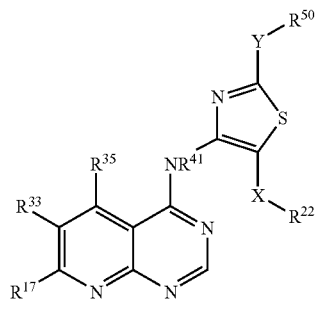

I(c)

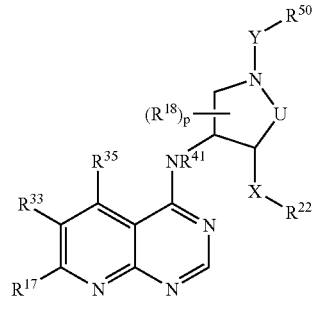

I(d)

wherein:
$R^{17}$, $R^{33}$ and $R^{35}$ are each independently selected from hydrogen, halogen, or $C_1$-$C_6$alkyl;
$R^{41}$ is selected from hydrogen or $C_1$-$C_6$alkyl;
X is —S—;
$R^{22}$ is $C_4$-$C_{12}$carbocyclyl or 4- to 12-membered heterocyclyl, and is optionally substituted with one or more $R^{26}$;
Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;
$R^{50}$ is -$L^1$-$A^1$, wherein:
  $L^1$ is $C_1$-$C_6$alkylene and is optionally substituted with one or more $R^{38}$, and $A^1$ is a $C_4$-$C_{12}$carbocyclyl or 4 to 12-membered heterocyclyl and is optionally substituted with one or more $R^{30}$;
  $L^1$ is a bond, and $A^1$ is a $C_4$-$C_{12}$carbocyclyl or 4- to 12-membered heterocyclyl and is optionally substituted with one more $R^{30}$; or
  $L^1$ is a bond, and $A^1$ is a bicyclic ring having from 6 to 12 ring atoms and is optionally substituted with one or more $R^{30}$;
$R^{18}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$-$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), and -$L_S$-N($R_S$)SO$_2$N($R_S R_{S''}$);
$R^{26}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N=C(N$R_S R_{S'}$)(N$R_S R_{S''}$), -$L_S$-N($R_S$)C(O)N($R_S R_{S''}$), -$L_S$-N($R_S$)SO$_2$$R_{S''}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-(3- to 18-membered-heterocyclyl);
$R^{30}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-(3- to 18-membered heterocyclyl);
$R^{38}$ is independently selected at each occurrence from the group consisting of halogen, hydroxy, mercapto, nitro, cyano, amino, carboxy, formyl, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S''}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q-$L_{E'}$-(3- to 18-membered heterocyclyl);
$L_S$ is independently selected at each occurrence from the group consisting of a bond, $C_1$-$C_6$alkylene, $C_2$-$C_6$alkenylene and $C_2$-$C_6$alkynylene;
$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, amino$C_1$-$C_6$alkyl, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

each $C_3$-$C_{18}$carbocyclyl and 3- to 18-membered heterocyclyl moiety in -$L_E$-Q-$L_{E'}$-($C_3$-$C_{18}$carbocyclyl) and -$L_E$-Q-$L_{E'}$-(3- to 18-membered heterocyclyl) is independently optionally substituted at each occurrence with at least one substituent selected from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

m is 0, 1, 2, or 3;
n is 0 or 1;
p is 0, 1, 2, or 3; and
U is —CH$_2$— or —CH$_2$—CH$_2$— and is optionally substituted with one or more $R^{18}$.

5. The compound, tautomer or pharmaceutically acceptable salt of claim 4, wherein:
$R^{22}$ is

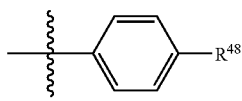

and is optionally substituted with one or more $R^{26}$, wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl; and $R^{50}$ is -$L^1$-$A^1$, wherein $L^1$ is $C_1$-$C_6$alkylene and is optionally substituted with one or more $R^{38}$, and $A^1$ is a $C_4$-$C_{12}$carbocyclyl or 4- to 12-membered heterocyclyl and is optionally substituted with one or more $R^{30}$.

6. The compound, tautomer or pharmaceutically acceptable salt of claim 5, wherein $R^{48}$ is amino and is optionally substituted with at least one $R^{26}$.

7. The compound, tautomer or pharmaceutically acceptable salt of claim 6, wherein $R^{48}$ is substituted with said at least one $R^{26}$ which is selected from —C(O)—O—$C_1$-$C_6$alkyl, —SO$_2$—$C_1$-$C_6$alkyl, —C(O)—$C_1$-$C_6$alkylene-$C_3$-$C_{18}$carbocyclyl or —C(O)—$C_1$-$C_6$alkylene-(3- to 18-membered heterocyclyl), and wherein $C_3$-$C_{18}$carbocyclyl in said —C(O)—$C_1$-$C_6$alkylene-$C_3$-$C_{18}$carbocyclyl and 3- to 18-membered heterocyclyl in said —C(O)—$C_1$-$C_6$alkylene-(3- to 18-membered heterocyclyl) are substituted or unsubstituted.

8. The compound, tautomer or pharmaceutically acceptable salt of claim 6, wherein $R^{17}$ is $C_1$-$C_6$alkyl, $R^{41}$, $R^{33}$ and $R^{35}$ are independently hydrogen or halogen, Y is —C(O)N($R^{15}$)—, and $A^1$ is $C_5$-$C_6$carbocyclyl or 5- to 6-membered heterocyclyl and is optionally substituted with one or more $R^{30}$.

9. The compound, tautomer or pharmaceutically acceptable salt of claim 8, wherein $R^{48}$ is substituted with at least one $R^{26}$ which is —C(O)—O—$C_1$-$C_6$alkyl, —SO$_2$—$C_1$-$C_6$alkyl, —C(O)—$C_1$-$C_6$alkylene-$C_3$-$C_{18}$carbocyclyl or —C(O)—$C_1$-$C_6$alkylene-(3- to 18-membered heterocyclyl), and wherein $C_3$-$C_{18}$carbocyclyl in said —C(O)—$C_1$-$C_6$alkylene-$C_3$-$C_{18}$carbocyclyl and 3- to 18-membered heterocyclyl in said —C(O)—$C_1$-$C_6$alkylene-(3- to 18-membered heterocyclyl) are substituted or unsubstituted.

10. The compound, tautomer or pharmaceutically acceptable salt of claim 4, wherein:
$R^{22}$ is

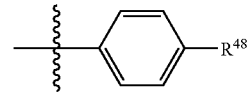

and is optionally substituted with one or more $R^{26}$, wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl; and $R^{50}$ is -$A^1$, wherein $A^1$ is a bicyclic ring having from 6 to 12 ring atoms and is optionally substituted with one or more $R^{30}$.

11. The compound, tautomer or pharmaceutically acceptable salt of claim 10, wherein $A^1$ is a bicyclic ring having from 9 to 11 ring atoms and is optionally substituted with one or more $R^{30}$, $R^{48}$ is amino and is optionally substituted with one or more $R^{26}$, Y is —C(O)N($R^{15}$)—, $R^{17}$ is $C_1$-$C_6$alkyl, and $R^{41}$, $R^{33}$ and $R^{35}$ are independently hydrogen or halogen.

12. The compound, tautomer or pharmaceutically acceptable salt of claim 4, wherein:
$R^{17}$ is $C_1$-$C_6$alkyl;
$R^{33}$ and $R^{35}$ are hydrogen;
$R^{41}$ is hydrogen;
$R^{22}$ is

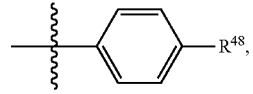

wherein $R^{48}$ is amino, and $R^{22}$ is optionally substituted with one or more $R^{26}$;

Y is —C(O)N($R^{15}$)—, wherein $R^{15}$ is hydrogen, $C_1$-$C_6$alkyl, $C_2$-$C_6$alkenyl or $C_2$-$C_6$alkynyl; and $R^{50}$ is -$L^1$-$A^1$, wherein:
$L^1$ is $C_1$-$C_6$alkylene and is optionally substituted with one or more $R^{38}$, wherein $A^1$ is phenyl, pyridinyl, thiazolyl, thienyl, furyl, tetrahydrofuryl, pyrrolyl, pyrazinyl, cyclobutyl, cyclohexyl or naphthyl, and is optionally substituted with one or more $R^{30}$, or $L^1$ is a bond, and $A^1$ is a bicyclic ring having from 9 to 11 ring atoms and is optionally substituted with one or more $R^{30}$.

13. The compound, tautomer or pharmaceutically acceptable salt of claim 1, wherein the compound has Formula I(e)

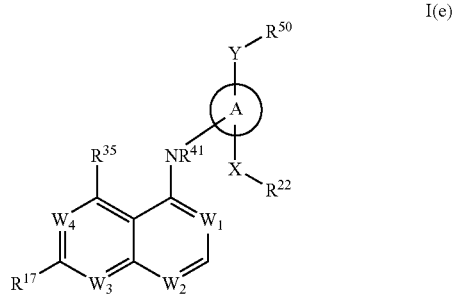

I(e)

wherein:

$R^{17}$, $R^{33}$ and $R^{35}$ are each independently selected at each occurrence from hydrogen, halogen, or $C_1$-$C_6$alkyl;

$R^{41}$ is selected from hydrogen or $C_1$-$C_6$alkyl;

A is a $C_5$-$C_{12}$carbocyclyl or 5- to 12-membered heterocyclyl, and is optionally substituted with one or more $R^{18}$;

X is —S—;

$R^{22}$ is $C_4$-$C_{12}$carbocyclyl or 5- to 12-membered heterocyclyl, and is optionally substituted with one or more $R^{26}$;

Y is a bond, —C(O)N($R^{15}$)— or —N($R^{15}$)C(O)—, wherein $R^{15}$ is hydrogen, $C_1$-$C_6$alkyl or $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or 4- to 12-membered heterocyclyl and is optionally substituted with one or more $R^{30}$; or $L^1$ is a bond, and $A^1$ is a $C_4$-$C_{12}$carbocyclyl or 4- to 12-membered heterocyclyl and is optionally substituted with one or more $R^{30}$; or $L^1$ is a bond, and $A^1$ is a bicyclic ring having from 6 to 12 ring atoms and is optionally substituted with one or more $R^{30}$;

$R^{18}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), and -$L_S$-N($R_S$)SO$_2$N($R_S$$R_{S''}$);

$R^{26}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S''}$, -$L_S$-C(=N$R_S$)N($R_S$$R_{S''}$), -$L_S$-N($R_{S'}$)C(=N$R_S$)$R_{S''}$, -$L_S$-N=C(N$R_S$$R_{S''}$)(N$R_S$$R_{S'}$), -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), -$L_E$-Q-$L_{E'}$-($C_3$-$C_{18}$carbocyclyl) and -$L_E$-Q-$L_{E'}$-(3- to 18-membered heterocyclyl);

$R^{30}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S''}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), -$L_E$-Q-$L_{E'}$-($C_3$-$C_{18}$carbocyclyl) and -$L_E$-Q-$L_{E'}$-(3- to 18-membered heterocyclyl);

$R^{38}$ is independently selected at each occurrence from the group consisting of halogen, hydroxy, mercapto, nitro, cyano, amino, carboxy, formyl, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=N$R_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S''}$, -$L_S$-C(=N$R_S$)N($R_S$$R_{S''}$), -$L_S$-N($R_{S'}$)C(=N$R_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q-$L_{E'}$-(3- to 18-membered heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, amino$C_1$-$C_6$alkyl, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—; and each $C_3$-$C_{18}$carbocyclyl and 3- to 18-membered heterocyclyl moiety in -$L_E$-Q-$L_{E'}$-($C_3$-$C_{18}$carbocyclyl) and -$L_E$-Q-$L_{E'}$-(3- to 18-membered heterocyclyl) is independently optionally substituted at each occurrence with at least one substituent selected from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, Cl -$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-

$C_6$alkyl, $C_1$-$C_6$alkoxycarbonylamino, and $C_1$-$C_6$alkoxycarbonylamino$C_1$-$C_6$alkyl.

14. The compound, tautomer or pharmaceutically acceptable salt of claim 1, wherein the compound has Formulae I(f),

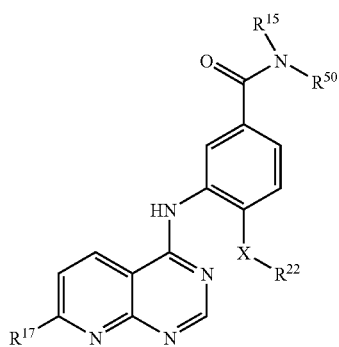

I(f)

wherein:

X is S;

$R^{50}$ is selected from the group consisting of

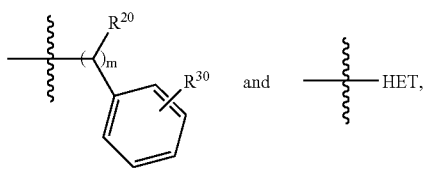

and ⸺HET, wherein HET is heterocyclo optionally substituted with $R^{30}$;

$R^{30}$ is one or more substituents independently selected from the group consisting of hydrogen, halogen, alkyl, haloalkyl, alkoxy, hydroxy, alkoxyiminoalkyl, cyano, alkylamino, haloalkylcycloalkyl, and aminocarbonyl;

$R^{20}$ is selected from the group consisting of hydrogen and alkyl;

m is an integer selected from the group consisting of zero and one;

or $R^{50}$ and $R^{15}$, taken together with the nitrogen to which they are bound, form a 5-12-membered monocyclic heterocycle containing one or more heteroatoms selected from the group consisting of O, N, and S; wherein the heterocycle is optionally substituted with at least one alkyl group; or $R^{15}$ is selected from the group consisting of hydrogen and alkyl;

$R^{17}$ is selected from the group consisting of hydrogen and alkyl;

$R^{22}$ is selected from the group consisting of aryl and heterocycle; wherein $R^{22}$ is optionally substituted with one or more substituents independently selected from $R^{26}$;

$R^{26}$ is selected from the group consisting of hydrogen, hydroxy, heteroaryl, alkoxycarbonylamino, amino, alkyl, heterocyclocarbonylamino, alkylheteroarylamino, aminocarbonylamino, alkoxycarbonylamino, halogen,alkylcarbonylamino, aminoalkylcarbonylamino, alkylsulfonylamino, haloalkoxycarbonylamino, alkylheteroarylamino, alkylamino, alkylaminocarbonyl, alkylaminoalkoxycarbonyl, morpholinoalkoxycarbonylamino, alkylheteroarylalkoxycarbonylamino, alkylaminoalkoxycarbonylamino, alkylaminohydroxyalkoxycarbonylamino, dialkylamino, monoalkylamino, alkoxycarbonylaminoimino, aminoimino, [2-(alkylheteroarylamino)-4-(haloheteroarylaminocarbonyl)]-(arylthio)arylureido, heteroarylcarbonylamino, arylalkylaminocarbonylamino, cycloalkylaminocarbonylamino, heteroarylalkylaminocarbonylamino, alkoxyalkylaminocarbonylamino, arylalkoxycarbonylamino, heteroarylalkoxycarbonylamino, heterocycloalkoxycarbonylamino, alkoxycarbonylaminopropylamino, arylcarbonylamino, alkoxyalkylcarbonylamino, alkoxyarylalkylcarbonylamino, hydroxyalkylarylalkylcarbonylamino, azido, alkylaminoalkyl, morpholinocarbonylamino, alkylaminocarbonylamino, arylalkylaminocarbonylamino, and cycloalkylalkylamino.

15. The compound, tautomer or pharmaceutically acceptable salt of claim 1, wherein the compound has Formula I(g),

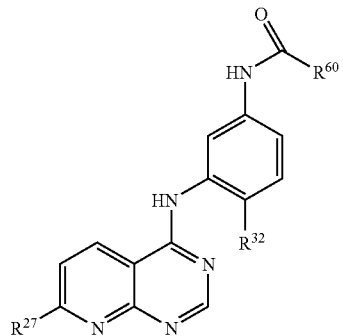

I(g)

wherein:

$R^{27}$ is selected from the group consisting of hydrogen and alkyl;

$R^{32}$ is arylsulfanyl; wherein $R^{32}$ is optionally substituted with one or more substituents independently selected from $R^{36}$;

$R^{36}$ is selected from the group consisting of hydrogen, hydroxy, amino, dialkylamino, haloalkoxycarbonylamino, alkyl, and arylalkoxy;

$R^{60}$ is selected from the group consisting of aryl and heterocyclo; wherein $R^{60}$ is optionally substituted with $R^{40}$;

$R^{40}$ is selected from the group consisting of hydrogen, halogen, haloalkyl, alkoxy, haloalkoxy, dialkylamino, monoalkylamino, hydroxy, alkylcarbonylamino, and alkyl.

16. The compound, tautomer or pharmaceutically acceptable salt of claim 1, wherein the compound has a formula I(h),

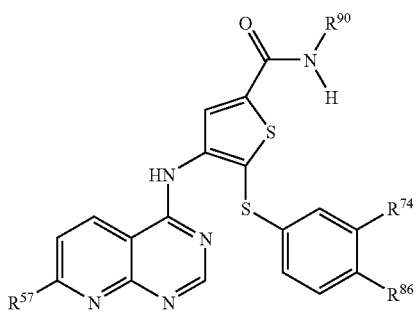

I(h)

wherein:

$R^{57}$ is selected from the group consisting of alkyl and hydroxyalkyl;

$R^{74}$ is selected from the group consisting of hydrogen and hydroxy;

$R^{86}$ is selected from the group consisting of hydrogen, hydroxy, haloalkoxycarbonylamino, and amino;

$R^{90}$ is selected from the group consisting of haloaryl and aryl.

17. A pharmaceutical composition comprising a compound, tautomer or salt according to claim 1.

18. A compound, a tautomer of said compound, or a pharmaceutically acceptable salt of said compound or tautomer, wherein said compound has a formula I,

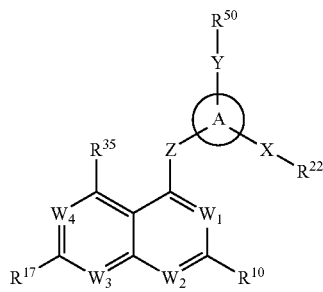

I wherein:

$W_1$, $W_2$ and $W_3$ are N;

$W_4$ is $C(R^{33})$;

Z is $-NR^{41}-$;

A is a $C_5$-$C_6$carbocyclyl or 5- to 6-membered heterocyclyl, and is optionally substituted with one or more $R^{18}$;

X is selected from the group consisting of a bond, $-L_S$-S-, $-L_S$-C(O)—, $-L_S$-N($R_S$)—, $-L_S$-N($R_S$)C(O)—, $-L_S$-C(O)N($R_S$)13 , $-L_S$-N($R_S$)C(O)O—, $-L_S$-OC(O)N($R_S$)—, $-L_S^{-N(R}_S)$C(O)N($R_{S'}$)-, $-L_S$-C(=N$R_S$)N($R_{S'}$)—, $-L_S$-N($R_S$)C(=N$R_S$)—, $-L_S$-S(O)—, $-L_S$-SO$_2$—, $-L_S$-C(O)O— and $-L_S$-OC(O)—;

$R^{22}$ is $C_3$-$C_{14}$carbocyclyl or 3- to 14-membered heterocyclyl, and is optionally substituted with one or more $R^{26}$;

Y is selected from the group consisting of —OS(O)$_2$—, —OS(O)—, —C(O)O—, —OC(O)—, —OC(O)O—, —C(O)N($R^{15}$)—, —N($R^{15}$)C(O)—, —C(O)N($R^{15}$)O—, —N($R^{15}$)C(O)O—, —C(O)N($R^{15}$)N($R^{15'}$)—, —C(S)—, —C(S)O—, —OC(S)—, —C(S)N($R^{15}$)—, —N($R^{15}$)C(S)—, —N($R^{15}$)—, —N($R^{15}$)S(O)—, —N($R^{15}$)S(O)$_2$—, —S(O)$_2$N($R^{15}$)—, —S(O)N($R^{15}$)—, —C(S)N($R^{15}$)O—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl and $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or 4- to 12-membered heterocyclyl and is optionally substituted with one or more $R^{30}$; or $L^1$ is a bond, and $A^1$ is a $C_4$-$C_{12}$carbocyclyl or 4- to 12-membered heterocyclyl and is optionally substituted with one or more $R^{30}$; or $L^1$ is a bond, and $A^1$ is a bicyclic ring having from 6 to 12 ring atoms and is optionally substituted with one or more $R^{30}$;

$R^{10}$ is hydrogen or halogen;

$R^{33}$ and $R^{35}$ are each independently selected at each occurrence from hydrogen, halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_3$-$C_6$carbocyclyl, 3- to 6-membered heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl), or -$L_E$-Q-$L_{E'}$-(3- to 18-membered heterocyclyl);

$R^{17}$ is independently selected at each occurrence from hydrogen, halogen, hydroxy, mercapto, nitro, cyano, amino, carboxy, formyl, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), or -$L_S$-N($R_S$)SO$_2$N($R_S R_{S''}$);

$R^{41}$ is selected from the group consisting of hydrogen, $C_1$-$C_6$alkyl, $C_2$-$C_6$alkenyl and $C_2$-$C_6$alkynyl;

$R^{18}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

$R^{26}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-

N=C(NR$_S$R$_{S'}$)(NR$_S$R$_{S'}$), -L$_S$-N(R$_S$)C(O)N(R$_S$R$_{S''}$), -L$_S$-N(R$_S$)SO$_2$R$_{S''}$, -L$_S$-SO$_2$N(R$_S$R$_{S'}$), -L$_S$-N(R$_S$)SO$_2$N (R$_S$R$_{S''}$), -L$_E$-Q-L$_{E'}$-(C$_3$-C$_{18}$carbocyclyl) and -L$_E$-Q-L$_{E'}$-(3- to 18-membered heterocyclyl);

R$^{30}$ is independently selected at each occurrence from the group consisting of halogen, hydroxy, mercapto, nitro, cyano, amino, carboxy, formyl, azido, C$_1$-C$_6$alkyl, C$_2$-C$_6$alkenyl, C$_2$-C$_6$alkynyl, C$_1$-C$_6$haloalkyl, -L$_S$-O—R$_S$, -L$_S$-S—R$_S$, -L$_S$-C(O)R$_S$, -L$_S$-OC(O)R$_S$, -L$_S$-C(O)OR$_S$, -L$_S$-N(R$_S$R$_{S'}$), -L$_S$-C(=NR$_S$)R$_{S'}$, -L$_S$-S(O)R$_S$, -L$_S$-SO$_2$R$_S$, -L$_S$-C(O)N(R$_S$R$_{S'}$), -L$_S$-N(R$_S$)C(O)R$_{S'}$, -L$_S$-C(=NR$_S$)N(R$_S$R$_{S''}$), -L$_S$-N(R$_{S'}$)C(=NR$_S$)R$_{S''}$, -L$_S$-N(R$_S$)C(O)N(R$_S$R$_{S''}$), -L$_S$-N(R$_S$)SO$_2$R$_{S''}$, -L$_S$-SO$_2$N(R$_S$R$_{S'}$), -L$_S$-N(R$_S$)SO$_2$N(R$_S$R$_{S''}$), -L$_E$-Q-L$_{E'}$-(C$_3$-C$_{18}$carbocyclyl) and -L$_E$-Q-L$_{E'}$-(3- to 18-membered heterocyclyl);

R$^{38}$ is independently selected at each occurrence from the group consisting of halogen, oxo, thioxo, hydroxy, mercapto, nitro, cyano, amino, carboxy, formyl, azido, C$_1$-C$_6$alkoxy, C$_1$-C$_6$thioalkoxy, C$_1$-C$_6$alkylcarbonyl, C$_1$-C$_6$alkoxycarbonyl, C$_1$-C$_6$alkylcarbonyloxy, C$_1$-C$_6$alkylamino, C$_1$-C$_6$alkoxycarbonylamino, -L$_S$-O—R$_S$, -L$_S$-S—R$_S$, -L$_S$-C(O)R$_S$, -L$_S$-OC(O)R$_S$, -L$_S$-C(O)OR$_S$, -L$_S$-N(R$_S$R$_{S'}$), -L$_S$-C(=NR$_S$)R$_{S'}$, -L$_S$-S(O)R$_S$, -L$_S$-SO$_2$R$_S$, -L$_S$-C(O)N(R$_S$R$_{S'}$), -L$_S$-N(R$_S$)C(O)R$_{S'}$, -L$_S$-C(=NR$_S$)N(R$_S$R$_{S''}$), -L$_S$-N(R$_{S'}$)C(=NR$_S$)R$_{S''}$, -L$_S$-N(R$_S$)C(O)N(R$_S$R$_{S''}$), -L$_S$-N(R$_S$)SO$_2$R$_{S''}$, -L$_S$-SO$_2$N(R$_S$R$_{S'}$), -L$_S$-N(R$_S$)SO$_2$N(R$_S$R$_{S''}$), carbocyclyl, heterocyclyl, carbocyclylC$_1$-C$_6$alkyl, heterocyclylC$_1$-C$_6$alkyl, -L$_E$-Q-L$_{E'}$-(C$_3$-C$_{18}$carbocyclyl) and -L$_E$-Q-L$_{E'}$-(3- to 18-membered heterocyclyl);

L$_S$ is independently selected at each occurrence from the group consisting of a bond, C$_1$-C$_6$alkylene, C$_2$-C$_6$alkenylene and C$_2$-C$_6$alkynylene;

R$_S$, R$_{S'}$ and R$_{S''}$ are each independently selected at each occurrence from the group consisting of hydrogen, C$_1$-C$_6$alkyl, C$_2$-C$_6$alkenyl, C$_2$-C$_6$alkynyl, C$_1$-C$_6$haloalkyl, C$_1$-C$_6$alkoxy, C$_1$-C$_6$thioalkoxy, C$_1$-C$_6$alkoxyC$_1$-C$_6$alkyl, C$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, aminoC$_1$-C$_6$alkyl, C$_1$-C$_6$alkylaminoC$_1$-C$_6$alkyl, C$_1$-C$_6$alkoxycarbonylamino, and C$_1$-C$_6$alkoxycarbonylaminoC$_1$-C$_6$alkyl;

L$_E$ and L$_{E'}$ are each independently selected at each occurrence from the group consisting of a bond, C$_1$-C$_6$alkylene, C$_2$-C$_6$alkenylene and C$_2$-C$_6$alkynylene;

Q is independently selected at each occurrence from the group consisting of a bond, C$_1$-C$_6$alkylene, C$_2$-C$_6$alkenylene, C$_2$-C$_6$alkynylene, —S—, —O—, —C(O)—, —N(R$_S$)—, —N(R$_S$)C(O)—, —C(O)N(R$_S$)—, —N(R$_S$)C(O)O—, —OC(O)N(R$_S$)—, —N(R$_S$)C(O)N(R$_{S'}$)—, —C(=NR$_S$)N(R$_{S'}$)—, —N(R$_{S'}$)C(=NR$_S$)—, —S(O)—, —SO$_2$—, —O—SO$_2$—, —SO$_2$—O—, —O—S(O)—, —S(O)—O—, —C(O)O— and —OC(O)—;

each C$_3$-C$_{18}$carbocyclyl and 3- to 18-membered heterocyclyl moiety in -L$_E$-Q-L$_{E'}$-(C$_3$-C$_{18}$carbocyclyl) and -L$_E$-Q-L$_{E'}$-(3- to 18-membered heterocyclyl) is independently optionally substituted at each occurrence with at least one substituent selected from the group consisting of halogen, hydroxy, mercapto, nitro, cyano, amino, carboxy, formyl, azido, C$_1$-C$_6$alkyl, C$_2$-C$_6$alkenyl, C$_2$-C$_6$alkynyl, C$_1$-C$_6$haloalkyl, C$_1$-C$_6$alkoxy, C$_1$-C$_6$thioalkoxy, C$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino, and C$_1$-C$_6$alkoxycarbonylaminoC$_1$-C$_6$alkyl.

19. The compound, tautomer or pharmaceutically acceptable salt of claim 18, wherein:

X is -L$_S$-S—;

Y is —C(O)N(R$^{15}$)— or —N(R$^{15}$)C(O)—.

20. A compound, a tautomer of said compound, or a pharmaceutically acceptable salt of said compound or tautomer, wherein said compound has a formula selected from the group consisting of Formulae I(a), I(b), I(c) and I(d),

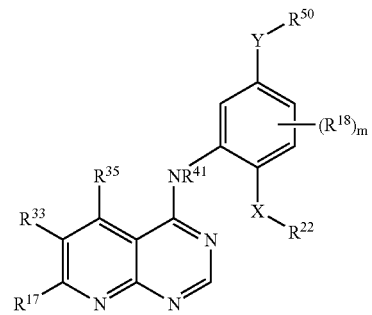

I(a)

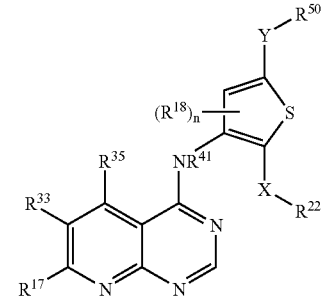

I(b)

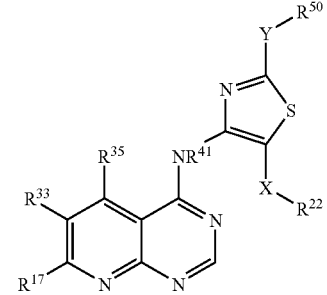

I(c)

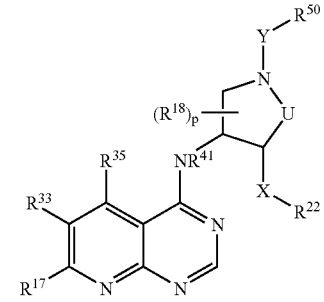

I(d)

wherein:

$R^{17}$, $R^{33}$ and $R^{35}$ are each independently selected from hydrogen, halogen, $C_1$-$C_6$alkyl or $C_3$-$C_6$cycloalkyl;

$R^{41}$ is selected from hydrogen or $C_1$-$C_6$alkyl;

X is —S—;

$R^{22}$ is $C_4$-$C_{12}$carbocyclyl or 4- to 12-membered heterocyclyl, and is optionally substituted with one or more $R^{26}$;

Y is —C(O)N($R^{15}$)— or —N($R^{15}$)C(O)—, wherein $R^{15}$ is hydrogen, $C_1$-$C_6$alkyl, $C_2$-$C_6$alkenyl or $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or 4- to 12-membered heterocyclyl and is optionally substituted with one or more $R^{30}$;

L' is a bond, and $A^1$ is a $C_4$-$C_{12}$carbocyclyl or 4- to 12-membered heterocyclyl and is optionally substituted with one or more $R^{30}$; or L' is a bond, and $A^1$ is a bicyclic ring having from 6 to 12 ring atoms and is optionally substituted with one or more $R^{30}$;

$R^{18}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

$R^{26}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N=C(N$R_S R_{S'}$)(N$R_S R_{S'}$), -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-(3- to 18-membered heterocyclyl);

$R^{30}$ is independently selected at each occurrence from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-(3- to 18-membered heterocyclyl);

$R^{38}$ is independently selected at each occurrence from the group consisting of halogen, oxo, thioxo, hydroxy, mercapto, nitro, cyano, amino, carboxy, formyl, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q-$L_{E'}$-(3- to 18-membered heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, amino$C_1$-$C_6$alkyl, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_S$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

each $C_3$-$C_{18}$carbocyclyl and 3- to 18-membered heterocyclyl moiety in -$L_E$-Q-$L_{E'}$-($C_3$-$C_{18}$carbocyclyl) and -$L_E$-Q-$L_{E'}$-(3- to 18-membered heterocyclyl) is independently optionally substituted at each occurrence with at least one substituent selected from the group consisting of halogen, hydroxy, mercapto, nitro, cyano, amino, carboxy, formyl, azido, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkylamino, $C_1$-$C_6$alkylamino$C_1$-$C_6$alkyl, $C_1$-$C_6$alkoxy carbonylamino, and $C_1$-$C_6$alkoxycarbonylamino$C_1$-$C_6$alkyl;

m is 0, 1, 2, or 3;

n is 0 or 1;

p is 0, 1, 2, or 3; and

U is —CH$_2$— or —CH$_2$—CH$_2$— and is optionally substituted with one or more $R^{18}$.

\* \* \* \* \*